United States Patent
Bonanomi et al.

(10) Patent No.: US 10,709,692 B2
(45) Date of Patent: Jul. 14, 2020

(54) ISOXAZOLIDINE DERIVED INHIBITORS OF RECEPTOR INTERACTING PROTEIN KINASE 1 (RIPK1)

(71) Applicant: Denali Therapeutics Inc., South San Francisco, CA (US)

(72) Inventors: Giorgio Bonanomi, Verona (IT); Anthony A. Estrada, San Mateo, CA (US); Jianwen A. Feng, San Mateo, CA (US); Brian Fox, Brisbane, CA (US); Colin Philip Leslie, Pozzolengo (IT); Joseph P. Lyssikatos, South San Francisco, CA (US); Carmela Napolitano, Verona (IT); Alfonso Pozzan, Monticello Conte Otto (IT); Anantha Sudhakar, Fremont, CA (US); Zachary K. Sweeney, Redwood City, CA (US); Federica Tonelli, Verona (IT); Javier de Vicente Fidalgo, Foster City, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 192 days.

(21) Appl. No.: 15/780,620

(22) PCT Filed: Dec. 2, 2016

(86) PCT No.: PCT/US2016/064818
§ 371 (c)(1),
(2) Date: Jan. 4, 2019

(87) PCT Pub. No.: WO2017/096301
PCT Pub. Date: Jun. 8, 2017

(65) Prior Publication Data
US 2018/0353480 A1    Dec. 13, 2018

Related U.S. Application Data

(60) Provisional application No. 62/364,814, filed on Jul. 20, 2016, provisional application No. 62/300,740, filed on Feb. 26, 2016, provisional application No. 62/263,481, filed on Dec. 4, 2015.

(51) Int. Cl.
| A61K 31/422 | (2006.01) |
| C07D 413/04 | (2006.01) |
| C07D 261/02 | (2006.01) |
| A61P 1/00 | (2006.01) |
| A61P 29/00 | (2006.01) |
| A61K 31/4439 | (2006.01) |

(52) U.S. Cl.
CPC ........ *A61K 31/422* (2013.01); *A61K 31/4439* (2013.01); *A61P 1/00* (2018.01); *A61P 29/00* (2018.01); *C07D 261/02* (2013.01); *C07D 413/04* (2013.01); *A61K 2121/00* (2013.01)

(58) Field of Classification Search
CPC ............. A61K 31/422; A61K 31/4439; A61K 2121/00; A61P 29/00; A61P 1/00; C07D 261/02; C07D 413/04
See application file for complete search history.

(56) References Cited

U.S. PATENT DOCUMENTS

| 3,853,903 A | 12/1974 | Sale |
| 9,556,152 B2 * | 1/2017 | Harris ................. C07D 403/14 |

FOREIGN PATENT DOCUMENTS

| DE | 2339185 | 2/1974 |
| WO | WO 2013/013826 | 1/2013 |
| WO | WO 2014/125444 | 8/2014 |
| WO | WO 2014/145022 | 9/2014 |
| WO | WO 2014/152182 | 9/2014 |

OTHER PUBLICATIONS

Database CA, Chemical Abstracts Service, Lemen, Georgia S. et al., "Influence of Hydroxylamine Conformation on Stereocontrol in Pd-Catalyzed Isoxazolidine-Forming Reactions", retrieved from STN Database accession No. 2009:244095, abstract, 2 pages, 2009.
Database CA, Chemical Abstracts Service, Romeo, Roberto et al., "Truncated Reverse Isoxazolidinyl Nucleosides: A New Class of Allosteric HIV-1 Reverse Transcriptase Inhibitors", retrieved from STN Database accession No. 2012:196899, abstract, 4 pages, 2012.
Gioia et al., "Organocatalytic Asymmetrical Formal 3+2|Cycloaddition with in Situ-Generated N-Carbamoyl Nitrones", Journal of the American Chemical Society, vol. 131, No. 28, 2009, pp. 9614-9615.
Harris et al., "Discovery of Small Molecule RIP1 Kinase Inhibitors for the Treatment of Pathologies Associated with Necroptosis", ACS Medicinal Chemistry Letters, vol. 4, No. 12, 2013, pp. 1238-1243.
International Search Report and Written Opinion for PCT/US2016/064818, dated Mar. 20, 2017, 14 pages.
Wang et al., "The use of Mosher derivatives for the determination of the absolute configuration of substituted isoxazolidines", Tetrahedron Asymmetry, vol. 24, No. 4, 2013, pp. 223-228.

* cited by examiner

Primary Examiner — Timothy R Rozof
(74) Attorney, Agent, or Firm — McNeill Baur PLLC

(57) ABSTRACT

The present disclosure relates generally to methods and compositions for preventing or arresting cell death and/or inflammation.

28 Claims, No Drawings

ISOXAZOLIDINE DERIVED INHIBITORS OF RECEPTOR INTERACTING PROTEIN KINASE 1 (RIPK1)

CROSS-REFERENCE TO RELATED APPLICATIONS

This application is a U.S. national stage application of International Application PCT/US2016/064818, filed Dec. 2, 2016, which claims the benefit under 35 U.S.C. 119(e) to U.S. Application Nos. 62/263,481, filed Dec. 4, 2015, 62/300,740, filed Feb. 26, 2016, and 62/364,814, filed Jul. 20, 2016, where the contents of each is incorporated herein by reference in its entirety.

FIELD

The present disclosure relates generally to methods and compositions for preventing or arresting cell death and/or inflammation.

BACKGROUND

Programmed necrotic cell death, also called necroptosis, is a form of cell death in which various stimuli such as TNFα, certain toll-like receptor (TLR) agonists and ischemia can induce cellular necrosis. Necroptosis is a highly inflammatory form of cell death and is thought to be an important contributor to pathology in multiple degenerative and inflammatory diseases. These diseases include neurodegenerative diseases, stroke, coronary heart disease and myocardial infarction, retinal degenerative diseases, inflammatory bowel disease, kidney disease, liver disease and others.

Necrosis is characterized by cell membrane and organelle disruption, cell swelling and mitochondrial impairment, followed by cell lysis. Also, cell lyses typically are accompanied by an inflammatory response. Some of the underlying biochemical events in this process are now understood and the activity of receptor interacting protein kinase 1 has been shown to be important for cells to undergo necroptosis. Furthermore, this activity is also known to promote the release of inflammatory mediators such as TNF alpha from cells which can induce inflammation and also promote further necroptosis. Therefore, identifying and preparing low molecular weight molecules that prevent necrotic cell death and/or inflammation by inhibiting this or by other mechanisms can provide useful compounds for therapeutic intervention in diseases characterized by necrotic cell death and/or inflammation.

While progress has been made, there remains a need in the art for improved compounds for preventing and treating diseases involving cell death and/or inflammation. The present disclosure provides this and related benefits.

SUMMARY

Provided herein is a method for inhibiting receptor interacting protein kinase 1 in a cell, comprising contacting the cell with a receptor interacting protein kinase 1 inhibitor. Also provided are compounds that are useful as inhibitors of receptor interacting protein kinase 1. The disclosure also provides compositions, including pharmaceutical compositions, kits that include the compounds and methods of using and making the compounds. The disclosure further provides compounds or compositions thereof for use in a method of treating a disease, disorder or condition that is mediated by receptor interacting protein kinase 1. Moreover, the disclosure provides uses of the compounds or compositions thereof in the manufacture of a medicament for the treatment of a disease, disorder or condition that is mediated by (or mediated, at least in part, by) receptor interacting protein kinase 1.

These and other aspects of the disclosure will be apparent upon reference to the following detailed description. To this end, various references are set forth herein which describe in more detail certain background information, procedures, compounds and/or compositions and are each hereby incorporated by reference in their entirety.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "C$_{u-v}$" indicates that the following group has from u to v carbon atoms. For example, "C$_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes tire indicated amount±10%. In certain embodiments, tire term "about" includes the indicated amount±5%. In certain embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 12 carbon atoms (i.e., C$_{1-12}$ alkyl), 1 to 8 carbon atoms (i.e., C$_{1-8}$ alkyl), 1 to 6 carbon atoms (i.e., C$_{1-6}$ alkyl) or 1 to 4 carbon atoms (i.e., C$_{1-8}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., C$_{2\text{-}20}$ alkenyl), 2 to 8 carbon atoms (i.e., C$_{2\text{-}8}$ alkenyl), 2 to 6 carbon atoms (i.e., C$_{2\text{-}6}$ alkenyl) or 2 to 4 carbon atoms (i.e., C$_{2\text{-}4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., C$_{2\text{-}20}$ alkynyl), 2 to 8 carbon atoms (i.e., C$_{2\text{-}8}$ alkynyl), 2 to 6 carbon atoms (i.e., C$_{2\text{-}6}$ alkynyl) or 2 to 4 carbon atoms (i.e., C$_{2\text{-}4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy and 1,2-dimethyl butoxy.

"Alkoxyalkyl" refers to the group "alkyl-O-alkyl".

"Alkylthio" refers to the group "alkyl-S—".

"Acyl" refers to a group —C(O)R, wherein R is hydrogen, alkyl, alkenyl, alkynyl, cycloalkyl, heterocyclyl, aryl, heteroalkyl or heteroaryl; each of which may be optionally substituted, as defined herein. Examples of acyl include formyl, acetyl, cyclohexylcarbonyl, cyclohexylmethyl-carbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C(NR)(NR$_2$), wherein each R is independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6\text{-}20}$ aryl), 6 to 18 carbon ring atoms (i.e., C$_{6\text{-}18}$ aryl), 6 to 12 carbon ring atoms (i.e., C$_{6\text{-}12}$ aryl) or 6 to 10 carbon ring atoms (i.e., C$_{6\text{-}10}$ aryl). Examples of aryl groups include phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)R and —C(O)OR, wherein R is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond). As used herein, cycloalkyl has from 3 to 20 ring carbon atoms (i.e., C$_{3\text{-}20}$ cycloalkyl), 3 to 15 ring carbon atoms (i.e., C$_{3\text{-}15}$ cycloalkyl), 3 to 12 ring carbon atoms (i.e., C$_{3\text{-}12}$ cycloalkyl), 3 to 10 ring carbon atoms (i.e., C$_{3\text{-}10}$ cycloalkyl), 3 to 8 ring carbon atoms (i.e., C$_{3\text{-}8}$ cycloalkyl) or 3 to 6 ring carbon atoms (i.e., C$_{3\text{-}6}$ cycloalkyl). Cycloalkyl also includes "spiro cycloalkyl" when there are two positions for substitution on the same carbon atom. Monocyclic radicals include, for example, cyclopropyl, cyclobutyl, cyclopentyl, cyclohexyl, cycloheptyl and cyclooctyl. Polycyclic radicals include, for example, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule.

"Cycloalkylalkyl" refers to the group "cycloalkyl-alkyl-".

"Guanidino" refers to —NRC(NR)(NR$_2$), wherein each R is hydrogen, alkyl, alkenyl, alkynyl, cycloalkyl, heterocyclyl, aryl, heteroalkyl or heteroaryl; each of which may be optionally substituted, as defined herein.

"Imino" refers to a group —C(NR)R, wherein each R is independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —C(O)NRC(O)R, wherein each R is independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" includes fluoro, chloro, bromo and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include trifluoromethyl, difluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more hydrogen atoms are replaced by a halogen.

"Hydroxyalkyl" refers to an alkyl group as defined above, wherein one or more hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include —CH$_2$OCH$_3$, —CH$_2$SCH$_3$, and —CH$_2$NRCH$_3$, where R is hydrogen, alkyl, alkenyl, alkynyl, cycloalkyl, heterocyclyl, aryl, heteroalkyl, or heteroaryl; each of which may be optionally substituted, as defined herein. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group (e.g., a 5-14 membered ring system) having a single ring, multiple rings or multiple fused rings, with one or more ring heteroatoms independently selected from nitrogen, oxygen and sulfur. As used herein, heteroaryl includes 1 to 20 ring carbon atoms (i.e., C$_{1-20}$ heteroaryl), 1 to 13 ring carbon atoms (i.e., C$_{3-12}$ heteroaryl), 3 to 12 ring carbon atoms (i.e., C$_{3-12}$ heteroaryl) or 3 to 8 carbon ring atoms (i.e., C$_{3-8}$ heteroaryl); and 1 to 6 heteroatoms, 1 to 5 heteroatoms, 1 to 4 heteroatoms, 1 to 3 ring heteroatoms, 1 to 2 ring heteroatoms or 1 ring heteroatom independently selected from nitrogen, oxygen and sulfur. Examples of heteroaryl groups include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl). Examples of the fused-heteroaryl rings include, but are not limited to, benzo[d]thiazolyl, quinolinyl, isoquinolinyl, benzothiophenyl, indazolyl, benzoimidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of die attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more oxo (C=O) or N-oxide (N—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl) or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms or 1 ring heteroatom independently selected from nitrogen, sulfur or oxygen. Examples of heterocyclyl groups include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl. Examples of the spiro-heterocyclyl rings include bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-".

"Oxime" refers to the group —CR(=NOH) wherein R is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —S(O)$_2$R, where R is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —S(O)R, where R is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NRR and —NRSO$_2$R, where each R is independently hydrogen, alkyl, alkenyl, alkynyl, cycloalkyl, heterocyclyl, aryl, heteroalkyl or heteroaryl; each of which may be optionally substituted, as defined herein.

"Alkylsulfonyl" refers to the group —S(O)$_2$R, where R is alkyl.

"Alkylsulfinyl" refers to the group —S(O)R, where R is alkyl.

The terms "optional" or "optionally" means that the subsequently described event or circumstance may or may not occur and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^{100}$)$_3$ wherein each $R^{100}$ is independently hydrogen, alkyl, alkenyl, alkynyl, heteroalkyl, cycloalkyl, aryl, heteroaryl or heterocyclyl.

The term "substituted" used herein means any of the above groups (i.e., alkyl, alkylene, alkoxy, haloalkoxy, aryl, cycloalkyl, haloalkyl, heterocyclyl, heteroaryl, hydroxylalkyl and/or alkoxyalkyl) wherein at least one hydrogen atom is replaced by a bond to a non-hydrogen atom such as, but not limited to: an alkyl group, a haloalkyl group, a halogen atom such as F, Cl, Br, and I; an alkenyl, a haloalkenyl group, an alkynyl group, a haloalkynyl group, a cyclic group such as an aryl, heteroaryl, cycloalkyl, or heterocyclyl group, an oxygen atom in groups such as hydroxyl groups, alkoxy groups, and ester groups; a sulfur atom in groups such as thiol groups, thioalkyl groups, thiohaloalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, formyl, carboxyl, carbonate, and ester groups; and nitrogen in groups such as imines, oximes, hydrazones, and nitriles.

In certain embodiments, "substituted" includes any of the above groups in which one or more hydrogen atoms are replaced with —NR$^g$R$^h$, —NR$^g$C(=O)R$^h$, —NR$^g$C(=O) NR$^g$R$^h$, —NR$^g$C(=O)OR$^h$, —NR$^g$SO$_2$R$^h$, —OC(=O) NR$^g$R$^h$, —OR$^g$, —SR$^g$, —SOR$^g$, —SO$_2$R$^g$, —OSO$_2$R$^g$, —SO$_2$OR$^g$, =NSO$_2$R$^g$, and —SO$_2$NR$^g$R$^h$. "Substituted" also means any of the above groups in which one or more hydrogen atoms are replaced with —C(=O)R$^g$, —C(=O) OR$^g$, —C(=O)NR$^g$R$^h$, —CH$_2$SO$_2$R$^g$, —CH$_2$SO$_2$NR$^g$R$^h$. "Substituted" further means any of the above groups in which one or more hydrogen atoms are replaced by —NR$^6$S(O)$_{1-2}$NR$^g$R$^h$. —CH$_2$S(O)R$^g$, —CH$_2$S(O)NR$^g$R$^h$, —OC(=O)OR$^g$, —SF$_5$, —SCF$_3$ or —OCF$_3$. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl group. In the foregoing, R$^g$ and R$^h$ and R$^i$ are the same or different and independently hydrogen, halo, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In an embodiment, each of said hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl are independently optionally-substituted with one or more oxo, alkyl, halo, amino, hydroxyl or alkoxyl. In addition, each of the foregoing substituents may also be optionally substituted with one or more of the above substituents.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in certain embodiments, the term "substituted alkyl" refers to an alkyl group having one or more substituents including hydroxy, halo, alkoxy, acyl, oxo, amino, cycloalkyl, heterocyclyl, aryl and heteroaryl. In certain embodiments, the one or more substituents may be further substituted with halo, alkyl, haloalkyl, hydroxy, alkoxy, cycloalkyl, heterocyclyl, aryl or heteroaryl, each of which is substituted. In certain embodiments, the substituents may be further substituted with halo, alkyl, haloalkyl, alkoxy, hydroxy, cycloalkyl, heterocyclyl, aryl or heteroaryl, each of which is unsubstituted.

Any compound or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^{3}$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN$(alkyl)$_2$), trialkyl amines (i.e., $N$(alkyl)$_3$), substituted alkyl amines (i.e., $NH_2$(substituted alkyl)), disubstituted alkyl) amines (i.e., $HN$(substituted alkyl)$_2$), trisubstituted alkyl) amines (i.e., trisubstituted alkyl)$_3$), alkenyl amines (i.e., $NH_2$(alkenyl)), dialkenyl amines (i.e., $HN$(alkenyl)$_2$), trialkenyl amines (i.e., $N$(alkenyl)$_3$), substituted alkenyl amines (i.e., $NH_2$(substituted alkenyl)), disubstituted alkenyl) amines (i.e., $HN$(substituted alkenyl)$_2$), trisubstituted alkenyl) amines (i.e., $N$(substituted alkenyl)$_3$, mono-, di- or tri-cycloalkyl amines (i.e., $NH_2$(cycloalkyl), $HN$(cycloalkyl)$_2$, $N$(cycloalkyl)$_3$), mono-, di- or tri-arylamines (i.e., $NH_2$(aryl), $HN$(aryl)$_2$, $N$(aryl)$_3$) or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, die compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

"Diastereoisomers" are stereoisomers that have at least two asymmetric atoms, but which are not mirror-images of each other.

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the patent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl or sulfhydryl group in a compound described herein is bonded to any group that may be cleaved in vivo to regenerate the free hydroxy, amino or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series: "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "necrotic cell disease" refers to diseases associated with or caused by cellular necrosis. Exemplary necrotic cell diseases include, but are not limited to, acute diseases such as trauma, ischemia, stroke, cardiac infarction, anthrax lethal toxin induced septic shock, sepsis, cell death induced by LPS and HIV induced T-cell death leading to immunodeficiency. The term "necrotic cell disease" also includes but is not limited to chronic neurodegenerative diseases, such as Parkinson's disease, Huntington's disease, amyotrophic lateral sclerosis, Alzheimer's disease, infectious encelopathies, dementia such as HIV associated dementia. The term "necrotic cell disease" also includes but is not limited to diseases such as inflammatory bowel disease and acute and chronic kidney disease which are characterized by inflammation and cell death.

The chemical names used herein are generated using the MarvinSketch Version 6.1.6 (ChemAxon) or the ChemDraw Ultra Version 13.0 software naming programs.

2. Compounds

Provided are compounds having the following structure (X):

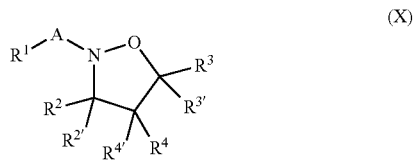

or a pharmaceutically acceptable salt, prodrug, stereoisomer or a mixture of stereoisomers thereof, wherein:
A is —C(=O)—, —S(=O)—, —S(=O)$_2$ or —S(=O)(=NH)—;
$R^1$ is —NR$^5$R$^6$, $C_{1-6}$ alkyl, $C_{3-6}$ alkoxy, $C_{3-10}$ cycloalkyl, heterocyclyl or heteroaryl;
$R^2$ is aryl or heteroaryl;
$R^{2'}$ is hydrogen or $R^2$ and $R^{2'}$ together form a $C_{3-10}$ cycloalkyl or heterocyclyl;
$R^3$ is hydrogen, deuterium, $C_{1-6}$ alkyl or $C_{3-10}$ cycloalkyl;
$R^{3'}$ is hydrogen, deuterium, or $R^3$ and $R^{3'}$ together form a $C_{3-10}$ cycloalkyl or heterocyclyl;
$R^4$ is hydrogen, halo, $C_{1-6}$ alkyl or $C_{3-10}$ cycloalkyl;
$R^{4'}$ is hydrogen or $R^4$ and $R^{4'}$ together form a $C_{3-10}$ cycloalkyl or heterocyclyl;
or $R^{2'}$ and $R^{4'}$ or $R^{3'}$ and $R^{4'}$ together form a $C_{3-10}$ cycloalkyl or heterocyclyl;
$R^5$ and $R^6$ are each independently H, $C_{1-6}$ alkyl, $C_{3-10}$ cycloalkyl, aryl, heteroaryl or heterocyclyl,
wherein each $C_{1-6}$ alkyl, $C_{3-6}$ alkoxy, $C_{3-10}$ cycloalkyl, heterocyclyl, heteroaryl and aryl group of $R^1$, $R^2$, $R^{2'}$, $R^3$, $R^{3'}$, $R^4$, $R^{4'}$, $R^5$ and $R^6$ is optionally substituted with one, two, three or four $R^{10}$;
$R^{10}$ in each instance is independently halo, hydroxy, cyano, nitro, $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl, heteroaryl, —C(=O)R$^{11}$, —C(=O)OR$^{11}$, —C(=O)NR$^{11}$R$^{11}$, —S(O)R$^{11}$, —S(=O)$_2$R$^{11}$, —NR$^{11}$R$^{11}$, —NR$^{11}$C(=O)R$^{11}$ or —NR$^{11}$C(=O)OR$^{11}$;
wherein the $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl and heteroaryl of $R^{10}$ are optionally substituted with one, two or three substituents independently selected from deuterium, halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and
$R^{11}$ in each instance independently is hydrogen, $C_{1-6}$ alkyl, $C_{3-10}$ cycloalkyl, heterocyclyl, heteroaryl or aryl;
wherein the $C_{1-6}$ alkyl of $R^{11}$ is optionally substituted with halo or oxo and wherein the $C_{3-10}$ cycloalkyl, heterocyclyl, heteroaryl or aryl of $R^{11}$ is optionally substituted with one, two or three $C_{1-6}$ alkyl;
provided the compound is not ethyl 3-phenylisoxazolidine-2-carboxylate, benzyl 3-(4-amino-2-oxopyrimidin-1(2H)-yl)isoxazolidine-2-carboxylate, 2-(methylsulfonyl)-3-phenyl-isoxazolidine, tert-butyl 5-benzyl-3-phenylisoxazolidine-2-carboxylate, tert-butyl 5-(naphthalen-2-ylmethyl)-3-phenylisoxazolidine-2-carboxylate, tert-butyl 5-([1,1-biphenyl]-4-ylmethyl)-3-phenylisoxazolidine-2-carboxylate, 2,2-dimethyl-1-(3-phenylisoxazolidin-2-yl)butan-1-one or 2,2-dimethyl-1-(3-phenylisoxazolidin-2-yl)but-3-en-1-one.

Also provided are compounds having structure (X), or a pharmaceutically acceptable salt, prodrug, stereoisomer or a mixture of stereoisomers thereof, wherein:

A is —C(=O)—, —S(=O)—, —S(=O)$_2$ or —S(=O)(=NH)—;

$R^1$ is —NR$^5$R$^6$, C$_{1-6}$ alkyl, C$_{3-6}$ alkoxy, C$_{3-10}$ cycloalkyl, heterocyclyl or heteroaryl;

$R^2$ is aryl or heteroaryl;

$R^{2'}$ is hydrogen or $R^2$ and $R^{2'}$ together form a C$_{3-10}$ cycloalkyl or heterocyclyl;

$R^3$ is hydrogen, deuterium, C$_{1-6}$ alkyl or C$_{3-10}$ cycloalkyl;

$R^{3'}$ is hydrogen, deuterium, or $R^3$ and $R^{3'}$ together form a C$_{3-10}$ cycloalkyl or heterocyclyl;

$R^4$ is hydrogen, halo, C$_{1-6}$ alkyl or C$_{3-10}$ cycloalkyl;

$R^{4'}$ is hydrogen or $R^4$ and $R^{4'}$ together form a C$_{3-10}$ cycloalkyl or heterocyclyl;

or $R^{2'}$ and $R^{4'}$ or $R^{3'}$ and $R^{4'}$ together form a C$_{3-10}$ cycloalkyl or heterocyclyl;

$R^5$ and $R^6$ are each independently H, C$_{1-6}$ alkyl, C$_{3-10}$ cycloalkyl, aryl, heteroaryl or heterocyclyl, wherein each C$_{1-6}$ alkyl, C$_{3-6}$ alkoxy, C$_{3-10}$ cycloalkyl, heterocyclyl, heteroaryl and aryl group of $R^1$, $R^2$, $R^{2'}$, $R^3$, $R^{3'}$, $R^4$, $R^{4'}$, $R^5$ and $R^6$ is optionally substituted with one, two, three or four $R^{10}$;

$R^{10}$ in each instance is independently halo, hydroxy, cyano, nitro, C$_{1-6}$ alkyl, C$_{1-6}$ alkoxy, C$_{2-6}$ alkenyl, C$_{2-6}$ alkynyl, C$_{3-10}$ cycloalkyl, heterocyclyl, aryl, heteroaryl, —C(=O)R$^{11}$, —C(=O)OR$^{11}$, —C(=O)NR$^{11}$R$^{11}$, —S(O)R$^{11}$, —S(=O)$_2$R$^{11}$, —NR$^{11}$R$^{11}$, —NR$^{11}$C(=O)R$^{11}$ or —NR$^{11}$C(=O)OR$^{11}$;

wherein the C$_{1-6}$ alkyl, C$_{1-6}$ alkoxy, C$_{2-6}$ alkenyl, C$_{2-6}$ alkynyl, C$_{3-10}$ cycloalkyl, heterocyclyl, aryl and heteroaryl of $R^{10}$ are optionally substituted with one, two or three substituents independently selected from deuterium, halo, hydroxy, cyano, amino, nitro, C$_{1-6}$ alkyl, C$_{1-6}$ alkoxy, C$_{1-6}$ haloalkoxy, C$_{2-6}$ alkenyl, C$_{2-6}$ alkynyl, C$_{3-10}$ cycloalkyl, heterocyclyl, aryl or heteroaryl; and $R^{11}$ in each instance independently is hydrogen, C$_{1-6}$ alkyl, C$_{3-10}$ cycloalkyl, heterocyclyl, heteroaryl or aryl;

wherein the C$_{1-6}$ alkyl of $R^{11}$ is optionally substituted with halo or oxo and wherein the C$_{3-10}$ cycloalkyl, heterocyclyl, heteroaryl or aryl of $R^{11}$ is optionally substituted with one, two or three C$_{1-6}$ alkyl;

provided the compound is not ethyl 3-phenylisoxazolidine-2-carboxylate, benzyl 3-(4-amino-2-oxopyrimidin-1(2H)-yl)isoxazolidine-2-carboxylate, 2-(methylsulfonyl)-3-phenyl-isoxazolidine, tert-butyl 5-benzyl-3-phenylisoxazolidine-2-carboxylate, tert-butyl 5-(naphthalen-2-ylmethyl)-3-phenylisoxazolidine-2-carboxylate, tert-butyl 5-([1,1-biphenyl]-4-ylmethyl)-3-phenylisoxazolidine-2-carboxylate, 2,2-dimethyl-1-(3-phenylisoxazolidin-2-yl)butan-1-one or 2,2-dimethyl-1-(3-phenylisoxazolidin-2-yl)but-3-en-1-one.

Also provided are compounds having structure (X), or a pharmaceutically acceptable salt, prodrug, stereoisomer or a mixture of stereoisomers thereof, wherein:

A is —C(=O)—, —S(=O)—, —S(=O)$_2$ or —S(=O)(=NH)—;

$R^1$ is —NR$^5$R$^6$, C$_{1-6}$ alkyl, C$_{3-6}$ alkoxy, C$_{3-10}$ cycloalkyl, heterocyclyl or heteroaryl;

$R^2$ is aryl or heteroaryl;

$R^{2'}$ is hydrogen or $R^2$ and $R^{2'}$ together form a C$_{3-10}$ cycloalkyl or heterocyclyl;

$R^3$ is hydrogen, deuterium, C$_{1-6}$ alkyl or C$_{3-10}$ cycloalkyl;

$R^{3'}$ is hydrogen, deuterium, or $R^3$ and $R^{3'}$ together form a C$_{3-10}$ cycloalkyl or heterocyclyl;

$R^4$ is hydrogen, halo, C$_{1-6}$ alkyl or C$_{3-10}$ cycloalkyl;

$R^{4'}$ is hydrogen or $R^4$ and $R^{4'}$ together form a C$_{3-10}$ cycloalkyl or heterocyclyl;

or $R^{2'}$ and $R^{4'}$ or $R^{3'}$ and $R^{4'}$ together form a C$_{3-10}$ cycloalkyl or heterocyclyl;

$R^5$ and $R^6$ are each independently H, C$_{1-6}$ alkyl, C$_{3-10}$ cycloalkyl, aryl, heteroaryl or heterocyclyl, wherein each C$_{1-6}$ alkyl, C$_{3-6}$ alkoxy, C$_{3-10}$ cycloalkyl, heterocyclyl, heteroaryl and aryl group of $R^1$, $R^2$, $R^{2'}$, $R^3$, $R^{3'}$, $R^4$, $R^{4'}$, $R^5$ and $R^6$ is optionally substituted with one, two, three or four $R^{10}$;

$R^{10}$ in each instance is independently halo, hydroxy, cyano, nitro, C$_{1-6}$ alkyl, C$_{1-6}$ alkoxy, C$_{2-6}$ alkenyl, C$_{2-6}$ alkynyl, C$_{3-10}$ cycloalkyl, heterocyclyl, aryl, heteroaryl, —C(=O)R$^{11}$, —C(=O)OR$^{11}$, —C(=O)NR$^{11}$R$^{11}$, —S(O)R$^{11}$, —S(=O)$_2$R$^{11}$, —NR$^{11}$R$^{11}$, —NR$^{11}$C(=O)R$^{11}$ or —NR$^{11}$C(=O)OR$^{11}$;

wherein the C$_{1-6}$ alkyl, C$_{1-6}$ alkoxy, C$_{2-6}$ alkenyl, C$_{2-6}$ alkynyl, C$_{3-10}$ cycloalkyl, heterocyclyl, aryl and heteroaryl of $R^{10}$ are optionally substituted with one, two or three substituents independently selected from deuterium, halo, hydroxy, cyano, amino, nitro, C$_{1-6}$ alkyl, C$_{1-6}$ alkoxy, C$_{1-6}$ haloalkoxy, C$_{2-6}$ alkenyl, C$_{2-6}$ alkynyl, C$_{3-10}$ cycloalkyl, heterocyclyl, aryl or heteroaryl; and $R^{11}$ in each instance independently is hydrogen, C$_{1-6}$ alkyl, C$_{3-10}$ cycloalkyl, heterocyclyl, heteroaryl or aryl;

provided the compound is not 2-(methylsulfonyl)-3-phenyl-isoxazolidine, tert-butyl 5-benzyl-3-phenylisoxazolidine-2-carboxylate, tert-butyl 5-(naphthalen-2-ylmethyl)-3-phenylisoxazolidine-2-carboxylate or tert-butyl 5-([1,1'-biphenyl]-4-ylmethyl)-3-phenylisoxazolidine-2-carboxylate. Further the compound is not ethyl 3-phenylisoxazolidine-2-carboxylate, benzyl 3-(4-amino-2-oxopyrimidin-(2H)-yl)isoxazolidine-2-carboxylate, 2,2-dimethyl-1-(3-phenylisoxazolidin-2-yl)butan-1-one or 2,2-dimethyl-1-(3-phenylisoxazolidin-2-yl)but-3-en-1-one.

Also provided herein are compounds having the following structure (Xa):

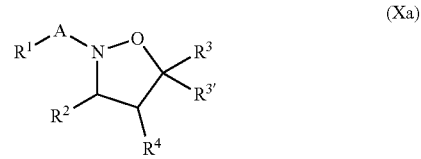

(Xa)

or a pharmaceutically acceptable salt, prodrug, stereoisomer or a mixture of stereoisomers thereof, wherein:

A is —C(=O)—, —S(=O)—, —S(=O)$_2$ or —S(=O)(=NH)—;

$R^1$ is —NR$^5$R$^6$, C$_{1-6}$ alkyl, C$_{3-6}$ alkoxy, C$_{3-10}$ cycloalkyl, heterocyclyl or heteroaryl;

$R^2$ is aryl or heteroaryl;

$R^{2'}$ is hydrogen or $R^2$ and $R^{2'}$ together form a C$_{3-10}$ cycloalkyl or heterocyclyl;

$R^3$ is hydrogen, deuterium, C$_{1-6}$ alkyl or C$_{3-10}$ cycloalkyl;

$R^{3'}$ is hydrogen or deuterium;

$R^4$ is hydrogen, halo, C$_{1-6}$ alkyl or C$_{3-10}$ cycloalkyl;

$R^5$ and $R^6$ are each independently H, C$_{1-6}$ alkyl, C$_{3-10}$ cycloalkyl, aryl, heteroaryl or heterocyclyl, wherein each C$_{1-6}$ alkyl, C$_{3-6}$ alkoxy, C$_{3-10}$ cycloalkyl, heterocyclyl, heteroaryl and aryl group of $R^1$, $R^2$, $R^3$, $R^{3'}$, $R^4$, $R^5$ and $R^6$ is optionally substituted with one, two, or three $R^{10}$;

$R^{10}$ in each instance is independently deuterium, halo, hydroxy, cyano, nitro, $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl, heteroaryl, —C(=O)$R^{11}$, —C(=O)O$R^{11}$, —C(=O)N$R^{11}R^{11}$, —S(O)$R^{11}$, —S(=O)$_2R^{11}$, —N$R^{11}R^{11}$, —N$R^{11}$C(=O)$R^{11}$ or —N$R^{11}$C(=O)O$R^{11}$;

wherein the $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl and heteroaryl of $R^{10}$ are optionally substituted with one, two or three substituents independently selected from halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and $R^{11}$ in each instance independently is hydrogen, $C_{1-6}$ alkyl, $C_{3-10}$ cycloalkyl, heterocyclyl, heteroaryl or aryl;

wherein the $C_{3-10}$ cycloalkyl, heterocyclyl, heteroaryl or aryl of $R^{11}$ is optionally substituted with one, two or three $C_{1-6}$ alkyl;

provided the compound is not 2-(methylsulfonyl)-3-phenyl-isoxazolidine, tert-butyl 5-benzyl-3-phenylisoxazolidine-2-carboxylate, tert-butyl 5-(naphthalen-2-ylmethyl)-3-phenylisoxazolidine-2-carboxylate, tert-butyl 5-([1,1'-biphenyl]-4-ylmethyl)-3-phenylisoxazolidine-2-carboxylate or 2,2-dimethyl-1-(3-phenylisoxazolidin-2-yl)butan-1-one or 2,2-dimethyl-1-(3-phenylisoxazolidin-2-yl)but-3-en-1-one.

Also provided herein are compounds having the following structure (I):

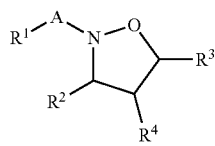

(I)

or a pharmaceutically acceptable salt, prodrug, stereoisomer or a mixture of stereoisomers thereof, wherein:

A is —C(=O)—, —S(=O)—, —S(=O)$_2$— or —S(=O)(=NH)—;

$R^1$ is —N$R^5R^6$, $C_{1-6}$ alkyl, $C_{3-6}$ alkoxy, $C_{3-10}$ cycloalkyl, heterocyclyl or heteroaryl;

$R^2$ is aryl or heteroaryl;

$R^3$ is hydrogen, $C_{1-6}$ alkyl or $C_{3-10}$ cycloalkyl;

$R^4$ is hydrogen, halo, $C_{1-6}$ alkyl or $C_{3-10}$ cycloalkyl;

$R^5$ and $R^6$ are each independently H, $C_{1-6}$ alkyl, $C_{3-10}$ cycloalkyl, aryl, heteroaryl or heterocyclyl, wherein each $C_{1-6}$ alkyl, $C_{3-6}$ alkoxy, $C_{3-10}$ cycloalkyl, heterocyclyl, heteroaryl and aryl group of $R^1$, $R^2$, $R^3$, $R^4$, $R^5$ and $R^6$ is optionally substituted with one, two or three $R^{10}$;

$R^{10}$ in each instance is independently halo, hydroxy, cyano, nitro, $C_{1-6}$ alkyl, $C_{1-6}$ alkoxy, $C_{2-6}$ alkenyl, $C_{2-6}$ alkanyl, $C_{3-10}$ cycloalkyl, heterocyclyl, aryl, heteroaryl, —C(=O)$R^{11}$, —C(=O)O$R^{11}$, —C(=O)N$R^{11}R^{11}$, —S(=O)$R^{11}$, —S(=O)$_2R^{11}$, —N$R^{11}R^{11}$, —N$R^{11}$C(=O)$R^{11}$ or —N$R^{11}$C(=O)O$R^{11}$;

wherein the $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl and heteroaryl of $R^{10}$ are optionally substituted with one, two or three substituents independently selected from halo, hydroxy, cyano, amino, nitro, $C_{1-6}$ alkyl, alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and $R^{11}$ in each instance is independently hydrogen, $C_{1-6}$ alkyl, $C_{3-10}$ cycloalkyl, heterocyclyl, heteroaryl or aryl;

provided the compound is not 2-(methylsulfonyl)-3-phenyl-isoxazolidine, tert-butyl 5-benzyl-3-phenylisoxazolidine-2-carboxylate, tert-butyl 5-(naphthalen-2-ylmethyl)-3-phenylisoxazolidine-2-carboxylate or tert-butyl 5-([1,1'-biphenyl]-4-ylmethyl)-3-phenylisoxazolidine-2-carboxylate.

In certain embodiments, the present disclosure is directed to a compound of structure (I), or a pharmaceutically acceptable salt, prodrug or stereoisomer thereof, wherein:

A is —C(=O)—, —S(=O)—, —S(=O)$_2$— or —S(=O)(=NH)—;

$R^1$ is —N$R^5R^6$, $C_{1-6}$ alkyl, $C_3$-$C_6$ alkoxy, $C_{3-10}$ cycloalkyl, heterocyclyl or heteroaryl;

$R^2$ is aryl or heteroaryl; and $R^3$ is hydrogen, $C_{1-6}$ alkyl or $C_{3-10}$ cycloalkyl;

$R^4$ is hydrogen, halo, $C_{1-6}$ alkyl or $C_{3-10}$ cycloalkyl;

$R^5$ and $R^6$ are each independently hydrogen, $C_{1-6}$ alkyl, $C_{3-10}$ cycloalkyl, aryl, heteroaryl or heterocyclyl, wherein each $C_{1-6}$ alkyl, $C_{3-6}$ alkoxy, $C_{3-10}$ cycloalkyl, heterocyclyl, heteroaryl and aryl group is optionally substituted with one or more substituent;

provided herein, the compound is not 2-(methylsulfonyl)-3-phenyl-isoxazolidine, tert-butyl 5-benzyl-3-phenylisoxazolidine-2-carboxylate, tert-butyl 5-(naphthalen-2-ylmethyl)-3-phenylisoxazolidine-2-carboxylate or tert-butyl 5-([1,1'-biphenyl]-4-ylmethyl)-3-phenylisoxazolidine-2-carboxylate.

Or alternatively, in certain embodiments, any $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl or heteroaryl group may be optionally substituted with one or more substituent as defined herein.

In certain embodiments, the present disclosure is directed to a compound having the following structure (II):

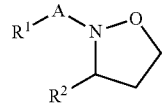

(II)

or a pharmaceutically acceptable salt, prodrug or stereoisomer thereof, wherein:

A is —C(=O)—, —S(=O)—, —S(=O)$_2$— or —S(=O)(=NH)—;

$R^1$ is —N$R^5R^6$, $C_{1-6}$ alkyl, $C_{3-6}$ alkoxy, $C_{3-10}$ cycloalkyl, heterocyclyl or heteroaryl;

$R^2$ is aryl or heteroaryl;

$R^5$ and $R^6$ are each independently H, $C_{1-6}$ alkyl, $C_{3-10}$ cycloalkyl, aryl, heteroaryl or heterocyclyl, wherein each $C_{1-6}$ alkyl, $C_{3-6}$ alkoxy, $C_{3-10}$ cycloalkyl, heterocyclyl, heteroaryl and aryl group of $R^1$, $R^2$, $R^5$ and $R^6$ is optionally substituted with one, two or three $R^{10}$;

$R^{10}$ in each instance is independently halo, hydroxy, cyano, nitro, $C_{1-6}$ alkyl, $C_{1-6}$ alkoxy, $C_{2-6}$ alkenyl, $C_{2-6}$ alkynyl, $C_{3-10}$cycloalkyl, heterocyclyl, aryl, heteroaryl, —C(=O)$R^{11}$, —C(=O)O$R^{11}$, —C(=O)N$R^{11}R^{11}$, —S(O)$R^{11}$, —S(=O)$_2R^{11}$, —N$R^{11}R^{11}$, —N$R^{11}$C(=O)$R^{11}$ or —N$R^{11}$C(=O)O$R^{11}$;

wherein the $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl and heteroaryl of $R^{10}$ are optionally substituted with one, two or three substituents independently selected from halo, hydroxy, cyano, amino, nitro, $C_{1-6}$ alkyl, alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and $R^{11}$ in each instance is independently hydrogen, $C_{1-6}$ alkyl, $C_{3-10}$ cycloalkyl, heterocyclyl, heteroaryl or aryl;

provided the compound is not 2-(methylsulfonyl)-3-phenyl-isoxazolidine.

In certain embodiments, the present disclosure is directed to a compound of structure (II), or a pharmaceutically acceptable salt, prodrug or stereoisomer thereof, wherein:

A is —C(=O)—, —S(=O)—, —S(=O)$_2$— or —S(=O)(=NH)—;

$R^1$ is —NR$^5$R$^6$, $C_{1-6}$ alkyl, $C_3$-$C_6$ alkoxy, $C_{3-10}$ cycloalkyl, heterocyclyl or heteroaryl;

$R^2$ is aryl or heteroaryl; and $R^5$ and $R^6$ are each independently hydrogen, $C_{1-6}$ alkyl, $C_{3-10}$ cycloalkyl, aryl, heteroaryl or heterocyclyl.

wherein each $C_{1-6}$ alkyl, $C_{3-6}$ alkoxy, $C_{3-10}$ cycloalkyl, heterocyclyl, heteroaryl and aryl group is optionally substituted with one or more substituent;

provided the compound is not 2-(methylsulfonyl)-3-phenyl-isoxazolidine.

In certain embodiments, the present disclosure is directed to a compound of structure (II), or a pharmaceutically acceptable salt, prodrug or stereoisomer thereof, wherein:

A is —C(=O)—, —S(=O)—, —S(=O)$_2$— or —S(=O)(=NH)—;

$R^1$ is —NR$^5$R$^6$, $C_{1-6}$ alkyl, $C_3$-$C_6$ alkoxy, $C_{3-10}$ cycloalkyl, heterocyclyl or heteroaryl;

$R^2$ is aryl or heteroaryl; and $R^5$ and $R^6$ are each independently hydrogen, $C_{1-6}$ alkyl, $C_{3-10}$ cycloalkyl, aryl, heteroaryl or heterocyclyl, wherein each $C_{1-6}$ alkyl, $C_{3-6}$ alkoxy, $C_{3-10}$ cycloalkyl, heterocyclyl, heteroaryl and aryl group is optionally substituted with one or more substituent.

Compounds of structure (I) in enantiomerically enriched or enantiomerically pure form are also provided in various embodiments. Accordingly, in certain embodiments the compound has one of the following structures (I') and (II'):

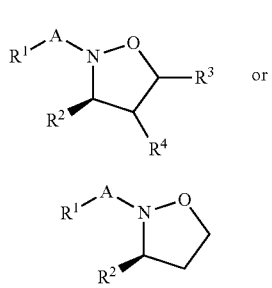

(I')

or (II')

where A, R$^1$, R$^2$, R$^3$ and R$^4$ are as defined herein. In certain embodiments the compound has one of the following structures (I") and (II"):

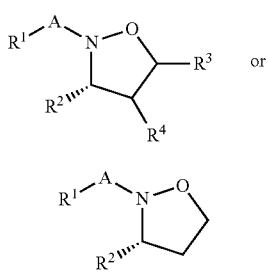

(I")

or (II")

where A, R$^1$, R$^2$, R$^3$ and R$^4$ are as defined herein.

In certain embodiments, the compound has structure (I'). In certain embodiments, the compound has structure (I"). In certain embodiments, the compound has structure (II'). In certain embodiments, the compound has structure (II").

In certain embodiments, the compound is not 2-(methylsulfonyl)-3-phenyl-isoxazolidine, tert-butyl 5-benzyl-3-phenylisoxazolidine-2-carboxylate, tert-butyl 5-(naphthalen-2-ylmethyl)-3-phenylisoxazolidine-2-carboxylate or tert-butyl 5-([1,1'-biphenyl]-4-ylmethyl)-3-phenylisoxazolidine-2-carboxylate.

In certain embodiments, the compound is not ethyl 3-phenylisoxazolidine-2-carboxylate, benzyl 3-(4-amino-2-oxopyrimidin-1(2H)-yl)isoxazolidine-2-carboxylate, 2,2-dimethyl-1-(3-phenylisoxazolidin-2-yl)butan-1-one or 2,2-dimethyl-1-(3-phenylisoxazolidin-2-yl)but-3-en-1-one. In certain embodiments, the compound is not 2,2-dimethyl-1-(3-phenylisoxazolidin-2-yl)butan-1-one or 2,2-dimethyl-1-(3-phenylisoxazolidin-2-yl)but-3-en-1-one. In certain embodiments, the compound is not 2,2-dimethyl-1-(3-phenylisoxazolidin-2-yl)butan-1-one. In certain embodiments, when $R^1$ is not pyrimidinyl substituted with one or more oxo and/or one or more hydroxy.

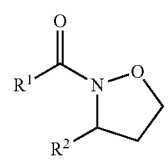

(Ia)

where $R^1$ and $R^2$ are as defined herein.

In certain embodiments, the compound has structure (Ia'):

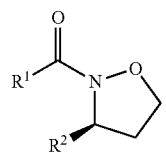

(Ia')

where $R^1$ and $R^2$ are as defined herein. In certain embodiments, the compound has structure (Ia"):

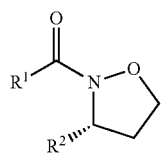

(Ia")

where $R^1$ and $R^2$ are as defined herein.

In certain embodiments, A is S(=O)— and the compound has the following structure (Ib):

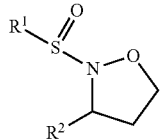
(Ib)

where $R^1$ and $R^2$ are as defined herein.

In certain embodiments, the compound has structure (Ib'):

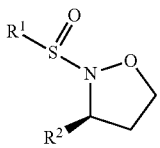
(Ib')

where $R^1$ and $R^2$ are as defined herein. In certain embodiments, the compound has structure (Ib"):

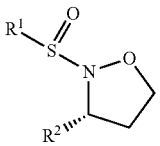
(Ib")

where $R^1$ and $R^2$ are as defined herein.

In certain embodiments, A is —S(=O)$_2$— and the compound has the following structure (Ic):

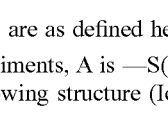
(Ic)

where $R^1$ and $R^2$ are as defined herein.

In certain embodiments, the compound has structure (Ic'):

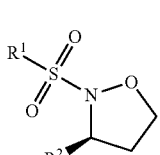
(Ic')

where $R^1$ and $R^2$ are as defined herein. In certain embodiments, the compound has structure (Ic"):

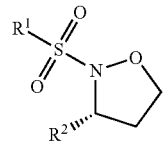
(Ic")

where $R^1$ and $R^2$ are as defined herein.

In certain embodiments, A is —S(=O)(=NH)— and the compound has the following structure (Id):

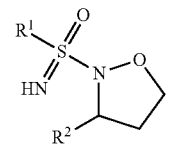
(Id)

where $R^1$ and $R^2$ are as defined herein.

In certain embodiments, the compound has structure (Id'):

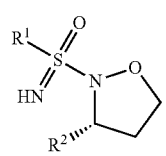
(Id')

where $R^1$ and $R^2$ are as defined herein. In certain embodiments, the compound has structure (Id"):

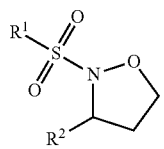
(Id")

where $R^1$ and $R^2$ are as defined herein.

The $R^1$ and $R^2$ moieties in any of the structures described herein, are optionally substituted with one or more substituents. In certain embodiments, the $R^1$ and $R^2$ moieties in any of the structures described herein, are optionally substituted with one, two, three or four substituents. In certain embodiments, $R^1$ and $R^2$ are both substituted. In certain embodiments, $R^1$ and $R^2$ are both unsubstituted. In certain embodiments, $R^1$ is substituted and $R^2$ is unsubstituted. In certain embodiments, $R^1$ is unsubstituted and $R^2$ is substituted. In certain embodiments, the optional substituents for $R^1$ and $R^2$ are selected from any of the optional substituents listed above with respect to the term "substituted." In certain embodiments, the optional substituents for $R^1$ and $R^2$ are selected from amino, hydroxy, cyano, halo (e.g., F, Cl or Br), optionally substituted $C_{1-6}$ alkyl, optionally substituted $C_{1-6}$ alkoxy, optionally substituted $C_{1-6}$ haloalkyl and optionally substituted $C_{1-6}$ haloalkoxy.

In certain embodiments, $R^1$ is substituted with at least one substituent selected from amino, hydroxy, cyano, halo (e.g., F, Cl or Br), optionally substituted $C_{1-6}$ alkyl, optionally substituted $C_{1-6}$ alkoxy, optionally substituted $C_{1-6}$ haloalkyl and optionally substituted $C_{1-6}$ haloalkoxy.

In certain embodiments, R² is substituted with at least one substituent selected from amino, hydroxy, cyano, halo (e.g., F, Cl or Br), optionally substituted $C_{1-6}$ alkyl, optionally substituted $C_{1-6}$ alkoxy, optionally substituted $C_{1-6}$ haloalkyl and optionally substituted haloalkoxy.

In certain embodiments, R¹ is $C_{1-6}$ alkyl, $C_3$-$C_6$ alkoxy, $C_{1-6}$ alkylaminyl, $C_{3-10}$ cycloalkyl, heterocyclyl, heteroaryl or arylaminyl. In certain embodiments, R¹ is optionally substituted $C_{1-6}$ alkyl, $C_{3-6}$ alkoxy, $C_{3-10}$ cycloalkyl or heterocyclyl. In certain embodiments, R¹ is optionally substituted $C_{1-6}$ alkyl. In certain embodiments, R¹ is optionally substituted $C_{10-20}$ alkyl.

In certain embodiments, R¹ is substituted with at least one substituent selected from deuterium, hydroxy, halo, $C_{1-6}$ alkyl, $C_{1-6}$ haloalkyl, $C_{1-6}$ alkoxy, $C_{1-6}$ haloalkoxy, cyano, $C_{3-10}$ cycloalkyl, heterocyclyl and heteroaryl, wherein the heterocyclyl or heteroaryl is optionally further substituted with one, two or three $C_{1-6}$ alkyl. In certain embodiments. R¹ is substituted with heterocyclyl or heteroaryl, wherein the heterocyclyl or heteroaryl is optionally further substituted with one, two or three substituents selected from deuterium, hydroxy, halo, $C_{1-6}$ alkyl, $C_{1-6}$ haloalkyl, $C_{1-6}$ alkoxy, $C_{1-6}$ haloalkoxy, cyano, $C_{3-10}$cycloalkyl, heterocyclyl and heteroaryl. In certain embodiments, R¹ is substituted with at least one substituent selected from hydroxy, halo, $C_{1-6}$ haloalkyl, $C_{1-6}$ alkoxy, $C_{1-6}$ haloalkoxy and cyano. In certain embodiments, R¹ is substituted with one, two, three or four substituents independently selected from hydroxy, halo, $C_{1-6}$ haloalkyl, $C_{1-6}$ alkoxy, $C_{1-6}$ haloalkoxy and cyano. In certain embodiments, R¹ is substituted with at least one substituent selected from hydroxy, alkoxy and cyano.

In certain embodiments, R¹ is optionally substituted branched $C_{1-6}$ alkyl. In certain embodiments, R¹ is of the formula:

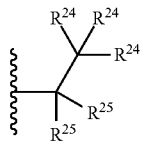

wherein each R²⁴ is independently hydrogen, halo, hydroxy, cyano, nitro, $C_{1-6}$ alkoxy, $C_{2-6}$ alkynyl, $C_{3-10}$ cycloalkyl, heterocyclyl, aryl, heteroaryl, —C(=O)R²⁶, —C(=O)OR²⁶, —C(=O)NR²⁶R²⁶, —S(=O)R²⁶, —S(=O)₂R²⁶, —NR²⁶R²⁶, —NR²⁶C(=O)R²⁶ or —NR²⁶C(=O)OR²⁶;

wherein the $C_{1-6}$ alkoxy, $C_{2-6}$ alkynyl, $C_{3-10}$cycloalkyl, heterocyclyl, aryl and heteroaryl of R²⁴ are optionally substituted with one, two or three substituents independently selected from deuterium, halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl;

each R²⁵ is independently hydrogen, halo, $C_{1-6}$ alkyl, $C_{3-10}$ cycloalkyl, heterocyclyl, heteroaryl or aryl; or two R²⁵ together with the atom to which they are attached form a $C_{3-10}$ cycloalkyl or heterocyclyl;

wherein the $C_{1-6}$ alkyl, $C_{3-10}$ cycloalkyl, heterocyclyl, heteroaryl or aryl of R²⁵ is optionally substituted with one, two or three substituents independently selected from deuterium, halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and R²⁶ in each instance independently is hydrogen, $C_{1-6}$ alkyl, $C_{3-10}$ cycloalkyl, heterocyclyl, heteroaryl or aryl;

wherein the $C_{1-6}$ alkyl of R²⁶ is optionally substituted with halo or oxo and wherein the $C_{3-10}$ cycloalkyl, heterocyclyl, heteroaryl or aryl of R²⁶ is optionally substituted with one, two or three $C_{1-6}$ alkyl;

provided that at least one of the following occurs: a) two R²⁵ together with the atom to which they are attached form a $C_{3-10}$ cycloalkyl or heterocyclyl, b) at least one R²⁴ is other than hydrogen, or c) both R²⁵ are optionally substituted $C_{1-6}$ alkyl.

In certain embodiments, two R²⁵ together with the atom to which they are attached form a $C_{3-10}$ cycloalkyl or heterocyclyl. In certain embodiments, at least one R²⁴ is other than hydrogen. In certain embodiments, both R²⁵ are optionally substituted $C_{1-6}$ alkyl. In certain embodiments, at least one R²⁵ is methyl. In certain embodiments, R¹ is of the formula:

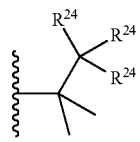

wherein each R²⁴ is independently hydrogen, halo, hydroxy, cyano, nitro, $C_{1-6}$ alkoxy, $C_{2-6}$ alkynyl, $C_{3-10}$ cycloalkyl, heterocyclyl, aryl, heteroaryl, —C(=O)R²⁶, —C(=O)OR²⁶, —C(=O)NR²⁶R²⁶, —S(=O)R²⁶, —S(=O)₂R²⁶, —NR²⁶R²⁶, —NR²⁶C(=O)R²⁶ or —NR²⁶C(=O)OR²⁶;

wherein the $C_{1-6}$ alkoxy, $C_{2-6}$ alkynyl, $C_{3-10}$cycloalkyl, heterocyclyl, aryl and heteroaryl of R²⁴ are optionally substituted with one, two or three substituents independently selected from deuterium, halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and R²⁶ in each instance independently is hydrogen, alkyl, $C_{3-10}$ cycloalkyl, heterocyclyl, heteroaryl or aryl;

wherein the $C_{1-6}$ alkyl of R²⁶ is optionally substituted with halo or oxo and wherein the $C_{3-10}$ cycloalkyl, heterocyclyl, heteroaryl or aryl of R²⁶ is optionally substituted with one, two or three $C_{1-6}$ alkyl;

provided that at least one R²⁴ is other than hydrogen.

In certain embodiments, each R²⁴ is independently selected from hydrogen, deuterium, hydroxy, halo, $C_{1-6}$ haloalkyl, $C_{1-6}$ alkoxy, $C_{1-6}$ haloalkoxy, cyano, $C_{3-10}$cycloalkyl, heterocyclyl and heteroaryl, wherein the heterocyclyl or heteroaryl is optionally further substituted with one, two or three halo, cyano $C_{1-6}$ alkyl or $C_{3-10}$cycloalkyl. In certain embodiments, each R²⁴ is independently selected from hydrogen, hydroxy, halo, haloalkyl, $C_{1-6}$ alkoxy, $C_{1-6}$ haloalkoxy and cyano. In certain embodiments, each R²⁴ is independently hydrogen, halo or cyano. In certain embodiments, one R²⁴ is hydrogen and the other two R²⁴ are halo.

In certain embodiments, R¹ may have one of the following structures:

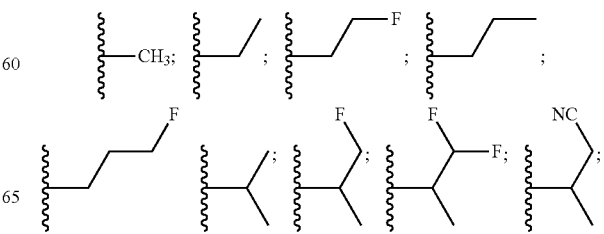

-continued
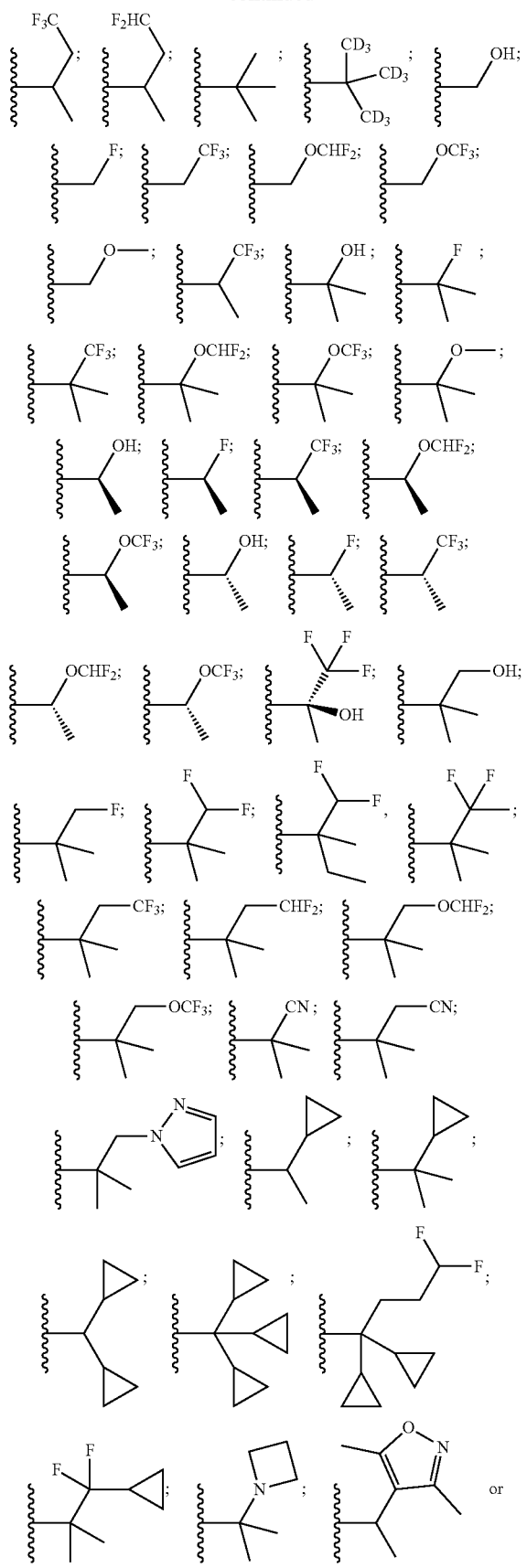
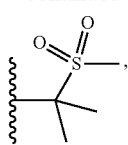
or a stereoisomer or mixture thereof.
In certain embodiments, R¹ may have one of the following structures:
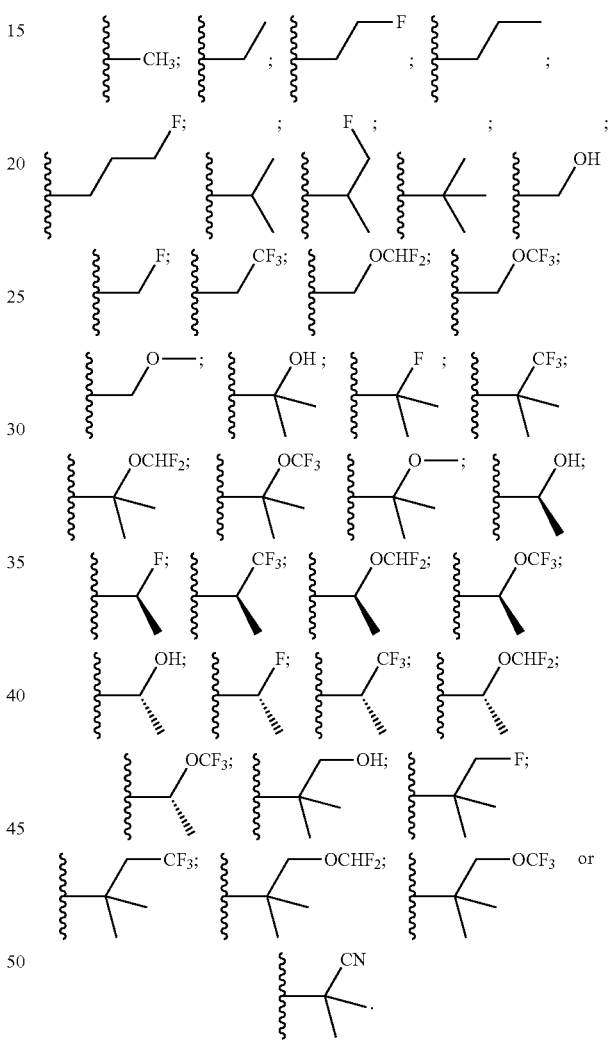
In certain embodiments, R¹ has one of the following structures:
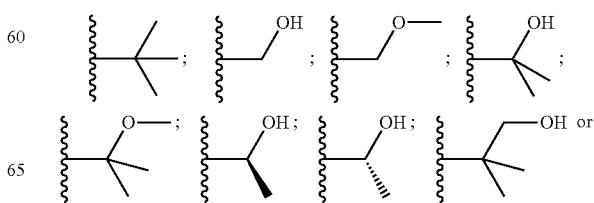

-continued

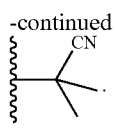

In certain embodiments, $R^1$ is optionally substituted $C_3$-$C_6$ alkoxy. For example, in certain embodiments $R^1$ is t-butoxy.

In certain embodiments, $R^1$ is —$NR^3R^4$. In certain embodiments, $R^1$ is —$NR^3R^4$ and at least one of $R^3$ or $R^4$ is optionally substituted $C_{1-6}$ alkyl or optionally substituted aryl. For example, in certain embodiments, $R^1$ is dimethylamino, t-butylamino or phenylamino.

In certain embodiments, $R^1$ is optionally substituted $C_{3-10}$ cycloalkyl. For example, in some of these embodiments the $C_{3-10}$ cycloalkyl is substituted with at least one substituent selected from hydroxy, halo, cyano, alkoxy, $C_{1-6}$ haloalkoxy $C_{1-6}$ alkyl, $C_{1-6}$ haloalkyl $C_{1-6}$ hydroxyalkyl and $C_{1-6}$ alkoxyalkyl. In certain embodiments the $C_{3-10}$ cycloalkyl is substituted with at least one substituent selected from embodiments the $C_{3-10}$ cycloalkyl is substituted with at least one substituent selected from hydroxy, halo, cyano, $C_{1-6}$ alkoxy, $C_{1-6}$ haloalkoxy $C_{1-6}$ alkyl, $C_{1-6}$ haloalkyl, $C_{1-6}$ hydroxyalkyl and alkoxyalkyl.

In certain embodiments, $R^1$ is $C_{3-10}$ cycloalkyl and $C_{3-10}$ cycloalkyl is cyclopropyl, cyclobutyl, bicyclo[1.1.1]pentyl. In certain embodiments, $R^1$ is $C_{3-10}$ cycloalkyl and cycloalkyl is cyclopropyl or cyclobutyl. For example, in certain embodiments R has one of the following structures:

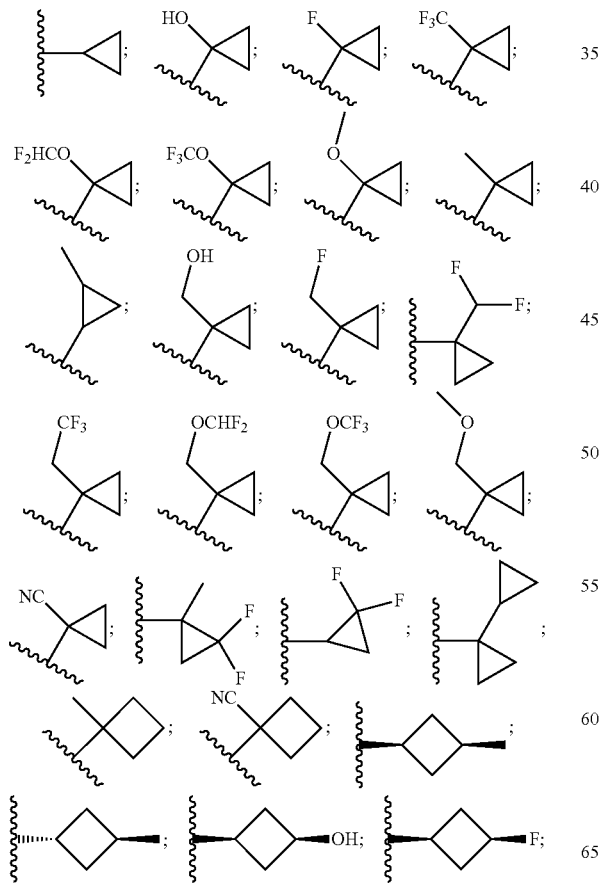

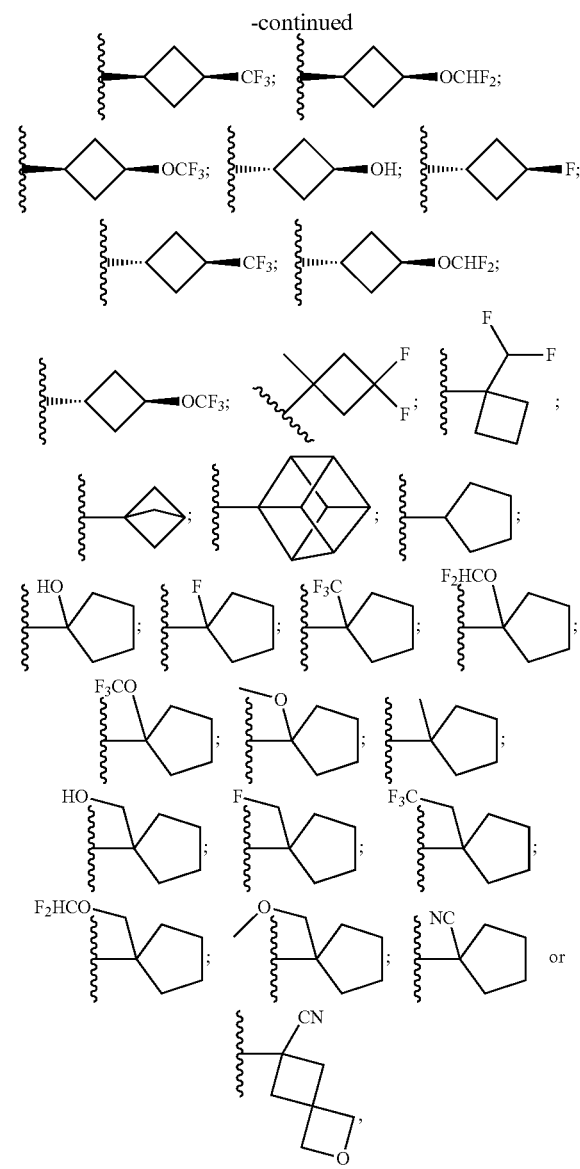

or a stereoisomer or mixture thereof.

In certain embodiments $R^1$ has one of the following structures:

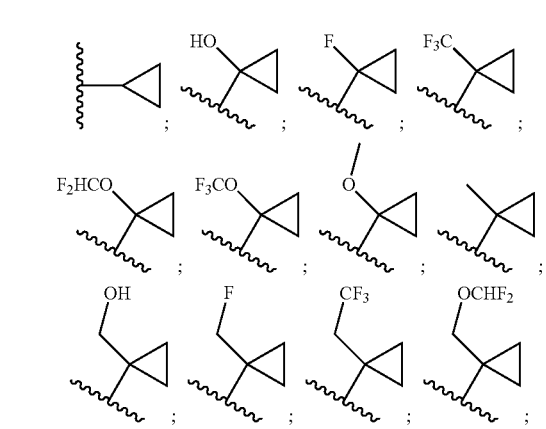

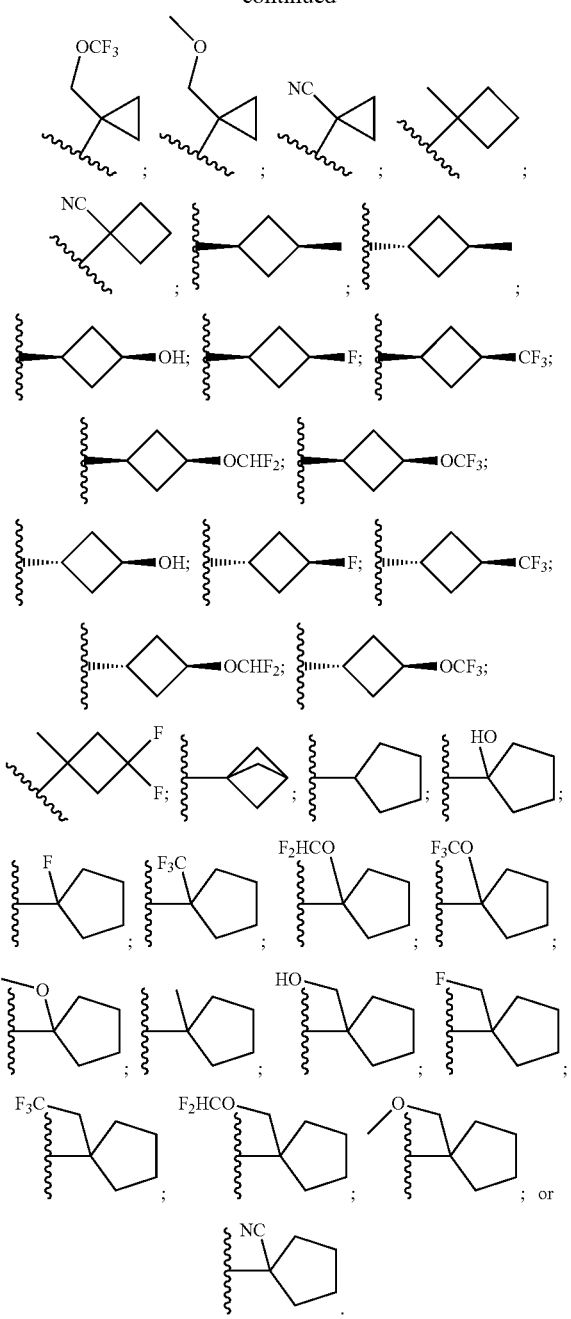
In certain embodiments, $R^1$ has one of the following structures:
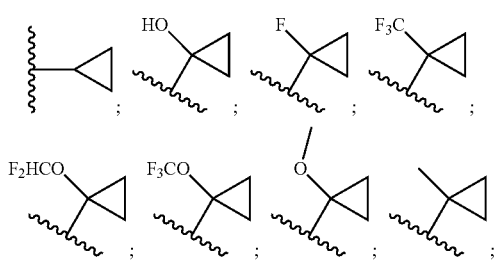
In some different embodiments, $R^1$ has one of the following structures:
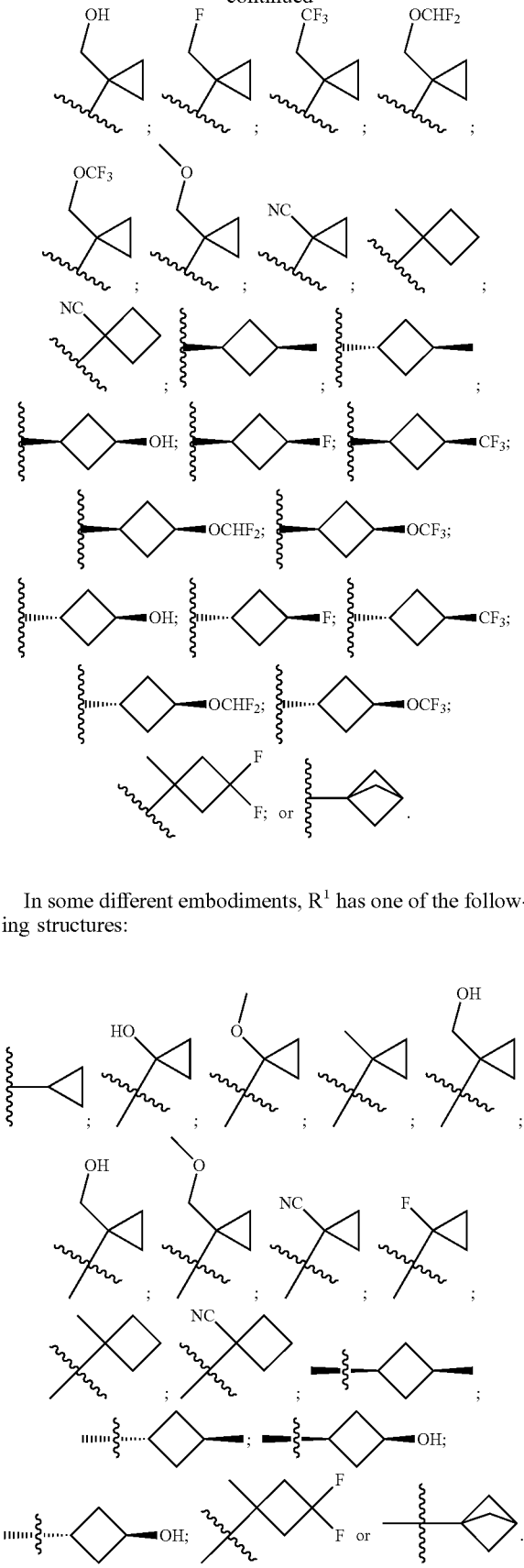

In certain embodiments, $R^1$ is optionally substituted heterocyclyl or optionally substituted heteroaryl. In certain embodiments, $R^1$ is oxetanyl, pyrrolidinyl, tetrahydropyranyl or azetidinyl. In certain embodiments $R^1$ is oxetanyl or pyrrolidinyl. In certain embodiments, $R^1$ is pyrrolyl, pyrazolopyridinyl or benzoisoxazolyl. In certain embodiments, $R^1$ is heterocyclyl or optionally substituted heteroaryl and $R^1$ is substituted with a substituent selected from $C_{1-6}$ alkyl and cyano. In certain embodiments, $R^1$ is heterocyclyl or optionally substituted heteroaryl and $R^1$ is substituted with a $C_{1-6}$ alkyl, cyano or both.

In certain embodiments, $R^1$ has one of the following structures:

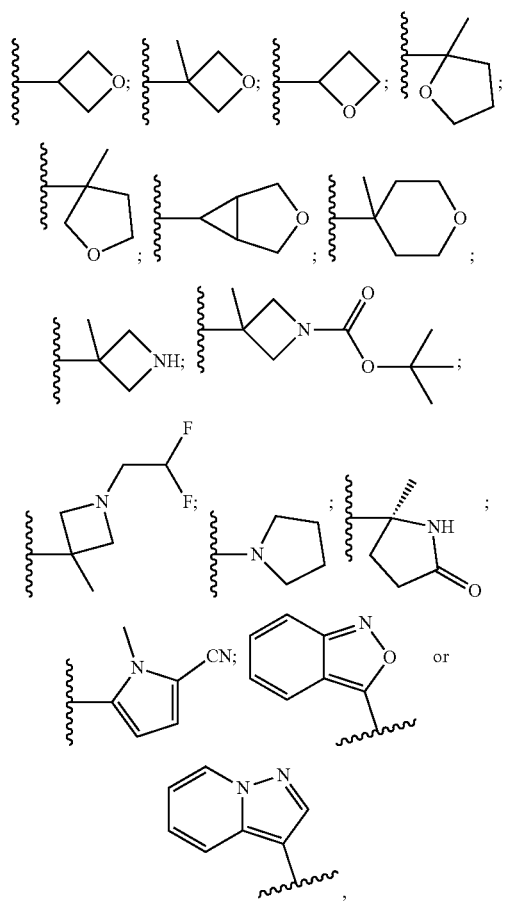

a stereoisomer or mixture thereof.

In certain embodiments, $R^1$ has one of the following structures:

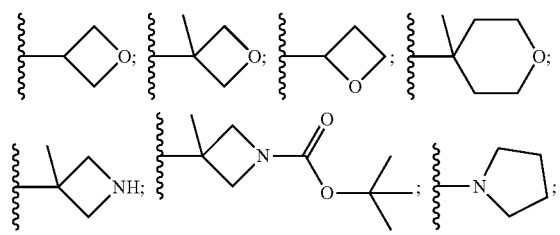

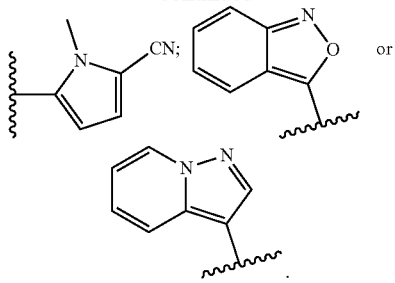

In certain embodiments, $R^1$ has one of the following structures:

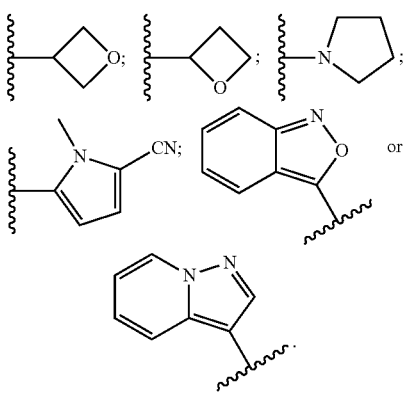

In certain embodiments, $R^2$ is aryl, such as phenyl. In certain embodiments, $R^2$ is heteroaryl, such as pyridinyl. In certain embodiments, $R^2$ is unsubstituted. In certain embodiments $R^2$ is substituted, for example with one or more halo, cyano, $C_{1-6}$ alkyl, $C_{1-6}$ haloalkyl, $C_{1-6}$ alkoxy, —$NH_2$ or $C_{3-10}$ cycloalkyl. In certain embodiments $R^2$ is substituted, for example with one or more halo atoms. In certain embodiments, $R^2$ has one of the following structures:

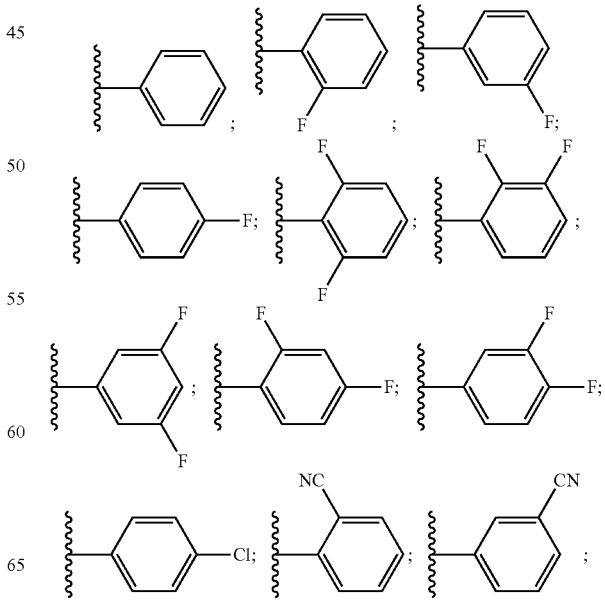

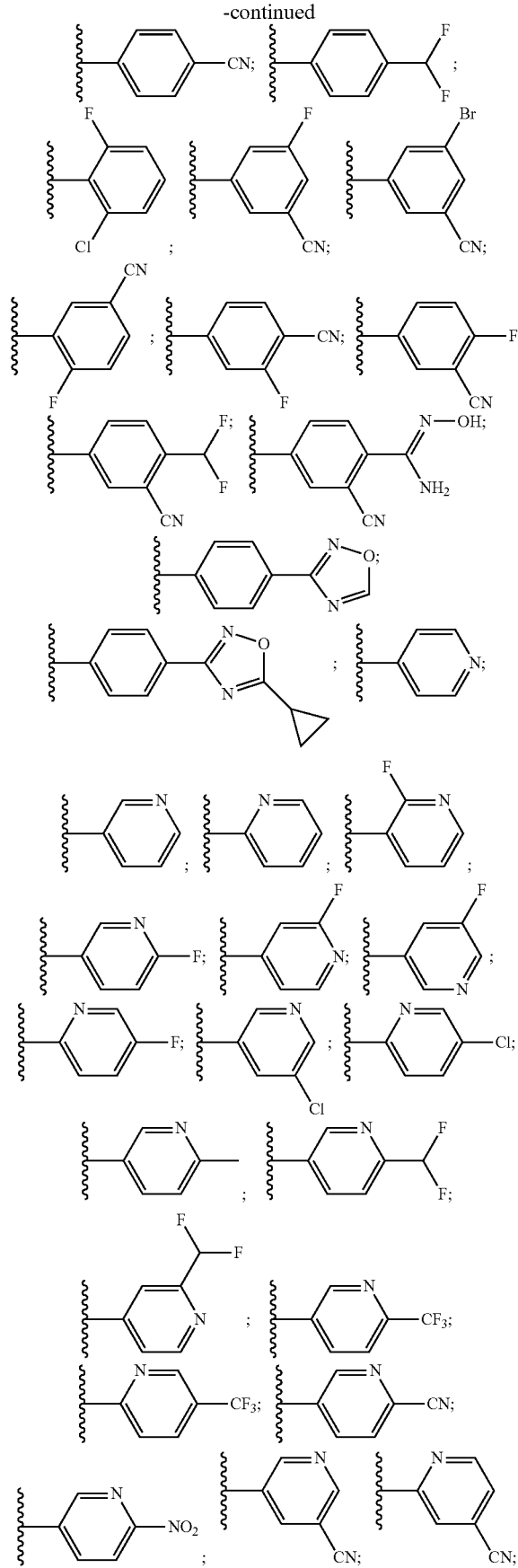
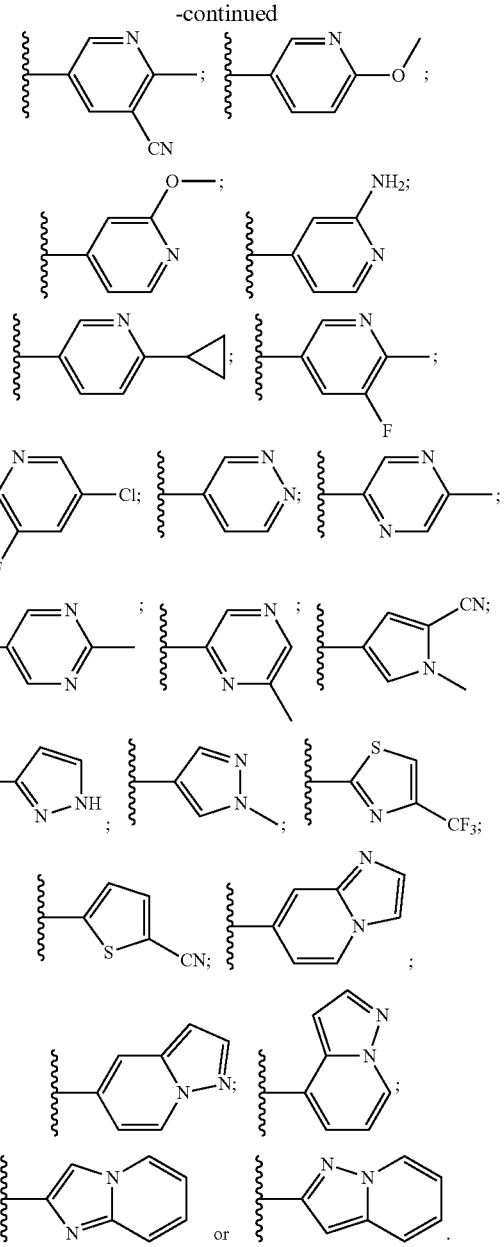
In certain embodiments, $R^2$ has one of the following structures:
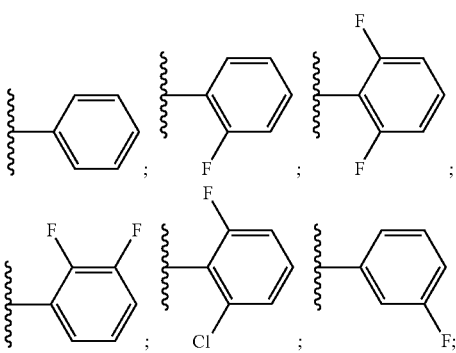

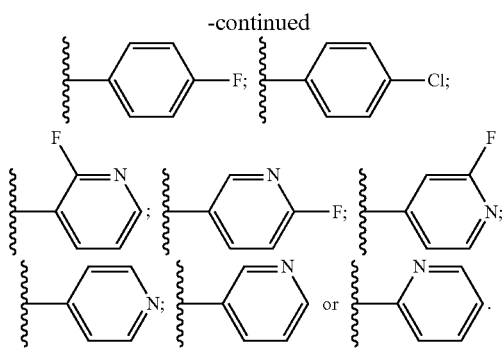

In certain embodiments, $R^2$ has one of the following structures:

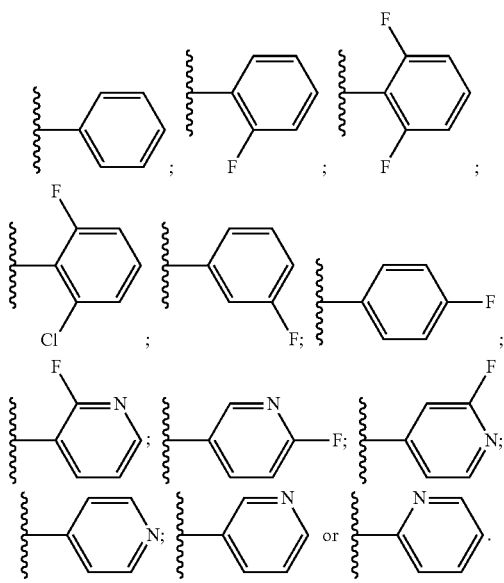

In certain embodiments, the present disclosure is directed to a compound having the following structure (III):

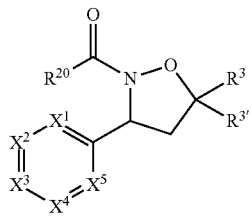

(III)

wherein:
each $X^1$, $X^2$, $X^3$, $X^4$ and $X^5$ is either N or $CR^{21}$;
$R^3$ is hydrogen, deuterium, $C_{1-6}$ alkyl or $C_{3-10}$ cycloalkyl;
$R^{3'}$ is hydrogen or deuterium;
$R^{20}$ is —$NR^5R^6$, $C_{1-6}$ alkyl, $C_{3-10}$ cycloalkyl, heterocyclyl or heteroaryl;
  wherein the $C_{1-6}$ alkyl, $C_{3-10}$ cycloalkyl, heterocyclyl or heteroaryl of $R^{20}$ are optionally substituted with one, two, three or four substituents independently selected from deuterium, halo, hydroxy, cyano, amino, —$S(=O)_2R^{11}$, nitro. $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl optionally further substituted with $C_{1-6}$ alkyl; and $R^5$ and $R^6$ are each independently H, $C_{1-6}$ alkyl, $C_{3-10}$ cycloalkyl, aryl, heteroaryl or heterocyclyl;
each $R^{21}$ is independently selected from hydrogen, halo, hydroxy, cyano, nitro, $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl, heteroaryl, —$C(=O)R^{11}$, —$C(=O)OR^{11}$, —$C(=O)NR^{11}R^{11}$, —$S(=O)R^{11}$, —$S(=O)_2R^{11}$, —$NR^{11}R^{11}$, —$NR^{11}C(=O)R^{11}$ or —$NR^{11}C(=O)OR^{11}$;
  wherein the $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl and heteroaryl of $R^{21}$ are optionally substituted with one, two or three substituents independently selected from halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and
$R^{11}$ in each instance is independently hydrogen, $C_{1-6}$ alkyl, $C_{3-10}$ cycloalkyl, heterocyclyl, heteroaryl or aryl.

In certain embodiments, the present disclosure is directed to a compound of structure (III), wherein:
each $X^1$, $X^2$, $X^3$, $X^4$ and $X^5$ is either N or $CR^{21}$;
$R^3$ is hydrogen, deuterium, $C_{1-6}$ alkyl or $C_{3-10}$ cycloalkyl;
$R^{3'}$ is hydrogen or deuterium;
$R^{20}$ is —$NR^5R^6$, $C_{1-6}$ alkyl. $C_{3-10}$ cycloalkyl, heterocyclyl or heteroaryl;
  wherein the $C_{1-6}$ alkyl, $C_{3-10}$ cycloalkyl, heterocyclyl or heteroaryl of $R^{20}$ are optionally substituted with one, two or three substituents independently selected from deuterium, halo, hydroxy, cyano, amino, —$S(=O)_2R^{11}$, nitro, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl optionally further substituted with $C_{1-6}$ alkyl; and
$R^5$ and $R^6$ are each independently H, $C_{1-6}$ alkyl, $C_{3-10}$ cycloalkyl, aryl, heteroaryl or heterocyclyl;
each $R^{21}$ is independently selected from hydrogen, halo, hydroxy, cyano, nitro, $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl, heteroaryl, —$C(=O)R^{11}$, —$C(=O)OR^{11}$, —$C(=O)NR^{11}R^{11}$, —$S(=O)R^{11}$, —$S(=O)_2R^{11}$, —$NR^{11}R^{11}$, —$NR^{11}C(=O)R^{11}$ or —$NR^{11}C(=O)OR^{11}$;
  wherein the $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl and heteroaryl of $R^{21}$ are optionally substituted with one, two or three substituents independently selected from halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and
$R^{11}$ in each instance is independently hydrogen, $C_{1-6}$ alkyl, $C_{3-10}$ cycloalkyl, heterocyclyl, heteroaryl or aryl.

In certain embodiments, the present disclosure is directed to a compound having the following structure (IIIa):

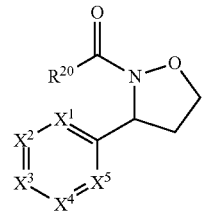

(IIIa)

wherein:

each $X^1$, $X^2$, $X^3$, $X^4$ and $X^5$ is either N or $CR^{21}$;

$R^{20}$ is $-NR^5R^6$, $C_{1-6}$ alkyl, $C_{3-10}$ cycloalkyl, heterocyclyl or heteroaryl;

$R^5$ and $R^6$ are each independently H, $C_{1-6}$ alkyl, $C_{3-10}$ cycloalkyl, aryl, heteroaryl or heterocyclyl;

each $R^{21}$ is independently selected from hydrogen, halo, hydroxy, cyano, nitro, $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl, heteroaryl, $-C(=O)R^{11}$, $-C(=O)OR^{11}$, $-C(=O)NR^{11}R^{11}$, $-S(=O)R^{11}$, $-S(=O)_2R^{11}$, $-NR^{11}R^{11}$, $-NR^{11}C(=O)R^{11}$ or $-NR^{11}C(=O)OR^{11}$;

wherein the $C_{1-6}$ alkyl, $C_{2-6}$ alkenyl, $C_{2-6}$ alkynyl, $C_{3-10}$ cycloalkyl, heterocyclyl, aryl and heteroaryl of $R^{21}$ are optionally substituted with one, two or three substituents independently selected from halo, hydroxy, cyano, amino, nitro, $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl or heteroaryl; and $R^{11}$ in each instance is independently hydrogen, $C_{1-6}$ alkyl, $C_{3-10}$ cycloalkyl, heterocyclyl, heteroaryl or aryl.

In certain embodiments, each of $X^1$, $X^2$, $X^3$, $X^4$ and $X^5$ is $CR^{21}$. In certain embodiments, at least one of $X^1$, $X^2$, $X^3$, $X^4$ or $X^5$ is N. In certain embodiments, $X^1$ is N. In certain embodiments, $X^2$ is N. In certain embodiments, $X^3$ is N. In certain embodiments, $X^4$ $X^5$ is N. In certain embodiments, $X^5$ is N. In certain embodiments, at least two of $X^1$, $X^2$, $X^3$, $X^4$ or $X^5$ is N.

In certain embodiments, each $R^{21}$ is independently hydrogen, halo, hydroxy, cyano, $C_{1-6}$ alkyl or $C_{1-6}$ alkoxy. In certain embodiments, at least one of $X^1$, $X^2$, $X^3$, $X^4$ and $X^5$ is $CR^{21}$ and $R^{21}$ is halo.

In certain embodiments, the present disclosure is directed to a compound having the following structure (IIIb) or (IIIc):

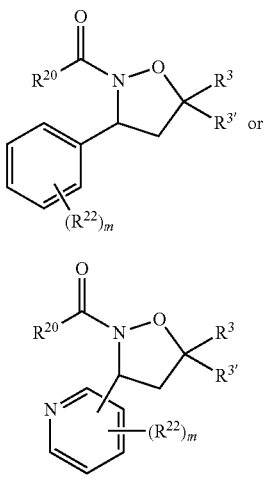

wherein $R^3$, $R^{3'}$, $R^{20}$ and $R^{22}$ are as defined herein;

m is 1 or 2; and each $R^{22}$ is independently selected from halo, hydroxy, cyano, nitro, $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl, heteroaryl, $-C(=O)R^{11}$, $-C(=O)OR^{11}$, $-C(=O)NR^{11}R^{11}$, $-S(=O)R^{11}$, $-S(=O)_2R^{11}$, $-NR^{11}R^{11}$, $-NR^{11}C(O)R^{11}$ or $-NR^{11}C(=O)OR^{11}$;

wherein the $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl and heteroaryl of $R^{22}$ are optionally substituted with one, two or three substituents independently selected from halo, hydroxy, cyano, amino, nitro, $C_{1-6}$ alkyl, alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and $R^{11}$ in each instance is independently hydrogen, $C_{1-6}$ alkyl, $C_{3-10}$ cycloalkyl, heterocyclyl, heteroaryl or aryl.

In certain embodiments, the present disclosure is directed to a compound having the following structure (IIIb') or (IIIc'):

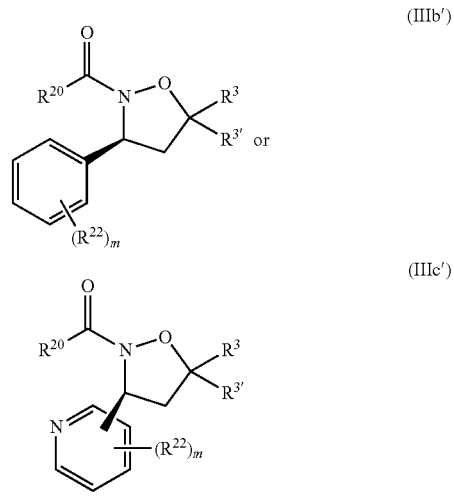

wherein m, $R^3$, $R^{3'}$, $R^{20}$ and $R^{22}$ are as defined herein.

In certain embodiments, the present disclosure is directed to a compound having the following structure (IIIb") or (IIIc"):

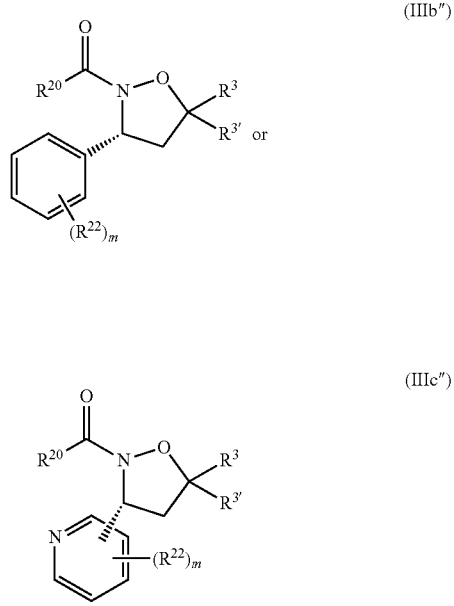

wherein m, $R^3$, $R^{3'}$, $R^{20}$ and $R^{22}$ are as defined herein.

In certain embodiments, the present disclosure is directed to a compound having the following structure (IVa), (IVb) or (IVc):

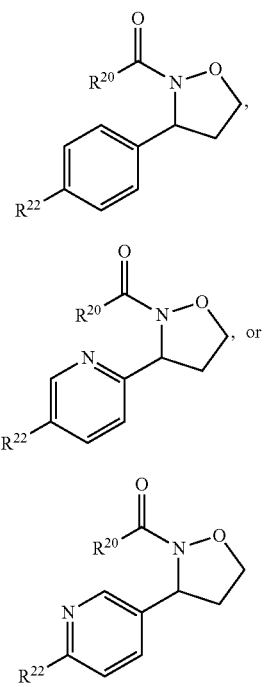

wherein R²⁰ and R²² are as defined herein.

In certain embodiments, the present disclosure is directed to a compound having the following structure (IVa'), (IVb') or (IVc'):

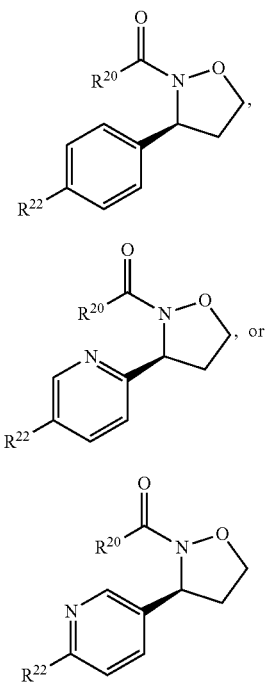

wherein R²⁰ and R²² are as defined herein.

In certain embodiments, the present disclosure is directed to a compound having the following structure (IVa″), (IVb″) or (IVc″):

wherein R²⁰ and R²² are as defined herein.

In certain embodiments, the present disclosure is directed to a compound having the following structure (IVd), (IVe), (IVf), (IVg) or (IVh):

(IVg)

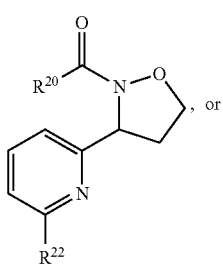

, or (IVh)

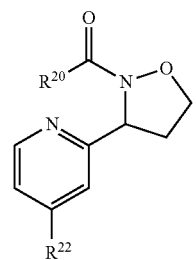

wherein $R^{20}$ and $R^{22}$ are as defined herein.

In certain embodiments, the present disclosure is directed to a compound having the following structure (IVd'), (IVe'), (IVf'), (IVg') or (IVh'):

(IVd')

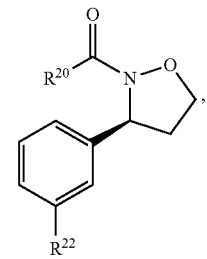

, (IVe')

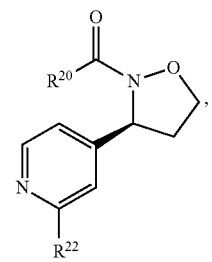

, (IVf')

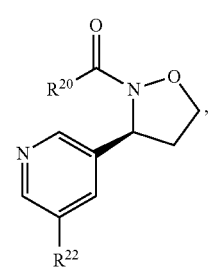

, (IVg')

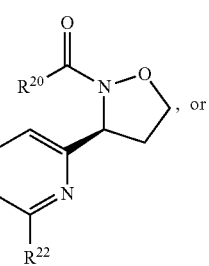

, or (IVh')

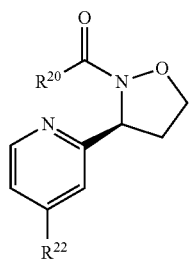

wherein $R^{20}$ and $R^{22}$ are as defined herein.

In certain embodiments, the present disclosure is directed to a compound having the following structure (IVd"), (IVe"), (IVf"), (IVg") or (IVh"):

(IVd")

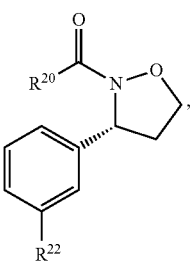

, (IVe")

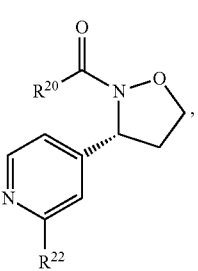

, (IVf")

-continued

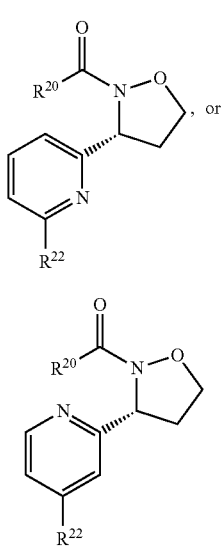

wherein $R^{20}$ and $R^{22}$ are as defined herein.

In certain embodiments, the present disclosure is directed to a compound having the following structure (IVi), (IVj), (IVk) or (IVl):

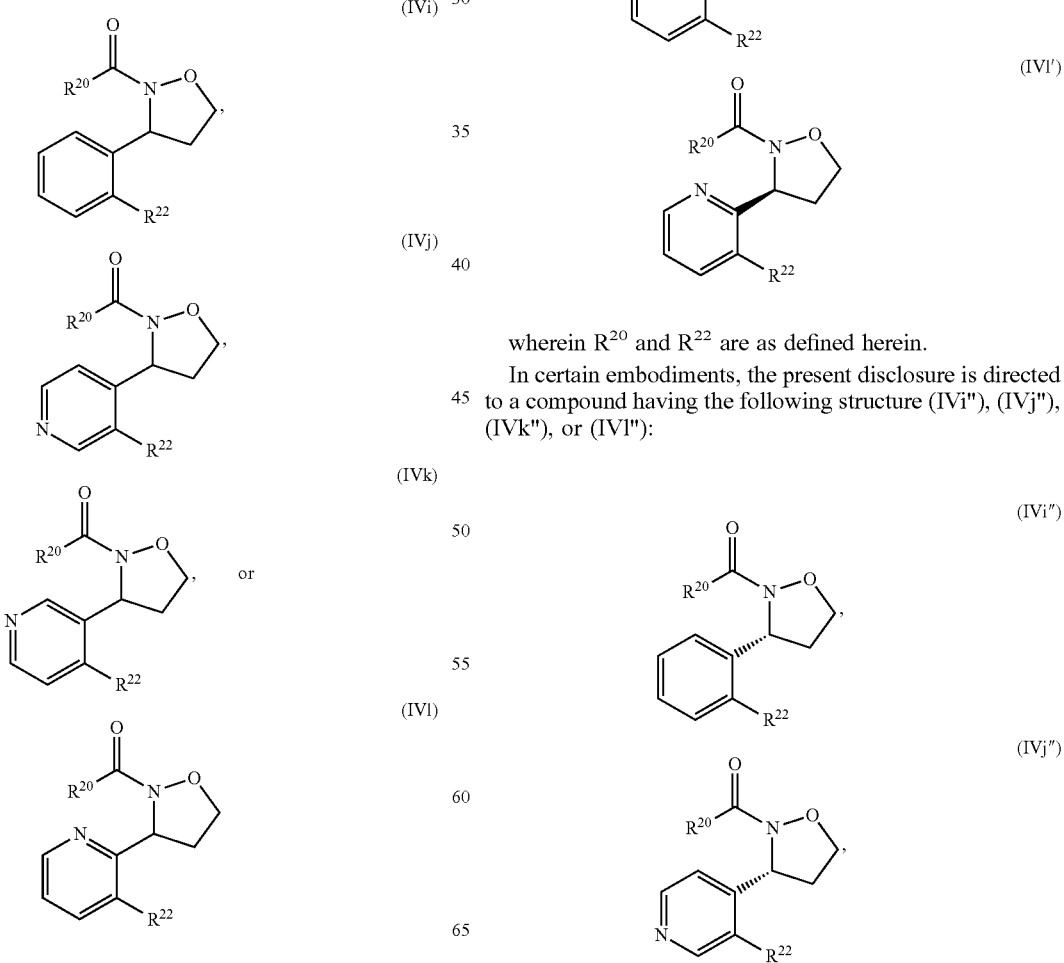

wherein $R^{20}$ and $R^{22}$ are as defined herein.

In certain embodiments, the present disclosure is directed to a compound having the following structure (IVi'), (IVj'), (IVk'), or (IVl'):

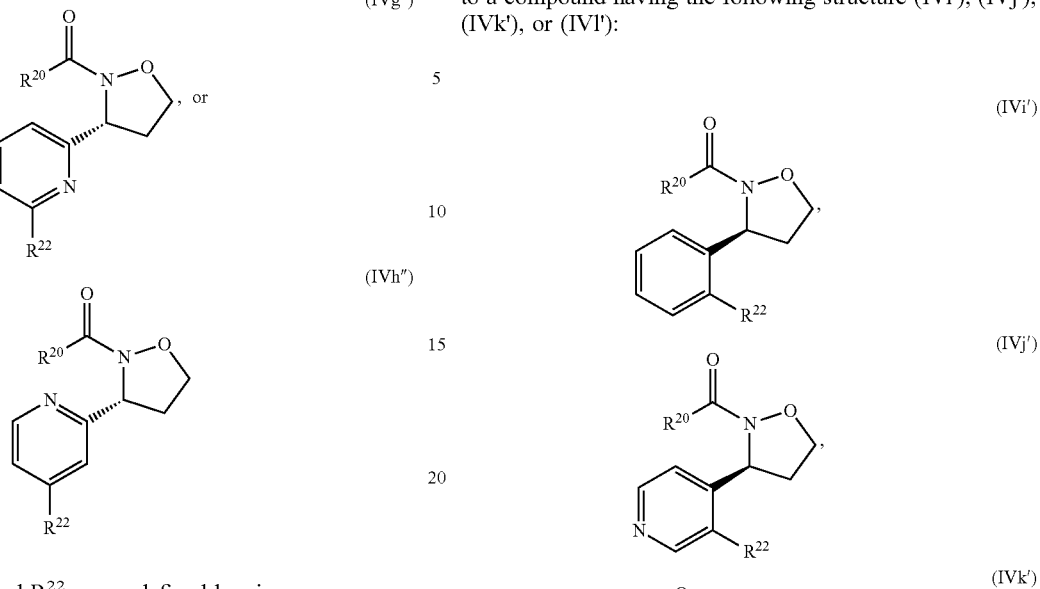

wherein $R^{20}$ and $R^{22}$ are as defined herein.

In certain embodiments, the present disclosure is directed to a compound having the following structure (IVi''), (IVj''), (IVk''), or (IVl''):

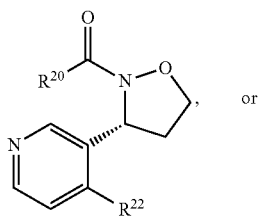

(IVk″)

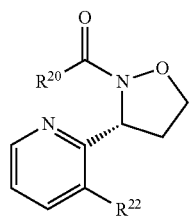

(IVl″)

wherein $R^{20}$ and $R^{22}$ are as defined herein.

In certain embodiments, the present disclosure is directed to a compound having the following structure (IVm), (IVn), (IVo), or (IVp):

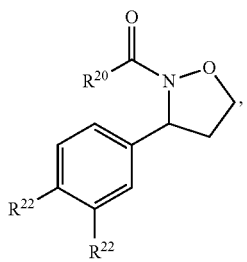

(IVm)

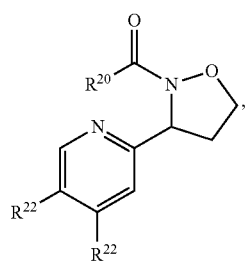

(IVn)

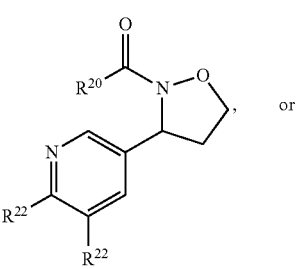

(IVo)

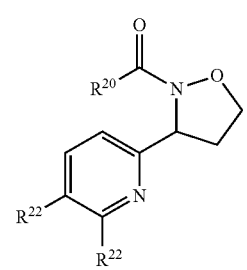

(IVp)

wherein $R^{20}$ and $R^{22}$ are as defined herein.

In certain embodiments, the present disclosure is directed to a compound having the following structure (IVm′), (IVn′), (IVo′), or (IVp′):

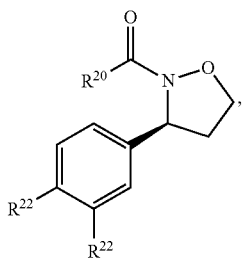

(IVm′)

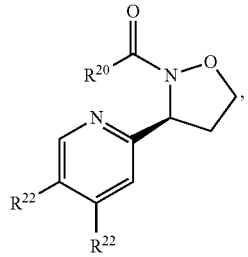

(IVn′)

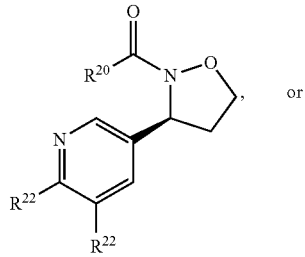

(IVo′) or

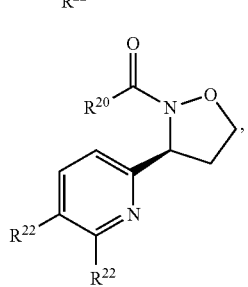

(IVp′)

wherein $R^{20}$ and $R^{22}$ are as defined herein.

In certain embodiments, the present disclosure is directed to a compound having the following structure (IVm″), (IVn″), (IVo″), or (IVp″):

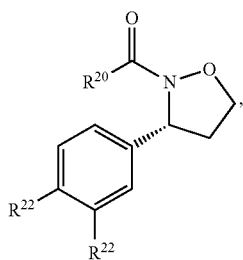
(IVm″)

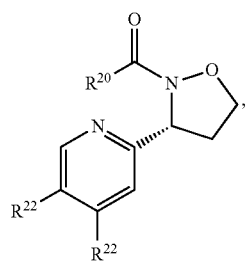
(IVn″)

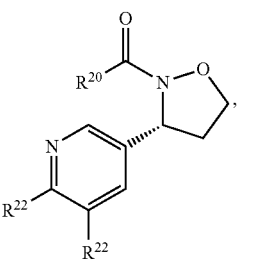
, or
(IVo″)

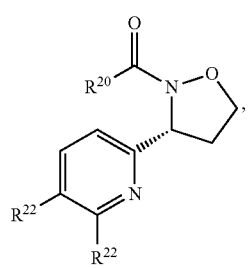
(IVp″)

wherein $R^{20}$ and $R^{22}$ are as defined herein.

In certain embodiments, the present disclosure is directed to a compound having the following structure (V):

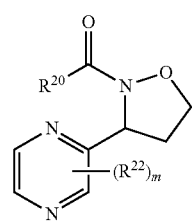
(V)

wherein m is 1 or 2; and $R^{20}$ and $R^{22}$ are as defined herein.

In certain embodiments, the present disclosure is directed to a compound having the following structure (V′):

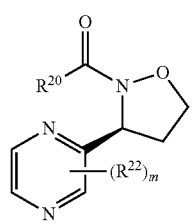
(V′)

wherein m, $R^{20}$ and $R^{22}$ are as defined herein.

In certain embodiments, the present disclosure is directed to a compound having the following structure (V″):

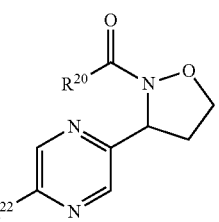
(V″)

wherein m, $R^{20}$ and $R^{22}$ are as defined herein.

In certain embodiments, the present disclosure is directed to a compound having the following structure (Va):

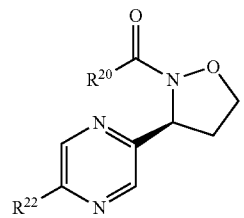
(Va)

wherein $R^{20}$ and $R^{22}$ are as defined herein.

In certain embodiments, the present disclosure is directed to a compound having the following structure (Va′):

(Va′)

wherein $R^{20}$ and $R^{22}$ are as defined herein.

In certain embodiments, the present disclosure is directed to a compound having the following structure (Va″):

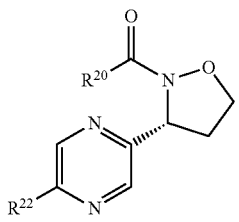
(Va″)

wherein $R^{20}$ and $R^{22}$ are as defined herein.

In certain embodiments, the present disclosure is directed to a compound having the following structure (Vb):

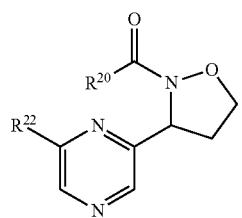
(Vb)

wherein $R^{20}$ and $R^{22}$ are as defined herein.

In certain embodiments, the present disclosure is directed to a compound having the following structure (Vb'):

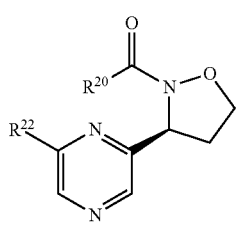
(Vb')

wherein $R^{20}$ and $R^{22}$ are as defined herein.

In certain embodiments, the present disclosure is directed to a compound having the following structure (Vb″):

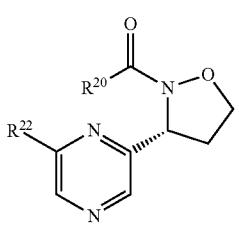
(Vb″)

wherein $R^{20}$ and $R^{22}$ are as defined herein.

In certain embodiments, the present disclosure is directed to a compound having the following structure (VI):

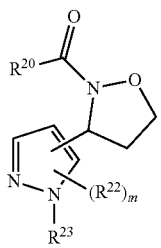
(VI)

wherein m is 1 or 2; $R^{20}$ and $R^{22}$ are as defined herein; and $R^{23}$ is hydrogen, deuterium, $C_{1-12}$ alkyl, —C(O)OC$_{1-12}$ alkyl, or $C_{3-10}$ cycloalkyl, wherein said alkyl and cycloalkyl are each independently optionally substituted with one or more oxo, halo, hydroxy, $C_{1-6}$ alkoxy, or amino.

In certain embodiments, the present disclosure is directed to a compound having the following structure (VI'):

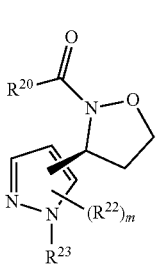
(VI')

wherein m, $R^{20}$, $R^{22}$ and $R^{23}$ are as defined herein.

In certain embodiments, the present disclosure is directed to a compound having the following structure (VI″):

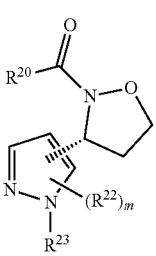
(VI″)

wherein m, $R^{20}$, $R^{22}$ and $R^{23}$ are as defined herein.

In certain embodiments, the present disclosure is directed to a compound having the following structure (VII):

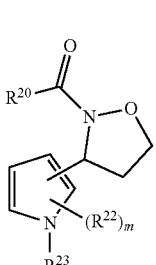
(VII)

wherein m is 1 or 2; $R^{20}$ and $R^{22}$ are as defined herein; and $R^{23}$ is hydrogen, deuterium, $C_{1-12}$ alkyl, —C(O)O$C_{1-12}$ alkyl, or $C_{3-10}$ cycloalkyl, wherein said alkyl and cycloalkyl are each independently optionally substituted with one or more oxo, halo, hydroxy, $C_{1-6}$ alkoxy, or amino.

In certain embodiments, the present disclosure is directed to a compound having the following structure (VII'):

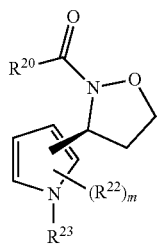

(VII')

wherein m, $R^{20}$, $R^{22}$ and $R^{23}$ are as defined herein.

In certain embodiments, the present disclosure is directed to a compound having the following structure (VII"):

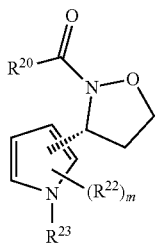

(VII")

wherein m, $R^{20}$, $R^{22}$ and $R^{23}$ are as defined herein.

In certain embodiments, the present disclosure is directed to a compound having the following structure (VIII):

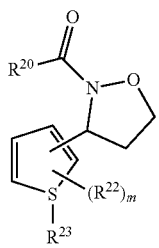

(VIII)

wherein m is 1 or 2; $R^{20}$ and $R^{22}$ are as defined herein; and $R^{23}$ is hydrogen, deuterium, $C_{1-12}$ alkyl, —C(O)O$C_{1-12}$ alkyl, or $C_{3-10}$ cycloalkyl, wherein said alkyl and cycloalkyl are each independently optionally substituted with one or more oxo, halo, hydroxy, $C_{1-6}$ alkoxy, or amino.

In certain embodiments, the present disclosure is directed to a compound having the following structure (VIII'):

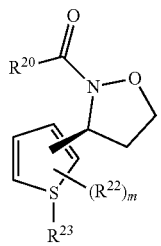

(VIII')

wherein m, $R^{20}$, $R^{22}$ and $R^{23}$ are as defined herein.

In certain embodiments, the present disclosure is directed to a compound having the following structure (VIII"):

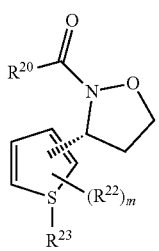

(VIII")

wherein m, $R^{20}$, $R^{22}$ and $R^{23}$ are as defined herein.

In certain embodiments, each $R^{22}$ is independently selected from halo, hydroxy, cyano, nitro, $C_{1-6}$ alkyl, $C_{1-6}$ alkoxy, $C_{3-10}$ cycloalkyl, or heterocyclyl. In certain embodiments, each $R^{22}$ is independently selected from halo. In certain embodiments, each $R^{22}$ is independently selected from hydroxy. In certain embodiments, each $R^{22}$ is independently selected from cyano. In certain embodiments, each $R^{22}$ is independently selected from $C_{1-6}$ alkyl. In certain embodiments, each $R^{22}$ is independently selected from $C_{3-10}$ cycloalkyl. In certain embodiments, each $R^{22}$ is independently selected from heterocyclyl.

In certain embodiments of the compounds of any structure above (e.g., any of structures (III)-(VIII) or a sub-structure thereof), each $R^{22}$ is independently fluoro, methyl, or cyano. In certain embodiments of the compounds of any structure above (e.g., any of structures (III)-(VIII) or a sub-structure thereof), one $R^{22}$ is cyano. In certain embodiments of the compounds of any structure above (e.g., any of structures (III)-(VIII) or a sub-structure thereof), one $R^{22}$ is fluoro. In certain embodiments, one $R^{22}$ is methyl.

In certain embodiments of the compounds of any structure above (e.g., any of structures (III)-(VIII) or a sub-structure thereof), $R^{20}$ is optionally substituted $C_{1-6}$ alkyl. In certain embodiments of the compounds of any structure above (e.g., any of structures (III)-(VIII) or a sub-structure thereof), $R^{20}$ is $C_{1-6}$ cyanoalkyl or $C_{1-6}$ haloalkyl. In certain embodiments of the compounds of any structure above (e.g., any of structures (III)-(VIII) or a sub-structure thereof), $R^{20}$ is $C_{1-6}$ haloalkyl.

In certain embodiments of the compounds of any structure above (e.g., any of structures (III)-(VIII) or a sub-structure thereof), $R^{20}$ is $C_{1-6}$ haloalkyl and, each $R^{22}$ is independently fluoro, methyl, or cyano. In certain embodiments of the compounds of any structure above (e.g., any of structures (III)-(VIII) or a sub-structure thereof), $R^{20}$ is $C_{1-6}$ haloalkyl and one $R^{22}$ is fluoro. In certain embodiments of the compounds of any structure above (e.g., any of structures (III)-(VIII) or a sub-structure thereof), $R^{20}$ is $C_{1-6}$ haloalkyl and one $R^{22}$ is cyano.

In certain embodiments of the compounds of any structure above (e.g., any of structures (III)-(VIII) or a sub-structure thereof), $R^{20}$ is optionally substituted $C_{3-10}$ cycloalkyl, or optionally substituted branched $C_{1-6}$ alkyl.

In certain embodiments of the compounds of any structure above (e.g., any of structures (III)-(VIII) or a sub-structure thereof), $R^{20}$ is optionally substituted branched $C_{1-6}$ alkyl. In certain embodiments of the compounds of any structure above (e.g., any of structures (III)-(VIII) or a sub-structure thereof), $R^{20}$ is of the formula:

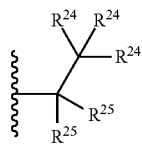

wherein each $R^{24}$ is independently hydrogen, halo, hydroxy, cyano, nitro, $C_{1-6}$ alkoxy, $C_{2-6}$ alkynyl, $C_{3-10}$ cycloalkyl, heterocyclyl, aryl, heteroaryl, —C(=O)$R^{26}$, —C(=O)O$R^{26}$, —C(=O)N$R^{26}R^{26}$, —S(=O)$R^{26}$, —S(=O)$_2R^{26}$, —N$R^{26}R^{26}$, —N$R^{26}$C(=O)$R^{26}$ or —N$R^{26}$C(=O)O$R^{26}$;

wherein the $C_{1-6}$ alkoxy, $C_{2-6}$ alkynyl, $C_{3-10}$ cycloalkyl, heterocyclyl, aryl and heteroaryl of $R^{24}$ are optionally substituted with one, two or three substituents independently selected from deuterium, halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl;

each $R^{25}$ is independently hydrogen, halo, $C_{1-6}$ alkyl, $C_{3-10}$ cycloalkyl, heterocyclyl, heteroaryl or aryl; or two $R^{25}$ together with the atom to which they are attached form a $C_{3-10}$ cycloalkyl or heterocyclyl;

wherein the $C_{1-6}$ alkyl, $C_{3-10}$ cycloalkyl, heterocyclyl, heteroaryl or aryl of $R^{25}$ is optionally substituted with one, two or three substituents independently selected from deuterium, halo, hydroxy, cyano, amino, nitro, alkyl, $C_{1-6}$ alkoxy, haloalkoxy, $C_{2-6}$ alkenyl, $C_{2-6}$ alkynyl, $C_{3-10}$ cycloalkyl, aryl or heteroaryl; and $R^{26}$ in each instance independently is hydrogen, $C_{1-6}$ alkyl, $C_{3-10}$ cycloalkyl, heterocyclyl, heteroaryl or aryl;

wherein the $C_{1-6}$ alkyl of $R^{26}$ is optionally substituted with halo or oxo and wherein the $C_{3-10}$ cycloalkyl, heterocyclyl, heteroaryl or aryl of $R^{26}$ is optionally substituted with one, two or three $C_{1-6}$ alkyl;

provided that at least one of the following occurs: a) two $R^{25}$ together with the atom to which they are attached form a $C_{3-10}$ cycloalkyl or heterocyclyl, b) at least one $R^{24}$ is other than hydrogen, or c) both $R^{25}$ are optionally substituted $C_{1-6}$ alkyl.

In certain embodiments of the compounds of any structure above (e.g., any of structures (III)-(VIII) or a sub-structure thereof), two $R^{25}$ together with the atom to which they are attached form a $C_{3-10}$ cycloalkyl or heterocyclyl. In certain embodiments of the compounds of any structure above (e.g., any of structures (III)-(VIII) or a sub-structure thereof), at least one $R^{24}$ is other than hydrogen. In certain embodiments of the compounds of any structure above (e.g., any of structures (III)-(VIII) or a sub-structure thereof), both $R^{25}$ are optionally substituted $C_{1-6}$ alkyl.

In certain embodiments of the compounds of any structure above (e.g., any of structures (III)-(VIII) or a sub-structure thereof), at least one $R^{25}$ is methyl. In certain embodiments of the compounds of any structure above (e.g., any of structures (III)-(VIII) or a sub-structure thereof), $R^{20}$ is of the formula:

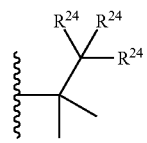

wherein each $R^{24}$ is independently hydrogen, halo, hydroxy, cyano, nitro, $C_{1-6}$ alkoxy, $C_{2-6}$ alkynyl, $C_{3-10}$ cycloalkyl, heterocyclyl, aryl, heteroaryl, —C(=O)$R^{26}$, —C(=O)O$R^{26}$, —C(=O)N$R^{26}R^{26}$, —S(=O)$R^{26}$, —S(=O)$_2R^{26}$, —N$R^{26}R^{26}$, —N$R^{26}$C(=O)$R^{26}$ or —N$R^{26}$C(=O)O$R^{26}$;

wherein the $C_{1-6}$ alkoxy, $C_{2-6}$ alkanyl, $C_{3-10}$ cycloalkyl, heterocyclyl, aryl and heteroaryl of $R^{24}$ are optionally substituted with one, two or three substituents independently selected from deuterium, halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and $R^{26}$ in each instance independently is hydrogen, $C_{1-6}$ alkyl, $C_{3-10}$ cycloalkyl, heterocyclyl, heteroaryl or aryl;

wherein the $C_{1-6}$ alkyl of $R^{26}$ is optionally substituted with halo or oxo and wherein the $C_{3-10}$ cycloalkyl, heterocyclyl, heteroaryl or aryl of $R^{26}$ is optionally substituted with one, two or three $C_{1-6}$ alkyl;

provided that at least one $R^{24}$ is other than hydrogen.

In certain embodiments, each $R^{24}$ is independently selected from hydrogen, deuterium, hydroxy, halo, $C_{1-6}$ haloalkyl, $C_{1-6}$ alkoxy, $C_{1-6}$ haloalkoxy, cyano, $C_{3-10}$ cycloalkyl, heterocyclyl and heteroaryl, wherein the heterocyclyl or heteroaryl is optionally further substituted with one, two or three halo, cyano $C_{1-6}$ alkyl or $C_{3-10}$ cycloalkyl. In certain embodiments, each $R^{24}$ is independently selected from hydrogen, hydroxy, halo, $C_{1-6}$ haloalkyl, $C_{1-6}$ alkoxy, $C_{1-6}$ haloalkoxy and cyano. In certain embodiments, each $R^{24}$ is independently hydrogen, halo or cyano. In certain embodiments, one $R^{24}$ is hydrogen and the other two $R^{24}$ are halo.

In certain embodiments, the present disclosure is directed to a compound having the following structure (IXa), (IXb), (IXc) or (IXd):

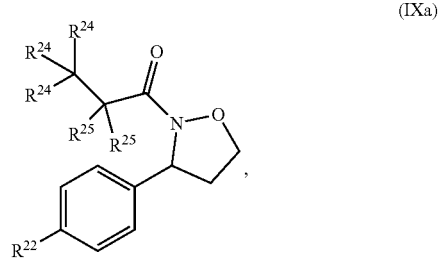

(IXa)

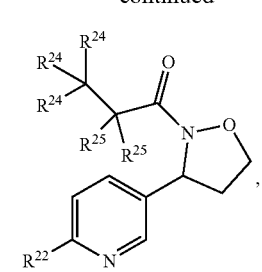

(IXb)

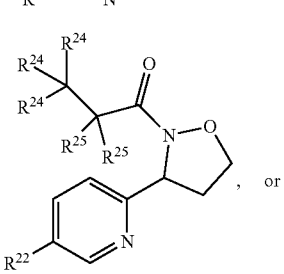

, or

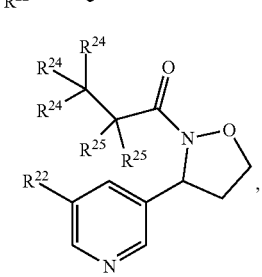

(IXd)

wherein:

$R^{22}$ is halo, hydroxy, cyano, nitro, $C_{1-6}$ alkyl, $C_{1-6}$ alkoxy, $C_{2-6}$ alkenyl, $C_{2-6}$ alkynyl, $C_{3-10}$ cycloalkyl, heterocyclyl, aryl, heteroaryl, —C(=O)$R^{26}$, —C(=O)O$R^{26}$, —C(=O)N$R^{26}R^{26}$, —S(=O)$R^{26}$, —S(=O)$_2R^{26}$, —N$R^{26}R^{26}$, —N$R^{26}$C(=O)$R^{26}$ or —N$R^{26}$C(=O)O$R^{26}$;

wherein the $C_{1-6}$ alkyl, $C_{1-6}$ alkoxy, $C_{1-6}$ alkenyl, $C_{2-6}$ alkynyl, $C_{3-10}$ cycloalkyl, heterocyclyl, aryl and heteroaryl of $R^{22}$ are optionally substituted with one, two or three substituents independently selected from halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl;

wherein each $R^{24}$ is independently hydrogen, halo, hydroxy, cyano, nitro, $C_{1-6}$ alkoxy, $C_{2-6}$ alkynyl, $C_{3-10}$ cycloalkyl, heterocyclyl, aryl, heteroaryl, —C(=O)$R^{26}$, —C(=O)O$R^{26}$, —C(=O)N$R^{26}R^{26}$, —S(=O)$R^{26}$, —S(=O)$_2R^{26}$, —N$R^{26}R^{26}$, —N$R^{26}$C(=O)$R^{26}$ or —N$R^{26}$C(=O)O$R^{26}$;

wherein the $C_{1-6}$ alkoxy, $C_{2-6}$ alkynyl, $C_{3-10}$ cycloalkyl, heterocyclyl, aryl and heteroaryl of $R^{24}$ are optionally substituted with one, two or three substituents independently selected from deuterium, halo, hydroxy, cyano, amino, nitro, $C_{1-6}$ alkyl, $C_{1-6}$ alkoxy, $C_{1-6}$ haloalkoxy, $C_{2-6}$ alkenyl, $C_{1-6}$ alkynyl, $C_{3-10}$ cycloalkyl, heterocyclyl, aryl or heteroaryl;

each $R^{25}$ is independently hydrogen, halo, $C_{1-6}$ alkyl, $C_{3-10}$ cycloalkyl, heterocyclyl, heteroaryl or aryl; or two $R^{25}$ together with the atom to which they are attached form a $C_{3-10}$ cycloalkyl or heterocyclyl;

wherein the $C_{1-6}$ alkyl, $C_{3-10}$ cycloalkyl, heterocyclyl, heteroaryl or aryl of $R^{25}$ is optionally substituted with one, two or three substituents independently selected from deuterium, halo, hydroxy, cyano, amino, nitro, $C_{1-6}$ alkyl, $C_{1-6}$ alkoxy, $C_{1-6}$ haloalkoxy, $C_{2-6}$ alkenyl, $C_{2-6}$ alkynyl, $C_{3-10}$ cycloalkyl, heterocyclyl, aryl or heteroaryl; and $R^{26}$ in each instance independently is hydrogen, $C_{1-6}$ alkyl, $C_{3-10}$cycloalkyl, heterocyclyl, heteroaryl or aryl;

wherein the $C_{1-6}$ alkyl of $R^{26}$ is optionally substituted with halo or oxo and wherein the $C_{3-10}$ cycloalkyl, heterocyclyl, heteroaryl or aryl of $R^{26}$ is optionally substituted with one, two or three $C_{1-6}$ alkyl;

provided that at least one of the following occurs: a) two $R^{25}$ together with the atom to which they are attached form a $C_{3-10}$ cycloalkyl or heterocyclyl, b) at least one $R^{24}$ is other than hydrogen, or c) both $R^{25}$ are optionally substituted $C_{1-6}$ alkyl.

In certain embodiments, the present disclosure is directed to a compound having the following structure (IXa'), (IXb'), (IXc') or (IXd'):

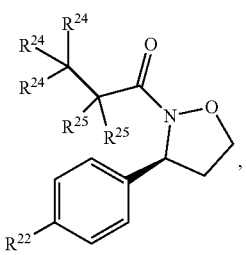
(IXa')

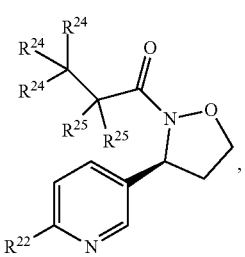
(IXb')

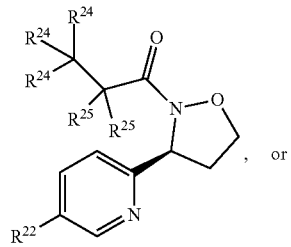
(IXc')
, or

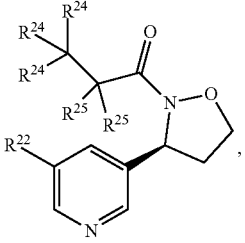
(IXd')

wherein $R^{22}$, $R^{24}$ and $R^{25}$ are as defined herein.

In certain embodiments, the present disclosure is directed to a compound having the following structure (IXa"), (IXb"), (IXc") or (IXd").

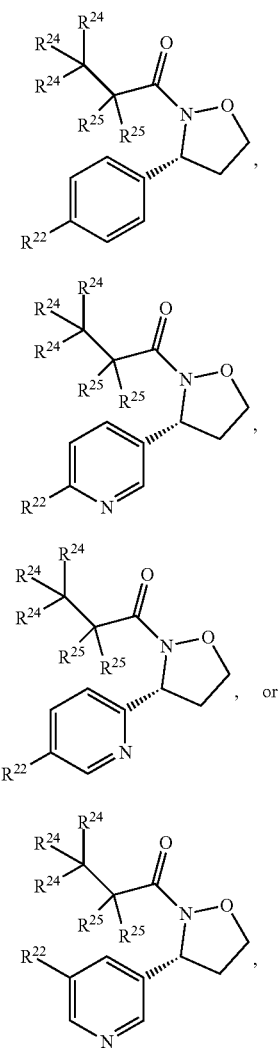

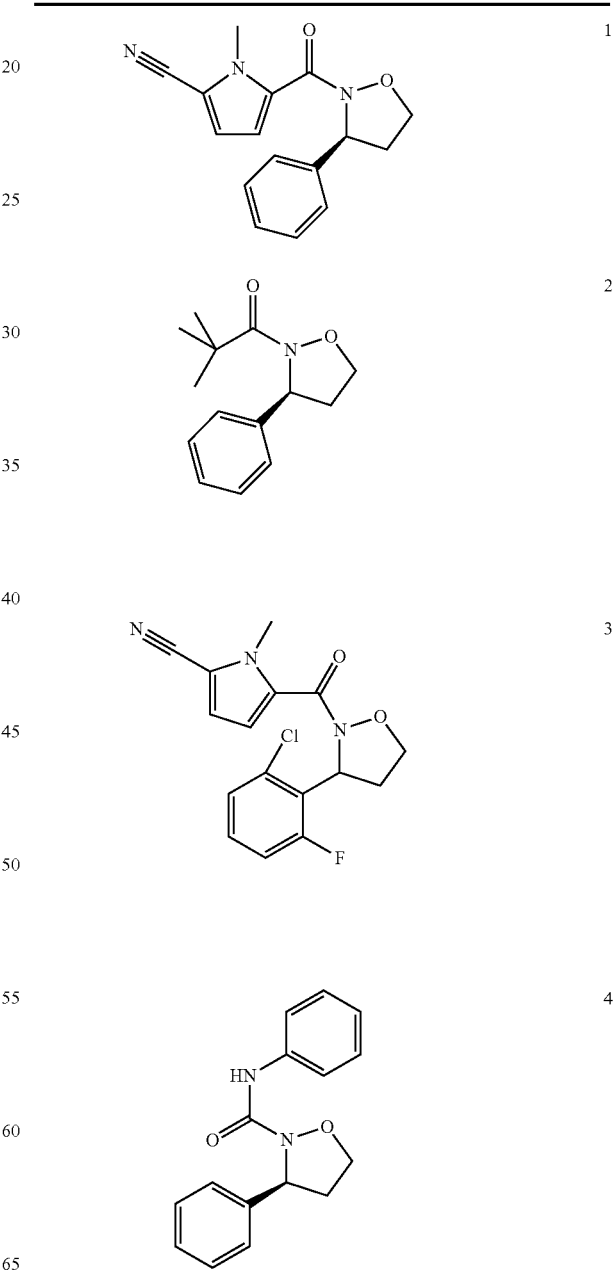

wherein $R^{22}$, $R^{24}$ and $R^{25}$ are as defined herein.

In certain embodiments of the compounds of structure (IX) or a sub-structure thereof, two $R^{25}$ together with the atom to which they are attached form a $C_{3-10}$ cycloalkyl or heterocyclyl. In certain embodiments of the compounds of structure (IX) or a sub-structure thereof, at least one $R^{24}$ is other than hydrogen. In certain embodiments of the compounds of structure (IX) or a sub-structure thereof, both $R^{25}$ are optionally substituted $C_{1-6}$ alkyl.

In certain embodiments of the compounds of any structure above (e.g., any of structures (III)-(IX) or a sub-structure thereof), $R^{22}$ is halo or cyano. In certain embodiments of the compounds of any structure above (e.g., any of structures (III)-(IX) or a sub-structure thereof), $R^{22}$ is halo. In certain embodiments, $R^{22}$ is fluoro. In certain embodiments of the compounds of any structure above (e.g., any of structures (III)-(IX) or a sub-structure thereof), $R^{22}$ is cyano.

In certain embodiments of the compounds of any structure above (e.g., any of structures (III)-(IX) or a sub-structure thereof), each $R^{24}$ is independently selected from hydrogen, deuterium, hydroxy, halo, $C_{1-6}$ haloalkyl, $C_{1-6}$ alkoxy, $C_{1-6}$ haloalkoxy, cyano, $C_{3-10}$ cycloalkyl, heterocyclyl and heteroaryl, wherein the heterocyclyl or heteroaryl is optionally further substituted with one, two or three $C_{1-6}$ alkyl. In certain embodiments of the compounds of any structure above (e.g., any of structures (III)-(IX) or a sub-structure thereof), each $R^{24}$ is independently selected from hydrogen, hydroxy, halo, $C_{1-6}$ haloalkyl, $C_{1-6}$ alkoxy, $C_{1-6}$ haloalkoxy and cyano. In certain embodiments of the compounds of any structure above (e.g., any of structures (III)-(IX) or a sub-structure thereof), each $R^{24}$ is independently hydrogen, halo or cyano. In certain embodiments of the compounds of any structure above (e.g., any of structures (III)-(IX) or a sub-structure thereof), one $R^{24}$ is hydrogen and the other two $R^{24}$ are halo. In certain embodiments, the compound is a compound selected from Table 1A, 1B or 1C. Also included within the disclosure are stereoisomers and mixtures of stereoisomers thereof.

TABLE 1A

TABLE 1A-continued
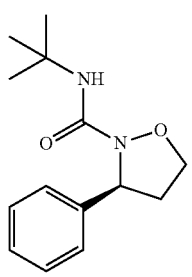 [SMILES: CC(C)(C)NC(=O)N1OCC[C@H]1c1ccccc1] 5
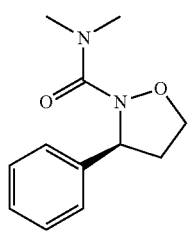 6
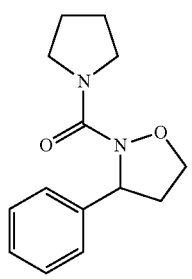 [SMILES: O=C(N1CCCC1)N1OCCC1c1ccccc1] 7
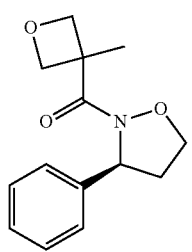 [SMILES: CC1(C(=O)N2OCC[C@H]2c2ccccc2)COC1] 8
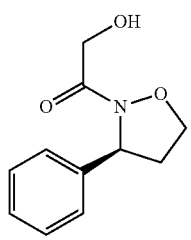 [SMILES: O=C(CO)N1OCC[C@H]1c1ccccc1] 9
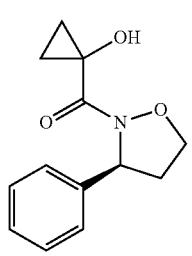 [SMILES: O=C(N1OCC[C@H]1c1ccccc1)C1(O)CC1] 10
TABLE 1A-continued
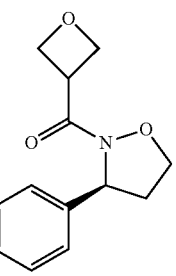 11
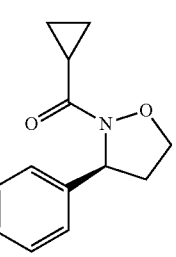 12
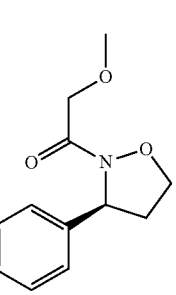 13
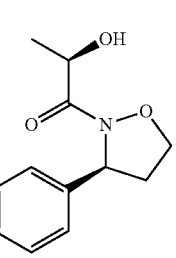 14
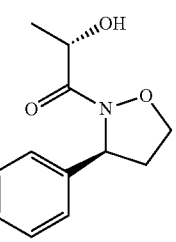 15
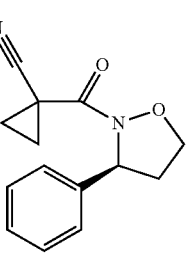 16

TABLE 1A-continued
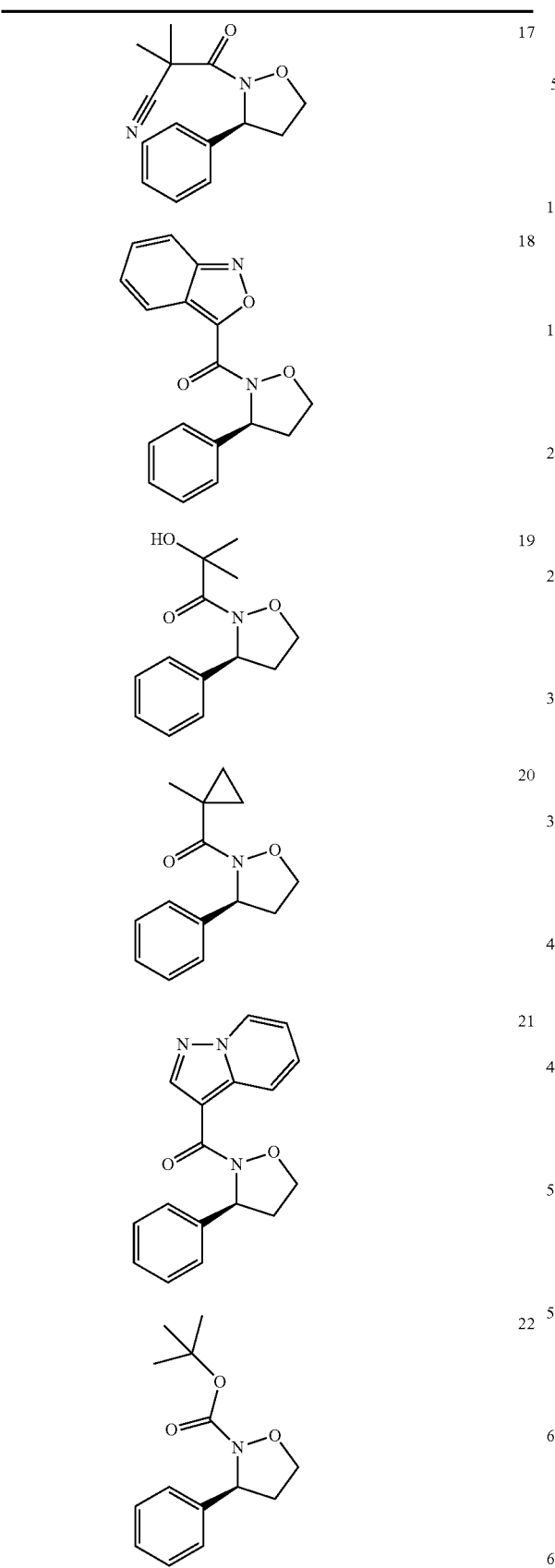
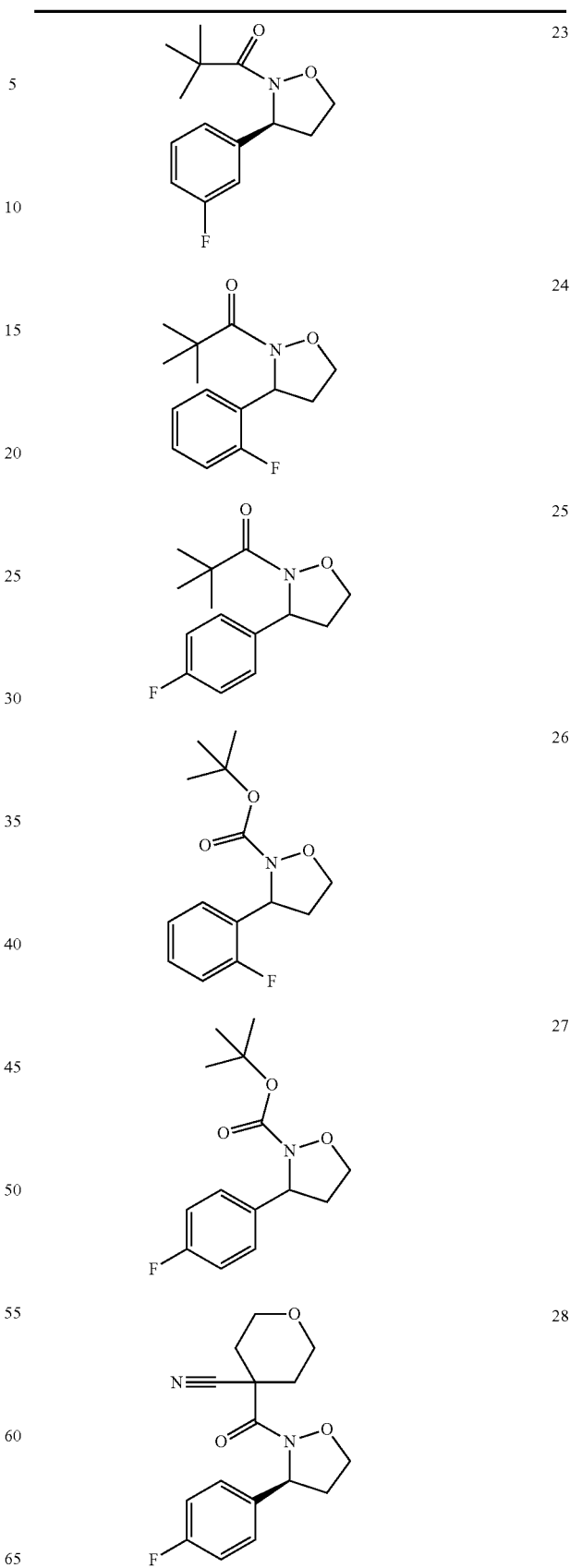

TABLE 1A-continued
| | |
|---|---|
| 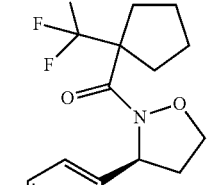 | 29 |
| 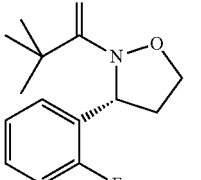 | 30 |
| 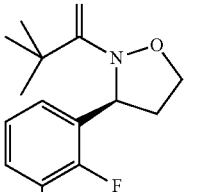 | 31 |
| 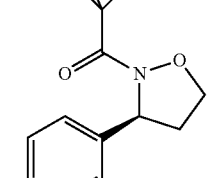 | 32 |
| 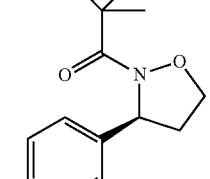 | 33 |
| 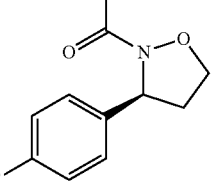 | 34 |
TABLE 1A-continued
| | |
|---|---|
| 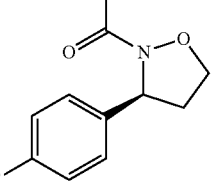 | |
| Diastereoisomer 2 | 35 |
| Diastereoisomer 1 | 36 |
| 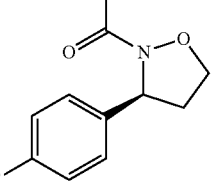 | 37 |
| 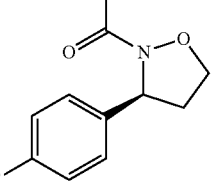 | 38 |
| 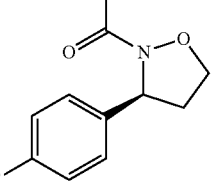 | 39 |
| 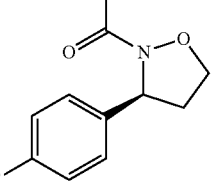 | |
| Diastereoisomer 1 | 40 |
| Diastereoisomer 2 | 41 |

TABLE 1A-continued
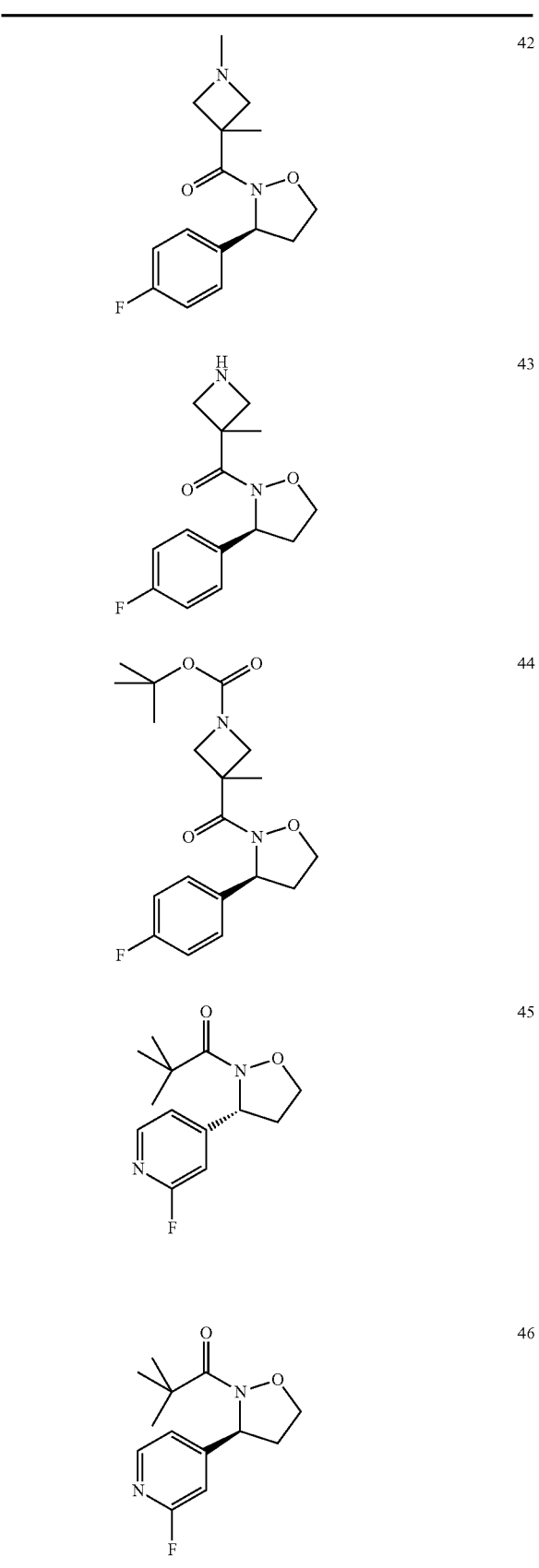
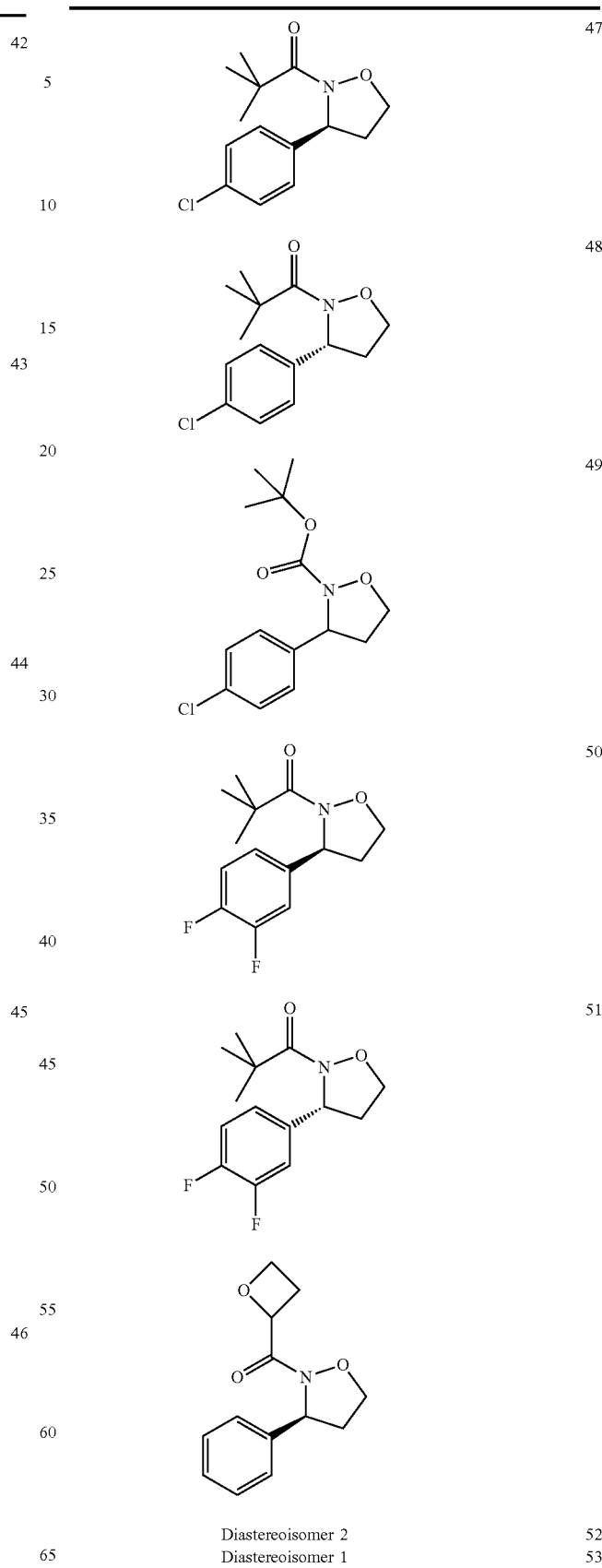
| | |
|---|---|
| Diastereoisomer 2 | 52 |
| Diastereoisomer 1 | 53 |

TABLE 1A-continued
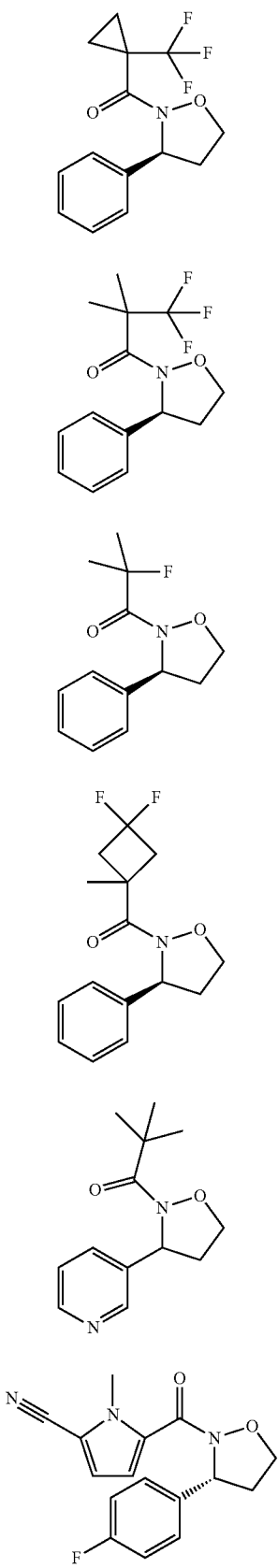
TABLE 1A-continued
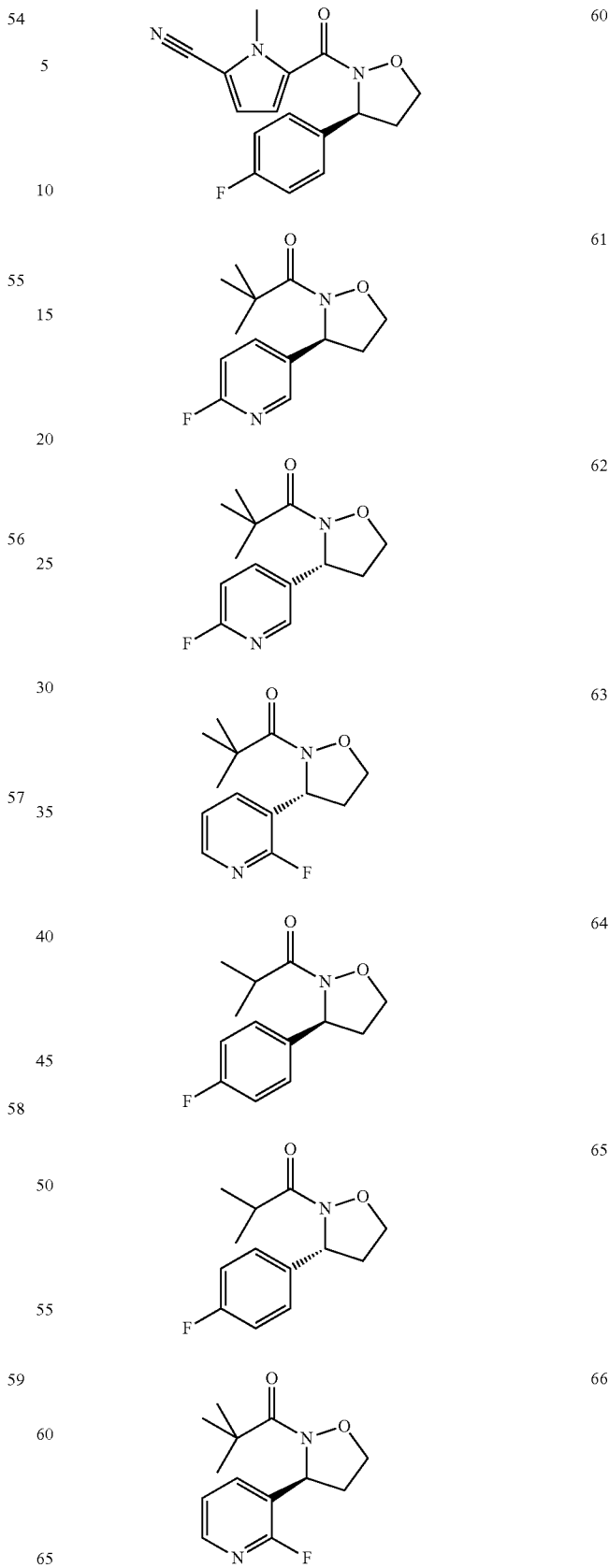

TABLE 1A-continued

| | |
|---|---|
| 67 | |
| 68 | |
| 69 | |
| 70 | |
| 71 | |
| 72 | |

TABLE 1A-continued

| | |
|---|---|
| Enantiomer 1 | 73 |
| Enantiomer 2 | 74 |
| 75 | |
| 76 | |
| 77 | |
| 78 | |
| 79 | |
| 80 | |

TABLE 1A-continued
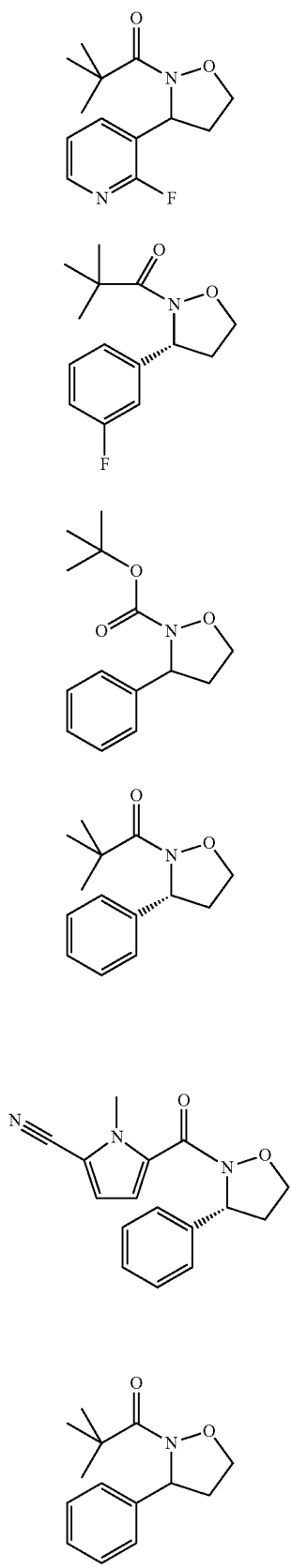
TABLE 1B
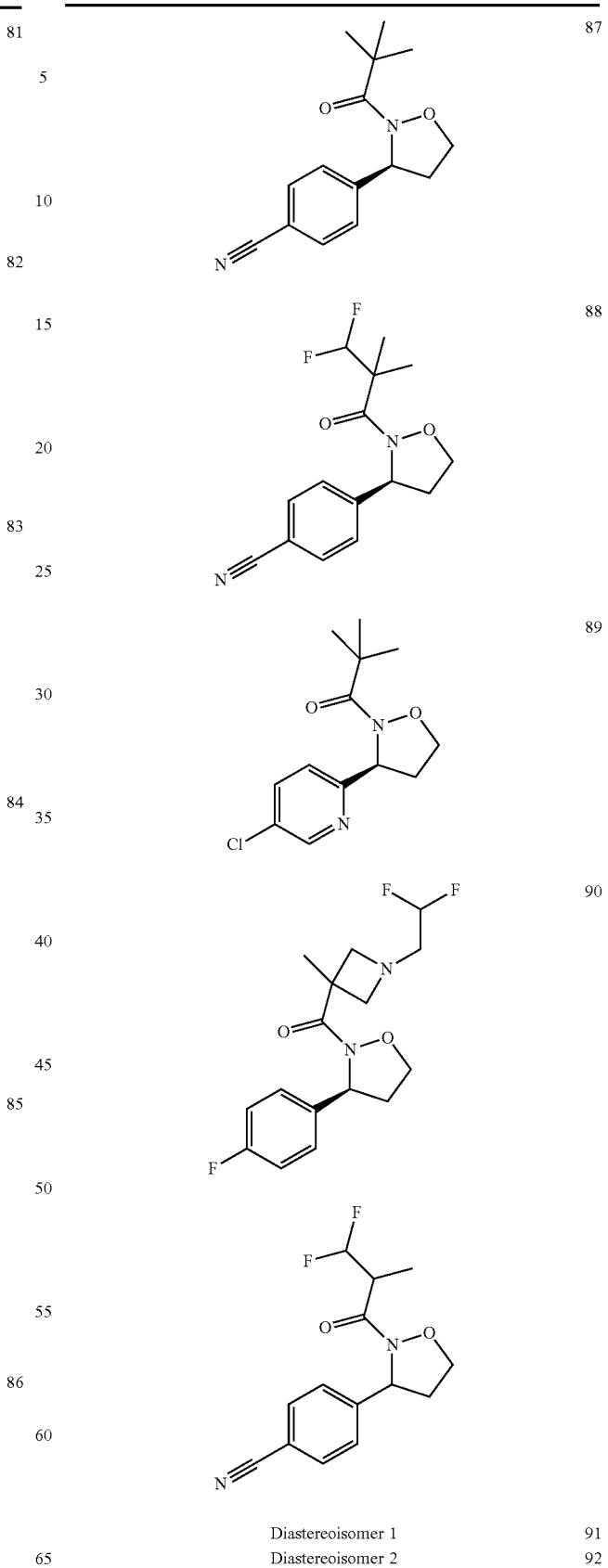
| Diastereoisomer 1 | 91 |
| Diastereoisomer 2 | 92 |

71
TABLE 1B-continued
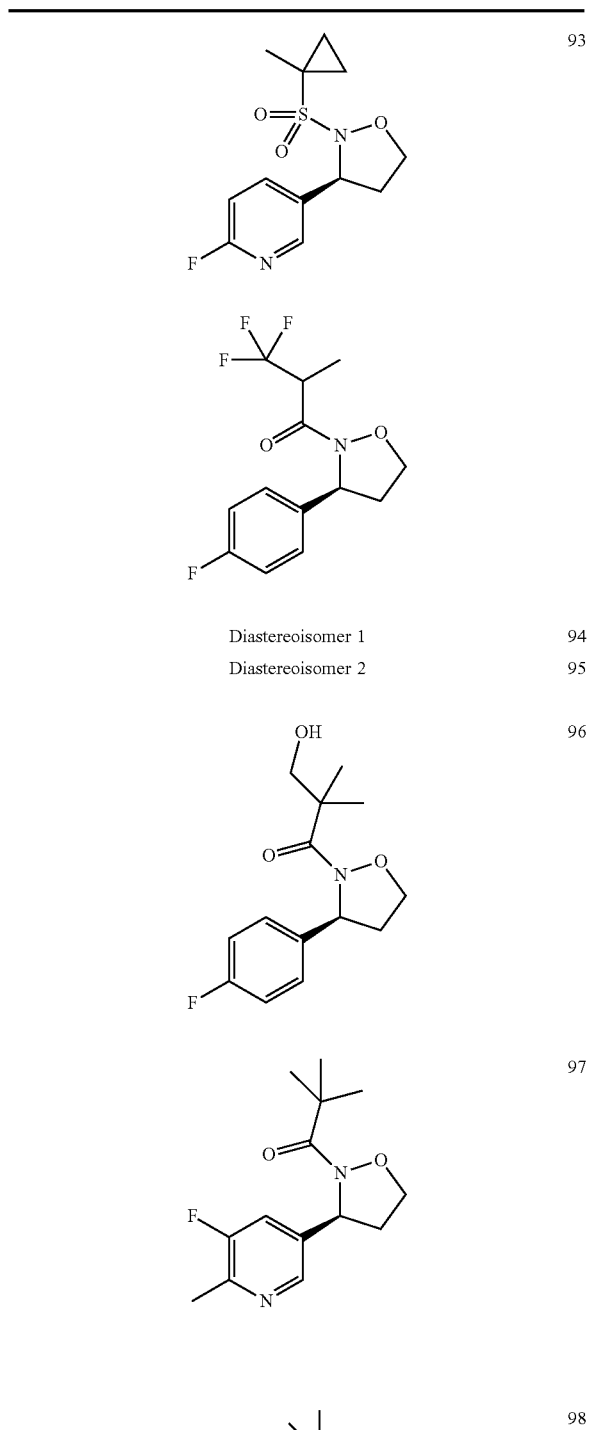
| | |
|---|---|
| Diastereoisomer 1 | 94 |
| Diastereoisomer 2 | 95 |
72
TABLE 1B-continued
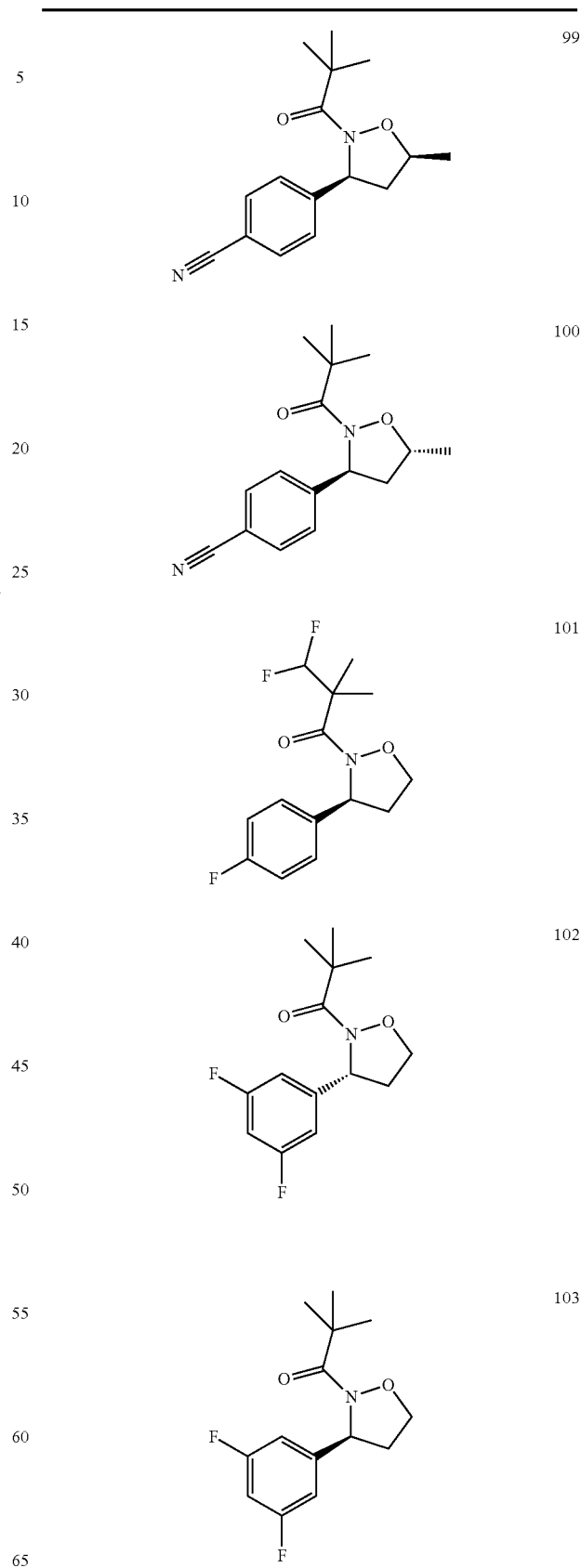

TABLE 1B-continued
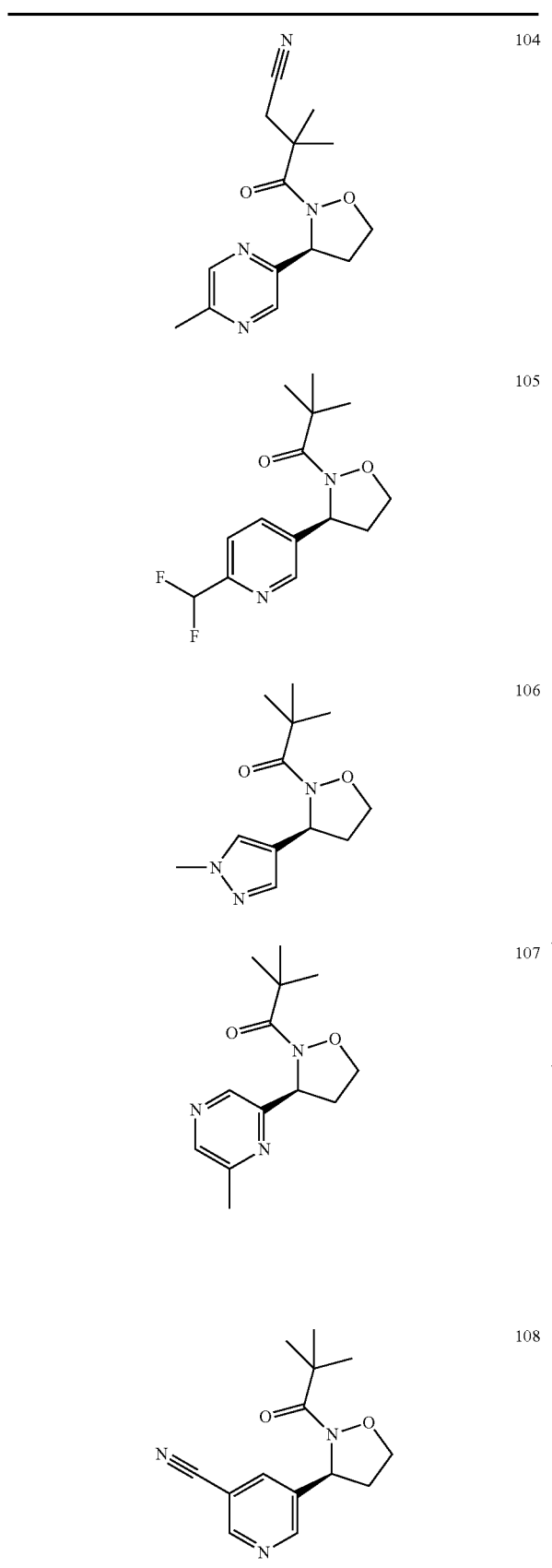
| | |
|---|---|
| 104 | |
| 105 | |
| 106 | |
| 107 | |
| 108 | |
TABLE 1B-continued
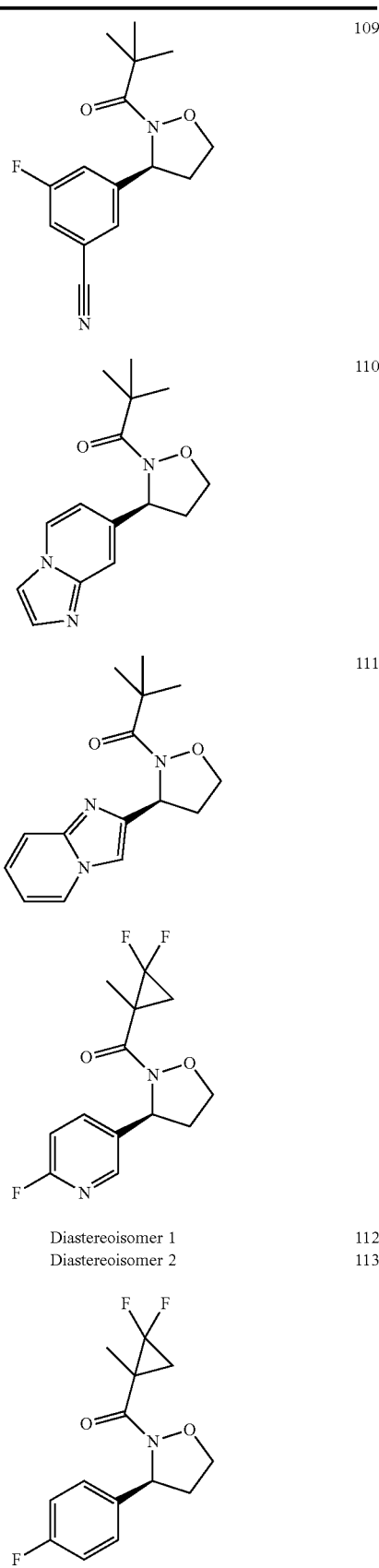
| | |
|---|---|
| 109 | |
| 110 | |
| 111 | |
| Diastereoisomer 1 | 112 |
| Diastereoisomer 2 | 113 |

| | |
|---|---|
| Diastereoisomer 1 | 114 |
| Diastereoisomer 2 | 115 |
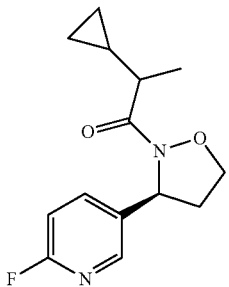 [SMILES: CC(C(=O)N1OCC[C@H]1c1ccc(F)nc1)C1CC1]
| | |
|---|---|
| Diastereoisomer 1 | 116 |
| Diastereoisomer 2 | 117 |
118
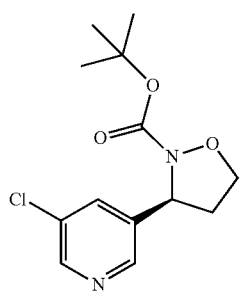 [SMILES: CC(C)(C)OC(=O)N1OCC[C@H]1c1cncc(Cl)c1]
119
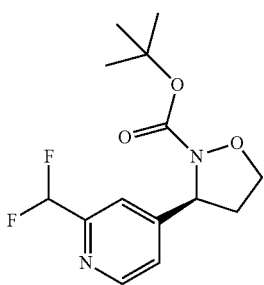 [SMILES: CC(C)(C)OC(=O)N1OCC[C@H]1c1ccnc(C(F)F)c1]
120
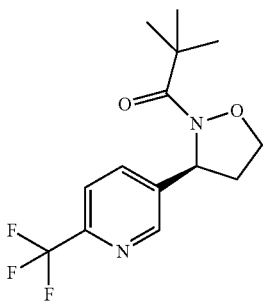 [SMILES: CC(C)(C)C(=O)N1OCC[C@H]1c1ccc(C(F)(F)F)nc1]
121
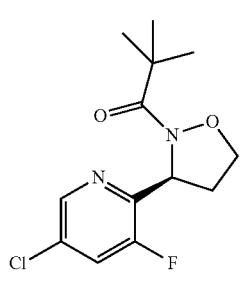 [SMILES: CC(C)(C)C(=O)N1OCC[C@H]1c1ncc(Cl)cc1F]
122
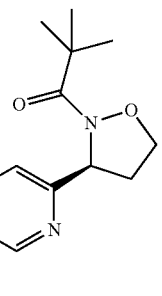
123
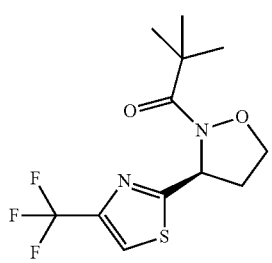 [SMILES: CC(C)(C)C(=O)N1OCC[C@H]1c1nc(C(F)(F)F)cs1]
124
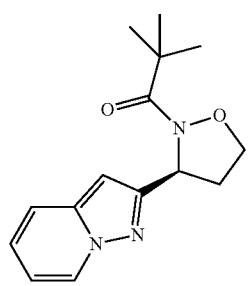 [SMILES: CC(C)(C)C(=O)N1OCC[C@H]1c1cc2ccccn2n1]
125
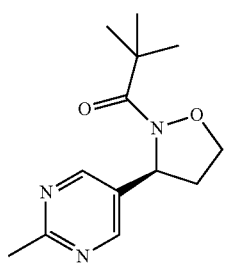 [SMILES: Cc1ncc([C@@H]2CCON2C(=O)C(C)(C)C)cn1]
126
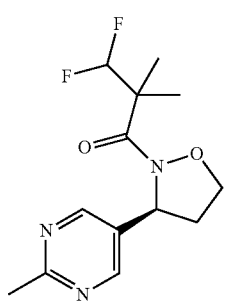 [SMILES: Cc1ncc([C@@H]2CCON2C(=O)C(C)(C)C(F)F)cn1]

TABLE 1B-continued
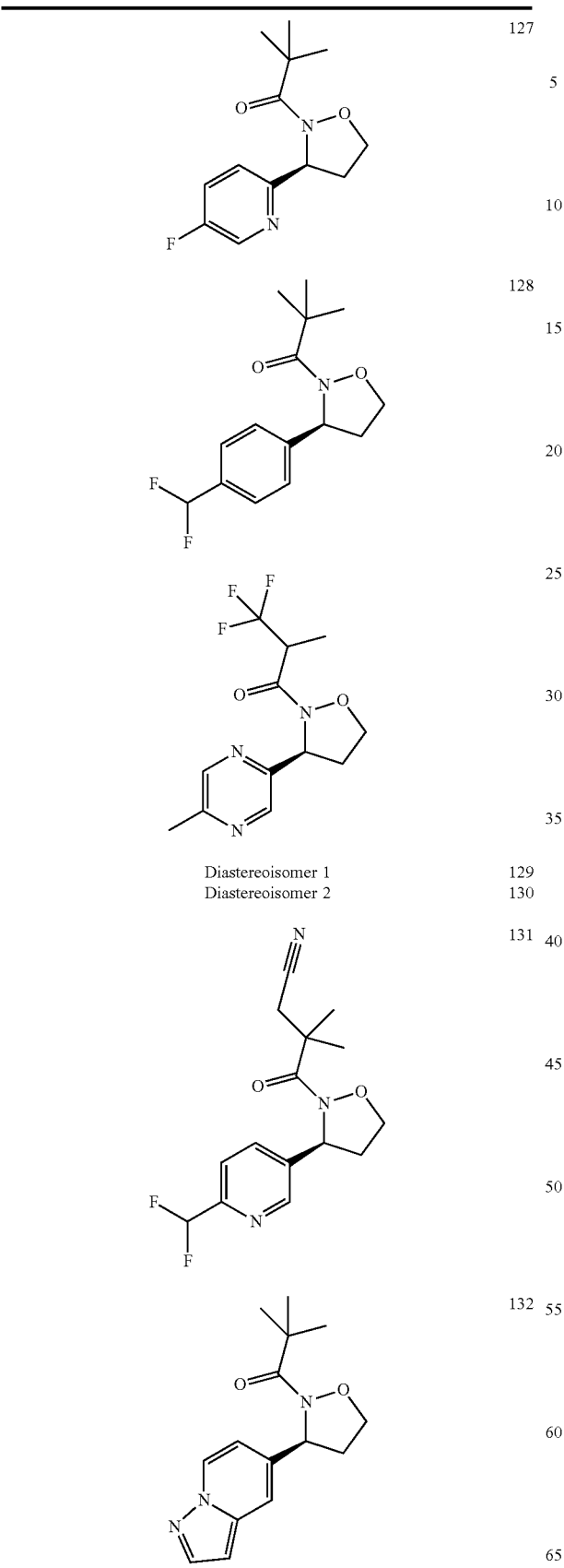
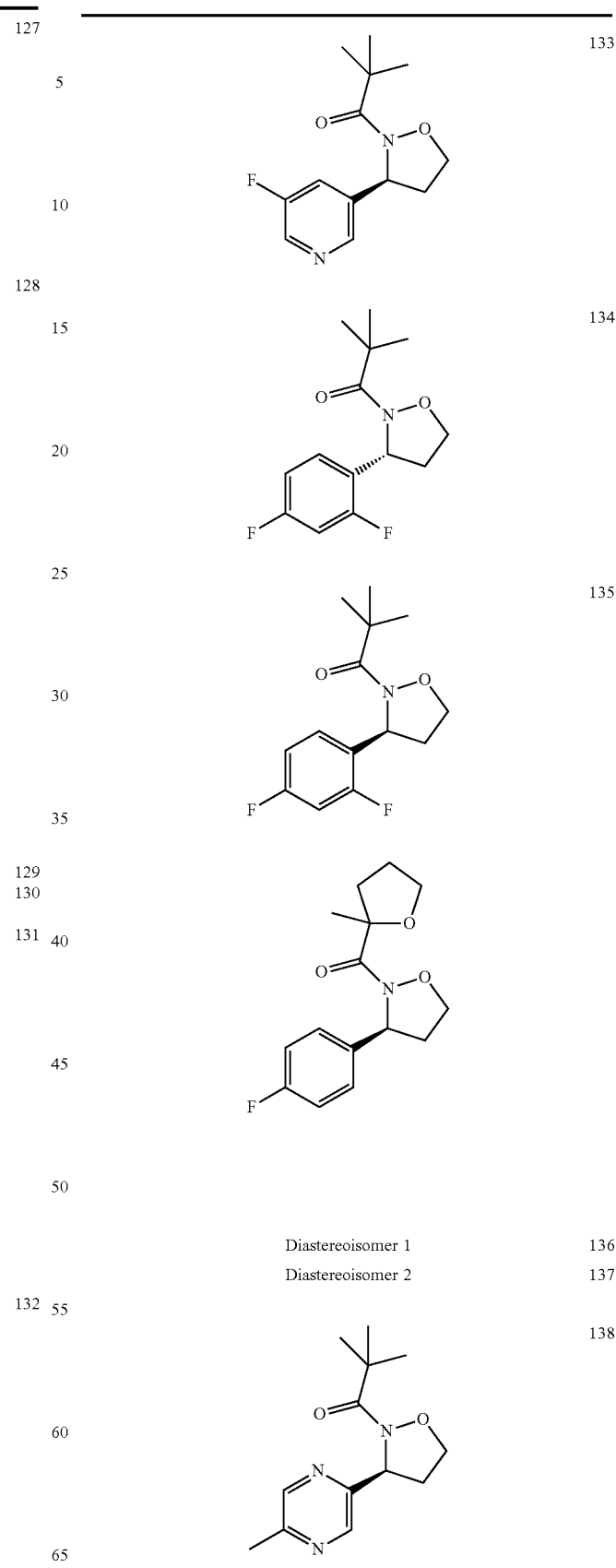

TABLE 1B-continued
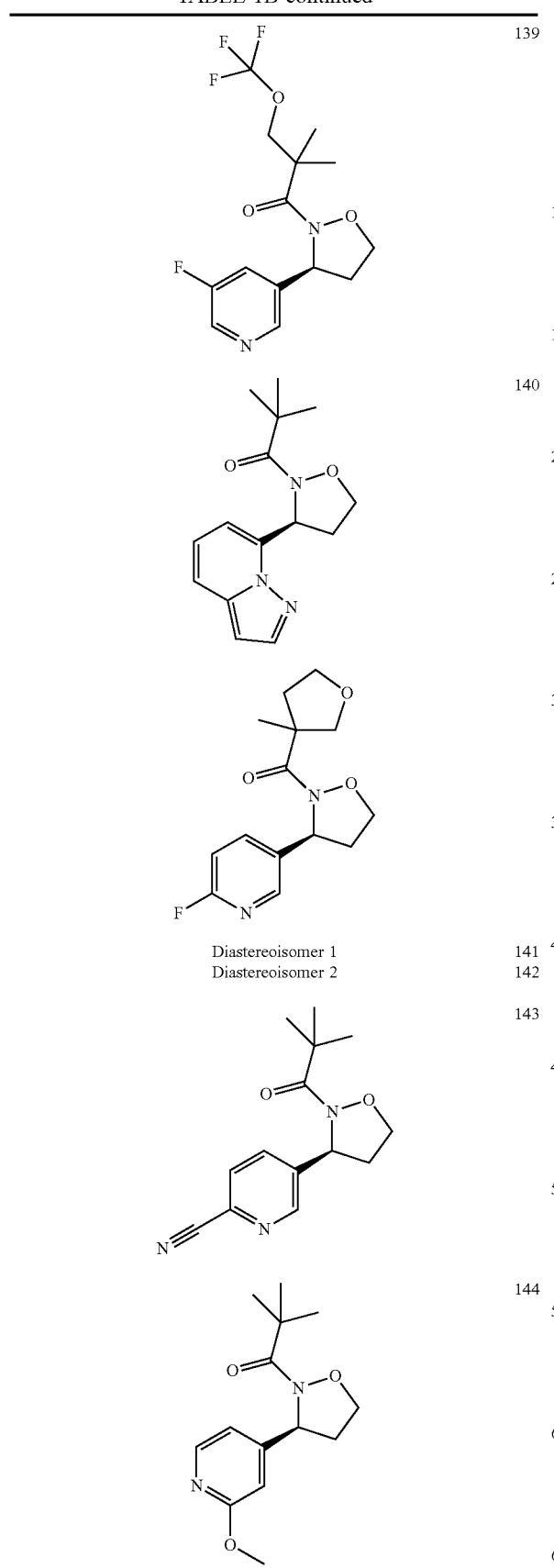
| | |
|---|---|
| 139 | |
| 140 | |
| Diastereoisomer 1 | 141 |
| Diastereoisomer 2 | 142 |
| 143 | |
| 144 | |
TABLE 1B-continued
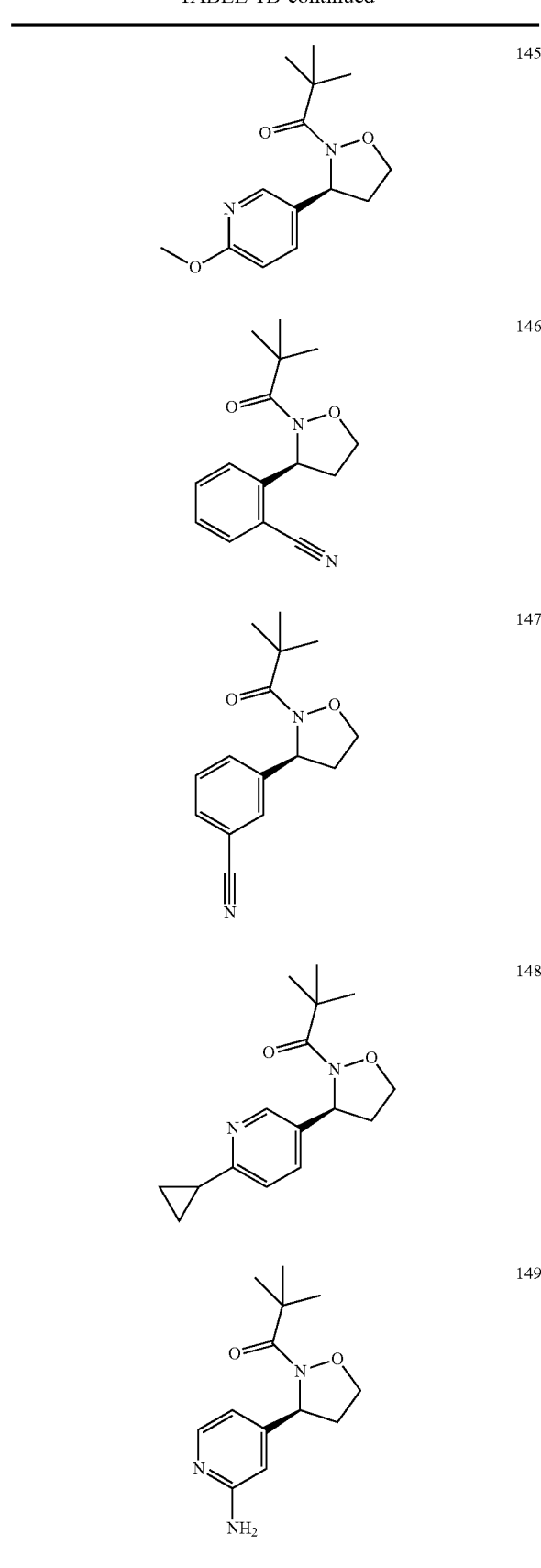
| | |
|---|---|
| 145 | |
| 146 | |
| 147 | |
| 148 | |
| 149 | |

TABLE 1B-continued
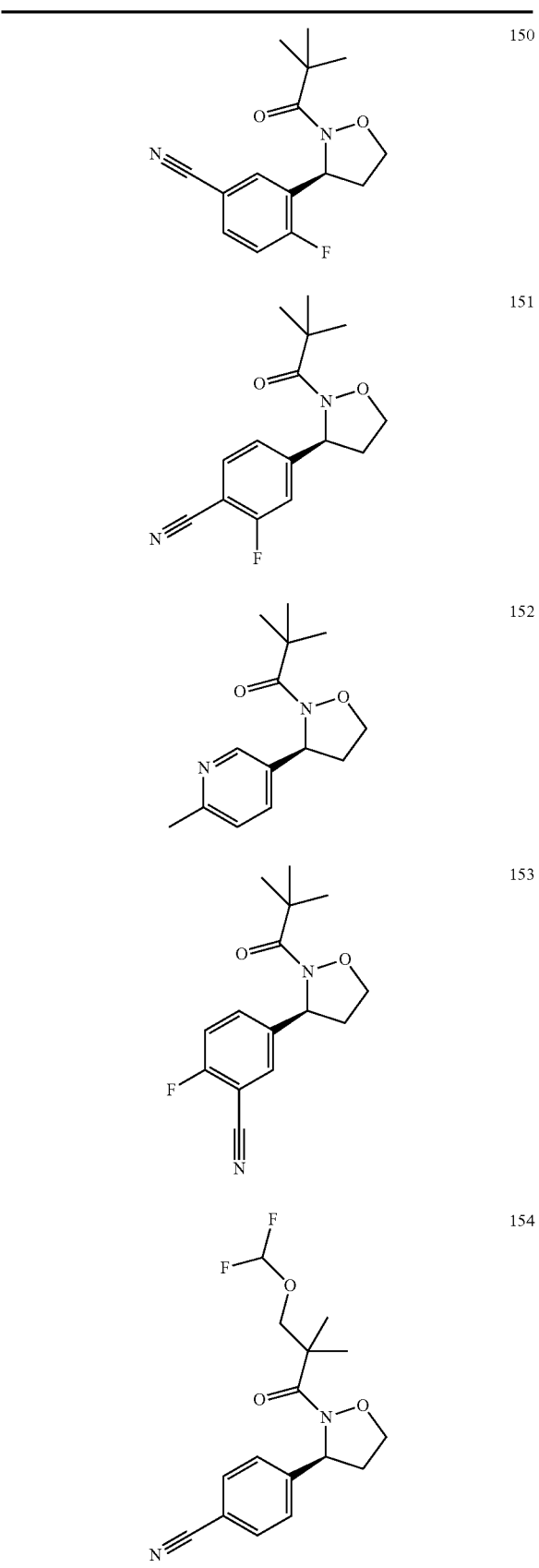
150
151
152
153
154
TABLE 1B-continued
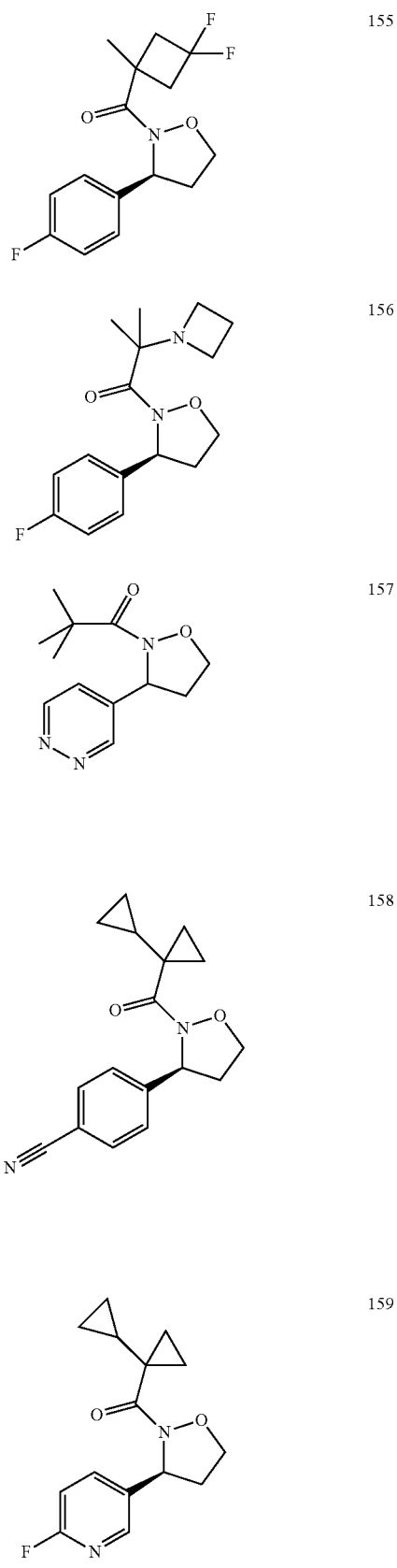
155
156
157
158
159

TABLE 1B-continued
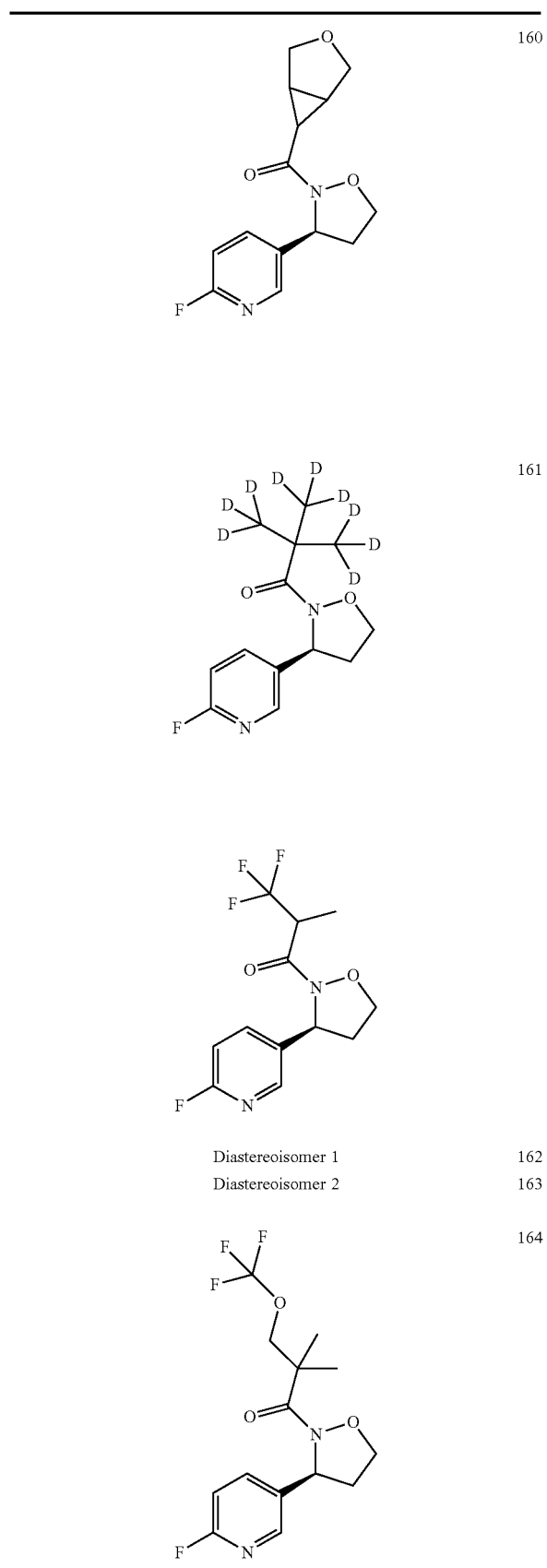
| | |
|---|---|
| | 160 |
| | 161 |
| Diastereoisomer 1 | 162 |
| Diastereoisomer 2 | 163 |
| | 164 |
TABLE 1B-continued
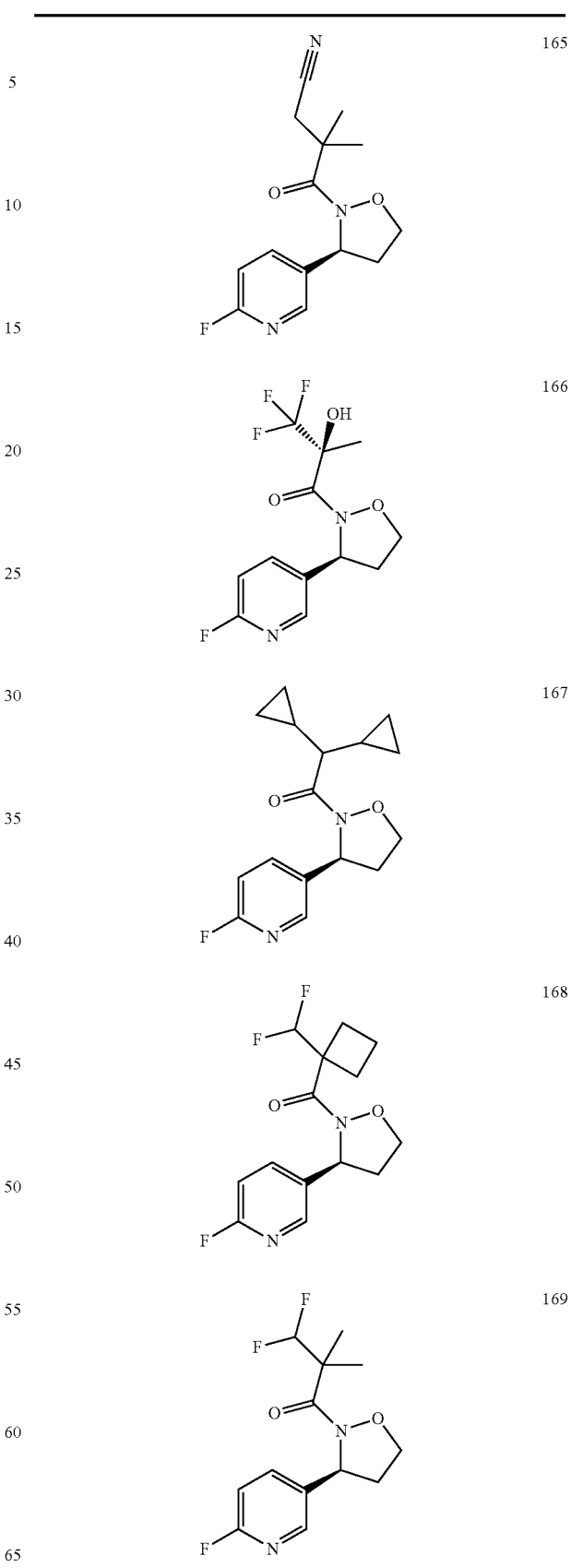
| | |
|---|---|
| | 165 |
| | 166 |
| | 167 |
| | 168 |
| | 169 |

TABLE 1B-continued
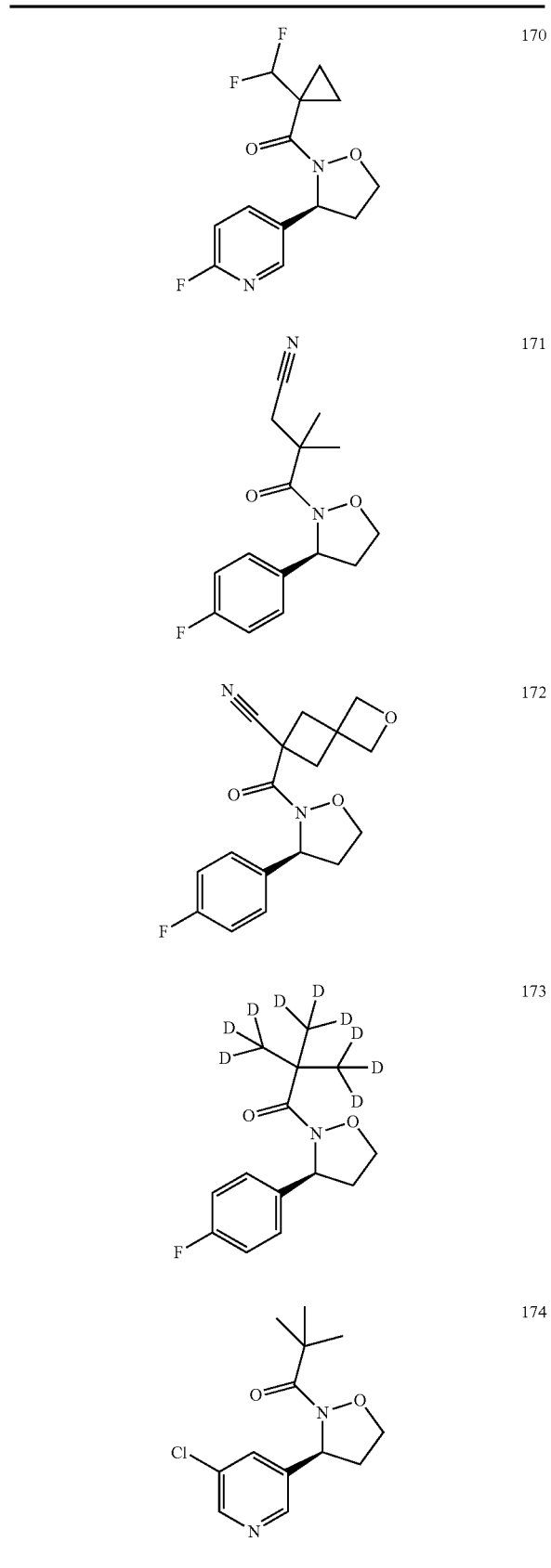
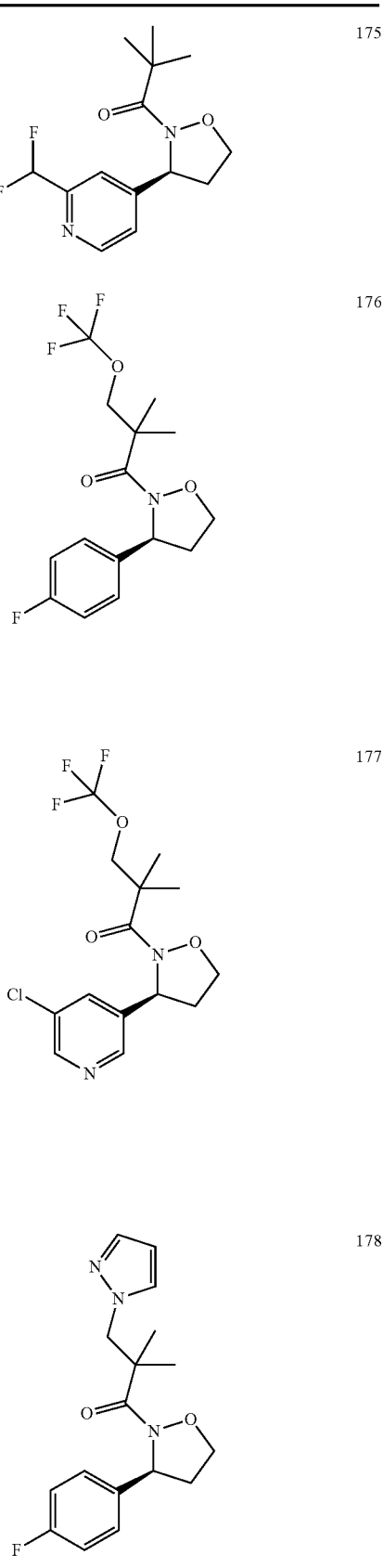

TABLE 1B-continued
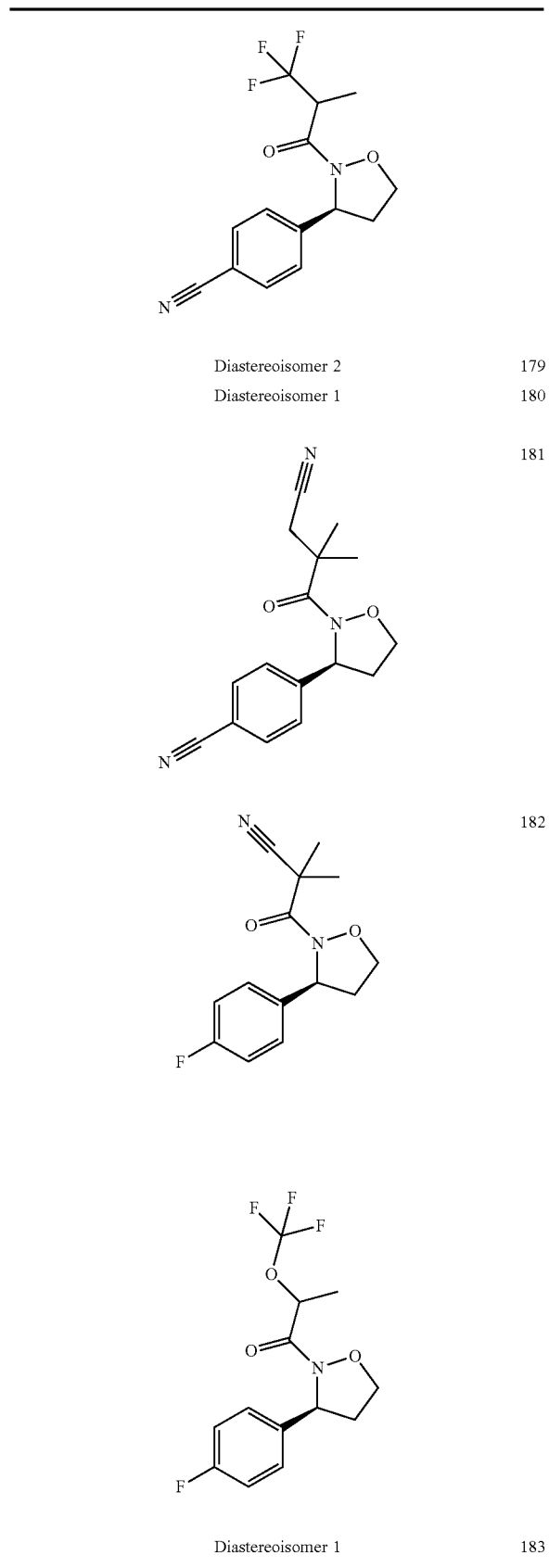
| | |
|---|---|
| Diastereoisomer 2 | 179 |
| Diastereoisomer 1 | 180 |
| | 181 |
| | 182 |
| Diastereoisomer 1 | 183 |
TABLE 1B-continued
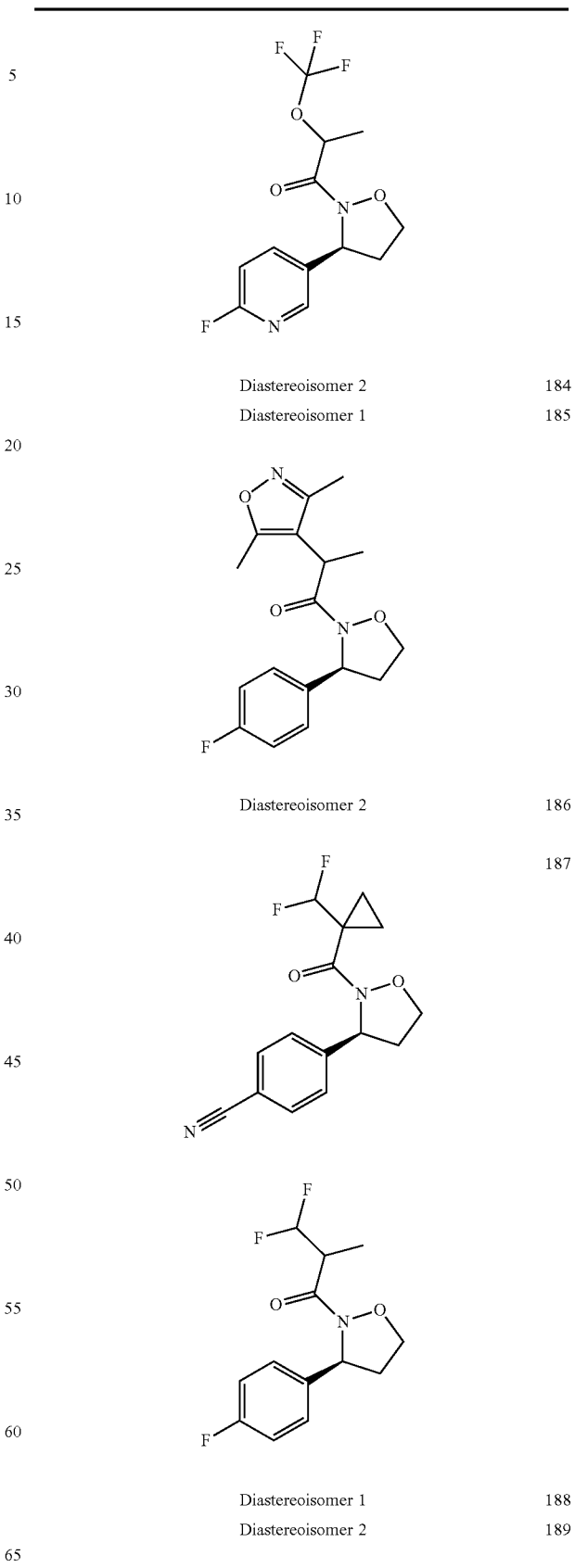
| | |
|---|---|
| Diastereoisomer 2 | 184 |
| Diastereoisomer 1 | 185 |
| | 186 |
| | 187 |
| Diastereoisomer 1 | 188 |
| Diastereoisomer 2 | 189 |

TABLE 1B-continued
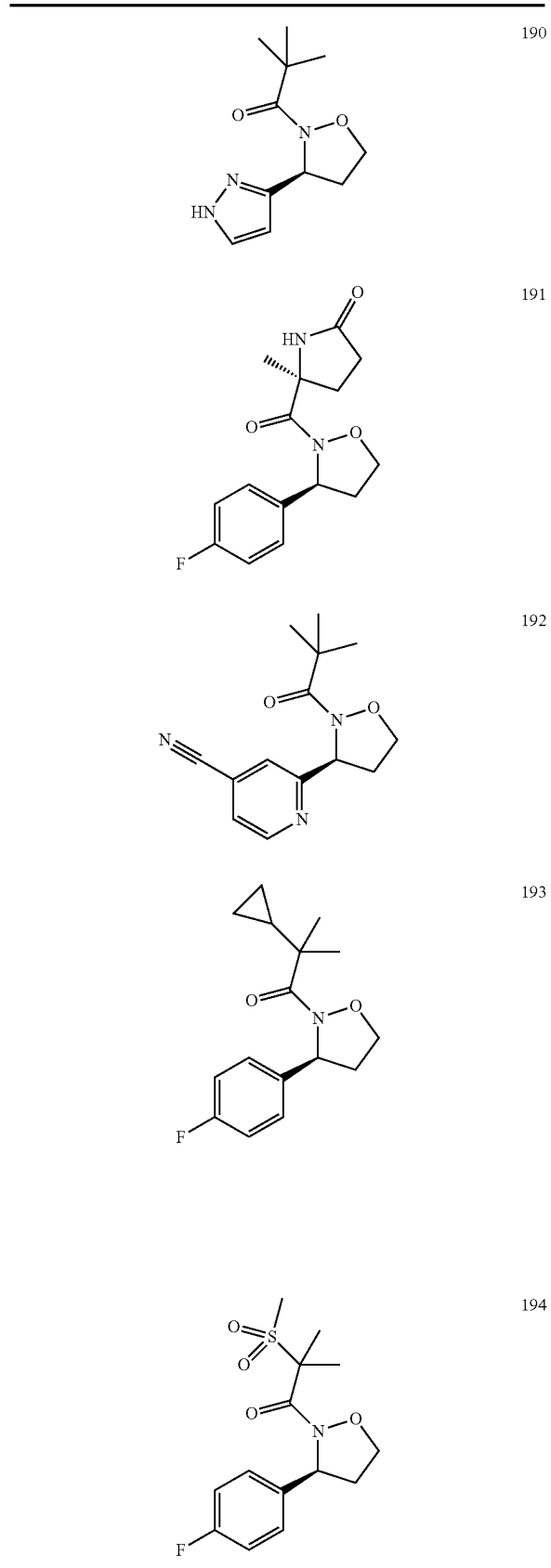
190
191
192
193
194
TABLE 1B-continued
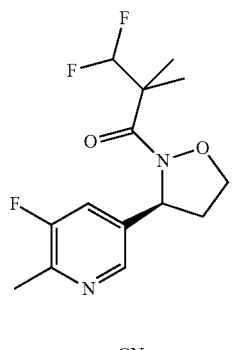
195
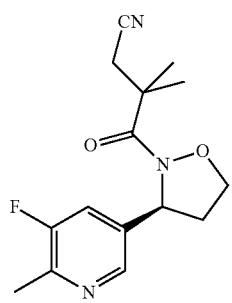 [SMILES: Cc1ncc([C@@H]2CCON2C(=O)C(C)(C)CC#N)cc1F]
196
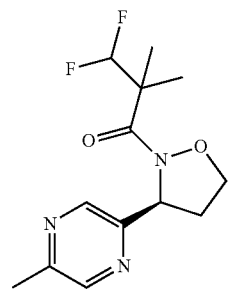 [SMILES: Cc1cnc([C@@H]2CCON2C(=O)C(C)(C)C(F)F)cn1]
197
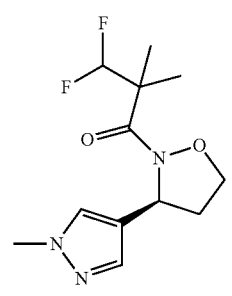 [SMILES: Cn1cc([C@@H]2CCON2C(=O)C(C)(C)C(F)F)cn1]
198
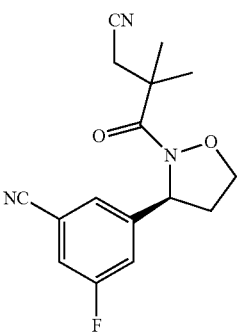 [SMILES: CC(C)(CC#N)C(=O)N1OCC[C@H]1c1cc(F)cc(C#N)c1]
199

TABLE 1B-continued
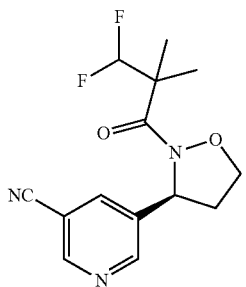 [SMILES: CC(C)(C(=O)N1OCC[C@H]1c1cncc(C#N)c1)C(F)F]
200
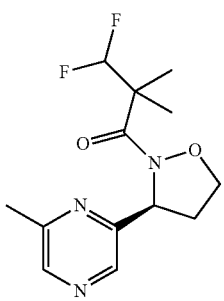 [SMILES: Cc1cncc([C@@H]2CCON2C(=O)C(C)(C)C(F)F)n1]
201
TABLE 1C
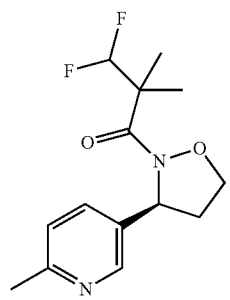 [SMILES: Cc1ccc([C@@H]2CCON2C(=O)C(C)(C)C(F)F)cn1]
202
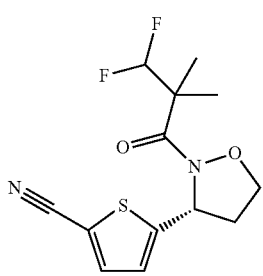 [SMILES: CC(C)(C(=O)N1OCC[C@@H]1c1ccc(C#N)s1)C(F)F]
203
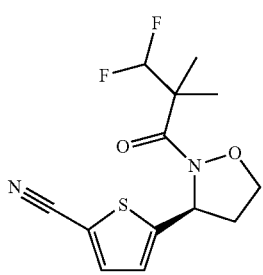 [SMILES: CC(C)(C(=O)N1OCC[C@H]1c1ccc(C#N)s1)C(F)F]
204
TABLE 1C-continued
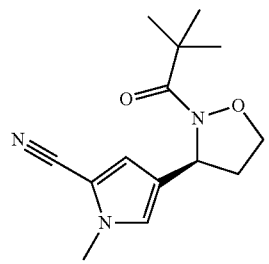 [SMILES: Cn1cc([C@@H]2CCON2C(=O)C(C)(C)C)cc1C#N]
205
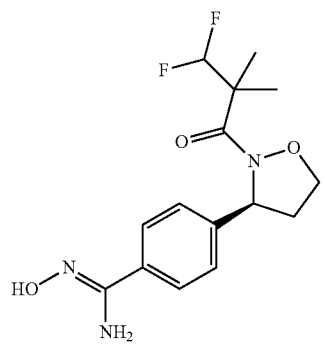 [SMILES: CC(C)(C(=O)N1OCC[C@H]1c1ccc(/C(N)=N/O)cc1)C(F)F]
206
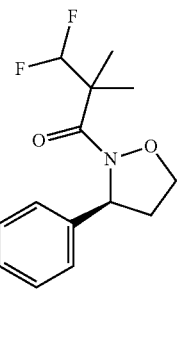
207
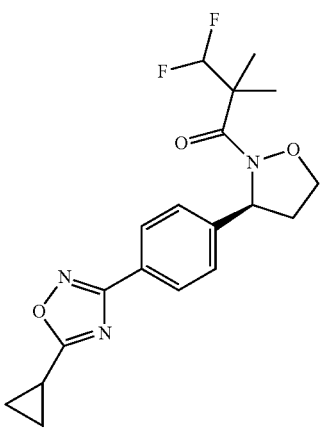 [SMILES: CC(C)(C(=O)N1OCC[C@H]1c1ccc(-c2noc(C3CC3)n2)cc1)C(F)F]
208
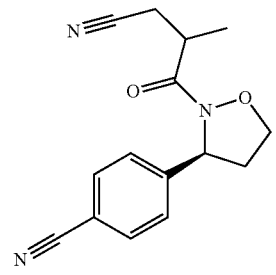 [SMILES: CC(CC#N)C(=O)N1OCC[C@H]1c1ccc(C#N)cc1]

TABLE 1C-continued
| | |
|---|---|
| Diastereoisomer 1 | 209 |
| Diastereoisomer 2 | 210 |
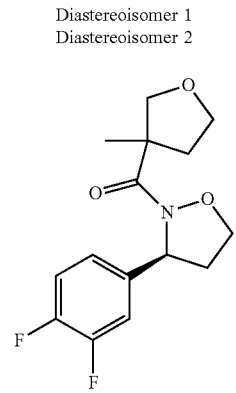
| | |
|---|---|
| Diastereoisomer 1 | 211 |
| Diastereoisomer 2 | 212 |
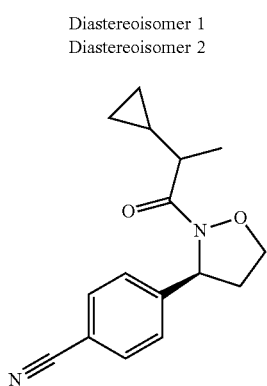
| | |
|---|---|
| Diastereoisomer 1 | 213 |
| Diastereoisomer 2 | 214 |
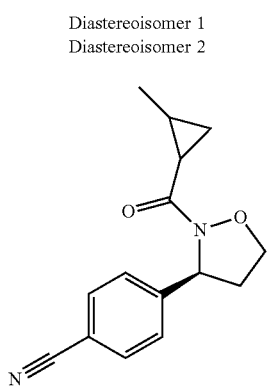
| | |
|---|---|
| Diastereoisomer 1 | 215 |
| Diastereoisomer 2 | 216 |
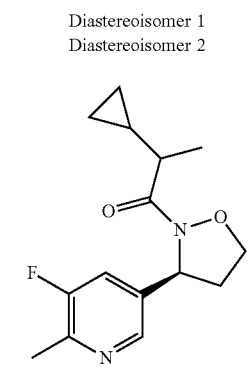
| | |
|---|---|
| Diastereoisomer 1 | 217 |
| Diastereoisomer 2 | 218 |
TABLE 1C-continued
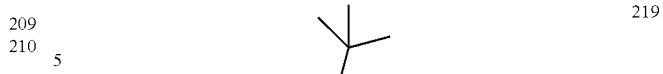
219
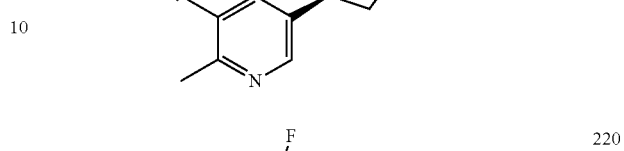
220
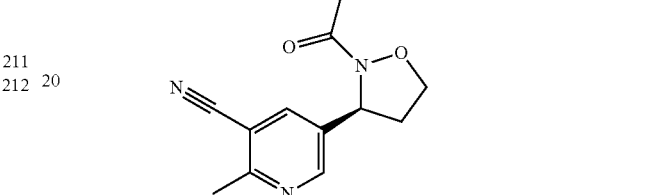
221
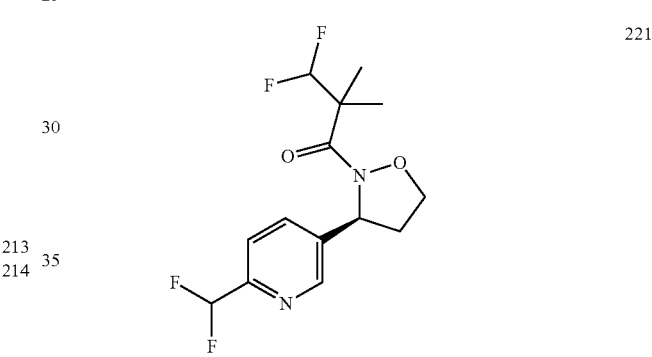
222
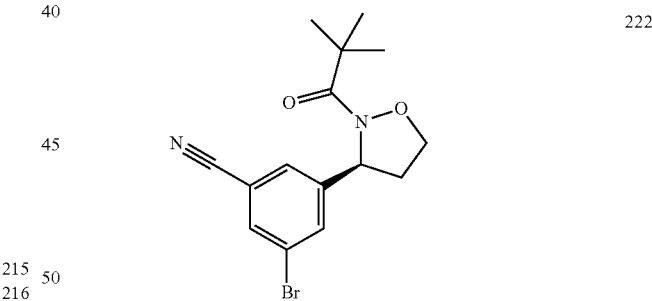
223
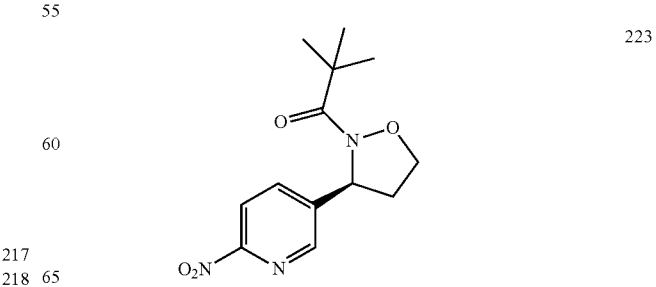

TABLE 1C-continued
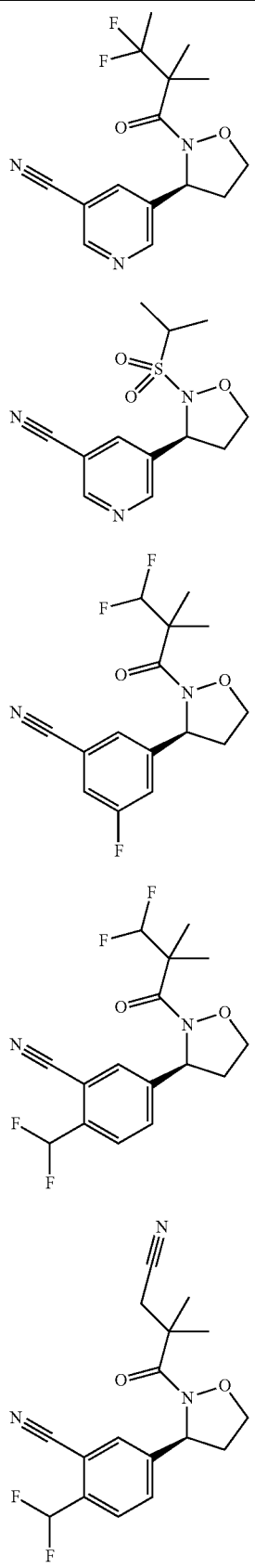
| | |
|---|---|
| | 224 |
| | 225 |
| | 226 |
| | 227 |
| | 228 |
TABLE 1C-continued
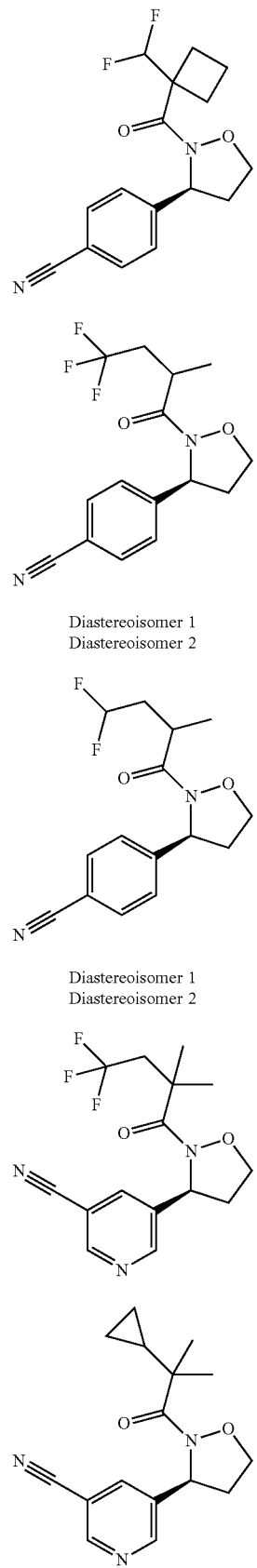
| | |
|---|---|
| | 229 |
| Diastereoisomer 1 | 230 |
| Diastereoisomer 2 | 231 |
| Diastereoisomer 1 | 232 |
| Diastereoisomer 2 | 233 |
| | 234 |
| | 235 |

TABLE 1C-continued
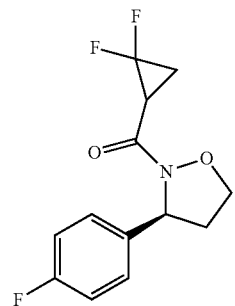 [SMILES: O=C(C1CC1(F)F)N1OCC[C@H]1c1ccc(F)cc1]
236 Diastereoisomer 1
237 Diastereoisomer 2
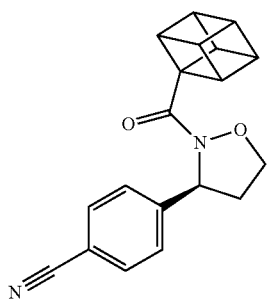 [SMILES: N#Cc1ccc([C@@H]2CCON2C(=O)C23C4C5C6C4C2C6C53)cc1] 238
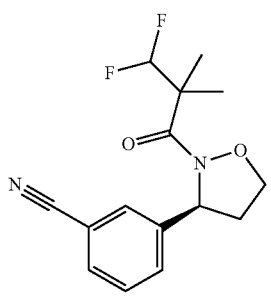 239
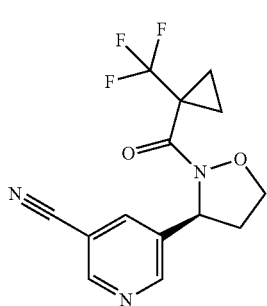 [SMILES: N#Cc1cncc([C@@H]2CCON2C(=O)C2(C(F)(F)F)CC2)c1] 240
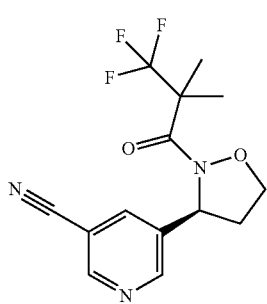 241
TABLE 1C-continued
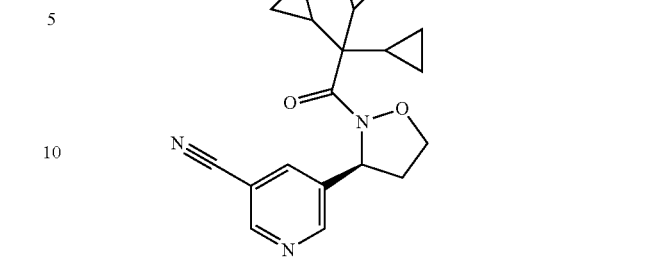 242
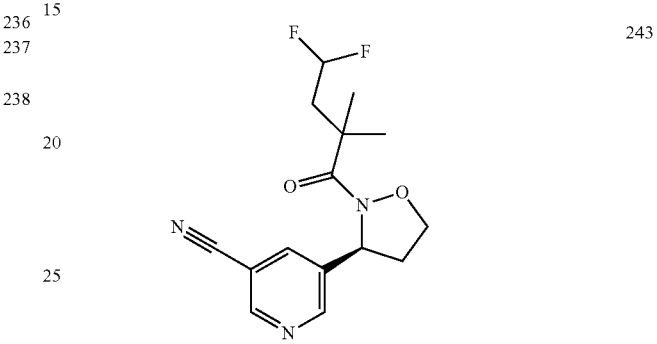 243
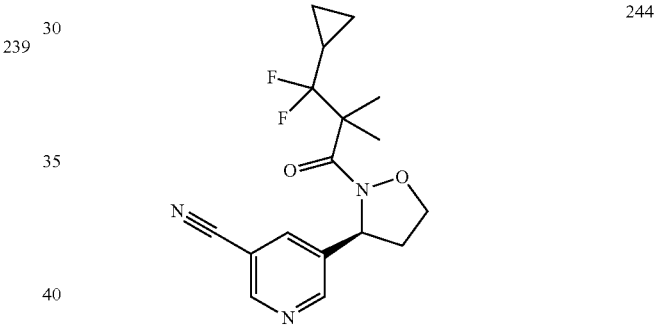 244
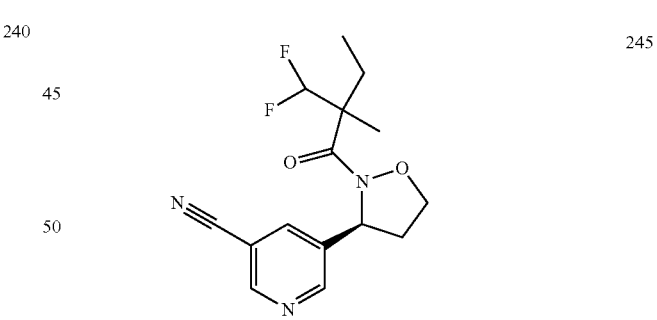 245
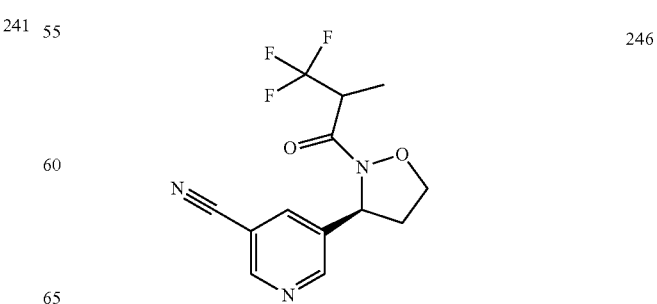 246

TABLE 1C-continued

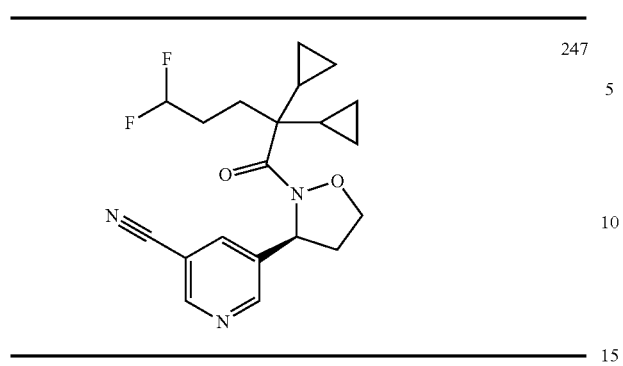

247

In certain embodiments, the compound of any structure or formula provided herein is provided in the form of a pharmaceutically acceptable salt. Exemplary salts for this purpose are described herein.

In certain embodiments, the disclosure provides a prodrug which converts to a compound of any structure provided herein in vivo. Exemplary prodrugs for this purpose are known in the art and described herein.

Enantiomerically enriched compositions of the compounds disclosed herein are also provided. In certain embodiments, the enantiomeric ratio of the composition is greater than 50:50. In certain embodiments, the enantiomeric ratio is calculated only with respect to a single stereocenter (e.g., $R^2$) without regard to other stereocenters which may be present on the molecule. In certain embodiments, die composition comprises a single enantiomer of the compound and is substantially free (i.e., having less than or about 40%, 30%, 25%, 20%, 15%, 10%, 5%, 1%, 0.05%, or 0.01%) of the other enantiomer (or diastereomers).

3. General Synthesis

In certain embodiments, provided is a method of preparing a compound of structure (X), comprising coupling a compound of formula (A-1):

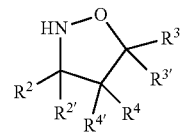

(A-1)

with a compound of formula (B-1):

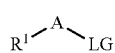

(B-1)

under conditions to provide the compound of structure (X), wherein A, $R^1$, $R^2$, $R^3$. $R^{3'}$, and $R^4$ are as defined herein and LG is a leaving group.

In certain embodiments, provided is a method of preparing a compound of structure (Xa), comprising coupling a compound of formula (A-2):

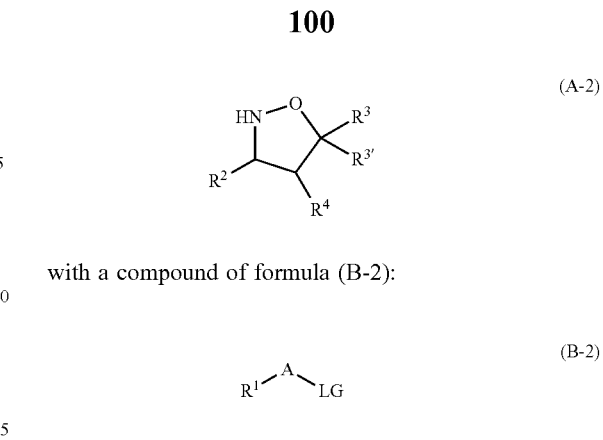

(A-2)

with a compound of formula (B-2):

(B-2)

$R^1 \diagup^A \diagdown LG$ under conditions to provide the compound of structure (Xa), wherein A, $R^1$, $R^2$, $R^3$, $R^{3'}$, and $R^4$ are as defined herein and LG is a leaving group.

The following General Reaction Scheme I further illustrates a method of making compounds of formula (I). Other methods for preparing compounds of structure (I) and related intermediates are provided in the Examples and/or known in the art. It is understood that one skilled in the art may be able to make these compounds by similar methods or by combining other methods known to one skilled in the art. In general, starting components and reagents may be obtained from sources such as Sigma Aldrich, Lancaster Synthesis, Inc., Maybridge, Matrix Scientific, TCI and Fluorochem USA, etc. or synthesized according to sources known to those skilled in the art (see, for example, Advanced Organic Chemistry: Reactions, Mechanisms and Structure, 5th edition (Wiley, December 2000)) or prepared as described in this disclosure.

Scheme I

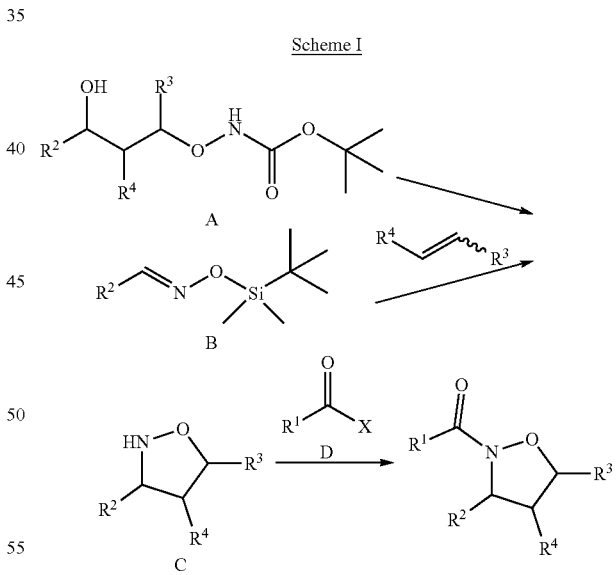

Referring to General Reaction Scheme 1, compounds of structure (I), wherein $R^1$ and $R^2$ are as defined herein and A is —(C═O)—, may be prepared from compound A or B. Appropriate compounds of structure A or B can be prepared according to the more specific methods described in the Examples which follow or by methods known to one of skill in the art. Treatment of compound A with an activating agent, such as methanesulfonyl chloride, followed by removal of the Boc protecting group under acidic conditions, results in oxazolidine C. Alternatively, compound C may be obtained by treatment of B with an appropriately substituted alkylene (e.g., ethylene gas) and an appropriate Lewis acid (e.g., $BF_3$). Treatment of C with an appropriate carbonyl compound (i.e., compound D, wherein X is halo or OH) under amide coupling conditions yields the desired product. It should be noted that although General Reaction Scheme 1 depicts an embodiment wherein A is —C(=O)—, other compounds of structure (I) wherein A is —S(=O)—, —S(=O)$_2$— or —S(=O)(=NH)— can be made via analogous procedures by substituting compound D with an appropriate sulfur-based analogue.

When enantiomerically pure or enriched compounds are desired, chiral chromatography and/or enantiomerially pure or enriched starting materials (e.g., compound A) may be used as described in the Examples It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl and the like. Suitable protecting groups for amino, amidino and guanidino include t-butoxycarbonyl, benzyloxycarbonyl and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". All prodrugs of compounds of this disclosure are included within the scope of the disclosure. Further, the above general scheme can be applied to any other structure or compound as described herein.

Furthermore, all compounds of structure (I) or any other structure or compound as described herein which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

4. Methods of Treatment

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition and/or diminishing the extent of the disease or condition); b) slowing or arresting die development of one or more clinical symptoms associated with the disease or condition (e.g., stabilizing the disease or condition, preventing or delaying the worsening or progression of the disease or condition and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in certain embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In certain embodiments, tire subject is a mammal. In certain embodiments, the subject is a human.

The term "therapeutically effective amount" or "effective amount" of a compound described herein or a pharmaceutically acceptable salt, tautomer, stereoisomer, mixture of stereoisomers, prodrug or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject and disease or condition being treated, the weight and age of the subject, the severity of the disease or condition and the manner of administering, which can readily be determined by one of ordinary skill in the art.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Experiments with knockout animal models and Necrostatin 1, a receptor interacting protein kinase 1 inhibitor, have demonstrated the effectiveness of receptor interacting protein kinase 1 inhibition in protecting tissues from inflammatory bowel diseases (e.g., ulcerative colitis and Crohn's disease), psoriasis, retinal-detachment-induced photoreceptor necrosis, retinitis pigmentosa, cerolein-induced acute pancreatits and sepsis/systemic inflammatory response syndrome (SIRS) and alleviating ischemic brain injury, retinal ischemia/reperfusion injury, Huntington's disease, renal ischemia reperfusion injury, cisplatin induced kidney injury, traumatic brain injury, hematological and solid organ malignancies, bacterial infections and viral infections (e.g., tuberculosis and influenza) and lysosomal storage diseases.

The receptor interacting protein kinase 1 inhibitors of the present disclosure are therefore useful for treating diseases and conditions mediated by receptor interacting protein kinase 1, including but not limited to inflammatory diseases or disorders, necrotic cell diseases, neurodegenerative diseases, central nerve system (CNS) diseases, ocular diseases, infections and malignancies. In certain embodiments, the receptor interacting protein kinase 1 inhibitors described herein can inhibit inflammation, protect tissue or cell from damage or undesired cell death (e.g., necrosis or apoptosis), ameliorate symptoms and improve immune response in a patient suffering from any of the prescribed diseases or conditions. Moreover, the compounds may be suitable for treatment of immune-mediated disease, such as but not limited to, allergic diseases, autoimmune diseases and prevention of transplant rejection.

Necrotic Cell Diseases

The compounds described herein may be used for the treatment of diseases/disorders caused or otherwise associated with cellular necrosis. In particular, the disclosure provides methods for preventing or treating a disorder associated with cellular necrosis in a mammal, comprising the step of administering to said mammal a therapeutically effective amount of a compound or composition described herein. The term "necrotic cell disease" refers to diseases associated with or caused by cellular necrosis, for example trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis or inflammatory bowel disease.

The necrotic cell diseases can be acute diseases such as trauma, ischemia, stroke, cardiac infarction, anthrax lethal toxin induced septic shock, sepsis, cell death induced by LPS and HIV induced T-cell death leading to immunodeficiency. In certain embodiments the disorder is an ischemic disease of organs including but not limited to brain, heart, kidney and liver.

The necrotic cell diseases also include chronic neurodegenerative diseases, such as Parkinson's disease, Huntington's disease, amyotrophic lateral sclerosis, Alzheimer's disease, infectious encelopathies, dementia such as HIV associated dementia.

In some different embodiments, the disorder is an ocular disorder such as retinal degenerative disease, glaucoma or age-related macular degeneration. In some different embodiments, the disorder is a central nervous system (CNS) disorder.

Inflammatory Diseases or Disorders

The receptor interacting protein kinase 1 inhibitors described herein may be used to treat inflammatory diseases and disorders. Inflammatory diseases and disorders typically exhibit high levels of inflammation in the connective tissues or degeneration of these tissues.

Non-limiting examples of inflammatory diseases and disorders include Alzheimer's disease, ankylosing spondylitis, arthritis including osteoarthritis, rheumatoid arthritis (RA), psoriasis, asthma, atherosclerosis, Crohn's disease, colitis, dermatitis, diverticulitis, fibromyalgia, hepatitis, irritable bowel syndrome (IBS), inflammatory bowel disease (IBD), systemic lupus erythematous (SLE), nephritis, Parkinson's disease and ulcerative colitis. In certain embodiments, the compounds and compositions of the present disclosure are useful for treating an autoimmune disorder, such as rheumatoid arthritis, psoriasis, psoriatic arthritis, encephalitis, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, sarcoidosis, scleroderma, and systemic lupus erythematosus. In an embodiment, the receptor interacting protein kinase 1 inhibitors described herein are useful for treating autoimmune encephalitis.

In certain embodiments, the compounds and compositions are useful for treating rheumatoid arthritis (RA). In certain embodiments, the compounds and compositions are useful for treating ulcerative colitis. In certain embodiments, the compounds and compositions are useful for treating psoriasis.

In certain embodiments, the disorder is an inflammatory disease of the intestines such as Crohn's disease or ulcerative colitis (both generally known together as inflammatory bowel disease). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity. Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

Ocular Conditions

The receptor interacting protein kinase 1 inhibitors described herein can also be used to treat ocular conditions, for example to reduce or prevent the loss of photoreceptor and/or retinal pigment epithelial cell viability.

In one aspect, the disclosure provides a method of preserving the visual function of an eye of a subject with an ocular condition, wherein a symptom of the ocular condition is the loss of photoreceptor cell viability in the retina of the eye with the condition. The method comprises administering to the eye of the subject an effective amount of a compound or composition described herein, thereby preserving the viability of the photoreceptor cells disposed within the retina of the eye. After administration, the visual function (e.g., visual acuity) of the eye may be preserved or improved relative to the visual function of the eye prior to administration.

The ocular condition may be a condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. AMD may be the neovascular or the dry form of AMD. Retinal detachment may be a rhegmatogenous, a serous or a tractional retinal detachment.

In another aspect, the disclosure provides a method of preserving the viability of retinal pigment epithelial (RPE) cells within the retina of a subject with an ocular condition, wherein a symptom of the ocular condition is the loss of retinal pigment epithelial cells in the retina of the eye with the condition. The method comprises administering to the eye of the subject an effective amount of a compound or composition described herein, thereby preserving the viability of the retinal pigment epithelial cells. The ocular condition may be selected from the group consisting of AMD, BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE) and other uveitis disorders.

The ocular condition may be a condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. Therefore, in certain embodiments, the method comprises administering to the eye an effective amount of a compound or composition described herein, thereby preserving the viability of the photoreceptor cells disposed within the retina of the subject with a condition.

In another aspect, the disclosure provides a method of preserving the viability of photoreceptor cells disposed within a retina of a mammalian eye following retinal detachment. The method comprises administering a compound or composition described herein to the eye in which a region of the retina has been detached in amounts sufficient to preserve the viability of photoreceptor cells disposed within the region of the detached retina.

In certain embodiments, the retinal detachment may be a rhegmatogenous retinal detachment, tractional retinal detachment or serous retinal detachment. In certain embodiments, the retinal detachment may occur as a result of a retinal tear, retinoblastoma, melanoma or other cancers, diabetic retinopathy, uveitis, choroidal neovascularization, retinal ischemia, pathologic myopia or trauma.

In another aspect, the disclosure provides a method of preserving visual function of an eye of a subject with an ocular condition selected from the group consisting of AMD. RP, macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy. North Carolina dystrophy, infectious retinitis, inflammatory retinitis, uveitis, toxic retinitis and light-induced toxicity, wherein a symptom of the ocular condition is the loss of photoreceptor cells viability in the retina of the eye, wherein the method comprises treating the subject with a compound or composition described herein to the subject.

In another aspect, the disclosure provides a method of preserving the visual function of an eye of a subject with an ocular condition, wherein a symptom of the ocular condition is the loss of photoreceptor cell viability and/or RPE viability in the retina of the eye wherein the method comprises treating the subject with a compound or composition described herein to the subject.

In certain embodiments is provided a method of preserving the visual function of an eye of a subject with ocular conditions, wherein a symptom of the ocular condition is the loss of retinal ganglion cell viability in the retina of the eye with the conditions. The method comprises administering to the eye of the subject an effective amount of a compound or composition, thereby preserving the viability of the retinal ganglion cells disposed within the retina of the eye. After administration of the compound or composition, the visual function of the eye may be preserved or improved relative to the visual function of the eye prior to administration. Further, after the administration, the preserved retinal ganglion cell is capable of supporting axonal regeneration.

In each of the foregoing methods, the ocular condition, wherein a symptom of the condition is the loss of retinal ganglion cell viability in the retina of the eye, includes but is not limited to glaucoma, optic nerve injury, optic neuritis, optic neuropathies, diabetic retinopathy, central retinal artery occlusion and central retinal vein occlusion. It is contemplated that the forgoing methods may be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy and hereditary optic neuropathy (e.g., Leber's optic neuropathy. Dominant Optic Atrophy, Behr's syndrome).

Also disclosed is a method of preserving the visual function of an eye of a subject with an ocular condition selected from the group consisting of glaucoma, optic nerve injury, optic neuropathies, diabetic retinopathy, central retinal artery occlusion and central retinal vein occlusion. The method comprises administering to the eye of the subject an effective amount of a compound or composition described herein, thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion and central retinal vein occlusion. The method comprises administering a compound or composition described herein to the eye in which a region of the retina has been affected in amounts sufficient to preserve the viability of retinal ganglion cells disposed within the region of the affected retina. The preserved retinal ganglion cell is capable of supporting axonal regeneration.

Also disclosed is a method for promoting axon regeneration in an eye of a subject with an ocular condition, wherein a symptom of the ocular condition is the loss of retinal ganglion cell viability in the retina of the eye with the condition. The method comprises administering to the eye of the subject an effective amount of a compound or composition described herein, thereby promoting axon regeneration of the retinal ganglion cell within the retina of the eye.

In each of the foregoing embodiments, it is understood that the methods and compositions described herein can be used to preserve the viability and/or promote axon regeneration of retinal ganglion cells during treatment of the underlying conditions including, but not limited to, glaucoma, optic nerve injury, optic neuritis, optic neuropathies, diabetic retinopathy, central retinal artery occlusion and central retinal vein occlusion.

Neurodegenerative and CNS Diseases

The receptor interacting protein kinase 1 inhibitors described herein may also be used to treat neurodegenerative diseases. Neurodegenerative diseases can affect many of the body's activities, such as balance, movement, talking, breathing and heart function. Neurodegenerative diseases can be genetic or caused by medical conditions such as alcoholism, tumors, strokes, toxins, chemicals and viruses.

Non-limiting examples of neurodegenerative diseases and CNS diseases include Niemann-Pick disease, type C1 (NPC1), Alzheimer's disease, amyotrophic lateral sclerosis (ALS), Friedreich's ataxia, Huntington's disease, Lewy body disease, Parkinson's disease and spinal muscular atrophy.

In an embodiment the receptor interacting protein kinase 1 inhibitors described herein may be used to treat NPC1 via inhibiting necroptosis that causes neuronal loss. In certain embodiments, tire compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS).

More generally, the receptor interacting protein kinase 1 inhibitors described herein can be used to preserve neuron viability and promote axon growth and nerve functions within the central nervous system (CNS). Accordingly, the compounds may be used to reduce or even reverse the loss of cognitive, motor and sensory functions associated with a CNS disease or disorder, by preserving neuron viability and/or promoting axon regeneration and/or nerve functions.

The receptor interacting protein kinase 1 inhibitors described herein can be used in a method for promoting axon regeneration in a CNS neuron, such as a CNS sensory neuron, a motor neuron, a cortical neuron, a cerebellar neuron, a hippocampal neuron and a midbrain neuron. The receptor interacting protein kinase 1 inhibitors described herein can be used in a method for promoting nerve function or preserving the viability following injury to a CNS neuron. In certain embodiments, these compounds can be used to promote regeneration of an axon in a CNS neuron that is degenerated in the CNS disease or disorder. The receptor interacting protein kinase 1 inhibitors may be administered by any conventional means, such as locally to the neuron or applied ex vivo before re-implantation.

Accordingly, in one aspect, the disclosure provides a method of treating a CNS disorder in a subject in need thereof, wherein a symptom of the CNS disorder is axon degeneration or injury within a CNS neuron. The method comprises administering to the subject an effective amount of a compound or composition disclosed herein thereby to promote regeneration of an axon in a CNS neuron affected by the CNS disorder. Following administration, neural functions may be measured, for example, as an indication of axon regeneration. It is also contemplated that, following administration of the compound or composition, the neuron function of the CNS neuron is preserved or improved relative to the neuron function prior to administration.

The CNS disorder includes, but is not limited to, brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabetic neuropathy, polyglutamine (polyQ) diseases, stroke, Fahr disease, Menke's disease, Wilson's disease, cerebral ischemia and a prion disorder. In exemplary embodiments, the CNS disorder is brain injury or spinal cord injury.

Also provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity or other physical injury to the brain or spinal cord) or neurodegenerative CNS disease, wherein a symptom of the disorder is axon degeneration (e.g., Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, prion disorder (e.g., Creutzfeldt-Jakob disease). In certain embodiments, the CNS disorder is brain injury (e.g., traumatic brain injury) or spinal cord injury (e.g., chronic, acute or traumatic spinal cord injury). In certain embodiments, the CNS disorder affects a subject's basic vital life functions such as breathing, heart beat and blood pressure, e.g., an injury to or aneurysm in the brain stem.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy and prion disorders.

In certain embodiments, the CNS disorder affects a subject's movement and/or strength, such as injury to the brain or spinal cord or a neurodegenerative CNS disorder such as Parkinson's disease, frontotemporal dementia, dementia with Lewy bodies, corticobasal degeneration, progress supranuclear palsy. Huntington's disease, multiple system atrophy, amyotrophic lateral sclerosis and hereditary spastic paresis.

In certain embodiments, the CNS disorder affects a subject's coordination, such as brain injury to the cerebellum or a neurodegenerative CNS disorder such as spinocerebellar atrophies, Friedreich's ataxia and prion disorders.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with Lewy bodies), corticobasal degeneration, progressive supranuclear palsy, multiple system atrophy, hereditary spastic paraparesis and spinocerebellar atrophies.

Tissue Injuries or Damages

The ability of the compounds described herein to inhibit inflammation and cell death makes them suitable for ameliorating tissue injuries or damages. The tissue injuries or damages may be a result of any of the diseases or conditions described above. For example, the compounds may be used for amelioration of brain tissue injury or damage following ischemic brain injury or traumatic brain injury- or for amelioration of heart tissue injury- or damage following myocardial infarction or for amelioration of brain tissue injury or damage associated with Huntington's disease, Alzheimer's disease or Parkinson's disease or for amelioration of liver tissue injury- or damage associated with non-alcohol steatohepatitis, alcohol steatohepatitis, autoimmune hepatitis autoimmune hepatobiliary diseases or primary sclerosing cholangitis or for the amelioration of liver tissue injury- or damage associated with overdose of acetaminophen or for amelioration of kidney tissue injury or damage following renal transplant or the administration of nephrotoxic drugs or substances.

Non-limiting examples of brain injury or damage include stroke (e.g., hemorrhagic and non-hemorrhagic), traumatic brain injury (TBI), cerebral hemorrhage, subarachnoid hemorrhage, intracranial hemorrhage secondary- to cerebral arterial malformation, cerebral infarction, perinatal brain injury, non-traumatic brain injury, Alzheimer's disease, Parkinson's disease, Huntington's disease, multiple sclerosis, amyotrophic lateral sclerosis, brain hemorrhage, brain infections, brain tumor, subclinical brain injury, spinal cord injury, anoxic-ischemic brain injury, focal cerebral ischemia, global cerebral ischemia, and hypoxic hypoxia.

In an embodiment, the compounds and compositions of the present disclosure may be used to treat peritoneal tissue injury. Non-limiting examples of peritoneal tissue injury include peritoneal deterioration, peritoneal sclerosis, and peritoneal cancer. For example, the receptor interacting protein kinase 1 inhibitors described herein may be used to treat peritoneal damage caused by peritoneal dialysis fluid (PDF) and PD-related side effects.

Liver Injury and Diseases

In an embodiment, the compounds and compositions of the present disclosure may be used to treat liver injury and diseases. Non-limiting examples of liver injury or damage include not only degeneration or necrosis of liver parenchyma cells which results from injury caused by a certain factor, but also undesirable phenomena caused by biological reactions to the injury, such as mobilization, infiltration, activation of Kupffer cells, leukocytes and the like, fibrosis of the liver tissue, etc., which reactions occur alone or in combination. In an embodiment, the receptor interacting protein kinase 1 inhibitors described herein may be used to treat steatohepatitis and hepatocellular carcinoma via inhibiting receptor interacting protein kinase 1 activity-dependent apoptosis of hepatocytes and hepatocarcinogenesis. In an embodiment, the receptor interacting protein kinase 1 inhibitors described herein may be used to treat acute cholestasis and liver injury.

Kidney Injury and Diseases

In an embodiment, the compounds and compositions of the present disclosure may be used to treat kidney injury and diseases. Non-limiting examples of kidney diseases include chronic kidney disease (CKD) (e.g., glomerular diseases, tubulointerstitial diseases, obstruction, polycystic kidney-disease), acute kidney injury (AKI), diabetic nephropathy, glomerulonephritis, focal glomerulosclerosis, immune complex nephropathy or lupus nephritis. Kidney disease may be caused by drug-induced renal injury or kidney graft rejection. Kidney disease may be characterized as nephrotic syndrome or renal insufficiency. In an embodiment, the receptor interacting protein kinase 1 inhibitors described herein may be used to treat kidney diseases (e.g., AKI) via inhibiting cell death pathway in kidney diseases. In an embodiment, the receptor interacting protein kinase 1 inhibitors described herein may be used to treat patient with kidney stones and to prevent crystal-induced cytotoxicity and acute kidney injury via inhibiting receptor interacting protein kinase 3-MLKL-mediated necroptosis.

Malignancies

In an embodiment, the compounds and compositions of the present disclosure are useful for treating malignancies/cancers such as carcinoma, sarcoma, melanoma, lymphoma or leukemia. Non-limiting examples of malignancies suitably treated by the receptor interacting protein kinase 1 inhibitors described herein include lung cancer (e.g. non-small cell lung cancer, small-cell lung cancer), hepatocellular cancer, melanoma, pancreatic cancer, urological cancer, bladder cancer, colorectal cancer, colon cancer, breast cancer, prostate cancer, renal cancer, thyroid cancer, gall bladder cancer, peritoneal cancer, ovarian cancer, cervical cancer, gastric cancer, endometrial cancer, esophageal cancer, head and neck cancer, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, vulval cancer, cancers of the adrenal cortex, ACTH producing tumors, lymphoma, and leukemia.

Infectious Diseases

In an embodiment the compounds and compositions of the present disclosure are useful for treating infectious diseases resulting from the presence of pathogenic agents, including pathogenic viruses, pathogenic bacteria, fungi, protozoa, multicellular parasites and aberrant proteins known as prions. Non-limiting examples of infectious diseases suitably treated by the receptor interacting protein kinase 1 inhibitors described herein include virus infectious diseases and bacterial infectious diseases. The virus infectious disease is not particularly limited and includes, for example, infectious diseases with respiratory infectious viruses (e.g., infectious diseases due to respiratory infectious viruses such as influenza virus, rhino virus, corona virus, parainfluenza virus, RS virus, adeno virus, reo virus and the like), herpes zoster caused by herpes virus, diarrhea caused by rotavirus, viral hepatitis, AIDS and die like. The bacterial infectious disease is not particularly limited and includes, for example, infectious diseases caused by *Bacillus cereus. Vibrio parahaemolyticus.* Enterohemorrhagic *Escherichia coli, Staphylococcus aureus*, MRSA, *Salmonella, Botulinus, Candida* and the like.

Bone Diseases

In an embodiment, the compounds and compositions of the present disclosure are useful for treating bone diseases that may result from a bone remodeling disorder whereby the balance between bone formation and bone resorption is shifted. Non-limiting examples of bone remodeling disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease. Additional examples of bone diseases suitably treated by the receptor interacting protein kinase 1 inhibitors described herein include bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment. Additional examples of diseases affecting bone or bone joints suitably treated by the receptor interacting protein kinase 1 inhibitors described herein include metastatic bone cancer, rheumatic diseases such as rheumatoid arthritis, osteoarthritis and other inflammatory arthropathies. In an embodiment, the receptor interacting protein kinase 1 inhibitors described herein may be used to treat postmenopausal osteoporosis via inhibiting osteocyte necroptosis and trabecular deterioration.

Cardiovascular Diseases

In an embodiment, the compounds and compositions of the present disclosure are useful for treating cardiovascular diseases that may be relate to the cardiovascular disorders of fragile plaque disorder, occlusive disorder and stenosis. Non-limiting cardiovascular diseases include coronary artery disorders and peripheral arterial disorders, including, among others, atherosclerosis, arterial occlusion, aneurysm formation, thrombosis, post-traumatic aneurysm formation, restenosis, and post-operative graft occlusion. It is believed that atherosclerosis results from maladaptive inflammation driven primarily by macrophages. Thus, the compounds and compositions of the present disclosure may be used to treat atherosclerosis via inhibiting macrophage necroptosis.

Transplantation

In an embodiment the compounds and compositions of the present disclosure are useful for treating transplant patients. Non-limiting examples of transplant patient suitably treated by the receptor interacting protein kinase 1 inhibitors described herein include patients with solid and non-solid organ and tissue transplantations and transplants, such as liver, heart, kidney, and heterologous and autologous bone marrow transplantations/transplants. Typically, immunosuppressive therapy is used to avoid graft rejection in recipients of solid organ transplants. Recipients of bone marrow transplants are usually subjected to extensive irradiation and chemotherapy prior to transplantation. It is believed that receptor interacting protein kinase 1 and NF-κB signaling in dying cells determines cross-priming of CD8$^+$ T cells. Thus, the receptor interacting protein kinase 1 inhibitors described herein may be used to treat transplant patient and avoid graft rejection by modulating cross-priming of CD8$^+$ T cells.

Other Diseases and Conditions

Additional examples of diseases and disorders suitably treated by the receptor interacting protein kinase 1 inhibitors described herein include Gaucher disease, organ failure, pancreatitis, atopic dermatitis, spondyloarthritis, gout, systemic onset juvenile idiopathic arthritis (SoJIA), systemic lupus erythematosus (SLE), Sjogren's syndrome, systemic scleroderma, anti-phospholipid syndrome (APS), vasculitis, primary sclerosing cholangitis (PSC), acetaminophen toxicity, kidney damage/injury (nephritis, renal transplant, surgery, administration of nephrotoxic drugs e.g. cisplatin, acute kidney injury (AKI)), Celiac disease, autoimmune idiopathic thrombocytopenic purpura (autoimmune ITP), cerebrovascular accident (CVA, stroke), myocardial infarction (MI), allergic diseases (including asthma), diabetes, Wegener's granulomatosis, pulmonary sarcoidosis, Behcet's disease, interleukin-1 converting enzyme (ICE/caspase-1) associated fever syndrome, chronic obstructive pulmonary disease (COPD), tumor necrosis factor receptor-associated periodic syndrome (TRAPS), peridontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (e.g., tuberculosis and influenza) and lysosomal storage diseases.

Non-limiting examples of lysosomal storage diseases include Gaucher disease, GM2 Gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs and Wolman disease.

In certain embodiments, provided are compounds and compositions for use in medicine. In certain embodiments, the compounds and compositions are for use in the treatment of a receptor interacting protein kinase 1-mediated disease or disorder. Also provided is a method of treating a receptor interacting protein kinase 1-mediated disease or disorder comprising administering a therapeutically effective amount of a compound or pharmaceutical composition disclosed herein to a subject in need thereof.

5. Compositions

For the purposes of administration, the compounds of the present disclosure may be administered as a raw chemical or may be formulated as pharmaceutical compositions. Pharmaceutical compositions of the present disclosure comprise a compound of structure (I) and a pharmaceutically acceptable carrier, diluent or excipient. Accordingly, different embodiments are directed to pharmaceutical compositions comprising any one or more of the foregoing compounds of structure (I) or a pharmaceutically acceptable salt, prodrug or stereoisomer thereof and a pharmaceutically acceptable carrier, diluent or excipient are also provided in various embodiments.

The pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual and systemic absorption, boluses, powders, granules, pastes for application to the tongue; parenteral administration, for example, by subcutaneous, intramuscular, intravenous or epidural injection as, for example, a sterile solution or suspension or sustained-release formulation; topical application, for example, as a cream, ointment or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions and/or dosage forms which are, within the scope of sound medical judgment suitable for use in contact with the tissues of human beings and animals without excessive toxicity, irritation, allergic response or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient or solvent encapsulating material, involved in carrying or transporting the subject compound from one organ or portion of the body, to another organ or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; surfactants, such as polysorbate 80 (i.e., Tween 80); powdered tragacanth; malt; gelatin; talc; excipients, such as cocoa butter and suppository waxes; oils, such as peanut oil, cottonseed oil, safflower oil, sesame oil, olive oil, corn oil and soybean oil: glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc. For example, in a certain embodiment the compounds of the disclosure can be used as 4 mM solution in 8% hydroxypropyl-beta-cyclodextrin in PBS for parenteral administration. In another certain embodiments, the compounds of the disclosure can be used as a suspension in 0.5% aqueous CMC containing 0.1% TWEEN 80.

As set out herein, certain embodiments of the present compounds may contain a basic functional group, such as amino or methylamino ($NCH_3$) and are, thus, capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present disclosure. These salts can be prepared in situ in the administration vehicle or the dosage form manufacturing process or by separately reacting a purified compound of the disclosure in its free base form with a suitable organic or inorganic acid and isolating the salt thus formed during subsequent purification. Representative salts include tire hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate and laurylsulphonate salts and the like. (See, for example, Berge et al. (1977) "Pharmaceutical Salts", J. Pharm. Sci. 66:1-19.)

The pharmaceutically acceptable salts of the subject compounds include the conventional nontoxic salts or quaternary ammonium salts of the compounds, e.g., from non-toxic organic or inorganic acids. For example, such conventional nontoxic salts include diose derived from inorganic acids such as hydrochloride, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic and die like.

In other cases, the compounds of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process or by separately reacting the purified compound in its free acid form with a suitable base, such as the hydroxide, carbonate or bicarbonate of a pharmaceutically-acceptable metal cation, with ammonia or with a pharmaceutically-acceptable organic primary, secondary or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol and the like; and metal chelating agents, such as citric acid, ethylenediamine tetraacetic acid (EDTA), sorbitol, tartaric acid, phosphoric acid and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in die art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present disclosure comprises an excipient selected from the group consisting of cyclodextrins, liposomes, micelle forming agents, e.g., bile acids and polymeric carriers, e.g., polyesters and polyanhydrides; and a compound of the present disclosure. In certain embodiments, an aforementioned formulation renders orally bioavailable a compound of die present disclosure.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers or finely divided solid carriers or both and then, if necessary, shaping the product.

Formulations of the disclosure suitable for oral administration may be in the form of capsules, cachets, pills, tablets, lozenges (using a flavored basis, usually sucrose and acacia or tragacanth), powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate and/or any of the following: fillers or extenders, such as starches, lactose, sucrose, glucose, mannitol and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates and sodium carbonate; solution retarding agents, such as paraffin; absorption accelerators, such as quaternary ammonium compounds; wetting agents, such as, for example, cetyl alcohol, glycerol monostearate and non-ionic surfactants; absorbents, such as kaolin and bentonite clay; lubricants, such a talc, calcium stearate, magnesium stearate, solid polyethylene glycols, sodium lauryl sulfate and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredients) only or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier and with any preservatives, buffers or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to a compound of this disclosure, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Dissolving or dispersing the compound in the proper medium can make such dosage forms.

Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically-acceptable sterile isotonic aqueous or nonaqueous solutions, dispersions, suspensions or emulsions or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

6. Dosing

The phrases "parenteral administration" and "administered parenterally" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other titan directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present disclosure, which may be used in a suitable hydrated form and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient that is effective to achieve the desired therapeutic response for a particular patient, composition and mode of administration, without being toxic to the patient.

The selected dosage level will depend upon a variety of factors including the activity of the particular compound of the present disclosure employed or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated and like factors well known in the medical arts. A daily, weekly or monthly dosage (or other time interval) can be used.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required to achieve the desired therapeutic effect and then gradually increasing the dosage until the desired effect is achieved.

In general, a suitable daily dose of a compound of the disclosure will be that amount of the compound that is the lowest dose effective to produce a therapeutic effect (e.g., inhibit necrosis). Such an effective dose will generally depend upon the factors described above. Generally doses of the compounds of this disclosure for a patient, when used for the indicated effects, will range from about 0.0001 to about 100 mg per kg of body weight per day. Preferably the daily dosage will range from 0.001 to 50 mg of compound per kg of body weight and even more preferably from 0.01 to 10 mg of compound per kg of body weight.

If desired, the effective daily dose of the active compound may be administered as two, three, four, five, six or more sub-doses administered separately at appropriate intervals throughout the day, optionally, in unit dosage forms.

In certain embodiments, the present disclosure relates to compounds for inhibiting cell death, wherein the compounds are represented by structures (I). In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar and most preferably at a concentration less than 1 micromolar.

The compounds of the disclosure can be tested in standard animal models of stroke and standard protocols such as described by Hara, H., et al. Proc Natl Acad Sci USA, 1997. 94(5): 2007-12.

When the compounds of the present disclosure are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds of the present application or the compositions thereof may be administered once, twice, three or four times daily, using any suitable mode described above. Also, administration or treatment with the compounds may be continued for a number of days; for example, commonly treatment would continue for at least 7 days, 14 days or 28 days, for one cycle of treatment. Treatment cycles are well known and are frequently alternated with resting periods of about 1 to 28 days, commonly about 7 days or about 14 days, between cycles. The treatment cycles, in certain embodiments, may also be continuous.

When administered orally, the total daily dosage for a human subject may be between 1 mg and 1,000 mg, between about 1,000-2,000 mg/day, between about 10-500 mg/day, between about 50-300 mg/day, between about 75-200 mg/day or between about 100-150 mg/day.

The daily dosage may also be described as a total amount of a compound described herein administered per dose or per day. Daily dosage of a compound may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day or between about 15 to 150 mg/day.

In certain embodiments, the method comprises administering to the subject an initial daily dose of about 1 to 800 mg of a compound described herein and increasing the dose by increments until clinical efficacy is achieved. Increments of about 5, 10, 25, 50 or 100 mg can be used to increase the dose. The dosage can be increased daily, every other day, twice per week or once per week.

In certain embodiments, a compound or pharmaceutical preparation is administered orally. In certain embodiments, the compound or pharmaceutical preparation is administered intravenously. Alternative routes of administration include sublingual, intramuscular and transdermal administrations.

The preparations of the present disclosure may be given orally, parenterally, topically or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. In certain embodiments, the administration is oral.

7. Combinations

In another aspect of the disclosure the compounds can be administered in combination with other agents, including (but not limited to) compounds that are apoptosis inhibitors; PARP poly(ADP-ribose) polymerase inhibitors; Src inhibitors; agents for the treatment of cardiovascular disorders; anti-inflammatory agents, anti-thrombotic agents; fibrinolytic agents; anti-platelet agents, lipid reducing agents, direct thrombin inhibitors; glycoprotein IIb/IIIa receptor inhibitors; calcium channel blockers; beta-adrenergic receptor blocking agents; cyclooxygenase (e.g., COX-1 and COX-2) inhibitors; angiotensin system inhibitor (e.g., angiotensin-converting enzyme (ACE) inhibitors); renin inhibitors; and/or agents that bind to cellular adhesion molecules and inhibit the ability of white blood cells to attach to such molecules (e.g., polypeptides, polyclonal and monoclonal antibodies).

Embodiments of the disclosure also provide combinations of two or more compounds that inhibit cellular necrosis (e.g., a compound as disclosed herein and an additional agent for inhibiting necrosis). The disclosure also provides combinations of one or more compounds that inhibit cellular necrosis combined with one or more additional agents or compounds (e.g., other therapeutic compounds for treating a disease, condition or infection such as an apoptosis inhibitor).

8. Kits

Provided herein are also kits that include a compound of the disclosure, combinations or a pharmaceutically acceptable salt, tautomer, stereoisomer, mixture of stereoisomers, prodrug or deuterated analog thereof and suitable packaging. In certain embodiments, a kit further includes instructions for use. In one aspect, a kit includes a compound of the disclosure or a pharmaceutically acceptable salt, tautomer, stereoisomer, mixture of stereoisomers, prodrug or deuterated analog thereof and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug or deuterated analog thereof in a suitable container. The container may be a vial, jar, ampoule, pre-loaded syringe and intravenous bag.

The kit can also contain instructions for using the compounds according to the disclosure. The kit can be compartmentalized to receive the containers in close confinement. As used herein, a kit such as a compartmentalized kit includes any kit in which compounds or agents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not limited to, a container that will accept a compound or combination of compounds and/or other agents of the disclosure. One or more compounds or agents can be provided as a powder (e.g. lyophilized powder) or precipitate. Such compound(s) can be resuspended prior to administration in a solution that may be provided as part of the kit or separately available. A kit can contain compounds or agents in other forms such as liquids, gels, solids, as described herein. Different compounds and/or agents may be provided in different forms in a single kit.

EXAMPLES

The examples and preparations provided below further illustrate and exemplify the compounds of the present disclosure and methods for testing such compounds. It is to be understood that the scope of the present disclosure is not limited in any way by the scope of the following examples. In the following examples and throughout the specification and claims, molecules with a chiral center, unless otherwise noted, exist as a racemic mixture. Single enantiomers may be obtained by methods known to those skilled in the art and described herein. Compounds were named by using either ChemBioDraw Ultra 13.0 or ChemAxon.

General Procedures

All solvents used were commercially available and were used without further purification. Reactions were typically run using anhydrous solvents under an inert atmosphere of nitrogen.

Analytical Methods $^1$H Nuclear magnetic resonance (NMR) spectroscopy was carried out using one of the following instruments: a Bruker Avance 400 Ultrashield™ instrument equipped with probe DUAL 400 MHz S1, a Bruker Avance 400 Ultrashield™ instrument equipped with probe 6 S1 400 MHz 5 mm $^1$H-$^{13}$C ID, a Bruker Avance III 400 Ultrashield™ instrument with nanobay equipped with probe Broadband BBFO 5 mm direct, a 400 MHz Agilent Direct Drive instrument with ID AUTO-X PFG probe, a Bruker Mercury Plus 400 instrument equipped with a Bruker 400 BBO probe, a Bruker Avance 400 Ultrashield™ instrument equipped with a BBO probe, a Bruker Avance 400 Ultrashield™ instrument equipped with a BBFO probe, all operating at 400 MHz, or a Bruker Avance III 300 Ultrashield™ instrument equipped with a BBFO probe operating at 300 MHz. All deuterated solvents contained typically 0.03% to 0.05% v/v tetramethylsilane, which was used as the reference signal (set at d 0.00 for both $^1$H and $^{13}$C). The spectra were acquired in the stated solvent at around room temperature unless otherwise stated. In all cases, NMR data were consistent with the proposed structures. Characteristic chemical shifts (5) are given in parts-per-million using conventional abbreviations for designation of major peaks: e.g. s, singlet; d, doublet; t, triplet; q, quartet; dd, doublet of doublets; dt, doublet of triplets; br, broad.

Where thin layer chromatography (TLC) has been used it refers to silica gel TLC using silica gel F254 (Merck) plates. Alternatively, thin layer chromatography (TLC) was performed on Alugram® (Silica gel 60 F254) from Mancherey-Nagel. Rf is the distance travelled by the compound divided by the distance travelled by the solvent on a TLC plate. UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24}.4H_2O$, 5 g $(NH_4)_2Ce(IV)(NO_3)_6$ in 450 mL water and 50 mL concentrated $H_2SO_4$) to visualize the compound.

Column chromatography was performed using an automatic flash chromatography (Biotage SP1 or Isolera) system over Biotage silica gel cartridges (KP-Sil or KP-NH) or in the case of reverse phase chromatography over Biotage C18 cartridges (KP-C18). Alternatively, column chromatography was performed using 40-63 μm (230-400 mesh) silica gel from Silicycle following analogous techniques to diose disclosed in Still, W. C.; Kahn, M.; and Mitra, M. Journal of Organic Chemistry, 1978, 43, 2923. Typical solvents used for column chromatography or thin layer chromatography were mixtures of chloroform/methanol, dichloromethane/methanol, ethyl acetate/methanol, hexanes/ethyl acetate, cyclohexane/ethyl acetate.

HPLC analyses were performed on a SHIMADZU UFLC with two LC20 AD pump and a SPD-M20A Photodiiode Array Detector. The column used was an XBridge C18, 3.5 μm, 4 60×100 mm. A linear gradient was applied, starting at 90% A (A: 0.05% TFA in water) and ending at 95% B (B: 0.05% TFA in MeCN) over 10 min with a total run time of 15 min. The column temperature was at 40° C. with the flow rate of 1.5 mL/min. The Diode Array Detector was scanned from 200-400 nm.

Unless otherwise stated, LCMS analyses were performed on LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s.

Liquid Chromatography—Mass Spectrometry Method A:

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ CSH, C18 column (50×2.1 mm, 1.7 μm particle size), column temperature 40° C., mobile phase: A—water+0.1% HCOOH/B—$CH_3CN$+0.1% HCOOH, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography—Mass Spectrometry Method B:

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ BEH, C18 column (50×2.1 mm, 1.7 μm particle size), column temperature 40° C., mobile phase: A—0.1% v/v aqueous ammonia solution pH 10/B—CH3CN, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography—Mass Spectrometry Method C:

The column used was an Shim-pack XR-ODS, 2.2 μm, 3.0×50 mm. A linear gradient was applied, starting at 95% A (A: 0.05% TFA in water) and ending at 100% B (B: 0.05% TFA in MeCN) over 1.8 min with a total run time of 2.1 min. The column temperature was at 45° C. with the flow rate of 1.2 mL/min.

Liquid Chromatography—Mass Spectrometry Method D:

The column used was an Shim-pack XR-ODS, 2.2 μm, 3.0×50 mm. A linear gradient was applied, starting at 95% A (A: 0.05% TFA in water) and ending at 100% B (B: 0.05%

TFA in MeCN) over 3.2 min with a total run time of 3.6 min. The column temperature was at 40° C. with the flow rate of 1.0 mL/min.

Liquid Chromatography—Mass Spectrometry Method E:

The column used was an Shim-pack XR-ODS, 2.2 μm, 3.0×50 mm. A linear gradient was applied, starting at 95% A (A: 0.05% TFA in water) and ending at 100% B (B: 0.05% TFA in MeCN) over 4.7 min with a total run time of 5.2 min. The column temperature was at 40° C. with the flow rate of 1.0 mL/min.

Liquid Chromatography—Mass Spectrometry Method F:

The column used was an Ascentis Express C18, 2.7 μm, 3.0×50 mm. A linear gradient was applied, starting at 95% A (A: 0.05% TFA in water) and ending at 100% B (B: 0.05% TFA in MeCN) over 2.8 min with a total run time of 3.0 min. The column temperature was at 45° C. with the flow rate of 1.5 mL/min.

Liquid Chromatography—Mass Spectrometry Method G:

The column used was an Poroshell HPH-C18, 2.7 μm, 3.0×50 mm. A linear gradient was applied, starting at 90% A (A: 0.05% $NH_4HCO_3$ in water) and ending at 95% B (B: 0.05% $NH_4HCO_3$ in MeCN) over 1.8 min with a total run time of 2 min. The column temperature was at 45° C. with the flow rate of 1.5 mL/min.

Liquid Chromatography—Mass Spectrometry Method H:

The column used was an Poroshell HPH-C18, 2.7 μm, 3.0×50 mm. A linear gradient was applied, starting at 90% A (A: 0.05% $NH_4HCO_3$ in water) and ending at 95% B (B: 0.05% $NH_4HCO_3$ in MeCN) over 2.7 min with a total run time of 3.0 min. The column temperature was at 45° C. with the flow rate of 1.5 mL/min.

Liquid Chromatography—Mass Spectrometry Method I:

The column used was an Poroshell HPH-C18, 2.7 μm, 3.0×50 mm. A linear gradient was applied, starting at 90% A (A: 0.05% $NH_4HCO_3$ in water) and ending at 95% B (B: 0.05% $NH_4HCO_3$ in MeCN) over 4.5 min with a total run time of 5.2 min. The column temperature was at 45° C. with the flow rate of 1.5 mL/min.

Liquid Chromatography—Mass Spectrometry Method J:

The column used was an Agilent Poroshell HPH-C18, 2.7 μm, 3.0×50 mm. A linear gradient was applied, starting at 90% A (A: 0.05% $NH_4HCO_3$ in water) and ending at 95% B (B: 0.05% $NH_4HCO_3$ in MeCN) over 2.7 min with a total run time of 3.0 min. The column temperature was at 45° C. with the flow rate of 1.5 mL/min.

Liquid Chromatography—Mass Spectrometry Method K:

The column used was an Ascentis Express C18, 2.7 μm, 3.0×50 mm. A linear gradient was applied, starting at 95% A (A: 0.05% TFA in water) and ending at 100% B (B: 0.05% TFA in MeCN) over 1.8 min with a total nm time of 2.0 min. The column temperature was at 45° C. with the flow rate of 1.5 mL/min.

Liquid Chromatography—Mass Spectrometry Method L:

The column used was an Ascentis Express C18, 2.7 μm, 3.0×50 mm. A linear gradient was applied, starting at 95% A (A: 0.05% TFA in water) and ending at 95% B (B: 0.05% TFA in MeCN) over 2.7 min with a total run time of 3.0 min. The column temperature was at 45° C. with the flow rate of 1.5 mL/min.

Liquid Chromatography—Mass Spectrometry Method M:

The column used was an Ascentis Express C18, 2.7 μm, 3.0×50 mm. A linear gradient was applied, starting at 95% A (A: 0.05% TFA in water) and ending at 100% B (B: 0.05% TFA in MeCN) over 1.8 min with a total run time of 2.0 min. The column temperature was at 40° C. with the flow rate of 1.5 mL/min.

Liquid Chromatography—Mass Spectrometry Method N:

The column used was an Ascentis Express C18, 2.7 μm, 3.0×50 mm. A linear gradient was applied, starting at 95% A (A: 0.05% TFA in water) and ending at 100% B (B: 0.05% TFA in MeCN) over 2.8 min with a total nm time of 3.0 min. The column temperature was at 40° C. with the flow rate of 1.5 mL/min.

Liquid Chromatography—Mass Spectrometry Method O:

The column used was an Shim-pack XR-ODS, 2.2 μm, 3.0×50 mm. A linear gradient was applied, starting at 95% A (A: 0.05% TFA in water) and ending at 100% B (B: 0.05% TFA in MeCN) over 3.2 min with a total run time of 3.6 min. The column temperature was at 40° C. with the flow rate of 1.0 mL/min.

Liquid Chromatography—Mass Spectrometry Method P:

The column used was an Kinetex 2.6u XB-C18, 2.6 μm, 3.0×50 mm. A linear gradient was applied, starting at 95% A (A: 0.05% TFA in water) and ending at 100% B (B: 0.05% TFA in MeCN) over 2.7 min with a total run time of 3.0 min. The column temperature was at 40° C. with the flow rate of 1.5 mL/min.

Liquid Chromatography—Mass Spectrometry Method Q:

The column used was a Kinetex XB-C18100A, 2.6 μm, 3.0×50 mm. A linear gradient was applied, starting at 90% A (A: 0.1% FA in water) and ending at 95% B (B: 0.1% formic acid in MeCN) over 2.7 min with a total run time of 3.0 min. The column temperature was at 45° C. with the flow rate of 1.5 mL/min.

Liquid Chromatography—Mass Spectrometry Method R:

The column used was an Ascentis Express C18, 2.7 μm, 3.0×50 mm. A linear gradient was applied, starting at 95% A (A: 0.05% TFA in water) and ending at 100% B (B: 0.05% TFA in MeCN) over 4.6 min with a total run time of 5.2 min. The column temperature was at 45° C. with the flow rate of 1.5 mL/min.

Liquid Chromatography—Mass Spectrometry Method S:

The column used was an Kinetex EVO C18, 2.6 μm, 3.0×50 mm. A linear gradient was applied, starting at 90% A (A: 5 mM $NH_4HCO_3$ in water) and ending at 95% B (MeCN) over 4.7 min with a total run time of 5.0 min. The column temperature was at 40° C. with the flow rate of 1.5 mL/min.

Liquid Chromatography—Mass Spectrometry Method T:

Total ion current (TIC) and DAD UV chromatographic traces together with MS and UV spectra associated with the peaks were taken on LCMS Agilent Technologies system equipped with DAD detector and coupled to an Agilent single quadrupole mass spectrometer operating in alternated positive and negative electrospray ionization mode. [LC/MS-ES (+): analyses performed using an Agilent Technologies 1200 Series, Atlantis dC18 column (50×4.6 mm, 5 μm particle size), column temperature 25° C., mobile phase: A-water+0.1% TFA/B-$CH_3CN$+0.1% TFA, flow rate 1.5 mL/min, total runtime=6.0 min, gradient: t=0 min, 10% B, t=2.5 min 95% B, t=4.5 min 95% B, t=4.6 min 10% B, t=6.0 min 10% B, stop time 6.0 min. Positive ES 100-900, UV detection DAD 220-400 nm].

Compound Preparation

Where the preparation of starting materials is not described, these are commercially available, known in the literature or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is a Biotage Initiator. The actual power supplied varies during the course of the reaction in order to maintain a constant temperature.

General Procedure A: Amide Coupling Conditions

N,N-Diisopropylethylamine (158 µL, 1.34 mmol), 1-hydroxybenzotriazole (70 mg, 0.52 mmol) and EDC-HCl (99 mg, 0.52 mmol) were added to a stirred solution of carboxylic acid (0.26 mmol) and (3S)-3-phenyl-1,2-oxazolidine (40 mg, 0.26 mmol) in $CH_2Cl_2$ (1.5 mL) and the resulting mixture was stirred at room temperature for 18 h. The reaction mixture was diluted with $CH_2Cl_2$ and washed twice with sat. $NaHCO_3$ solution. The organic portion was dried over $Na_2SO_4$, filtered and concentrated under reduced pressure. The crude product was purified by column chromatography to afford the title compound.

Exemplary compounds of the disclosure and intermediates made in the following examples are summarized herein, including inhibitory activity for receptor interacting protein kinase 1 ($IC_{50}$, micromolar) for representative compounds together with LCMS method (M), LC retention time (RT) in minutes and Mass Spec m/z values (molecular weight).

Intermediate 1

Preparation of tert-Butyl N-[(3R)-3-hydroxy-3-phenylpropoxy]carbamate

NaH (180 mg, 4.51 mmol) was added to a solution of tert-butyl N-hydroxycarbamate (542 mg, 4.10 mmol) in DMF (10 mL) which had been pre-cooled to 0° C. After 20 min, a solution of (1R)-3-chloro-1-phenylpropan-1-ol (350 mg, 2.05 mmol) in DMF (3 mL) was added dropwise. The reaction mixture was stirred at 0° C. for 10 min, warmed up to room temperature, stirred for 72 h and quenched with sat. $NH_4Cl$ solution. The aqueous portion was extracted with EtOAc. The organic portion was dried over $Na_2SO_4$, filtered and concentrated under reduced pressure. The crude product was purified by column chromatography (cyclohexane-EtOAc, 100:0 to 50:50) to afford the title compound (450 mg, 82%) as a colorless wax. $^1H$ NMR (400 MHz, DMSO-$d_6$) δ 10.02-9.90 (br s, 1H), 7.37-7.28 (m, 4H), 7.26-7.19 (m, 1H), 5.22 (d, J=4.5 Hz, 1H), 4.72-4.64 (m, 1H), 3.82 (dt, J=9.8, 7.0 Hz, 1H), 3.69 (dt, J=9.7, 6.3 Hz, 1H), 1.87-1.74 (m, 2H), 1.40 (s, 9H). LC-MS (Method A): m/z=268.3 $[M+H]^+$, 0.91 min.

Intermediate 2

Preparation of 3-Phenyl-1,2-oxazolidine

Methanesulfonyl chloride (153 µL, 1.98 mmol) was added to a solution of tert-butyl N-[(3R)-3-hydroxy-3-phenylpropoxy]carbamate (459 mg, 1.72 mmol) and $Et_3N$ (478 µL, 3.44 mmol) in $CH_2Cl_2$ (40 mL) which had been pre-cooled to 0° C. The reaction mixture was stirred at 0° C. for 1.5 h. The reaction mixture was diluted with $CH_2Cl_2$ and washed with water. The organic portion was dried over $Na_2SO_4$, filtered and concentrated under reduced pressure to afford crude tert-butyl 3-phenyl-1,2-oxazolidine-2-carboxylate, which was directly progressed to the next step. LC-MS (Method A): m/z=250.3 $[M+H]^+$, 194.2 $[M+H-tBu]^+$, 1.03 min.

TFA (5 mL) was added to a solution of the crude tert-butyl 3-phenyl-1,2-oxazolidine-2-carboxylate in $CH_2Cl_2$ (50 mL). The reaction mixture was stirred at room temperature for 30 min and concentrated under reduced pressure. The residue was dissolved in $CH_2Cl_2$ and the organic portion was washed with sat. $NaHCO_3$, dried over $Na_2SO_4$, filtered and concentrated under reduced pressure. The crude product was purified by reverse phase chromatography (water-$CH_3CN$, 100:0 to 50:50) to afford the title compound (150 mg, 58%) as a colorless oil. $^1H$ NMR (400 MHz, DMSO-$d_6$) δ 7.42-7.16 (m, 5H), 6.52-6.12 (br s, 1H) 4.47-4.23 (br s, 1H), 3.91 (td, J=8.0, 5.3 Hz, 1H), 3.85-3.66 (br s, 1H), 2.64-2.53 (m, 1H), 2.09 (dddd, J=12.1, 8.7, 6.7, 5.5 Hz, 1H). LC-MS (Method A): m/z=150.1 $[M+H]^+$, 0.40 min.

Examples 1 and 2, which were prepared from this intermediate, were formed as ~85:15 mixtures of enantiomers. It is therefore assumed that this batch of 3-phenyl-1,2-oxazolidine has ~70% enantiomeric excess (e.e.).

Intermediate 3

Preparation of (3S)-3-Phenyl-1,2-oxazolidine

TFA (5 mL) was added to a solution of tert-butyl (3S)-3-phenyl-1,2-oxazolidine-2-carboxylate in $CH_2Cl_2$ (50 mL). The reaction mixture was stirred at room temperature for 30 min and concentrated under reduced pressure. The residue was dissolved in $CH_2Cl_2$ and the organic portion was washed with sat. $NaHCO_3$, dried over $Na_2SO_4$, filtered and concentrated under reduced pressure to afford the title compound (1.76 g, 99%). $^1H$ NMR (400 MHz, DMSO-$d_6$) δ 7.41-7.35 (m, 2H), 7.35-7.28 (m, 2H), 7.27-7.21 (m, 1H), 6.67-6.33 (br. s, 1H), 4.40-4.29 (m, 1H), 3.92 (dt, J=5.3, 8.0 Hz, 1H), 3.84-3.70 (m, 1H), 2.59 (dtd, J=5.4, 8.5, 11.8 Hz, 1H), 2.54-2.54 (m, 1H), 2.10 (dddd, J=5.8, 6.6, 8.8, 12.2 Hz, 1H). LC-MS (Method A): m/z=150.1 [M+H]+, 0.41 min.

A batch of Example 1 prepared from this intermediate was formed as a ~98:2 mixture of enantiomers. It is therefore assumed that this batch of (3S)-3-phenyl-1,2-oxazolidine has 96% enantiomeric excess (e.e.).

Intermediate 4

Preparation of (E)-N-[(2-Chloro-6-fluorophenyl) methylidene] Hydroxylamine

An aqueous solution of NaOH (1.13 g, 28.5 mmol) in water (1 mL) was added to a stirred mixture of 2-chloro-6-fluorobenzaldehyde (1.5 g, 9.5 mmol), EtOH (3 mL), ice and water (9 mL) and hydroxylamine hydrochloride (849 mg, 12.3 mmol). The mixture was stirred at room temperature for 1.5 h and extracted with $Et_2O$ to remove impurities. The aqueous layer was neutralized with 2M aq HCl solution and extracted three times with $Et_2O$. The combined organic portions were dried over $Na_2SO_4$, filtered and concentrated under reduced pressure to afford the crude title compound (1.3 g), which was directly progressed to the next step. $^1H$ NMR (400 MHz, DMSO-$d_6$) δ 11.85 (s, 1H), 8.23 (s, 1H), 7.50-7.37 (m, 2H), 7.35-7.27 (m, 1H). LC-MS (Method A): m/z=174.1 $[M+H]^+$, 0.83 min.

Intermediate 5

Preparation of (E)-[(tert-Butyldimethylsilyl)oxy][(2-chloro-6-fluorophenyl)methylidene]amine TBSCl (520 mg, 3.5 mmol) and imidazole (472 mg, 6.9 mmol) were added to a solution of (E)-N-[(2-chloro-6-fluorophenyl)methylidene]hydroxylamine (400 mg, 2.3 mmol) in DMF (20 mL). The reaction was stirred at room temperature for 50 h, diluted with EtOAc and washed twice with water. The organic portion was dried over Na$_2$SO$_4$, filtered and concentrated under reduced pressure The crude product was purified by column chromatography (cyclohexane-EtOAc, 100:0 to 95:5) to afford the title compound (400 mg, 60%) as a colorless oil. LC-MS (Method A): m/z=288.2 [M+H]+, 1.61 min.

Intermediate 6

Preparation of 3-(2-Chloro-6-fluorophenyl)-1,2-oxazolidine

Ethylene (purity ≥99.95% GC, 00489 Sigma-Aldrich) was bubbled for 30 min through a solution of (E)-[(tert-butyldimethylsilyl)oxy][(2-chloro-6-fluorophenyl)methylidene]amine (100 mg, 0.35 mmol) in CH$_2$Cl$_2$ (7 mL) which had been pre-cooled to −78° C. The reaction was warmed to room temperature and BF$_3$.Et$_2$O (98 µL, 0.77 mmol) was added. The solution was stirred at 60° C. for 16 h under an ethylene atmosphere, cooled to room temperature, diluted with CH$_2$Cl$_2$ and washed with sat. NaHCO$_3$ solution. The organic portion was dried over Na$_2$SO$_4$, filtered and concentrated under reduced pressure. The crude reaction mixture (147 mg) was joined together with the crude reaction mixture (132 mg) from a second reaction identical to that described above in all premises but with a longer heating time of 48 h. The resulting mixture was purified by column chromatography (cyclohexane-EtOAc, 100:0 to 70:30) to afford the title compound (7 mg). $^1$H NMR (400 MHz, CDCl$_3$) δ 7.26-7.21 (m, 2H), 7.06-6.99 (m, 1H), 4.97 (t, J=8.5 Hz, 1H), 4.25 (dt, J=5.4, 8.1 Hz, 1H), 4.08 (q, J=8.0 Hz, 1H), 2.67-2.55 (m, 1H), 2.50-2.38 (m, 1H). LC-MS (Method A): m/z=202.1 [M+H]+, 0.69 min.

Intermediate 7

Preparation of 1-(3-Fluorophenyl)prop-2-en-1-ol

Vinylmagnesium bromide (1M solution in THF, 12.0 mL, 12.0 mmol) was added dropwise to a solution of 3-fluorobenzaldehyde (1.0 g, 8.0 mmol) in THF (10 mL), which had been pre-cooled to −78° C. The reaction was stirred at −78° C. for 2 h and quenched with sat. NH$_4$Cl solution. The aqueous portion was extracted twice with EtOAc. The combined organic portions were dried over Na$_2$SO$_4$, filtered and concentrated under reduced pressure. The crude product was purified by column chromatography (cyclohexane-EtOAc, 80:20) to afford the title compound (800 mg, 66%) as a yellow oil. $^1$H NMR (400 MHz, CDCl$_3$) δ 7.34 (td, J=7.9, 5.8 Hz, 1H), 7.18-7.08 (m, 2H), 6.98 (tdd, J=8.4, 2.5, 1.0 Hz, 1H), 6.11-5.94 (m, 1H), 5.37 (dt, J=17.3, 1.3 Hz, 1H), 5.27-5.18 (m, 2H), 1.96 (d, J=3.8 Hz, 1H). LC-MS (Method A): m/z=135.0 [M−H$_2$O+H]+, 0.81 min.

Intermediate 8

Preparation of 1-(3-Fluorophenyl)prop-2-en-1-one

Dess-Martin periodinane (3.35 g, 7.9 mmol) was added to a solution of 1-(3-fluorophenyl)prop-2-en-1-ol (800 mg, 5.3 mmol) in CH$_2$Cl$_2$ (20 mL). The reaction mixture was stirred at room temperature for 1.5 h, diluted with CH$_2$Cl$_2$ and quenched with a 1:1 sat. NaHCO$_3$ solution/2M Na$_2$S$_2$O$_3$ solution (30 mL). The mixture was vigorously stirred at room temperature for 30 min. The layers were separated and the organic portion was washed with sat. NaHCO$_3$ solution, dried over Na$_2$SO$_4$, filtered and concentrated under reduced pressure to afford crude title compound (779 mg), which was directly progressed to the next step. $^1$H NMR (400 MHz, CDCl$_3$) δ 7.75 (dq, J=7.8, 0.8 Hz, 1H), 7.66 (ddd, J=9.3, 2.4, 1.5 Hz, 1H), 7.49 (td, J=8.0, 5.5 Hz, 1H), 7.35-7.28 (m, 1H), 7.14 (dd, J=17.2, 10.7 Hz, 1H), 6.52-6.45 (m, 1H), 6.00 (dd, J=10.5, 1.5 Hz, 1H). LC-MS (Method A): m/z=151.0 [M+H]+, 0.92 min.

Intermediate 9

Preparation of 3-Chloro-1-(3-fluorophenyl)propan-1-one

Hydrochloric acid (4M solution in dioxane, 30 mL) was added to a solution of 1-(3-fluorophenyl)prop-2-en-1-one (779 mg) in CH$_2$Cl$_2$ (60 mL), which had been pre-cooled to 0° C. The reaction mixture was stirred at 0° C. for 1 h and concentrated under reduced pressure to afford the title compound as a brown oil, which was directly progressed to the next step. $^1$H NMR (400 MHz, CDCl$_3$) δ 7.80-7.74 (m, 1H), 7.67 (dt, J=9.3, 2.0 Hz, 1H), 7.50 (td, J=8.0, 5.5 Hz, 1H), 7.32 (td, J=8.2, 2.5 Hz, 1H), 3.95 (t, J=6.7 Hz, 2H), 3.47 (t, J=6.8 Hz, 2H).

Intermediate 10

Preparation of 3-Chloro-1-(3-fluorophenyl)propan-1-ol

Sodium borohydride (201 mg, 5.3 mmol) was added to a solution of 3-chloro-1-(3-fluorophenyl)propan-1-one in MeOH (40 mL). The reaction was stirred at room temperature for 30 min, concentrated to half of its initial volume under reduced pressure and diluted with EtOAc. The organic portion was washed with sat. NH$_4$Cl solution, dried over Na$_2$SO$_4$, filtered and concentrated under reduced pressure. The crude product was purified by column chromatography (cyclohexane-EtOAc, 100:0 to 30:70) to afford the title compound (778 mg, 78% over three steps) as an orange oil. $^1$H NMR (400 MHz, CDCl$_3$) δ 7.35 (td, J=7.9, 5.8 Hz, 1H), 7.20-7.08 (m, 2H), 7.00 (tdd, J=8.4, 2.6, 0.9 Hz, 1H), 4.99 (dt, J=8.4, 4.1 Hz, 1H), 3.77 (ddd, J=11.0, 8.3, 5.3 Hz, 1H), 3.63-3.54 (m, 1H), 2.28-2.17 (m, 1H), 2.02-2.16 (m, 2H).

Intermediate 11

Preparation of tert-Butyl N-[3-(3-fluorophenyl)-3-hydroxypropoxy]carbamate

Sodium hydride (60% dispersion in mineral oil, 413 mg, 10.3 mmol) was added in two portions to a stirred solution of tert-butyl N-hydroxycarbamate (1.10 g, 8.27 mmol) in DMF (18 mL), which had been pre-cooled to 0° C. The reaction mixture was stirred at 0° C. for 30 min. A solution of 3-chloro-1-(3-fluorophenyl)propan-1-ol (778 mg, 4.14 mmol) in DMF (5 mL) was added dropwise. The reaction was gradually allowed to reach room temperature, stirred for 16 h and quenched with sat. NH$_4$Cl solution. The aqueous portion was extracted twice with EtOAc. The combined organic portions were dried over Na$_2$SO$_4$, filtered and concentrated under reduced pressure. The crude product was purified by column chromatography (cyclohexane-EtOAc, 100:0 to 50:50) to afford the title compound (1.10 g, 93%) as a yellow solid. $^1$H NMR (400 MHz, DMSO-d$_6$) δ 9.98 (br. s, 1H), 7.36 (td, J=7.9, 6.0 Hz, 1H), 7.22-7.12 (m, 2H), 7.09-6.98 (m, 1H), 5.37 (d, J=4.8 Hz, 1H), 4.73 (dt, J=8.7, 4.5 Hz, 1H), 3.84 (d, J=9.8, 6.9 Hz, 1H), 3.68 (ddd, J=9.9, 6.7, 5.3 Hz, 1H), 1.91-1.68 (m, 2H), 1.41 (s, 9H). LC-MS (Method A): m/z=286.1 [M+H]$^+$, 0.97 min.

Intermediate 12

Preparation of 3-(3-Fluorophenyl)-1,2-oxazolidine

Methanesulfonyl chloride (358 μL, 4.63 mmol) was added to a solution of tert-butyl N-[3-(3-fluorophenyl)-3-hydroxypropoxy]carbamate (1.10 g, 3.86 mmol) and Et$_3$N (1.1 mL, 7.71 mmol) in CH$_2$Cl$_2$ (40 mL), which had been pre-cooled to 0° C. The reaction mixture was stirred at 0° C. for 1 h, diluted with CH$_2$Cl$_2$ and washed with sat. NaHCO$_3$ solution and sat. NH$_4$Cl solution. The organic portion was dried over Na$_2$SO$_4$, filtered and concentrated under reduced pressure to afford the title compound in a mixture with tert-butyl 3-(3-fluorophenyl)-1,2-oxazolidine-2-carboxylate (1.22 g). This mixture was dissolved in CH$_2$Cl$_2$ (40 mL) and treated with trifluoroacetic acid (5 mL). The reaction mixture was stirred at room temperature for 1 h and concentrated under reduced pressure. The erode product was dissolved in CH$_2$Cl$_2$ and the organic portion was washed twice with sat. NaHCO$_3$ solution, dried over Na$_2$SO$_4$, filtered and concentrated under reduced pressure. The crude product was purified by reverse phase chromatography (water-CH$_3$CN, 100:0 to 20:80) to afford the title compound (253 mg, 39% over two steps) as a pale yellow wax. $^1$H NMR (400 MHz, DMSO-d$_6$) δ 7.45-7.29 (m, 1H), 7.27-7.15 (m, 2H), 7.12-6.97 (m, 1H), 6.59-6.29 (m, 1H), 4.54-4.30 (m, 1H), 3.91 (td, J=8.0, 5.1 Hz, 1H), 3.82-3.57 (m, 1H), 2.68-2.55 (m, 1H), 2.08 (dddd, J=12.0, 8.5, 7.0, 5.1 Hz, 1H). LC-MS (Method A): m/z=168.2 [M+H]$^+$, 0.57 min.

Intermediate 13

Preparation of 3-Chloro-1-(2-fluorophenyl)propan-1-one

To a solution of 1-bromo-2-fluorobenzene (5.0 g, 28.5 mmol) in dry THF (7.0 mL) was added dropwise at 0° C. isopropylmagnesium chloride lithium chloride complex (1.3M solution in THF, 24.1 mL, 31.3 mmol). The mixture was stirred at this temperature for 4 h, then diluted with THF (50 mL) and the resulting solution was added dropwise over 20 min to a solution of 3-chloropropionyl chloride (3.8 g, 30 mmol) in dry THF (25 mL) at 0° C. The mixture was then stirred at 0° C. for 1 h 40 min then a sat. aqueous NH$_4$Cl solution was added and the mixture was extracted twice with EtOAc. The combined organic phases were washed with sat. aqueous NaHCO$_3$ solution-water (1:1) and then with brine, dried over Na$_2$SO$_4$, filtered and concentrated under reduced pressure. The crude product was purified by column chromatography (cyclohexane-EtOAc, 100:0 to 80:20) to afford the title compound (313 mg) contaminated with unknown impurities (estimated purity ~70% by $^1$NMR) as a pale yellow oil. $^1$H NMR (400 MHz, DMSO-d$_6$) δ 7.93 (dt, J=8.0, 2.0 Hz, 1H), 7.61-7.54 (m, 1H), 7.31-7.25 (m, 1H), 7.21-7.15 (m, 1H), 3.93 (t, J=8.0 Hz, 2H), 3.50 (dt, J=8.0, 4.0 Hz, 2H). LC-MS (Method A): m/z=187 [M+H]$^+$, 1.00 min.

Intermediate 14

Preparation of 3-Chloro-1-(2-fluorophenyl)propan-1-ol

Sodium borohydride (20 mg, 0.53 mmol) was added at 0° C. to a solution of 3-chloro-1-(2-fluorophenyl)propan-1-one (100 mg, 0.53 mmol) in dry THF (1.5 mL). The mixture was then stirred at this temperature for 1 h 30 min. Sat. aqueous NH$_4$Cl solution was added and the mixture was stirred at room temperature for 20 min, then extracted twice with EtOAc. The combined organic phases were dried over Na$_2$SO$_4$, filtered and concentrated under reduced pressure to give crude title compound as a yellow-oil (72 mg).

In a second experiment, sodium borohydride (39 mg, 1.03 mmol) was added at 0° C. to a solution of 3-chloro-1-(2-fluorophenyl)propan-1-one (193 mg, 1.03 mmol) in dry MeOH (3.5 mL). The mixture was then stirred at this temperature for 30 min. Sat. aqueous NH$_4$Cl solution was added and the mixture was stirred at 0° C. for 20 min, then extracted three times with ethyl acetate. The combined organic phases were dried over Na$_2$SO$_4$, filtered and concentrated under reduced pressure to give crude title compound as a yellow oil (188 mg).

The two crudes obtained above were combined and purified by column chromatography (cyclohexane-EtOAc, 95:5 to 60:40) to afford the title compound (154 mg) contaminated with unknown impurities (estimated purity ~70% by $^1$NMR) as a colorless oil. $^1$H NMR (400 MHz, DMSO-d$_6$) δ 7.49 (dt, J=8.0, 2.0 Hz, 1H), 7.34-7.27 (m, 1H), 7.22-7.16 (m, 1H), 7.10-7.02 (m, 1H), 5.30-5.23 (m, 1H), 3.83-3.75 (m, 1H), 3.70-3.62 (m, 1H), 2.33-2.18 (m, 2H), 2.12 (d, J=4.7 Hz, 1H).

Intermediate 15

Preparation of tert-Butyl N-[3-(2-fluorophenyl)-3-hydroxypropoxy]carbamate

NaH (60% dispersion in mineral oil, 72 mg, 1.80 mmol) was added to a solution of tert-butyl N-hydroxycarbamate (218 mg, 1.63 mmol) in dry DMF (2.6 mL) which had been pre-cooled to 0° C. After 20 min, a solution of 3-chloro-1-(2-fluorophenyl)propan-1-ol (154 mg, 0.82 mmol) in dry DMF (1.5 mL) was added dropwise. The reaction was stirred at 0° C. for 45 min, then warmed to room temperature. After 4 h 30 min the mixture was quenched with sat. aqueous NH$_4$Cl solution and extracted three times with EtOAc. The combined organic phases were dried over Na$_2$SO$_4$, filtered and concentrated under reduced pressure. The crude product (340 mg) was purified by column chromatography (cyclohexane-EtOAc, 93:7 to 40:60) to afford the title compound (185 mg, 2% over 3 steps) as a colorless oil. $^1$H NMR (400 MHz, CDCl$_3$) δ 7.62 (dt, J=8.0, 1.7 Hz, 1H), 7.32 (br. s, 1H), 7.28-7.21 (m, 1H), 7.20-7.15 (m, 1H), 7.05-6.99 (m, 1H), 5.35-5.29 (m, 1H), 4.16-4.05 (m, 2H), 2.17-2.09 (m, 1H), 2.01-1.91 (m, 1H), 1.52 (s, 9H). LC-MS (Method A): m/z=286.1 [M+H]$^+$, 0.94 min.

Intermediate 16

Preparation of 3-(2-Fluorophenyl)-1,2-oxazolidine

Trifluoroacetic acid (0.166 mL, 2.17 mmol) was added at 0° C. to a solution of tert-butyl 3-(2-fluorophenyl)-1,2-oxazolidine-2-carboxylate (58 mg, 0.217 mmol) in dry CH$_2$Cl$_2$ (2 mL). The mixture was then stirred at room temperature for 3 h, then concentrated under reduced pressure. The residue was dissolved in CH$_2$Cl$_2$ and the organic portion was washed twice with sat. aqueous NaHCO$_3$ solution, dried over Na$_2$SO$_4$, filtered and concentrated under reduced pressure to give the title compound as a colorless oil (31 mg, 85%). This was used in the following experiment without further purification. $^1$H NMR (400 MHz, CDCl$_3$) δ

7.53 (dt, J=8.0, 1.0 Hz, 1H), 7.31-7.23 (m, 1H), 7.15 (dt, J=8.0, 1.0 Hz, 1H), 7.06 (ddd, J=10.6, 8.2, 1.0 Hz, 1H), 4.80-4.71 (m, 1H), 4.15-4.06 (m, 1H), 4.02-3.92 (m, 1H), 2.78-2.67 (m, 1H), 2.35-2.24 (m, 1H) LC-MS (Method A): m/z=168.2 [M+H]$^+$, 0.57 min.

Intermediate 17

Preparation of 3-Chloro-1-(4-fluorophenyl)propan-1-ol

NaBH$_4$ (200 mg, 5.37 mmol) was added portionwise to a solution of 3-chloro-1-(4-fluorophenyl)propan-1-one (1 g, 5.37 mmol) in MeOH (10 mL) at 0° C. The reaction mixture was allowed to reach room temperature and stirred at this temperature for 1 h. A sat. NH$_4$Cl solution was added and the mixture was stirred at 0° C. for 20 min, then extracted twice with EtOAc. The combined organic phases were dried over Na$_2$SO$_4$, filtered and concentrated under reduced pressure. The crude product was purified by column chromatography (cyclohexane-EtOAc, 100:0 to 50:50) to afford title compound (830 mg, 82% yield) as colorless oil. $^1$H NMR (400 MHz, CDCl$_3$) δ 7.40-7.31 (m, 2H), 7.13-7.01 (m, 2H), 4.97 (dt, J=8.4, 4.1 Hz, 1H), 3.76 (ddd, J=0.9, 8.3, 5.5 Hz, 1H), 3.57 (dt, J=11.0, 5.9 Hz, 1H), 2.24 (ddt, J=14.4, 8.5, 5.7 Hz, 1H), 2.14-2.02 (m, 2H). LC-MS (Method A): m/z=171.0 [M−H$_2$O]$^+$, 0.97 min.

Intermediate 18

Preparation of tert-butyl n-[3-(×4-fluorophenyl)-3-hydroxypropoxy]carbamate

NaH (60% dispersion in mineral oil, 186 mg, 4.66 mmol) was added to a solution of tert-butyl N-hydroxycarbamate (566 mg, 4.25 mmol) in DMF (5 mL) which had been pre-cooled to 0° C. After 20 min, a solution of 3-chloro-1-(4-fluorophenyl)propan-1-ol (400 mg, 2.12 mmol) in DMF (2 mL) was added dropwise. The reaction mixture was stirred at 0° C. for 10 min, warmed to room temperature, stirred for 5 h and quenched with sat. NH$_4$Cl solution. The aqueous portion was extracted with EtOAc. The organic portion was dried over Na$_2$SO$_4$, filtered and concentrated under reduced pressure. The crude product was purified by column chromatography (cyclohexane-EtOAc, 100:0 to 50:50) to afford the title compound (430 mg, 71% yield) as a white solid. $^1$H NMR (400 MHz, CDCl$_3$) δ 7.44-7.34 (m, 2H), 7.29 (s, 1H), 7.10-6.99 (m, 2H), 5.02 (dt, J=8.4, 3.9 Hz, 1H), 4.19-3.99 (m, 2H), 2.10-1.88 (m, 2H), 1.52 (s, 9H). LC-MS (Method A): m/z=308.1 [M+Na]$^+$, 1.03 min.

Intermediate 19

Preparation of 3-(4-Fluorophenyl)-1,2-oxazolidine

TFA (0.66 mL) was added to a solution of tert-butyl 3-(4-fluorophenyl)-1,2-oxazolidine-2-carboxylate (232 mg, 0.87 mmol) in CH$_2$Cl$_2$ (7 mL) which had been pre-cooled to 0° C. The reaction mixture was stirred at room temperature for 1.5 h and concentrated under reduced pressure. The residue was dissolved in CH$_2$Cl$_2$ and the organic portion was washed with sat. NaHCO$_3$, dried over Na$_2$SO$_4$, filtered and concentrated under reduced pressure. The crude product was purified by reverse phase chromatography (water-CH$_3$CN, 100:0 to 50:50) to afford the title compound (90 mg, 62% yield) as a colorless oil. $^1$H NMR (400 MHz, CDCl$_3$) δ 7.45-7.33 (m, 2H), 7.15-6.96 (m, 2H), 4.58-4.42 (m, 1H), 4.18-3.94 (m, 2H), 2.80-2.56 (m, 1H), 2.40-2.16 (m, 1H). LC-MS (Method A): m/z=168.2 [M+H]$^+$, 0.57 min.

Intermediate 20

Preparation of 1-(6-fluoropyridin-3-yl)prop-2-en-1-ol

Vinylmagnesium bromide (1M solution in THF, 24.8 mL, 24.8 mmol) was added dropwise to a solution of 6-fluoropyridine-3-carbaldehyde (1.00 g, 8.00 mmol) in THF (10 mL) which had been pre-cooled to 0° C. The reaction was stirred at 0° C. for 2 h and quenched with sat. NH$_4$Cl solution. The aqueous portion was extracted twice with EtOAc. The combined organic portions were dried over Na$_2$SO$_4$, filtered and concentrated under reduced pressure to afford the crude title compound (1.09 g), which was directly progressed to the next step. $^1$H NMR (400 MHz, CDCl$_3$) δ 8.23 (d, J=2.3 Hz, 1H), 7.84 (td, J=8.2, 2.5 Hz, 1H), 6.95 (dd, J=8.4, 2.9 Hz, 1H), 6.11-5.97 (m, 1H), 5.47-5.37 (m, 1H), 5.34-5.26 (m, 2H), 2.08 (br s, 1H). LC-MS (Method A): m/z=154.0 [M+H]$^+$, 0.57 min.

Intermediate 21

Preparation of 1-(6-fluoropyridin-3-yl)prop-2-en-1-one

Dess-Martin periodinane (3.35 g, 7.90 mmol) was added to a solution of 1-(6-fluoropyridin-3-yl)prop-2-en-1-ol (1.09 g) in CH$_2$Cl$_2$ (70 mL). The reaction was stirred at room temperature for 16 h, and quenched with a 1:1 mixture of sat. NaHCO$_3$ solution/2M Na$_2$S$_2$O$_3$ solution. After being stirred vigorously for 30 min, the layers were separated. The organic portion was washed with sat. NaHCO$_3$ solution, dried over Na$_2$SO$_4$, filtered and concentrated under reduced pressure to afford the crude title compound, which was directly progressed to the next step. LC-MS (Method A): m/z=152.0 [M+H]0.67 min.

Intermediate 22

Preparation of 3-Chloro-1-(6-fluoropyridin-3-yl)propan-1-one

A solution of hydrochloric acid (4M in dioxane, 30 mL) was added to a solution of 1-(6-fluoropyridin-3-yl)prop-2-en-1-one in CH$_2$Cl$_2$ (60 mL) which had been pre-cooled to 0° C. The reaction was stirred at 0° C. for 40 min and concentrated under reduced pressure to give the crude title compound, which was directly progressed to tire next step. LC-MS (Method A): m/z=188.0 [M+H]$^+$, 0.80 min.

Intermediate 23

Preparation of 3-Chloro-1-(6-fluoropyridin-3-yl)propan-1-ol

Sodium borohydride (273 mg, 7.18 mmol) was added to a solution of 3-chloro-1-(6-fluoropyridin-3-yl)propan-1-one in MeOH (50 mL) which had been pre-cooled to 0° C. The reaction was stirred at 0° C. for 20 min. Volatiles were removed under reduced pressure. The crude product was purified by column chromatography (cyclohexane-EtOAc, 100:0 to 20:80) to give the title compound (590 mg, 26% over four steps) as a pale yellow oil. $^1$H NMR (400 MHz, CDCl$_3$) δ 8.24 (d, J=2.5 Hz, 1H), 7.85 (td, J=8.0, 2.4 Hz, 1H), 6.97 (dd, J=8.4, 2.9 Hz, 1H), 5.08 (dt, J=8.8, 4.1 Hz, 1H), 3.84-3.77 (m, 1H), 3.61 (dt, J=11.1, 5.6 Hz, 1H), 2.31-2.21 (m, 1H), 2.16 (d, J=3.8 Hz, 1H), 2.14-2.03 (m, 1H). LC-MS (Method A): m/z=190.0 [M+H]$^+$, 0.74 min.

Intermediate 24

Preparation of tert-Butyl N-[3-(6-fluoropyridin-3-yl)-3-hydroxypropoxy]carbamate Sodium hydride (60% dispersion in mineral oil, 237 mg, 5.93 mmol) was added to a stirred solution of tert-butyl N-hydroxycarbamate (391 mg, 2.96 mmol) in DMF (8 mL) which had been pre-cooled to 0° C. The reaction mixture was stirred at 0° C. for 10 min. A solution of 3-chloro-1-(6-fluoropyridin-3-yl)propan-1-ol (590 mg, 3.12 mmol) in DMF (5 mL) was then added dropwise. The reaction mixture was gradually allowed to reach room temperature, stirred for 5 h and quenched with sat. NH$_4$Cl solution. The aqueous portion was extracted twice with EtOAc. The combined organic portions were dried over Na$_2$SO$_4$, filtered and concentrated under reduced pressure. The crude product was purified by column chromatography (cyclohexane-EtOAc, 100:0 to 20:80) to afford the title compound (366 mg, 41%) as a yellow oil. LC-MS (Method A): m/z=287.2 [M+H]$^+$, 0.78 min.

Intermediate 25

Preparation of tert-Butyl 3-(6-fluoropyridin-3-yl)-1,2-oxazolidine-2-carboxylate Methanesulfonyl chloride (148 μL, 1.90 mmol) was added to a solution of N-[3-(6-fluoropyridin-3-yl)-3-hydroxypropoxy]carbamate (366 mg, 1.28 mmol) and Et$_3$N (355 μL, 2.55 mmol) in CH$_2$Cl$_2$ (7 mL) which had been pre-cooled to 0° C. The reaction mixture was gradually allowed to reach room temperature and stirred for 1 h. The reaction mixture was diluted with CH$_2$Cl$_2$ and washed with sat. NH$_4$Cl solution. The organic portion was dried over Na$_2$SO$_4$, filtered and concentrated under reduced pressure. The crude product was purified by column chromatography (cyclohexane-EtOAc, 100:0 to 20:80) to afford the title compound (161 mg, 47%) as a mixture of enantiomers as a pale yellow oil. $^1$H NMR (400 MHz, CDCl$_3$) δ 8.24-8.18 (m, 1H), 7.84 (td, J=8.0, 2.5 Hz, 1H), 6.94 (dd, J=8.4, 2.9 Hz, 1H), 5.26 (dd, J=8.8, 5.8 Hz, 1H), 4.27-4.20 (m, 1H), 3.98-3.88 (m, 1H), 2.91-2.77 (m, 1H), 2.34-2.24 (m, 1H), 1.50 (s, 9H). LC-MS (Method A): m/z=269.2 [M+H]$^+$, 0.90 min.

Intermediate 26

Preparation of (2E)-3-(6-fluoropyridin-3-yl)prop-2-enal

6-Fluoropyridine-3-carbaldehyde (2.0 g, 16.0 mmol) was added to a solution of (triphenylphosphoranylidene)acetaldehyde (6.32 g, 20.8 mmol) in CH$_2$Cl$_2$ (100 mL) and the resulting mixture was stirred at room temperature for 18 h. The reaction was diluted with CH$_2$Cl$_2$ and the organic portion was washed with water, dried over Na$_2$SO$_4$, filtered and concentrated under reduced pressure. The crude product was purified by column chromatography (cyclohexane-EtOAc, 100:0 to 30:70) to afford the title compound (1.17 g, 48%) as a pale yellow solid. $^1$H NMR (400 MHz, CDCl$_3$) δ 9.76 (d, J=7.3 Hz, 1H), 8.44 (d, J=2.5 Hz, 1H), 8.09-7.98 (m, 1H), 7.50 (d, J=16.1 Hz, 1H), 7.06 (dd, J=8.5, 3.0 Hz, 1H), 6.74 (dd, J=16.2, 7.4 Hz, 1H). LC-MS (Method A): m/z=152.0 [M+H]$^+$, 0.61 min.

Intermediate 27

Preparation of tert-butyl N-[(1S)-1-(6-fluoropyridin-3-yl)-3-hydroxypropyl]-N-hydroxycarbamate (2E)-3-(6-Fluoropyridin-3-yl)prop-2-enal (1.17 g, 7.75 mmol) and tert-butyl N-hydroxycarbamate (1.23 g, 9.30 mmol) were sequentially added to a solution of (S)-(-)-α,α-diphenyl-2-pyrrolidinemethanol trimethylsilyl ether (504 mg, 1.55 mmol) in CH$_2$Cl$_2$ (30 mL). The resulting mixture was stirred at room temperature for 5 h, diluted with MeOH (30 mL) and cooled to 0° C. Sodium borohydride (442 mg, 11.6 mmol) was added in three portions and the resulting mixture was stirred at 0° C. for 45 min before being quenched with sat. NH$_4$Cl solution. The layers were separated and the aqueous portion was extracted twice with CH$_2$Cl$_2$. The combined organic portions were dried over Na$_2$SO$_4$, filtered and concentrated under reduced pressure. The crude product was purified by column chromatography (cyclohexane-EtOAc, 100:0 to 30:70) to give the desired compound (745 mg, 34%) as a colorless wax. $^1$H NMR (400 MHz, CDCl$_3$) δ 8.25 (d, J=2.5 Hz, 1H), 7.95 (td, J=8.0, 2.5 Hz, 1H), 6.94 (dd, J=8.4, 2.9 Hz, 1H), 5.30 (dd, J=10.9, 5.1 Hz, 1H), 3.92-3.77 (m, 2H), 2.44 (dddd, J=14.5, 10.9, 7.2, 3.5 Hz, 1H), 2.12-1.95 (m, 1H), 1.49 (s, 9H). LC-MS (Method A): m/z=287.2 [M+H]$^+$, 0.69 min.

Intermediate 28

Preparation of tert-butyl (3S)-3-(6-fluoropyridin-3-yl)-1,2-oxazolidine-2-carboxylate Diisopropyl azodicarboxylate (511 μL, 2.60 mmol) was added dropwise to a solution of tert-butyl N-[(1S)-1-(6-fluoropyridin-3-yl)-3-hydroxypropyl]-N-hydroxycarbamate (745 mg, 2.60 mmol) and triphenylphosphine (817 mg, 3.12 mmol) in THF (30 mL), which had been pre-cooled to 0° C. The reaction mixture was stirred at 0° C. for 5 min, diluted with EtOAc and washed with brine. The organic portion was dried over Na$_2$SO$_4$, filtered and concentrated under reduced pressure. The crude product was purified by reverse phase chromatography (water-CH$_3$CN, 100:0 to 0:100) to give the title compound (560 mg, 80%) as a colorless oil. $^1$H NMR (400 MHz, CDCl$_3$) δ 8.21 (d, J=2.3 Hz, 1H), 7.84 (td, J=8.1, 2.6 Hz, 1H), 6.94 (dd, J=8.4, 2.9 Hz, 1H), 5.26 (dd, J=8.7, 5.6 Hz, 1H), 4.23 (td, J=8.0, 3.4 Hz, 1H), 3.92 (td, J=8.7, 7.2 Hz, 1H), 2.84 (dddd, J=12.3, 8.8, 7.0, 3.5 Hz, 1H), 2.29 (dddd, J=12.3, 9.0, 7.8, 5.5 Hz, 1H), 1.50 (s, 9H). LC-MS (Method A): m/z=269.2 [M+H]$^+$, 0.90 min. e.e.=90.6% as determined on a Chiralpak AD-H (25×0.46 cm), 5 μm column using a mobile phase of n-hexane/EtOH 50/50% v/v.

Intermediate 29

Preparation of 2-fluoro-5-[(3S)-1,2-oxazolidin-3-yl]pyridine

Trifluoroacetic acid (1 mL) was added to a solution of tertbutyl (3S)-3-(6-fluoropyridin-3-yl)-1,2-oxazolidine-2-carboxylate (560 mg, 2.09 mmol) in CH$_2$Cl$_2$ (5 mL) which had been pre-cooled to 0° C. The reaction mixture was stirred at 0° C. for 20 min, warmed to room temperature and stirred for a further 3 h. Volatiles were removed under reduced pressure. The residue was partitioned between $CH_2Cl_2$ and 1M NaOH solution. The layers were separated and the aqueous portion was extracted twice with $CH_2Cl_2$. The combined organic portions were dried over $Na_2SO_4$, filtered and concentrated under reduced pressure to afford the title compound (320 mg) as a colorless oil which was directly used in the synthesis of Compound 61 (Example 31B). $^1H$ NMR (400 MHz, $CDCl_3$) δ 8.23 (d, J=1.5 Hz, 1H), 7.89 (td, J=8.0, 2.5 Hz, 1H), 6.94 (dd, J=8.4, 2.9 Hz, 1H), 5.77-5.15 (m, 1H), 4.74-4.47 (m, 1H), 4.20-4.11 (m, 1H), 4.06-3.82 (m, 1H), 2.81-2.70 (m, 1H), 2.39-2.21 (m, 1H). LC-MS (Method A): m/z=169.0 [M+H]$^+$, 0.39 min.

Intermediate 30

Preparation of (2E)-3-(5-chloropyridin-2-yl)prop-2-enal

5-Chloropyridine-2-carbaldehyde (2.0 g, 14.2 mmol) was added to a solution of 2-(triphenylphosphoranylidene)acetaldehyde (5.6 g, 18.4 mmol) in $CH_2Cl_2$ (100 mL). The reaction was stirred at room temperature for 18 h, diluted with $CH_2Cl_2$ and washed with water. The organic portion was dried over $Na_2SO_4$, filtered and concentrated under reduced pressure. The crude product was purified by column chromatography (cyclohexane-EtOAc, 100:0 to 30:70) to afford the title compound (1.25 g, 53%) as a light brown solid. $^1H$ NMR (400 MHz, $CDCl_3$) δ 9.82 (d, J=7.5 Hz, 1H), 8.67 (d, J=2.5 Hz, 1H), 7.76 (dd, J=8.4, 2.4 Hz, 1H), 7.53-7.47 (m, 2H), 7.09 (dd, J=15.8, 7.8 Hz, 1H). LC-MS (Method A): m/z=168.0 [M+H]$^+$, 0.77 min.

Intermediate 31

Preparation of tert-butyl N-[(1S)-1-(5-chloropyridin-2-yl)-3-oxopropyl]-N-hydroxycarbamate (2E)-3-(5-chloropyridin-2-yl)prop-2-enal (1.25 g, 7.48 mmol) and tert-butyl N-hydroxycarbamate (1.19 g, 8.98 mmol) were sequentially added to a solution of (S)-(−)-α,α-diphenyl-2-pyrrolidinemethanol trimethylsilyl ether (608 mg, 1.87 mmol) in $CH_2Cl_2$ (30 mL). The resulting solution was stirred at room temperature for 24 h, diluted with $CH_2Cl_2$ and washed with sat. $NH_4Cl$ solution and brine. The organic portion was dried over $Na_2SO_4$, filtered and concentrated under reduced pressure. The crude product was purified by column chromatography (cyclohexane-EtOAc, 100:0 to 30:70) to afford an impure fraction of the title compound (1.10 g), which was progressed to the next step without any further purification. LC-MS (Method A): m/z=301.1 [M+H]$^+$, 0.88 min.

Intermediate 32

Preparation of tert-butyl N-[(1S)-1-(5-chloropyridin-2-yl)-3-hydroxypropyl]-N-hydroxycarbamate Sodium borohydride (139 mg, 3.67 mmol) was added in three portions to a solution of tert-butyl N-[(1S)-1-(5-chloropyridin-2-yl)-3-oxopropyl]-N-hydroxycarbamate (1.10 g) in MeOH (35 mL), which had been pre-cooled to 0° C. The reaction was stirred at 0° C. for 45 min and quenched with sat. $NH_4Cl$ solution. The aqueous portion was extracted twice with $CH_2Cl_2$. The combined organic portions were dried over $Na_2SO_4$, filtered and concentrated under reduced pressure. The crude product was purified by column chromatography (cyclohexane-EtOAc, 100:0 to 30:70) to afford the title compound (850 mg, 38% over two steps) as a yellow wax. $^1H$ NMR (400 MHz, $CDCl_3$) δ 8.47 (d, J=2.0 Hz, 1H), 8.08-7.94 (m, 1H), 7.71 (dd, J=8.3, 2.5 Hz, 1H), 7.34-7.28 (m, 1H), 5.47 (dd, J=10.8, 4.3 Hz, 1H), 3.86-3.78 (m, 2H), 2.41-2.29 (m, 2H), 2.17-2.07 (m, 1H), 1.49 (s, 9H). LC-MS (Method A): m/z=303.2 [M+H]$^+$, 0.80 min.

Intermediate 33

Preparation of tert-butyl (3S)-3-(5-chloropyridin-2-yl)-1,2-oxazolidine-2-carboxylate DIAD (556 µL, 2.83 mmol) was added dropwise to a solution of tert-butyl N-[(1S)-1-(5-chloropyridin-2-yl)-3-hydroxypropyl]-N-hydroxycarbamate (850 mg, 2.83 mmol) and triphenylphosphine (890 mg, 3.40 mmol) in THF (30 mL), which had been pre-cooled to 0° C. The reaction was stirred at 0° C. for 5 min, diluted with EtOAc and washed with brine. The organic portion was dried over $Na_2SO_4$, filtered and concentrated under reduced pressure. The crude product was purified by column chromatography (cyclohexane-EtOAc, 100:0 to 50:50) to afford the title compound (700 mg, 87%) as a 5.5:94.5 mixture of enantiomers. This mixture was resolved by chiral HPLC on a Chiralpak AD-H (25×2.0 cm), 5 µm column using a mobile phase of n-hexane/ethanol 50/50% v/v and a flow rate of 18 mL/min to afford the title compound (599 mg, 74%) as a pale yellow wax. $^1H$ NMR (400 MHz, $CDCl_3$) δ 8.52 (dd, J=2.5, 0.5 Hz, 1H), 7.66 (dd, J=8.5, 2.5 Hz, 1H), 7.49 (d, J=8.5 Hz, 1H), 5.34 (dd, J=8.9, 4.9 Hz, 1H), 4.19-4.11 (m, 1H), 3.93 (q, J=8.3 Hz, 1H), 2.85-2.74 (m, 1H), 2.57 (dtd, J=12.7, 8.0, 4.9 Hz, 1H), 1.50 (s, 9H). LC-MS (Method A): m/z=285.1 [M+H]$^+$, 1.01 min. e.e.=100% as determined on a Chiralpak AD-H (25×0.46 cm), 5 µm column using a mobile phase of n-hexane/ethanol 50/50% v/v, flow rate=1.0 mL/min, retention time: 12.2 min.

Intermediate 34

Preparation of 5-chloro-2-[(3S)-1,2-oxazolidin-3-yl]pyridine

TFA (1 mL) was added to a solution of tert-butyl (3S)-3-(5-chloropyridin-2-yl)-1,2-oxazolidine-2-carboxylate (599 mg, 2.10 mmol) in $CH_2Cl_2$ (5 mL). The reaction was stirred at room temperature for 3 h. Volatiles were removed under reduced pressure. The crude residue was dissolved in $CH_2Cl_2$ and the organic portion was washed with 1M NaOH solution and water, dried over $Na_2SO_4$, filtered and concentrated under reduced pressure to afford the title compound (348 mg) as a pale yellow wax. $^1H$ NMR (400 MHz, $CDCl_3$) δ 8.51 (d, J=2.3 Hz, 1H), 7.65 (dd, J=8.3, 2.5 Hz, 1H), 7.58-7.32 (m, 1H), 6.08-5.36 (m, 1H), 4.72-4.41 (m, 1H), 4.21-3.82 (m, 2H), 2.80-2.56 (m, 1H), 2.53-2.33 (m, 1H). LC-MS (Method A), m/z=185.0 [M+H]$^+$, 0.52 min.

Intermediate 35

Preparation of 3,3-difluoro-2-methylprop-2-enoic Acid

Sodium borohydride (250 mg, 6.57 mmol) was added to a solution of 2-(trifluoromethyl)prop-2-enoic acid (460 mg, 3.28 mmol) in THF (10 mL) which had been pre-cooled to 0° C. The reaction mixture was stirred at 0° C. for 30 min and quenched with 1M HCl solution. The organic solvent was evaporated under reduced pressure and the aqueous portion was extracted twice with EtOAc. The combined organic portions were dried over Na₂SO₄, filtered and concentrated under reduced pressure to afford a 3:2 mixture of 3,3,3-trifluoro-2-methylpropanoic acid and the title 3,3-difluoro-2-methylprop-2-enoic acid (270 mg). This mixture was progressed to the next step without further purification. Analytical data for 3,3-difluoro-2-methylprop-2-enoic acid: LC-MS (Method A): m/z=120.9 [M–H]⁻, 0.57 min.

Intermediate 36

Preparation of 3,3-difluoro-2-methylpropanoic Acid

Pd/C (10% wt Degussa type) was added to a solution of the mixture containing 3,3-difluoro-2-methylprop-2-enoic acid (270 mg) in MeOH (7 mL) and the resulting mixture was stirred under an atmosphere of H₂ for 20 h. The mixture was filtered from the catalyst and the filtrate was concentrated under reduced pressure to afford a 2:1 mixture of 3,3,3-trifluoro-2-methylpropanoic acid and the title 3,3-difluoro-2-methylpropanoic acid (100 mg). This mixture was progressed to the next step without further purification. Analytical data for 3,3-difluoro-2-methylpropanoic acid: LC-MS (Method A): m/z=122.9 [M–H]⁻, 0.53 min.

Intermediate 37

Preparation of 3-cyano-2,2-dimethylpropanoic Acid

To a stirred solution of methyl 3-cyano-2,2-dimethylpropanoate (100 mg, 0.7 mmol) in a mixture of THF/MeOH/H₂O (2:1:1, 4 mL), LiOH (34 mg, 1.4 mmol) was added and the mixture was stirred at room temperature for 1.5 h. The mixture was concentrated under reduced pressure. The residue was diluted with water and extracted with EtOAc. The organic portion was acidified to pH 5 with 1N HCl solution and then extracted twice with EtOAc. The combined organic phases were dried over Na₂SO₄ and evaporated under reduced pressure to afford the title compound (68 mg, 76%) as a white solid. ¹H NMR (400 MHz, CDCl₃) δ 2.65 (s, 2H), 1.44 (s, 6H). LC-MS (Method A): m/z=127.9 [M+H]⁺, 0.50 min.

Intermediate 38

Preparation of tert-butyl N-[(1S)-1-(4-fluorophenyl)-3-hydroxypropyl]-N-hydroxycarbamate To a solution of (S)-(−)-α,α-diphenyl-2-pyrrolidinemethanol trimethylsilyl ether (1.3 g, 4 mmol) in CH₂Cl₂ (45 mL) was added 4-fluorocinnamaldehyde (3.0 g, 20 mmol) and tert-butyl N-hydroxycarbamate (3.19 g, 24 mmol) and the mixture was stirred at room temperature for 20 h. The reaction mixture was diluted with MeOH (45 mL) and cooled to 0° C., then NaBH₄ (1.56 g, 40 mmol) was added portionwise. The reaction mixture was stirred for 30 min at room temperature, then cooled again to 0° C. and quenched with 1N HCl solution. The reaction mixture was extracted twice with CH₂Cl₂ and the organic phase was dried over Na₂SO₄ and concentrated under reduced pressure. The crude product was purified by column chromatography (cyclohexane-EtOAc, 100:0 to 70:30) to afford the title compound (1.7 g, 30%) as a white solid. ¹H NMR (400 MHz, CDCl₃) δ 7.43-7.36 (m, 2H), 7.06-6.98 (m, 2H), 5.21 (dd, J=10.3, 5.2 Hz, 1H), 3.88-3.73 (m, 2H), 2.46-2.39 (m, 1H), 2.08-1.99 (m, 1H), 1.45 (s, 9H).

Intermediate 39

Preparation of tert-butyl 3-(4-fluorophenyl)-1,2-oxazolidine-2-carboxylate

To a solution of tert-butyl N-[(1S)-1-(4-fluorophenyl)-3-hydroxypropyl]-N-hydroxycarbamate (1.7 g, 6 mmol) and triphenylphosphine (1.88 g, 7.2 mmol) in anhydrous THF (20 mL) at 0° C., DIAD (1.17 mL, 6 mmol) was added dropwise. The mixture was stirred for 15 min then concentrated under reduced pressure and the crude product was purified by column chromatography (cyclohexane-EtOAc, 100:0 to 70:30) to afford the title compound (1.4 g) as a 18.3:81.7 mixture of enantiomers as a white solid. This mixture of enantiomers was resolved by chiral HPLC on a Chiralcel OJ-H (25×3.0 cm), 5 μm column using a mobile phase of n-hexane/ethanol 70/30% v/v and a flow rate of 18 mL/min to afford the tide compound (940 mg, 58%) as a white solid. ¹H NMR (400 MHz, CDCl₃) δ 7.39-7.29 (m, 2H), 7.10-6.98 (m, 2H), 5.19 (dd, J=8.7, 5.5 Hz, 1H), 4.24-4.14 (m, 1H), 3.90 (ddd, J=8.9, 8.1, 7.0 Hz, 1H), 2.78 (dddd, J=12.3, 8.7, 7.0, 3.7 Hz, 1H), 2.28 (dddd, J=12.2, 9.0, 7.7, 5.6 Hz, 1H), 1.47 (s, 9H). Chiralcel OJ-H (25×0.46 cm), 5 μm column using a mobile phase of n-hexane/ethanol 70/30% v/v, flow rate: 1 mL/min, retention time: 7.3 min.

Intermediate 40

Preparation of (3S)-3-(4-fluorophenyl)-1,2-oxazolidine

Trifluoroacetic acid (2.5 mL) was added at 0° C. to a solution of tert-butyl 3-(4-fluorophenyl)-1,2-oxazolidine-2-carboxylate (900 mg, 3.37 mmol) in CH₂Cl₂ (15 mL). The mixture was stirred at room temperature for 4 h, then concentrated under reduced pressure. The residue was dissolved in CH₂Cl₂ and the organic portion was washed twice with sat. NaHCO₃ solution, dried over Na₂SO₄, filtered and concentrated under reduced pressure to afford the title compound (380 mg, 67%) as a colorless oil. ¹H NMR (400 MHz, CDCl₃) δ 7.43-7.31 (m, 2H), 7.12-6.98 (m, 2H), 4.49 (dd, J=8.1, 6.1 Hz, 1H), 4.14-3.94 (m, 2H), 2.68 (dtd, J=12.2, 8.3, 5.6 Hz, 1H), 2.27 (dddd, J=12.5, 8.7, 6.8, 6.1 Hz, 1H).

Intermediate 41

Preparation of 4-[(1E)-3-oxoprop-1-en-1-yl]benzonitrile

4-Cyanobenzaldehyde (20 g, 152 mmol) was added to a solution of (triphenylphosphoranylidene) acetaldehyde (60.3 g, 198 mmol) in CH₂Cl₂ (500 mL). The reaction was stirred at room temperature for 20 hours. The reaction was concentrated under reduced pressure. The crude product was triturated with Et₂O and the solid was filtered off washing several times with Et₂O. The filtrate and washings were evaporated under reduced pressure and the resulting crude product was purified by column chromatography (cyclohexane-EtOAc, 100:0 to 80:20) to afford the title compound (9.97 g, 41%) as a light yellow solid. ¹H NMR (400 MHz, CDCl₃) δ 9.78 (d, J=7.4 Hz, 1H), 7.78-7.72 (m, 2H), 7.71-7.65 (m, 2H), 7.48 (d, J=16.1 Hz, 1H), 6.79 (dd, J=16.1, 7.2 Hz, 1H). LC-MS (Method A): m/z=158.0 [M+H]⁺, 0.76 min.

Intermediate 42

Preparation of tert-butyl N-[1-(4-cyanophenyl)-3-hydroxypropyl]-N-hydroxycarbamate To a solution of catalyst (S)-(−)-α,α-diphenyl-2-pyrrolidinemethanol trimethylsilyl ether (3.9 g, 12 mmol) in $CH_2Cl_2$ (400 mL) was added 4-[(1E)-3-oxoprop-1-en-1-yl] benzonitrile (9.97 g, 60 mmol) and tert-butyl N-hydroxycarbamate (9.57 g, 72 mmol) and mixture was stirred at room temperature for 24 h. The reaction mixture was concentrated under reduced pressure, then diluted with MeOH (300 mL) and cooled to 0° C. $NaBH_4$ (4.7 g, 120 mmol) was added portionwise, then the mixture was stirred for 30 min at 0° C. and at room temperature for 2 h. The mixture was cooled to 0° C. and quenched with 1N HCl solution. The mixture was extracted twice with $CH_2Cl_2$ and the combined organic phases were dried over $Na_2SO_4$ and evaporated under reduced pressure. The crude product was purified by column chromatography (cyclohexane-EtOAc, 100: to 30:70) to afford the title compound (6.97 g, 39%) as a yellow oil. $^1$H NMR (400 MHz, $CDCl_3$) δ 7.66-7.60 (m, 2H), 7.56-7.51 (m, 2H), 5.26 (dd, J=10.9, 4.9 Hz, 1H), 3.92-3.74 (m, 2H), 2.40 (dddd, J=14.6, 11.0, 7.5, 3.6 Hz, 1H), 2.08-1.98 (m, 1H), 1.43 (s, 9H).

Intermediate 43

Preparation of tert-butyl (3S)-3-(4-cyanophenyl)-1,2-oxazolidine-2-carboxylate

To a solution of tert-butyl N-[1-(4-cyanophenyl)-3-hydroxypropyl]-N-hydroxycarbamate (6.9 g, 23.8 mmol) and triphenylphosphine (7.48 g, 28.56 mmol) in anhydrous THF (150 mL) at 0° C., DIAD (4.67 mL, 23.8 mmol) was added dropwise. The mixture was stirred for 1.5 h allowing the temperature to gradually reach room temperature. The mixture was concentrated under reduced pressure, and the crude product was dissolved in the minimum quantity of $CH_2Cl_2$. Cyclohexane was added until a white solid, that resulted to be triphenylphosphine oxide, precipitated. The solid was filtered off and die filtrate was concentrated under reduced pressure. The crude product was purified by column chromatography (cyclohexane-EtOAc, 100:0 to 50:50) to afford the title compound as a 6:94 mixture of enantiomers (5.2 g, 79%). 1.7 g of this mixture of enantiomers was resolved by chiral HPLC on a Chiralpak AD-H (25×2.0 cm), 5 μm column using a mobile phase of n-hexane/(ethanol+0.1% isopropylamine) 50/50 v/v and a flow rate of 18 mL/min to afford the title compound (1.43 g) as a colorless oil. $^1$H NMR (400 MHz, $CDCl_3$) δ 7.68-7.62 (m, 2H), 7.52-7.47 (m, 2H), 5.27 (dd, J=8.8, 5.7 Hz, 1H), 4.24-4.16 (m, 1H), 3.95-3.86 (m, 1H), 2.85 (dddd, J=12.3, 8.8, 6.9, 3.4 Hz, 1H), 2.26 (dddd, J=12.2, 9.1, 7.7, 5.6 Hz, 1H), 1.48 (s, 9H).

Intermediate 44

Preparation of 4-(1,2-oxazolidin-3-yl)benzonitrile

Trifluoroacetic acid (9.77 mL) was added at 0° C. to a solution of tert-butyl 3-(4-cyanophenyl)-1,2-oxazolidine-2-carboxylate (6:94 mixture of enantiomers, 3.5 g, 12.77 mmol) in $CH_2Cl_2$ (50 mL). The mixture was stirred at room temperature for 2 h. The mixture was then concentrated under reduced pressure. The residue was dissolved in $CH_2Cl_2$ and washed twice with sat. $NaHCO_3$ solution, dried over $Na_2SO_4$, filtered and concentrated under reduced pressure. The crude product was purified by column chromatography (cyclohexane-EtOAc, 100:0 to 30:70) to afford the title compound (1.45 g, 65%) as a colorless oil. $^1$H NMR (400 MHz, $CDCl_3$) δ 7.68-7.60 (m, 2H), 7.57-7.49 (m, 2H), 5.47 (br.s, 1H), 4.61 (br.s, 1H), 4.13 (td, J=8.2, 5.0 Hz, 1H), 3.89 (br.s, 1H), 2.76 (dtd, J=12.2, 8.5, 5.0 Hz, 1H), 2.27 (dddd, J=12.3, 8.5, 7.3, 4.9 Hz, 1H). LC-MS (Method A): m/z=175.1 [M+H]$^+$, 0.54 min.

Intermediate 45

Preparation of methyl 3-bromo-2,2-dimethylpropanoate

To a solution of 3-bromo-2,2-dimethylpropanoic acid (900 mg, 5 mmol) in toluene/methanol (4:1, 20 mL) at 0° C. was added (trimethylsilyl)diazomethane (2 M in hexane, 5 mL, 10 mmol) slowly under a nitrogen atmosphere. The reaction mixture was allowed to warm to room temperature and stirred overnight. The reaction mixture was diluted with water and extracted with EtOAc. The organic phase was dried over $Na_2SO_4$ and evaporated under reduced pressure to afford the title compound (450 mg, 46%) as a colorless oil. $^1$H NMR (400 MHz, $CDCl_3$) δ 3.73 (s, 3H), 3.51 (s, 2H), 1.33 (s, 6H).

Intermediate 46

Preparation of 2,2-dimethyl-3-(1H-pyrazol-1-yl)propanoic Acid

A suspension of methyl 3-bromo-2,2-dimethylpropanoate (195 mg, 1 mmol), pyrazole (82 mg, 1.2 mmol), $Cs_2CO_3$ (390 mg, 1.2 mmol) and tetrabutylammonium iodide (184 mg, 0.5 mmol) in DMF (2 mL) was stirred at 60° C. for 4 h. The mixture was filtered and the organic phase was evaporated under reduced pressure. The residue was redissolved in a 2:1 mixture of THF/$H_2O$ (2.5 mL), LiOH (96 mg, 4 mmol) was added and the mixture was stirred at room temperature overnight. The reaction mixture was washed with EtOAc, the aqueous phase was acidified to pH~5 with 1N HCl solution and then extracted with EtOAc. The organic portion was dried over $Na_2SO_4$ and evaporated under reduced pressure. The crude product was purified by reverse phase column chromatography (water-acetonitrile, 100:0 to 60:40) to afford the title compound (50 mg, 30%). $^1$H NMR (400 MHz, $CDCl_3$) δ 7.55 (d, J=2.0 Hz, 1H), 7.46 (d, J=2.0 Hz, 1H), 6.26 (t, J=2.1 Hz, 1H), 4.35 (s, 2H), 1.23 (s, 6H).

Intermediate 47

Preparation of 6-chloro-5-fluoropyridine-3-carbaldehyde

Butyllithium (2.5 M in hexane, 13.8 mL, 34.4 mmol) was added to a solution of 5-bromo-2-chloro-3-fluoro-pyridine (5.14 g, 24.6 mmol) in anhydrous diethyl ether (80 mL) at −78° C. After 30 minutes, anhydrous DMF (24.8 mL, 320 mmol) was added and the mixture was stirred at −78° C. After 30 min water was added and the mixture was extracted three times with EtOAc. The combined organic phases were washed with brine, dried over $Na_2SO_4$, and concentrated under reduced pressure. The crude product was purified by column chromatography (cyclohexane-EtOAc, 95:5 to 60:40) to afford the title compound (2.19 g) as a pale yellow solid. LC-MS (Method A): m/z=177.9 [M+H+H₂O]⁺, 0.71 min.

Intermediate 48

Preparation of (2E)-3-(5-fluoro-6-methylpyridin-3-yl)prop-2-enal

6-Chloro-5-fluoropyridine-3-carbaldehyde (2.19 g) was dissolved in 1,4-dioxane (24 mL) and trimethylboroxine (2.32 ml, 16.4 mmol) was added, followed by K₂CO₃ (5.68 g, 41.1 mmol). The mixture was degassed by applying alternatively vacuum and nitrogen. Pd(PPh₃)₄ (791 mg, 0.68 mmol) was then added. The mixture was then heated at 100° C. for 1 h30 min, then cooled to room temperature and filtered over a pad of Celite. The solvent was evaporated under reduced pressure to give a red solid (3.33 g). This solid was dissolved in CH₂Cl₂ (50 mL) and (triphenylphosphoranylidene)acetaldehyde (5.0 g, 16.4 mmol) was then added at 10° C. The mixture was allowed to warm to room temperature and stirred overnight. The mixture was then concentrated under reduced pressure and the crude product was purified by column chromatography (cyclohexane-EtOAc, 88:12 to 0:100) to afford the title compound (1.21 g, 30% yield over 3 steps) as a yellow solid. ¹H NMR (400 MHz, CDCl₃) δ 9.76 (d, J=7.3 Hz, 1H), 8.50 (s, 1H), 7.56-7.45 (m, 2H), 6.74 (dd, J=16.0, 7.3 Hz, 1H), 2.61 (d, J=3.0 Hz, 3H). LC-MS (Method A): m/z=166.0 [M+H]⁺, 0.67 min.

Intermediate 49

Preparation of tert-butyl N-[(1S)-1-(5-fluoro-6-methylpyridin-3-yl)-3-hydroxypropyl]-N-hydroxycarbamate To a solution of (S)-(-)-α,α-diphenyl-2-pyrrolidinemethanol trimethylsilyl ether (241 mg, 0.74 mmol) in anhydrous CH₂Cl₂ (10 mL) were added a solution of (2E)-3-(5-fluoro-6-methylpyridin-3-yl)prop-2-enal (612 mg, 3.70 mmol) in anhydrous CH₂Cl₂ (8 mL) and tert-butyl N-hydroxycarbamate (592 mg, 4.45 mmol) and the mixture was stirred at room temperature. After 27 h the reaction mixture was diluted with MeOH (13 mL) and cooled to 0° C. NaBH₄ (280 mg, 7.4 mmol) was added portionwise then the mixture was stirred at 0° C. for 10 min and quenched with sat. NH₄Cl solution and stirred at room temperature for 10 min. The mixture was then extracted twice with CH₂Cl₂ and twice with EtOAc. The combined organic phases were dried over Na₂SO₄ and evaporated under reduced pressure. The crude product was purified by column chromatography (cyclohexane-EtOAc, 80:20 to 0:100) to afford the title compound (206 mg, 18% yield) as a brown oil. ¹H NMR (400 MHz, CDCl₃) δ 8.22 (s, 1H), 7.46 (dd, J=10.0, 2.0 Hz, 1H), 5.33 (dd, J=10.5, 5.0 Hz, 1H), 3.84-3.73 (m, 2H), 2.54-2.34 (m, 1H), 2.43 (d, J=3.0 Hz, 3H), 2.06-1.96 (m, 1H), 1.49 (s, 9H). LC-MS (Method A): m/z=301.2 [M+H]⁺, 0.66 min.

Intermediate 50

Preparation of tert-butyl (3S)-3-(5-fluoro-6-methylpyridin-3-yl)-1,2-oxazolidine-2-carboxylate To a solution of tert-butyl N-[(1S)-1-(5-fluoro-6-methylpyridin-3-yl)-3-hydroxypropyl]-N-hydroxycarbamate (206 mg, 0.68 mmol) and PPh₃ (214 mg, 0.816 mmol) in anhydrous THF (7 mL) at 0° C., DIAD (0.135 mL, 0.68 mmol) was added dropwise. After 10 min a further addition of DIAD (0.045 mL, 0.23 mmol) was made. The mixture was then concentrated under reduced pressure and the crude product was purified twice by column chromatography (first column cyclohexane-EtOAc, 88:12 to 0:100; second column cyclohexane-EtOAc, 70:30 to 0:100) to afford the title compound as a colorless oil (120 mg, 62% yield). ¹H NMR (400 MHz, CDCl₃) δ 8.30 (s, 1H), 7.39 (dd, J=10.0, 1.5 Hz, 1H), 5.25 (dd, J=8.5, 5.5 Hz, 1H), 4.21 (dd, J=8.0, 3.5 Hz, 1H), 3.95-3.88 (m, 1H), 2.87-2.78 (m, 1H), 2.53 (d, J=3.0 Hz, 3H), 2.34-2.24 (m, 1H), 1.50 (s, 9H). LC-MS (Method A), m/z=283.3 [M+H]⁺, 0.89 min.

Intermediate 51

Preparation of 3-fluoro-2-methyl-5-[(3S)-1,2-oxazolidin-3-yl]pyridine

Trifluoroacetic acid (0.49 mL, 6.38 mmol) was added at 0° C. to a solution of tert-butyl (3S)-3-(5-fluoro-6-methylpyridin-3-yl)-1,2-oxazolidine-2-carboxylate (120 mg, 0.42 mmol) in anhydrous CH₂Cl₂ (4 mL). The mixture was stirred at room temperature for 3 h30 min then concentrated under reduced pressure. The residue was dissolved in CH₂Cl₂ and washed twice with sat. NaHCO₃ solution, dried over Na₂SO₄, filtered and concentrated under reduced pressure to give the title compound as a pale yellow oil (65 mg, 85% yield), which was used in the following experiment without further purification. ¹H NMR (400 MHz, CDCl₃) δ 8.30 (s, 1H), 7.46 (d, J=10.0, 1H), 5.43 (br.s, 1H), 4.58 (br.s, 1H), 4.18-4.10 (m, 1H), 3.93 (br.s, 1H), 2.80-2.68 (m, 1H), 2.53 (d, J=3.0 Hz, 3H), 2.34-2.24 (m, 1H). LC-MS (Method A): m/z=183.1 [M+H]⁺, 0.40 min.

Intermediate 52

Preparation of 6-cyano-2-oxaspiro[3.3]heptane-6-carboxylic Acid

To a stirred solution of methyl 6-cyano-2-oxaspiro[3.3]heptane-6-carboxylate (181 mg, 1 mmol) in a mixture of THF/MeOH/H₂O 2:1:1 (4 mL) was added LiOH (48 mg, 2 mmol) and the mixture was stirred at room temperature overnight. The mixture was concentrated under reduced pressure, the residue was diluted with water and washed with EtOAc. The organic portion was acidified to pH ~5 with 1N HCl solution and then extracted twice with EtOAc. The combined organic phases were dried over Na₂SO₄ and evaporated under reduced pressure but very little product was recovered. The aqueous phase was then evaporated under reduced pressure to afford the title compound (163 mg, 97%) as white solid. ¹H NMR (400 MHz, DMSO-d₆) δ 4.51 (d, J=8.4 Hz, 4H), 2.68-2.60 (m, 2H), 2.50-2.45 (m, 2H). LC-MS (Method A): m/z=168.0 [M+H]⁺, 0.44 min Intermediate 53

4-[(1E)-3-hydroxy(3,3-²H₂)prop-1-en-1-yl]benzonitrile

A suspension of (2E)-3-(4-cyanophenyl)prop-2-enoic acid (750 mg, 4.33 mmol), oxalyl chloride (0.385 mL, 4.54 mmol) and 1 drop of DMF in CH₂Cl₂ (15 mL) was stirred at room temperature for 30 min to give a clear solution. After checking the complete formation of the acyl chloride, the mixture was evaporated and the residue was dissolved in THF (15 mL), then NaBD₄ (544 mg, 13 mmol) was added at room temperature. The resulting mixture was stirred at room temperature for 15 min, then CD₃OD (3.75 mL) was added dropwise over 1 h. The reaction was quenched with D₂O, then with 1N HCl solution, and the aqueous phase was extracted with Et₂O. The organic phase was separated and washed with brine, dried over Na₂SO₄ and filtered. The solvent was evaporated under reduced pressure to give a white solid. The crude product purified by column chromatography (cyclohexane-EtOAc, 85:15 to 65:35) to afford the title compound (350 mg, 50%) as a white solid. ¹H NMR (400 MHz, DMSO-d₆) δ 7.86-7.73 (m, 2H), 7.68-7.56 (m, 2H), 6.73-6.53 (m, 2H), 4.99-4.86 (m, 1H). LC-MS (Method A): m/z=162.1 [M+H]⁺, 0.70 min.

Intermediate 54

4-[(1E)-3-oxo(3,3-²H₂)prop-1-en-1-yl]benzonitrile

A suspension of 4-[(1E)-3-hydroxy(3,3-²H₂)prop-1-en-1-yl]benzonitrile (350 mg, 2.17 mmol) and MnO₂ (943 mg, 10.8 mmmol) in CH₂Cl₂ (20 mL) was stirred at room temperature for 6 h. Further MnO₂ (313 mg, 3.6 mmol) was added, and the mixture was stirred at room temperature overnight. Further MnO₂ (383 mg, 4.4 mmol) was added and the mixture was stirred at room temperature overnight. Further MnO₂ (380 mg, 4.4 mmol) was added and the mixture was stirred for 5 h. The suspension was filtered and the solvent was evaporated under reduced pressure to give the title compound (303 mg, 88%) as a white solid. ¹H NMR (400 MHz, DMSO-d₆) δ 7.98-7.91 (m, 4H), 7.85-7.77 (m, 1H), 7.01 (d, J=16.1 Hz, 1H). LC-MS (Method A): m/z=159.0 [M+H]⁺, 0.78 min.

Intermediate 55 tert-butyl N-[(1S)-1-(4-cyanophenyl)-3-hydroxy(3, 3-²H₂)propyl]-N-hydroxycarbamate tert-Butyl N-hydroxycarbamate (305 mg, 2.29 mmol) was added to a solution of 4-[(1E)-3-oxo(3-²H)prop-1-en-1-yl]benzonitrile (303 mg, 1.91 mmol) and (S)-(−)-α,α-diphenyl-2-pyrrolidinemethanol trimethylsilyl ether (190 mg, 0.58 mmol) in CH₂Cl₂ (9 mL). The mixture was stirred at room temperature for 6 h, then CD₃OD (5 mL) was added and the mixture was cooled to 0° C. and NaBD₄ (120 mg, 2.86 mmol) was added in small portions. The resulting mixture was stirred at 0° C. for 30 min. The mixture was quenched with D₂O, then with sat. NH₄Cl solution. The layers were separated and the aqueous portion was extracted twice with CH₂Cl₂. The combined organic portions were dried over Na₂SO₄, filtered and concentrated under reduced pressure. The crude product was purified by column chromatography (cyclohexane-EtOAc, 80:20 to 25:75) to afford the title compound (145 mg, 42%) as a pale yellow oil. ¹H NMR (400 MHz, DMSO-d₆) δ 9.24 (s, 1H), 7.85-7.73 (m, 2H), 7.56-7.48 (m, 2H), 5.20 (dd, J=6.0, 9.0 Hz, 1H), 4.50 (s, 1H), 2.11 (dd, J=13.7, 8.9 Hz, 1H), 1.86 (dd, J=13.8, 6.0 Hz, 1H), 1.35 (s, 9H). LC-MS (Method A): m/z=295.2 [M+H]⁺, 0.77 min.

Intermediate 56 tert-butyl N-[(1S)-1-(4-cyanophenyl)-3-hydroxy(3, 3-²H₂)propyl]-N-hydroxycarbamate A solution of DIAD (0.1 mL, 0.49 mmol) in anhydrous THF (1 mL) was added dropwise to a solution of tert-butyl N-[(1S)-1-(4-cyanophenyl)-3-hydroxy(3,3-²H₂)propyl]-N-hydroxycarbamate (145 mg, 0.49 mmol) and triphenylphosphine (154 mg, 0.59 mmol) in anhydrous THF (12 mL) which had been pre-cooled to 0° C. The reaction was stirred at 0° C. for 15 min, diluted with EtOAc and washed with brine. The organic portion was dried over Na₂SO₄, filtered and concentrated under reduced pressure. The crude product was purified by column chromatography (cyclohexane-EtOAc, 75:25 to 60:40) to afford the title compound in a ~1:1 mixture with N'-[(propan-2-yloxy)carbonyl](propan-2-yloxy)carbohydrazide (190 mg) as a white solid. This mixture was progressed in the following step without further purification. ¹H NMR (400 MHz, CDCl₃) δ 7.69-7.60 (m, 2H), 7.53-7.43 (m, 2H), 5.25 (dd, J=8.8, 5.5 Hz, 1H), 2.82 (dd, J=12.3, 9.0 Hz, 1H), 2.24 (dd, J=12.4, 5.6 Hz, 1H), 1.47 (s, 9H). LC-MS (Method A): m/z=277.0 [M+H]⁺, 1.00 min.

Intermediate 57

4-[(3S)-(5,5-²H₂)-1,2-oxazolidin-3-yl]benzonitrile

A solution of tert-butyl (3S)-3-(4-cyanophenyl)(5,5-²H₂)-1,2-oxazolidine-2-carboxylate (190 mg) in CH₂Cl₂ (15 mL) and TFA (3 mL) was stirred at 0° C. for 30 minutes, then at room temperature for 3 h. The mixture was evaporated to dryness. The residue was purified by ion exchange chromatography (SCX, MeOH then 0.2M NH₃ in MeOH) to afford the title compound (60 mg, 69% over two steps) as a colorless oil. ¹H NMR (400 MHz, DMSO-d6) δ 7.82-7.73 (m, 2H), 7.58 (d, J=8.3 Hz, 2H), 6.55 (br.s, 1H), 4.52 (br.s, 1H), 2.72-2.58 (m, 1H), 2.05 (dd, J=12.0, 4.5 Hz, 1H). LC-MS (Method A): m/z=177.0 [M+H]⁺, 0.53 min.

Intermediate 58 tert-butyl (3S)-3-(4-cyanophenyl)-5-hydroxy-1,2-oxazolidine-2-carboxylate tert-Butyl N-hydroxycarbamate (631 mg, 4.74 mmol) was added to a solution of 4-[(1E)-3-oxo(3-²H)prop-1-en-1-yl]benzonitrile (622 mg, 3.95 mmol) and (S)-(−)-α,α-diphenyl-2-pyrrolidinemethanol trimethylsilyl ether (321 mg, 0.98 mmol) in CH₂Cl₂ (30 mL). The mixture was stirred at room temperature overnight. The solution was concentrated under reduced pressure and the crude product was purified by column chromatography (cyclohexane-EtOAc, 80:20 to 65:35) to afford the title compound (689 mg, 60%) as a pale yellow solid as a mixture of isomers. ¹H NMR (400 MHz, DMSO-d6) δ 7.86-7.76 (m, 2H), 7.55-7.45 (m, 2H), 6.95 (br.s, 1H), 5.62 (br.s, 1H), 5.30 (t, J=8.3 Hz, 1H), 2.64 (dd, J=12.4, 8.4 Hz, 1H), 2.07 (ddd, J=12.5, 8.1, 4.5 Hz, 1H), 1.47-1.36 (m, 9H). LC-MS (Method A): m/z=291.1 [M+H]⁺, 0.90 min.

Intermediate 59 tert-butyl N-[(1S)-1-(4-cyanophenyl)-3-hydroxybutyl]-N-hydroxycarbamate

MeMgBr (3M solution in diethyl ether, 0.67 mL, 2.01 mmol) was added dropwise to a solution of tert-butyl (3S)-3-(4-cyanophenyl)-5-hydroxy-1,2-oxazolidine-2-carboxylate (585 mg, 2.01 mmol) in anhydrous THF (25 mL) under nitrogen at −20° C. The mixture was stirred at −20° C. for 1 h, then at 0° C. for 2 h. Further MeMgBr (0.67 mL, 2.01 mmol) was added and the mixture was allowed to warm to room temperature and stirred overnight. The reaction was quenched with sat. NH₄Cl solution, then the aqueous phase was extracted with EtOAc. The combined organic phases were washed with brine, dried over Na₂SO₄, filtered and concentrated under reduced pressure. The crude product was purified by column chromatography (cyclohexane-EtOAc, 70:30 to 50:50) to afford the title compound (190 mg, 31%) as a ~65:35 mixture of diastereoisomers. $^1$H NMR (400 MHz, DMSO-76) δ 9.22 (s, 1H), 7.85-7.76 (m, 2H), 7.58-7.46 (m, 2H), 5.32-5.12 (m, 1H), 4.61-4.45 (m, 1H), 3.76-3.34 (m, 1H), 2.15-1.83 (m, 2H), 1.40-1.32 (m, 9H), 1.13-1.04 (m, 3H). LC-MS (Method A): m/z=307.2 [M+H]⁺, 0.86 min.

Intermediate 60

4-[(3S)-5-methyl-1,2-oxazolidin-3-yl]benzonitrile

A solution of DIAD (0.122 mL, 0.62 mmol) in anhydrous THF (2 mL) was added dropwise to a solution of tert-butyl N-[(1S)-1-(4-cyanophenyl)-3-hydroxybutyl]-N-hydroxycarbamate (190 mg, 0.62 mmol) and triphenylphosphine (195 mg, 0.744 mmol) in anhydrous THF (13 mL) which had been pre-cooled to 0° C. The reaction was stirred at 0° C. for 15 min, then it was concentrated under reduced pressure to give a yellow oil. The residue was dissolved in CH₂Cl₂ (12 mL) and TFA (3 mL) was added. The resulting solution was stirred at room temperature for 1 h then the solvent was evaporated under reduced pressure. The crude product was purified by SCX cartridge. The desired product was purified by ion exchange chromatography (SCX, MeOH then 0.2M NH₃ in MeOH) to afford the title compound (100 mg, 85%) as a mixture of diastereoisomers as a yellow oil. LC-MS (Method A): m/z=189.1 [M+H]⁺, 0.62 min.

Intermediate 61

Tert-butyl 2-(azetidin-1-yl)-2-methylpropanoate

A mixture of tert-butyl α-bromoisobutyrate (0.5 mL, 5.4 mmol), azetidine (0.43 mL, 6.4 mmol) and potassium carbonate (2.23 g, 16.2 mmol) in anhydrous DMF (10 mL) was stirred at 60° C. under nitrogen for 1 h 30 min. The mixture was diluted with EtOAc and washed with water. The organic phase was separated, washed several times with brine, dried over Na₂SO₄ and filtered. The solvent was evaporated under reduced pressure to give a colorless oil which was purified by column chromatography (cyclohexane-EtOAc, 20:80 to 40:60) to afford the title compound (300 mg, 56%) a colorless oil. $^1$H NMR (400 MHz, CDCl₃) δ 3.49-3.37 (m, 4H), 2.07-1.91 (m, 2H), 1.50 (s, 9H), 1.14 (s, 6H). LC-MS (Method A): m/z=200.2 [M+H]⁺, 0.36 min.

Intermediate 62

2-(azetidin-1-yl)-2-methylpropanoic Acid Hydrochloride

A solution of tert-butyl 2-(azetidin-1-yl)-2-methylpropanoate (300 mg, 1.5 mmol) in HCl (4M in dioxane, 12 mL) was stirred at 0° C. for 30 min, then at room temperature overnight. Further HCl (4M in dioxane, 5 mL) was added and the mixture was stirred at room temperature for 2 h. The volatiles were evaporated under reduced pressure, and the resulting solid residue was triturated with Et₂O and filtered to afford the title compound (214 mg, 79%) as a white solid. $^1$H NMR (400 MHz, DMSO-d6) δ 14.55-13.71 (br.s, 1H), 11.27 (br.s, 1H), 4.07 (br.s, 4H), 2.42-2.14 (m, 2H), 1.46 (s, 6H). LC-MS (Method A): m/z=144.0 [M+H]⁺, 0.15 min.

Intermediate 63

Preparation of (2E)-3-[6-(difluoromethyl)pyridin-3-yl]prop-2-enal

A mixture of 5-bromo-2-(difluoromethyl)pyridine (1770 mg, 8.5 mmol), trans-di(μ-acetato)bis[o-(di-o-tolyl-phosphino)benzyl]dipalladium(II) (1600 mg, 1.7 mmol) and sodium acetate (797 mg, 9.35 mmol) was placed in a microwave tube under nitrogen. The lube was dried under vacuum, then acetonitrile (15 mL) and 2-propenal (4.66 mL, 30.6 mmol) was added consecutively to the reaction mixture. The mixture heated in a Biotage Initiator microwave oven at 140° C. (7 cycles of 15 min each). The solids were filtered off and washed with MeOH. The filtrate was concentrated under reduced pressure and the crude product was purified by column chromatography (cyclohexane-EtOAc, 100:0 to 0:100) to afford unreacted 5-bromo-2-(difluoromethyl)pyridine (690 mg) and the title compound (700 mg, 26% yield) as an orange oil. LC-MS (Method A): m/z=184.1 [M+H]⁺, 0.69 min.

Intermediate 64

Preparation of tert-Butyl N-[(1S)-1-[6-(difluoromethyl)pyridin-3-yl]-3-hydroxypropyl]-N-hydroxycarbamate To a solution of catalyst (S)-(−)-α,α-diphenyl-2-pyrrolidinemethanol trimethylsilyl ether (0.540 mg, 1.66 mmol) in CH₂Cl₂ (40 mL), were added 3-[6-(difluoromethyl)pyridine-3-yl]prop-2-enal (0.76 g, 4.15 mmol) and tert-butyl N-hydroxycarbamate (662 mg, 5 mmol). The mixture was stirred at room temperature for 20 h. The reaction was diluted with MeOH (40 mL), and NaBH₄ (0.324 g, 8.3 mmol) was added portionwise. The mixture was then stirred for 1.5 hour at room temperature. Volatiles were removed under reduced pressure and the crude product was purified by column chromatography (CH₂Cl₂-MeOH, 100:0 to 95:5) to afford a first batch of the title compound (97 mg, 5%) as a yellow oil. LC-MS (Method A): m/z=319.2 [M+H]⁺, 0.92 min. The column was eluted further with CH₂Cl₂-MeOH 80:20 to afford a second batch of the title compound (310 mg, 16%) as an orange oil. UPLC LC-MS (Method A): m/z=319.2 [M+H]+, 0.92 min.

Intermediate 65

Preparation of tert-butyl (3S)-3-[6-(difluoromethyl) pyridin-3-yl]-1,2-oxazolidine-2-carboxylate To a solution of tert-butyl N-[(1S)-1-[6-(difluoromethyl) pyridine-3-yl]-3-hydroxypropyl]-N-hydroxycarbamate (407 mg, 1.27 mmol) and PPh₃ (499 mg, 1.92 mmol) in anhydrous THF (9 mL) at room temperature, was added DIAD (0.377 mL, 1.92 mmol) dropwise. The mixture was stirred at the same temperature for 1 hour, than it was concentrated under reduced pressure. The crude product was purified by column chromatograpy (cyclohexane-EtOAc, 100:0 to 50:50) to afford the title compound (154 mg, 40 mmol) as a yellow oil. $^1$H NMR (400 MHz, CDCl₃) δ 8.65 (d, J=2.0 Hz, 1H), 7.88 (dd, J=8.2, 2.1 Hz, 1H), 7.64 (d, J=8.0 Hz, 1H), 6.81-6.49 (t, 1H), 5.31 (dd, J=8.7, 5.6 Hz, 1H), 4.23 (dt, J=3.4, 8.0 Hz, 1H), 3.93 (dt, J=7.0, 8.7 Hz, 1H), 2.87 (dddd, J=12.3, 8.8, 7.0, 3.5 Hz, 1H), 2.30 (dddd, J=12.3, 9.1, 7.7, 5.8 Hz, 1H), 1.49 (s, 9H). LC-MS (Method A): m/z=301.2 [M+H]+, 0.94 min.

Intermediate 66

Preparation of 2-(difluoromethyl)-5-[(3S)-1,2-oxazolidin-3-yl]pyridine

To a solution of tert-butyl (3S)-3-[6-(difluoromethyl)-pyridin-3-yl]-1,2-oxazolidine-2-carboxylate (154 mg, 0.51 mmol) in CH$_2$Cl$_2$, trifluoroacetic acid (0.5 mL, 6.6 mmol) was added. The mixture was stirred for 2 h. Sat. NaHCO$_3$ solution was added and the mixture was extracted twice with CH$_2$Cl$_2$. The combined organic phases were concentrated under reduced pressure and the crude product was purified by column chromatography (cyclohexane-EtOAc, 100:0 to 30:70) to afford the title compound (49 mg, 45%) as a yellow oil. $^1$H NMR (400 MHz, CDCl$_3$), δ 8.66 (d, J=1.5 Hz, 1H), 7.94 (dd, J=8.2, 1.9 Hz, 1H), 7.63 (d, J=8.0 Hz, 1H), 6.81-6.48 (t, J=55.2 Hz, 1H), 5.63-5.35 (m, 1H), 4.65 (br.s, 1H), 4.22-4.10 (m, 1H), 3.92 (br.s, 1H), 2.85-2.72 (m, 1H), 2.38-2.24 (m, 1H). LC-MS (Method A), m/z=201.1 [M+H]+, 0.51 min.

Intermediate 67

Preparation of (2E)-3-(1-methyl-1H-pyrazol-4-yl)prop-2-enal

To a solution of 1-methyl-1H-pyrazole-4-carbaldehyde (4 g, 36.3 mmol) in N,N-dimethylformamide (50 mL) was added (formylmethylene)triphenylphosphorane (12.17 g, 40.0 mmol). The reaction mixture was heated to 120° C. and stirred overnight. After being cooled to room temperature, the reaction mixture was quenched by the addition of water (50 mL), and extracted with EtOAc (3×50 mL). The combined organic layers was washed with brine (50 mL), dried over Na$_2$SO$_4$, filtered and concentrated under reduced pressure. The crude product was purified by reverse phase column chromatography (water-acetonitrile, 5:1) to afford the title compound (1.00 g, 20%) as a yellow solid. $^1$H NMR (300 MHz, CDCl$_3$) δ 9.59 (d, J=7.8 Hz, 1H), 7.74 (s, 1H), 7.64 (s, 1H), 7.36 (d, J=15.9 Hz, 1H), 6.50-6.42 (m, 1H), 3.96 (s, 3H).

Intermediate 68

Preparation of tert-butyl N-hydroxy-N-[(1S)-3-hydroxy-1-(1-methyl-1H-pyrazol-4-yl)propyl]carbamate To a stirred solution of (S)-2-(diphenyl(trimethylsilyloxy)methyl)pyrrolidine (383 mg, 1.18 mmol) in CHCl$_3$ (20 mL) were added (2E)-3-(1-methyl-1H-pyrazol-4-yl)prop-2-enal (800 mg, 5.90 mmol) and tert-butyl N-hydroxycarbamate (940 mg, 7.00 mmol). After being stirred at room temperature for 9.5 days, the reaction mixture was diluted with methanol (20 mL) and cooled to 0° C. NaBH$_4$ (447 mg, 11.8 mmol) was added portionwise. After being stirred at room temperature for 30 min, the mixture was cooled to 0° C., quenched with sat. NH$_4$Cl solution (60 mL) and extracted with CH$_2$Cl$_2$ (3×50 mL). The combined organic layers was washed with brine (60 mL), dried over Na$_2$SO$_4$, filtered and concentrated under reduced pressure. The crude product was purified by column chromatography (EtOAc-petroleum ether, 1:1) to afford the title compound (200 mg, 12%) as a yellow oil. $^1$H NMR (300 MHz, DMSO-d$_6$) δ 9.09 (s, 1H), 7.98 (d, J=1.2 Hz, 1H), 7.61 (d, J=1.2 Hz, 1H), 5.12-5.07 (m, 1H), 4.49-4.46 (m, 1H), 3.85 (s, 3H), 3.44-3.39 (m, 1H), 3.33-3.28 (m, 1H), 2.01-1.94 (m, 1H), 1.83-1.76 (m, 1H), 1.39 (s, 9H). LC-MS (Method M): m/z=272.2 [M+H]+, 0.77 min.

Intermediate 69

Preparation of tert-Butyl (3S)-3-(1-methyl-1H-pyrazol-4-yl)-1,2-oxazolidine-2-carboxylate To a stirred solution of tert-butyl N-hydroxy-N-[(1S)-3-hydroxy-1-(1-methyl-1H-pyrazol-4-yl)propyl]carbamate (200 mg, 0.74 mmol) and triphenylphosphine (640 mg, 2.44 mmol) in anhydrous THF (10 mL) was added DIAD (448 mg, 2.22 mmol) dropwise. After being stirred overnight at room temperature, the reaction mixture was concentrated under reduced pressure. The crude product was purified by column chromatography (EtOAc-petroleum ether, 1:2) to afford the title compound (100 mg, 53%) as a white solid. LC-MS (Method M): m/z=254.2 [M+H]+, 0.79 min.

Intermediate 70

Preparation of (3S)-3-(1-methyl-1H-pyrazol-4-yl)-1,2-oxazolidine hydrochloride

To a solution of tert-butyl (3S)-3-(1-methyl-1H-pyrazol-4-yl)-1,2-oxazolidine-2-carboxylate (100 mg, 0.9 mmol) in 1,4-dioxane (2 mL) was added a solution of hydrogen chloride in 1,4-dioxane (4 M, 5 mL). After being stirred overnight at room temperature, the reaction mixture was concentrated under reduced pressure to afford the title compound (90.0 mg, crude) as a yellow solid, which was used directly in the next step without further purification. LC-MS (Method M): m/z=154.3 [M+H]+, 0.30 min.

Intermediate 71

Preparation of (6-methylpyrazin-2-yl)methanol

To a solution of 6-methylpyrazine-2-carboxylic acid (8.00 g, 58.0 mmol) in N,N-dimethylformamide (50 mL) were added Cs$_2$CO$_3$ (37.8 g, 116 mmol) and iodomethane (12.3 g, 87.0 mmol). After being stirred overnight at room temperature, the reaction mixture was quenched with water (100 mL) and extracted with EtOAc (5×150 mL). The combined organic layers were washed with brine (100 mL), dried over Na$_2$SO$_4$, filtered and concentrated under reduced pressure. The residue was dien diluted with water (50 mL). NaBH$_4$ (12.5 g, 330 mmol) was added portionwise at 0° C. After addition, the resulting mixture was stirred at room temperature for 30 min, cooled to 0° C., diluted with water (150 mL) and extracted with EtOAc (8×100 mL). The combined organic layers were washed with brine (200 mL), dried over Na$_2$SO$_4$, filtered and concentrated under reduced pressure to afford the title compound (2.9 g, crude) as a yellow solid. $^1$H NMR (400 MHz, DMSO-d$_6$) δ 8.50 (s, 1H), 8.42 (s, 1H), 5.55 (t, J=5.8 Hz, 1H), 4.59 (d, J=5.5 Hz, 2H), 2.47 (s, 3H).

Intermediate 72

Preparation of 6-methylpyrazine-2-carbaldehyde

To a solution of (6-methylpyrazin-2-yl)methanol (1.50 g, 12.1 mmol) in CH$_2$Cl$_2$ (30 mL) was added Dess-Martin periodinane (7.70 g, 18.1 mmol) at −15° C. After being stirred at −15° C. for 3 hours, the reaction mixture was quenched by the addition of water (50 mL) and extracted with EtOAc (3×50 mL). The combined organic layers were washed with brine (60 mL), dried over $Na_2SO_4$, filtered and concentrated under reduced pressure. The crude product was purified by column chromatography (EtOAc-petroleum ether, 1:9) to afford the title compound (540 mg, 36%) as a yellow solid. $^1$H NMR (300 MHz, DMSO-$d_6$) δ 10.02 (s, 1H), 8.91 (s, 1H), 8.82 (s, 1H), 2.61 (s, 3H).

Intermediate 73

Preparation of (2E)-3-(6-methylpyrazin-2-yl)prop-2-enal

To a solution of 6-methylpyrazine-2-carbaldehyde (620 mg, 5.10 mmol) in THF (20 mL) was added (formylmethylene)triphenylphosphorane (1.70 g, 5.60 mmol). After being stirred overnight at room temperature, the reaction mixture was quenched by the addition of water (50 mL) and extracted with EtOAc (3×50 mL). The combined organic layers were washed with brine (50 mL), dried over $Na_2SO_4$, filtered and concentrated under reduced pressure. The crude product was purified by column chromatography (EtOAc-petroleum ether, 1:3) to afford the title compound (370 mg, 49%) as a yellow solid. $^1$H NMR (300 MHz, DMSO-$d_6$) δ 9.81 (d, J=7.9 Hz, 1H), 8.85 (s, 1H), 8.61 (s, 1H), 7.83 (d, J=15.8 Hz, 1H), 7.16-7.08 (m, 1H), 2.57 (s, 3H).

Intermediate 74

Preparation of N-hydroxy-N-[(1S)-3-hydroxy-1-(6-methylpyrazin-2-yl)propyl]-2,2-dimethylpropanamide To a stirred solution of (S)-2-(diphenyl(trimethylsilyloxy)methyl)pyrrolidine (198 mg, 0.60 mmol) in $CHCl_3$ (30 mL) were added (2E)-3-(6-methylpyrazin-2-yl)prop-2-enal (300 mg, 2.00 mmol) and N-hydroxypivalamide (284 mg, 2.4 mmol). After being stirred overnight at room temperature, the reaction mixture was diluted with MeOH (15 mL) and cooled to 0° C. NaBH (154 mg, 4.00 mmol) was added. The reaction mixture was stirred at room temperature for 30 min, then cooled to 0° C. and quenched with sat. $NH_4Cl$ solution (30 mL). The mixture was extracted with $CH_2Cl_2$ (3×30 mL). The combined organic layers were washed with brine (30 mL), dried over $Na_2SO_4$, filtered and concentrated under reduced pressure. The crude product was purified by column chromatography (EtOAc-petroleum ether, 4:1) to afford the title compound (180 mg, 33%) as a yellow oil. $^1$H NMR (400 MHz, DMSO-$d_6$) δ 9.28 (s, 1H), 8.40 (s, 1H), 8.32 (s, 1H), 5.71-5.67 (m, 1H), 4.60 (t, J=4.9 Hz, 1H), 3.54-3.39 (m, 2H), 2.46 (s, 3H), 2.28-2.00 (m, 2H), 1.20 (s, 9H). LC-MS (Method K): m/z=268.3 [M+H]$^+$, 0.75 min.

Intermediate 75

Preparation of 5-formylpyridine-3-carbonitrile

A mixture of of 5-bromopyridine-3-carbaldehyde (10 g, 53.8 mmol) and cuprous cyanide (7.20 g, 80.6 mmol) in N,N-dimethylformamide (40 mL) was heated to 140° C. and stirred under a nitrogen atmosphere overnight. After being cooled to room temperature, the reaction mixture was diluted with water (80 mL) and filtered. The filtrate was extracted with EtOAc (3×50 mL). The combined organic layers were dried over $Na_2SO_4$, filtered and concentrated under reduced pressure. The crude product was purified by column chromatography (EtOAc-petroleum ether, 1:4) to afford the title compound (1.86 g, 26%) as a yellow solid. $^1$H NMR (400 MHz, $CDCl_3$) δ 10.17 (s, 1H), 9.30 (s, 1H), 9.14 (s, 1H), 8.45 (t, J=2.0 Hz, 1H).

Intermediate 76

Preparation of 5-[(1E)-3-oxoprop-1-en-1-yl]pyridine-3-carbonitrile

A mixture of 5-formylpyridine-3-carbonitrile (1.82 g, 13.78 mmol) and (formylmethylene)triphenylphosphorane (4.28 g, 14.06 mmol) in DMSO (15 mL) was stirred overnight at 120° C. under a nitrogen atmosphere. After being cooled to room temperature, the reaction mixture was diluted with water (30 mL) and extracted with EtOAc (3×20 mL). The combined organic layers were dried over $Na_2SO_4$ and concentrated under reduced pressure. The crude product was purified by column chromatography (EtOAc-petroleum ether, 1:3) to afford the title compound (490 mg, 22%) as a white solid. $^1$H NMR (300 MHz, $CDCl_3$) δ 9.79 (d, J=7.2 Hz, 1H), 8.99 (d, J=2.1 Hz, 1H), 8.92 (d, J=2.1 Hz, 1H) 8.14 (m, 1H), 7.52 (d, J=15.6 Hz, 1H), 6.87-6.79 (m, 1H).

Intermediate 77

Preparation of tert-butyl N-[(1S)-1-(5-cyanopyridin-3-yl)-3-hydroxypropyl]-N-hydroxycarbamate To a solution of (S)-2-(diphenyl(trimethylsilyloxy)methyl)pyrrolidine (280 mg, 0.86 mmol) in $CHCl_3$ (20 mL) were added 5-[(1E)-3-oxoprop-1-en-1-yl]pyridine-3-carbonitrile (450 mg, 2.85 mmol) and tert-butyl N-hydroxycarbamate (570 mg, 4.28 mmol). The reaction mixture was stirred overnight at room temperature. MeOH (10 mL) was added to the reaction solution, then NaBH (220 mg, 5.82 mmol) was added at 0° C. After being stirred at room temperature for 30 min. the reaction mixture was quenched by the addition of sat. $NH_4Cl$ solution (30 mL) and extracted with $CH_2Cl_2$ (3×20 mL). The combined organic layers were dried over $Na_2SO_4$ and concentrated under reduced pressure. The erode product was purified by column chromatography (EtOAc-petroleum ether, 3:1) to afford the title compound (280 mg, 30%) as a yellow solid. LC-MS (Method K): m/z=294.3 [M+H]$^+$, 0.67 min.

Intermediate 78

Preparation of tert-butyl (3S)-3-(5-cyanopyridin-3-yl)-1,2-oxazolidine-2-carboxylate To a stirred solution of tert-butyl N-[(1S)-1-(5-cyanopyridin-3-yl)-3-hydroxypropyl]-N-hydroxycarbamate (280 mg, 0.95 mmol) and triphenylphosphine (300 mg, 1.14 mmol) in THF (5 mL) was added dropwise DIAD (193 mg, 0.95 mmol) at 0° C. The reaction mixture was stirred overnight at room temperature under a nitrogen atmosphere. Upon concentration under reduced pressure, the crude product was purified by preparative thin layer chromatography (EtOAc-petroleum ether, 2:3) to afford the title compound (130 mg, 49%) as a yellow solid. LC-MS (Method K): m/z=276.3 [M+H]$^+$, 0.83 min.

The title compound was isolated by chiral HPLC on a Chiralpak IC (25×2.0 cm), 5 μm column using a mobile phase of n-hexane/ethanol 60/40% v/v, flow rate: 18 mL/min. ¹H NMR (400 MHz, CDCl₃) δ 8.82 (d, J=2.0 Hz, 2H), 8.02 (t, J=2.0 Hz, 1H), 5.34 (dd, J=8.8, 5.5 Hz, 1H), 4.25 (dt, J=3.4, 8.0 Hz, 1H), 3.93 (dt, J=7.0, 8.8 Hz, 1H), 2.90 (dddd, J=12.3, 8.9, 7.2, 3.3 Hz, 1H), 2.35-2.24 (m, 1H), 1.52 (s, 9H). LC-MS (Method A): m/z=276.2 [M+H]⁺, 0.85 min. e.e.=100% as determined on a Chiralpak IC (25×0.46 cm), 5 µm column using a mobile phase of n-hexane/ethanol 60/40% v/v, flow rate: 1.0 mL/min, retention time: 8.9 min.

Intermediate 79

Preparation of 5-[(3S)-1,2-oxazolidin-3-yl]pyridine-3-carbonitrile trifluoroacetate Trifluoroacetic acid (5 mL) was added to a solution of tert-butyl (3S)-3-(5-cyanopyridin-3-yl)-1,2-oxazolidine-2-carboxylate (100 mg, 0.36 mmol) in CH₂Cl₂ (10 mL). After being stirred at room temperature for 1 hour, the mixture was concentrated under reduced pressure to afford the title compound (105 mg, crude) as a yellow solid. LC-MS (Method C): m/z=176.1 [M+H]⁺, 0.76 min.

Intermediate 80

Preparation of 3-fluoro-5-[(1E)-3-oxoprop-1-en-1-yl]benzonitrile

A mixture of 3-fluoro-5-formylbenzonitrile (1 g, 6.71 mmol) and (formylmethylene)triphenylphosphorane (2.04 g, 6.70 mmol) in THF (20 mL) was stirred overnight at 75 C under a nitrogen atmosphere. After being cooled to room temperature, the reaction mixture was diluted with water (30 mL) and extracted with EtOAc (3×20 mL). The combined organic layers were dried over Na₂SO₄ and concentrated under reduced pressure. The crude product was purified by column chromatography (EtOAc-petroleum ether, 1:5) to afford the title compound (830 mg, 71%) as a yellow solid. ¹H NMR (300 MHz, DMSO-d₆) δ 9.69 (d, J=7.6 Hz, 1H), 8.15 (s, 1H), 8.08-8.04 (m, 1H) 7.98-7.94 (m, 1H), 7.72 (d, J=16.0 Hz, 1H), 7.09-7.02 (m, 1H).

Intermediate 81

Preparation of N-[(1S)-1-(3-cyano-5-fluorophenyl)-3-hydroxypropyl]-N-hydroxy-2,2-dimethylpropanamide To a solution of (S)-2-(diphenyl(trimethylsilyloxy)methyl)pyrrolidine (110 mg, 0.34 mmol) in CHCl₃ (10 mL) were added 3-fluoro-5-[(1E)-3-oxoprop-1-en-1-yl]benzonitrile (200 mg, 1.14 mmol) and N-hydroxypivalamide (200 mg, 1.71 mmol). The reaction mixture was stirred overnight at room temperature. MeOH (10 mL) was added to the mixture, then NaBH₄ (90 mg, 2.38 mmol) was added at 0° C. After being stirred at room temperature for 30 min, the reaction mixture was quenched by the addition of sat. NH₄Cl solution (20 mL) and extracted with CH₂Cl₂ (3×15 mL). The combined organic layers were dried over Na₂SO₄, filtered and concentrated under reduced pressure. The crude product was purified by column chromatography (EtOAc-petroleum ether, 1:2) to afford the title compound (100 mg, 29%) as a yellow solid. LC-MS (Method G): m/z=294.9 [M+H]⁺, 0.89 min.

Intermediate 82

Preparation of tert-butyl (3S)-3-(5-methylpyrazin-2-yl)-1,2-oxazolidine-2-carboxylate The title compound was isolated by chiral HPLC on a Chiralpak AD-H (25×2.0 cm), 5 µm column using a mobile phase of n-hexane/(ethanol+0.1% isopropylamine) 50/50% v/v, flow rate: 18 mL/min. ¹H NMR (400 MHz, CDCl₃) δ 8.65 (d, J=1.5 Hz, 1H), 8.40 (d, J=0.8 Hz, 1H), 5.36 (dd, J=8.9, 5.1 Hz, 1H), 4.24-4.16 (m, 1H), 4.00-3.91 (m, 1H), 2.78 (dddd, J=12.3, 8.6, 7.5, 4.1 Hz, 1H), 2.67-2.56 (m, 4H), 1.51 (s, 9H). LC-MS (Method A): m/z=266.1 [M+H]⁺, 0.76 min. e.e.=100% as determined on a Chiralpak AD-H (25× 0.46 cm), 5 µm column using a mobile phase of n-hexane/(ethanol+0.1% isopropylamine) 50/50% v/v, flow rate: 1 mL/min, retention time: 23.8 min.

Intermediate 83

Preparation of (2E)-3-[6-(difluoromethyl)pyridin-3-yl]prop-2-enal

A mixture of 5-bromo-2-(difluoromethyl)pyridine (1770 mg, 8.5 mmol), trans-di(p-acetato)bis[o-(di-o-tolyl-phosphino)benzyl]dipalladium(II) (1600 mg, 1.7 mmol) and sodium acetate (797 mg, 9.35 mmol) was introduced into a microwave reaction tube under nitrogen. The tube was dried under vacuum, then acetonitrile (10 mL) and 2-propenal (4.66 mL, 30.6 mmol) were added consecutively to the reaction mixture. The mixture was heated in a microwave oven to 140° C. (7 cycles of 15 min each). After cooling, the solid was filtered and washed with MeOH, and the filtrate was concentrated under reduced pressure. The crude product was purified by column chromatography (cyclohexane/EtOAc, 100:0 to 0:100) to afford the title compound (825 mg, 47%) as an orange oil. ¹H NMR (400 MHz, CDCl₃) δ 9.78 (d, J=7.5 Hz, 1H), 8.83 (d, J=1.0 Hz, 1H), 8.05 (dd, J=8.2, 2.1 Hz, 1H), 7.74 (d, J=8.3 Hz, 1H), 7.53 (d, J=16.3 Hz, 1H), 6.89-6.52 (m, 2H). LC-MS (Method A): m/z=184.1 [M+H]⁺, 0.69 min.

Intermediate 84

Preparation of 2-methyl-5-[(1E)-3-oxoprop-1-en-1-yl]pyridine-3-carbonitrile

A solution of 5-bromo-2-methylnicotinonitrile (1000 mg, 5.08 mmol) and 3,3-diethoxyprop-1-ene (2.78 mL, 18.27 mmol) in anhydrous MeCN (15 mL) was degassed by applying alternatively vacuum and nitrogen for 3 cycles. Palladium(II) acetate (342 mg, 1.5 mmol), tri(o-tolyl)phosphine (541 mg, 1.78 mmol) and Et₃N (1.9 mL, 13.7 mmol) were then added and the mixture was heated in a microwave oven to 100° C. (4 cycles of 15 min each). After cooling, the solid was filtered and washed with methanol, and the filtrate was concentrated under reduced pressure. The residue was purified by column chromatography (cyclohexane/EtOAc, 100:0 to 0:100) to afford the intermediate 5-[(1E)-3,3-diethoxyprop-1-en-1-yl]-2-methylpyridine-3-carbonitrile (360 mg) as an orange oil. This intermediate was dissolved in THF (10 mL) and treated with hydrochloric acid solution (10 mL, 10% in water) at room temperature. After 4 h, the solution was basified with sat. NaHCO₃ solution and extracted twice with CH₂Cl₂. The combined organic layers were dried over Na₂SO₄, and concentrated under reduced pressure to afford the title compound (320 mg, 35%) as a yellow solid. $^1$H NMR (400 MHz, CDCl$_3$) δ 9.77 (d, J=7.3 Hz, 1H), 8.86 (d, J=2.3 Hz, 1H), 8.08 (d, J=2.3 Hz, 1H), 7.46 (d, J=16.3 Hz, 1H), 6.80 (dd, J=16.2, 7.4 Hz, 1H), 2.85 (s, 3H). LC-MS (Method A): m/z=173.1 [M+H]$^+$, 0.64 min.

Intermediate 85

Preparation of 3-bromo-5-formylbenzonitrile

Isopropylmagnesium chloride solution (2M in THF, 20.9 mL, 41.88 mmol) was added at 0° C. to a stirred solution of 3,5-dibromobenzonitrile (9.036 g, 34.9 mmol) in anhydrous THF (36 mL). After 30 min, anhydrous DMF (8.14 mL, 104.7 mmol) was added at 0° C. and the mixture was stirred at this temperature for 1 h then water (200 mL) and diethyl ether (150 mL) were added to the mixture. The mixture was stirred and acidified to pH 2-3 with 6N aqueous HCl solution. The clear biphasic mixture thus obtained was separated and the aqueous phase was extracted twice again with diethyl ether. The combined organic phases were washed twice with brine, dried over Na$_2$SO$_4$ and evaporated under reduced pressure to give a yellow solid (7.39 g). This crude product was pooled with the crude product (0.73 g) isolated from a similar reaction run on 1.0 g of 3,5-dibromobenzonitrile and together they were purified by column chromatography (cyclohexane/EtOAc, 100:0 to 30:70) to afford the title compound (6.41 g, 79%). $^1$H NMR (400 MHz, CDCl$_3$) δ 10.01 (s, 1H), 8.25 (t, J=1.5 Hz, 1H), 8.11 (t, J=1.4 Hz, 1H), 8.05 (t, J=2.0 Hz, 1H).

Intermediate 86

Preparation of (2E)-3-(6-nitropyridin-3-yl)prop-2-enal

A mixture of 5-bromo-2-nitropyridine (1.92 g, 9.53 mmol), 3,3-diethoxy-1-propenylboronic acid pinacol ester (2.93 g, 11.43 mmol) and cesium carbonate (6.21 g, 19.06 mmol) in 1,4-dioxane (28 mL) was degassed by alternatively applying vacuum and nitrogen for 3 cycles. Water (4 mL) and [1,1'-bis(diphenylphosphino)ferrocene]dichloropalladium(II) (0.695 g, 0.95 mmol) were then added and the mixture was stirred at 100° C. for 4 h. The mixture was filtered over a pad of Celite, diluted with EtOAc and washed twice with water. The organic phase was combined with the organic phase from a second reaction run in parallel on the same scale and using the same conditions. The pooled organic phases were dried over Na$_2$SO$_4$, filtered and concentrated under reduced pressure to afford a brown oil (7.23 g). This material was dissolved in THF (75 mL) and treated with 1M aqueous HCl solution (75 mL). The mixture was stirred at room temperature for 1 h then extracted three times with EtOAc. The combined organic portions were dried over Na$_2$SO$_4$, filtered and concentrated under reduced pressure to afford a brown solid (5.2 g). The crude product was purified by column chromatography (cyclohexane/EtOAc, 80:20 to 0:100) to give the title compound (2.28 g, 67%) as an orange solid. $^1$H NMR (400 MHz, CDCl$_3$) δ 9.84 (d, J=7.0 Hz, 1H), 8.83 (d, J=2.3 Hz, 1H), 8.36 (d, J=8.5 Hz, 1H), 8.23 (dd, J=8.4, 2.1 Hz, 1H), 7.59 (d, J=16.3 Hz, 1H), 6.91 (dd, J=16.2, 7.2 Hz, 1H). LC-MS (Method A): m/z=179.1 [M+H]$^+$, 0.60 min.

Intermediate 87

Preparation of tert-butyl 3-(6-methylpyridin-3-yl)-5-oxo-1,2-oxazolidine-2-carboxylate To a stirred solution of 6-methylpyridine-3-carbaldehyde (1 g, 8.26 mmol) in EtOAc (20 mL) were added 2,2-dimethyl-1,3-dioxane-4,6-dione (1.19 g, 8.26 mmol), 1,4-diazabicyclo[2.2.2]octane (93 mg, 0.83 mmol) and tert-butyl N-hydroxycarbamate (1.10 g, 8.26 mmol). After being stirred at room temperature for 16 h, the reaction mixture was quenched with water (50 mL), and extracted with EtOAc (3×30 mL). The combined organic layers were washed with brine (30 mL), dried over Na$_2$SO$_4$ and concentrated under reduced pressure to afford the title compound (2.10 g, crude) as a yellow oil. LC-MS (Method G): m/z=279.3 [M+H]$^+$, 0.843 min.

Intermediate 88

Preparation of tert-butyl N-hydroxy-N-[3-hydroxy-1-(6-methylpyridin-3-yl)propyl]carbamate To a stirred solution of tert-butyl 3-(6-methylpyridin-3-yl)-5-oxo-1,2-oxazolidine-2-carboxylate (2.10 g, 7.55 mmol) in THF (30 mL) was added lithium borohydride (493 mg, 22.6 mmol) in portions. After being stirred at room temperature for 5 min, the reaction mixture was quenched by the addition of water (50 mL), and extracted with EtOAc (3×50 mL). The combined organic layers were washed with brine (50 mL), dried over Na$_2$SO$_4$ and concentrated under reduced pressure to afford the title compound (2.10 g, crude) as a yellow oil. LC-MS (Method G): m/z=283.3 [M+H]$^+$, 0.795 min.

Intermediate 89

Preparation of tert-butyl 3-(6-methylpyridin-3-yl)-1,2-oxazolidine-2-carboxylate To a stirred solution of tert-butyl N-hydroxy-N-[3-hydroxy-1-(6-methylpyridin-3-yl)propyl]carbamate (2.10 g, 7.44 mmol) and triphenylphosphine (2.93 g, 11.2 mmol) in THF (30 mL) under a nitrogen atmosphere was added dropwise DIAD (2.26 g, 11.2 mmol) at 5° C. After being stirred at 5° C. for 10 min, the mixture was concentrated under reduced pressure to afford the title compound (7.50 g, crude) as a brown oil. LC-MS (Method G): m/z=265.3 [M+H]$^+$, 0.967 min.

Intermediate 90

Preparation of 2-methyl-5-(1,2-oxazolidin-3-yl)pyridine

A mixture of tert-butyl 3-(6-methylpyridin-3-yl)-1,2-oxazolidine-2-carboxylate (7.50 g, crude) and 4 M hydrogen chloride in dioxane (50 mL) was stirred at room temperature for 30 min. The solvent was removed under reduced pressure. The residue was diluted with water (30 mL) and washed with CH$_2$Cl$_2$(4×30 mL). The aqueous layer was basified with sat. Na$_2$CO$_3$ solution and extracted with CH$_2$Cl$_2$(4×30 mL). The combined organic layers were dried over Na$_2$SO$_4$ and concentrated under reduced pressure to afford the title compound (1.20 g, crude) as a yellow oil. LC-MS (Method G): m/z=165.3 [M+H]$^+$, 0.464 min.

Intermediate 91

Preparation of tert-butyl 3-(5-cyanothiophen-2-yl)-5-oxo-1,2-oxazolidine-2-carboxylate This compound was synthesized by the same method as described for tert-butyl 3-(6-methylpyridin-3-yl)-5-oxo-1,2- oxazolidine-2-carboxylate except 5-formylthiophene-2-carbonitrile (1 g, 7.30 mmol) was used instead of 6-methylpyridine-3-carbaldehyde to afford the title compound (1.6 g, 74%). LC-MS (Method C): m/z=295.1 [M+H]$^+$, 0.793 min.

Intermediate 92

Preparation of tert-butyl N-[1-(5-cyanothiophen-2-yl)-3-hydroxypropyl]-n-hydroxycarbamate This compound was synthesized by the same method as described for tert-butyl N-hydroxy-N-[3-hydroxy-1-(6-methylpyridin-3-yl)propyl]carbamate except tert-butyl 3-(5-cyanothiophen-2-yl)-5-oxo-1,2-oxazolidine-2-carboxylate (1.4 g, 4.76 mmol) was used instead of tert-butyl 3-(6-methylpyridin-3-yl)-5-oxo-1,2-oxazolidine-2-carboxylate to afford the title compound (900 mg, 63%). LC-MS (Method C): m/z=299.1 [M+H]$^+$, 0.730 min.

Intermediate 93

Preparation of tert-butyl 3-(5-cyanothiophen-2-yl)-1,2-oxazolidine-2-carboxylate This compound was synthesized by the same method as described for tert-butyl 3-(6-methylpyridin-3-yl)-1,2-oxazolidine-2-carboxylate except tert-butyl N-[1-(5-cyanothiophen-2-yl)-3-hydroxypropyl]-N-hydroxycarbamate (900 mg, 3.02 mmol) was used instead of tert-butyl N-hydroxy-N-[3-hydroxy-1-(6-methylpyridin-3-yl)propyl]carbamate to afford the title compound (2.00 g, crude). LC-MS (Method Q): m/z=281.1 [M+H]$^+$, 0.636 min.

Intermediate 94

Preparation of 5-(1,2-oxazolidin-3-yl)thiophene-2-carbonitrile

This compound was synthesized by the same method as described for 2-methyl-5-(1,2-oxazolidin-3-ylpyridine except tert-butyl 3-(5-cyanothiophen-2-yl)-1,2-oxazolidine-2-carboxylate (500 mg, crude) was used instead of tert-butyl 3-(6-methylpyridin-3-yl)-1,2-oxazolidine-2-carboxylate to afford the title compound (50 mg). LC-MS (Method Q): m/z=181.1 [M+H]$^+$, 0.536 min.

Intermediate 95

Preparation of tert-butyl 3-(5-cyano-1-methyl-1H-pyrrol-3-yl)-5-oxo-1,2-oxazolidine-2-carboxylate This compound was synthesized by the same method as described for tert-butyl 3-(6-methylpyridin-3-yl)-5-oxo-1,2-oxazolidine-2-carboxylate except 4-formyl-1-methyl-1H-pyrrole-2-carbonitrile (1 g, 7.46 mmol) was used instead of 6-methylpyridine-3-carbaldehyde to afford the title compound (1.4 g, 64%). LC-MS (Method M): m/z=192.2 [M–Boc+H]$^+$, 0.973 min.

Intermediate 96

Preparation of tert-butyl N-[1-(5-cyano-1-methyl-1H-pyrrol-3-yl)-3-hydroxypropyl]-N-hydroxycarbamate This compound was synthesized by the same method as described for tert-butyl N-hydroxy-N-[3-hydroxy-1-(6-methylpyridin-3-yl)propyl]carbamate except tert-butyl 3-(5-cyano-1-methyl-1H-pyrrol-3-yl)-5-oxo-1,2-oxazolidine-2-carboxylate (1.4 g, 4.81 mmol) was used instead of tert-butyl 3-(6-methylpyridin-3-yl)-5-oxo-1,2-oxazolidine-2-carboxylate to afford the title compound (1.15 g, 80%). LC-MS (Method G): m/z=196.2 [M–Boc+H]$^+$, 0.727 min.

Intermediate 97

Preparation of tert-butyl 3-(5-cyano-1-methyl-1H-pyrrol-3-yl)-1,2-oxazolidine-2-carboxylate This compound was synthesized by the same method as described for tert-butyl 3-(6-methylpyridin-3-yl)-5-oxo-1,2-oxazolidine-2-carboxylate except tert-butyl N-[1-(5-cyano-1-methyl-1H-pyrrol-3-yl)-3-hydroxypropyl]-N-hydroxycarbamate (500 mg, 1.69 mmol) was used instead of 6-methylpyridine-3-carbaldehyde to afford the title compound (620 mg, crude). LC-MS (Method G): m/z=178.3 [M–Boc+H]$^+$, 0.922 min.

Intermediate 98

Preparation of 1-methyl-4-(1,2-oxazolidin-3-yl)-1H-pyrrole-2-carbonitrile

This compound was synthesized by the same method as described for 2-methyl-5-(1,2-oxazolidin-3-yl)pyridine except tert-butyl 3-(5-cyano-1-methyl-1 h-pyrrol-3-yl)-1,2-oxazolidine-2-carboxylate (620 mg, crude) was used instead of tert-butyl 3-(6-methylpyridin-3-yl)-1,2-oxazolidine-2-carboxylate to afford the title compound (150 mg, crude). Lc-ms (method g): m/z=178.2 [m+h]$^+$, 0.488 min.

Example 1

Preparation of 1-Methyl-5-[(3S)-3-phenyl-1,2-oxazolidine-2-carbonyl]-1H-pyrrole-2-carbonitrile (1)

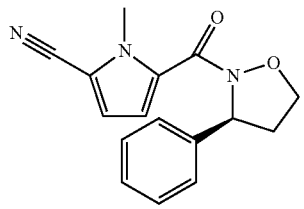 [SMILES: Cn1c(C#N)ccc1C(=O)N1OCC[C@H]1c1ccccc1]

N,N-Diisopropylethylamine (233 µL, 1.34 mmol), 1-hydroxybenzotriazole (91 mg, 0.67 mmol) and EDC-HCl (129 mg, 0.67 mmol) were added to a stirred solution of 5-cyano-1-methyl-1H-pyrrole-2-carboxylic acid (50 mg, 0.33 mmol) and 3-phenyl-1,2-oxazolidine (50 mg, 0.33 mmol) in THF (2 mL) and the resulting mixture was stirred at room temperature for 18 h. The reaction mixture was diluted with EtOAc and washed twice with sat. NaHCO$_3$ solution. The organic portion was dried over Na$_2$SO$_4$, filtered and concentrated under reduced pressure. The erode product was purified by reverse phase chromatography (water-CH$_3$CN, 100:0 to 20:80) to afford an 84:16 mixture of enantiomers (80.3 mg, 86%) as a white solid. This mixture was resolved by chiral HPLC on a Whelk O-1 (R,R) (25×2.0 cm), 10 µm column using a mobile phase of n-hexane/(EtOH/CH$_2$Cl$_2$ 9/1+0.1% isopropylamine) 10/90% v/v and a flow rate of 20 mL/min to afford the title compound. $^1$H NMR (400 MHz, CDCl$_3$) δ

7.41-7.29 (m, 5H), 6.98 (d, J=4.3 Hz, 1H), 6.77 (d, J=4.5 Hz, 1H), 5.60 (dd, J=8.7, 6.2 Hz, 1H), 4.34 (td, J=7.8, 3.9 Hz, 1H), 4.06-3.96 (m, 4H), 2.96-2.84 (m, 1H), 2.49-2.39 (m, 1H). LC-MS (Method A): m/z=282.2 [M+H]⁺, 1.03 min. e.e.=100% as determined on a Whelk O-1 (R,R) (25×0.46 cm), 10 μm column using a mobile phase of n-hexane/(EtOH+0.1% isopropylamine) 20/80% v/v, flow rate: 1 mL/min, retention time: 6.4 min.

Example 2

Preparation of 2,2-dimethyl-1-[(3S)-3-phenyl-1,2-oxazolidin-2-yl]propan-1-one (2)

Pivaloyl chloride (53 μL, 0.433 mmol) was added to a solution of 3-phenyl-1,2-oxazolidine (40 mg, 0.268 mmol) and pyridine (54 μL, 0.670 mmol) in CH₂Cl₂ (2.5 mL). The reaction mixture was stirred at room temperature for 4 h. Volatiles were removed under reduced pressure. The crude product was purified by reverse phase chromatography (water-CH₃CN, 100:0 to 20:80) to afford an 85:15 mixture of enantiomers (45 mg, 72%) as a colorless oil. This mixture was resolved by chiral HPLC on a Chiralpak IC (25×2.0 cm), 5 μm column using a mobile phase of n-hexane/EtOH 70/30% v/v to afford the title compound. ¹H NMR (400 MHz, DMSO-4) δ 7.38-7.31 (m, 2H), 7.29-7.21 (m, 3H), 5.31 (dd, J=8.7, 6.9 Hz, 1H), 4.28 (td, J=7.7, 2.3 Hz, 1H), 3.84 (ddd, J=10.0, 8.0, 6.4 Hz, 1H), 2.87 (dddd, J=12.0, 9.0, 6.4, 2.8 Hz, 1H), 2.19-2.07 (m, 1H), 1.22 (s, 9H). LC-MS (Method A): m/z=234.3 [M+H]⁺, 1.08 min. e.e.=97.6% as determined on a Chiralpak IC (25×0.46 cm), 5 μm column using a mobile phase of n-hexane/EtOH 70/30% v/v.

Example 3

Preparation of 5-[3-(2-chloro-6-fluorophenyl)-1,2-oxazolidine-2-carbonyl]-1-methyl-1H-pyrrole-2-carbonitrile (3)

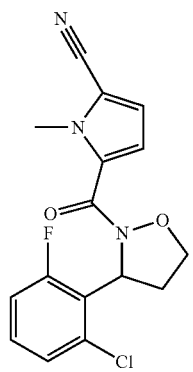 [SMILES: Cn1c(C#N)ccc1C(=O)N1OCCC1c1c(F)cccc1Cl]

N,N-Diisopropylethylamine (18 μL, 0.10 mmol), 1-hydroxybenzotriazole (6.7 mg, 0.05 mmol) and EDC-HCl (9.6 mg, 0.05 mmol) were added to a stirred solution of 5-cyano-1-methyl-1H-pyrrole-2-carboxylic acid (3.7 mg, 0.025 mmol) and 3-(2-chloro-6-fluorophenyl)-1,2-oxazolidine (5.0 mg, 0.025 mmol) in THF (2 mL) and the resulting mixture was stirred at room temperature for 72 h. The reaction mixture was diluted with EtOAc and washed twice with sat. NaHCO₃ solution. The organic portion was dried over Na₂SO₄, filtered and concentrated under reduced pressure. The crude product was purified by column chromatography (cyclohexane-EtOAc, 100:0 to 50:50) to afford an impure fraction of the title compound. This material was further purified by reverse phase chromatography (water-CH₃CN, 100:0 to 30:70) to afford the title compound as a mixture of enantiomers. ¹H NMR (400 MHz, CDCl₃) δ 7.24-7.20 (m, 2H), 7.05-6.96 (m, 2H), 6.75 (d, J=4.3 Hz, 1H), 6.01 (t, J=8.7 Hz, 1H), 4.51-4.43 (m, 1H), 3.97-4.05 (m, 4H), 2.93-2.81 (m, 1H), 2.66-2.53 (m, 1H). LC-MS (Method A): m/z=334.2 [M+H]⁺, 1.09 min.

Example 4

Preparation of (3S)—N,3-diphenyl-1,2-oxazolidine-2-carboxamide (4)

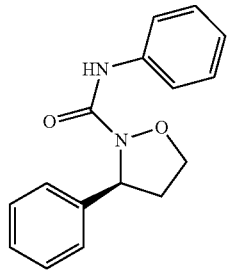 [SMILES: O=C(Nc1ccccc1)N1OCC[C@H]1c1ccccc1]

A solution of (3S)-3-phenyl-1,2-oxazolidine (25 mg, 0.16 mmol) in CH₂Cl₂ (0.5 mL) was added to a solution of phenyl isocyanate (18 μL, 0.16 mmol) in CH₂Cl₂ (0.5 mL) which had been pre-cooled to 0° C. The resulting reaction mixture was allowed to warm to room temperature and stirred for 1 h. Volatiles were removed under reduced pressure. The crude product was purified by column chromatography (cyclohexane-EtOAc, 95:5 to 70:30) to afford the title compound. ¹H NMR (400 MHz, DMSO-d₆) δ 9.36 (s, 1H), 7.66-7.62 (m, 2H), 7.42-7.34 (m, 4H), 7.31-7.25 (m, 3H), 7.05-7.00 (m, 1H), 5.43 (dd, J=8.5, 5.8 Hz, 1H), 4.24 (td, J=8.0, 3.1 Hz, 1H), 3.92-3.85 (m, 1H), 2.85 (dddd, J=12.1, 8.7, 7.1, 3.3 Hz, 1H), 2.23 (dddd, J=12.0, 9.4, 7.9, 5.8 Hz, 1H). LC-MS (Method A): m/z=269.2 [M+H]⁺, 1.07 min.

Example 5

Preparation of (3S)—N-tert-Butyl-3-phenyl-1,2-oxazolidine-2-carboxamide (5)

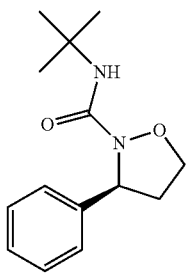 [SMILES: CC(C)(C)NC(=O)N1OCC[C@H]1c1ccccc1]

A solution of (3S)-3-phenyl-1,2-oxazolidine (25 mg, 0.16 mmol) in CH₂Cl₂ (0.5 mL) was added to a solution of tert-butyl isocyanate (18 µL, 0.16 mmol) in CH₂Cl₂ (0.5 mL) which had been pre-cooled 15 to 0° C. The resulting reaction mixture was allowed to warm to room temperature and stirred overnight. Volatiles were removed under reduced pressure. The crude product was purified by column chromatography (cyclohexane-EtOAc, 95:5 to 70:30) to afford the title compound. $^1$H NMR (400 MHz, DMSO-$d_6$) δ 7.35-7.29 (m, 4H), 7.28-7.21 (m, 1H), 6.49 (br. s, 1H), 5.30 (dd, J=8.5, 5.5 Hz, 1H), 4.14-4.08 (m, 1H), 3.77-3.70 (m, 1H), 2.78-2.67 (m, 1H), 2.14 (dddd, J=12.0, 9.3, 7.8, 5.5 Hz, 1H), 1.30 (s, 9H). LC-MS (Method A): m/z=249.3 [M+H]⁺, 1.05 min.

Example 6

Preparation of (3S)—N,N-dimethyl-3-phenyl-1,2-oxazolidine-2-carboxamide (6)

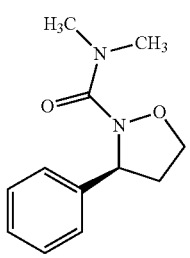 [SMILES: CN(C)C(=O)N1OCC[C@H]1c1ccccc1]

4-(Dimethylamino)pyridine (2 mg, 0.016 mmol) was added to a stirred solution of (3S)-3-phenyl-1,2-oxazolidine (50 mg, 0.33 mmol), dimethylcarbamyl chloride (46 µL, 0.50 mmol) and pyridine (180 µL) in CH₂Cl₂ (1.0 mL) and the resulting mixture was stirred at room temperature for 18 h. The reaction mixture was diluted with CH₂Cl₂ and washed twice with sat. NH₄Cl solution. The organic portion was dried over Na₂SO₄, filtered and concentrated under reduced pressure. The crude product was purified by column chromatography (cyclohexane-EtOAc, 95:5 to 50:50) to afford the title compound. $^1$H NMR (400 MHz, DMSO-$d_6$) δ 7.40-7.31 (m, 4H), 7.28-7.22 (m, 1H), 5.25 (dd, J=8.7, 4.6 Hz, 1H), 4.05 (td, J=7.9.4.3 Hz, 1H), 3.83 (q, J=8.0 Hz, 1H), 2.89 (s, 6H), 2.71 (dtd, J=12.4, 8.1, 4.0 Hz, 1H), 2.20-2.10 (m, 1H). LC-MS (Method A): m/z=221.2 [M+H]⁺, 0.85 min.

Example 7

Preparation of (3S)-3-phenyl-2-(pyrrolidine-1-carbonyl)-1,2-oxazolidine (7)

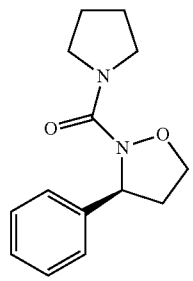 [SMILES: O=C(N1CCCC1)N1OCC[C@H]1c1ccccc1]

4-(Dimethylamino)pyridine (2 mg, 0.016 mmol) was added to a stirred solution of (3S)-3-phenyl-1,2-oxazolidine (50 mg, 0.33 mmol), 1-pyrrolidinecarbonyl chloride (55 µL, 0.50 mmol) and pyridine (180 µL) in CH₂Cl₂ (1.0 mL) and the resulting mixture was stirred at room temperature for 18 h. The reaction mixture was diluted with CH₂Cl₂ and washed twice with sat. NH₄Cl solution. The organic portion was dried over Na₂SO₄, filtered and concentrated under reduced pressure. The crude product was purified by column chromatography (cyclohexane-EtOAc, 95:5 to 50:50) to afford the title compound. $^1$H NMR (400 MHz, DMSO-$d_6$) δ 7.40-7.30 (m, 4H), 7.27-7.21 (m, 1H), 5.38 (dd, J=8.7, 4.9 Hz, 1H), 4.07 (td, J=7.8, 4.0 Hz, 1H), 3.76 (q, J=7.8 Hz, 1H), 3.38 (t, J=5.6 Hz, 4H), 2.77-2.67 (m, 1H), 2.15 (dtd, J=12.1, 8.3, 4.9 Hz, 1H), 1.85-1.69 (m, 4H). LC-MS (Method A): m/z=247.3 [M+H]⁺, 0.94 min.

Example 8

Preparation of (3S)-2-(3-Methyloxetane-3-carbonyl)-3-phenyl-1,2-oxazolidine (8)

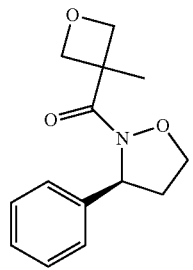 [SMILES: CC1(C(=O)N2OCC[C@H]2c2ccccc2)COC1]

3-Methyloxetane-3-carboxylic acid (30 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-$d_6$) δ 7.39-7.33 (m, 2H), 7.31-7.25 (m, 3H), 5.32 (dd, J=8.5, 6.5 Hz, 1H), 4.86 (d, J=6.3 Hz, 1H), 4.74 (d, J=6.0 Hz, 1H), 4.29-4.20 (m, 3H), 3.97-3.88 (m, 1H), 2.92 (ddt, J=15.3, 8.9, 3.2 Hz, 1H), 2.24-2.13 (m, 1H), 1.60 (s, 3H). LC-MS (Method A): m/z=248.1 [M+H]⁺, 0.81 min.

Example 9

Preparation of 2-hydroxy-1-[(3S)-3-phenyl-1,2-oxazolidin-2-yl]ethan-1-one (9)

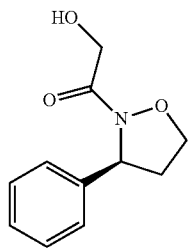 [SMILES: O=C(CO)N1OCC[C@H]1c1ccccc1]

Glycolic acid (19 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-d$_6$) δ 7.38-7.33 (m, 2H), 7.32-7.25 (m, 3H), 5.32 (dd, J=8.7, 6.1 Hz, 1H), 4.82 (t, J=6.3 Hz, 1H), 4.29-4.13 (m, 3H), 3.86 (ddd, J=9.5, 8.0, 6.7 Hz, 1H), 2.92-2.84 (m, 1H), 2.18 (dddd, J=12.2, 9.5, 7.5, 6.1 Hz, 1H). LC-MS (Method A): m/z=208.0 [M+H]$^+$, 0.65 min.

Example 10

Preparation of 1-[(3S)-3-Phenyl-1,2-oxazolidine-2-carbonyl]cyclopropan-1-ol (10)

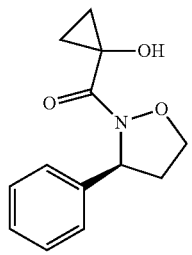 [SMILES: O=C(N1OCC[C@H]1c1ccccc1)C1(O)CC1]

1-Hydroxycyclopropane-1-carboxylic acid (26 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-d$_6$) δ 7.38-7.31 (m, 4H), 7.29-7.23 (m, 1H), 6.01 (s, 1H), 5.59 (dd, J=8.8, 4.8 Hz, 1H), 4.15 (td, J=7.7, 3.9 Hz, 1H), 3.86 (q, J=7.8 Hz, 1H), 2.86-2.78 (m, 1H), 2.28-2.19 (m, 1H), 1.09-0.97 (m, 2H), 0.84 (dd, J=4.8, 1.8 Hz, 1H), 0.78 (dd, J=5.3, 2.0 Hz, 1H). LC-MS (Method A): m/z=234.3 [M+H]$^+$, 0.71 min.

Example 11

Preparation of (3S)-2-(Oxetane-3-carbonyl)-3-phenyl-1,2-oxazolidine (11)

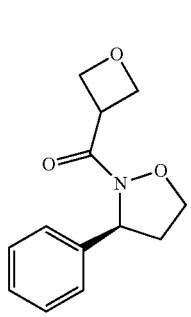 [SMILES: O=C(C1COC1)N1OCC[C@H]1c1ccccc1]

Oxetane-3-carboxylic acid (26 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-d$_6$) δ 7.39-7.24 (m, 5H), 5.33 (dd, J=8.4, 6.7 Hz, 1H), 4.76-4.63 (m, 4H), 4.19 (td, J=7.7, 3.1 Hz, 2H), 3.88-3.80 (m, 1H), 2.89 (dddd, J=12.2, 8.8, 6.6, 3.3 Hz, 1H), 2.18 (dddd, J=12.1, 9.5, 7.5, 6.3 Hz, 1H). LC-MS (Method A): m/z=234.0 [M+H]$^+$, 0.73 min.

Example 12

Preparation of (3S)-2-Cyclopropanecarbonyl-3-phenyl-1,2-oxazolidine (12)

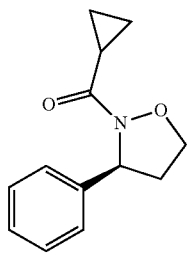 [SMILES: O=C(C1CC1)N1OCC[C@H]1c1ccccc1]

Cyclopropanecarboxylic acid (20 μL, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-d$_6$) δ 7.39-7.23 (m, 5H), 5.35 (dd, J=8.7, 6.1 Hz, 1H), 4.28 (td, J=7.7, 3.1 Hz, 1H), 3.86 (ddd, J=9.3, 8.0, 6.8 Hz, 1H), 2.88 (dddd, J=12.1, 8.8, 6.7, 3.3 Hz, 1H), 2.21 (dddd, J=12.1, 9.4, 7.6, 6.0 Hz, 2H), 0.89-0.73 (m, 4H). LC-MS (Method A): m/z=218.4 [M+H]$^+$, 0.90 min.

Example 13

Preparation of 2-Methoxy-1-[(3S)-3-phenyl-1,2-oxazolidin-2-yl]ethan-1-one (13)

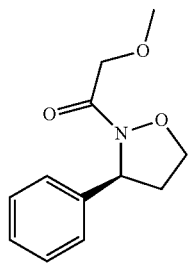 [SMILES: COCC(=O)N1OCC[C@H]1c1ccccc1]

2-Methoxyacetic acid (19 µL, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-$d_6$) δ 7.39-7.24 (m, 5H), 5.31 (dd, J=8.7, 6.4 Hz, 1H), 4.28-4.18 (m, 3H), 3.88 (ddd, J=9.6, 8.0, 6.5 Hz, 1H), 3.30 (s, 3H), 2.88 (dddd, J=12.1, 9.1, 6.5, 3.0 Hz, 1H), 2.17 (dddd, J=12.1, 9.6, 7.5, 6.4 Hz, 1H). LC-MS (Method A): m/z=222.3 [M+H]$^+$, 0.77 min.

Example 14

Preparation of (2R)-2-Hydroxy-1-[(3S)-3-phenyl-1,2-oxazolidin-2-yl]propan-1-one (14)

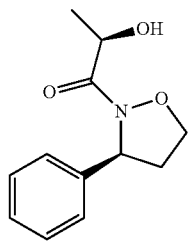 [SMILES: C[C@@H](O)C(=O)N1OCC[C@H]1c1ccccc1]

D-(−)-Lactic acid (23 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-$d_6$) δ 7.39-7.24 (m, 5H), 5.36-5.27 (m, 1H), 5.04-4.97 (m, 1H), 4.53-4.42 (m, 1H), 4.30-4.21 (m, 1H), 3.88 (ddd, J=9.2, 8.0, 6.7 Hz, 1H), 2.88 (dddd, J=12.2, 8.8, 6.7, 3.4 Hz, 1H), 2.21 (dddd, J=12.2, 9.2, 7.5, 6.1 Hz, 1H), 1.12-1.22 (m, 3H). LC-MS (Method A): m/z=222.0 [M+H]$^+$, 0.68 min.

Example 15

Preparation of (2S)-2-hydroxy-1-[(3S)-3-phenyl-1,2-oxazolidin-2-yl]propan-1-one (15)

L-(+)-Lactic acid (23 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-$d_6$) δ 7.40-7.23 (m, 5H), 5.34 (dd, J=6.4, 8.9 Hz, 1H), 4.84 (d, J=7.0 Hz, 1H), 4.54-4.44 (m, 1H), 4.25 (dt, J=2.6, 7.8 Hz, 1H), 3.86 (ddd, J=6.8, 8.0, 9.5 Hz, 1H), 2.93-2.85 (m, 1H), 2.18 (dddd, J=6.3, 7.6, 9.6, 12.2 Hz, 1H), 1.30 (d, J=6.8 Hz, 3H). LC-MS (Method A): m/z=222.2 [M+H]$^+$, 0.73 min.

Example 16

Preparation of 1-[(3S)-3-phenyl-1,2-oxazolidine-2-carbonyl]cyclopropane-1-carbonitrile (16)

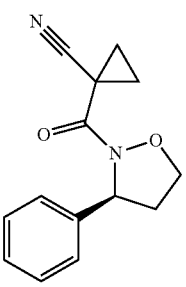 [SMILES: N#CC1(C(=O)N2OCC[C@H]2c2ccccc2)CC1]

1-Cyanocyclopropane-1-carboxylic acid (41 mg, 0.37 mmol) was reacted with (3S)-3-phenyl-1,2-oxazolidine (50 mg, 0.33 mmol) using general procedure A for amide coupling with DMF as solvent to afford the title compound. $^1$H NMR (400 MHz, CDCl$_3$) δ 7.23-7.45 (m, 5H), 5.43 (dd, J=8.5, 6.0 Hz, 1H), 4.45 (td, J=7.9, 3.3 Hz, 1H), 4.03-4.21 (m, 1H), 2.93 (dddd, J=12.3, 8.9, 6.9, 3.5 Hz, 1H), 2.47 (dddd, J=12.4, 9.3, 7.7, 6.0 Hz, 1H), 1.66-1.77 (m, 1H), 1.49-1.64 (m, 3H). LC-MS (Method A): m/z=243.3 [M+H]$^+$, 0.87 min.

Example 17

Preparation of 2,2-Dimethyl-3-oxo-3-[(3S)-3-phenyl-1,2-oxazolidin-2-yl]propanenitrile (17)

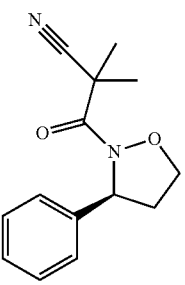 [SMILES: CC(C)(C#N)C(=O)N1OCC[C@H]1c1ccccc1]

2-Cyano-2,2-dimethylacetic acid (42 mg, 0.37 mmol) was reacted with (3S)-3-phenyl-1,2-oxazolidine (50 mg, 0.33 mmol) using general procedure A for amide coupling with DMF as solvent to afford the title compound. $^1$H NMR (400 MHz, CDCl$_3$) δ 7.22-7.43 (m, 5H), 5.41 (dd, J=8.9, 6.4 Hz, 1H), 4.39 (td, J=8.2, 2.8 Hz, 1H), 4.18 (ddd, J=9.7, 8.2, 6.7 Hz, 1H), 2.87-2.99 (m, 1H), 2.46 (dddd, J=12.4, 9.8, 7.8, 6.4 Hz, 1H), 1.73 (s, 3H), 1.61 (s, 3H). LC-MS (Method A): m/z=245.1 [M+H]$^+$, 0.95 min.

Example 18

Preparation of 3-[(3S)-3-phenyl-1,2-oxazolidine-2-carbonyl]-2,1-benzoxazole (18)

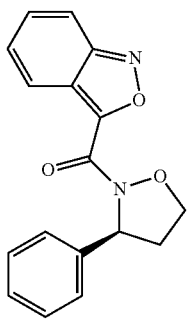 [SMILES: O=C(c1onc2ccccc12)N1OCC[C@H]1c1ccccc1]

2,1-Benzoxazole-3-carboxylic acid (42 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-d$_6$) δ 7.91 (td, J=0.9, 9.0 Hz, 1H), 7.78 (d, J=9.3 Hz, 1H), 7.51 (ddd, J=0.9, 6.3, 9.1 Hz, 1H), 7.45-7.37 (m, 4H), 7.34-7.27 (m, 2H), 5.71 (dd, J=6.3, 8.3 Hz, 1H), 4.40 (dt, J=3.5, 7.5 Hz, 1H), 4.09 (ddd, J=6.8, 8.0, 9.0 Hz, 1H), 3.01 (dddd, J=3.5, 6.8, 8.7, 12.1 Hz, 1H), 2.34 (dddd, J=6.0, 7.4, 9.0, 12.2 Hz, 1H). LC-MS (Method A): m/z=295.1 [M+H]$^+$, 1.03 min.

Example 19

Preparation of 2-Hydroxy-2-methyl-1-[(3S)-3-phenyl-1,2-oxazolidin-2-yl]propan-1-one (19)

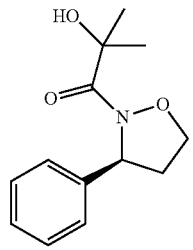 [SMILES: CC(C)(O)C(=O)N1OCC[C@H]1c1ccccc1]

2-Hydroxy-2-methylpropanoic acid (27 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-d$_6$) δ 7.39-7.23 (m, 5H), 5.39 (dd, J=6.5, 8.3 Hz, 1H), 4.77 (s, 1H), 4.27 (dt, J=3.1, 7.8 Hz, 1H), 3.92-3.84 (m, 1H), 2.94-2.84 (m, 1H), 2.24-2.11 (m, 1H), 1.39 (s, 3H), 1.37 (s, 3H). LC-MS (Method A): m/z=236.3 [M+H]$^+$, 0.84 min.

Example 20

Preparation of (3S)-2-(1-Methylcyclopropanecarbonyl)-3-phenyl-1,2-oxazolidine (20)

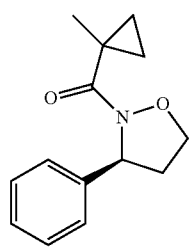 [SMILES: CC1(C(=O)N2OCC[C@H]2c2ccccc2)CC1]

1-Methylcyclopropane-1-carboxylic acid (26 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-d$_6$) δ 7.38-7.23 (m, 5H), 5.33 (dd, J=6.3, 8.8 Hz, 1H), 4.25 (dt, J=3.0, 7.5 Hz, 1H), 3.85 (ddd, J=6.7, 7.9, 9.5 Hz, 1H), 2.85 (dddd, J=3.0, 6.5, 9.0, 12.0 Hz, 1H), 2.16 (dddd, J=6.3, 7.7, 9.6, 12.1 Hz, 1H), 1.35 (s, 3H), 1.05-0.98 (m, 1H), 0.88 (ddd, J=4.0, 6.0, 9.9 Hz, 1H), 0.62-0.56 (m, 1H), 0.53-0.48 (m, 1H). LC-MS (Method A): m/z=232.3 [M+H]$^+$, 0.96 min.

Example 21

Preparation of (3S)-3-phenyl-2-{pyrazolo[1,5-a]pyridine-3-carbonyl}-1,2-oxazolidine (21)

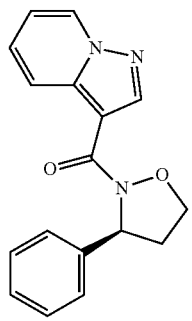 [SMILES: O=C(c1cnn2ccccc12)N1OCC[C@H]1c1ccccc1]

Pyrazolo[1,5-a]pyridine-3-carboxylic acid (42 mg, 0.26 mmol) was reacted with (3S)-3-phenyl-1,2-oxazolidine (40 mg, 0.26 mmol) using general procedure A for amide coupling to afford the title compound. $^1$H NMR (400 MHz, DMSO-$d_6$) δ 8.86 (td, J=1.0, 7.0 Hz, 1H), 8.64 (s, 1H), 8.25 (td, J=1.2, 8.8 Hz, 1H), 7.55 (ddd, J=1.0, 6.8, 9.0 Hz, 1H), 7.43-7.36 (m, 4H), 7.31-7.26 (m, 1H), 7.15 (dt, J=1.3, 6.9 Hz, 1H), 5.62 (dd, J=6.3, 8.5 Hz, 1H), 4.37 (dt, J=2.9, 7.7 Hz, 1H), 3.88 (ddd, J=6.8, 8.0, 9.5 Hz, 1H), 2.92 (dddd, J=3.0, 6.5, 9.0, 12.0 Hz, 1H), 2.27 (dddd, J=6.3, 7.7, 9.6, 12.1 Hz, 1H). LC-MS (Method A): m/z=294.3 [M+H]$^+$, 0.98 min.

Example 22

Preparation of tert-Butyl (3S)-3-phenyl-1,2-oxazolidine-2-carboxylate (22)

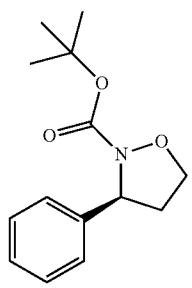 [SMILES: CC(C)(C)OC(=O)N1OCC[C@H]1c1ccccc1]

Methanesulfonyl chloride (1.4 mL, 18.91 mmol) was added to a solution of tert-butyl N-[(3R)-3-hydroxy-3-phenylpropoxy]carbamate (4.4 g, 16.45 mmol) and Et$_3$N (4.5 mL, 32.9 mmol) in CH$_2$Cl$_2$ (383 mL) which had been pre-cooled to 0° C. The reaction was stirred at 0° C. for 1.5 h. The reaction was diluted with CH$_2$Cl$_2$ and washed with water. The organic portion was dried over Na$_2$SO$_4$, filtered and concentrated under reduced pressure. The crude product was purified by column chromatography (cyclohexane-EtOAc, 100:0 to 50:50) to afford the title compound. $^1$H NMR (400 MHz, DMSO-$d_6$) δ 7.40-7.18 (m, 5H), 5.15 (dd, J=5.9, 8.7 Hz, 1H), 4.14 (dt, J=2.9, 8.1 Hz, 1H), 3.72 (ddd, J=6.9, 8.0, 9.4 Hz, 1H), 2.80 (dddd, J=3.1, 6.8, 8.8, 12.1 Hz, 1H), 2.20-2.07 (m, 1H), 1.38 (s, 9H). LC-MS (Method A): m/z=194.1 [M+H−tBu]$^+$ and 250.3 [M+H]$^+$, 1.07 min.

Example 23

Preparation of 1-[3-(3-Fluorophenyl)-1,2-oxazolidin-2-yl]-2,2-dimethylpropan-1-one (23)

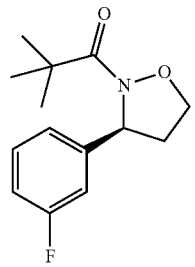 [SMILES: CC(C)(C)C(=O)N1OCC[C@H]1c1cccc(F)c1]

Pivaloyl chloride (53 μL, 0.430 mmol) was added to a solution 3-(3-fluorophenyl)-1,2-oxazolidine (60 mg, 0.359 mmol) and Et$_3$N (75 μL, 0.539 mmol) in CH$_2$Cl$_2$ (2.5 mL). The reaction mixture was stirred at room temperature for 40 min, diluted with CH$_2$Cl$_2$ and washed with sat. NH$_4$Cl solution. The organic portion was dried over Na$_2$SO$_4$, filtered and concentrated under reduced pressure. The mixture of enantiomers was resolved by chiral HPLC on a Chiralcel OJ-H (25×2.0 cm), 5 μm column using a mobile phase of n-hexane/2-propanol 90/10% v/v to afford the title compound. $^1$H NMR (400 MHz, CDCl$_3$) δ 7.34-7.27 (m, 1H), 7.11-7.07 (m, 1H), 7.02 (dt, J=9.8, 2.0 Hz, 1H), 6.95 (tdd, J=8.4, 2.6, 0.9 Hz, 1H), 5.42 (dd, J=8.8, 6.5 Hz, 1H), 4.31-4.24 (m, 1H), 3.90 (ddd, J=9.8, 8.0, 6.5 Hz, 1H), 2.83 (dddd, J=12.1, 9.1, 6.4, 2.8 Hz, 1H), 2.30 (dddd, J=12.3, 9.8, 7.7, 6.4 Hz, 1H), 1.31 (s, 9H). LC-MS (Method A): m/z=252.2 [M+H]$^+$, 1.14 min. e.e.=100% as determined on a Chiralcel OJ-H (25×0.46 cm), 5 μm column using a mobile phase of n-hexane/2-propanol 90/10% v/v.

Example 24

Preparation of 1-[3-(2-Fluorophenyl)-1,2-oxazolidin-2-yl]-2,2-dimethylpropan-1-one (24)

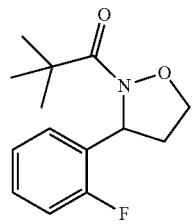 [SMILES: CC(C)(C)C(=O)N1OCCC1c1ccccc1F]

3-(2-Fluorophenyl)-1,2-oxazolidine (31 mg, 0.18 mmol) was dissolved in dry CH$_2$Cl$_2$ (1.76 mL). Pyridine (30 μL, 0.36 mmol) and a solution of pivaloyl chloride (27 μL, 0.216 mmol) in dry CH$_2$Cl$_2$ (0.1 mL) were then added at 0° C. The mixture was stirred at room temperature for 3 h, then a second addition of pyridine (15 μL, 0.18 mmol) and a solution of pivaloyl chloride (13.5 μL, 0.108 mmol) in dry CH$_2$Cl$_2$ (0.05 mL) was made. The reaction mixture was stirred at room temperature for a further 3 h then the mixture was concentrated under reduced pressure. The residue was dissolved in EtOAc and washed with sat. aqueous NH$_4$Cl solution, with sat. aqueous NaHCO$_3$ solution and with brine.

The organic phase was dried over Na₂SO₄, filtered and concentrated under reduced pressure. The crude product (44 mg) was purified by column chromatography (cyclohexane-EtOAc, 95:5 to 60:40) to afford the title compound as a mixture of enantiomers. ¹H NMR (400 MHz, CDCl₃) δ 7.31-7.21 (m, 2H), 7.14-7.02 (m, 2H), 5.69 (dd, J=8.8, 8.0 Hz, 1H), 4.25 (dt, J=8.5, 3.0 Hz, 1H), 3.96-3.88 (m, 1H), 2.95-2.85 (m, 1H), 2.32-2.22 (m, 1H), 1.33 (s, 9H). LC-MS (Method A): m/z=252.3 [M+H]⁺, 1.14 min.

Example 25

Preparation of 1-[3-(4-Fluorophenyl)-1-oxazolidin-2-yl]-2,2-dimethylpropan-1-one (25)

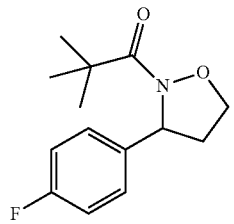 [SMILES: CC(C)(C)C(=O)N1OCCC1c1ccc(F)cc1]

Pivaloyl chloride (0.1 mL, 0.8 mmol) was added to a solution of 3-(4-fluorophenyl)-1,2-oxazolidine (90 mg, 0.54 mmol) and pyridine (0.1 mL, 1.35 mmol) in CH₂Cl₂ (4 mL). The reaction mixture was stirred at room temperature for 2 h. Volatiles were removed under reduced pressure. The crude product was purified by reverse phase chromatography (water-CH₃CN, 100:0 to 70:30) to afford the title compound as a mixture of enantiomers. ¹H NMR (400 MHz, CDCl₃) δ 7.34-7.22 (m, 2H), 7.08-6.96 (m, 2H), 5.40 (dd, J=8.8, 6.5 Hz, 1H), 4.27 (tdd, J=7.8, 2.9, 0.8 Hz, 1H), 3.89 (ddd, J=9.9, 8.0, 6.5 Hz, 1H), 2.88-2.74 (m, 1H), 2.30 (dddd, J=12.3, 9.9, 7.7, 6.5 Hz, 1H), 1.30 (s, 9H). LC-MS (Method A): m/z=252.2 [M+H]⁺, 1.17 min.

Example 26

Preparation of tert-Butyl 3-(2-fluorophenyl)-1,2-oxazolidine-2-carboxylate (26)

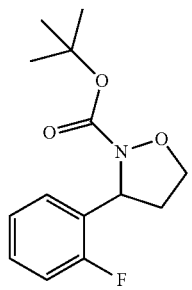 [SMILES: CC(C)(C)OC(=O)N1OCCC1c1ccccc1F]

Methanesulfonyl chloride (57 μL, 0.746 mmol) was added to a solution of tert-butyl N-[3-(2-fluorophenyl)-3-hydroxypropoxy]carbamate (185 mg, 0.65 mmol) and Et₃N (0.182 mL, 1.3 mmol) in dry CH₂Cl₂ (15 mL) at 0° C. The reaction mixture was stirred at 0° C. for 2 h then a second addition of methanesulfonyl chloride (0.011 mL, 0.15 mmol) and Et₃N (36 μL, 0.26 mmol) was made. After 5 h the reaction was diluted with CH₂Cl₂ and washed with sat. aqueous NaHCO₃ solution and sat. aqueous NH₄Cl solution. The organic portion was dried over Na₂SO₄, filtered and concentrated under reduced pressure. The crude product (178 mg) was purified by column chromatography (cyclohexane-EtOAc, 95:5 to 60:40) to afford the title compound as a mixture of enantiomers. ¹H NMR (400 MHz, CDCl₃) δ 7.50 (dt, J=8.0, 1.5 Hz, 1H), 7.28-7.22 (m, 1H), 7.17-7.11 (m, 1H), 7.08-7.01 (m, 1H), 5.54-5.48 (m, 1H), 4.17 (dt, J=8.0, 3.7 Hz, 1H), 3.96-3.88 (m, 1H), 2.90-2.80 (m, 1H), 2.30-2.20 (m, 1H), 1.48 (s, 9H). LC-MS (Method A): m/z=268.1 [M+H]⁺, 1.17 min.

Example 27

Preparation of tert-Butyl 3-(4-fluorophenyl)-1,2-oxazolidine-2-carboxylate (27)

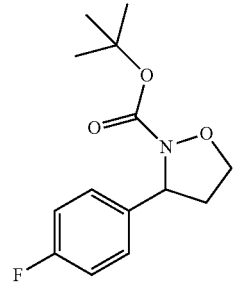 [SMILES: CC(C)(C)OC(=O)N1OCCC1c1ccc(F)cc1]

Methanesulfonyl chloride (130 μL, 1.73 mmol) was added to a solution of tert-butyl N-[3-(4-fluorophenyl)-3-hydroxypropoxy]carbamate (430 mg, 1.5 mmol) and Et₃N (410 μL, 3.0 mmol) in CH₂Cl₂ (15 mL) which had been pre-cooled to 0° C. The reaction mixture was stirred at 0° C. for 1 h and at room temperature for 1 h. The reaction mixture was diluted with CH₂Cl₂ and washed with sat. NaHCO₃ solution and sat. NH₄Cl solution. The organic portions were combined, dried over Na₂SO₄, filtered and concentrated under reduced pressure. The crude product was purified by column chromatography (cyclohexane-EtOAc, 100:0 to 80:20) to afford the title compound as a mixture of enantiomers. ¹H NMR (400 MHz, CDCl₃) δ 7.40-7.30 (m, 2H), 7.09-6.97 (m, 2H), 5.20 (dd, J=8.7, 5.5 Hz, 1H), 4.28-4.13 (m, 1H), 3.91 (ddd, J=8.9, 8.2, 7.0 Hz, 1H), 2.79 (dddd, J=12.3, 8.7, 7.0, 3.7 Hz, 1H), 2.28 (dddd, J=12.2, 8.9, 7.6, 5.6 Hz, 1H), 1.48 (s, 9H). LC-MS (Method A): m/z=212.2 [M−tBu]⁺, 1.10 min.

Examples 28 and 29

Preparation of 1-[(3R)-3-(6-fluoropyridin-3-yl)-1-oxazolidin-2-yl]-2-dimethylpropan-1-one and 1-[(3S)-3-(6-fluoropyridin-3-yl)-1,2-oxazolidin-2-yl]-2,2-dimethylpropan-1-one (62 and 61)

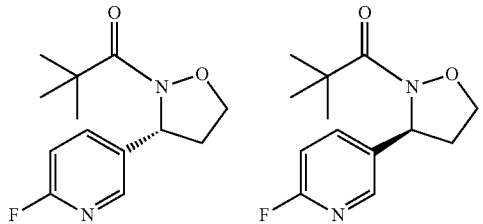 [SMILES: CC(C)(C)C(=O)N1OCC[C@@H]1c1ccc(F)nc1 ; CC(C)(C)C(=O)N1OCC[C@H]1c1ccc(F)nc1]

Trifluoroacetic acid (500 μL) was added to a solution of tert-butyl 3-(6-fluoropyridin-3-yl)-1,2-oxazolidine-2-carboxylate (161 mg, 0.60 mmol) in CH₂Cl₂ (5 mL). The reaction was stirred at room temperature for 30 min and concentrated under reduced pressure to give crude 2-fluoro-5-(1,2-oxazolidin-3-yl)pyridine as its trifluoracetic acid salt (157 mg). Et₃N (300 μL, 2.15 mmol) and pivaloyl chloride (100 μL, 0.851 mmol) were sequentially added to a solution of the crude 2-fluoro-5-(1,2-oxazolidin-3-yl)pyridine trifluoroacetic acid salt (75 mg) in CH₂Cl₂ (3 mL). The reaction was stirred at room temperature for 1 h, diluted with CH₂Cl₂ and washed twice with sat. NaHCO₃ solution. The organic portion was dried over Na₂SO₄, filtered and concentrated under reduced pressure. The crude product was purified by reverse phase chromatography (water-CH₃CN, 100:0 to 20:80) to afford the title compound as a mixture of enantiomers. This mixture was resolved by chiral HPLC on a Chiralpak AD-H (25×2.0 cm), 5 μm column using a mobile phase of n-hexane/2-propanol 80/20% v/v to afford the two separated enantiomers.

First eluting enantiomer, 1-[(3R)-3-(6-fluoropyridin-3-yl)-1,2-oxazolidin-2-yl]-2,2-dimethylpropan-1-one. ¹H NMR (400 MHz, CDCl₃) δ 8.20 (d, J=2.5 Hz, 1H), 7.74 (td, J=8.0, 2.4 Hz, 1H), 6.92 (dd, J=8.4, 2.9 Hz, 1H), 5.45 (dd, J=8.8, 6.8 Hz, 1H), 4.35-4.28 (m, 1H), 3.93 (ddd, J=10.0, 8.1, 6.5 Hz, 1H), 2.87 (dddd, J=12.4, 8.9, 6.4, 2.6 Hz, 1H), 2.32 (dddd, J=12.4, 10.0, 7.7, 6.8 Hz, 1H), 1.30 (s, 9H). LC-MS (Method A): m/z=253.2 [M+H]⁺, 0.92 min. e.e.=100% as determined on a Chiralpak AD-H (25×0.46 cm), 5 μm column using a mobile phase of n-hexane/2-propanol 80/20% v/v.

Second eluting enantiomer, 1-[(3S)-3-(6-fluoropyridin-3-yl)-1,2-oxazolidin-2-yl]-2,2-dimethylpropan-1-one. ¹H NMR (400 MHz, CDCl₃) δ 8.22-8.18 (m, 1H), 7.74 (td, J=7.9, 2.5 Hz, 1H), 6.92 (dd, J=8.4, 2.9 Hz, 1H), 5.51-5.41 (m, 1H), 4.32 (td, J=8.0.2.4 Hz, 1H), 3.98-3.85 (m, 1H), 2.94-2.80 (m, 1H), 2.39-2.25 (m, 1H), 1.30 (s, 9H). LC-MS (Method A): m/z=253.3 [M+H]⁺, 0.92 min. e.e.=100% as determined on a Chiralpak AD-H (25×0.46 cm), 5 μm column using a mobile phase of n-hexane/2-propanol 80/20% v/v.

Example 30

Preparation of 1-[(3S)-3-(6-fluoropyridin-3-yl)-1,2-oxazolidin-2-yl]-2,2-dimethylpropan-1-one (61)

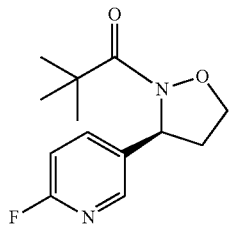 [SMILES: CC(C)(C)C(=O)N1OCC[C@H]1c1ccc(F)nc1]

Pivaloyl chloride (256 μL, 2.09 mmol) was added to a solution of 2-fluoro-5-[(3S)-1,2-oxazolidin-3-yl]pyridine (320 mg) and Et₃N (396 μL, 2.85 mmol) in CH₂Cl₂ (10 mL) which had been pre-cooled to 0° C. The reaction mixture was stirred at 0° C. for 30 min, then diluted with CH₂Cl₂ and washed with water. The organic portion was dried over Na₂SO₄, filtered and concentrated under reduced pressure. The crude product was purified by column chromatography (cyclohexane-EtOAc, 100:0 to 0:100) to give the title compound (452 mg) as a 4.7:95.3 mixture of enantiomers. This mixture was resolved by chiral HPLC on a Chiralpak AD-H (25×2.0 cm), 5 μm column using a mobile phase of n-hexane/2-propanol 80/20% v/v to afford the title compound. ¹H NMR (400 MHz, CDCl₃) δ 8.20 (d, J=2.5 Hz, 1H), 7.74 (td, J=8.0, 2.6 Hz, 1H), 6.92 (dd, J=8.5, 3.0 Hz, 1H), 5.45 (dd, J=8.8, 6.8 Hz, 1H), 4.32 (td, J=7.8, 2.6 Hz, 1H), 3.93 (ddd, J=10.0, 8.2, 6.4 Hz, 1H), 2.92-2.83 (m, 1H), 2.32 (dddd, J=12.4, 10.0, 7.6, 6.9 Hz, 1H), 1.30 (s, 9H). LC-MS (Method A): m/z=253.2 [M+H]⁺, 0.92 min. e.e.=100% as determined on a Chiralpak AD-H (25×2.0 cm), 5 μm column using a mobile phase of n-hexane/2-propanol 80/20% v/v.

Example 31 and 32

Preparation of 1-[3-(4-Fluorophenyl)-1,2-oxazolidin-2-yl]-2,2-dimethylpropan-1-one Enantiomer 1 and Enantiomer 2 (73 and 74)

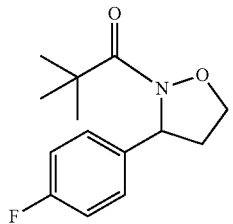 [SMILES: CC(C)(C)C(=O)N1OCCC1c1ccc(F)cc1]

Pivaloyl chloride (0.1 mL, 0.8 mmol) was added to a solution of 3-(4-fluorophenyl)-1,2-oxazolidine (90 mg, 0.54 mmol) and pyridine (0.1 mL, 1.35 mmol) in CH₂Cl₂ (4 mL). The reaction mixture was stirred at room temperature for 2 h. Volatiles were removed under reduced pressure. The crude product was purified by reverse phase chromatography (water-CH₃CN, 100:0 to 70:30) to afford (S)-1-[3-(4-fluorophenyl)-1,2-oxazolidin-2-yl]-2,2-dimethylpropan-1-one and (R)-1-[3-(4-fluorophenyl)-1,2-oxazolidin-2-yl]-2,2- dimethylpropan-1-one as a mixture of enantiomers. This mixture was resolved by chiral HPLC on a Chiralcel OJ-H (25×2.0 cm), 5 μm column using a mobile phase of n-hexane/(EtOH/MeOH 1/1+0.1% isopropylamine) 85/15% v/v to afford the two title compounds as separated enantiomers.

First eluting enantiomer, Enantiomer 1. ¹H NMR (400 MHz, CDCl₃) δ 7.36-7.22 (m, 3H), 7.11-6.92 (m, 2H), 5.40 (dd, J=8.8, 6.5 Hz, 1H), 4.27 (dt, J=7.9, 2.8 Hz, 1H), 3.90 (ddd, J=9.9, 7.9, 6.5 Hz, 1H), 2.82 (dddd, J=12.1, 9.1, 6.4, 2.8 Hz, 1H), 2.30 (dddd, J=12.3, 9.9, 7.6, 6.7 Hz, 1H), 1.30 (s, 9H). LC-MS (Method A): m/z=252.2 [M+H]⁺, 1.10 min. e.e.=100% as determined on a Chiralcel OJ-H (25×0.46 cm), 5 μm column using a mobile phase of n-hexane/(EtOH/MeOH 1/1+0.1% isopropylamine) 85/15% v/v Second eluting enantiomer, Enantiomer 2. ¹H NMR (400 MHz, CDCl₃) δ 7.33-7.24 (m, 2H), 7.07-6.98 (m, 2H), 5.40 (dd, J=8.8, 6.8 Hz, 1H), 4.27 (dt, J=2.8, 7.8 Hz, 1H), 3.90 (ddd, J=9.9, 8.0, 6.5 Hz, 1H), 2.82 (dddd, J=12.2, 9.1, 6.4, 2.9 Hz, 1H), 2.30 (dddd, J=12.3, 9.9, 7.6, 6.7 Hz, 1H), 1.30 (s, 9H). LC-MS (Method A): m/z=252.2 [M+H]⁺, 1.11 min. e.e.=100% as determined on a Chiralcel OJ-H (25×0.46 cm), 5 μm column using a mobile phase of n-hexane/(EtOH/MeOH 1/1+0.1% isopropylamine) 85/15% v/v.

Example 33

Preparation of 4-[(3S)-2-(2,2-dimethylpropanoyl)-1,2-oxazolidin-3-yl]benzonitrile (87)

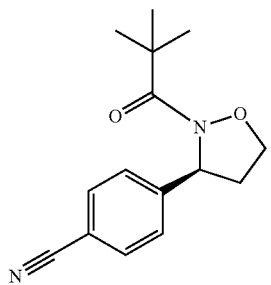 [SMILES: CC(C)(C)C(=O)N1OCC[C@H]1c1ccc(C#N)cc1]

Pivaloyl chloride (1.52 mL, 12.5 mmol) was added to a solution of 4-(1,2-oxazolidin-3-yl)benzonitrile (1.45 g, 8.33 mmol) and pyridine (1.68 mL, 20.82 mmol) in CH₂Cl₂ (20 mL). The reaction mixture was stirred at room temperature for 1 h. Volatiles were removed under reduced pressure. The crude product was purified by column chromatography (cyclohexane-EtOAc, 100:0 to 70:30) to afford the title compound (2.06 g, 96%) as a mixture of enantiomers. This mixture was resolved by chiral HPLC on a Chiralpak AD-H (25×2.0 cm) 5 μm column using a mobile phase of n-hexane/(ethanol+0.1% isopropylamine) 70/30 v/v and a flow rate of 18 mL/min to afford the title compound. ¹H NMR (400 MHz, CDCl₃) δ 7.68-7.60 (m, 2H), 7.45-7.37 (m, 2H), 5.43 (dd, J=9.0, 6.8 Hz, 1H), 4.34-4.24 (m, 1H), 3.91 (ddd, J=10.1, 8.1, 6.3 Hz, 1H), 2.87 (dddd, J=12.3, 8.9, 6.4, 2.6 Hz, 1H), 2.27 (dddd, J=12.3, 10.0, 7.7, 6.8 Hz, 1H), 1.30 (s, 9H). LC-MS (Method A): m/z=259.2 [M+H]⁺, 1.03 min.

Example 34

Preparation of 4-[(3S)-2-(3,3-difluoro-2,2-dimethylpropanoyl)-1,2-oxazolidin-3-yl]benzonitrile (88)

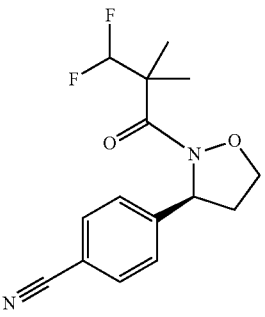 [SMILES: CC(C)(C(=O)N1OCC[C@H]1c1ccc(C#N)cc1)C(F)F]

To a solution of 3,3-difluoro-2,2-dimethylpropanoic acid (43 mg, 0.316 mmol) in CH₂Cl₂ (2 mL) were added oxalylchloride (26 μL, 0.316 mmol) and a drop of DMF. The mixture was stirred at room temperature for 2 h, then concentrated under reduced pressure. The residue was redissolved in CH₂Cl₂ (2 mL) and this solution was then added slowly to a stirred solution of 4-(1,2-oxazolidin-3-yl)benzonitrile (50 mg, 0.28 mmol) and DIPEA (0.12 mL, 0.70 mmol) in CH₂Cl₂ (2 mL) at 0° C. The mixture was stirred at room temperature for 2 h, then the solvent was evaporated under reduced pressure. The crude product was purified by column chromatography (cyclohexane-EtOAc, 1:1) to afford the title compound. ¹H NMR (400 MHz, CDCl₃) δ 7.69-7.61 (m, 2H), 7.43-7.35 (m, 2H), 6.32 (t, J=57.2 Hz, 1H), 5.44 (dd, J=8.9, 6.8 Hz, 1H), 4.38-4.28 (m, 1H), 3.97 (ddd, J=9.8, 8.1, 6.4 Hz, 1H), 2.91 (dddd, J=12.0, 9.1, 6.4, 2.9 Hz, 1H), 2.31 (dddd, J=12.4, 9.9, 7.6, 6.7 Hz, 1H), 1.42-1.36 (m, 6H). LC-MS (Method A): m/z=295.1 [M+H]⁺, 1.03 min.

Example 35

Preparation of 1-[(3S)-3-(5-chloropyridin-2-yl)-1,2-oxazolidin-2-yl]-2,2-dimethylpropan-1-one (89)

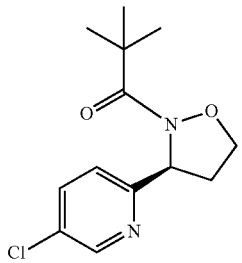 [SMILES: CC(C)(C)C(=O)N1OCC[C@H]1c1ccc(Cl)cn1]

Pivaloyl chloride (22 μL, 0.179 mmol) was added to a solution of 5-chloro-2-[(3 S)-1,2-oxazolidin-3-yl]pyridine (32 mg, 0.174 mmol) and triethylamine (34 μL, 0.244 mmol) in CH₂Cl₂ (3 mL), which had been pre-cooled to 0° C. The reaction was stirred at 0° C. for 30 min, diluted with CH₂Cl₂ and washed with water. The organic portion was dried over Na₂SO₄, filtered and concentrated under reduced pressure. The crude product was purified by column chromatography (cyclohexane-EtOAc, 100:0 to 0:100) to afford the title compound. $^1$H NMR (400 MHz, CDCl$_3$) δ 8.54-8.52 (m, 1H), 7.63 (dd, J=8.5, 2.5 Hz, 1H), 7.32 (d, J=8.5 Hz, 1H), 5.50 (dd, J=9.0, 6.3 Hz, 1H), 4.33-4.22 (m, 1H), 3.94 (ddd, J=9.4, 7.9, 6.8 Hz, 1H), 2.85-2.75 (m, 1H), 2.71-2.60 (m, 1H), 1.31 (s, 9H). LC-MS (Method A): m/z=269.1 [M+H]$^+$, 1.02 min.

Example 36

Preparation of (3S)-2-[1-(2,2-difluoroethyl)-3-methylazetidine-3-carbonyl]-3-(4-fluorophenyl)-1,2-oxazolidine (90)

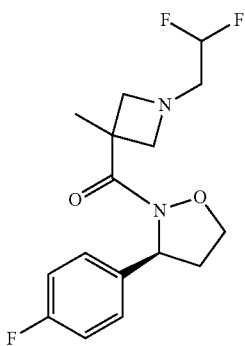 [SMILES: CC1(C(=O)N2OCC[C@H]2c2ccc(F)cc2)CN(CC(F)F)C1]

Et$_3$N (37 µL, 0.264 mmol) and 2,2-difluoroethyl methanesulfonate (28 mg, 0.132 mmol) were sequentially added to a solution of (3S)-3-(4-fluorophenyl)-2-(3-methylazetidine-3-carbonyl)-1,2-oxazolidine (24 mg, 0.088 mmol) in CH$_2$Cl$_2$ (5 mL) which had been pre-cooled to 0° C. The reaction was stirred at 0° C. for 2 h, diluted with CH$_2$Cl$_2$ and washed with water. The organic portion was dried over Na$_2$SO$_4$, filtered and concentrated under reduced pressure. The crude product was purified by column chromatography (KP-NH, cyclohexane-EtOAc, 100:0 to 50:50) to afford the title compound. $^1$H NMR (400 MHz, CDCl$_3$) δ 7.31-7.25 (m, 2H), 7.09-7.01 (m, 2H), 5.74 (tt, J=56.2, 5.0 Hz, 1H), 5.37 (dd, J=8.7, 6.1 Hz, 1H), 4.24 (td, J=7.6, 3.6 Hz, 1H), 3.92 (ddd, J=9.0, 8.0, 6.8 Hz, 1H), 3.57 (d, J=7.5 Hz, 1H), 3.42-3.37 (m, 3H), 2.73-2.91 (m, 3H), 2.35 (dddd, J=12.4, 9.2, 7.5, 6.3 Hz, 1H), 1.65 (s, 3H). LC-MS (Method A): m/z=329.2 [M+H]$^+$, 0.50 min.

Examples 37 and 38

Preparation of 4-[(3S)-2-(3,3-difluoro-2-methylpropanoyl)-1,2-oxazolidin-3-yl]benzonitriles (91) and (92)

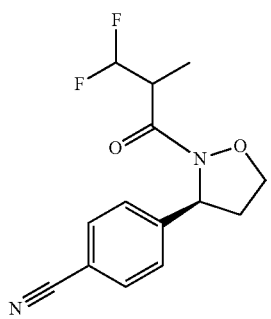 [SMILES: CC(C(=O)N1OCC[C@H]1c1ccc(C#N)cc1)C(F)F]

DMF (20 µL) and oxalyl chloride (50 µL, 0.590 mmol) were sequentially added to a solution of the mixture containing 3,3-difluoro-2-methylpropanoic acid (100 mg) and the reaction was stirred at room temperature for 1 h. A solution of 4-[(3S)-1,2-oxazolidin-3-yl]benzonitrile (100 mg, 0.575 mmol) and DIPEA (250 µL, 1.44 mmol) in CH$_2$Cl$_2$ (2 mL) was added. The reaction was stirred at room temperature for 1.5 h, diluted with CH$_2$Cl$_2$ and washed twice with water. The organic portion was dried over Na$_2$SO$_4$, filtered and concentrated under reduced pressure to provide 4-[(3S)-2-((S)-3,3-difluoro-2-methylpropanoyl)-1,2-oxazolidin-3-yl]benzonitrile and 4-[(3S)-2-((R)-3,3-difluoro-2-methylpropanoyl)-1,2-oxazolidin-3-yl]benzonitrile. The crude product was purified by column chromatography (cyclohexane-EtOAc, 100:0 to 0:100) to afford the first eluting diastereoisomer of the title compound and a mixture of the second eluting diastereoisomer with several byproducts. The latter was further purified by semi-preparative HPLC to afford the second eluting diastereoisomer of the title compound (2.1 mg).

First eluting diastereoisomer, Diastereoisomer 1: $^1$H NMR (400M Hz, DMSO-d$_6$) δ 7.89-7.80 (m, 2H), 7.53-7.45 (m, 2H), 6.13 (td, J=55.7, 6.3 Hz, 1H), 5.51-5.37 (m, 1H), 4.30 (td, J=7.5, 2.5 Hz, 1H), 3.99-3.85 (m, 1H), 3.52-3.36 (m, 1H), 3.06-2.84 (m, 1H), 2.29-2.10 (m, 1H), 1.24 (d, J=7.0 Hz, 3H). LC-MS (Method A): m/z=281.2 [M+H]$^+$, 0.95 min.

Second eluting diastereoisomer, Diastereoisomer 2: $^1$H NMR (400 MHz, DMSO-d$_6$) δ 7.91-7.80 (m, 2H), 7.51-7.44 (m, 2H), 6.19 (td, J=60.5, 9.5 Hz, 1H), 5.42 (t, J=7.7 Hz, 1H), 4.29 (td, J=7.8, 3.1 Hz, 1H), 3.97 (ddd, J=9.4, 8.0, 6.4 Hz, 1H), 3.56-3.38 (m, 1H), 2.95 (dddd, J=12.2, 9.1, 6.2, 3.1 Hz, 1H), 2.28-2.10 (m, 1H), 1.14 (d, J=7.0 Hz, 3H). LC-MS (Method A): m/z=281.2 [M+H]$^+$, 0.94 min.

Example 39

Preparation of 2-fluoro-5-[(3S)-2-[(1-methylcyclopropyl)sulfonyl]-1,2-oxazolidin-3-yl]pyridine (93)

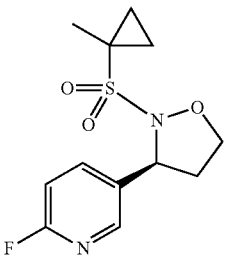 [SMILES: CC1(S(=O)(=O)N2OCC[C@H]2c2ccc(F)nc2)CC1]

A solution of 2-fluoro-5-[(3S)-1,2-oxazolidin-3-yl]pyridine (30 mg, 0.179 mmol), 1-methylcyclopropane-1-sulfonyl chloride (30 mg, 0.197 mmol), pyridine (40 µL, 0.358 mmol) and DMAP (5 mg, 0.041 mmol) in CH$_2$Cl$_2$ (1.5 mL) was stirred at room temperature for 20 h. Although not complete, the reaction was diluted with CH$_2$Cl$_2$ and washed with 0.5M HCl solution. The organic portion was washed with 1M HCl solution and sat. NaHCO$_3$ solution, dried over Na$_2$SO$_4$, filtered and concentrated under reduced pressure. The crude product was purified by column chromatography (cyclohexane-EtOAc, 100:0 to 70:30) to afford the title compound. $^1$H NMR (400 MHz, CDCl$_3$) δ 8.29-8.24 (m, 1H), 7.84 (td, J=8.0, 2.3 Hz, 1H), 6.95 (dd, J=8.5, 2.8 Hz, 1H), 5.44 (dd, J=8.3, 5.5 Hz, 1H), 4.43-4.34 (m, 1H), 4.24-4.16 (m, 1H), 2.98-2.87 (m, 1H), 2.35 (dtd, J=12.3, 8.2, 5.5 Hz, 1H), 1.68-1.58 (m, 4H), 1.48 (ddd, J=10.6, 6.5, 5.5 Hz, 1H), 1.03 (ddd, J=9.1, 6.8, 5.4 Hz, 1H), 0.86 (ddd, J=9.0, 7.0, 5.3 Hz, 1H). LC-MS (Method A): m/z=287.1 [M+H]⁺, 0.90 min.

Examples 40 and 41

Preparation of 3,3,3-trifluoro-1-[(3S)-3-(4-fluorophenyl)-1,2-oxazolidin-2-yl]-2-methylpropan-1-ones (94) and (95)

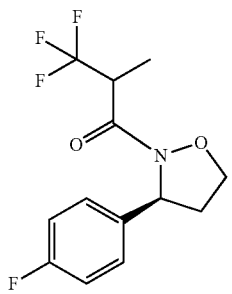 [SMILES: CC(C(=O)N1OCC[C@H]1c1ccc(F)cc1)C(F)(F)F]

A solution of (3S)-3-(4-fluorophenyl)-1,2-oxazolidine (30 mg, 0.179 mmol), 3,3,3-trifluoro-2-methylpropanoic acid (28 mg, 0.197 mmol), T₃P (50% wt solution in EtOAc, 234 μL, 0.394 mmol) and pyridine (40 μL, 0.537 mmol) in EtOAc (1 mL) was stirred at room temperature for 1.5 h. The reaction was diluted with EtOAc and the organic portion was washed with 1M HCl solution and sat. NaHCO₃ solution, dried over Na₂SO₄, filtered and concentrated under reduced pressure to provide (R)-3,3,3-trifluoro-1-[(3S)-3-(4-fluorophenyl)-1,2-oxazolidin-2-yl]-2-methylpropan-1-one and (S)-3,3,3-trifluoro-1-[(3S)-3-(4-fluorophenyl)-1,2-oxazolidin-2-yl]-2-methylpropan-1-one. The crude product was purified by chiral HPLC on a Chiralcel OJ-H (25×2.0 cm), 5 μm column using a mobile phase of n-hexane/(ethanol/methanol+0.1% isopropylamine) 30/70% v/v and a flow rate of 18 mL/min to afford the two separated diastereoisomers of the title compound.

First eluting diastereoisomer. Diastereoisomer 1: ¹H NMR (400 MHz, CDCl₃) δ 7.31-7.22 (m, 2H), 7.00-7.08 (m, 2H), 5.41 (dd, J=8.5, 5.8 Hz, 1H), 4.31 (td, J=7.6, 3.9 Hz, 1H), 4.03-3.93 (m, 1H), 3.92-3.79 (m, 1H), 2.88 (dddd, J=12.4, 8.7, 6.8, 4.0 Hz, 1H), 2.44-2.34 (m, 1H), 1.38 (d, J=7.0 Hz, 3H). LC-MS (Method A): m/z=292.1 [M+H]⁺, 1.05 min.

Second eluting diastereoisomer, Diastereoisomer 2: ¹H NMR (400 MHz, CDCl₃) δ 7.29-7.21 (m, 2H), 7.06-6.98 (m, 2H), 5.37 (dd, J=8.8, 5.3 Hz, 1H), 4.32 (td, J=7.7, 4.5 Hz, 1H), 4.05 (td, J=8.2, 7.0 Hz, 1H), 2.96-2.85 (m, 1H), 2.42-2.31 (m, 1H), 1.97-1.85 (m, 1H), 1.48 (br. s., 3H). LC-MS (Method A): m/z=292.1 [M+H]⁺, 1.07 min.

Example 42

Preparation of 1-[(3S)-3-(4-fluorophenyl)-1,2-oxazolidin-2-yl]-3-hydroxy-2,2-dimethylpropan-1-one (96)

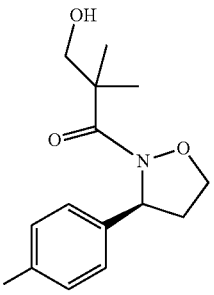

A mixture of (3S)-3-(4-fluorophenyl)-1,2-oxazolidine (100 mg, 0.6 mmol), 3-hydroxy-2,2-dimethylpropanoic acid (85 mg, 0.72 mmol), HATU (456 mg, 1.2 mmol) and DIPEA (0.2 mL, 1.2 mmol) in CH₂Cl₂ (7 mL) was stirred at room temperature for 6 h. The mixture was evaporated under reduced pressure and the crude product was purified twice by column chromatography (first column CH₂Cl₂-MeOH, 100:0 to 90:10; second column cyclohexane-EtOAc, 100:0 to 50:50) and then by Prep-HPLC with the following conditions: column: Gemini C18 110A AXIA Column, 100×30 mm, 5 μm; Mobile Phase A: 10 mmol/L ammonium bicarbonate aqueous solution adjusted to pH 10 with ammonia; Mobile Phase B: acetonitrile (20% to 70% over 10 min); Detector, UV 210 to 350 nm to afford the title compound. ¹H NMR (400 MHz, CDCl₃) δ 7.31-7.21 (m, 2H), 7.09-6.99 (m, 2H), 5.38 (dd, J=8.8, 6.3 Hz, 1H), 4.35-4.26 (m, 1H), 3.94 (ddd, J=9.7, 8.0, 6.5 Hz, 1H), 3.62-3.48 (m, 2H), 3.09 (t, J=7.1 Hz, 1H), 2.84 (dddd, J=12.1, 8.9, 6.6, 3.1 Hz, 1H), 2.30 (dddd, J=12.4, 9.7, 7.6, 6.3 Hz, 1H), 1.37 (s, 3H), 1.29 (s, 3H). LC-MS (Method B): m/z=267.0 [M+H]⁺, 0.86 min.

Example 43

1-[(3S)-3-(5-fluoro-6-methylpyridin-3-yl)-1,2-oxazolidin-2-yl]-2,2-dimethylpropan-1-one (97)

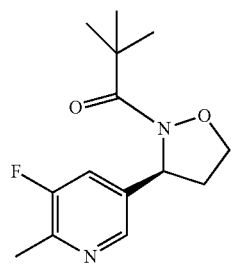 [SMILES: Cc1ncc([C@@H]2CCON2C(=O)C(C)(C)C)cc1F]

3-Fluoro-2-methyl-5-[(3S)-1,2-oxazolidin-3-yl]pyridine (38 mg, 0.208 mmol) was dissolved in CH₂Cl₂ (1.0 mL). A solution of pyridine (0.034 mL, 0.416 mmol) in CH₂Cl₂ (0.5 mL) and a solution of pivaloyl chloride (0.033 mL, 0.27 mmol) in CH₂Cl₂ (0.5 mL) were then added at 0° C. The mixture was then stirred at room temperature for 30 min then the mixture was concentrated under reduced pressure. The residue was dissolved in EtOAc and washed with sat. NH$_4$Cl solution, twice with sat. NaHCO$_3$ solution and with brine. The organic phase was dried over Na$_2$SO$_4$, filtered and concentrated under reduced pressure. The crude product was purified by column chromatography (cyclohexane-EtOAc, 88:12 to 0:100) to afford the title compound as an unequal mixture of enantiomers. This mixture was resolved by chiral HPLC on a Chiralpak AD-H (25×2.0 cm) 5 µm column using a mobile phase of n-hexane/(ethanol+0.1% isopropylamine) 75/25% v/v and a flow rate of 18 mL/min.

Second eluting enantiomer. Enantiomer 2: $^1$H NMR (400 MHz, CDCl$_3$) δ 8.29 (s, 1H), 7.27 (m, 1H), 5.43 (dd, J=8.8, 6.8 Hz, 1H), 4.30 (td, J=8.0, 2.5 Hz, 1H), 3.96-3.88 (m, 1H), 2.91-2.82 (m, 1H), 2.51 (d, J=3.0 Hz, 3H), 2.36-2.26 (m, 1H), 1.30 (s, 9H). LC-MS (Method A): m/z=267.2 [M+H]$^+$, 0.92 min. e.e.=98.8% as determined on a Chiralpak IC (25×0.46 cm) 5 µm column using a mobile phase of n-hexane/(ethanol+0.1% isopropylamine) 75/25% v/v, flow rate: 1 mL/min, retention time: 7.4 min.

Example 44

4-[(3S)-2-(2,2-dimethylpropanoyl)(5,5-$^2$H$_2$)-1,2-oxazolidin-3-yl]benzonitrile (98)

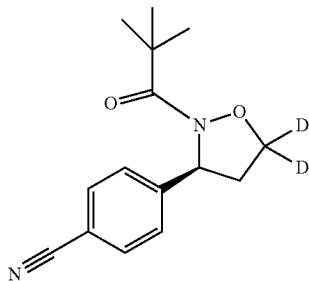 [SMILES: [2H]C1([2H])C[C@@H](c2ccc(C#N)cc2)N(C(=O)C(C)(C)C)O1]

A solution of 4-[(3S)-(5,5-$^2$H$_2$)-1,2-oxazolidin-3-yl]benzonitrile (30 mg, 0.17 mmol), pivaloyl chloride (0.023 mL, 0.19 mmol) and Et$_3$N (0.035 ml, 0.25 mmol) in CH$_2$Cl$_2$ (4 mL) was stirred at room temperature for 1 h. The mixture was diluted with CH$_2$Cl$_2$ and washed with brine. The organic phase was separated, dried over Na$_2$SO$_4$, filtered and evaporated under reduced pressure. The crude product was resolved by chiral HPLC on a Chiralpak AD-H (25×2.0 cm) 5 µm column using a mobile phase of n-hexane/(ethanol+0.1% isopropylamine) 65/35% v/v and a flow rate of 18 mL/min.

Second eluting enantiomer, Enantiomer 2: $^1$H NMR (400 MHz, CDCl$_3$) δ 7.68-7.58 (m, 2H) 7.45-7.35 (m, 2H) 5.43 (dd, J=9.0, 6.8 Hz, 1H) 2.84 (dd, J=12.3, 9.0 Hz, 1H) 2.32-2.18 (m, 1H) 1.30 (s, 9H). LC-MS (Method A): m/z=261.2 [M+H]$^+$, 1.03 min. e.e.=100% as determined on a Chiralpak AD-H (25×0.46 cm) 5 µm column using a mobile phase of n-hexane/(ethanol+0.1% isopropylamine) 65/35% v/v, flow rate: 1 mL/min, retention time: 7.3 min.

Examples 45 and 46

4-[(3S,5S)-2-(2,2-dimethylpropanoyl)-5-methyl-1,2-oxazolidin-3-yl]benzonitrile (99) and 4-[(3S,5R)-2-(2,2-dimethylpropanoyl)-5-methyl-1,2-oxazolidin-3-yl]benzonitrile (100)

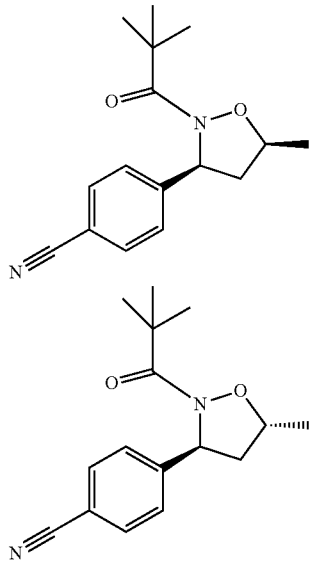

A solution of 4-[(3S)-5-methyl-1,2-oxazolidin-3-yl]benzonitrile (50 mg, 0.26 mmol), pivaloyl chloride (0.036 mL, 0.29 mmol) and Et$_3$N (0.054 mL, 0.39 mmol) in CH$_2$Cl$_2$ (4 mL) was stirred at room temperature for 1 h 30 min. The mixture was diluted with CH$_2$Cl$_2$ and washed with 0.5M HCl solution and brine. The organic phase was separated, dried over Na$_2$SO$_4$, filtered and concentrated under reduced pressure. The crude products were purified by column chromatography (cyclohexane-EtOAc, 90:10 to 65:35) to give a mixture of diastereoisomers as a colorless oil. This mixture was resolved by chiral HPLC on a Chiralpak AD-H (25×2.0 cm) 5 µm column using a mobile phase of n-hexane/(ethanol+0.1% isopropylamine) 70/30% v/v and a flow rate of 18 mL/min.

4-[(3S,5S)-2-(2,2-dimethylpropanoyl)-5-methyl-1,2-oxazolidin-3-yl]benzonitrile (First eluted diastereoisomer): $^1$H NMR (400 MHz, CDCl$_3$) δ 7.62 (d, J=8.4 Hz, 2H), 7.40 (d, J=8.0 Hz, 2H), 5.43 (t, J=8.41 Hz, 1H), 4.16 (dquin, J=11.0, 5.6 Hz, 1H), 2.93 (ddd, J=12.3, 8.9, 5.1 Hz, 1H), 1.85 (ddd, J=12.3, 10.5, 8.0 Hz, 1H), 1.42 (d, J=5.8 Hz, 3H), 1.29 (s, 9H). LC-MS (Method A): m/z=273.2 [M+H]+, 1.11 min. e.e.=100% as determined on a Chiralpak AD-H (25×0.46 cm), 5 µm column using a mobile phase of n-hexane/(ethanol+0.1% isopropylamine) 70/30% v/v, flow rate: 1 mL/min, retention time: 6.5 min.

4-[(3S,5R)-2-(2,2-dimethylpropanoyl)-5-methyl-1,2-oxazolidin-3-yl]benzonitrile (Second eluted diastereoisomer): $^1$H NMR (400 MHz, CDCl$_3$) δ 7.63 (d, J=8.4 Hz, 2H), 7.38 (d, J=8.2 Hz, 2H), 5.39 (dd, J=8.8, 5.2 Hz, 1H), 4.61 (sextet, J=6.0 Hz, 1H), 2.44 (ddd, J=12.3, 8.9, 5.2 Hz, 1H), 2.29 (dt, J=12.1, 5.9 Hz, 1H), 1.36 (d, J=6.2 Hz, 3H), 1.29 (s, 9H). LC-MS (Method A): m/z=273.2 [M+H]+, 1.09 min. e.e=100% as determined on a Chiralpak AD-H (25×0.46 cm), 5 µm column using a mobile phase of n-hexane/

Example 47

3,3-difluoro-1-[(3S)-3-(4-fluorophenyl)-1,2-oxazolidin-2-yl]-2,2-dimethylpropan-1-one (101)

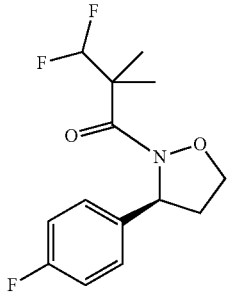 [SMILES: CC(C)(C(=O)N1OCC[C@H]1c1ccc(F)cc1)C(F)F]

A solution of 3,3-difluoro-2,2-dimethylpropanoic acid (55 mg, 0.4 mmol), oxayl chloride (0.034 mL, 0.4 mmol) and DMF (1 drop) in anhydrous $CH_2Cl_2$ (4 mL) was stirred at room temperature 1 h 30 min, then a solution of (3S)-3-(4-fluorophenyl)-1,2-oxazolidine (60 mg, 0.36 mmol) and DIPEA (0.157 mL) 0.9 mmol) in anhydrous $CH_2Cl_2$ (3 mL) was added and the resulting mixture was stirred at room temperature for 1 h. The mixture was diluted with $CH_2Cl_2$ and washed with HCl solution, sat. $NaHCO_3$ solution and brine. The organic phase was separated, dried over $Na_2SO_4$, filtered and concentrated under reduced pressure. The crude product was purified by column chromatography (cyclohexane-EtOAc, 90:10 to 70:30) to give the title compound containing some residual 3,3-difluoro-2,2-dimethylpropanoic acid. This mixture was dissolved in $CH_2Cl_2$ and washed with 0.1N NaOH solution and brine. The organic phase was concentrated under reduced pressure to give the title compound. $^1$H NMR (400 MHz, $CDCl_3$) δ 7.29-7.21 (m, 2H), 7.08-6.97 (m, 2H), 6.50-6.14 (m, 1H), 5.40 (dd, J=8.8, 6.5 Hz, 1H), 4.30 (dt, J=3.3, 7.5 Hz, 1H), 3.95 (ddd, J=9.5, 8.0, 6.5 Hz, 1H), 2.91-2.76 (m, 1H), 2.33 (dddd, J=12.4, 9.6, 7.6, 6.5 Hz, 1H), 1.40-1.32 (m, 6H). LC-MS (Method A): m/z=288.2 [M+H]$^+$, 1.10 min.

Examples 48 and 49

Preparation of 1-(3R)-3-(3,5-difluorophenyl)-1,2-oxazolidin-2-yl-2,2-dimethylpropan-1-one and 1-[(3S)-3-(3,5-difluorophenyl)-1,2-oxazolidin-2-yl]-2,2-dimethylpropan-1-one (102) and (103)

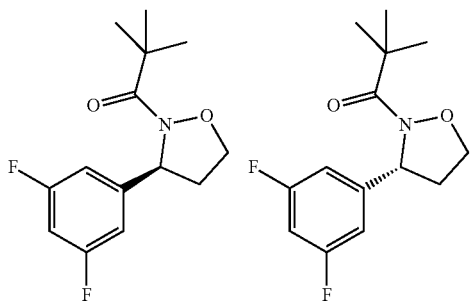

Hydrochloric acid solution (4M in dioxane, 3 mL, 12 mmol), was added at room temperature to a solution of tert-butyl 3-(3,5-difluorophenyl)-1,2-oxazolidine-2-carboxylate (50 mg, 0.17 mmol) in anhydrous $CH_2Cl_2$ (2 mL). The mixture was then stirred at room temperature for 2 h. The mixture was concentrated under reduced pressure. The residue was dissolved in $CH_2Cl_2$ (5 mL) and pivaloyl chloride (0.031 mL, 0.255 mmol) was added followed by sat. $NaHCO_3$ solution (5 mL). The mixture was stirred for 18 h then the organic portion was separated and washed with sat. $NaHCO_3$ solution, dried over $Na_2SO_4$, filtered and concentrated under reduced pressure to afford the title compounds as a mixture of enantiomers. This mixture of enantiomers was resolved by chiral HPLC on Chiralpak AS-H (25×2.0 cm), 5 μm column using a mobile phase of n-hexane/2-propanol 90/10% v/v and a flow rate of 18 mL/min to afford the two separated title compounds.

First eluting enantiomer, 1-[(3R)-3-(3,5-difluorophenyl)-1,2-oxazolidin-2-yl]-2,2-dimethylpropan-1-one. $^1$H NMR (400 MHz, $CDCl_3$) δ 6.83 (dd, J=8.3, 2.0 Hz, 2H), 6.74-6.65 (m, 1H), 5.38 (dd, J=8.9, 6.7 Hz, 1H), 4.32-4.18 (m, 1H), 3.95-3.82 (m, 1H), 2.89-2.76 (m, 1H), 2.33-2.22 (m, 1H), 1.31 (s, 9H). LC-MS (Method A): m/z=269.0 [M+H]$^+$, 1.18 min. e.e.=100% as determined on a Chiralpak AS-H (25× 0.46 cm) 5 μm column using a mobile phase of n-hexane/ 2-propanol 90/10% v/v, flow rate: 18 mL/min, retention time: 4.2 min.

Second eluting enantiomer, 1-[(3S)-3-(3,5-difluorophenyl)-1,2-oxazolidin-2-yl]-2,2-dimethylpropan-1-one. $^1$H NMR (400 MHz, $CDCl_3$), δ 6.79-6.89 (m, 2H), 6.69 (tt, J=8.9, 2.4 Hz, 1H), 5.38 (dd, J=8.8, 6.5 Hz, 1H), 4.26 (td, J=7.9, 2.8 Hz, 1H), 3.89 (ddd, J=9.8, 8.0, 6.5 Hz, 1H), 2.83 (dddd, J=12.2, 9.2, 6.5, 2.8 Hz, 1H), 2.27 (dddd, J=12.3, 9.8, 7.6, 6.7 Hz, 1H), 1.31 (s, 9H). LC-MS (Method A): m/z=269.0 [M+H]$^+$, 1.18 min. e.e.=99% as determined on a Chiralpak AS-H (25×0.46 cm) 5 μm column using a mobile phase of n-hexane/2-propanol 90/10% v/v, flow rate: 18 mL/min, retention time: 5.5 min.

Example 50

Preparation of 3,3-dimethyl-4-[(3S)-3-(5-methylpyrazin-2-yl)-1,2-oxazolidin-2-yl]-4-oxobutanenitrile (104)

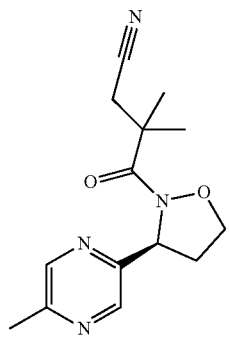 [SMILES: Cc1cnc([C@@H]2CCON2C(=O)C(C)(C)CC#N)cn1]

Thionyl chloride (0.029 mL, 0.39 mmol) was added to a solution of 3-cyano-2,2-dimethylpropanoic acid (45 mg, 0.35 mmol) and DMF in $CH_2Cl_2$ (2 mL). The reaction was stirred at room temperature for 2 h. A solution of tert-butyl (3S)-3-[4-(difluoromethyl)phenyl]-1,2-oxazolidine-2-carboxylate (45 mg, 0.35 mmol) and $Et_3N$ (0.13 mL, 1.08 mmol) in CH₂Cl₂ was added to the reaction and stirring was continued at room temperature for 1 h. The reaction was diluted with CH₂Cl₂ and washed with sat. NaHCO₃ solution. The organic phase was concentrated under reduced pressure and the crude product was purified by column chromatography (cyclohexane-EtOAc, 100:0 to 0:100) to afford the title compound as a mixture of enantiomers. This mixture was resolved by chiral HPLC on a Chiralpak IC (25×2.0 cm) 5 μm column using a mobile phase of n-hexane/(ethanol+ 0.1% isopropylamine) 50/50% v/v and a flow rate of 18 mL/min to afford the title compound. ¹H NMR (400 MHz, CDCl₃) δ 8.53 (d, J=1.3 Hz, 1H), 8.42 (d, J=0.8 Hz, 1H), 5.51 (dd, J=8.8, 6.0 Hz, 1H), 4.41 (dt, J=4.0, 7.5 Hz, 1H), 4.15-3.95 (m, 1H), 2.88-2.76 (m, 1H), 2.73-2.62 (m, 3H), 2.57 (s, 3H), 1.49 (s, 3H), 1.47 (s, 3H). LC-MS (Method A): m/z=275.3 [M+H]⁺, 0.68 min. e.e.=97.3% as determined on a Chiralpak IC (25×0.46 cm) 5 μm column using a mobile phase of n-hexane/(ethanol+0.1% isopropylamine) 50/50% v/v, flow rate: 1 mL/min, retention time: 11.2 min.

Example 51

Preparation of 1-[(3S)-3-[6-(difluoromethyl)pyridin-3-yl]-1,2-oxazolidin-2-yl]-2,2-dimethylpropan-1-one (105)

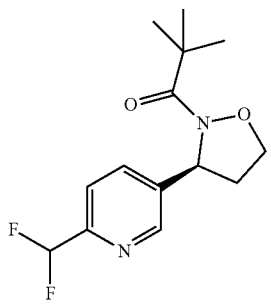 [SMILES: CC(C)(C)C(=O)N1OCC[C@H]1c1ccc(C(F)F)nc1]

To a solution of tert-butyl (3S)-3-[6-(difluoromethyl)pyridine-3-yl]-1,2-oxazolidine-2-carboxylate (24 mg, 0.11 mmol) in CH₂Cl₂ (2 mL) were added Et₃N (0.031 mL, 0.22 mmol) and pivaloylchloride (0.015 mL, 0.12 mmol). The mixture was stirred for 2 h. The volatiles were removed under reduced pressure to afford the title compound as a mixture of enantiomers. This mixture was resolved by chiral HPLC on a Chiralpak AD-H (25×2 cm) 5 μm column using a mobile phase of n-hexane/ethanol 70/30% v/v and a flow rate of 18 mL/min to afford then purified further by column chromatography (cyclohexane-EtOAc, 100:0 to 50:50) to afford the title compound. ¹H NMR (400 MHz, CDCl₃), δ 8.62 (d, J=2.0 Hz, 1H), 7.77 (dd, J=8.0, 2.3 Hz, 1H), 7.62 (d, J=8.0 Hz, 1H), 6.79-6.47 (m, 1H), 5.48 (dd, J=8.5, 7.0 Hz, 1H), 4.32 (dt, J=2.3, 7.9 Hz, 1H), 3.94 (ddd, J=10.0, 8.2, 6.4 Hz, 1H), 2.96-2.85 (m, 1H), 2.38-2.26 (m, 1H), 1.30 (s, 9H). LC-MS (Method A): m/z=285.93 [M+H]⁺, 0.97 min. e.e.=100% as determined on a Chiralpak AD-H (25×0.46 cm) 5 μm column using a mobile phase of n-hexane/ethanol 60/40% v/v, flow rate: 1 mL/min, retention time: 7.2 min.

Example 52

Preparation of 2,2-dimethyl-1-[(3S)-3-(1-methyl-1h-pyrazol-4-yl)-1,2-oxazolidin-2-yl]propan-1-one (106)

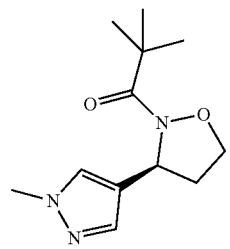 [SMILES: Cn1cc([C@@H]2CCON2C(=O)C(C)(C)C)cn1]

To a stirred mixture of (3S)-3-(1-methyl-1H-pyrazol-4-yl)-1,2-oxazolidine hydrochloride (90 mg, 0.47 mmol) and Et₃N (143 mg, 1.42 mmol) in CH₂Cl₂ (10 mL) was added dropwise pivaloyl chloride (57 mg, 0.47 mmol) at 0° C. The resulting mixture was warmed to room temperature and stirred for 1 hour. The reaction mixture was quenched with water (15 mL) and extracted with CH₂Cl₂ (2×15 mL). The combined organic layers were washed with brine (20 mL), dried over Na₂SO₄, filtered and concentrated under reduced pressure. The crude product was purified by Prep-HPLC with the following conditions: column: XBridge Prep C18 Column, 150×19 mm, 5 μm; Mobile Phase A: water (10 mmol/L ammonium bicarbonate); Mobile Phase B: acetonitrile (25% to 75% over 7 min); Detector, UV 220 & 254 nm to afford the title compound (35 mg, 31%) as a mixture of enantiomers. This mixture was resolved by chiral HPLC on a Chiralpak IC (25×2 cm), 5 μm column using a mobile phase of hexane/ethanol 70/30% v/v and a flow rate of 20 mL/min to afford the title compound. First eluting enantiomer. ¹H NMR (400 MHz, DMSO-d₆) δ 7.57 (s, 1H), 7.31 (s, 1H), 5.26-5.22 (m, 1H), 4.25-4.20 (m, 1H), 3.82-3.76 (m, 4H), 2.70-2.60 (m, 1H), 2.30-2.22 (m, 1H), 1.15 (s, 9H). LC-MS (Method F): m/z=238.0 [M+H]⁺, 1.00 min. e.e.=99.9% as determined on a Chiralpak IC-3 (10×0.46 cm), 3 μm column using a mobile phase of (n-hexane+0.1% trifluoroacetic acid)/ethanol 70/30% v/v, flow rate: 1.0 mL/min, retention time: 5.58 min.

Example 53

Preparation of 2,2-dimethyl-1-[(3S)-3-(6-methyl-pyrazin-2-yl)-1,2-oxazolidin-2-yl]propan-1-one (107)

To a solution of N-hydroxy-N-[(1S)-3-hydroxy-1-(6-methylpyrazin-2-yl)propyl]-2,2-dimethylpropanamide (170 mg, 0.64 mmol) and triphenylphosphine (566 mg, 2.10 mmol) in anhydrous THF (10 mL) was added DIAD (387 mg, 1.90 mmol) dropwise at room temperature. After being stirred overnight at room temperature, the reaction mixture was concentrated under reduced pressure. The crude product was purified by Prep-HPLC with the following conditions: column: XBridge Prep C18 Column, 150×19 mm, 5 μm; Mobile Phase A: Water (10 mmol/L NH$_4$HCO$_3$); Mobile Phase B: Acetonitrile (20% to 50% over 7 min); Detector, UV 220 & 254 nm to afford the title compound as a mixture of enantiomers. This mixture was resolved by chiral HPLC on a Phenomenex Lux 5u Cellulose-4AXIA Packed (25× 2.12 cm), 5 μm column using a mobile phase of hexane/ethanol 95/5% v/v and a flow rate of 20 mL/min to afford the title compound. First eluted enantiomer. $^1$H NMR (400 MHz, CD$_3$OD) δ 8.39 (s, 1H), 8.34 (s, 1H), 5.44-5.40 (m, 1H), 4.45-4.31 (m, 1H), 4.07-4.01 (m, 1H), 2.99-2.78 (m, 1H), 2.68-2.43 (m, 4H), 1.27 (s, 9H). LC-MS (Method N): m/z=250.2 [M+H]$^+$, 1.12 min. e.e.=99.9% as determined on a Lux Cellulose-4 (5×0.46 cm), 3 μm column using a mobile phase of (n-hexane+0.1% diethylamine)/ethanol 95/5% v/v, flow rate: 1.0 mL/min, retention time: 3.23 min.

Example 54

Preparation of 5-[(3S)-2-(2,2-dimethylpropanoyl)-1,2-oxazolidin-3-yl]pyridine-3-carbonitrile (108)

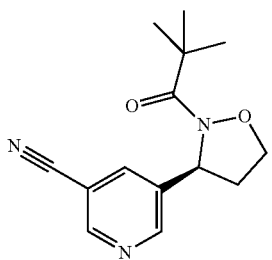 [SMILES: CC(C)(C)C(=O)N1OCC[C@H]1c1cncc(C#N)c1]

To a stirred mixture of 5-[(3S)-1,2-oxazolidin-3-yl]pyridine-3-carbonitrile trifluoroacetate (105 mg, 0.36 mmol) and Et$_3$N (163 mg, 1.61 mmol) in CH$_2$Cl$_2$ (10 mL) was added pivaloylchloride (44 mg, 0.36 mmol) at 0° C. After being stirred at room temperature for 1 hour, the reaction mixture was quenched by tire addition of water (15 mL) and extracted with CH$_2$Cl$_2$ (3×15 mL). The combined organic layers were dried over Na$_2$SO$_4$ and concentrated under reduced pressure. The crude product was purified by Prep-HPLC with the following conditions: Column, XBridge Prep C18 OBD Column, 5 μm, 150×19 mm; Mobile phase: Phase A: Water (10 mmol/L ammonium bicarbonate); Phase B: Acetonitrile (25% up to 55% in 7 min); Detector, UV 254 & 220 nm to afford the title compound. $^1$H NMR (300 MHz, DMSO-d$_6$) δ 8.92 (d, J=1.8 Hz, 1H), 8.73 (d, J=2.1 Hz, 1H), 8.16-8.15 (m, 1H), 5.39 (t, J=7.2 Hz, 1H), 4.35-4.29 (m, 1H), 3.92-3.84 (m, 1H), 2.90-2.85 (m, 1H), 2.28-2.21 (m, 1H), 1.19 (s, 9H). LC-MS (Method H): m/z=260.0 [M+H]$^+$, 1.22 min. e.e.=95.9% as determined on a Chiralpak IA-3 (5×0.46 cm), 3 μm column using a mobile phase of (n-hexane+0.1% diethylamine)/ethanol 70/30% v/v, flow rate: 1.0 mL/min, retention time: 1.94 min.

Example 55

Preparation of 3-[(3S)-2-(2,2-dimethylpropanoyl)-1,2-oxazolidin-3-yl]-5-fluorobenzonitrile (109)

To a stirred solution of N-[(1S)-1-(3-cyano-5-fluorophenyl)-3-hydroxypropyl]-N-hydroxy-2,2-dimethylpropanamide (100 mg, 0.34 mmol) and triphenylphosphine (213 mg, 0.81 mmol) in THF (10 mL) was added dropwise DIAD (137 mg, 0.68 mmol) at 0° C. After being stirred overnight at room temperature under a nitrogen atmosphere, the reaction mixture was concentrated under reduced pressure. The crude product was purified by preparative thin layer chromatography (EtOAc-petroleum ether, 1:3) to afford the title compound as a mixture of enantiomers. This mixture was resolved by chiral HPLC on a Chiralpak IC (25×2 cm) 5 μm column using a mobile phase of hexane/ethanol 80/20% v/v and a flow-rate of 20 mL/min to afford the title compound. Second eluting enantiomer. $^1$H NMR (300 MHz, DMSO-d$_6$) δ 7.79-7.75 (m, 1H), 7.58 (s, 1H), 7.46-7.41 (m, 1H) 5.37 (t, J=7.2 Hz, 1H), 4.32-4.27 (m, 1H), 3.90-3.82 (m, 1H), 2.90-2.86 (m, 1H), 2.22-2.14 (m, 1H), 1.21 (s, 9H). LC-MS (Method H): m/z=276.9 [M+H]$^+$, 1.56 min. e.e.=99.9% as determined on a Chiralpak IC-3 (10×0.46 cm), 3 μm column using a mobile phase of (n-hexane+0.1% diethylamine)/ethanol 80/20% v/v, flow rate: 1.0 mL/min, retention time: 3.54 min.

Example 56

Preparation of 1-[(3S)-3-{imidazo[1,2-A]pyridin-7-yl}-1-oxazolidin-2-yl]-2,2-dimethylpropan-1-one (110)

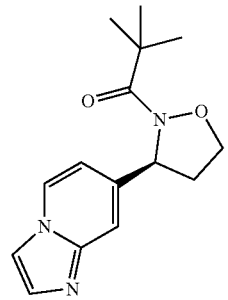 [SMILES: CC(C)(C)C(=O)N1OCC[C@H]1c1ccn2ccnc2c1]

The title compound was isolated by chiral HPLC on a Chiralpak AD-H (25×2.0 cm), 5 μm column using a mobile phase of n-hexane/(ethanol/methanol 1/1+0.1% isopropylamine) 40/60% v/v, flow rate: 18 mL/min. ¹H NMR (400 MHz, CDCl₃) δ 8.09 (dd, J=7.0, 0.8 Hz, 1H), 7.62 (d, J=1.3 Hz, 1H), 7.57-7.53 (m, 2H), 6.77 (dd, J=7.0, 1.8 Hz, 1H), 5.45 (dd, J=9.0, 6.5 Hz, 1H), 4.33-4.26 (m, 1H), 3.93 (ddd, J=9.6, 8.1, 6.7 Hz, 1H), 2.85 (dddd, J=12.1, 9.1, 6.5, 2.9 Hz, 1H), 2.34 (dddd, J=12.3, 9.7, 7.7, 6.7 Hz, 1H), 1.31 (s, 9H). LC-MS (Method A): m/z=274.2 [M+H]⁺, 0.43 min. e.e.=100% as determined on a Chiralpak AD-H (25×0.46 cm), 5 μm column using a mobile phase of n-hexane/(ethanol/methanol 1/1+0.1% isopropylamine) 40/60% v/v, flow rate: 1 mL/min, retention time: 5.0 min.

Example 57

Preparation of 1-(3S)-3-{imidazo[1,2-A]pyridin-2-yl}-1,2-oxazolidin-2-yl-2,2-dimethylpropan-1-one (111)

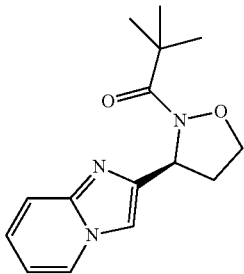 [SMILES: CC(C)(C)C(=O)N1OCC[C@H]1c1cn2ccccc2n1]

The title compound was isolated by chiral HPLC on a Chiralpak AD-H (25×2.0 cm), 5 μm column using a mobile phase of n-hexane/(ethanol+0.1% isopropylamine) 40/60% v/v, flow rate: 18 mL/min. ¹H NMR (400 MHz, CDCl₃) δ 8.04 (dt, J=6.8, 1.2 Hz, 1H), 7.61-7.54 (m, 2H), 7.15 (ddd, J=9.2, 6.8, 1.3 Hz, 1H), 6.76 (td, J=6.8, 1.0 Hz, 1H), 5.69 (dd, J=8.9, 5.9 Hz, 1H), 4.38-4.30 (m, 1H), 3.96 (ddd, J=9.2, 7.8, 6.9 Hz, 1H), 2.99-2.86 (m, 1H), 2.84-2.74 (m, 1H), 1.32 (s, 9H). LC-MS (Method A): m/z=274.2 [M+H]⁺, 0.46 min. e.e.=100% as determined on a Chiralpak AD-H (25×0.46 cm), 5 μm column using a mobile phase of n-hexane/(ethanol+0.1% isopropylamine) 40/60% v/v, flow rate: 1 mL/min, retention time: 5.5 min.

Examples 58 and 59

Preparation of 5-[(3S)-2-(2,2-difluoro-1-methylcyclopropanecarbonyl)-1,2-oxazolidin-3-yl]-2-fluoropyridines (112) and (113)

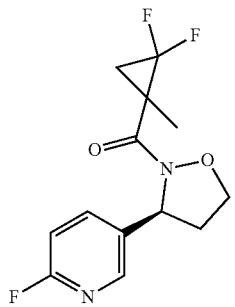 [SMILES: CC1(C(=O)N2OCC[C@H]2c2ccc(F)nc2)CC1(F)F]

The title compounds ((S)-5-[(3S)-2-(2,2-difluoro-1-methylcyclopropanecarbonyl)-1,2-oxazolidin-3-yl]-2-fluoropyridine and (R)-5-[(3S)-2-(2,2-difluoro-1-methylcyclopropanecarbonyl)-1,2-oxazolidin-3-yl]-2-fluoropyridine) were isolated by chiral HPLC on a Chiralpak AD-H (25×2.0 cm), 5 μm column using a mobile phase of n-hexane/ethanol 70/30% v/v, flow rate: 18 mL/min.

First eluting diastereoisomer, Diastereoisomer 1. ¹H NMR (400 MHz, CDCl₃) δ 8.18 (d, J=2.5 Hz, 1H), 7.70 (td, J=8.0, 2.6 Hz, 1H), 6.92 (dd, J=8.5, 3.0 Hz, 1H), 5.42 (dd, J=8.8, 5.5 Hz, 1H), 4.41-4.31 (m, 1H), 4.08 (td, J=8.4, 6.8 Hz, 1H), 2.97 (dddd, J=12.4, 8.9, 6.8, 4.0 Hz, 1H), 2.47-2.32 (m, 1H), 1.90 (ddd, J=13.7, 8.6, 4.5 Hz, 1H), 1.50 (dd, J=2.8, 1.3 Hz, 3H), 1.26 (ddd, J=11.4, 8.3, 5.1 Hz, 1H). LC-MS (Method A): m/z=287.1 [M+H]⁺, 0.84 min. Chiralpak AD-H (25×0.46 cm), 5 μm column using a mobile phase of n-hexane/ethanol 70/30% v/v, flow rate: 1 mL/min. retention time: 10.8 min.

Second eluting diastereoisomer, Diastereoisomer 2. ¹H NMR (400 MHz, CDCl₃) δ 8.25-8.18 (m, 1H), 7.76 (td, J=7.8, 2.4 Hz, 1H), 6.94 (dd, J=8.7, 2.9 Hz, 1H), 5.43 (dd, J=8.5, 6.8 Hz, 1H), 4.34 (td, J=7.8, 3.0 Hz, 1H), 4.02 (ddd, J=9.9, 8.2, 6.5 Hz, 1H), 2.93-2.83 (m, 1H), 2.37 (ddt, J=12.4, 9.9, 7.2 Hz, 1H), 2.04 (ddd, J=14.2, 8.3, 4.6 Hz, 1H), 1.59 (dd, J=3.0, 1.5 Hz, 3H), 1.24 (ddd, J=11.4, 8.3, 5.1 Hz, 1H). LC-MS (Method A): m/z=287.1 [M+H]+, 0.90 min. Chiralpak AD-H (25×0.46 cm), 5 μm column using a mobile phase of n-hexane/ethanol 70/30% v/v, flow rate: 1 mL/min, retention time: 12.1 min.

Examples 60 and 61

Preparation of (3S)-2-(2-difluoro-1-methylcyclopropanecarbonyl)-3-(4-fluorophenyl)-1,2-oxazolidines (114) and (115)

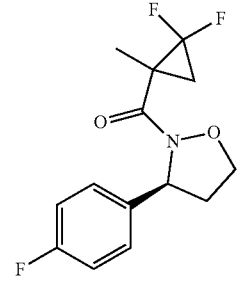 [SMILES: CC1(C(=O)N2OCC[C@H]2c2ccc(F)cc2)CC1(F)F]

The title compounds ((3S)-2-((R)-2,2-difluoro-1-methylcyclopropanecarbonyl)-3-(4-fluorophenyl)-1,2-oxazolidine and (3S)-2-((S)-2,2-difluoro-1-methylcyclopropanecarbonyl)-3-(4-fluorophenyl)-1,2-oxazolidine) were isolated by chiral HPLC on a Chiralpak AD-H (25×2.0 cm), 5 μm column using a mobile phase of n-hexane/ethanol 50/50% v/v, flow rate: 18 mL/min.

First eluting diastereoisomer, Diastereoisomer 1. ¹H NMR (400 MHz, CDCl₃) δ 7.34-7.26 (m, 2H), 7.00-7.09 (m, 2H), 5.38 (dd, J=8.5, 6.5 Hz, 1H), 4.30 (td, J=7.8, 3.0 Hz, 1H), 4.04-3.94 (m, 1H), 2.87-2.78 (m, 1H), 2.35 (ddt, J=12.2, 9.6, 7.2 Hz, 1H), 2.03 (ddd, J=14.1, 8.3, 4.8 Hz, 1H), 1.60 (dd, J=3.0, 1.5 Hz, 3H), 1.21 (ddd, J=11.5, 8.3, 5.0 Hz, 1H). LC-MS (Method A): m/z=286.1 [M+H]⁺, 1.06 min. Chiralpak AD-H (25×0.46 cm), 5 μm column using a mobile phase of n-hexane/ethanol 50/50% v/v, flow rate: 1 mL/min, retention time: 4.9 min.

Second eluting diastereoisomer. Diastereoisomer 2. ¹H NMR (400 MHz, CDCl₃) δ 7.29-7.21 (m, 2H), 7.06-6.98 (m, 2H), 5.37 (dd, J=8.8, 5.3 Hz, 1H), 4.32 (td, J=7.7, 4.5 Hz, 1H), 4.05 (td, J=8.2, 7.0 Hz, 1H), 2.96-2.85 (m, 1H), 2.42-2.31 (m, 1H), 1.97-1.85 (m, 1H), 1.48 (br. s., 3H), 1.29-1.19 (m, 1H). LC-MS (Method A): m/z=286.1 [M+H]⁺, 1.00 min. Chiralpak AD-H (25×0.46 cm), 5 µm column using a mobile phase of n-hexane/ethanol 50/50% v/v, flow rate: 1 mL/min, retention time: 6.6 min.

Examples 62 and 63

Preparation of 2-cyclopropyl-1-[(3S)-3-(6-fluoro-pyridin-3-yl)-1,2-oxazolidin-2-yl]propan-1-ones (116) and (117)

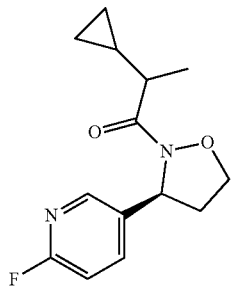 [SMILES: CC(C(=O)N1OCC[C@H]1c1ccc(F)nc1)C1CC1]

The title compounds ((R)-2-cyclopropyl-1-[(3S)-3-(6-fluoropyridin-3-yl)-1,2-oxazolidin-2-yl]propan-1-one and (S)-2-cyclopropyl-1-[(3S)-3-(6-fluoropyridin-3-yl)-1,2-oxazolidin-2-yl]propan-1-one) were isolated by chiral HPLC on a Chiralpak AD-H (25×2.0 cm), 5 µm column using a mobile phase of n-hexane/(ethanol+0.1% isopropylamine) 70/30% v/v, flow rate: 18 mL/min.

First eluting diastereoisomer. Diastereoisomer 1. ¹H NMR (400 MHz, CDCl₃) δ 8.23-8.20 (m, 1H), 7.76 (td, J=8.0, 2.5 Hz, 1H), 6.93 (dd, J=8.4, 2.9 Hz, 1H), 5.49 (dd, J=8.8, 6.3 Hz, 1H), 4.26 (td, J=7.8, 3.5 Hz, 1H), 3.88 (ddd, J=9.3, 8.2, 6.8 Hz, 1H), 2.94-2.81 (m, 1H), 2.42-2.26 (m, 2H), 1.21 (d, J=6.8 Hz, 3H), 1.09-0.97 (m, 1H), 0.61-0.43 (m, 2H), 0.43-0.34 (m, 1H), 0.19 (dt, J=9.5, 4.7 Hz, 1H). LC-MS (Method A): m/z=265.2 [M+H]⁺, 0.90 min. Chiralpak AD-H (25×0.46 cm), 5 µm column using a mobile phase of n-hexane/(ethanol+0.1% isopropylamine) 70/30% v/v, flow rate: 1 mL/min, retention time: 6.5 min.

Second eluting diastereoisomer, Diastereoisomer 2. ¹H NMR (400 MHz, CDCl₃) δ 8.20 (d, J=2.5 Hz, 1H), 7.75 (td, J=8.0, 2.5 Hz, 1H), 6.92 (dd, J=8.5, 2.8 Hz, 1H), 5.49 (dd, J=9.0, 6.3 Hz, 1H), 4.28 (td, J=8.0, 2.6 Hz, 1H), 3.88 (ddd, J=9.6, 8.1, 6.7 Hz, 1H), 2.89 (dddd, J=12.3, 9.2, 6.3, 3.0 Hz, 1H), 2.35 (dddd, J=12.3, 9.6, 7.7, 6.3 Hz, 1H), 2.30-2.19 (m, 1H), 1.28 (d, J=7.0 Hz, 3H), 1.04 (dtt, J=9.8, 8.1, 5.0 Hz, 1H), 0.61-0.47 (m, 2H), 0.25-0.11 (m, 2H). LC-MS (Method A): m/z=265.2 [M+H]⁺, 0.89 min. Chiralpak AD-H (25×0.46 cm), 5 µm column using a mobile phase of n-hexane/(ethanol+0.1% isopropylamine) 70/30% v/v, flow rate: 1 mL/min, retention time: 8.0 min.

Example 64

Preparation of tert-butyl (3S)-3-(5-chloropyridin-3-yl)-isoxazolidine-2-carboxylate (118)

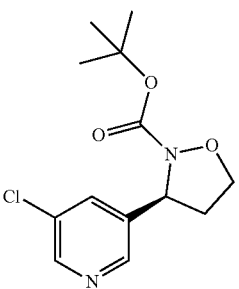 [SMILES: CC(C)(C)OC(=O)N1OCC[C@H]1c1cncc(Cl)c1]

The title compound was isolated by chiral SFC on a Chiralpak AD-H (25×2.0 cm) 5 µm column using a mobile phase of 7% isopropanol in CO₂, flow rate: 45 mL/min. ¹H NMR (400 MHz, CDCl₃) δ 8.49 (d, J=2.3 Hz, 1H), 8.47 (d, J=2.0 Hz, 1H), 7.77-7.70 (m, 1H), 5.26 (dd, J=8.8, 5.5 Hz, 1H), 4.27-4.18 (m, 1H), 3.91 (ddd, J=9.0, 8.3, 7.0 Hz, 1H), 2.85 (dddd, J=12.3, 8.9, 7.0, 3.4 Hz, 1H), 2.29 (dddd, J=12.3, 9.1, 7.8, 5.6 Hz, 1H), 1.49 (s, 9H). SFC on a Chiralpak AD-H (25×0.46 cm) 5 µm column using a mobile phase of 7% isopropanol in CO₂, flow rate: flow rate: 2.5 mL/min, retention time: 8.4 min.

Example 65

Preparation of tert-butyl (3S)-3-[2-(difluoromethyl) pyridin-4-yl]-1,2-oxazolidine-2-carboxylate (119)

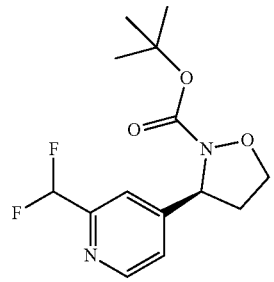 [SMILES: CC(C)(C)OC(=O)N1OCC[C@H]1c1ccnc(C(F)F)c1]

The title compound was isolated by chiral HPLC on a Chiralpak IA (25×2.0 cm), 5 µm column using a mobile phase of n-hexane/ethanol 75/25 v/v, flow rate: 18 mL/min. ¹H NMR (400 MHz, CDCl₃) δ 8.63 (d, J=5.0 Hz, 1H), 7.65 (s, 1H), 7.44 (dd, J=5.0, 0.8 Hz, 1H), 6.66 (t, J=55.0 Hz, 1H), 5.29 (dd, J=8.9, 5.6 Hz, 1H), 4.21 (dt, J=3.3, 7.9 Hz, 1H), 3.92 (dt, J=7.0, 8.7 Hz, 1H), 2.88 (dddd, J=12.3, 8.9, 7.0, 3.4 Hz, 1H), 2.28 (dddd, J=12.3, 9.0, 7.7, 5.6 Hz, 1H), 1.50 (s, 9H). LC-MS (Method A): m/z=301.1 [M+H]⁺, 0.93 min. Chiralpak IA (25×0.46 cm), 5 µm column using a mobile phase of n-hexane/ethanol 75/25 v/v, flow rate: 1 mL/min, retention time: 6.7 min.

Example 66

Preparation of 2,2-dimethyl-1-(3S)-3-[6-(trifluoromethyl)pyridin-3-yl]-1,2-oxazolidin-2-yl)propan-1-one (120)

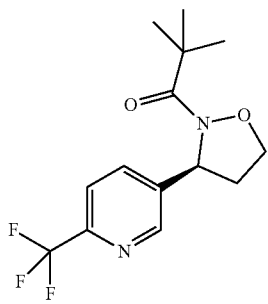 [SMILES: CC(C)(C)C(=O)N1OCC[C@H]1c1ccc(C(F)(F)F)nc1]

The title compound was isolated by chiral SFC on a Chiralpak AD-H (25×2.0 cm), 5 µm column using a mobile phase of 5% isopropanol in $CO_2$, flow rate: 45 mL/min. $^1$H NMR (400 MHz, CDCl$_3$) δ 8.70 (d, J=2.0 Hz, 1H), 7.79 (dd, J=8.3, 2.0 Hz, 1H), 7.67 (d, J=8.3 Hz, 1H), 5.50 (dd, J=9.0, 7.0 Hz, 1H), 4.33 (td, J=8.3, 2.0 Hz, 1H), 4.0-3.91 (m, 1H), 2.96-2.87 (m, 1H), 2.37-2.27 (m, 1H), 1.30 (s, 9H). LC-MS (Method A): m/z=303.2 [M+H]$^+$, 1.07 min. e.e.=100% as determined on a Chiralpak AD-H (25×0.46 cm), 5 µm column using a mobile phase of 5% isopropanol in $CO_2$, flow rate: 2.5 mL/min, retention time: 7.6 min.

Example 67

Preparation of 1-[(3S)-3-(5-chloro-3-fluoropyridin-2-yl)-1,2-oxazolidin-2-yl]-2,2-dimethylpropan-1-one (121)

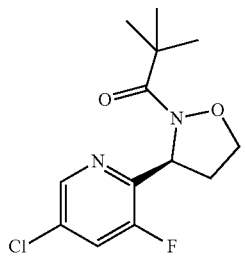 [SMILES: CC(C)(C)C(=O)N1OCC[C@H]1c1ncc(Cl)cc1F]

The title compound was isolated by chiral HPLC on a Chiralpak IC (25×2.0 cm), 5 µm column using a mobile phase of n-hexane/(ethanol+0.1% isopropylamine) 75/25% v/v, flow rate: 18 mL/min. $^1$H NMR (400 MHz, CDCl$_3$) δ 8.38 (d, J=2.0 Hz, 1H), 7.43 (dd, J=9.0, 2.0 Hz, 1H), 5.67 (dd, J=8.8, 6.8 Hz, 1H), 4.44 (td, J=8.0, 2.5 Hz, 1H), 4.04-3.97 (m, 1H), 2.80-2.70 (m, 1H), 2.62-2.52 (m, 1H), 1.26 (s, 9H). LC-MS (Method A): m/z=287.2 [M+H]$^+$, 1.04 min. e.e.=100% as determined on a Chiralpak IC (25×0.46 cm), 5 µm column using a mobile phase of n-hexane/(ethanol+0.1% isopropylamine) 75/25% v/v, flow rate: 1 mL/min, retention time: 6.4 min.

Example 68

Preparation of 2,2-dimethyl-(3S)-3-[5-(trifluoromethyl)pyridin-2-yl-1,2-oxazolidin-2-yl]propan-1-one (122)

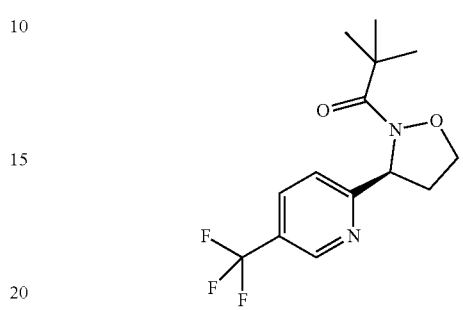

The title compound was isolated by chiral SFC on a Chiralpak AD-H (25×2.0 cm), 5 µm column using a mobile phase of 6% isopropanol in $CO_2$, flow rate: 45 mL/min. $^1$H NMR (400 MHz, CDCl$_3$) δ 8.84 (s, 1H), 7.91 (dd, J=8.3, 2.0 Hz, 1H), 7.48 (d, J=8.3 Hz, 1H), 5.57 (dd, J=9.0, 6.3 Hz, 1H), 4.31 (td, J=7.0, 3.2 Hz, 1H), 4.0-3.91 (m, 1H), 2.90-2.81 (m, 1H), 2.70-2.60 (m, 1H), 1.32 (s, 9H). LC-MS (Method A): m/z=303.2 (M+H)*, 1.08 min. e.e.=100% as determined on a Chiralpak AD-H (25×0.46 cm), 5 µm column using a mobile phase of 5% isopropanol in $CO_2$, flow rate: 2.5 mL/min, retention time: 7.7 min.

Example 69

Preparation of 2,2-dimethyl-1-[(3S)-3-[4-(trifluoromethyl)-1,3-thiazol-2-yl]-1,2-oxazolidin-2-yl]propan-1-one (123)

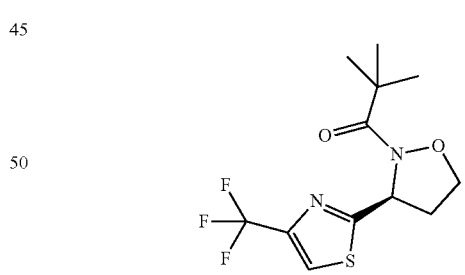

The title compound was isolated by chiral HPLC on a Whelk O-1 (R,R) (25×2.0 cm), 10 µm column using a mobile phase of n-hexane/(ethanol+0.1% isopropylamine) 80/20% v/v, flow rate: 18 mL/min. $^1$H NMR (400 MHz, CDCl$_3$) δ 7.72 (s, 1H), 5.78 (dd, J=8.8, 5.5 Hz, 1H), 4.31 (td, J=7.8, 4.0 Hz, 1H), 3.98 (q, J=7.8 Hz, 1H), 3.0-2.82 (m, 2H), 1.33 (s, 9H). LC-MS (Method A): m/z=309.2 [M+H]$^+$, 1.13 min. e.e.=100% as determined on a Whelk O-1 (R,R) (25×0.46 cm), 10 µm column using a mobile phase of n-hexane/(ethanol+0.1% isopropylamine) 80/20% v/v, flow rate: 1 mL/min, retention time: 5.2 min.

Example 70

Preparation of 2,2-dimethyl-1-[(3S)-3-{pyrazolo[1,5-A]pyridin-2-yl}-1,2-oxazolidin-2-yl]propan-1-one (124)

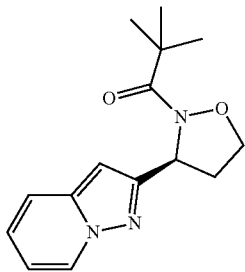 [SMILES: CC(C)(C)C(=O)N1OCC[C@H]1c1cc2ccccn2n1]

The title compound was isolated by chiral HPLC on a Chiralpak AD-H (25×2.0 cm), 5 µm column using a mobile phase of n-hexane/(ethanol+0.1% isopropylamine) 65/35% v/v, flow rate: 18 mL/min. $^1$H NMR (400 MHz, CDCl$_3$) δ 8.40 (dd, J=6.0, 1.0 Hz, 1H), 7.46 (dt, J=8.8, 1.0 Hz, 1H), 7.08 (ddd, J=7.8, 6.8, 1.0 Hz, 1H), 6.7 (td, J=7.0, 1.5 Hz, 1H), 6.49 (s, 1H), 5.78 (dd, J=7.8, 6.5 Hz, 1H), 4.36-4.30 (m, 1H), 3.97 (q, J=7.5 Hz, 1H), 2.84-2.77 (m, 2H), 1.33 (s, 9H). LC-MS (Method A): m/z=274.2 [M+H]$^+$, 0.97 min. e.e.=100% as determined on a Chiralpak AD-H (25×0.46 cm), 5 µm column using a mobile phase of n-hexane/(ethanol+0.1% isopropylamine) 65/35% v/v, flow rate: 1 mL/min, retention time: 7.0 min.

Example 71

Preparation of 2,2-dimethyl-1-[(3S)-3-(2-methylpyrimidin-5-yl)-1,2-oxazolidin-2-yl]propan-1-one (125)

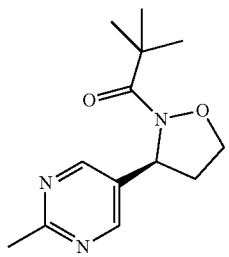 [SMILES: Cc1ncc([C@@H]2CCON2C(=O)C(C)(C)C)cn1]

The title compound was isolated by chiral HPLC on a Chiralpak AD-H (25×2.0 cm), 5 µm column using a mobile phase of n-hexane/(ethanol/methanol 1/1+0.1% isopropylamine) 40/60% v/v, flow rate: 18 mL/min. $^1$H NMR (400 MHz, CDCl$_3$) δ 8.59 (s, 2H), 5.40 (dd, J=6.8, 8.8 Hz, 1H), 4.32 (dt, J=2.8, 7.9 Hz, 1H), 3.94 (ddd, J=6.5, 8.2, 9.9 Hz, 1H), 2.87 (dddd, J=2.8, 6.4, 9.2, 12.3 Hz, 1H), 2.75-2.69 (m, 3H), 2.32 (tdd, J=7.3, 9.7, 12.2 Hz, 1H), 1.32-1.23 (m, 9H). LC-MS (Method A): m/z=250.2 [M+H]$^+$, 0.75 min e.e.=100% as determined on a Chiralpak AD-H (25×0.46 cm), 5 µm column using a mobile phase of n-hexane/(ethanol/methanol 1/1+0.1% isopropylamine) 40/60 v/v, flow rate: 1 mL/min, retention time: 12.0 min.

Example 72

Preparation of 3,3-difluoro-2,2-dimethyl-1-[(3S)-3-(2-methylpyrimidin-5-yl)-1,2-oxazolidin-2-yl]propan-1-one (126)

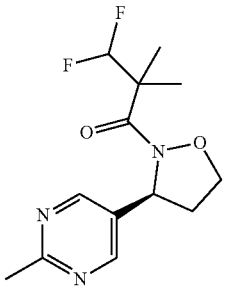 [SMILES: Cc1ncc([C@@H]2CCON2C(=O)C(C)(C)C(F)F)cn1]

The title compound was isolated by chiral HPLC on a Chiralpak AD-H (25×2.0 cm), 5 µm column using a mobile phase of n-hexane/(ethanol/methanol 1/1+0.1% isopropylamine) 40/60% v/v, flow rate: 18 mL/min. $^1$H NMR (400 MHz, CDCl$_3$) δ 8.58 (s, 2H), 6.48-6.09 (m, 1H), 5.40 (dd, J=8.8, 6.8 Hz, 1H), 4.36 (dt, J=2.8, 8.0 Hz, 1H), 4.00 (ddd, J=9.7, 8.2, 6.3 Hz, 1H), 2.91 (dddd, J=12.3, 9.2, 6.4, 3.0 Hz, 1H), 2.78-2.68 (m, 3H), 2.44-2.29 (m, 1H), 1.37 (s, 3H), 1.36 (s, 3H). LC-MS (Method A): m/z=286.2 [M+H]$^+$, 0.77 min. e.e.=100% as determined on a Chiralpak AD-H (25×0.46 cm), 5 µm column using a mobile phase of n-hexane/(ethanol/methanol 1/1+0.1% isopropylamine) 40/60 v/v, flow rate: 1 mL/min, retention time: 14.7 min.

Example 73

Preparation of 1-[(3S)-3-(5-fluoropyridin-2-yl)-1,2-oxazolidin-2-yl]-2,2-dimethylpropan-1-one (127)

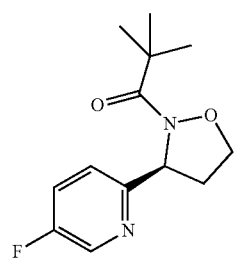 [SMILES: CC(C)(C)C(=O)N1OCC[C@H]1c1ccc(F)cn1]

The title compound was isolated by chiral HPLC on a Chiralpak AD-H (25×2.0 cm), 5 µm column using a mobile phase of n-hexane/ethanol 85/15% v/v, flow rate: 18 mL/min. $^1$H NMR (400 MHz, CDCl$_3$) δ 8.46-8.38 (m, 1H), 7.40-7.33 (m, 2H), 5.51 (dd, J=8.9, 6.1 Hz, 1H), 4.33-4.25 (m, 1H), 3.93 (ddd, J=9.4, 7.9, 6.8 Hz, 1H), 2.83-2.59 (m, 2H), 1.30 (s, 9H). LC-MS (Method A): m/z=253.2 [M+H]$^+$, 0.91 min. e.e.=100% as determined on a Chiralpak AD-H (25×0.46 cm), 5 µm column using a mobile phase of n-hexane/ethanol 85/15% v/v, flow rate: 1 mL/min, retention time: 8.0 min.

Example 74

Preparation of 1-[(3S)-3-[4-(difluoromethyl)phenyl]-1,2-oxazolidin-2-yl]-2,2-dimethylpropan-1-one (128)

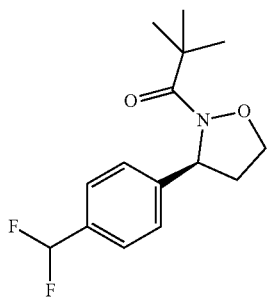 [SMILES: CC(C)(C)C(=O)N1OCC[C@H]1c1ccc(C(F)F)cc1]

The title compound was isolated by chiral HPLC on a Chiralpak IC (25×2.0 cm) 5 μm column using a mobile phase of n-hexane/(ethanol+0.1% isopropylamine) 85/15% v/v, flow rate: 18 mL/min. $^1$H NMR (400 MHz, CDCl$_3$) δ 7.52-7.45 (m, 2H), 7.43-7.36 (m, 2H), 6.79-6.46 (m, 1H), 5.45 (dd, J=8.7, 6.9 Hz, 1H), 4.28 (dt, J=2.6, 7.8 Hz, 1H), 3.91 (ddd, J=10.0, 8.0, 6.4 Hz, 1H), 2.84 (dddd, J=12.2, 9.1, 6.3, 2.8 Hz, 1H), 2.30 (dddd, J=12.2, 9.9, 7.5, 6.8 Hz, 1H), 1.31 (s, 9H). LC-MS (Method A): m/z=284.2 [M+H]$^+$, 1.13 min. e.e.=100% as determined on a Chiralpak IC (25×2.0 cm) 5 μm column using a mobile phase of n-hexane/(ethanol+0.1% isopropylamine) 85/15% v/v, flow rate: 1.0 mL/min, retention time: 7.4 min.

Example 75

Preparation of 3,3,3-trifluoro-2-methyl-1-[(3S)-3-(5-methylpyrazin-2-yl)-1,2-oxazolidin-2-yl]propan-1-one (129)

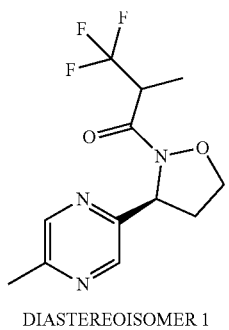 [SMILES: Cc1cnc([C@@H]2CCON2C(=O)C(C)C(F)(F)F)cn1]

DIASTEREOISOMER 1

The title compound was isolated by chiral HPLC on a Chiralcel OJ-H (25×2 cm) 5 μm column using a mobile phase of n-hexane/(ethanol+0.1% isopropylamine) 75/25% v/v, and a flow rate of 18 mL/min. First eluting diastereoisomer. Diastereoisomer 1. $^1$H NMR (400 MHz, CDCl$_3$) δ 8.55 (d, J=1.5 Hz, 1H), 8.43 (d, J=1.0 Hz, 1H), 5.54 (dd, J=8.5, 6.3 Hz, 1H), 4.38 (dt, J=3.9, 7.5 Hz, 1H), 4.11-3.99 (m, 1H), 3.89 (dd, J=8.0, 7.3 Hz, 1H), 2.93-2.69 (m, 2H), 2.58 (s, 3H), 1.41 (d, J=7.0 Hz, 3H). LC-MS (Method A): m/z=290.2 [M+H]$^+$, 0.80 min. e.e.=100% as determined on a Chiralcel OJ-H (25×0.46 cm) 5 μm column using a mobile phase of n-hexane/(ethanol+0.1% isopropylamine) 75/25% v/v, flow rate: 1 mL/min, retention time: 6.1 min.

Example 76

Preparation of 3,3,3-trifluoro-2-methyl-1-[(3S)-3-(5-methylpyrazin-2-yl)-1,2-oxazolidin-2-yl]propan-1-one (130)

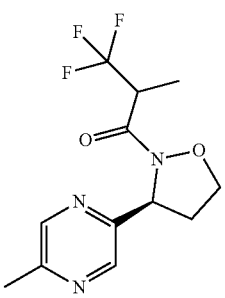

DIASTEREOISOMER 2

The title compound was isolated by chiral HPLC on a Chiralpak AD-H (25×2.0 cm) 5 μm column using a mobile phase of n-hexane/(ethanol+0.1% isopropylamine) 50/50% v/v and a flow rate of 18 mL/min. Second eluting diastereoisomer, Diastereoisomer 2. $^1$H NMR (400 MHz, CDCl$_3$) δ 8.54 (d, J=1.3 Hz, 1H), 8.42 (s, 1H), 5.51 (dd, J=8.8, 5.5 Hz, 1H), 4.38 (dt, J=7.7, 4.8 Hz, 1H), 4.09-4.00 (m, 1H), 3.86 (td, J=7.5, 15.4 Hz, 1H), 2.91-2.81 (m, 1H), 2.80-2.70 (m, 1H), 2.58 (s, 3H), 1.41 (d, J=7.3 Hz, 3H). LC-MS (Method A): m/z=290.2 [M+H]$^+$, 0.79 min. e.e.=100% as determined on a Chiralpak AD-H (25×0.46 cm) 5 μm column using a mobile phase of n-hexane/(ethanol+0.1% isopropylamine) 50/50% v/v, flow rate: 1 mL/min, retention time: 10.9 min.

Example 77

Preparation of 4-(3S)-3-[6-(difluoromethyl)pyridin-3-yl]-1,2-oxazolidin-2-yl-3,3-dimethyl-4-oxobutanenitrile (131)

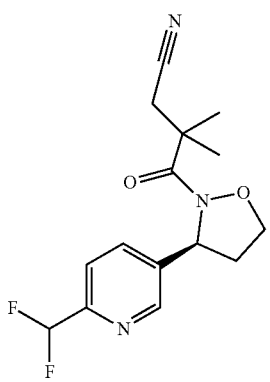 [SMILES: CC(C)(CC#N)C(=O)N1OCC[C@H]1c1ccc(C(F)F)nc1]

The title compound was isolated by chiral HPLC on a Chiralpak AD-H (25×2.0 cm) 5 μm column using a mobile phase of n-hexane/(ethanol/methanol 1/1+0.1% isopropylamine) 40/60% v/v and a flow rate of 18 mL/min. $^1$H NMR (400 MHz, CDCl$_3$) δ 8.62 (d, J=1.8 Hz, 1H), 7.77 (dd, J=8.2, 2.1 Hz, 1H), 7.64 (d, J=8.3 Hz, 1H), 6.80-6.47 (m, 1H), 5.48 (dd, J=8.5, 7.0 Hz, 1H), 4.39 (dt, J=2.9, 7.8 Hz, 1H), 4.02 (ddd, J=9.7, 8.2, 6.4 Hz, 1H), 2.95 (dddd, J=12.3, 9.2, 6.3, 2.9 Hz, 1H), 2.78-2.62 (m, 2H), 2.37 (tdd, J=12.4, 9.5, 7.3 Hz, 1H), 1.51-1.49 (m, 3H), 1.49-1.46 (m, 3H). LC-MS (Method A): m/z=310.23 [M+H]$^+$, 0.85 min. e.e.=95% as determined on a Chiralpak AD-H (25×0.46 cm) 5 μm column using a mobile phase of n-hexane/(ethanol/methanol 1/1+0.1% isopropylamine) 40/60% v/v, flow rate: 1 mL/min, retention time: 24.1 min.

Example 78

Preparation of 2,2-dimethyl-1-[(3S)-3-{pyrazolo[1,5-a]pyridin-5-yl}-1,2-oxazolidin-2-yl]propan-1-one (132)

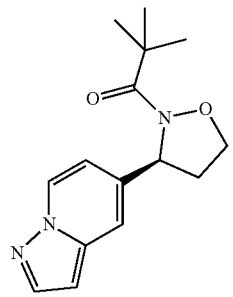 [SMILES: CC(C)(C)C(=O)N1OCC[C@H]1c1ccn2nccc2c1]

The title compound was isolated by chiral HPLC on a Chiralpak AD-H (25×2.0 cm) 5 μm column using a mobile phase of n-hexane/(ethanol/methanol 1/1+0.1% isopropylamine) 50/50% v/v and a flow rate of 18 mL/min. $^1$H NMR (400 MHz, CDCl$_3$) δ 8.43 (d, J=7.3 Hz, 1H), 7.93 (d, J=2.3 Hz, 1H), 7.50-7.40 (m, 1H), 6.70 (dd, J=7.3, 1.8 Hz, 1H), 6.47 (dd, J=2.3, 0.8 Hz, 1H), 5.42 (dd, J=8.8, 6.8 Hz, 1H), 4.30 (td, J=7.7, 2.8 Hz, 1H), 3.91 (ddd, J=10.0, 8.1, 6.5 Hz, 1H), 2.91-2.75 (m, 1H), 2.34 (dddd, J=12.3, 9.9, 7.6, 6.8 Hz, 1H), 1.32 (s, 9H). LC-MS (Method A): m/z=274.2 [M+H]$^+$, 0.93 min. e.e.=100% as determined on a Chiralpak AD-H (25×0.46 cm) 5 μm column using a mobile phase of n-hexane/(ethanol/methanol 1/1+0.1% isopropylamine) 50/50% v/v, flow rate: 1 mL/min, retention time: 12.9 min.

Example 79

Preparation of 1-[(3S)-3-(5-fluoropyridin-3-yl)-1,2-oxazolidin-2-yl]-2,2-dimethylpropan-1-one (133)

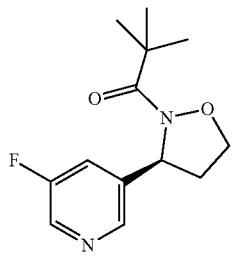 [SMILES: CC(C)(C)C(=O)N1OCC[C@H]1c1cncc(F)c1]

The title compound was isolated by chiral HPLC on a Chiralpak AD-H (25×2.0 cm) 5 μm column using a mobile phase of n-hexane/ethanol 70/30% v/v and a flow rate of 18 mL/min. $^1$H NMR (400 MHz, CDCl$_3$) δ 8.42 (t, J=1.5 Hz, 1H), 8.38 (d, J=2.8 Hz, 1H), 7.34 (dt, J=9.2, 2.1 Hz, 1H), 5.47 (dd, J=8.9, 6.7 Hz, 1H), 4.34-4.27 (m, 1H), 3.92 (ddd, J=10.0, 8.1, 6.5 Hz, 1H), 2.94-2.83 (m, 1H) 2.32 (dddd, J=12.4, 9.9, 7.7, 6.7 Hz, 1H) 1.30 (s, 9H). LC-MS (Method B): m/z=252.0 [M+H]$^+$, 0.90 min. e.e.=98.2% as determined on a Chiralpak AD-H (25×0.46 cm) 5 μm column using a mobile phase of n-hexane/ethanol 70/30% v/v, flow rate: 1 mL/min, retention time: 7.7 min.

Examples 80 and 81

Preparation of 1-[(3R)-3-(2,4-difluorophenyl)-1,2-oxazolidin-2-yl]-2,2-dimethylpropan-1-one and 1-[(3S)-3-(2,4-difluorophenyl)-1,2-oxazolidin-2-yl]-2,2-dimethylpropan-1-one (134) and (135)

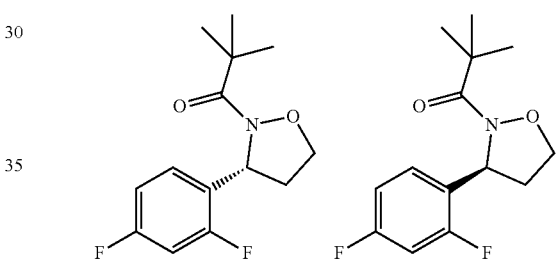

The title compounds were isolated by chiral HPLC on a Chiralpak IC (25×2.0 cm), 5 μm column using a mobile phase of n-hexane/2-propanol 90/10% v/v, flow rate: 17 mL/min.

1-[(3R)-3-(2,4-difluorophenyl)-1,2-oxazolidin-2-yl]-2,2-dimethylpropan-1-one. $^1$H NMR (400 MHz, CDCl$_3$) δ 7.24 (td, J=8.6, 6.4 Hz, 1H), 6.89-6.76 (m, 2H), 5.61 (dd, J=8.7, 6.7 Hz, 1H), 4.25 (td, J=7.7, 2.6 Hz, 1H), 3.90 (ddd, J=9.8, 8.0, 6.5 Hz, 1H), 2.94-2.80 (m, 1H), 2.34-2.16 (m, 1H), 1.31 (s, 9H). LC-MS (Method B): m/z=269.0 [M+H], 1.16 min. e.e.=95.8% as determined on a Chiralpak IC (25×0.46 cm), 5 μm column using a mobile phase of n-hexane/2-propanol 90/10% v/v, flow rate: 1 mL/min, retention time: 6.4 min.

1-[(3S)-3-(2,4-difluorophenyl)-1,2-oxazolidin-2-yl]-2,2-dimethylpropan-1-one. $^1$H NMR (400 MHz, CDCl$_3$) δ 7.27-7.20 (m, 1H), 6.88-6.77 (m, 2H), 5.62 (dd, J=8.7, 6.7 Hz, 1H), 4.25 (td, J=7.7, 2.5 Hz, 1H), 3.91 (ddd, J=9.8, 8.0, 6.5 Hz, 1H), 2.90-2.85 (m, 1H), 2.32-2.17 (m, 1H), 1.32 (s, 9H). LC-MS (Method B): m/z=269.0 [M+H]$^+$, 1.16 min. e.e.=100% as determined on a Chiralpak IC (25×0.46 cm), 5 μm column using a mobile phase of n-hexane/2-propanol 90/10% v/v, flow rate: 1 mL/min, retention time: 9.6 min.

Examples 82 and 83

Preparation of (3S)-3-(4-fluorophenyl)-2-(2-methyl-oxolane-2-carbonyl)-1,2-oxazolidines (136) and (137)

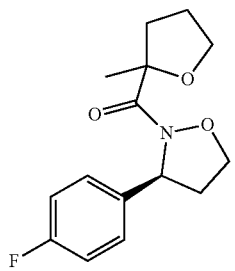 [SMILES: CC1(C(=O)N2OCC[C@H]2c2ccc(F)cc2)CCCO1]

The title compounds ((3S)-3-(4-fluorophenyl)-2-((S)-2-methyloxolane-2-carbonyl)-1,2-oxazolidine and (3S)-3-(4-fluorophenyl)-2-((R)-2-methyloxolane-2-carbonyl)-1,2-oxazolidine) were isolated by chiral HPLC on a Chiralpak OJ-H (25×2.0 cm), 5 μm column using a mobile phase of n-hexane/ethanol 50/50% v/v, flow rate: 18 mL/min.

First eluting diastereoisomer, Diastereoisomer 1. $^1$H NMR (400 MHz, CDCl$_3$) δ 7.34-7.24 (m, 2H), 7.08-6.98 (m, 2H), 5.57-5.45 (m, 1H), 4.25 (td, J=7.8, 4.0 Hz, 1H), 3.98 (q, J=8.0 Hz, 1H), 3.89-3.80 (m, 1H), 3.79-3.68 (m, 1H), 3.68-3.57 (m, 1H), 2.82 (dddd, J=12.3, 8.7, 7.2, 4.0 Hz, 1H), 2.66-2.55 (m, 1H), 2.39-2.24 (m, 1H), 1.96-1.73 (m, 3H), 1.56 (s, 3H). LC-MS (Method B): m/z=280.1 [M+H]$^+$, 0.89 min. e.e.=100% as determined on a Chiralpak OJ-H (25×0.46 cm), 5 μm column using a mobile phase of n-hexane/ethanol 50/50% v/v, flow rate: 1 mL/min, retention time: 6.0 min.

Second eluting diastereoisomer. Diastereoisomer 2. $^1$H NMR (400 MHz, CDCl$_3$) δ 7.32-7.26 (m, 2H), 7.06-6.99 (m, 2H), 5.52-5.45 (m, 1H), 4.32-4.23 (td, J=7.8, 3.5 Hz, 1H), 4.04-3.92 (m, 2H), 3.92-3.83 (m, 1H), 2.83 (dddd, J=12.2, 8.7, 6.9, 3.8 Hz, 1H), 2.51-2.41 (m, 1H), 2.34 (dddd, J=12.3, 9.1, 7.6, 5.9 Hz, 1H), 2.02-1.78 (m, 3H), 1.50 (s, 3H). LC-MS (Method B): m/z=280.1 [M+H]$^+$, 0.90 min. e.e.=100% as determined on a Chiralpak OJ-H (25×0.46 cm), 5 μm column using a mobile phase of n-hexane/ethanol 50/50% v/v, flow rate: 1 mL/min, retention time: 6.9 min.

Example 84

Preparation of 2,2-dimethyl-1-[(3S)-3-(5-methyl-pyrazin-2-yl)-1,2-oxazolidin-2-yl]propan-1-one (138)

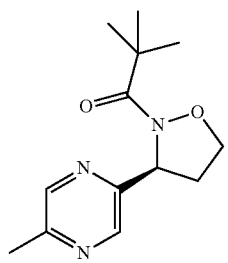 [SMILES: Cc1cnc([C@@H]2CCON2C(=O)C(C)(C)C)cn1]

The title compound was isolated by chiral HPLC on a Chiralpak AD-H (25×2.0 cm), 5 μm column using a mobile phase of n-hexane/ethanol 60/40% v/v, flow rate: 18 mL/min. $^1$H NMR (400 MHz, CDCl$_3$) δ 8.53 (d, J=1.3 Hz, 1H), 8.41 (d, J=1.0 Hz, 1H), 5.53 (dd, J=8.8, 6.3 Hz, 1H), 433 (td, J=7.4, 3.3 Hz, 1H), 3.97 (ddd, J=9.4, 7.9, 6.5 Hz, 1H), 2.86-2.74 (m, 1H), 2.64 (dddd, J=12.3, 9.4, 7.7, 6.3 Hz, 1H), 2.56 (s, 3H), 1.30 (s, 9H). LC-MS (Method A): m/z=250.2 [M+H]$^+$, 0.80 min. e.e.=100% as determined on a Chiralpak AD-H (25×0.46 cm), 5 μm column using a mobile phase of n-hexane/ethanol 60/40 v/v, flow rate: 1 mL/min, retention time: 9.8 min.

Example 85

Preparation of 1-[(3S)-3-(5-fluoropyridin-3-yl)-1,2-oxazolidin-2-yl]-2,2-dimethyl-3-(trifluoromethoxy)propan-1-one (139)

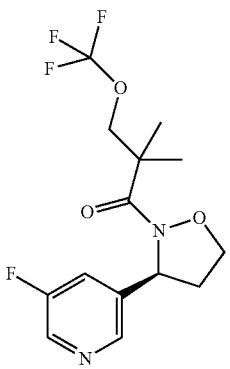 [SMILES: CC(C)(COC(F)(F)F)C(=O)N1OCC[C@H]1c1cncc(F)c1]

The title compound was isolated by chiral HPLC on a Chiralpak AD-H (25×2.0 cm), 5 μm column using a mobile phase of n-hexane/(ethanol+0.1% isopropylamine) 70/30% v/v, flow rate: 18 mL/min. $^1$H NMR (400 MHz, CDCl$_3$) δ 8.43-8.38 (m, 2H), 7.36-7.30 (m, 1H), 5.49 (dd, J=8.8, 7.0 Hz, 1H), 4.40-4.27 (m, 1H), 4.16 (s, 2H), 3.99 (ddd, J=9.6, 8.1, 6.4 Hz, 1H), 2.92 (ddd, J=12.4, 5.9, 3.3 Hz, 1H), 2.42-2.23 (m, 1H), 1.36 (s, 6H). LC-MS (Method A): m/z=336.0 [M+H]$^+$, 1.04 min. e.e.=100% as determined on a Chiralpak AD-H (25×0.46 cm), 5 μm column using a mobile phase of n-hexane/(ethanol+0.1% isopropylamine) 70/30% v/v, flow rate: 1 mL/min, retention time: 9.0 min.

Example 86

Preparation of 2,2-dimethyl-1-[(3S)-3-{pyrazolo[1,5-a]pyridin-7-yl}-1,2-oxazolidin-2-yl]propan-1-one (140)

The title compound was isolated by chiral HPLC on a Chiralpak AD-H (25×2.0 cm), 5 μm column using a mobile phase of n-hexane/(ethanol+0.1% isopropylamine) 40/60% v/v, flow rate: 18 mL/min. $^1$H NMR (400 MHz, CDCl$_3$) δ 7.99 (d, J=2.3 Hz, 1H), 7.56-7.46 (m, 1H), 7.13 (dd, J=8.9, 6.9 Hz, 1H), 6.74 (d, J=7.0 Hz, 1H), 6.58 (d, J=2.3 Hz, 1H), 6.16 (dd, J=8.8, 6.0 Hz, 1H), 4.29-4.17 (m, 1H), 4.01 (ddd, J=9.3, 8.0, 6.8 Hz, 1H), 3.34-3.17 (m, 1H), 2.30 (dddd, J=12.5, 9.3, 7.8, 5.8 Hz, 1H), 1.38 (s, 9H). LC-MS (Method A): m/z=274.2 [M+H]$^+$, 1.05 min. e.e.=100% as determined on a Chiralpak AD-H (25×0.46 cm), 5 μm column using a mobile phase of n-hexane/(ethanol+0.1% isopropylamine) 40/60% v/v, flow rate: 1 mL/min, retention time: 5.1 min.

Examples 87 and 88

Preparation of 2-fluoro-5-(3S)-2-(3-methyloxolane-3-carbonyl)-1,2-oxazolidin-3-yl)pyridines (141) and (142)

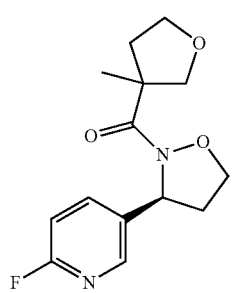 [SMILES: CC1(C(=O)N2OCC[C@H]2c2ccc(F)nc2)CCOC1]

The title compounds (2-fluoro-5-[(3S)-2-((S)-3-methyloxolane-3-carbonyl)-1,2-oxazolidin-3-yl]pyridine and 2-fluoro-5-[(3S)-2-((R)-3-methyloxolane-3-carbonyl)-1,2-oxazolidin-3-yl]pyridine) were isolated by chiral HPLC on a Chiralpak AD-H (25×2.0 cm), 5 μm column using a mobile phase of n-hexane/(ethanol/methanol 1/1+01% isopropylamine) 10/90% v/v, flow rate: 16 mL/min.

First eluting diastereoisomer, Diastereoisomer 1. $^1$H NMR (400 MHz, CDCl$_3$) δ 8.20 (d, J=2.8 Hz, 1H), 7.73 (td, J=8.0, 2.6 Hz, 1H), 6.93 (dd, J=8.5, 3.0 Hz, 1H), 5.44 (dd, J=8.8, 6.5 Hz, 1H), 4.33 (td, J=7.9, 3.0 Hz, 1H), 4.17 (d, J=9.0 Hz, 1H), 4.01-3.79 (m, 3H), 3.73 (d, J=9.0 Hz, 1H), 2.91 (ddt, J=15.4, 9.0, 3.2 Hz, 1H), 2.56-2.30 (m, 2H), 1.86 (ddd, J=12.7, 7.3, 5.5 Hz, 1H), 1.43 (s, 3H). LC-MS (Method B): m/z=280.0 [M+H]$^+$, 0.72 min. Chiralpak AD-H (25×0.46 cm), 5 μm column using a mobile phase of n-hexane/(ethanol/methanol 1/1+0.1% isopropylamine) 10/90% v/v flow rate: 1 mL/min, retention time: 17.8 min.

Second eluting diastereoisomer. Diastereoisomer 2. $^1$H NMR (400 MHz, CDCl$_3$) δ 8.20 (d, J=2.3 Hz, 1H), 7.73 (dt, J=2.5, 8.0 Hz, 1H), 6.92 (dd, J=8.5, 3.0 Hz, 1H), 5.42 (dd, J=8.7, 6.7 Hz, 1H), 4.33 (td, J=7.8, 2.9 Hz, 1H), 4.04-3.72 (m, 5H), 2.91 (dddd, J=12.3, 9.1, 6.2, 3.0 Hz, 1H), 2.60 (ddd, J=12.9, 8.1, 6.9 Hz, 1H), 2.36 (dddd, J=12.5, 9.7, 7.6, 6.7 Hz, 1H), 1.81 (ddd, J=12.9, 7.4, 5.8 Hz, 1H), 1.46 (s, 3H). LC-MS (Method B): m/z=280.1 [M+H]$^+$, 0.90 min. Chiralpak AD-H (25×0.46 cm), 5 μm column using a mobile phase of n-hexane/(ethanol/methanol 1/1+0.1% isopropylamine) 10/90% v/v, flow rate: 1 mL/min, retention time: 19.6 min.

Example 89

Preparation of 5-[(3S)-2-(2,2-dimethylpropanoyl)-1,2-oxazolidin-3-yl]pyridine-2-carbonitrile (143)

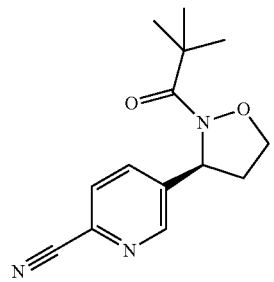 [SMILES: CC(C)(C)C(=O)N1OCC[C@H]1c1ccc(C#N)nc1]

The title compound was isolated by chiral HPLC on a Chiralpak IA (25×2.0 cm), 5 μm column using a mobile phase of n-hexane/ethanol 50/50% v/v, flow rate: 15 mL/min. $^1$H NMR (300 MHz, DMSO-d$_6$) δ 8.66 (d, J=1.8 Hz, 1H), 8.02 (d, J=7.8 Hz, 1H), 7.88 (dd, J=7.8, 2.1 Hz, 1H), 5.43 (t, J=8.1 Hz, 1H), 4.36-4.30 (m, 1H), 3.94-3.86 (m, 1H), 2.94-2.90 (m, 1H), 2.24-2.17 (m, 1H), 1.21 (s, 9H). LC-MS (Method E): m/z=260.1 [M+H]$^+$, 2.67 min. e.e.=99.9% as determined on a Chiralpak IA-3 (5×0.46 cm), 3 μm column using a mobile phase of (n-hexane+0.1% diethylamine)/ethanol 70/30% v/v, flow-rate: 1.0 mL/min, retention time: 3.02 min.

Example 90

Preparation of 1-[(3S)-3-(2-methoxypyridin-4-yl)-1,2-oxazolidin-2-yl]-2,2-dimethylpropan-1-one (144)

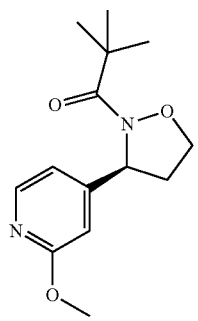 [SMILES: COc1cc([C@@H]2CCON2C(=O)C(C)(C)C)ccn1]

The title compound was isolated by chiral HPLC on a Chiralpak IC (25×2.0 cm), 5 μm column using a mobile phase of n-hexane/ethanol 80/20% v/v, flow rate: 20 mL/min. $^1$H NMR (400 MHz, DMSO-$d_6$) δ 8.10 (d, J=5.2 Hz, 1H), 6.84 (dd, J=5.2, 1.2 Hz, 1H), 6.60 (s, 1H), 5.27-5.23 (m, 1H), 4.27-4.22 (m, 1H), 3.85-3.79 (m, 4H), 2.87-2.82 (m, 1H), 2.10-2.04 (m, 1H), 1.19 (s, 9H). LC-MS (Method F): m/z=265.0 [M+H]$^+$, 1.04 min. e.e.=99.9% as determined on a Chiralpak IC-3 (5×0.46 cm), 5 μm column using a mobile phase of (n-hexane+0.1% diethylamine)/ethanol 80/20% v/v, flow rate: 1.0 mL/min, retention time: 2.59 min.

Example 91

Preparation of 1-[(3S)-3-(6-methoxypyridin-3-yl)-1,2-oxazolidin-2-yl]-2,2-dimethylpropan-1-one (145)

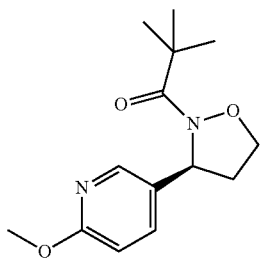 [SMILES: COc1ccc([C@@H]2CCON2C(=O)C(C)(C)C)cn1]

The title compound was isolated by chiral SFC on a Chiralart Amylose-SA (25×2.0 cm), 5 μm column using a mobile phase of carbon dioxide/(methanol+2 mM ammonia) 80/20% v/v, flow rate: 40 mL/min. $^1$H NMR (400 MHz, DMSO-$d_6$) δ 8.03 (d, J=2.4 Hz, 1H), 7.55 (dd, J=8.4, 2.4 Hz, 1H), 6.79 (d, J=8.8 Hz, 1H), 5.28-5.25 (m, 1H), 4.29-4.27 (m, 1H), 3.85-3.79 (m, 4H), 2.82-2.79 (m, 1H), 2.23-2.10 (m, 1H), 1.17 (s, 9H). LC-MS (Method O): m/z=265.1 [M+H]$^+$, 1.82 min. e.e.=99.9% as determined on a Chiralpak AD-3 (3×100 mm), 3 μm column using a mobile phase of carbon dioxide/(methanol+0.1% diethylamine) 95/5% v/v, flow rate: 2.0 mL/min, retention time: 1.54 min.

Example 92

Preparation of 2-[(3S)-2-(2,2-dimethylpropanoyl)-1,2-oxazolidin-3-yl]benzonitrile (146)

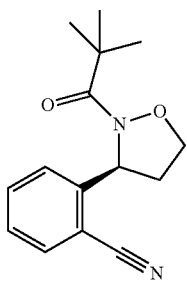 [SMILES: CC(C)(C)C(=O)N1OCC[C@H]1c1ccccc1C#N]

The title compound was isolated by chiral HPLC on a Chiralpak IC (25×2.0 cm), 5 μm column using a mobile phase of n-hexane/isopropanol 70/30% v/v, flow rate: 20 mL/min. $^1$H NMR (400 MHz, DMSO-$d_6$) δ 7.83 (dd, J=7.6, 1.2 Hz, 1H), 7.73-7.69 (m, 1H), 7.49-7.41 (m, 2H), 5.49 (t, J=8.0 Hz, 1H), 4.37-4.33 (m, 1H), 3.96-3.90 (m, 1H), 2.99-2.96 (m, 1H), 2.14-2.09 (m, 1H), 1.21 (s, 9H). LC-MS (Method H): m/z=258.9 [M+H]$^+$, 1.48 min. e.e.=98.9% as determined on a Chiralpak IC-3 (5×0.46 cm), 3 μm column using a mobile phase of (n-hexane+0.1% diethylamine)/isopropanol 70/30% v/v, flow rate: 1.0 mL/min, retention time: 2.59 min.

Example 93

Preparation of 3-[(3S)-2-(2,2-dimethylpropanoyl)-1,2-oxazolidin-3-yl]benzonitrile (147)

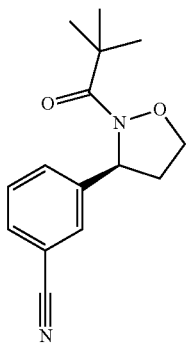 [SMILES: CC(C)(C)C(=O)N1OCC[C@H]1c1cccc(C#N)c1]

The title compound was isolated by chiral HPLC on a Chiralpak IC (25×2.0 cm), 5 μm column using a mobile phase of n-hexane/ethanol 80/20% v/v, flow rate: 20 mL/min. $^1$H NMR (300 MHz, DMSO-$d_6$) δ 7.76-7.64 (m, 2H), 7.60-7.51 (m, 2H), 5.36-5.31 (m, 1H), 4.25-4.31 (m, 1H), 3.88-3.80 (m, 4H), 2.92-2.82 (m, 1H), 2.20-2.08 (m, 1H), 1.19 (s, 9H). LC-MS (Method F): m/z=259.0 [M+H]$^+$, 1.31 min. e.e.=99.9% as determined on a Chiralpak IC-3 (5×0.46 cm), 5 μm column using a mobile phase of (n-hexane+0.1% diethylamine)/ethanol 80/20% v/v, flow rate: 1.0 mL/min. retention time: 2.32 min.

Example 94

Preparation of 1-[(3S)-3-(6-cyclopropylpyridin-3-yl)-1,2-oxazolidin-2-yl]-2,2-dimethylpropan-1-one (148)

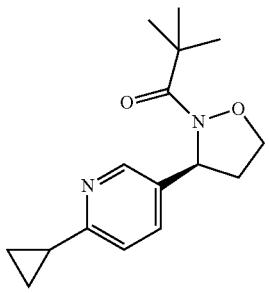 [SMILES: CC(C)(C)C(=O)N1OCC[C@H]1c1ccc(C2CC2)nc1]

The title compound was isolated by chiral HPLC on a Chiralpak IC (25×2.0 cm), 5 μm column using a mobile phase of n-hexane/ethanol 80/20% v/v, flow rate: 20 mL/min. $^1$H NMR (300 MHz, DMSO-$d_6$) δ 8.26 (d, J=2.1 Hz, 1H), 7.47 (dd, J=8.1, 2.1 Hz, 1H), 7.23 (d, J=7.8 Hz, 1H), 5.34-5.18 (m, 1H), 4.31-4.25 (m, 1H), 3.87-3.79 (m, 1H), 2.88-2.70 (m, 1H), 2.24-1.92 (m, 2H), 1.17 (s, 9H), 0.96-0.82 (m, 4H). LC-MS (Method F): m/z=275.0 [M+H]$^+$, 0.80 min. e.e.=99.9% as determined on a Chiralpak IC-3 (5×0.46 cm), 5 μm column using a mobile phase of (n-hexane+0.1% diethylamine)/ethanol 80/20% v/v, flow rate: 1.0 mL/min, retention time: 2.89 min.

Example 95

Preparation of 1-[(3S)-3-(2-aminopyridin-4-yl)-1,2-oxazolidin-2-yl]-2,2-dimethylpropan-1-one (149)

The title compound was isolated by chiral HPLC on a Chiralpak IA (25×2.0 cm), 5 μm column using a mobile phase of n-hexane/ethanol 80/20% v/v, flow rate: 20 mL/min. $^1$H NMR (300 MHz, DMSO-$d_6$) δ 7.83 (d, J=5.4 Hz, 1H), 6.37 (dd, J=5.4, 1.5 Hz, 1H), 6.31 (s, 1H), 6.05 (br s, 2H), 5.15-5.10 (m, 1H), 4.25-4.24 (m, 1H), 3.82-3.78 (m, 1H), 2.85-2.80 (m, 1H), 2.07-2.00 (m, 1H), 1.21 (s, 9H). LC-MS (Method J): m/z=250.3 [M+H]$^+$, 1.01 min. e.e.=99.9% as determined on a Chiralpak IA-3 (5×0.46 cm), 3 μm column using a mobile phase of (n-hexane+0.2% isopropylamine)/ethanol 80/20% v/v, flow rate: 1.0 mL/min, retention time: 2.57 min.

Example 96

Preparation of 3-[(3S)-2-(2,2-dimethylpropanoyl)-1,2-oxazolidin-3-yl]-4-fluorobenzonitrile (150)

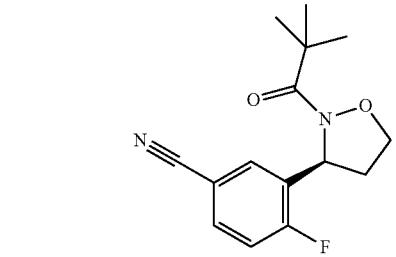 [SMILES: CC(C)(C)C(=O)N1OCC[C@H]1c1cc(C#N)ccc1F]

The title compound was isolated by chiral HPLC on a Lux 5u Cellulose-3, AXIA Packed (25×2.12 cm), 5 μm column using a mobile phase of n-hexane/ethanol 90/10% v/v, flow rate: 20 mL/min. $^1$H NMR (300 MHz, DMSO-$d_6$) δ 7.89-7.83 (m, 1H), 7.61 (dd, J=6.9, 1.8 Hz, 1H), 7.50-7.43 (m, 1H), 5.47-5.42 (m, 1H), 4.34-4.29 (m, 1H), 3.91-3.83 (m, 1H), 2.95-2.79 (m, 1H), 2.18-2.11 (m, 1H), 1.20 (s, 9H). LC-MS (Method H): m/z=276.9 [M+H]$^+$, 1.51 min. e.e.=99.9% as determined on a Lux Cellulose-3 (15×0.46 cm), 3 μm column using a mobile phase of (n-hexane+0.1% diethylamine)/isopropanol 70/30% v/v, flow rate: 1.0 mL/min, retention time: 3.19 min.

Example 97

Preparation of 4-[(3S)-2-(2,2-dimethylpropanoyl)-1,2-oxazolidin-3-yl]-2-fluorobenzonitrile (151)

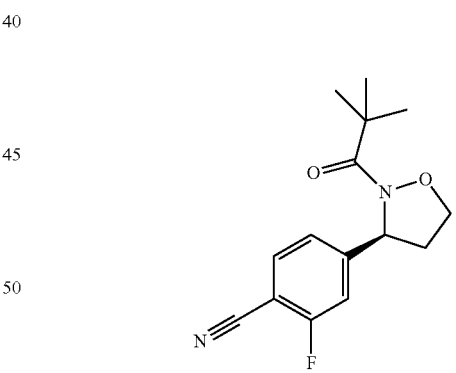

The title compound was isolated by chiral HPLC on a Chiralpak IF (25×2.0 cm), 5 μm column using a mobile phase of n-hexane/ethanol 70/30% v/v, flow rate: 18 mL/min. $^1$H NMR (300 MHz, DMSO-$d_6$) δ 7.94-7.89 (m, 1H), 7.39-7.27 (m, 2H), 5.42-5.36 (m, 1H), 4.37-4.24 (m, 1H), 3.90-3.82 (m, 1H), 2.92-2.88 (m, 1H), 2.10-2.17 (m, 1H), 1.22 (s, 9H). LC-MS (Method D): m/z=277.1 [M+H]$^+$, 2.07 min. e.e.=99.9% as determined on a Chiralpak IF-3 (10×0.46 cm), 3 μm column using a mobile phase of (n-hexane+0.1% diethylamine)/ethanol 70/30% v/v, flow rate: 1.0 mL/min, retention time: 3.36 min.

Example 98

Preparation of 2,2-dimethyl-1-[(3S)-3-(6-methyl-pyridin-3-yl)-1,2-oxazolidin-2-yl]propan-1-one (152)

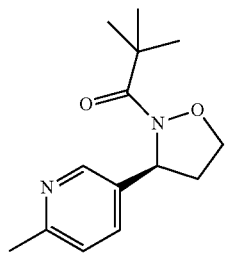 [SMILES: Cc1ccc([C@@H]2CCON2C(=O)C(C)(C)C)cn1]

The title compound was isolated by chiral HPLC on a Chiralpak IC (25×2.0 cm), 5 μm column using a mobile phase of n-hexane/ethanol 70/30% v/v, flow rate: 20 mL/min. ¹H NMR (300 MHz, DMSO-d₆) δ 8.32 (d, J=2.1 Hz, 1H), 7.50 (dd, J=8.1, 2.4 Hz, 1H), 7.20 (d, J=8.1 Hz, 1H), 5.29 (t, J=6.9 Hz, 1H) 4.32-4.26 (m, 1H), 3.88-3.80 (m, 1H), 2.86-2.82 (m, 1H), 2.42 (s, 3H), 2.21-2.11 (m, 1H), 1.18 (s, 9H). LC-MS (Method J): m/z=249.3 [M+H]⁺, 1.20 min. e.e.=99.9% as determined on a Chiralpak IC-3 (10× 0.46 cm), 3 μm column using a mobile phase of (n-hexane+ 0.1% diethylamine)/ethanol 70/30% v/v, flow rate: 1.0 mL/min, retention time: 4.17 min.

Example 99

Preparation of 5-[(3S)-2-(2,2-dimethylpropanoyl)-1,2-oxazolidin-3-yl]-2-fluorobenzonitrile (153)

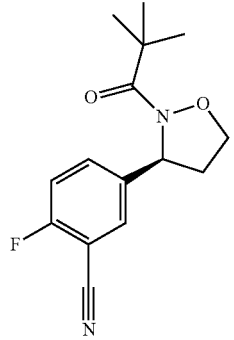

The title compound was isolated by chiral HPLC on a Phenomenex Lux 5u Cellulose-4, AXIA Packed (25×2.12 cm), 5 μm column using a mobile phase of n-hexane/ethanol 70/30% v/v, flow rate: 20 mL/min. ¹H NMR (400 MHz, DMSO-d₆) δ 7.79-7.77 (m, 1H), 7.66-7.62 (m, 1H), 7.54-7.49 (m, 1H), 5.34 (t, J=8.4 Hz, 1H), 4.32-4.28 (m, 1H), 3.88-3.82 (m, 1H), 2.88-2.85 (m, 1H), 2.19-2.14 (m, 1H), 1.20 (s, 9H). LC-MS (Method L): m/z=277.2 [M+H]⁺, 1.56 min. e.e.=99.9% as determined on a Lux Cellulose-3 (10× 0.46 cm), 3 μm column using a mobile phase of (n-hexane+ 0.1% diethylamine)/ethanol 70/30% v/v, flow rate: 1.0 mL/min, retention time: 2.44 min.

Example 100

Preparation of 4-[(3S)-2-[3-(difluoromethoxy)-2,2-dimethylpropanoyl]-1,2-oxazolidin-3-yl]benzonitrile (154)

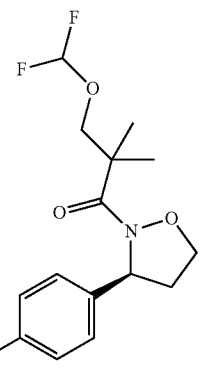

The title compound was isolated by chiral HPLC on a EnantioPak A1-5 (25×2.12 cm), 5 μm column using a mobile phase of n-hexane/ethanol 70/30% v/v, flow rate: 20 mL/min. ¹H NMR (300 MHz, CD₃OD) 7.72 (d, J=8.4 Hz, 2H), 7.50 (d, J=8.1 Hz, 2H), 6.42 (t, J=75.6 Hz, 1H), 5.44 (t, J=7.2 Hz, 1H), 4.40-4.34 (m, 1H), 4.13-4.00 (m, 3H), 3.03-2.93 (m, 1H), 2.32-2.26 (m, 1H), 1.33 (s, 6H). LC-MS (Method D): m/z=325.1 [M+H]⁺, 2.00 min. e.e.=99.9% as determined on a Chiralpak IC-3 (5×0.46 cm), 3 μm column using a mobile phase of (n-hexane+0.1% diethylamine)/ ethanol 70/30% v/v, flow rate: 1.0 mL/min, retention time: 1.53 min.

Example 101

Preparation of 3,3-difluoro-1-[(3S)-3-(5-fluoro-6-methylpyridin-3-yl)-1,2-oxazolidin-2-yl]-2*2-dimethylpropan-1-one (195)

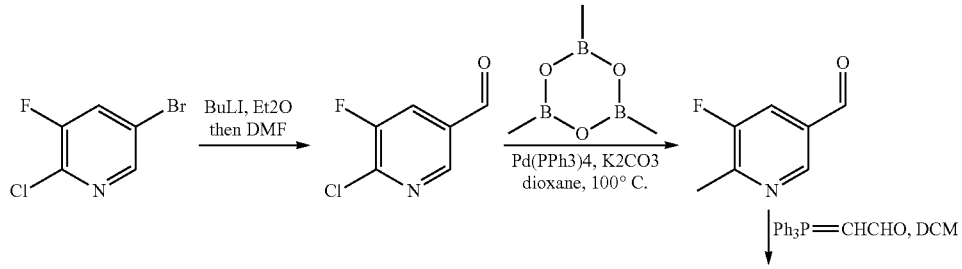

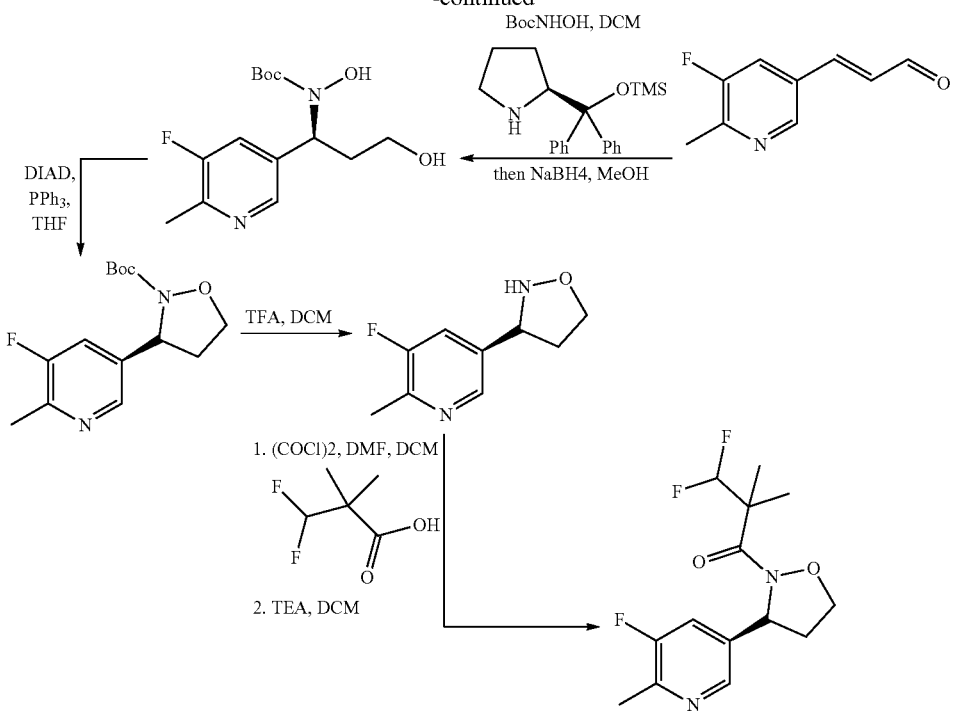

The title compound was isolated by chiral HPLC on a Chiralpak AD-H (25×2.0 cm), 5 μm column using a mobile phase of n-hexane/ethanol 50/50% v/v, flow rate: 18 mL/min. $^1$H NMR (400 MHz, CDCl$_3$) δ 8.28 (s, 1H), 7.24 (dd, J=9.8, 1.8 Hz, 1H), 6.32 (t, J=57.7 Hz, 1H), 5.44 (dd, J=8.7, 6.7 Hz, 1H), 4.35 (td, J=7.8, 3.0 Hz, 1H), 3.98 (ddd, J=9.5, 8.3, 6.5 Hz, 1H), 2.90 (dddd, J=12.4, 9.2, 6.3, 3.3 Hz, 1H), 2.52 (d, J=3.0 Hz, 3H), 2.35 (dddd, J=12.4, 9.6, 7.6, 6.8 Hz, 1H), 1.40-1.36 (m, 6H). LC-MS (Method A): m/z=302.9 [M+H]$^+$, 0.93 min. e.e.=100% as determined on a Chiralpak AD-H (25×0.46 cm), 5 μm column using a mobile phase of n-hexane/ethanol 50/50% v/v, flow rate: 1 mL/min, retention time: 5.5 min.

Example 102

Preparation of 4-[(3S)-3-(5-fluoro-6-methylpyridin-3-yl)-1,2-oxazolidin-2-yl]-3,3-dimethyl-4-oxobutanenitrile (196)

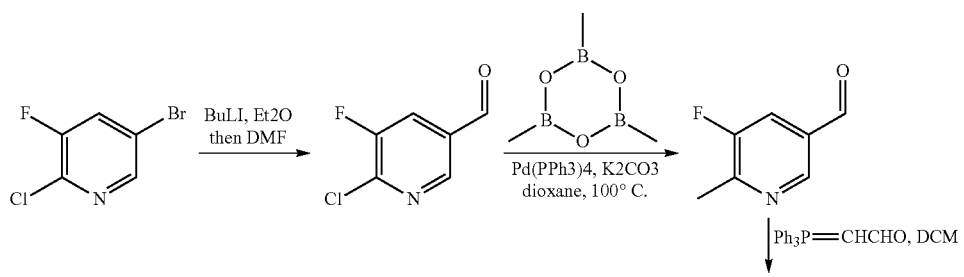

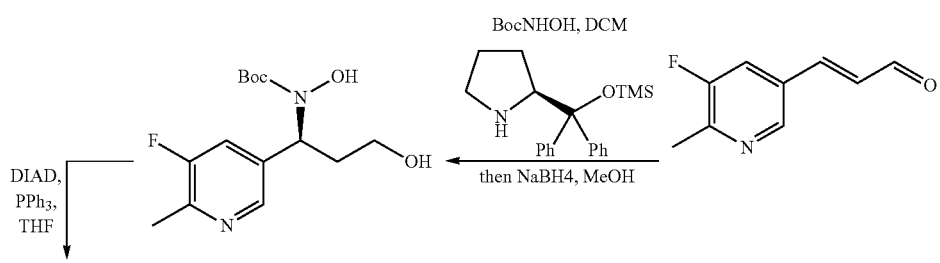

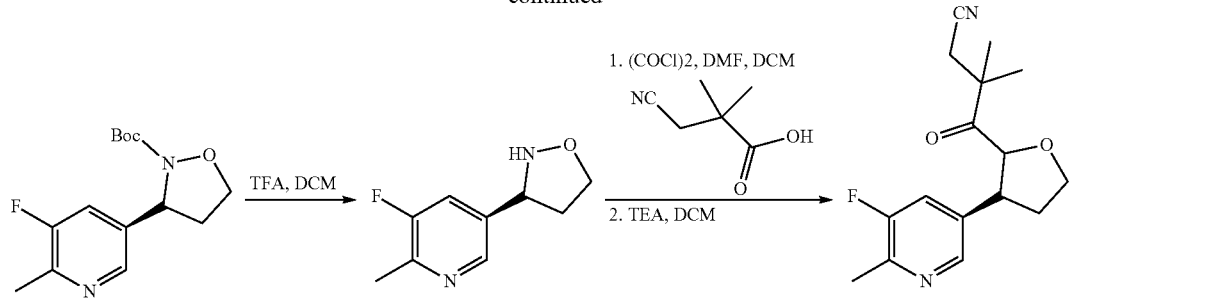

The title compound was isolated by chiral HPLC on a Chiralcel OJ-H (25×2.0 cm), 5 μm column using a mobile phase of n-hexane/ethanol 50/50% v/v, flow rate: 18 mL/min. $^1$H NMR (400 MHz, CDCl$_3$) δ 8.30-8.27 (m, 1H), 7.26 (dd, J=9.8, 1.8 Hz, 1H), 5.43 (dd, J=8.7, 6.7 Hz, 1H), 4.41-4.32 (m, 1H), 4.01 (ddd, J=9.5, 8.0, 6.5 Hz, 1H), 2.91 (dddd, J=12.3, 9.2, 6.4, 3.0 Hz, 1H), 2.73 (d, J=16.8 Hz, 1H), 2.67 (d, J=17.1 Hz, 1H), 2.52 (d, J=2.8 Hz, 3H), 2.36 (dddd, J=12.5, 9.6, 7.5, 6.5 Hz, 1H), 1.50 (s, 3H), 1.48 (s, 3H). LC-MS (Method A): m/z=291.9 [M+H]$^+$, 0.79 min.

e.e.=100% as determined on a Chiralcel OJ-H (25×0.46 cm), 5 μm column using a mobile phase of n-hexane/ethanol 65/35% v/v, flow-rate: 1 mL/min, retention time: 6.4 min.

Example 103

3,3-difluoro-2,2-dimethyl-1-[(3S)-3-(5-methyl-pyrazin-2-yl)-1,2-oxazolidin-2-yl]propan-1-one (197)

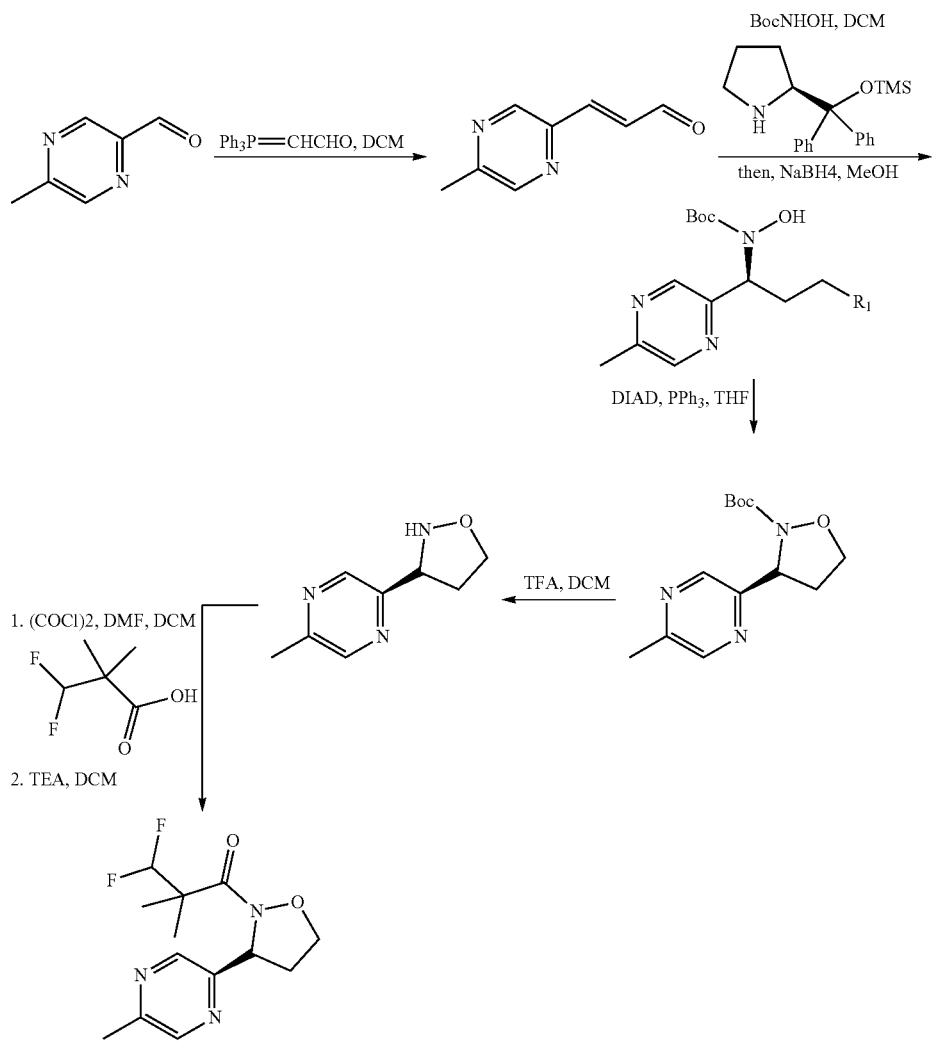

¹H NMR (400 MHz, CDCl₃) δ 8.51 (d, J=1.5 Hz, 1H), 8.41 (d, J=1.0 Hz, 1H), 6.32 (t, J=58.2 Hz, 1H), 5.51 (dd, J=8.9, 6.1 Hz, 1H), 4.39 (td, J=7.8, 3.9 Hz, 1H), 4.03 (ddd, J=9.0, 7.9, 6.7 Hz, 1H), 2.88-2.77 (m, 1H), 2.74-2.62 (m, 1H), 2.57 (s, 3H), 1.39-1.34 (m, 6H). LC-MS (Method A): m/z=286.4 [M+H]⁺, 0.81 min.

Example 104

Preparation of (S)-3,3-difluoro-2,2-dimethyl-1-(3-(1-methyl-1H-pyrazol-4-yl)isoxazolidin-2-yl)propan-1-one (198)

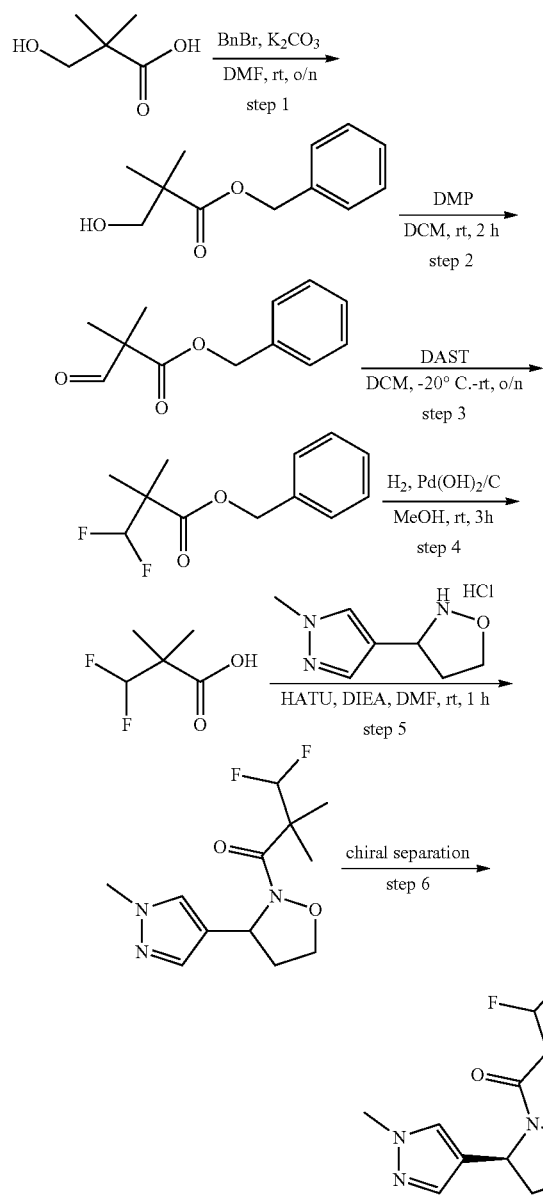

The title compound was isolated by chiral HPLC on a Chiralpak IC (25×2.0 cm), 5 μm column using a mobile phase of n-hexane/ethanol 70/30% v/v, flow rate: 20 mL/min. ¹H NMR (400 MHz, DMSO-d₆) δ 7.59 (s, 1H), 7.32 (s, 1H), 6.33 (t, J=56.9 Hz, 1H), 5.28-5.24 (m, 1H), 4.30-4.25 (m, 1H), 3.90-3.84 (m, 1H), 3.76 (s, 3H), 2.73- 2.65 (m, 1H), 2.33-2.25 (m, 1H), 1.21 (s, 6H). LC-MS (Method F): m/z=273.9 [M+H]⁺, 0.98 min. e.e.=99.9% as determined on a Chiralpak IC-3 (5×0.46 cm), 3 μm column using a mobile phase of (n-hexane+0.1% diethylamine)/ethanol 70/30% v/v, flow rate: 1.0 mL/min, retention time: 1.86 min.

Example 105

Preparation of (S)-3-(2-(3-cyano-2,2-dimethylpropanoyl)isoxazolidin-3-yl)-5-fluorobenzonitrile (199)

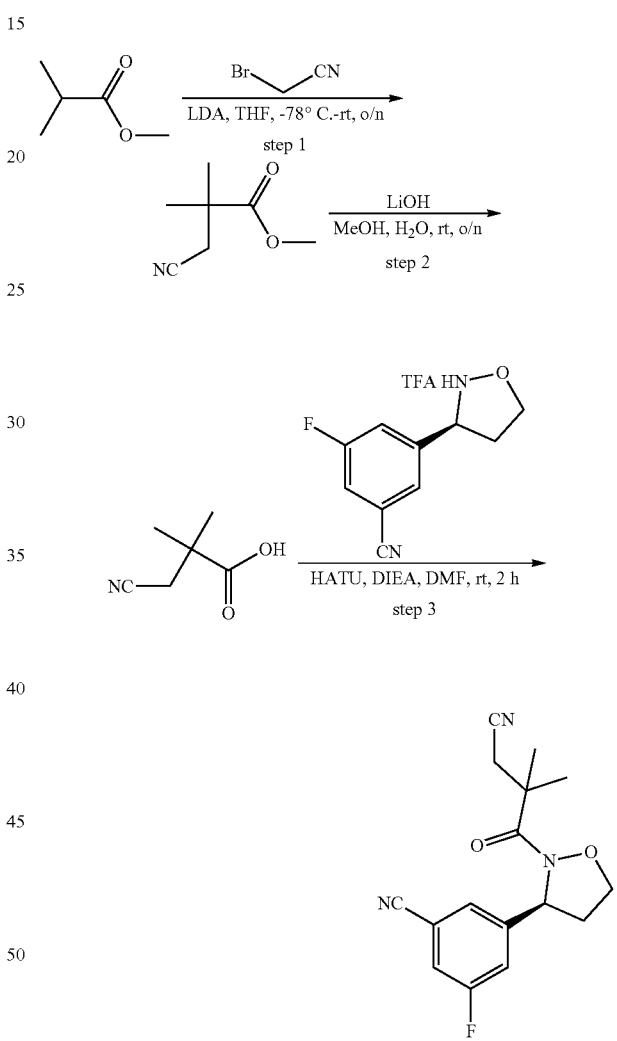

The title compound was isolated by chiral HPLC on a Chiralpak IA (25×2.0 cm), 5 μm column using a mobile phase of n-hexane/ethanol 70/30% v/v, flow rate: 20 mL/min. ¹H NMR (300 MHz, CD₃OD) δ 7.55-7.53 (m, 1H), 7.51-7.39 (m, 2H), 5.49-5.36 (m, 1H), 4.46-4.33 (m, 1H), 4.08-3.99 (m, 1H), 3.07-2.91 (m, 1H), 2.91-2.70 (m, 2H), 2.37-2.25 (m, 1H), 1.47 (s, 3H), 1.43 (s, 3H). LC-MS (Method Q): m/z=302.0 [M+H]⁺, 1.33 min. e.e.=99.9% as determined on a Chiralpak IA-3 (5×0.46 cm), 3 μm column using a mobile phase of (n-hexane+0.1% diethylamine)/ethanol 60/40% v/v, flow-rate: 1.0 mL/min, retention time: 1.99 min.

Example 106

Preparation of (S)-5-(2-(3,3-difluoro-2,2-dimethyl-propanoyl)isoxazolidin-3-yl)nicotinonitrile (200)

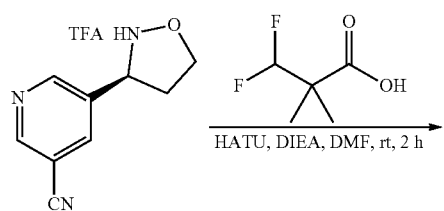

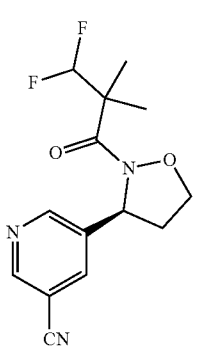

The title compound was isolated by chiral HPLC on a EnantioPak A1-5 (25×2.12 cm), 5 μm column using a mobile phase of n-hexane/ethanol 70/30% v/v, flow rate: 20 mL/min. $^1$H NMR (400 MHz, DMSO-d$_6$) δ 8.94 (d, J=2.0 Hz, 1H), 8.74 (d, J=2.2 Hz, 1H), 8.18-8.16 (m, 1H), 6.38 (t, J=56.7 Hz, 1H), 5.52-5.34 (m, 1H), 4.39-4.34 (m, 1H), 3.99-3.93 (m, 1H), 2.94-2.87 (m, 1H), 2.33-2.24 (m, 1H), 1.27 (s, 3H), 1.25 (s, 3H). LC-MS (Method F): m/z=295.9 [M+H]$^+$, 1.11 min. e.e.=97.0% as determined on a Chiralpak AS-3 (5×0.46 cm), 3 μm column using a mobile phase of (n-hexane+0.1% diethylamine)/ethanol 50/50% v/v, flow rate: 1.0 mL/min, retention time: 1.37 min.

Example 107

Preparation of (S)-3,3-difluoro-2,2-dimethyl-1-(3-(6-methylpyrazin-2-yl)isoxazolidin-2-yl)propan-1-one (201)

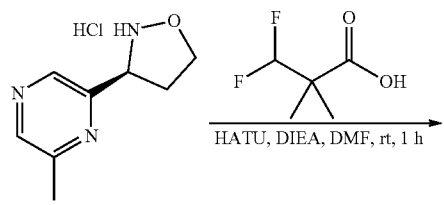

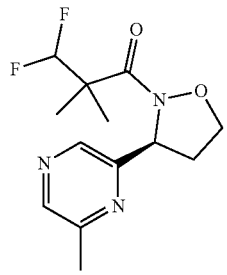

The title compound was isolated by chiral HPLC on a Chiralcel OJ-H (25×2.0 cm), 5 μm column using a mobile phase of n-hexane/ethanol 80/20% v/v, flow rate: 20 mL/min. $^1$H NMR (400 MHz, CD$_3$OD) δ 8.40 (s, 1H), 8.34 (s, 1H), 6.36 (t, J=57.1 Hz, 1H), 5.46-5.42 (m, 1H), 4.45-4.40 (m, 1H), 4.12-4.07 (m, 1H), 2.93-2.85 (m, 1H), 2.59-2.50 (m, 4H), 1.34-1.32 (m, 6H). LC-MS (Method R): m/z=286.0 [M+H]$^+$, 2.55 min. e.e.=99.9% as determined on a Chiralpak IA-3 (5×0.46 cm), 3 μm column using a mobile phase of (n-hexane+0.1% diethylamine)/ethanol 70/30% v/v, flow rate: 1.0 mL/min, retention time: 1.56 min.

Example 108

Preparation of 3,3-difluoro-2,2-dimethyl-(3S)-3-(6-methylpyridin-3-yl)-1,2-oxazolidin-2-yl)propan-1-one (202)

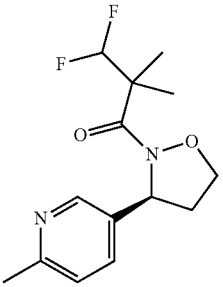 [SMILES: Cc1ccc([C@@H]2CCON2C(=O)C(C)(C)C(F)F)cn1]

To a stirred solution of 3,3-difluoro-2,2-dimethylpropanoic acid (150 mg, 1.09 mmol), N,N,N',N'-tetramethyl-O-(7-azabenzotriazol-1-yl)uronium hexafluorophospate (619 mg, 1.63 mmol) and N,N-diisopropylethylamine (421 mg, 3.26 mmol) in DMF (6 mL) was added 2-methyl-5-(1,2-oxazolidin-3-yl)pyridine (357 mg, 2.17 mmol). After being stirred at room temperature for 4 h, the reaction mixture was quenched by the addition of water (20 mL), and extracted with EtOAc (3×20 mL). The combined organic layers were washed with brine (20 mL), dried over anhydrous Na$_2$SO$_4$ and concentrated under reduced pressure. The residue was purified by preparative-HPLC with the following conditions: column: Xbridge Prep C18, 19×150 mm, 5 μm; Mobile phase: Phase A: water (10 mmol/L NH$_4$HCO$_3$); Phase B: acetonitrile (20% to 85% over 10 min); Detector, UV 220 & 254 nm to afford 3,3-difluoro-2,2-dimethyl-1-[3-(6-methylpyridin-3-yl)-1,2-oxazolidin-2-yl]propan-1-one as a mixture of enantiomers (180 mg, 58%) as a white solid. This mixture was resolved by chiral HPLC on a Chiralpak IC (25×2.0 cm), 5 μm column using a mobile phase of n-hexane/ethanol 80/20% v/v and a flow rate of 20 mL/min to afford the title compound. $^1$H NMR (400 MHz, DMSO-d$_6$) δ 8.34 (d, J=2.0 Hz, 1H), 7.52 (dd, J=8.0, 2.4 Hz, 1H), 7.23 (d, J=8.0 Hz, 1H), 6.39 (t, J=56.8 Hz, 1H), 5.35-5.31 (m, 1H), 4.38-4.33 (m, 1H), 3.96-3.90 (m, 1H), 2.93-2.85 (m, 1H), 2.44 (s, 3H), 2.24-2.17 (m, 1H), 1.27 (s, 3H), 1.26 (s, 3H). LC-MS (Method J): m/z=285.4 [M+H]$^+$, 1.156 min. e.e. =99.9% as determined on a Chiralpak IC-3 (5×0.46 cm), 3 µm column using a mobile phase of (n-hexane+0.1% diethylamine)/ethanol 80/20% v/v, flow rate: 1.0 mL/min, retention time: 2.056 min.

Examples 109 and 110

Preparation of 5-[(3R)-2-(3,3-difluoro-2,2-dimethylpropanoyl)-1,2-oxazolidin-3-yl]thiophene-2-carbonitrile and 5-[(3S)-2-(3,3-difluoro-2,2-dimethylpropanoyl)-1,2-oxazolidin-3-yl]thiophene-2-carbonitrile (203 and 204)

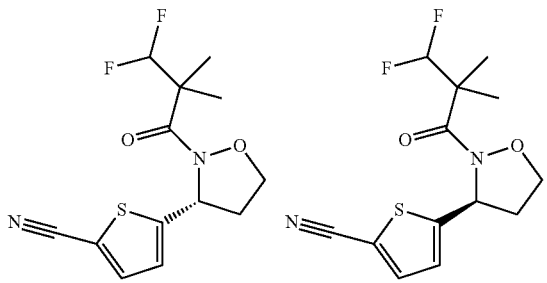

These compound was synthesized by the same method as described for 3,3-difluoro-2,2-dimethyl-1-[(3S)-3-(6-methylpyridin-3-yl)-1,2-oxazolidin-2-yl]propan-1-one except 5-(1,2-oxazolidin-3-yl)thiophene-2-carbonitrile (50 mg, 0.28 mmol) was used instead of 2-methyl-5-(1,2-oxazolidin-3-yl)pyridine. The title compounds were isolated by chiral HPLC on a CHIRALART Cellulose-SB-KSB99S05-2520WX12806 (25×2.0 cm), 5 µm column using a mobile phase of n-hexane/ethanol 85/15% v/v, flow rate: 20 mL/min.

5-[(3R)-2-(3,3-difluoro-2,2-dimethylpropanoyl)-1,2-oxazolidin-3-yl]thiophene-2-carbonitrile. $^1$H NMR (400 MHz, CD$_3$OD) δ 7.62 (d, J=4.0 Hz, 1H), 7.13 (d, J=3.6 Hz, 1H), 6.33 (t, J=57.2 Hz, 1H), 5.72-5.68 (m, 1H), 4.41-4.36 (m, 1H), 4.06-4.00 (m, 1H), 2.98-2.92 (m, 1H), 2.52-2.45 (m, 1H), 1.33 (s, 6H). LC-MS (Method D): m/z=301.1 [M+H]$^+$, 1.751 min. e.e.=97.7% as determined on a CHIRAL Cellulose-SB (0.46×15 cm) 5 µm column using a mobile phase of (n-hexane+0.1% diethylamine)/ethanol 80/20% v/v, flow rate: 1.0 mL/min, retention time: 4.296 min.

5-[(3S)-2-(3,3-difluoro-2,2-dimethylpropanoyl)-1,2-oxazolidin-3-yl]thiophene-2-carbonitrile. $^1$H NMR (400 MHz, CD$_3$OD) δ 7.62 (d, J=4.0 Hz, 1H), 7.13 (d, J=4.0 Hz, 1H), 6.33 (t, J=57.2 Hz, 1H), 5.72-5.68 (m, 1H), 4.41-4.36 (m, 1H), 4.06-4.00 (m, 1H), 2.99-2.91 (m, 1H), 2.52-2.45 (m, 1H), 1.32 (s, 6H). LC-MS (Method D): m/z=301.1 [M+H]$^+$, 1.751 min. e.e.=99.7% as determined on a CHIRAL Cellulose-SB (0.46×15 cm) 5 nm column using a mobile phase of (n-hexane+0.1% diethylamine)/ethanol 80/20% v/v, flow rate: 1.0 mL/min, retention time: 4.786 min.

Example 111

Preparation of 4-[(3S)-2-(2,2-dimethylpropanoyl)-1,2-oxazolidin-3-yl]-1-methyl-1 h-pyrrole-2-carbonitrile (205)

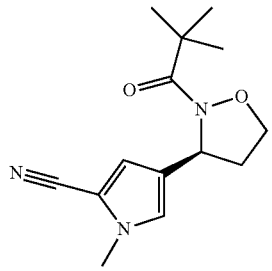 [SMILES: Cn1cc([C@@H]2CCON2C(=O)C(C)(C)C)cc1C#N]

The title compound was isolated by chiral HPLC on a Chiralpak IC (25×2.0 cm), 5 µm column using a mobile phase of n-hexane/ethanol 70/30% v/v, flow rate: 20 mL/min. $^1$H NMR (300 MHz. DMSO-d$_6$) δ 7.09 (d, J=1.8 Hz, 1H), 6.83 (d, J=1.8 Hz, 1H), 5.24-5.18 (m, 1H), 4.25-4.20 (m, 1H), 3.83-3.75 (m, 1H), 3.70 (s, 3H), 2.73-2.60 (m, 1H), 2.27-2.17 (m, 1H), 1.16 (s, 9H). LC-MS (Method F): m/z=262.0 [M+H]$^+$, 1.233 min. e.e.=99.9% as determined on a Lux Cellulose-4 (10×0.46 cm), 3 µm column using a mobile phase of (n-hexane+0.1% diethylamine)/ethanol 70/30% v/v, flow rate: 1.0 mL/min, retention time: 2.939 min.

Example 112

Preparation of (Z)-4-(3S)-2-(3,3-difluoro-2,2-dimethylpropanoyl)-1,2-oxazolidin-3-yl-N'-hydroxybenzene-1-carboximidamide (206)

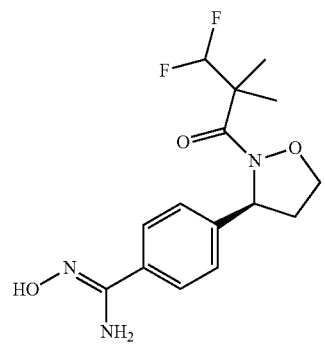 [SMILES: CC(C)(C(=O)N1OCC[C@H]1c1ccc(/C(N)=N/O)cc1)C(F)F]

To a solution of 4-[(3S)-2-(3,3-difluoro-2,2-dimethylpropanoyl)-1,2-oxazolidin-3-yl]benzonitrile (1 g, 3.4 mmol) in DMF (10 mL) was added hydroxylamine (50% aq. solution) (1.12 mL, 16 mmol). The reaction mixture was allowed to stir at room temperature for 2 h. After completion of the reaction, DMF was removed under reduced pressure. The residue was diluted with EtOAc (50 mL) and washed with sat. NaHCO$_3$ solution (20 mL). The aqueous layer was extracted further with EtOAc (3×30 mL). The combined organic layers were washed with brine and dried over anhydrous Na$_2$SO$_4$ and evaporated under reduced pressure. The crude product was purified by column chromatography (Petroleum ether/EtOAc, 60:40 to 57:43) to afford the title compound (960 mg, 86%) as a white solid. ¹H NMR (400 MHz, DMSO-d6) δ 9.61 (s, 1H), 7.63 (d, J=8.4 Hz, 2H), 7.24 (d, J=8.4 Hz, 2H), 6.41 (t, J=56.8 Hz, 1H), 5.79 (s, 2H), 5.37-5.30 (m, 1H), 4.50-4.31 (m, 1H), 3.97-3.87 (m, 1H), 2.94-2.86 (m, 1H), 2.26-2.12 (m, 1H), 1.32-1.24 (m, 6H). LC-MS (Method T): m/z=328.3 [M+H]⁺, 2.014 min. Melting range=67.3°-75.6° C., [α]$_D^{23.7}$=-132.89° (c=0.152, MeOH). e.e.=100% as determined on a Lux C2 (25×0.46 cm), 5 μm column using a mobile phase of (n-hexane+0.1% diethylamine)/ethanol 60/40% v/v, flow rate: 1.0 mL/min, retention time: 9.439 min.

Example 113

Preparation of 3,3-difluoro-2,2-dimethyl-1-[(3S)-3-[4-(1,2,4-oxadiazol-3-yl)phenyl]-1,2-oxazolidin-2-yl]propan-1-one (207)

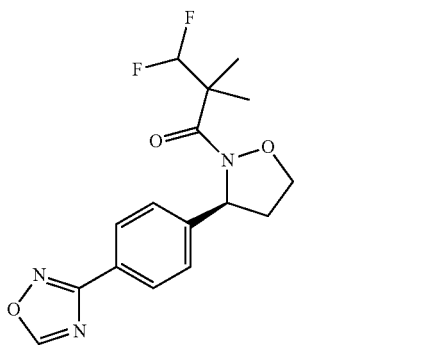 [SMILES: CC(C)(C(=O)N1OCC[C@H]1c1ccc(-c2ncon2)cc1)C(F)F]

(Z)-4-[(3S)-2-(3,3-Difluoro-2,2-dimethylpropanoyl)-1,2-oxazolidin-3-yl]-N'-hydroxybenzene-1-carboximidamide (3.4 g, 10.4 mmol) was suspended in ethanol (10.2 mL) and triethyl orthoformate (10.2 mL). The reaction mixture was heated to 100° C. for 2 days in a sealed tube. After completion of the reaction, the reaction mixture was cooled to room temperature and ethanol was removed under reduced pressure. The crude product was purified by column chromatography (petroleum ether/EtOAc, 75:25 to 72:27) and then by preparative HPLC with the following conditions: column: Sunfire OBD, C18; 250×30 mm, 5 μM; Mobile phase: 0.1% TFA in H₂O/ACN, Flow rate: 22 mL/min, to afford the title compound (950 mg, 27%) as an off-white solid. ¹H NMR (400 MHz, CDCl₃) δ 8.77 (s, 1H), 8.18-8.07 (m, 2H), 7.48-7.39 (m, 2H), 6.35 (t, J=57.0 Hz, 1H), 5.55-5.43 (m, 1H), 4.40-4.30 (m, 1H), 4.05-3.94 (m, 1H), 2.98-2.87 (m, 1H), 2.47-2.33 (m, 1H), 1.46-1.34 (m, 6H). LC-MS (Method T): m/z=338.3 [M+H]2.696 min. Melting range=87.9°-88.9° C., [α]$_D^{28.4}$=-156.87° (c=0.160, MeOH). e.e.=100% as determined on a Lux C2 (25×0.46 cm), 5 μm column using a mobile phase of (n-hexane+0.1% diethylamine)/ethanol 60/40% v/v, flow rate: 1.0 mL/min, retention time: 6.708 min.

Example 114

Preparation of 1-[(3S)-3-[4-(5-cyclopropyl-1,2,4-oxadiazol-3-yl)phenyl]-1,2-oxazolidin-1-yl]-3,3-difluoro-2,2-dimethylpropan-1-one (208)

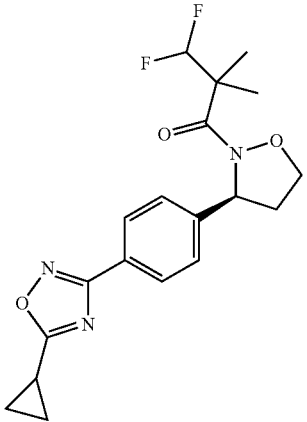 [SMILES: CC(C)(C(=O)N1OCC[C@H]1c1ccc(-c2noc(C3CC3)n2)cc1)C(F)F]

To a solution of cyclopropane carboxylic acid (421 mg, 4.9 mol) and (S)-4-(2-(3,3-difluoro-2,2-dimethylpropanoyl)isoxazolidin-3-yl)-N-hydroxybenzimidamide (1 g, 3.1 mmol) in EtOAc (10 mL) was added Et₃N (2.11 mL, 15.1 mmol) followed by T3P (50% solution in EtOAc, 5.8 mL, 7 mmol). The reaction mixture was heated to 80° C. under an inert atmosphere for 20 h. The reaction mixture was cooled to room temperature, diluted with ice water (30 mL) and extracted with EtOAc (3×50 mL). The combined organic layers were washed with brine and dried over Na₂SO₄. The crude product was purified twice by column chromatography (petroleum ether/EtOAc, 80:20 to 75:25) to afford the title compound (360 mg, 31%) as an off-white solid. ¹H NMR (400 MHz, CDCl₃) δ 8.08-7.98 (m, 2H), 7.43-7.33 (m, 2H), 6.34 (t, J=57.2 Hz, 1H), 5.52-5.41 (m, 1H), 4.38-4.28 (m, 1H), 4.03-3.92 (m, 1H), 2.95-2.82 (m, 1H), 2.44-2.30 (m, 1H), 2.30-2.20 (m, 1H), 1.45-1.18 (m, 10H). LC-MS (Method T): m/z=378.3 [M+H]⁺, 2.924 min. Melting range=92.1°-95.6° C., [α]$_D^{25.2}$=-147.61° (c=0.105, MeOH). e.e.=99.3% as determined on a Chiralcel OD-H (25×0.46 cm), 5 μm column using a mobile phase of n-heptane/ethanol 70/30% v/v, flow rate: 1.0 mL/min, retention time: 6.141 min.

Example 115

Preparation of 4-[(3S)-2-[(2S)-3-cyano-2-methyl-propanoyl]-1,2-oxazolidin-3-yl]benzonitrile Diastereoisomer 1 (209)

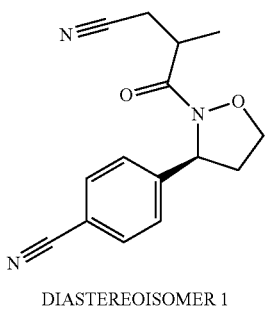 [SMILES: CC(CC#N)C(=O)N1OCC[C@H]1c1ccc(C#N)cc1]

DIASTEREOISOMER 1

The title compound was isolated by chiral HPLC on a Chiralpak AS-H (25×2.0 cm), 5 μm column using a mobile phase of n-hexane/(ethanol+0.1% isopropylamine) 50/50% v/v, flow rate: 18 mL/min. $^1$H NMR (400 MHz, CDCl$_3$) δ 7.69-7.64 (m, 2H), 7.44-7.39 (m, 2H), 5.45 (dd, J=8.8, 6.3 Hz, 1H), 4.32 (dt, J=3.1, 7.8 Hz, 1H), 4.00 (ddd, J=9.5, 8.2, 6.7 Hz, 1H), 3.36 (sextet, J=7.2 Hz, 1H), 3.01-2.88 (m, 1H), 2.69 (dd, J=16.8, 7.8 Hz, 1H), 2.45 (dd, J=16.8, 6.8 Hz, 1H), 2.35 (dddd, J=12.5, 9.5, 7.6, 6.3 Hz, 1H), 1.40 (d, J=7.0 Hz, 3H). LC-MS (Method A): m/z=270.2 [M+H]$^+$, 0.84 min. e.e.=100% as determined on a Chiralpak AS-H (25×0.46 cm) 5 μm column using a mobile phase of n-hexane/(ethanol+0.1% isopropylamine) 50/50% v/v, flow rate: 1.0 mL/min, retention time: 7.7 min.

Example 116

Preparation of 4-[(3S)-2-[(2S)-3-cyano-2-methyl-propanoyl]-1,2-oxazolidin-3-yl]benzonitrile Diastereoisomer 2 (210)

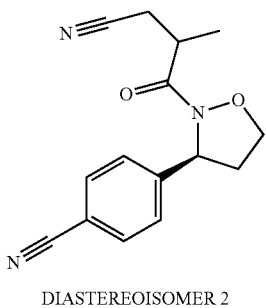 [SMILES: CC(CC#N)C(=O)N1OCC[C@H]1c1ccc(C#N)cc1]

DIASTEREOISOMER 2

The title compound was isolated by chiral HPLC on a Chiralpak AS-H (25×2.0 cm), 5 μm column using a mobile phase of n-hexane/(ethanol+0.1% isopropylamine) 50/50% v/v, flow rate: 18 mL/min. $^1$H NMR (400 MHz, CDCl$_3$) δ 7.70-7.63 (m, 2H), 7.47-7.40 (m, 2H), 5.41 (dd, J=8.8, 6.3 Hz, 1H), 4.34 (dt, J=3.9, 7.7 Hz, 1H), 4.06-3.95 (m, 1H), 3.37 (sextet, J=7.0 Hz, 1H), 3.00-2.87 (m, 1H), 2.69 (dd, J=16.6, 6.5 Hz, 1H), 2.54 (dd, J=17.3, 8.0 Hz, 1H), 2.37 (dddd, J=12.5, 9.1, 7.4, 6.1 Hz, 1H), 1.31 (d, J=7.0 Hz, 3H). LC-MS (Method A): m/z=270.2 [M+H]$^+$, 0.81 min. e.e.=100% as determined on a Chiralpak AS-H (25×0.46 cm) 5 μm column using a mobile phase of n-hexane/(ethanol+0.1% isopropylamine) 50/50% v/v, flow rate: 1.0 mL/min, retention time: 6.6 min.

Example 117

Preparation of (3S)-3-(3,4-difluorophenyl)-2-(3-methyloxolane-3-carbonyl)-1,2-oxazolidine diastereoisomer 1 (211)

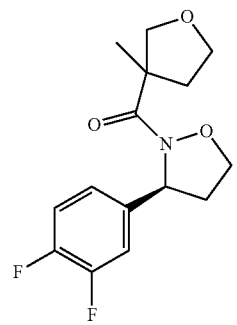

DIASTEREOISOMER 1

The title compound was isolated by chiral HPLC on a Chiralpak AD-H (25×2.0 cm), 5 μm column using a mobile phase of n-hexane/(ethanol+0.1% isopropylamine) 60/40% v/v, flow rate: 18 mL/min. $^1$H NMR (400 MHz, CDCl$_3$) δ 7.18-7.07 (m, 2H), 7.06-6.99 (m, 1H), 5.35 (dd, J=8.7, 6.4 Hz, 1H), 4.28 (dt, J=3.1, 7.8 Hz, 1H), 4.18 (d, J=9.0 Hz, 1H), 4.00-3.79 (m, 3H), 3.73 (d, J=9.0 Hz, 1H), 2.86 (dddd, J=12.2, 9.2, 6.3, 3.1 Hz, 1H), 2.47 (td, J=7.8, 12.7 Hz, 1H), 2.32 (dddd, J=12.5, 9.6, 7.5, 6.5 Hz, 1H), 1.86 (ddd, J=12.8, 7.3, 5.5 Hz, 1H), 1.43 (s, 3H). LC-MS (Method A): m/z=298.2 [M+H]$^+$, 0.96 min. e.e.=97.5% as determined on a Chiralpak AD-H (25×0.46 cm), 5 μm column using a mobile phase of n-hexane/(ethanol+0.1% isopropylamine) 60/40% v/v, flow rate: 1.0 mL/min, retention time: 7.8 min.

Example 118

Preparation of (3S)-3-(3,4-difluorophenyl)-2-(3-methyloxolane-3-carbonyl)-1,2-oxazolidine diastereoisomer 2 (212)

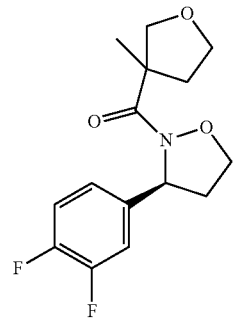

DIASTEREOISOMER 2

The title compound was isolated by chiral HPLC on a Chiralpak AD-H (25×2.0 cm), 5 μm column using a mobile phase of n-hexane/(ethanol+0.1% isopropylamine) 60/40% v/v, flow rate: 18 mL/min. ¹H NMR (400 MHz, CDCl₃) δ 7.18-7.08 (m, 2H), 7.07-7.00 (m, 1H), 5.34 (dd, J=8.8, 6.5 Hz, 1H), 4.29 (dt, J=3.0, 7.9 Hz, 1H), 3.98 (d, J=9.0 Hz, 1H), 3.96-3.88 (m, 2H), 3.84 (dt, J=5.8, 8.3 Hz, 1H), 3.77 (d, J=9.0 Hz, 1H), 2.91-2.81 (m, 1H), 2.62 (ddd, J=12.8, 8.2, 6.9 Hz, 1H), 2.32 (dddd, J=12.5, 9.6, 7.5, 6.5 Hz, 1H), 1.81 (ddd, J=13.0, 7.3, 6.0 Hz, 1H), 1.48 (s, 3H). LC-MS (Method A): m/z=298.2 [M+H]⁺, 0.97 min. e.e.=100% as determined on a Chiralpak AD-H (25×0.46 cm), 5 μm column using a mobile phase of n-hexane/(ethanol+0.1% isopropylamine) 60/40% v/v, flow rate: 1.0 mL/min, retention time: 8.7 min.

Example 119

Preparation of 4-[(3S)-2-(2-cyclopropylpropanoyl)-1,2-oxazolidin-3-yl]benzonitrile diastereoisomer 1 (213)

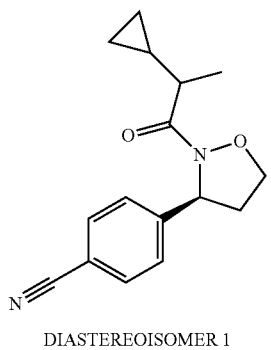 [SMILES: CC(C(=O)N1OCC[C@H]1c1ccc(C#N)cc1)C1CC1]

DIASTEREOISOMER 1

The title compound was isolated by chiral HPLC on a Chiralpak OJ-H (25×2.0 cm), 5 μm column using a mobile phase of n-hexane/(ethanol+0.1% isopropylamine) 50/50% v/v, flow rate: 18 mL/min. ¹H NMR (400 MHz, CDCl₃) δ 7.70-7.62 (m, 2H), 7.47-7.42 (m, 2H), 5.48 (dd, J=9.0, 6.3 Hz, 1H), 4.24 (dt, J=3.1, 7.8 Hz, 1H), 3.87 (ddd, J=9.5, 8.1, 6.8 Hz, 1H), 2.94-2.83 (m, 1H), 2.41-2.24 (m, 2H), 1.22 (d, J=7.0 Hz, 3H), 1.12-0.98 (m, 1H), 0.62-0.36 (m, 3H), 0.26-0.15 (m, 1H). LC-MS (Method A): m/z=271.2 [M+H]⁺, 1.01 min. e.e.=100% as determined on a Chiralpak OJ-H (25×0.46 cm), 5 μm column using a mobile phase of n-hexane/(ethanol+0.1% isopropylamine) 50/50% v/v, flow rate: 1.0 mL/min, retention time: 7.0 min.

Example 120

Preparation of 4-[(3S)-2-(2-cyclopropylpropanoyl)-1,2-oxazolidin-3-yl]benzonitrile diastereoisomer 2 (214)

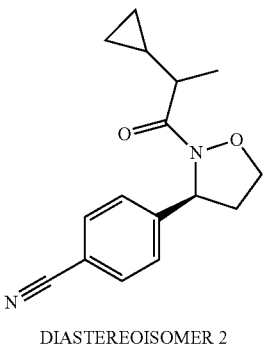 [SMILES: CC(C(=O)N1OCC[C@H]1c1ccc(C#N)cc1)C1CC1]

DIASTEREOISOMER 2

The title compound was isolated by chiral HPLC on a Chiralpak OJ-H (25×2.0 cm), 5 μm column using a mobile phase of n-hexane/(ethanol+0.1% isopropylamine) 50/50% v/v, flow rate: 18 mL/min. ¹H NMR (400 MHz, CDCl₃) δ 7.68-7.61 (m, 2H), 7.47-7.40 (m, 2H), 5.48 (dd, J=8.8, 6.5 Hz, 1H), 4.25 (dt, J=2.6, 7.7 Hz, 1H), 3.88 (ddd, J=9.7, 8.0, 6.7 Hz, 1H), 2.90 (dddd, J=12.2, 9.2, 6.5, 3.0 Hz, 1H), 2.39-2.19 (m, 2H), 1.29 (d, J=7.0 Hz, 3H), 1.04 (ttd, J=8.1, 5.0, 9.7 Hz, 1H), 0.63-0.45 (m, 2H), 0.24-0.12 (m, 2H). LC-MS (Method A): m/z=271.2 [M+H]⁺, 1.01 min. e.e.=100% as determined on a Chiralpak OJ-H (25×0.46 cm), 5 μm column using a mobile phase of n-hexane/(ethanol+0.1% isopropylamine) 50/50% v/v, flow rate: 1.0 mL/min, retention time: 9.6 min.

Example 121

Preparation of 4-[(3S)-2-(2-trans-methylcyclopropanecarbonyl)-1,2-oxazolidin-3-yl]benzonitrile Diastereoisomer 1 (215)

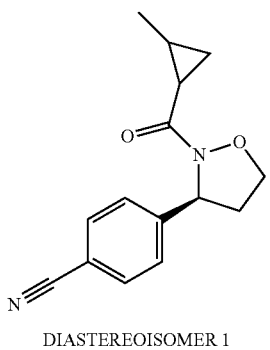 [SMILES: CC1CC1C(=O)N1OCC[C@H]1c1ccc(C#N)cc1]

DIASTEREOISOMER 1

The title compound was isolated by chiral HPLC on a Chiralpak AD-H (25×2.0 cm), 5 μm column using a mobile phase of n-hexane/(ethanol/methanol 1/1+0.1% isopropylamine) 30/70% v/v, flow rate: 17 mL/min. ¹H NMR (400 MHz, DMSO-d6) δ 7.86-7.79 (m, 2H), 7.54-7.46 (m, 2H), 5.41 (dd, J=8.8, 6.3 Hz, 1H), 4.28 (dt, J=3.0, 7.9 Hz, 1H), 3.85 (ddd, J=9.5, 8.0, 6.8 Hz, 1H), 2.92 (dddd, J=12.1, 9.1, 6.5, 2.9 Hz, 1H), 2.19 (dddd, J=12.2, 9.5, 7.7, 6.3 Hz, 1H), 1.97 (br.s., 1H), 1.26-1.16 (m, 1H), 1.10 (d, J=6.0 Hz, 3H), 1.04-0.94 (m, 1H), 0.75-0.66 (m, 1H). LC-MS (Method A): m/z=257.1 [M+H]+, 0.90 min.

Example 122

Preparation of 4-[(3S)-2-(2-trans-methylcyclopropanecarbonyl)-1,2-oxazolidin-3-yl]benzonitrile Diastereoisomer 2 (216)

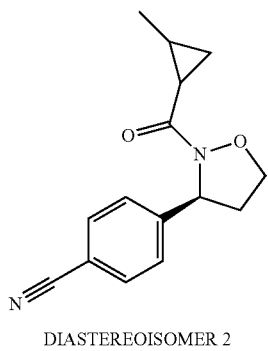 [SMILES: CC1CC1C(=O)N1OCC[C@H]1c1ccc(C#N)cc1]

DIASTEREOISOMER 2

The title compound was isolated by chiral HPLC on a Chiralpak AD-H (25×2.0 cm), 5 μm column using a mobile phase of n-hexane/(ethanol/methanol 1/1+0.1% isopropylamine) 30/70% v/v, flow rate: 17 mL/min. ¹H NMR (400 MHz, DMSO-d6) δ 7.87-7.78 (m, 2H), 7.52-7.46 (m, 2H), 5.43 (dd, J=8.8, 6.3 Hz, 1H), 4.29 (dt, J=2.8, 7.8 Hz, 1H), 3.86 (ddd, J=9.5, 8.0, 6.8 Hz, 1H), 2.93 (dddd, J=12.2, 9.2, 6.5, 3.0 Hz, 1H), 2.19 (dddd, J=12.1, 9.5, 7.7, 6.0 Hz, 1H), 1.96 (br.s., 1H), 1.24-1.15 (m, 1H), 1.11-1.04 (m, 3H), 0.99 (ddd, J=8.5, 4.8, 3.5 Hz, 1H), 0.77-0.68 (m, 1H). LC-MS (Method A): m/z=257.1 [M+H]+, 0.89 min.

Example 123

Preparation of 2-cyclopropyl-1-[(3S)-3-(5-fluoro-6-methylpyridin-3-yl)-1,2-oxazolidin-2-yl]propan-1-one Diastereoisomer 1 (217)

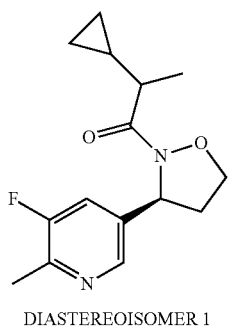 [SMILES: Cc1ncc([C@@H]2CCON2C(=O)C(C)C2CC2)cc1F]

DIASTEREOISOMER 1

The title compound was isolated by chiral HPLC on a Chiralpak AD-H (25×2.0 cm), 5 μm column using a mobile phase of n-hexane/ethanol 80/20% v/v, flow rate: 17 mL/min. ¹H NMR (400 MHz, CDCl₃) δ 8.31 (s, 1H), 7.30 (dd, J=9.8, 1.8 Hz, 1H), 5.47 (dd, J=8.8, 6.0 Hz, 1H), 4.25 (dt, J=3.4, 7.7 Hz, 1H), 3.88 (ddd, J=9.1, 8.1, 6.9 Hz, 1H), 2.88 (dddd, J=12.3, 8.9, 6.7, 3.4 Hz, 1H), 2.52 (d, J=2.8 Hz, 3H), 2.39-2.29 (m, 2H), 1.22 (d, J=7.0 Hz, 3H), 1.09-0.99 (m, 1H), 0.61-0.38 (m, 3H), 0.20 (qd, J=4.8, 9.4 Hz, 1H). LC-MS (Method A): m/z=279.3 [M+H]+, 0.91 min. e.e.=100% as determined on a Chiralpak AD-H (25×0.46 cm), 5 μm column using a mobile phase of n-hexane/ethanol 80/20% v/v, flow rate: 1.0 mL/min, retention time: 9.8 min.

Example 124

Preparation of 2-cyclopropyl-1-[(3S)-3-(5-fluoro-6-methylpyridin-3-yl)-1 (2-oxazolidin-2-yl]propan-1-one Diastereoisomer 2 (218)

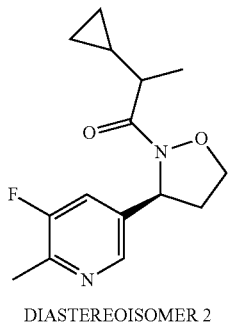 [SMILES: Cc1ncc([C@@H]2CCON2C(=O)C(C)C2CC2)cc1F]

DIASTEREOISOMER 2

The title compound was isolated by chiral HPLC on a Chiralpak AD-H (25×2.0 cm), 5 μm column using a mobile phase of n-hexane/ethanol 80/20% v/v, flow rate: 17 mL/min. ¹H NMR (400 MHz, CDCl₃) δ 8.30 (s, 1H), 7.31-7.27 (m, 1H), 5.48 (dd, J=8.8, 6.3 Hz, 1H), 4.27 (dt, J=2.9, 7.7 Hz, 1H), 3.89 (ddd, J=9.3, 8.1, 6.7 Hz, 1H), 2.93-2.84 (m, 1H), 2.52 (d, J=3.0 Hz, 3H), 2.41-2.21 (m, 2H), 1.29 (d, J=6.8 Hz, 3H), 1.10-1.00 (m, 1H), 0.62-0.48 (m, 2H), 0.24-0.13 (m, 2H). LC-MS (Method A): m/z=279.3 [M+H]+, 0.90 min. e.e.=100% as determined on a Chiralpak AD-H (25×0.46 cm), 5 μm column using a mobile phase of n-hexane/ethanol 80/20% v/v, flow rate: 1.0 mL/min. retention time: 14.8 min.

Example 125

Preparation of 5-[(3S)-2-(2,2-dimethylpropanoyl)-1,2-oxazolidin-3-yl)-2-methyl]pyridine-3-carbonitrile (219)

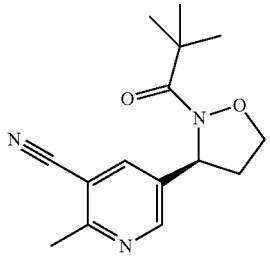 [SMILES: Cc1ncc([C@@H]2CCON2C(=O)C(C)(C)C)cc1C#N]

The title compound was isolated by chiral HPLC on a Chiralpak AD-H (25×2.0 cm), 5 μm column using a mobile phase of n-hexane/ethanol 70/30% v/v, flow rate: 18 mL/min. ¹H NMR (400 MHz, CDCl₃) δ 8.65 (d, J=2.5 Hz, 1H), 7.82 (d, J=2.3 Hz, 1H), 5.42 (dd, J=8.8, 7.0 Hz, 1H), 4.33 (dt, J=2.5, 7.9 Hz, 1H), 3.93 (ddd, J=10.1, 8.2, 6.3 Hz, 1H), 2.89 (dddd, J=12.4, 8.8, 6.3, 2.5 Hz, 1H), 2.77 (s, 3H), 2.29 (tdd, J=7.4, 12.2, 9.9 Hz, 1H), 1.29 (s, 9H). LC-MS (Method A): m/z=274.1 [M+H]$^+$, 0.90 min. e.e.=100% as determined on a Chiralpak AD-H (25×0.46 cm), 5 μm column using a mobile phase of n-hexane/ethanol 70/30% v/v, flow rate: 1.0 mL/min, retention time: 24.0 min.

Example 126

Preparation of 5-[(3S)-2-(3,3-difluoro-2,2-dimethyl-propanoyl)-1,2-oxazolidin-3-yl]-2-methylpyridine-3-carbonitrile (220)

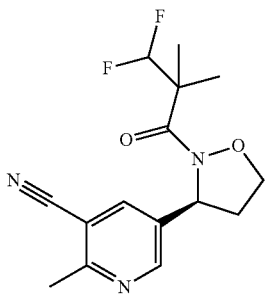 [SMILES: Cc1ncc([C@@H]2CCON2C(=O)C(C)(C)C(F)F)cc1C#N]

The title compound was isolated by chiral HPLC on a Chiralpak AD-H (25×2.0 cm), 5 μm column using a mobile phase of n-hexane/(ethanol+0.1% isopropylamine) 50/50% v/v, flow rate: 18 mL/min. $^1$H NMR (400 MHz, CDCl$_3$) δ 8.64 (d, J=2.3 Hz, 1H), 7.79 (d, J=2.5 Hz, 1H), 6.30 (t, J=57.0 Hz, 1H), 5.43 (dd, J=8.8, 7.0 Hz, 1H), 4.38 (dt, J=2.8, 7.7 Hz, 1H), 3.99 (ddd, J=9.9, 8.2, 6.3 Hz, 1H), 2.94 (dddd, J=12.5, 8.9, 6.2, 2.8 Hz, 1H), 2.78 (s, 3H), 2.34 (tdd, J=7.4, 12.4, 9.8 Hz, 1H), 1.39-1.35 (m, 6H). LC-MS (Method A): m/z=310.3 [M+H]$^+$, 0.94 min. e.e.=100% as determined on a Chiralpak AD-H (25×0.46 cm), 5 μm column using a mobile phase of n-hexane/(ethanol+0.1% isopropylamine) 50/50% v/v, flow rate: 1.0 mL/min, retention time: 17.9 min.

Example 127

Preparation of 1-[(3S)-3-[6-(difluoromethyl)pyridin-3-yl]-1,2-oxazolidin-2-yl]-3,3-difluoro-2,2-dimethyl-propan-1-one (221)

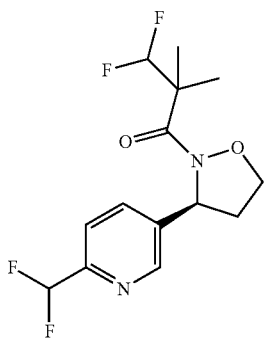 [SMILES: CC(C)(C(=O)N1OCC[C@H]1c1ccc(C(F)F)nc1)C(F)F]

The title compound was isolated by chiral HPLC on a Chiralpak AD-H (25×2.0 cm), 5 μm column using a mobile phase of n-hexane/(ethanol+0.1% isopropylamine) 50/50% v/v, flow rate: 18 mL/min. $^1$H NMR (400 MHz, CDCl$_3$) δ 8.61 (d, J=2.3 Hz, 1H), 7.75 (dd, J=8.0, 2.3 Hz, 1H), 7.64 (d, J=8.0 Hz, 1H), 6.64 (t, J=55.5 Hz, 1H), 6.31 (t, J=57.0 Hz, 1H), 5.49 (dd, J=8.5, 7.0 Hz, 1H), 4.37 (dt, J=2.6, 7.7 Hz, 1H), 4.00 (ddd, J=9.8, 8.2, 6.4 Hz, 1H), 2.94 (dddd, J=12.2, 9.2, 6.3, 2.9 Hz, 1H), 2.37 (dddd, J=12.3, 9.8, 7.5, 6.8 Hz, 1H), 1.41-1.36 (m, 6H). LC-MS (Method A): m/z=321.0 [M+H]$^+$, 0.96 min. e.e.=100% as determined on a Chiralpak AD-H (25×0.46 cm), 5 μm column using a mobile phase of n-hexane/(ethanol+0.1% isopropylamine) 50/50% v/v, flow rate: 1.0 mL/min, retention time: 7.4 min.

Example 128

Preparation of 3-bromo-5-[(3S)-2-(2,2-dimethylpro-panoyl)-1,2-oxazolidin-3-yl]benzonitrile (222)

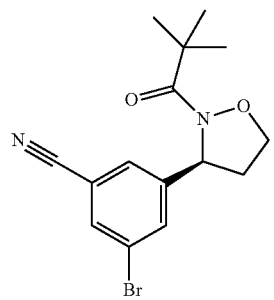 [SMILES: CC(C)(C)C(=O)N1OCC[C@H]1c1cc(Br)cc(C#N)c1]

The title compound was isolated by chiral HPLC on a Chiralpak IC (25×2.0 cm), 5 μm column using a mobile phase of n-hexane/ethanol 70/30% v/v, flow rate: 17 mL/min. $^1$H NMR (400 MHz, CDCl$_3$) δ 7.71-7.64 (m, 2H), 7.53 (t, J=1.3 Hz, 1H), 5.37 (dd, J=8.9, 6.9 Hz, 1H), 4.29 (dt, J=3.0, 7.5 Hz, 1H), 3.90 (ddd, J=10.2, 8.2, 6.3 Hz, 1H), 2.87 (dddd, J=12.5, 8.9, 6.3, 2.5 Hz, 1H), 2.32-2.19 (m, 1H), 1.30 (s, 9H). LC-MS (Method A): m/z=336.0 [M+H]$^+$, 1.19 min. e.e.=100% as determined on a Chiralpak IC (25×0.46 cm), 5 μm column using a mobile phase of n-hexane/ethanol 70/30% v/v, flow-rate: 1.0 mL/min, retention time: 8.2 min.

Example 129

Preparation of 2,2-dimethyl-1-[(3S)-3-(6-nitropyri-din-3-yl)-1,2-oxazolidin-2-yl]propan-1-one (223)

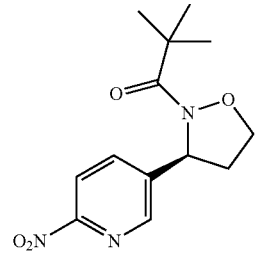 [SMILES: CC(C)(C)C(=O)N1OCC[C@H]1c1ccc([N+](=O)[O-])nc1]

The title compound was isolated by chiral HPLC on a Chiralpak IA (25×2.0 cm), 5 μm column using a mobile phase of n-hexane/(ethanol+0.1% isopropylamine) 50/50% v/v, flow rate: 18 mL/min. $^1$H NMR (400 MHz, CDCl$_3$) δ

8.61 (d, J=2.3 Hz, 1H), 8.24 (d, J=8.3 Hz, 1H), 7.96 (dd, J=8.3, 2.3 Hz, 1H), 5.56 (dd, J=9.0, 7.0 Hz, 1H), 4.36 (dt, J=2.4, 8.0 Hz, 1H), 3.98 (ddd, J=10.0, 8.3, 6.3 Hz, 1H), 3.02-2.91 (m, 1H), 2.34 (tdd, J=7.4, 12.3, 10.0 Hz, 1H), 1.31 (s, 9H). LC-MS (Method A), m/z=280.3 [M+H]$^+$, 0.92 min. e.e.=100% as determined on a Chiralpak IA (25×0.46 cm), 5 μm column using a mobile phase of n-hexane/(ethanol+ 0.1% isopropylamine) 50/50% v/v, flow rate: 1.0 mL/min, retention time: 11.3 min.

Example 130

5-[(3S)-2-(3,3-difluoro-2,2-dimethylbutanoyl)-1,2-oxazolidin-3-yl]pyridine-3-carbonitrile (224)

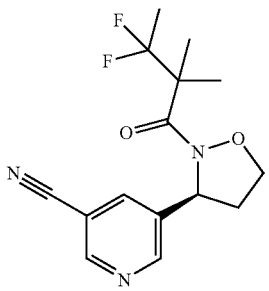 [SMILES: CC(F)(F)C(C)(C)C(=O)N1OCC[C@H]1c1cncc(C#N)c1]

$^1$H NMR (400 MHz, DMSO-d6) δ 8.95 (d, J=1.8 Hz, 1H), 8.76 (d, J=2.3 Hz, 1H), 8.19 (t, J=2.0 Hz, 1H), 5.45 (dd, J=8.5, 7.0 Hz, 1H), 4.35 (dt, J=2.4, 7.8 Hz, 1H), 3.94 (ddd, J=9.9, 8.0, 6.4 Hz, 1H), 3.01-2.82 (m, 1H), 2.27 (tdd, J=7.4, 12.2, 9.9 Hz, 1H), 1.67 (t, J=19.7 Hz, 3H), 1.42 (s, 3H), 1.37 (s, 3H). LC-MS (Method A): m/z=310.2 [M+H]$^+$, 0.93 min.

Example 131

Preparation of 5-[(3S)-2-(propane-2-sulfonyl)-1,2-oxazolidin-3-yl]pyridine-3-carbonitrile (225)

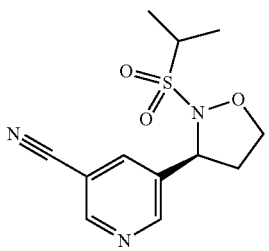 [SMILES: CC(C)S(=O)(=O)N1OCC[C@H]1c1cncc(C#N)c1]

The title compound was isolated by chiral HPLC on a Chiralpak IA (15×2.12 cm), 5 μm column using a mobile phase of n-hexane/ethanol 70/30% v/v, flow rate: 20 mL/min. $^1$H NMR (400 MHz, DMSO-d$_6$) δ 8.97 (d, J=1.6 Hz, 1H), 8.87 (d, J=2.0 Hz, 1H), 8.29-8.24 (m, 1H), 5.52-5.46 (m, 1H), 4.33-4.12 (m, 2H), 3.80-3.66 (m, 1H), 2.96-2.82 (m, 1H), 2.42-2.30 (m, 1H), 1.36-1.28 (m, 6H). LC-MS (Method F): m/z=281.9 [M+H]$^+$, 1.024 min. e.e.=99.3% as determined on a Chiralpak AS-3 (5×0.46 cm), 3 μm column using a mobile phase of (n-hexane+0.1% diethylamine)/ ethanol 50/50% v/v, flow rate: 1.0 mL/min, retention time: 3.39 min.

Example 132

Preparation of 3-[(3S)-2-(3,3-difluoro-2,2-dimethylpropanoyl)-1,2-oxazolidin-3-yl]-5-fluorobenzonitrile (226)

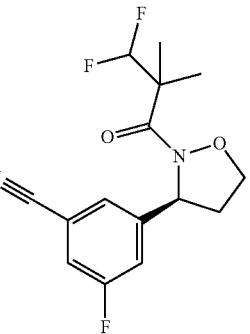

The title compound was isolated by chiral HPLC on a Lux 5u Cellulose-4, AXIA Packed (25×2.12 cm), 5 μm column using a mobile phase of n-hexane/ethanol 70/30% v/v, flow rate: 20 mL/min. $^1$H NMR (300 MHz, CD$_3$OD) δ 7.50-7.46 (m, 2H), 7.40-7.35 (m, 1H), 6.39 (t, J=57.0 Hz, 1H), 5.45-5.40 (m, 1H), 4.43-4.37 (m, 1H), 4.06-3.98 (m, 1H), 3.00-2.95 (m, 1H), 2.34-2.27 (m, 1H), 1.36 (s, 3H), 1.34 (s, 3H). LC-MS (Method D): m/z=313.1 [M+H]$^+$, 1.796 min. e.e.=99.9% as determined on a Lux Cellulose-4 (5×0.46 cm), 3 μm column using a mobile phase of (n-hexane+0.1% diethylamine)/ethanol 70/30% v/v, flow rate: 1.0 mL/min, retention time: 1.543 min.

Example 133

Preparation of 5-[(3S)-2-(3,3-difluoro-2,2-dimethylpropanoyl)-1,2-oxazolidin-3-yl]-2-(difluoromethyl) benzonitrile (227)

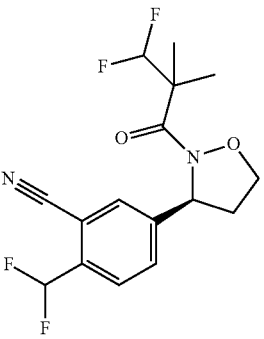 [SMILES: CC(C)(C(=O)N1OCC[C@H]1c1ccc(C(F)F)c(C#N)c1)C(F)F]

The title compound was isolated by chiral HPLC on a Phenomenex Lux (25×2.1 cm), 5 μm column using a mobile phase of n-hexane/ethanol 75/25% v/v, flow rate: 20 mL/min. $^1$H NMR (300 MHz, DMSO-d$_6$) δ 7.92 (s, 1H), 7.84 (d, J=8.1 Hz, 1H), 7.73 (d, J=8.2 Hz, 1H), 7.26 (t, J=54.2 Hz, 1H), 6.42 (t, J=56.8 Hz, 1H), 5.50-5.40 (m, 1H), 4.45-4.31 (m, 1H), 4.10-3.92 (m, 1H), 3.03-2.90 (m, 1H), 2.33-2.16 (m, 1H), 1.30 (s, 3H), 1.29 (s, 3H). LC-MS (Method D): m/z=345.1 [M+H]$^+$, 1.804 min. e.e.=99.9% as determined on a Chiralpak IF-3 (5×0.46 cm), 3 μm column using a mobile phase of (n-hexane+0.1% diethylamine)/ ethanol 50/50% v/v, flow rate: 1.0 mL/min, retention time: 3.05 min.

Example 134

Preparation of 5-[(3S)-2-(3-cyano-2,2-dimethylpropanoyl)-1,2-oxazolidin-3-yl]-2-(difluoromethyl)benzonitrile (228)

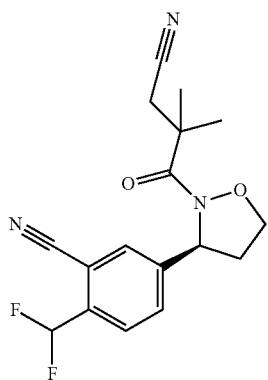 [SMILES: CC(C)(CC#N)C(=O)N1OCC[C@H]1c1ccc(C(F)F)c(C#N)c1]

The title compound was isolated by chiral HPLC on a Chiralpak IA (15×2.1 cm), 5 μm column using a mobile phase of n-hexane/2-propanol 50/50% v/v, flow rate: 20 mL/min. $^1$H NMR (300 MHz, CD$_3$OD) δ 7.82 (s, 1H), 7.80-7.71 (m, 2H), 7.01 (t, J=54.6 Hz, 1H), 5.52-5.41 (m, 1H), 4.46-4.34 (m, 1H), 4.11-4.00 (m, 1H), 3.10-2.93 (m, 1H), 2.91-2.70 (m, 2H), 2.37-2.21 (m, 1H), 1.46 (s, 3H), 1.43 (s, 3H). LC-MS (Method S): m/z=334.4 [M+H]$^+$, 2.349 min. e.e.=99.9% as determined on a Chiralpak IA-3 (5×0.46 cm), 3 μm column using a mobile phase of (n-hexane+0.1% diethylamine)/ethanol 50/50% v/v, flow rate: 1.0 mL/min, retention time: 1.60 min.

The following compounds were prepared according to the Examples above and/or general procedures described herein.

| Comp. No. | Name | Structure | $^1$H NMR | M + H$^+$ |
|---|---|---|---|---|
| 28 | 4-[(3S)-3-(4-Fluorophenyl)-1,2-oxazolidine-2-carbonyl]oxane-4-carbonitrile | 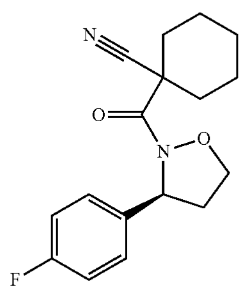 [SMILES: N#CC1(C(=O)N2OCC[C@H]2c2ccc(F)cc2)CCCCC1] | $^1$H NMR (500 MHz, CDCl$_3$) δ 7.32-7.24 (m, 2H), 7.05 (t, J = 8.7 Hz, 2H), 5.39 (dd, J = 8.7, 6.7 Hz, 1H), 4.38 (td, J = 8.1, 2.7 Hz, 1H), 4.17 (ddd, J = 9.8, 8.3, 6.9 Hz, 1H), 4.05-3.91 (m, 2H), 3.85-3.78 (m, 2H), 2.93 (dddd, J = 12.2, 9.1, 6.5, 2.9 Hz, 1H), 2.47-2.33 (m, 2H), 2.19 (ddd, J = 13.9, 11.6, 4.4 Hz, 1H), 2.07 (ddd, J = 13.7, 11.4, 4.3 Hz, 1H), 2.00 (dq, J = 2.3, 14.0 Hz, 1H). | (Method B): m/z = 304.0 [M + H]$^+$, 0.93 min |
| 29 | (3S)-3-(4-fluorophenyl)-2-[1-(trifluoromethyl)cyclopentanecarbonyl]-1,2-oxazolidine | 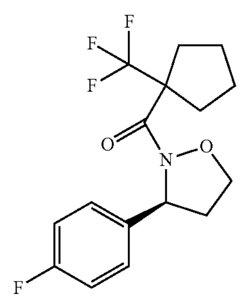 [SMILES: O=C(N1OCC[C@H]1c1ccc(F)cc1)C1(C(F)(F)F)CCCC1] | $^1$H NMR (400 MHz, CDCl$_3$) δ 7.33-7.26 (m, 2H), 7.07-7.00 (m, 2H), 5.41 (dd, J = 8.8, 6.8 Hz, 1H), 4.29 (td, J = 8.0, 2.8 Hz, 1H), 4.00-3.91 (m, 1H), 2.89-2.80 (m, 1H), 2.47-2.28 (m, 3H), 2.24-2.11 (m, 2H), 1.80-1.60 (m, 4H). | (Method A): m/z = 332.2 [M + H]$^+$, 1.24 min |
| 30 | 1-[(3R)-3-(2,3-Difluorophenyl)-12-oxazolidin-2-yl]-2,2-dimethylpropan-1-one | 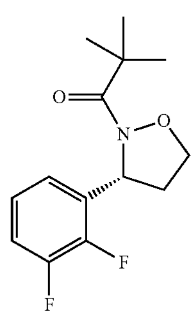 [SMILES: CC(C)(C)C(=O)N1OCC[C@@H]1c1cccc(F)c1F] | $^1$H NMR (400 MHz, CDCl$_3$) δ 7.12-7.00 (m, 3H), 5.68 (dd, J = 8.8, 6.8 Hz, 1H), 4.27 (td, J = 8.0, 2.8 Hz, 1H), 3.96-3.89 (m, 1H), 2.97-2.88 (m, 1H), 2.33-2.22 (m, 1H), 1.33 (s, 9H). | (Method A): m/z = 270.3 [M + H]$^+$, 1.16 min |

| Comp. No. | Name | Structure | ¹H NMR | M + H⁺ |
|---|---|---|---|---|
| 31 | 1-[(3S)-3-(2,3-Difluorophenyl)-1,2-oxazolidin-2-yl]-2,2-dimethylpropan-1-one | 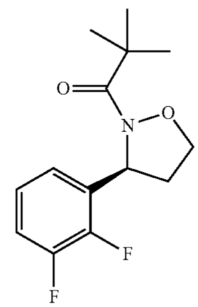 [SMILES: CC(C)(C)C(=O)N1OCC[C@H]1c1cccc(F)c1F] | ¹H NMR (400 MHz, CDCl₃) δ 7.12-7.00 (m, 3H), 5.68 (dd, J = 8.8, 6.8 Hz, 1H), 4.27 (td, J = 8.0, 2.8 Hz, 1H), 3.96-3.89 (m, 1H), 2.97-2.88 (m, 1H), 2.33-2.22 (m, 1H), 1.33 (s, 9H). | (Method A): m/z = 270.3 [M + H]⁺, 1.16 min |
| 32 | (3S)-2-{Bicyclo[1.1.1]pentane-1-carbonyl}-3-(4-fluorophenyl)-1,2-oxazolidine | 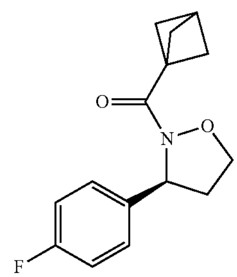 [SMILES: O=C(N1OCC[C@H]1c1ccc(F)cc1)C12CC(C1)C2] | ¹H NMR (400 MHz, CDCl₃) δ 7.34-7.25 (m, 2H), 7.07-6.99 (m, 2H), 5.42 (dd, J = 8.7, 5.9 Hz, 1H), 4.25 (td, J = 7.8, 3.1 Hz, 1H), 3.89-3.77 (m, 1H), 2.82 (dddd, J = 12.2, 8.9, 7.0, 3.3 Hz, 1H), 2.49 (br s, 1H), 2.33 (dddd, J = 12.3, 9.3, 7.7, 5.8 Hz, 1H), 2.19 (br s, 6H). | LC-MS (Method A): m/z = 262.2 [M + H]⁺, 1.02 min |
| 33 | (3S)-3-(4-Fluorophenyl)-2-(3-methyloxetane-3-carbonyl)-1,2-oxazolidine | 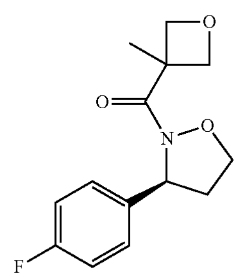 [SMILES: CC1(C(=O)N2OCC[C@H]2c2ccc(F)cc2)COC1] | ¹H NMR (400 MHz, CDCl₃) δ 7.33-7.23 (m, 2H), 7.12-7.00 (m, 2H), 5.39 (dd, J = 8.5, 6.0 Hz, 1H), 5.08 (d, J = 6.3 Hz, 1H), 4.91 (d, J = 6.0 Hz, 1H), 4.41 (d, J = 6.3 Hz, 1H), 4.38 (d, J = 6.5 Hz, 1H), 4.25 (td, J = 7.9, 3.8 Hz, 1H), 3.93 (ddd, J = 9.0, 8.0, 6.8 Hz, 1H), 2.92-2.82 (m, 1H), 2.42-2.31 (m, 1H), 1.71 (s, 3H). | LC-MS (Method A): m/z = 266.2 [M + H]⁺, 0.83 min |
| 34 | (3S)-2-(1-Fluorocyclopropane-carbonyl)-3-(4-fluorophenyl)-1,2-oxazolidine | 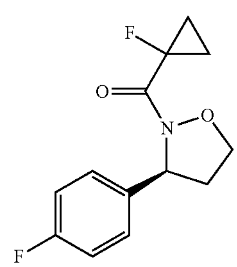 [SMILES: O=C(N1OCC[C@H]1c1ccc(F)cc1)C1(F)CC1] | ¹H NMR (400 MHz, CDCl₃) δ 7.37-7.30 (m, 2H), 7.10-7.00 (m, 2H), 5.60-5.48 (m, 1H), 4.31 (dd, J = 15.4, 4.6 Hz, 1H), 4.10-4.02 (m, 1H), 2.95-2.86 (m, 1H), 2.40 (dtd, J = 12.5, 7.8, 5.0 Hz, 1H), 1.50-1.39 (m, 1H), 1.36-1.11 (m, 3H). | LC-MS (Method A): m/z = 254.1 [M + H]⁺, 0.91 min |
| 35 | (3S)-3-(4-Fluorophenyl)-2-[3-methyloxane-3-carbonyl]-1,2-oxazolidine diastereoisomer 2 (Second eluting diastereoisomer) | DIASTEREOISOMER 2 | ¹H NMR (400 MHz, CDCl₃) δ 7.31-7.26 (m, 5H) 7.02 (t, J = 8.8 Hz, 2H) 5.50-5.38 (m, 1H) 4.24 (s, 2H) 3.96-3.86 (m, 1H) 3.64 (d, J = 5.3 Hz, 2H) 3.51 (d, J = 11.5 Hz, 1H) 2.87-2.75 (m, 1H) 2.36-2.24 (m, 1H) 2.22-2.12 (m, 1H) 1.71-1.59 (m, 3H) 1.29 (s, 3H) | |

| Comp. No. | Name | Structure | ¹H NMR | M + H⁺ |
|---|---|---|---|---|
| 36 | (3S)-3-(4-Fluorophenyl)-2-[3-methyloxane-3-carbonyl]-1,2-oxazolidine diastereoisomer 1 (First eluting diastereoisomer) | DIASTEREOISOMER 1 | ¹H NMR (400 MHz, CDCl₃) δ 7.29-7.25 (m, 2H), 7.04-6.98 (m, 2H), 5.43 (dd, J = 8.8, 6.6 Hz, 1H), 4.27 (td, J = 7.7, 2.5 Hz, 1H), 4.18 (dd, J = 11.5, 1.4 Hz, 1H), 3.92 (ddd, J = 9.8, 8.0, 6.6 Hz, 1H), 3.73-3.64 (m, 1H), 3.61-3.53 (m, 1H), 3.37 (d, J = 11.4 Hz, 1H), 2.82 (dddd, J = 12.1, 9.1, 6.4, 2.9 Hz, 1H), 2.36-2.21 (m, 2H), 1.81-1.68 (m, 1H), 1.68-1.59 (m, 2H), 1.26 (s, 3H). | |
| 37 | (3S)-3-(4-Fluorophenyl)-2-[1-(trifluoromethyl)cyclopropanecarbonyl]-1,2-oxazolidine | 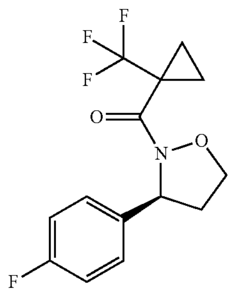 [SMILES: O=C(N1OCC[C@H]1c1ccc(F)cc1)C1(C(F)(F)F)CC1] | ¹H NMR (400 MHz, CDCl₃) δ 7.32-7.22 (m, 2H), 7.10-7.00 (m, 2H), 5.42 (dd, J = 8.8, 6.0 Hz, 1H), 4.31 (td, J = 7.7, 3.3 Hz, 1H), 3.99 (ddd, J = 9.2, 8.1, 6.8 Hz, 1H), 2.87 (dddd, J = 12.3, 8.8, 6.9, 3.5 Hz, 1H), 2.37 (dddd, J = 12.3, 9.2, 7.7, 6.0 Hz, 1H), 1.41-1.16 (m, 4H). | (Method A): m/z = 304.1 [M + H]⁺, 1.06 min |
| 38 | (3S)-2-(3-Ethyloxetane-3-carbonyl)-3-(4-fluorophenyl)-1,2-oxazolidine | 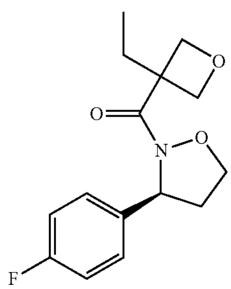 [SMILES: CCC1(C(=O)N2OCC[C@H]2c2ccc(F)cc2)COC1] | ¹H NMR (400 MHz, CDCl₃) δ ppm 7.32-7.25 (m, 2H) 7.05 (t, J = 8.7 Hz, 2H) 5.44-5.38 (m, 1H) 5.07-5.02 (m, 1H) 4.83 (d, J = 6.5 Hz, 1H) 4.45 (d, J = 6.5 Hz, 1H) 4.39 (d, J = 6.5 Hz, 1H) 4.26-4.19 (m, 1H) 3.94-3.84 (m, 1H) 2.92-2.78 (m, 1H) 2.42-2.29 (m, 1H) 2.24-2.05 (m, 2H) 0.94 (t, J = 7.5 Hz, 3H). | (Method A): m/z = 280.1 [M + H]⁺, 0.97 min |
| 39 | (3S)-3-(4-Fluorophenyl)-2-[1-(trifluoromethyl)cyclobutanecarbonyl]-1,2-oxazolidine | 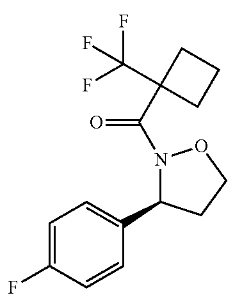 [SMILES: O=C(N1OCC[C@H]1c1ccc(F)cc1)C1(C(F)(F)F)CCC1] | ¹H NMR (400 MHz, CDCl₃) δ 7.33-7.26 (m, 2H), 7.10-7.01 (m, 2H), 5.41 (dd, J = 8.8, 6.5 Hz, 1H), 4.26 (td, J = 7.8, 3.5 Hz, 1H), 3.98-3.90 (m, 1H), 2.90-2.73 (m, 2H), 2.67-2.49 (m, 3H), 2.40-2.30 (m, 1H), 2.17-2.03 (m, 1H), 1.92-1.80 (m, 1H). | (Method A): m/z = 318.2 [M + H]⁺, 1.15 min |
| 40 | (3S)-3-(4-Fluorophenyl)-2-(3-methyloxolane-3-carbonyl)-1,2-oxazolidine diastereoisomer 1 (First eluting diastereoisomer) | DIASTEREOISOMER 1 | ¹H NMR (500 MHz, CDCl₃) δ 7.32-7.22 (m, 2H), 7.03 (t, J = 8.8 Hz, 2H), 5.36 (dd, J = 8.6, 6.6 Hz, 1H), 4.28 (td, J = 7.8, 3.4 Hz, 1H), 3.98 (d, J = 9.3 Hz, 1H), 3.95-3.87 (m, 2H), 3.83 (td, J = 8.3, 5.9 Hz, 1H), 3.77 (d, J = 8.8 Hz, 1H), 2.84 (dddd, J = 12.2, 9.1, 6.4, 3.2 Hz, 1H), 2.61 (dt, J = 12.7, 7.6 Hz, 1H), 2.39-2.29 (m, 1H), 1.80 (dt, J = 12.8, 6.5 Hz, 1H), 1.46 (s, 3H). | (Method B): m/z = 279.0 [M + H]⁺, 0.92 min |

| Comp. No. | Name | Structure | ¹H NMR | M + H⁺ |
|---|---|---|---|---|
| 41 | (3S)-3-(4-Fluorophenyl)-2-(3-methyloxolane-3-carbonyl)-1,2-oxazolidine diastereoisomer 2 (Second eluting diastereoisomer) | DIASTEREOISOMER 2 | ¹H NMR (500 MHz, CDCl₃) δ 7.31-7.24 (m, 2H), 7.03 (t, J = 8.8 Hz, 2H), 5.38 (dd, J = 8.6, 6.6 Hz, 1H), 4.28 (td, J = 7.7, 3.2 Hz, 1H), 4.18 (d, J = 8.8 Hz, 1H), 3.73 (d, J = 8.8 Hz, 1H), 3.97-3.78 (m, 3H), 2.84 (ddt, J = 15.4, 9.0, 3.2 Hz, 1H), 2.48 (dt, J = 12.7, 7.6 Hz, 1H), 2.39-2.29 (m, 1H), 1.85 (ddd, J = 12.8, 7.2, 5.9 Hz, 1H), 1.43 (s, 3H). | (Method B): m/z = 279.0 [M + H]⁺, 0.91 min |
| 42 | (3S)-2-(1,3-Dimethylazetidine-3-carbonyl)-3-(4-fluorophenyl)-1,2-oxazolidine | 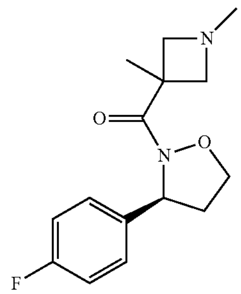 [SMILES: CN1CC(C)(C(=O)N2OCC[C@H]2c2ccc(F)cc2)C1] | ¹H NMR (400 MHz, DMSO-d₆) δ 7.36-7.27 (m, 2H), 7.22-7.13 (m, 2H), 5.29 (dd, J = 8.5, 6.8 Hz, 1H), 4.23 (td, J = 7.8, 3.3 Hz, 1H), 3.86 (ddd, J = 9.6, 8.0, 6.5 Hz, 1H), 3.23 (d, J = 7.0 Hz, 1H), 3.10 (s, 2H), 3.06 (d, J = 7.0 Hz, 1H), 2.88 (dddd, J = 12.0, 9.0, 6.3, 3.0 Hz, 1H), 2.22-2.11 (m, 4H), 1.49 (s, 3H). | LC-MS (Method A): m/z = 279.1 [M + H]⁺, 0.47 min |
| 43 | (3S)-3-(4-Fluorophenyl)-2-(3-methylazetidine-3-carbonyl)-1,2-oxazolidine | 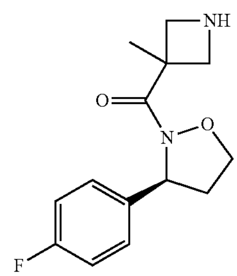 [SMILES: CC1(C(=O)N2OCC[C@H]2c2ccc(F)cc2)CNC1] | ¹H NMR (400 MHz, CDCl₃) δ 7.35-7.25 (m, 2H), 7.12-6.99 (m, 2H), 5.39 (dd, J= 8.7, 6.1 Hz, 1H), 4.24 (td, J = 7.8, 3.6 Hz, 1H), 4.17 (d, J = 8.5 Hz, 1H), 4.00 (d, J = 8.3 Hz, 1H), 3.96-3.86 (m, 1H), 3.42-3.33 (m, 2H), 2.92-2.80 (m, 1H), 2.42-2.28 (m, 1H), 1.68 (s, 3H). | LC-MS (Method A): m/z = 265.2 [M + H]⁺, 0.43 min |
| 44 | tert-Butyl 3-[(3S)-3-(4-fluorophenyl)-1,2-oxazolidine-2-carbonyl]-3-methylazetidine-1-carboxylate | 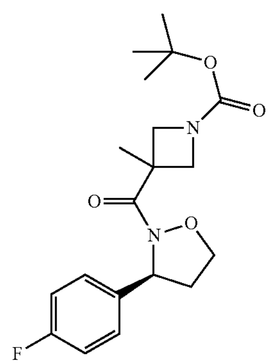 [SMILES: CC(C)(C)OC(=O)N1CC(C)(C(=O)N2OCC[C@H]2c2ccc(F)cc2)C1] | ¹H NMR (400 MHz, CDCl₃) δ 7.34-7.24 (m, 2H), 7.10-7.01 (m, 2H), 5.37 (dd, J = 8.7, 6.1 Hz, 1H), 4.35 (d, J = 8.8 Hz, 1H), 4.27 (td, J = 7.7, 3.5 Hz, 1H), 4.16 (d, J = 8.8 Hz, 1H), 3.96 (ddd, J = 9.0, 8.0, 6.8 Hz, 1H), 3.71 (d, J = 8.8 Hz, 1H), 3.67 (d, J = 9.0 Hz, 1H), 2.92-2.82 (m, 1H), 2.42-2.31 (m, 1H), 1.62 (s, 3H), 1.46 (s, 9H). | LC-MS (Method A): m/z = 365.3 [M + H]⁺, 1.13 min |
| 45 | 1-[(3R)-3-(2-Fluoropyridin-4-yl)-1,2-oxazolidin-2-yl]-2,2-dimethylpropan-1-one | 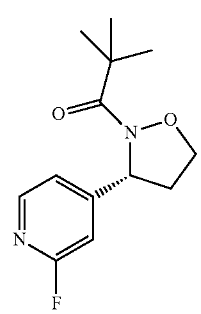 [SMILES: CC(C)(C)C(=O)N1OCC[C@@H]1c1ccnc(F)c1] | ¹H NMR (400 MHz, CDCl₃) δ 8.19 (d, J = 5.3 Hz, 1H), 7.14-7.10 (m, 1H), 6.87 (s, 1H), 5.43 (dd, J = 6.8, 8.8 Hz, 3H), 4.29 (td, J = 7.8, 2.2 Hz, 1H), 3.96-3.89 (m, 1H), 2.93-2.84 (m, 1H), 2.33-2.22 (m, 1H), 1.32 (s, 9H). | (Method A): m/z = 253.2 [M + H]⁺, 0.93 min |

| Comp. No. | Name | Structure | ¹H NMR | M + H⁺ |
|---|---|---|---|---|
| 46 | 1-[(3S)-3-(2-Fluoropyridin-4-yl)-1,2-oxazolidin-2-yl]-2,2-dimethylpropan-1-one | 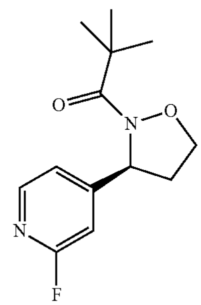 [SMILES: CC(C)(C)C(=O)N1OCC[C@H]1c1ccnc(F)c1] | ¹H NMR (400 MHz, CDCl₃) δ 8.19 (d, J = 5.3 Hz, 1H), 7.14-7.10 (m, 1H), 6.87 (s, 1H), 5.43 (dd, J = 6.8, 8.8 Hz, 1H), 4.29 (td, J = 7.8, 2.2 Hz, 1H), 3.96-3.89 (m, 1H), 2.93-2.84 (m, 1H), 2.33-2.22 (m, 1H), 1.32 (s, 9H). | (Method A): m/z = 253.2 [M + H]⁺, 0.93 min |
| 47 | 1-[(3S)-3-(4-Chlorophenyl)-1,2-oxazolidin-2-yl]-2,2-dimethylpropan-1-one | 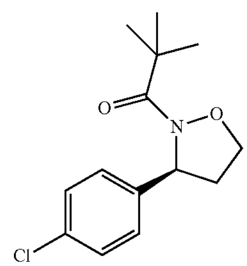 [SMILES: CC(C)(C)C(=O)N1OCC[C@H]1c1ccc(Cl)cc1] | ¹H NMR (400 MHz, CDCl₃) δ 7.34-7.29 (m, 2H), 7.28-7.23 (m, 2H), 5.39 (dd, J = 8.8, 6.5 Hz, 1H), 4.27 (td, J = 7.7, 2.6 Hz, 1H), 3.90 (ddd, J = 9.9, 8.0, 6.4 Hz, 1H), 2.82 (dddd, J = 12.2, 9.1, 6.3, 2.8 Hz, 1H), 2.29 (dddd, J = 12.3, 9.9, 7.7, 6.8 Hz, 1H), 1.30 (s, 9H). | LC-MS (Method A): m/z = 268.2 [M + H]⁺, 1.11 min |
| 48 | 1-[(3R)-3-(4-Chlorophenyl)-1,2-oxazolidin-2-yl]-2,2-dimethylpropan-1-one | 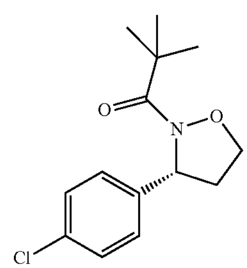 [SMILES: CC(C)(C)C(=O)N1OCC[C@@H]1c1ccc(Cl)cc1] | ¹H NMR (400 MHz, CDCl₃) δ 7.35-7.29 (m, 2H), 7.28-7.23 (m, 2H), 5.39 (dd, J = 8.9, 6.7 Hz, 1H), 4.27 (td, J = 7.8, 2.3 Hz, 1H), 3.90 (ddd, J = 9.8, 8.0, 6.5 Hz, 1H), 2.82 (dddd, J = 12.1, 9.1, 6.4, 2.8 Hz, 1H), 2.29 (dddd, J = 12.3, 9.9, 7.7, 6.5 Hz, 1H), 1.30 (s, 9H). | LC-MS (Method A): m/z = 268.2 [M + H]⁺, 1.12 min |
| 49 | tert-Butyl 3-(4-chlorophenyl)-1,2-oxazolidine-2-carboxylate | 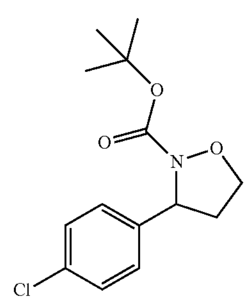 [SMILES: CC(C)(C)OC(=O)N1OCCC1c1ccc(Cl)cc1] | ¹H NMR (400 MHz, CDCl₃) δ 7.36-7.28 (m, 4H), 5.19 (dd, J = 5.5, 8.5 Hz, 1H), 4.20 (dt, J = 3.3, 7.8 Hz, 1H), 3.91 (dt, J = 7.0, 8.5 Hz, 1H), 2.79 (dddd, J = 3.6, 7.0, 8.7, 12.2 Hz, 1H), 2.33-2.22 (m, 1H), 1.48 (s, 9H). | LC-MS (Method A): m/z = 284.1 [M + H]⁺, 1.13 min |
| 50 | 1-[(3S)-3-(3,4-Difluorophenyl)-1,2-oxazolidin-2-yl]-2,2-dimethylpropan-1-one | 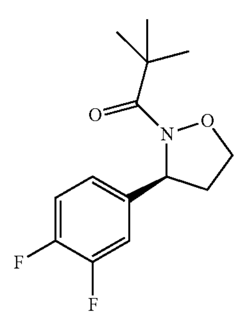 [SMILES: CC(C)(C)C(=O)N1OCC[C@H]1c1ccc(F)c(F)c1] | ¹H NMR (400 MHz, CDCl₃) δ 7.18-7.07 (m, 2H), 7.06-7.00 (m, 1H), 5.37 (dd, J = 8.7, 6.9 Hz, 1H), 4.27 (td, J = 7.8, 2.6 Hz, 1H), 3.89 (ddd, J = 9.8, 8.0, 6.5 Hz, 1H), 2.88-2.76 (m, 1H), 2.27 (dddd, J = 12.3, 9.9, 7.5, 6.7 Hz, 1H), 1.30 (s, 9H). | LC-MS (Method A): m/z = 270.1 [M + H]⁺, 1.09 min. |

| Comp. No. | Name | Structure | ¹H NMR | M + H⁺ |
|---|---|---|---|---|
| 51 | 1-[(3R)-3-(3,4-Difluorophenyl)-1,2-oxazolidin-2-yl]-2,2-dimethylpropan-1-one | 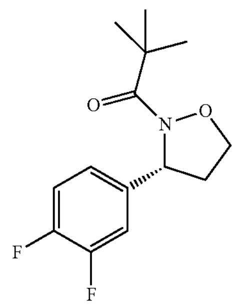 [SMILES: CC(C)(C)C(=O)N1OCC[C@@H]1c1ccc(F)c(F)c1] | ¹H NMR (400 MHz, CDCl₃) δ 7.18-7.08 (m, 2H), 7.07-7.00 (m, 1H), 5.37 (dd, J = 8.8, 6.8 Hz, 1H), 4.28 (td, J = 7.8, 2.8 Hz, 1H), 3.89 (ddd, J = 10.0, 8.1, 6.5 Hz, 1H), 2.82 (dddd, J = 12.1, 9.1, 6.4, 2.8 Hz, 1H), 2.28 (dddd, J = 12.3, 9.9, 7.7, 6.5 Hz, 1H), 1.30 (s, 9H). | LC-MS (Method A): m/z = 270.1 [M + H]⁺, 1.09 min. |
| 52 | (3S)-2-(Oxetane-2-carbonyl)-3-phenyl-1,2-oxazolidine diastereoisomer 2 (Second eluting diastereoisomer) | DIASTEREOISOMER 2 | ¹H NMR (400 MHz, CDCl₃) δ 7.40-7.29 (m, 5H), 5.63-5.45 (m, 2H), 4.80-4.66 (m, 2H), 4.26 (dt, J = 7.5, 4.5 Hz, 1H), 3.92 (br s, 1H), 3.02-2.76 (m, 3H), 2.47-2.35 (m, 1H). | (Method A): m/z = 234.1 [M + H]⁺, 0.73 min |
| 53 | (3S)-2-(Oxetane-2-carbonyl)-3-phenyl-1,2-oxazolidine diastereoisomer 1 (First eluting diastereoisomer) | DIASTEREOISOMER 1 | ¹H NMR (400 MHz, CDCl₃) δ 7.40-7.29 (m, 5H), 5.58-5.48 (m, 2H), 4.73 (t, J = 7.5 Hz, 2H), 4.24 (dt, J = 7.7, 3.6 Hz, 1H), 3.91 (q, J = 7.9 Hz, 1H), 3.07-2.82 (m, 3H), 2.45-2.35 (m, 1H). | (Method A): m/z = 234.1 [M + H]⁺, 0.75 min |
| 54 | (3S)-3-Phenyl-2-[1-(trifluoromethyl)cyclopropanecarbonyl]-1,2-oxazolidine | 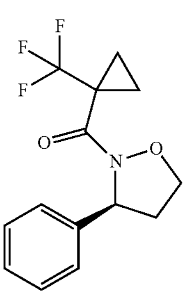 [SMILES: O=C(N1OCC[C@H]1c1ccccc1)C1(C(F)(F)F)CC1] | ¹H NMR (400 MHz, DMSO-d₆) δ 7.39-7.33 (m, 2H), 7.30-7.24 (m, 3H), 5.34 (dd, J = 8.8, 6.5 Hz, 1H), 4.29 (dt, J = 3.3, 7.7 Hz, 1H), 3.94 (ddd, J = 9.7, 7.9, 6.5 Hz, 1H), 2.91 (s, 1H), 2.24-2.12 (m, 1H), 1.29 (dd, J = 7.2, 2.4 Hz, 4H). | (Method A): m/z = 286.2 [M + H]⁺, 1.08 min |
| 55 | 3,3,3-Trifluoro-2,2-dimethyl-1-[(3S)-3-phenyl-1,2-oxazolidin-2-yl]propan-1-one | 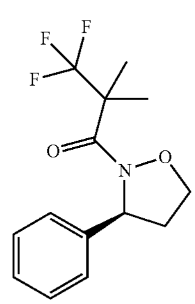 [SMILES: CC(C)(C(=O)N1OCC[C@H]1c1ccccc1)C(F)(F)F] | ¹H NMR (400 MHz, CDCl₃) δ 7.38-7.28 (m, 5H), 5.45 (dd, J = 8.8, 6.5 Hz, 1H), 4.31 (dt, J = 8.0, 2.8 Hz, 1H), 3.94 (ddd, J = 9.7, 8.0, 6.7 Hz, 1H), 2.84 (dddd, J = 12.0, 9.1, 6.5, 3.0 Hz, 1H), 2.36 (dddd, J = 12.3, 9.8, 7.8, 6.5 Hz, 1H), 1.58 (s, 3H), 1.57-1.56 (m, 3H). | (Method A): m/z = 288.1 [M + H]⁺, 1.19 min |

-continued

| Comp. No. | Name | Structure | ¹H NMR | M + H⁺ |
|---|---|---|---|---|
| 56 | 2-Fluoro-2-methyl-1-[(3S)-3-phenyl-1,2-oxazolidin-2-yl]propan-1-one | 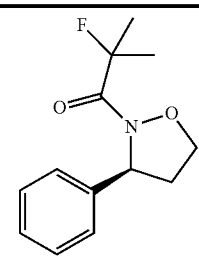 | ¹H NMR (400 MHz, DMSO-$d_6$) δ 7.39-7.34 (m, 2H), 7.30-7.25 (m, 3H), 5.37 (dd, J = 8.5, 6.5 Hz, 1H), 4.29 (dt, J = 7.7, 3.3 Hz, 1H), 3.89 (ddd, J = 9.5, 7.9, 6.7 Hz, 1H), 2.91 (dddd, J = 12.2, 9.1, 6.3, 3.0 Hz, 1H), 2.19 (dddd, J = 12.1, 9.6, 7.7, 6.5 Hz, 1H), 1.61 (s, 3H), 1.55 (s, 3H). | (Method A): m/z = 238.2 [M + H]⁺, 1.19 min |
| 57 | (3S)-2-(3,3-difluoro-1-methylcyclobutane-carbonyl)-3-phenyl-1,2-oxazolidine | 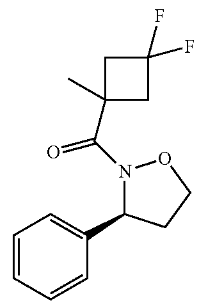 [SMILES: CC1(C(=O)N2OCC[C@H]2c2ccccc2)CC(F)(F)C1] | ¹H NMR (400 MHz, CDCl₃) δ 7.41-7.29 (m, 5H), 5.41 (dd, J = 8.9, 6.1 Hz, 1H), 4.28 (dt, J = 7.9, 4.0 Hz, 1H), 3.96 (ddd, J = 9.0, 8.0, 6.8 Hz, 1H), 3.25-3.11 (m, 1H), 3.02-2.82 (m, 2H), 2.59-2.34 (m, 3H), 1.58 (s, 3H). | (Method A): m/z = 282.3 [M + H]⁺, 1.11 min |
| 58 | 2,2-Dimethyl-1-[3-(pyridin-3-yl)-1,2-oxazolidin-2-yl]propan-1-one | 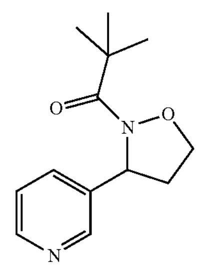 [SMILES: CC(C)(C)C(=O)N1OCCC1c1cccnc1] | ¹H NMR (400 MHz, DMSO-$d_6$) δ 8.50-8.45 (m, 2H), 7.64 (dt, J = 8.0, 1.8 Hz, 1H), 7.41-7.34 (m, 1H), 5.36 (dd, J = 8.8, 7.0 Hz, 1H), 4.32 (td, J = 7.7, 2.5 Hz, 1H), 3.88 (ddd, J = 10.0, 8.0, 6.4 Hz, 1H), 2.95-2.84 (m, 1H), 2.19 (ddt, J = 12.0, 9.9, 7.3 Hz, 1H), 1.21 (s, 9H). | LC-MS (Method A): m/z = 235.2 [M + H]⁺, 0.50 min |
| 59 | 5-[(3R)-3-(4-fluorophenyl)-1,2-oxazolidine-2-carbonyl]-1-methyl-1H-pyrrole-2-carbonitrile | 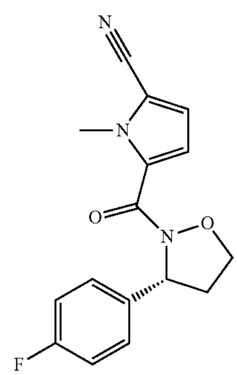 [SMILES: Cn1c(C#N)ccc1C(=O)N1OCC[C@@H]1c1ccc(F)cc1] | ¹H NMR (400 MHz, CDCl₃) δ 7.41-7.32 (m, 2H), 7.07 (t, J = 8.6 Hz, 2H), 7.00 (d, J = 4.3 Hz, 1H), 6.78 (dd, J = 4.3, 0.7 Hz, 1H), 5.63-5.54 (m, 1H), 4.35 (td, J = 7.8, 3.5 Hz, 1H), 4.04-3.94 (m, 4H), 2.95-2.85 (m, 1H) 2.48-2.34 (m, 1H). | (Method A): m/z = 300.2 [M + H]⁺, 1.05 min |
| 60 | 5-[(3S)-3-(4-fluorophenyl)-1,2-oxazolidine-2-carbonyl]-1-methyl-1H-pyrrole-2-carbonitrile | 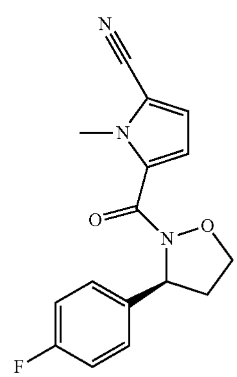 [SMILES: Cn1c(C#N)ccc1C(=O)N1OCC[C@H]1c1ccc(F)cc1] | ¹H NMR (400 MHz, CDCl₃) δ 7.41-7.31 (m, 2H), 7.12-7.01 (m, 2H), 7.00 (d, J = 4.3 Hz, 1H) 6.77 (d, J = 4.3 Hz, 1H), 5.58 (dd, J = 8.7, 6.1 Hz, 1H), 4.39-4.29 (m, 1H), 4.01 (s, 3H), 4.02-3.93 (m, 1H), 2.89 (dddd, J = 12,2, 8.7, 6.7, 3.5 Hz, 1H), 2.40 (dddd, J = 12.4, 9.3, 7.5, 6.1 Hz, 1H). | (Method A): m/z = 300.2 [M + H]⁺, 1.05 min |

| Comp. No. | Name | Structure | ¹H NMR | M + H⁺ |
|---|---|---|---|---|
| 64 | 1-[(3S)-3-(4-Fluorophenyl)-1,2-oxazolidin-2-yl]-2-methylpropan-1-one | 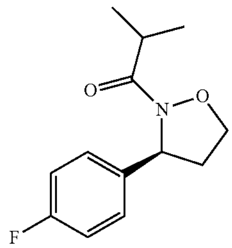 [SMILES: CC(C)C(=O)N1OCC[C@H]1c1ccc(F)cc1] | ¹H NMR (400 MHz, CDCl₃) δ 7.34-7.27 (m, 2H), 7.09-6.98 (m, 2H), 5.40 (dd, J = 8.8, 5.9 Hz, 1H), 4.32-4.22 (m, 1H), 3.90 (ddd, J = 9.2, 8.0, 6.8 Hz, 1H), 3.08-2.99 (m, 1H), 2.83 (dddd, J = 12.3, 8.8, 6.8, 3.5 Hz, 1H), 2.35 (dddd, J = 12.2, 9.2, 7.6, 5.9 Hz, 1H), 1.22 (d, J = 6.9 Hz, 3H), 1.12 (d, J = 6.8 Hz, 3H). | (Method A): m/z = 238.2 [M + H]⁺, 0.97 min. |
| 65 | 1-[(3R)-3-(4-Fluorophenyl)-1,2-oxazolidin-2-yl]-2-methylpropan-1-one | 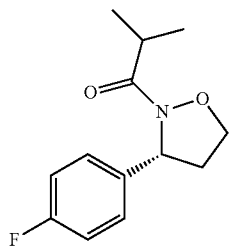 [SMILES: CC(C)C(=O)N1OCC[C@@H]1c1ccc(F)cc1] | ¹H NMR (400 MHz, CDCl₃) δ 7.35-7.25 (m, 2H), 7.09-6.98 (m, 2H), 5.40 (dd, J = 8.8, 5.9 Hz, 1H), 4.31-4.22 (m, 1H), 3.90 (ddd, J = 9.2, 8.0, 6.8 Hz, 1H), 3.08-2.99 (m, 1H), 2.83 (dddd, J = 12.3, 8.8, 6.8, 3.5 Hz, 1H), 2.34 (dddd, J = 12.3, 9.2, 7.5, 5.9 Hz, 1H), 1.22 (d, J = 6.9 Hz, 3H), 1.12 (d, J = 6.9 Hz, 3H). | (Method A): m/z = 238.2 [M + H]⁺, 0.96 min. |
| 63 | 1-[(3R)-3-(2-Fluoropyridin-3-yl)-1,2-oxazolidin-2-yl]-2,2-dimethylpropan-1-one | 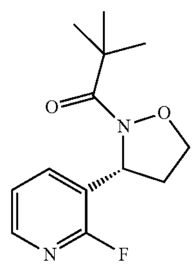 [SMILES: CC(C)(C)C(=O)N1OCC[C@@H]1c1cccnc1F] | ¹H NMR (400 MHz, CDCl₃) δ 8.13 (dt, J = 4.8, 1.5 Hz, 1H), 7.72-7.65 (m, 1H), 7.18 (td, J = 5.0, 2.4 Hz, 1H), 5.59 (dd, J = 8.7, 6.9 Hz, 1H), 4.26 (td, J = 7.9, 2.8 Hz, 1H), 3.93 (ddd, J = 9.8, 8.0, 6.5 Hz, 1H), 3.00-2.90 (m, 1H), 2.35-2.21 (m, 1H), 1.34 (s, 9H). | |
| 66 | 1-[(3S)-3-(2-Fluoropyridin-3-yl)-1,2-oxazolidin-2-yl]-2,2-dimethylpropan-1-one | 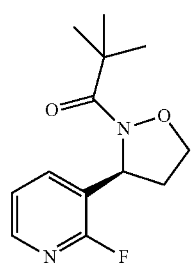 [SMILES: CC(C)(C)C(=O)N1OCC[C@H]1c1cccnc1F] | ¹H NMR (400 MHz, CDCl₃) δ 8.12 (dt, J = 4.8, 1.5 Hz, 1H), 7.68 (ddt, J = 9.7, 6.7, 1.3 Hz, 1H), 7.18 (ddd, J = 7.2, 5.1, 1.8 Hz, 1H), 5.59 (dd, J = 8.9, 6.7 Hz, 1H), 4.29-4.22 (m, 1H), 3.93 (ddd, J = 9.8, 8.0, 6.5 Hz, 1H), 3.00-2.87 (m, 1H), 2.34-2.22 (m, 1H), 1.33 (s, 9H). | LC-MS (Method A): m/z = 253.2 [M + H]⁺, 0.92 min |
| 67 | 1-[(3R)-3-(2,6-Difluorophenyl)-1,2-oxazolidin-2-yl]-2,2-dimethylpropan-1-one | 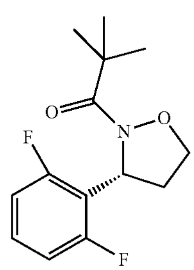 [SMILES: CC(C)(C)C(=O)N1OCC[C@@H]1c1c(F)cccc1F] | ¹H NMR (400 MHz, CDCl₃) δ 7.26-7.16 (m, 1H), 6.92-6.83 (m, 2H), 5.68 (t, J = 8.8, 1H), 4.40 (td, J = 7.8, 1.8 Hz, 1H), 3.95-3.87 (m, 1H), 2.81-2.73 (m, 1H), 2.56-2.45 (m, 1H), 1.27 (s, 9H). | (Method A): m/z = 270.2 [M + H]⁺, 1.09 min |
| 68 | 1-[(3S)-3-(2,6-Difluorophenyl)-1,2-oxazolidin-2-yl]-2,2-dimethylpropan-1-one | 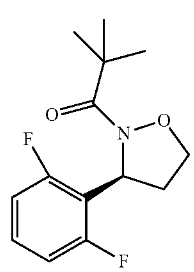 [SMILES: CC(C)(C)C(=O)N1OCC[C@H]1c1c(F)cccc1F] | ¹H NMR (400 MHz, CDCl₃) δ 7.26-7.16 (m, 1H), 6.92-6.83 (m, 2H), 5.68 (t, J = 8.8, 1H), 4.40 (td, J = 7.8, 1.8 Hz, 1H), 3.95-3.87 (m, 1H), 2.81-2.73 (m, 1H), 2.56-2.45 (m, 1H), 1.27 (s, 9H). | (Method A): m/z = 270.2 [M + H]⁺, 1.09 min |

-continued

| Comp. No. | Name | Structure | ¹H NMR | M + H⁺ |
|---|---|---|---|---|
| 69 | (3S)-2-(4-methyloxane-4-carbonyl)-3-phenyl-1,2-oxazolidine | 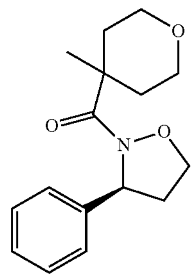 [SMILES: CC1(C(=O)N2OCC[C@H]2c2ccccc2)CCOCC1] | ¹H NMR (400 MHz, CDCl₃) δ 7.41-7.23 (m, 5H) 5.48 (dd, J = 8.8, 6.5 Hz, 1H), 4.27 (td, J = 7.5, 3.3 Hz, 1H) 3.91 (ddd, J = 9.5, 8.0, 6.5 Hz, 1H) 3.85-3.72 (m, 2H) 3.59 (dddd, J = 11.9, 9.3, 6.3, 2.9 Hz, 2H) 2.90-2.77 (m, 1H) 2.47-2.27 (m, 2H) 2.21 (ddt, J = 13.6, 4.7, 2.6 Hz, 1H) 1.86-1.46 (m, 2H) 1.34 (s, 3H). | LC-MS (Method B): m/z = 275.00 [M + H]⁺, 0.94 min |
| 75 | (1r,3r)-3-[(3S)-3-Phenyl-1,2-oxazolidine-2-carbonyl]cyclobutan-1-ol | 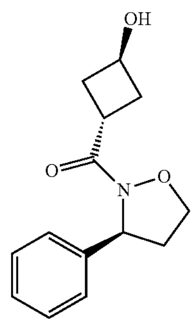 [SMILES: O=C([C@H]1C[C@H](O)C1)N1OCC[C@H]1c1ccccc1] | ¹H NMR (400 MHz, CDCl₃) δ 7.39-7.29 (m, 5H), 5.49-5.36 (m, 1H), 4.58-4.49 (m, 1H), 4.24 (dt, J = 7.8, 3.8 Hz, 1H), 3.91-3.82 (m, 1H), 3.49 (br s, 1H), 2.84 (dddd, J = 12.3, 8.8, 6.8, 3.8 Hz, 1H), 2.71-2.55 (m, 2H), 2.38 (dddd, J = 12.3, 9.0, 7.5, 5.8 Hz, 1H), 2.32-2.23 (m, 1H), 2.18 (br s, 1H), 1.78 (d, J = 5.3 Hz, 1H). | (Method A): m/z = 248.2 [M + H]⁺, 0.71 min |
| 76 | (3S)-2-[1-(Methoxymethyl)cyclopropanecarbonyl]-3-phenyl-1,2-oxazolidine | 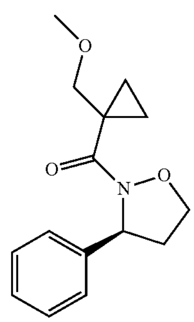 [SMILES: COCC1(C(=O)N2OCC[C@H]2c2ccccc2)CC1] | ¹H NMR (400 MHz, DMSO-d₆) δ 7.39-7.22 (m, 5H), 5.36 (dd, J = 8.7, 6.1 Hz, 1H), 4.24 (dt J = 7.8, 3.0 Hz, 1H), 3.89-3.80 (m, 2H), 3.35-3.33 (m, 1H), 3.23 (s, 3H), 2.86 (tdd, J = 15.2, 9.0, 3.2 Hz, 1H), 2.16 (dddd, J = 12.1, 9.6, 7.7, 6.3 Hz, 1H), 1.07-1.00 (m, 1H), 0.91 (dt, J = 6.0, 2.8 Hz, 1H), 0.75-0.66 (m, 2H). | (Method A): m/z = 262.3 [M + H]⁺, 0.90 min |
| 77 | (3S)-2-(1-Methylcyclobutane-carbonyl)-3-phenyl-1,2-oxazolidine | 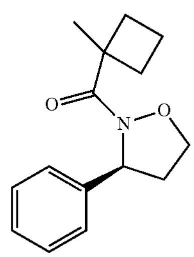 [SMILES: CC1(C(=O)N2OCC[C@H]2c2ccccc2)CCC1] | ¹H NMR (400 MHz, DMSO-d₆) δ 7.39-7.21 (m, 5H), 5.29 (dd, J = 8.8, 6.5 Hz, 1H), 4.21 (dt, J = 7.8, 3.0 Hz, 1H), 3.84 (ddd, J = 9.7, 7.9, 6.5 Hz, 1H), 2.94-2.82 (m, 1H), 2.48-2.41 (m, 1H), 2.37-2.28 (m, 1H), 2.15 (dddd, J = 12.1, 9.7, 7.5, 6.5 Hz, 1H), 2.02-1.88 (m, 1H), 1.84-1.59 (m, 3H), 1.43 (s, 3H). | (Method A): m/z = 246.1 [M + H]⁺, 1.08 min |
| 78 | 2-Methyl-1-[(3S)-3-phenyl-1,2-oxazolidin-2-yl]propan-1-one | 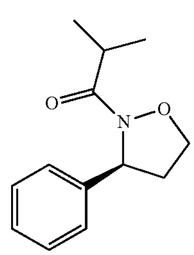 [SMILES: CC(C)C(=O)N1OCC[C@H]1c1ccccc1] | ¹H NMR (400 MHz, DMSO-d₆) δ 7.39-7.23 (m, 5H), 5.31 (dd, J = 8.8, 6.3 Hz, 1H), 4.25 (dt, J = 7.7, 2.9 Hz, 1H), 3.86 (ddd, J = 9.4, 8.0, 6.7 Hz, 1H), 3.03-2.92 (m, 1H), 2.92-2.83 (m, 1H), 2.24-2.12 (m, 1H), 1.10 (d, J = 7.0 Hz, 3H), 1.00 (d, J = 6.8 Hz, 3H). | (Method A): m/z = 220.0 [M + H]⁺, 0.95 min |

| Comp. No. | Name | Structure | ¹H NMR | M + H⁺ |
|---|---|---|---|---|
| 79 | 1-[(3S)-3-Phenyl-1,2-oxazolidine-2-carbonyl]cyclobutane-1-carbonitrile | 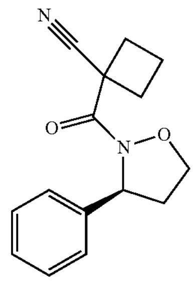 [SMILES: N#CC1(C(=O)N2OCC[C@H]2c2ccccc2)CCC1] | ¹H NMR (400 MHz, DMSO-d₆) δ 7.43-7.34 (m, 2H), 7.33-7.25 (m, 3H), 5.36 (dd, J = 8.5, 6.8 Hz, 1H), 4.34 (dt, J = 7.7, 2.5 Hz, 1H), 3.99 (ddd, J = 9.9, 7.9, 6.5 Hz, 1H), 2.97 (dddd, J = 12.0, 9.0, 6.3, 2.8 Hz, 1H), 2.77-2.62 (m, 2H), 2.61-2.45 (m, 2H), 2.31-2.08 (m, 2H), 1.91 (ttd, J = 1.4, 9.4, 5.6 Hz, 1H) | (Method A): m/z = 257.2 [M + H]⁺, 0.98 min |
| 80 | 2-Methoxy-2-methyl-1-[(3S)-3-phenyl-1,2-oxazolidin-2-yl]propan-1-one | 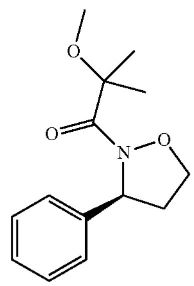 [SMILES: COC(C)(C)C(=O)N1OCC[C@H]1c1ccccc1] | ¹H NMR (400 MHz, DMSO-d₆) δ 7.39-7.22 (m, 5H), 5.40 (dd, J = 8.5, 6.5 Hz, 1H), 4.26 (dt, J = 7.7, 3.0 Hz, 1H), 3.86 (ddd, J = 9.4, 7.9, 6.8 Hz, 1H), 3.13 (s, 3H), 2.87 (dddd, J = 12.1, 9.1, 6.5, 3.0 Hz, 1H), 2.15 (dddd, J = 12.1, 9.5, 7.5, 6.3 Hz, 1H), 1.37 (s, 3H), 1.36 (s, 3H). | (Method A): m/z = 250.1 [M + H]⁺, 0.87 min |
| 15 | (2S)-2-Hydroxy-1-[(3S)-3-phenyl-1,2-oxazolidin-2-yl]propan-1-one | 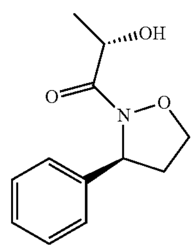 [SMILES: C[C@H](O)C(=O)N1OCC[C@H]1c1ccccc1] | ¹H NMR (400 MHz, DMSO-d₆) δ 7.40-7.23 (m, 5H), 5.34 (dd, J = 8.9, 6.4 Hz, 1H), 4.84 (d, J = 7.0 Hz, 1H), 4.54-4.44 (m, 1H), 4.25 (dt, J = 7.8, 2.6 Hz, 1H), 3.86 (ddd, J = 9.5, 8.0, 6.8 Hz, 1H), 2.93-2.85 (m, 1H), 2.18 (dddd, J = 12.2, 9.6, 7.6, 6.3 Hz, 1H), 1.30 (d, J = 6.8 Hz, 3H). | (Method A): m/z = 222.2 [M + H]⁺, 0.73 min. |
| 81 | 1-(3-(2-fluoropyridin-3-yl)isoxazolidin-2-yl)-2,2-dimethylpropan-1-one | 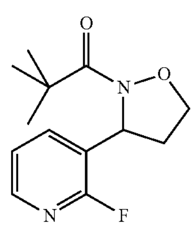 [SMILES: CC(C)(C)C(=O)N1OCCC1c1cccnc1F] | | |
| 82 | (R)-1-(3-(3-fluorophenyl)isoxazolidin-2-yl)-2,2-dimethylpropan-1-one | 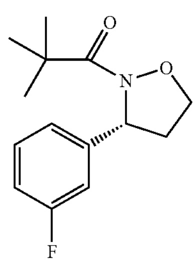 [SMILES: CC(C)(C)C(=O)N1OCC[C@@H]1c1cccc(F)c1] | | |
| 83 | tert-butyl 3-phenylisoxazolidine-2-carboxylate | 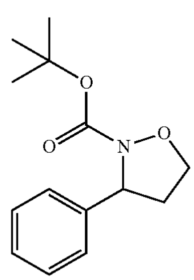 [SMILES: CC(C)(C)OC(=O)N1OCCC1c1ccccc1] | | |

-continued

| Comp. No. | Name | Structure | ¹H NMR | M + H⁺ |
|---|---|---|---|---|
| 84 | (R)-2,2-dimethyl-1-(3-phenylisoxazolidin-2-yl)propan-1-one | 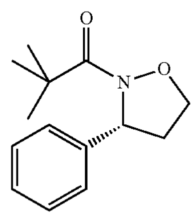 [SMILES: CC(C)(C)C(=O)N1OCC[C@@H]1c1ccccc1] | | |
| 85 | (R)-1-methyl-5-(3-phenylisoxazolidine-2-carbonyl)-1H-pyrrole-2-carbonitrile | 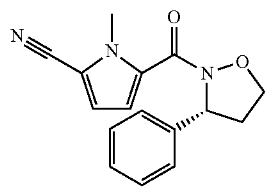 [SMILES: Cn1c(C#N)ccc1C(=O)N1OCC[C@@H]1c1ccccc1] | | |
| 86 | 2,2-dimethyl-1-(3-phenylisoxazolidin-2-yl)propan-1-one | 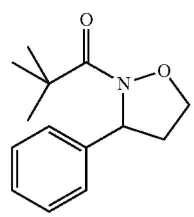 [SMILES: CC(C)(C)C(=O)N1OCCC1c1ccccc1] | | |
| 155 | (3S)-2-(3,3-difluoro-1-methylcyclobutane-carbonyl)-3-(4-fluorophenyl)-1,2-oxazolidine | 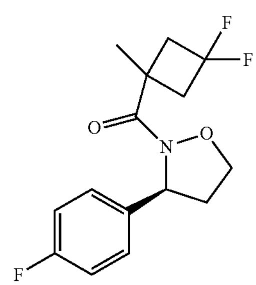 | ¹H NMR (400 MHz, CDCl₃) δ 7.33-7.23 (m, 2H), 7.11-6.98 (m, 2H), 5.38 (dd, J = 8.7, 6.1 Hz, 1H), 4.28 (dt, J = 3.6, 7.6 Hz, 1H), 3.95 (ddd, J = 9.2, 8.0, 6.7 Hz, 1H), 3.25-3.07 (m, 1H), 3.02-2.79 (m, 2H), 2.62-2.29 (m, 3H), 1.57 (s, 3H) | LC-MS (Method A): m/z = 287.2 [M + H]⁺, 1.18 min |
| 156 | 2-(azetidin-1-yl)-1-[(3S)-3-(4-fluorophenyl)-1,2-oxazolidin-2-yl]-2-methylpropan-1-one | 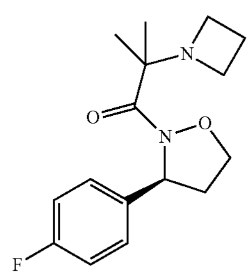 [SMILES: CC(C)(C(=O)N1OCC[C@H]1c1ccc(F)cc1)N1CCC1] | ¹H NMR (500 MHz, CDCl₃) δ 7.32-7.23 (m, 2 H), 7.05-6.96 (m, 2H), 5.59-5.44 (m, 1H), 4.24 (td, J = 7.8, 2.7 Hz, 1H), 3.96-3.84 (m, 1H), 3.53-3.35 (m, 4H), 2.84-2.75 (m, 1H), 2.33-2.24 (m, 1H), 2.01 (quin, J = 7.1 Hz, 2 H), 1.36-1.28 (m, 6H) | LC-MS (Method A): m/z = 293.2 [M + H]⁺, 0.91 min |
| 157 | 2,2-dimethyl-1-[3-(pyridazin-4-yl)-1,2-oxazolidin-2-yl]propan-1-one | 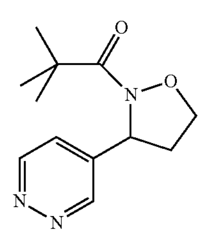 [SMILES: CC(C)(C)C(=O)N1OCCC1c1ccnnc1] | ¹H NMR (400 MHz, CDCl₃) δ 9.2-9.13 (m, 2H), 7.39 (dd, J = 5.3, 2.2 Hz, 1H), 5.44 (dd, J = 8.8, 6.8 Hz, 1H), 4.31 (td, J = 8.0, 2.5 Hz, 1H), 4.0-3.91 (m, 1H), 2.97-2.89 (m, 1H), 2.36-2.26 (m, 1H), 1.32 (s, 9H). | LC-MS (Method A): m/z = 236.2 [M + H]⁺, 0.69 min. |

-continued

| Comp. No. | Name | Structure | ¹H NMR | M + H⁺ |
|---|---|---|---|---|
| 158 | 4-[(3S)-2-(1-cyclopropylcyclopropanecarbonyl)-1,2-oxazolidin-3-yl]benzonitrile | 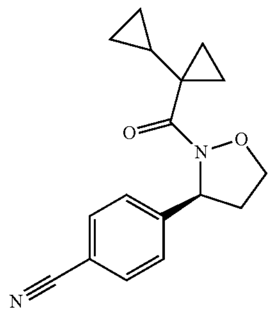 [SMILES: N#Cc1ccc([C@@H]2CCON2C(=O)C2(C3CC3)CC2)cc1] | ¹H NMR (400 MHz, CDCl₃) δ 7.66 (d, J = 8.3 Hz, 2H), 7.47 (d, J = 8.5 Hz, 2H), 5.51 (dd, J = 8.8, 6.0 Hz, 1H), 4.29 (td, J = 8.0, 3.3 Hz, 1H), 4.0-3.94 (m, 1H), 2.94-2.85 (m, 1H), 2.38-2.28 (m, 1H), 1.66-1.58 (m, 1H), 1.06-0.99 (m, 1H), 0.90-0.84 (m, 1H), 0.68-0.61 (m, 1H), 0.55-0.39 (m, 3H), 0.27-0.15 (m, 2H). | LC-MS (Method A): m/z = 283.2 [M + H]⁺, 1.00 min. |
| 159 | 5-[(3S)-2-(1-cyclopropylcyclopropanecarbonyl)-1,2-oxazolidin-3-yl]-2-fluoropyridine | 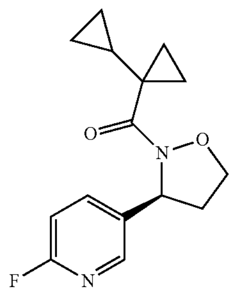 [SMILES: O=C(N1OCC[C@H]1c1ccc(F)nc1)C1(C2CC2)CC1] | ¹H NMR (400 MHz, CDCl₃) δ 8.23 (d, J = 2.5 Hz, 1H), 7.78 (td, J = 8.0, 2.5 Hz, 1H), 6.93 (dd, J = 8.0, 2.5 Hz, 1H), 5.51 (dd, J = 9.0, 6.0 Hz, 1H), 4.32 (td, J = 8.0, 3.3 Hz, 1H), 4.0-3.94 (m, 1H), 2.94-2.85 (m, 1H), 2.41-2.31 (m, 1H), 1.66-1.58 (m, 1H), 1.06-0.99 (m, 1H), 0.90-0.84 (m, 1H), 0.68-0.61 (m, 1H), 0.55-0.39 (m, 3H), 0.27-0.15 (m, 2H). | LC-MS (Method A): m/z = 277.2 [M + H]⁺, 0.91 min. |
| 160 | 2-fluoro-5-[(3S)-2-{3-oxabicyclo[3.1.0]hexane-6-carbonyl}-1,2-oxazolidin-3-yl]pyridine | 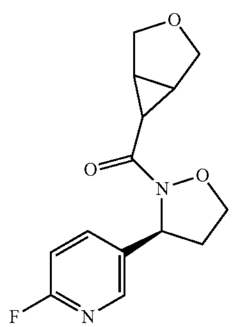 [SMILES: O=C(C1C2COCC21)N1OCC[C@H]1c1ccc(F)nc1] | ¹H NMR (400 MHz, CDCl₃) δ 8.21 (d, J = 2.0 Hz, 1H), 7.78 (td, J = 8.1, 2.4 Hz, 1H), 6.92 (dd, J = 8.4, 2.9 Hz, 1H), 5.46 (dd, J = 8.9, 5.9 Hz, 1H), 4.35-4.29 (m, 1H), 3.99 (d, J = 8.8 Hz, 1H), 3.98-3.89 (m, 2H), 3.81-3.77 (m, 2H), 2.94-2.83 (m, 1H), 2.43-2.25 (m, 2H), 2.21-2.17 (m, 2H). | LC-MS (Method A): m/z = 279.2 [M + H]⁺, 0.66 min. |
| 161 | 1-[(3S)-3-(6-fluoropyridin-3-yl)-1,2-oxazolidin-2-yl]-2,2-bis(²H₃)methyl(²H₃)propan-1-one | 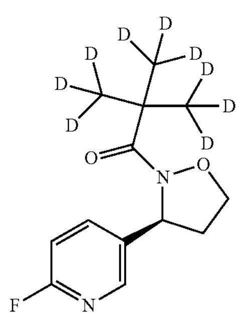 | ¹H NMR (400 MHz, CDCl₃) δ 8.20 (d, J = 2.3 Hz, 1H), 7.74 (td, J = 7.9, 2.5 Hz, 1H), 6.92 (dd, J = 8.4, 2.9 Hz, 1H), 5.46 (dd, J = 8.9, 6.9 Hz, 1H), 4.35-4.28 (m, 1H), 3.93 (ddd, J = 9.9, 8.1, 6.4 Hz, 1H), 2.87 (dddd, J = 12.1, 9.1, 6.4, 2.8 Hz, 1H), 2.38-2.26 (m, 1H). | LC-MS (Method A): m/z = 262.2 [M + H]⁺, 0.92 min. |
| 162 | 3,3,3-trifluoro-1-[(3S)-3-(6-fluoropyridin-3-yl)-1,2-oxazolidin-2-yl]-2-methylpropan-1-one | DIASTEREOISOMER 2 | ¹H NMR (400 MHz, CDCl₃) δ 8.19 (d, J = 2.5 Hz, 1H), 7.72 (td, J = 8.0, 2.6 Hz, 1H), 6.93 (dd, J = 8.4, 2.9 Hz, 1H), 5.45 (dd, J = 8.8, 6.0 Hz, 1H), 4.34 (td, J = 7.8, 3.6 Hz, 1H), 3.98 (td, J = 8.7, 6.8 Hz, 1H), 3.85 (dt, J = 15.2, 7.6 Hz, 1H), 2.98-2.89 (m, 1H), 2.40 (dddd, J = 12.5, 9.0, 7.5, 6.1 Hz, 1H), 1.39 (d, J = 7.0 Hz, 3H). | LC-MS (Method A): m/z = 293.1 [M + H]⁺, 0.89 min. |

| Comp. No. | Name | Structure | ¹H NMR | M + H⁺ |
|---|---|---|---|---|
| 163 | 3,3,3-trifluoro-1-[(3S)-3-(6-fluoropyridin-3-yl)-1,2-oxazolidin-2-yl]-2-methylpropan-1-one | DIASTEREOISOMER 1 | ¹H NMR (400 MHz, CDCl₃) δ 8.21 (d, J = 2.5 Hz, 1H), 7.75 (td, J = 7.9, 2.5 Hz, 1H), 6.94 (dd, J = 8.5, 3.0 Hz, 1H), 5.49 (dd, J = 8.8, 6.3 Hz, 1H), 4.34 (td, J = 8.0, 2.9 Hz, 1H), 3.99 (ddd, J = 9.7, 8.2, 6.8 Hz, 1H), 3.94-3.84 (m, 1H), 2.93 (dddd, J = 12.3, 9.2, 6.5, 2.9 Hz, 1H), 2.42 (dddd, J = 12.5, 9.7, 7.7, 6.5 Hz, 1H), 1.43 (d, J = 7.3 Hz, 3H). | LC-MS (Method A): m/z = 293.1 [M + H]⁺, 0.91 min. |
| 164 | 1-[(3S)-3-(6-fluoropyridin-3-yl)-1,2-oxazolidin-2-yl]-2,2-dimethyl-3-(trifluoromethoxy)propan-1-one | 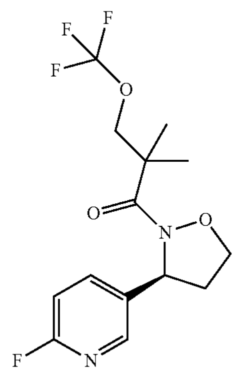 [SMILES: CC(C)(COC(F)(F)F)C(=O)N1OCC[C@H]1c1ccc(F)nc1] | ¹H NMR (400 MHz, CDCl₃) δ 8.19 (d, J = 2.5 Hz, 1H), 7.76-7.68 (m, 1H), 6.92 (dd, J = 8.4, 2.9 Hz, 1H), 5.46 (dd, J = 8.8, 6.5 Hz, 1H), 4.39-4.31 (m, 1H), 4.16 (s, 2H), 3.99 (ddd, J = 9.7, 8.1, 6.5 Hz, 1H), 2.89 (dddd, J = 12.2, 9.2, 6.3, 2.9 Hz, 1H), 2.39-2.27 (m, 1H), 1.34-1.36 (m, 6H). | LC-MS (Method A): m/z = 337.2 [M + H]⁺, 1.06 min. |
| 165 | 4-[(3S)-3-(6-fluoropyridin-3-yl)-1,2-oxazolidin-2-yl]-3,3-dimethyl-4-oxobutanenitrile | 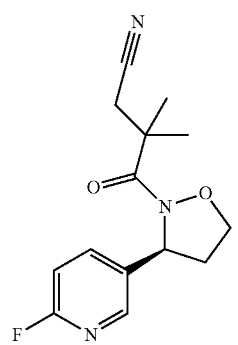 [SMILES: CC(C)(CC#N)C(=O)N1OCC[C@H]1c1ccc(F)nc1] | ¹H NMR (400 MHz, CDCl₃) δ 8.19 (d, J = 2.5 Hz, 1H), 7.73 (td, J = 8.0, 2.6 Hz, 1H), 6.93 (dd, J = 8.5, 3.0 Hz, 1H), 5.45 (dd, J = 8.7, 6.9 Hz, 1H), 4.38 (td, J = 7.9, 2.5 Hz, 1H), 4.00 (ddd, J = 9.7, 8.1, 6.5 Hz, 1H), 2.92 (dddd, J = 12.3, 9.2, 6.3, 2.9 Hz, 1H), 2.73 (d, J = 16.6 Hz, 1H), 2.66 (d, J = 16.6 Hz, 1H), 2.36 (dddd, J = 12.5, 9.7, 7.5, 6.7 Hz, 1H), 1.49 (s, 3H), 1.47 (s, 3H). | LC-MS (Method A): m/z = 278.2 [M + H]⁺, 0.79 min. |
| 166 | (2S)-3,3,3-trifluoro-1-[(3S)-3-(6-fluoropyridin-3-yl)-1,2-oxazolidin-2-yl]-2-hydroxy-2-methylpropan-1-one | 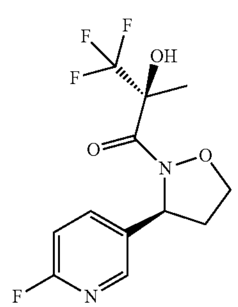 [SMILES: C[C@](O)(C(=O)N1OCC[C@H]1c1ccc(F)nc1)C(F)(F)F] | ¹H NMR (400 MHz, CDCl₃) δ 8.23 (d, J = 1.8 Hz, 1H), 7.75 (ddd, J = 8.3, 7.5, 2.8 Hz, 1H), 6.97 (dd, J = 8.4, 3.4 Hz, 1H), 5.48 (dd, J = 8.7, 6.9 Hz, 1H), 4.70 (s, 1H), 4.42 (td, J = 8.2, 2.4 Hz, 1H), 4.04 (ddd, J = 10.2, 8.4, 6.5 Hz, 1H), 2.98 (dddd, J = 12.6, 8.9, 6.7, 2.4 Hz, 1H), 2.43 (dddd, J = 12.7, 10.2, 7.8, 6.7 Hz, 1H), 1.76 (s, 3H). | LC-MS (Method A): m/z = 309.2 [M + H]⁺, 0.80 min. |

| Comp. No. | Name | Structure | ¹H NMR | M + H⁺ |
|---|---|---|---|---|
| 167 | 2,2-dicyclopropyl-1-[(3S)-3-(6-fluoropyridin-3-yl)-1,2-oxazolidin-2-yl]ethan-1-one | 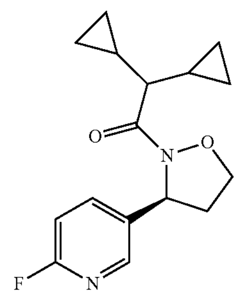 [SMILES: O=C(C(C1CC1)C1CC1)N1OCC[C@H]1c1ccc(F)nc1] | ¹H NMR (400 MHz, CDCl₃) δ 8.21 (d, J = 2.5 Hz, 1H), 7.76 (td, J = 8.1, 2.9 Hz, 1H), 6.93 (dd, J = 8.5, 2.8 Hz, 1H), 5.52 (dd, J = 8.7, 6.1 Hz, 1H), 4.24 (td, J = 7.8, 2.8 Hz, 1H), 3.85 (ddd, J = 9.5, 8.0, 6.8 Hz, 1H), 2.95-2.84 (m, 1H), 2.34 (dddd, J = 12.3, 9.6, 7.6, 6.1 Hz, 1H), 1.68 (t, J = 9.4 Hz, 1H), 1.26-1.07 (m, 2H), 0.68-0.55 (m, 2H), 0.54-0.38 (m, 2H), 0.36-0.24 (m, 3H), 0.17-0.04 (m, 1H). | LC-MS (Method A): m/z = 291.2 [M + H]⁺, 0.99 min. |
| 168 | 5-[(3S)-2-[1-(difluoromethyl)cyclobutanecarbonyl]-1,2-oxazolidin-3-yl]-2-fluoropyridine | 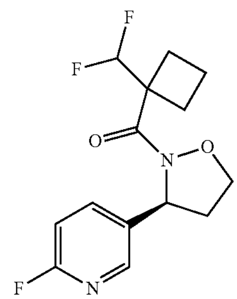 [SMILES: O=C(N1OCC[C@H]1c1ccc(F)nc1)C1(C(F)F)CCC1] | ¹H NMR (400 MHz, CDCl₃) δ 8.19 (d, J = 2.3 Hz, 1H), 7.72 (td, J = 8.0, 2.6 Hz, 1H), 6.93 (dd, J = 8.5, 2.8 Hz, 1H), 6.24 (t, J = 57.5 Hz, 1H), 5.47 (dd, J = 8.5, 6.5 Hz, 1H), 4.29 (td, J = 7.9, 3.3 Hz, 1H), 3.96 (ddd, J = 9.4, 8.2, 6.5 Hz, 1H), 3.01-2.83 (m, 1H), 2.69-2.58 (m, 1H), 2.54-2.29 (m, 4H), 2.08-1.94 (m, 1H), 1.94-1.81 (m, 1H). | LC-MS (Method A): m/z = 301.2 [M + H]⁺, 0.95 min. |
| 169 | 3,3-difluoro-1-[(3S)-3-(6-fluoropyridin-3-yl)-1,2-oxazolidin-2-yl]-2,2-dimethylpropan-1-one | 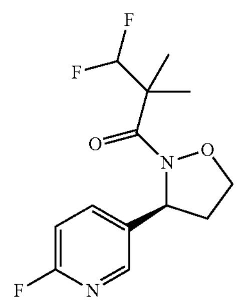 [SMILES: CC(C)(C(=O)N1OCC[C@H]1c1ccc(F)nc1)C(F)F] | ¹H NMR (400 MHz, CDCl₃) δ 8.19 (d, J = 2.5 Hz, 1H), 7.72 (td, J = 7.9, 2.5 Hz, 1H), 6.93 (dd, J = 8.4, 2.9 Hz, 1H), 6.32 (t, J = 58.0 Hz, 1H), 5.46 (dd, J = 8.5, 6.8 Hz, 1H), 4.36 (td, J = 7.7, 2.6 Hz, 1H), 3.99 (ddd, J = 9.7, 8.1, 6.5 Hz, 1H), 2.91 (dddd, J = 12.3, 9.1, 6.3, 2.9 Hz, 1H), 2.36 (dddd, J = 12.5, 9.7, 7.5, 6.8 Hz, 1H), 1.40-1.36 (m, 6H). | LC-MS (Method A): m/z = 289.2 [M + H]⁺, 0.94 min. |
| 170 | 5-[(3S)-2-[1-(difluoromethyl)cyclopropanecarbonyl]-1,2-oxazolidin-3-yl]-2-fluoropyridine | 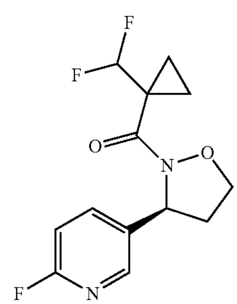 [SMILES: O=C(N1OCC[C@H]1c1ccc(F)nc1)C1(C(F)F)CC1] | ¹H NMR (400 MHz, CDCl₃) δ 8.20 (d, J = 2.5 Hz, 1H), 7.75 (td, J = 8.0, 2.6 Hz, 1H), 6.94 (dd, J = 8.4, 2.9 Hz, 1H), 6.65 (dd, J = 59.5, 58.5 Hz, 1H), 5.51 (dd, J = 8.8, 6.5 Hz, 1H), 4.36 (td, J = 7.9, 3.0 Hz, 1H), 3.98 (ddd, J = 9.5, 8.3, 6.8 Hz, 1H), 2.99-2.83 (m, 1H), 2.38 (dddd, J = 12.5, 9.5, 7.7, 6.5 Hz, 1H), 1.44-1.33 (m, 1H), 1.31-1.09 (m, 3H). | LC-MS (Method A): m/z = 287.1 [M + H]⁺, 0.88 min. |
| 171 | 4-[(3S)-3-(4-fluorophenyl)-1,2-oxazolidin-2-yl]-3,3-dimethyl-4-oxobutanenitrile | 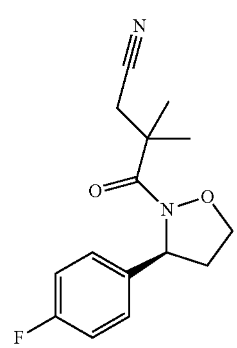 [SMILES: CC(C)(CC#N)C(=O)N1OCC[C@H]1c1ccc(F)cc1] | ¹H NMR (400 MHz, CDCl₃) δ 7.33-7.23 (m, 2H), 7.10-6.99 (m, 2H), 5.40 (dd, J = 8.8, 6.5 Hz, 1H), 4.34 (td, J = 7.8, 3.1 Hz, 1H), 3.98 (ddd, J = 9.6, 8.1, 6.5 Hz, 1H), 2.86 (dddd, J = 12.2, 8.7, 6.5, 3.1 Hz, 1H), 2.79-2.63 (m, 2H), 2.34 (dddd, J = 12.4, 9.6, 7.6, 6.5 Hz, 1H), 1.49 (s, 6H). | LC-MS (Method A): m/z = 277.2 [M + H]⁺, 0.97 min. |

| Comp. No. | Name | Structure | ¹H NMR | M + H⁺ |
|---|---|---|---|---|
| 172 | 6-[(3S)-3-(4-fluorophenyl)-1,2-oxazolidine-2-carbonyl]-2-oxaspiro[3.3]heptane-6-carbonitrile | 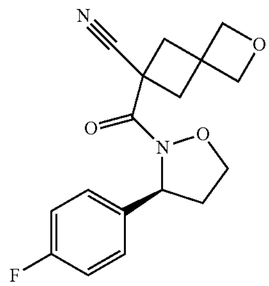 [SMILES: N#CC1(C(=O)N2OCC[C@H]2c2ccc(F)cc2)CC2(COC2)C1] | ¹H NMR (400 MHz, CDCl₃) δ 7.33-7.24 (m, 2H), 7.12-7.00 (m, 2H), 5.33 (dd, J = 8.8, 6.2 Hz, 1H), 4.82 (s, 2H), 4.64-4.52 (m, 2H), 4.41-4.31 (m, 1H), 4.18-4.07 (m, 1H), 3.06-2.86 (m, 4H), 2.81 (dd, J = 13.0, 2.5 Hz, 1H), 2.43 (dddd, J = 12.5, 9.4, 7.6, 6.1 Hz, 1H). | LC-MS (Method A): m/z = 317.2 [M + H]⁺, 0.89 min |
| 173 | 1-[(3S)-3-(4-fluorophenyl)-1,2-oxazolidin-2-yl]-2,2-bis(²H₃)methyl(²H₃)propan-1-one | 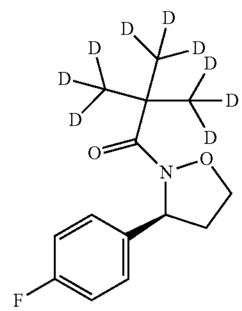 [SMILES: [2H]C([2H])([2H])C(C(=O)N1OCC[C@H]1c1ccc(F)cc1)(C([2H])([2H])[2H])C([2H])([2H])[2H]] | ¹H NMR (400 MHz, CDCl₃) δ 7.33-7.24 (m, 2H), 7.08-6.97 (m, 2H), 5.41 (dd, J = 8.8, 6.5 Hz, 1H), 4.27 (tdd, J = 7.8, 2.9, 0.7 Hz, 1H), 3.89 (ddd, J = 9.8, 8.0, 6.5 Hz, 1H), 2.88-2.75 (m, 1H), 2.30 (dddd, J = 12.2, 9.8, 7.7, 6.4 Hz, 1H). | LC-MS (Method A): m/z = 261.2 [M + H]⁺, 1.09 min |
| 174 | 1-[(3S)-3-(5-chloropyridin-3-yl)-1,2-oxazolidin-2-yl]-2,2-dimethylpropan-1-one | 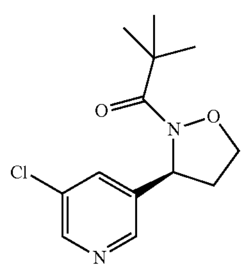 [SMILES: CC(C)(C)C(=O)N1OCC[C@H]1c1cncc(Cl)c1] | ¹H NMR (400 MHz, CDCl₃) δ 8.49 (d, J = 2.3 Hz, 1H), 8.47 (d, J = 2.0 Hz, 1H), 7.60 (t, J = 2.1 Hz, 1H) 5.43 (dd, J = 8.9, 6.7 Hz, 1H), 4.36-4.26 (m, 1H), 3.92 (ddd, J = 10.0, 8.1, 6.4 Hz, 1H), 2.88 (dddd, J = 12.4, 9.0, 6.4, 2.6 Hz, 1H), 2.31 (dddd, J = 12.3, 10.0, 7.7, 6.7 Hz, 1H), 1.31 (s, 9H). | LC-MS (Method A): m/z = 269.1 [M + H]⁺, 0.97 min |
| 175 | 1-[(3S)-3-[2-(difluoromethyl)pyridin-4-yl]-1,2-oxazolidin-2-yl]-2,2-dimethylpropan-1-one | 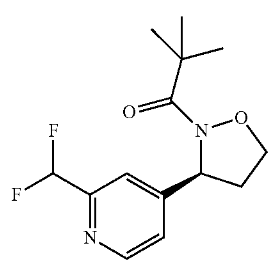 [SMILES: CC(C)(C)C(=O)N1OCC[C@H]1c1ccnc(C(F)F)c1] | ¹H NMR (400 MHz, CDCl₃) δ 8.65-8.58 (m, 1H), 7.56 (s, 1H), 7.34-7.33 (m, 1H), 6.64 (t, J = 55.6 Hz, 1H), 5.45 (dd, J = 9.0, 6.7 Hz, 1H), 4.35-4.25 (m, 1H), 3.93 (ddd, J = 9.9, 8.1, 6.4 Hz, 1H), 2.96-2.84 (m, 1H), 2.35-2.21 (m, 1H), 1.32 (s, 9H). | LC-MS (Method A): m/z = 285.2 [M + H]⁺, 0.95 min |
| 176 | 1-[(3S)-3-(4-fluorophenyl)-1,2-oxazolidin-2-yl]-2,2-dimethyl-3-(trifluoromethoxy)propan-1-one | 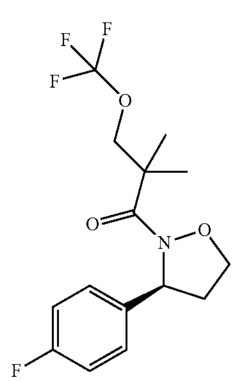 [SMILES: CC(C)(COC(F)(F)F)C(=O)N1OCC[C@H]1c1ccc(F)cc1] | ¹H NMR (400 MHz, CDCl₃) δ 7.31-7.22 (m, 2H), 7.08-6.97 (m, 2H), 5.41 (dd, J = 8.8, 6.4 Hz, 1H), 4.30 (td, J = 7.9, 3.3 Hz, 1H), 4.16 (s, 2H), 3.96 (ddd, J = 9.5, 8.0, 6.6 Hz, 1H), 2.83 (dddd, J = 12.2, 8.8, 6.5, 3.2 Hz, 1H), 2.31 (dddd, J = 12.3, 9.5, 7.6, 6.4 Hz, 1H), 1.35 (s, 6H). | LC-MS (Method A): m/z = 336.2 [M + H]⁺, 1.20 min |

| Comp. No. | Name | Structure | ¹H NMR | M + H⁺ |
|---|---|---|---|---|
| 177 | 1-[(3S)-3-(5-chloropyridin-3-yl)-1,2-oxazolidin-2-yl]-2,2-dimethyl-3-(trifluoromethoxy)propan-1-one | 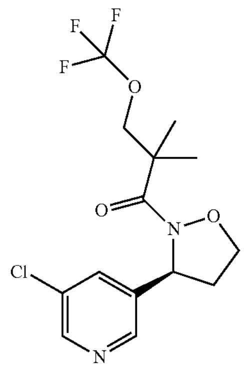 [SMILES: CC(C)(COC(F)(F)F)C(=O)N1OCC[C@H]1c1cncc(Cl)c1] | ¹H NMR (400 MHz, CDCl₃) δ 8.50 (d, J = 2.5 Hz, 1H), 8.46 (d, J = 2.0 Hz, 1H), 7.60 (t, J = 1.9 Hz, 1H), 5.45 (dd, J = 8.9, 6.6 Hz, 1H), 4.35 (td, J = 7.7, 2.8 Hz, 1H), 4.16 (s, 2H), 4.04-3.93 (m, 1H), 2.91 (dddd, J = 12.1, 9.2, 6.4, 3.0 Hz, 1H), 2.34 (dddd, J = 12.4, 9.7, 7.5, 6.5 Hz, 1H), 1.36 (s, 6H) | LC-MS (Method A): m/z = 353.2 [M + H]⁺, 1.09 min |
| 178 | 1-[(3S)-3-(4-fluorophenyl)-1,2-oxazolidin-2-yl]-2,2-dimethyl-3-(1H-pyrazol-1-yl)propan-1-one | 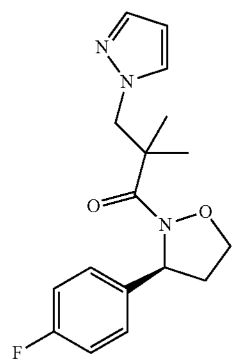 [SMILES: CC(C)(Cn1cccn1)C(=O)N1OCC[C@H]1c1ccc(F)cc1] | ¹H NMR (400 MHz, CDCl₃) δ 7.47 ( J = 1.9, 0.7 Hz, 1H), 7.39 (dd, J = 2.3, 0.7 Hz, 1H), 7.35-7.26 (m, 2H), 7.08-6.97 (m, 2H), 6.19 (t, J = 2.1 Hz, 1H), 5.41 (dd, J = 8.8, 6.6 Hz, 1H), 4.58 (d, J = 14.0 Hz, 1H), 4.38-4.25 (m, 2H), 4.15 (ddd, J = 9.7, 7.8, 6.5 Hz, 1H), 2.88 (dddd, J = 12.0, 8.8, 6.5, 3.1 Hz, 1H), 2.33 (dddd, J = 12.2, 9.6, 7.6, 6.6 Hz, 1H), 1.33 (s, 3H), 1.26 (s, 3H). | LC-MS (Method A): m/z = 318.2 [M + H]⁺, 0.94 min |
| 179 | 4-[(3S)-2-(3,3,3-trifluoro-2-methylpropanoyl)-1,2-oxazolidin-3-yl]benzonitrile (Second eluting diastereoisomer) | DIASTEREOISOMER 2 | ¹H NMR (400 MHz, CDCl₃) δ 7.70-7.63 (m, 2H), 7.44-7.38 (m, 2H), 5.45 (dd, J = 8.9, 6.1 Hz, 1H), 4.33 (td, J = 7.8, 3.6 Hz, 1H), 3.99 (td, J = 8.6, 6.6 Hz, 1H), 3.92-3.83 (m, 1H), 3.01-2.88 (m, 1H), 2.44-2.31 (m, 1H), 1.39 (d, J = 7.1 Hz, 3H). | LC-MS (Method A): m/z = 299.1 [M + H]⁺, 0.99 min |
| 180 | 4-[(3S)-2-(3,3,3-trifluoro-2-methylpropanoyl)-1,2-oxazolidin-3-yl]benzonitrile (First eluting diastereoisomer) | DIASTEREOISOMER 1 | ¹H NMR (400 MHz, CDCl₃) δ 7.70-7.62 (m, 2H), 7.46-7.38 (m, 2H), 5.48 (dd, J = 8.9, 6.5 Hz, 1H), 4.37-4.27 (m, 1H), 4.04-3.82 (m, 2H), 3.00-2.87 (m, 1H), 2.38 (dddd, J = 12.4, 9.8, 7.7, 6.5 Hz, 1H), 1.45 (d, J = 7.2 Hz, 3H). | LC-MS (Method A): m/z = 299.1 [M + H]⁺, 1.00 min |

-continued

| Comp. No. | Name | Structure | ¹H NMR | M + H⁺ |
|---|---|---|---|---|
| 181 | 4-[(3S)-2-(3-cyano-2,2-dimethylpropanoyl)-1,2-oxazolidin-3-yl]benzonitrile | 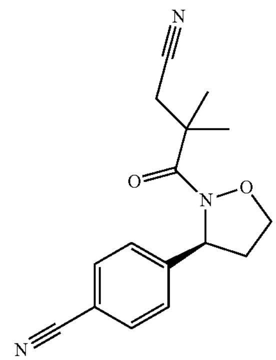 [SMILES: CC(C)(CC#N)C(=O)N1OCC[C@H]1c1ccc(C#N)cc1] | ¹H NMR (400 MHz, CDCl₃) δ 7.70-7.61 (m, 2H), 7.45-7.37 (m, 2H), 5.44 (dd, J = 8.9, 6.8 Hz, 1H), 4.40-4.30 (m, 1H), 3.99 (ddd, J = 9.8, 8.1, 6.3 Hz, 1H), 2.91 (dtd, J = 12.0, 6.3, 3.2 Hz, 1H), 2.78-2.63 (m, 2H), 2.32 (dddd, J = 12.4, 9.8, 7.6, 6.8 Hz, 1H), 1.50 (s, 3H), 1.47 (s, 3H). | LC-MS (Method A): m/z = 284.2 [M + H]⁺, 0.89 min |
| 182 | 3-[(3S)-3-(4-fluorophenyl)-1,2-oxazolidin-2-yl]-2,2-dimethyl-3-oxopropanenitrile | 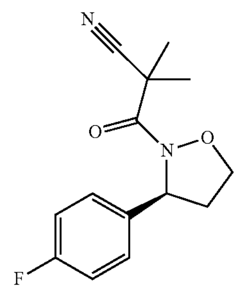 [SMILES: CC(C)(C#N)C(=O)N1OCC[C@H]1c1ccc(F)cc1] | ¹H NMR (400 MHz, CDCl₃) δ 7.32-7.25 (m, 2 H), 7.09-7.00 (m, 2 H), 5.37 (dd, J = 8.8, 6.5 Hz, 1 H), 4.42-4.34 (m, 1 H), 4.16 (ddd, J = 9.8, 8.3, 6.8 Hz, 1 H), 2.99-2.87 (m, 1 H), 2.43 (dddd, J = 12.5, 9.9, 7.8, 6.5 Hz, 1 H), 1.71 (s, 3 H), 1.60 (s, 3 H). | LC-MS (Method A): m/z = 263.2 [M + H]⁺, 0.97 min. |
| 183 | 1-[(3S)-3-(4-fluorophenyl)-1,2-oxazolidin-2-yl]-2-(trifluoromethoxy)propan-1-one (First eluting diastereoisomer) DIASTEREOISOMER 1 | 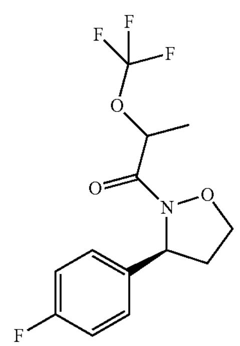 | ¹H NMR (400 MHz, CDCl₃) δ 7.33-7.22 (m, 2H), 7.09-7.00 (m, 2H), 5.45-5.32 (m, 1H), 5.26-5.14 (m, 1H), 4.30 (td, J = 7.6, 4.1 Hz, 1H), 3.99 (td, J = 8.2, 6.9 Hz, 1H), 2.88 (dddd, J = 12.5, 8.6, 6.8, 4.3 Hz, 1H), 2.49-2.30 (m, 1H), 1.54 (d, J = 6.5 Hz, 3H). | LC-MS (Method A): m/z = 308.1 [M + H]⁺, 1.07 min. |
| 184 | 1-[(3S)-3-(6-fluoropyridin-3-yl)-1,2-oxazolidin-2-yl]-2-(trifluoromethoxy)propan-1-one (Second eluting diastereoisomer) DIASTEREOISOMER 2 | 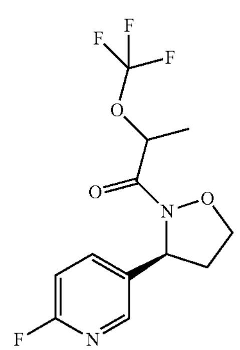 | ¹H NMR (400 MHz, CDCl₃) δ 8.19 (d, J = 2.5 Hz, 1H), 7.73 (dt, J = 2.6, 8.0 Hz, 1H), 6.94 (dd, J = 2.9, 8.4 Hz, 1H), 5.41 (dd, J = 8.7, 6.1 Hz, 1H), 5.20 (q, J = 6.8 Hz, 1H), 4.35 (dt, J = 4.0, 7.7 Hz, 1H), 4.00 (dt, J = 6.8, 8.5 Hz, 1H), 3.02-2.86 (m, 1H), 2.51-2.36 (m, 1H), 1.58-1.50 (m, 3H). | LC-MS (Method A): m/z = 309.1 [M + H]⁺, 0.91 min. |

-continued

| Comp. No. | Name | Structure | ¹H NMR | M + H⁺ |
|---|---|---|---|---|
| 185 | 1-[(3S)-3-(6-fluoropyridin-3-yl)-1,2-oxazolidin-2-yl]-2-(trifluoromethoxy)propan-1-one (First eluting diastereoisomer) | 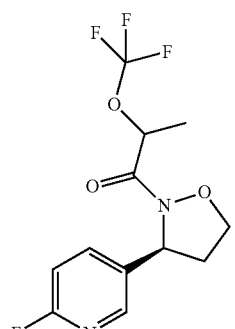<br>DIASTEREOISOMER 1 | ¹H NMR (400 MHz, CDCl₃) δ 8.22-8.17 (m, 1H), 7.74 (dt, J = 2.6, 8.0 Hz, 1H), 6.94 (dd, J = 8.5, 2.8 Hz, 1H), 5.50 (dd, J = 8.7, 6.4 Hz, 1H), 5.24 (q, J = 6.8 Hz, 1H), 4.36 (dt, J = 2.6, 7.8 Hz, 1H), 3.95 (ddd, J = 9.8, 8.3, 6.8 Hz, 1H), 2.99-2.88 (m, 1H), 2.41 (dddd, J = 12.5, 9.7, 7.7, 6.3 Hz, 1H), 1.65-1.57 (m, 3H) | LC-MS (Method A): m/z = 274.2 [M + H]⁺, 1.05 min. |
| 186 | 2-(dimethyl-1,2-oxazol 4-yl)-1-[(3S)-3-(4-fluorophenyl)-1,2-oxazolidin-2-yl]propan-1-one (Second eluting diastereoisomer) | 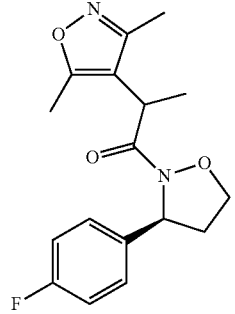<br>DIASTEREOISOMER 2 | ¹H NMR (400 MHz, CDCl₃) δ 7.16-7.08 (m, 2H), 7.03-6.94 (m, 2H), 5.35 (dd, J = 8.5, 6.0 Hz, 1H), 4.21 (td, J = 7.8, 3.8 Hz, 1H), 3.98-3.82 (m, 2H), 2.90-2.76 (m, 1H), 2.34-2.24 (m, 4H), 2.20 (s, 3H), 1.35 (d, J = 7.3 Hz, 3H) | LC-MS (Method A): m/z = 319.2 [M + H]⁺, 0.97 min. |
| 187 | 4-[(3S)-2-[1-(difluoromethyl)cyclopropanecarbonyl]-1,2-oxazolidin-3-yl]benzonitrile | 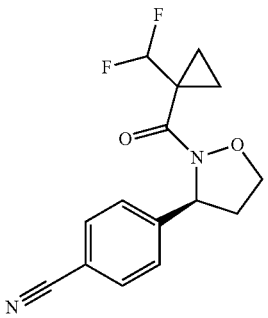 [SMILES: N#Cc1ccc([C@@H]2CCON2C(=O)C2(C(F)F)CC2)cc1] | ¹H NMR (400 MHz, CDCl₃) δ 7.69-7.62 (m, 2H), 7.45-7.39 (m, 2H), 6.83-6.49 (m, 1H), 5.50 (dd, J = 8.9, 6.4 Hz, 1H), 4.33 (dt, J = 2.8, 7.8 Hz, 1H), 3.97 (ddd, J = 9.6, 8.1, 6.7 Hz, 1H), 2.91 (dddd, J = 12.2, 9.2, 6.5, 3.0 Hz, 1H), 2.33 (dddd, J = 12.3, 9.6, 7.7, 6.5 Hz, 1H), 1.43-1.32 (m, 1H), 1.29-1.12 (m, 3H) | LC-MS (Method A): m/z = 293.17 [M + H]⁺, 0.97 min |
| 188 | 3,3-difluoro-1-[(3S)-3-(4-fluorophenyl)-1,2-oxazolidin-2-yl]-2-methylpropan-1-one (First eluting diastereoisomer) | 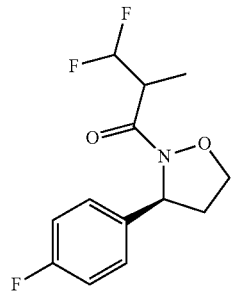<br>DIASTEREOISOMER 1 | ¹H NMR (400 MHz, CDCl₃) δ 7.32-7.24 (m, 2H), 7.09-7.00 (m, 2H), 5.95 (ddd, J = 56.2, 54.7, 6.8 Hz, 2H), 5.42 (dd, J = 9.2, 5.9 Hz, 1H), 4.33-4.25 (m, 1H), 3.94 (ddd, J = 9.4, 8.0, 6.9 Hz, 1H), 3.60-3.44 (m, 1H), 2.86 (dddd, J = 12.2, 8.8, 6.8, 3.3 Hz, 1H), 2.37 (dddd, J = 12.3, 9.5, 7.8, 6.0 Hz, 1H), 1.34 (d, J = 7.3 Hz, 3H). | LC-MS (Method A): m/z = 296.0 [M + Na]⁺, 1.02 min. |

-continued

| Comp. No. | Name | Structure | ¹H NMR | M + H⁺ |
|---|---|---|---|---|
| 189 | 3,3-difluoro-1-[(3S)-3-(4-fluorophenyl)-1,2-oxazolidin-2-yl]-2-methylpropan-1-one (Second eluting diastereoisomer) | 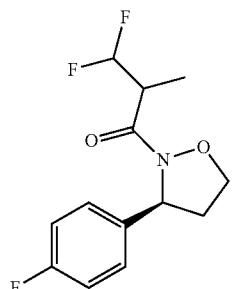<br>DIASTEREOISOMER 2 | ¹H NMR (400 MHz, CDCl₃) δ 7.34-7.22 (m, 2H), 7.08-7.01 (m, 2H), 6.00 (td, J = 56.7, 7.5 Hz, 1H), 5.40 (dd, J = 8.7, 5.9 Hz, 1H), 4.38-4.22 (m, 1H), 4.04-3.91 (m, 1H), 3.58-3.35 (m, 1H), 2.97-2.78 (m, 1H), 2.48-2.30 (m, 1H), 1.27 (d, J = 6.5 Hz, 3H). | LC-MS (Method A): m/z = 296.0 [M + Na]⁺, 1.00 min. |
| 190 | 2,2-dimethyl-1-[(3S)-3-(1H-pyrazol-5-yl)-1,2-oxazolidin-2-yl]propan-1-one | 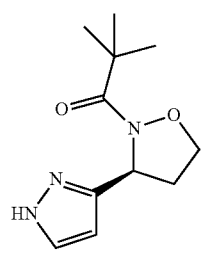 | ¹H NMR (400 MHz, CDCl₃) δ 8.10 (brs, 1H), 7.67 (d, J = 2.2 Hz, 1H), 6.32 (d, J = 2.2 Hz, 1H), 5.58 (t, J = 7.7 Hz, 1H), 4.35-4.31 (m, 1H), 3.99-3.85 (m, 1H), 2.85-2.79 (m, 1H), 2.72-2.65 (m, 1H), 1.27 (s, 9H). | LC-MS (Method F): m/z = 224.0 [M + H]⁺, 0.90 min. |
| 191 | (5S)-5-[(3S)-3-(4-fluorophenyl)-1,2-oxazolidine-2-carbonyl]-5-methylpyrrolidin-2-one | 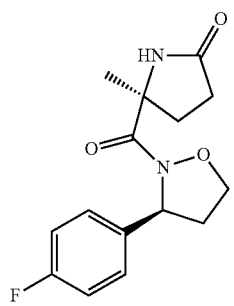 | ¹H NMR (300 MHz, DMSO-d₆) δ 7.80 (s, 1H), 7.31-7.26 (m, 2H), 7.18-7.12(m, 2H), 5.29 (t, J = 7.7 Hz, 1H), 4.28-4.23 (m, 1H), 3.95-3.87 (m, 1H), 2.89-2.85 (m, 1H), 2.49-2.10 (m, 5H), 1.46 (s, 3H). | LC-MS (Method H): m/z = 585.0 [2M + H]⁺, 1.03 min. |
| 192 | 2-[(3S)-2-(2,2-dimethylpropanoyl)-1,2-oxazolidin-3-yl]pyridine-4-carbonitrile | 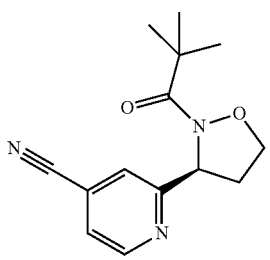 [SMILES: CC(C)(C)C(=O)N1OCC[C@H]1c1cc(C#N)ccn1] | ¹H NMR (400 MHz, DMSO-d₆) δ 8.80 (dd, J = 4.5, 1.5 Hz, 1H), 7.79 (dd, J = 4.5, 1.5 Hz, 1H), 7.66 (s, 1H), 5.42-5.38 (m, 1H), 4.35-4.30 (m, 1H), 3.95-3.89 (m, 1H), 2.85-2.80 (m, 1H), 2.41-2.36 (m, 1H), 1.22 (s, 9H). | LC-MS (Method H): m/z = 260.0 [M + H]⁺, 1.23 min. |
| 193 | 2-cyclopropyl-1-[(3S)-3-(4-fluorophenyl)-1,2-oxazolidin-2-yl]-2-methylpropan-1-one | 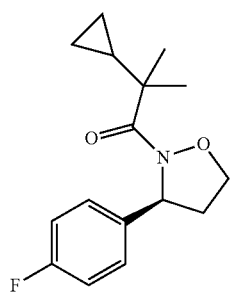 [SMILES: CC(C)(C(=O)N1OCC[C@H]1c1ccc(F)cc1)C1CC1] | ¹H NMR (300 MHz, CD₃OD) δ 7.36-7.31 (m, 2H), 7.10-7.04 (m, 2H), 5.40-5.37 (m, 1H), 4.36-4.31 (m, 1H), 4.03-3.94 (m, 1H), 2.93-2.87 (m, 1H), 2.30-2.22 (m, 1H), 1.43-1.38 (m, 1H), 1.14 (s, 3H), 1.10 (s, 3H), 0.40-0.31 (m, 4H). | LC-MS (Method P): m/z = 278.2 [M + H]⁺, 1.66 min. |

| Comp. No. | Name | Structure | ¹H NMR | M + H⁺ |
|---|---|---|---|---|
| 194 | 1-[(3S)-3-(4-fluorophenyl)-1,2-oxazolidin-2-yl]-2-methanesulfonyl-2-methylpropan-1-one | 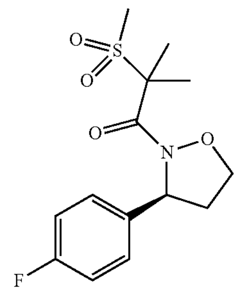 [SMILES: CC(C)(C(=O)N1OCC[C@H]1c1ccc(F)cc1)S(C)(=O)=O] | ¹H NMR (300 MHz, CD₃OD) δ 7.37-7.33 (m, 2H), 7.09 (d, J = 8.7 Hz, 2H), 5.44-5.39 (m, 1H), 4.40-4.34 (m, 1H), 4.11-4.03 (m, 1H), 3.06 (s, 3H), 2.98-2.88 (m, 1H), 2.36-2.24 (m, 1H), 1.62 (s, 6H). | LC-MS (Method P): m/z = 316.2 [M + H]⁺, 1.22 min. |
| 229 | 4-[(3S)-2-[1-(difluoromethyl)cyclobutanecarbonyl]-1,2-oxazolidin-3-yl]benzonitrile | 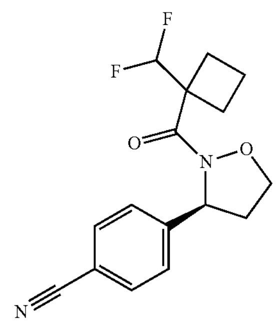 [SMILES: N#Cc1ccc([C@@H]2CCON2C(=O)C2(C(F)F)CCC2)cc1] | ¹H NMR (400 MHz, CDCl₃) δ 7.66 (d, J = 8.2 Hz, 2H), 7.40 (d, J = 8.6 Hz, 2H), 6.03-6.58 (m, 1H), 5.46 (dd, J = 8.6, 6.7 Hz, 1H), 4.26 (dt, J = 3.1, 7.8 Hz, 1H), 3.94 (ddd, J = 9.4, 8.2, 6.7 Hz, 1H), 2.92 (dddd, J = 12.3, 9.2, 6.3, 3.1 Hz, 1H), 2.73-2.58 (m, 1H), 2.52-2.26 (m, 4H), 2.11-1.94 (m, 1H), 1.93-1.80 (m, 1H). | LC-MS (Method B): m/z = 307.2 [M + H]⁺, 1.03 min. |
| 230 | 4-[(3S)-2-(4,4,4-trifluoro-2-methylbutanoyl)-1,2-oxazolidin-3-yl]benzonitrile Diastereoisomer 1 | DIASTEREOISOMER 1 | ¹H NMR (400 MHz, CDCl₃) δ 7.69-7.62 (m, 2H), 7.45-7.38 (m, 2H), 5.44 (dd, J = 8.8, 6.3 Hz, 1H), 4.29 (dt, J = 3.8, 7.8 Hz, 1H), 3.92 (ddd, J = 9.5, 8.0, 6.8 Hz, 1H), 3.47-3.35 (m, 1H), 2.95-2.86 (m, 1H), 2.77 (dqd, J = 15.1, 11.0, 8.8 Hz, 1H), 2.33 (dddd, J = 12.4, 9.6, 7.7, 6.3 Hz, 1H), 2.10 (dqd, J = 15.2 10.9, 4.5 Hz, 1H), 1.33 (d, J = 7.0 Hz, 3H) | LC-MS (Method B): m/z = 312.0 [M + H]⁺, 1.03 min. |
| 231 | 4-[(3S)-2-(4,4,4-trifluoro-2-methylbutanoyl)-1,2-oxazolidin-3-yl]benzonitrile Diastereoisomer 2 | DIASTEREOISOMER 2 | ¹H NMR (400 MHz, CDCl₃) δ 7.71-7.61 (m, 2H), 7.44-7.38 (m, 2H), 5.41 (dd, J = 8.8, 6.3 Hz, 1H), 4.31 (dt, J = 3.4, 7.7 Hz, 1H), 4.03-3.94 (m, 1H), 3.47-3.30 (m, 1H), 2.98-2.87 (m, 1H), 2.73 (dqd, J = 15.0, 11.1, 7.8 Hz, 1H), 2.35 (dddd, J = 12.4, 9.2, 7.3, 6.3 Hz, 1H), 2.23-2.07 (m, 1H), 1.24 (d, J = 7.0 Hz, 3H) | LC-MS (Method B): m/z = 312.0 [M + H]⁺, 1.01 min. |

-continued

| Comp. No. | Name | Structure | ¹H NMR | M + H⁺ |
|---|---|---|---|---|
| 232 | 4-[(3S)-2-(4,4-difluoro-2-methylbutanoyl)-1,2-oxazolidin-3-yl]benzonitrile Diastereoisomer 1 | DIASTEREOISOMER 1 | ¹H NMR (400 MHz, CDCl₃) δ 7.70-7.61 (m, 2H), 7.45-7.38 (m, 2H), 6.07-5.73 (m, 1H), 5.43 (dd, J = 8.8, 6.3 Hz, 1H), 4.28 (dt, J = 2.8, 7.8 Hz, 1H), 3.93 (ddd, J = 9.5, 8.2, 6.7 Hz, 1H), 3.37-3.22 (m, 1H), 2.95-2.85 (m, 1H), 2.47-2.26 (m, 2H), 1.87 (tdt, J = 16.9, 14.5, 4.8 Hz, 1H), 1.31 (d, J = 7.3 Hz, 3H). | LC-MS (Method B): m/z = 294.0 [M + H]⁺, 0.98 min. |
| 233 | 4-[(3S)-2-(4,4-difluoro-2-methylbutanoyl)-1,2-oxazolidin-3-yl]benzonitrile Diastereoisomer 2 | DIASTEREOISOMER 2 | ¹H NMR (400 MHz, CDCl₃) δ 7.72-7.61 (m, 2H), 7.44-7.38 (m, 2H), 6.01-5.68 (m, 1H), 5.42 (dd, J = 8.8, 6.3 Hz, 1H), 4.31 (dt, J = 3.5, 7.8 Hz, 1H), 4.02-3.93 (m, 1H), 3.37-3.18 (m, 1H), 2.97-2.87 (m, 1H), 2.46-2.27 (m, 2H), 1.93 (ttd, J = 15.1, 5.3, 17.3 Hz, 1H), 1.21 (d, J = 7.0 Hz, 3H). | LC-MS (Method B): m/z = 294.0 [M + H]⁺, 0.95 min. |
| 234 | 5-[(3S)-2-(4,4,4-trifluoro-2,2-dimethylbutanoyl)-1,2-oxazolidin-3-yl]pyridine-3-carbonitrile | 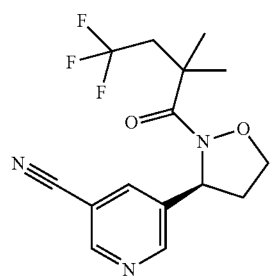 [SMILES: CC(C)(CC(F)(F)F)C(=O)N1OCC[C@H]1c1cncc(C#N)c1] | ¹H NMR (400 MHz, CDCl₃) δ 8.82 (d, J = 2.0 Hz, 1H), 8.79 (d, J = 2.3 Hz, 1H), 7.88 (t, J = 1.9 Hz, 1H), 5.49-5.39 (m, 1H), 4.37 (dt, J = 2.6, 8.0 Hz, 1H), 4.04 (ddd, J = 9.9, 8.1, 6.4 Hz, 1H), 2.95 (dddd, J = 12.2, 9.1, 6.3, 2.8 Hz, 1H), 2.80 (qd, J = 11.5, 15.4 Hz, 1H), 2.58 (qd, J = 11.3, 15.5 Hz, 1H), 2.35 (tdd, J = 7.3, 12.4, 9.8 Hz, 1H), 1.43 (s, 3H), 1.39 (s, 3H). | LC-MS (Method A): m/z = 328.3 [M + H]⁺, 0.95 min. |
| 235 | 5-[(3S)-2-(2-cyclopropyl-2-methylpropanoyl)-1,2-oxazolidin-3-yl]pyridine-3-carbonitrile | 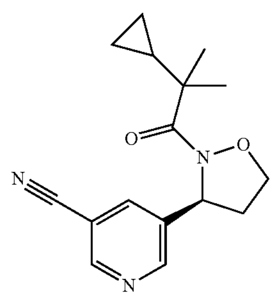 [SMILES: CC(C)(C(=O)N1OCC[C@H]1c1cncc(C#N)c1)C1CC1] | ¹H NMR (400 MHz, CDCl₃) δ 8.80 (t, J = 1.9 Hz, 2H), 7.91 (t, J = 1.9 Hz, 1H), 5.51 (dd, J = 8.8, 7.0 Hz, 1H), 4.34 (dt, J = 2.8, 7.8 Hz, 1H), 3.99 (ddd, J = 10.2, 8.2, 6.5 Hz, 1H), 3.01-2.89 (m, 1H), 2.38-2.25 (m, 1H), 1.41-1.32 (m, 1H), 1.17 (s, 3H), 1.12 (s, 3H), 0.49-0.31 (m, 4H). | LC-MS (Method A): m/z = 286.3 [M + H]⁺, 0.96 min. |
| 236 | (3S)-2-(2,2-difluorocyclopropane-carbonyl)-3-(4-fluorophenyl)-1,2-oxazolidine Diastereoisomer 1 | DIASTEREOISOMER 1 | ¹H NMR (400 MHz, CDCl₃) δ 7.36-7.29 (m, 2H), 7.08-7.01 (m, 2H), 5.45 (dd, J = 8.7, 6.1 Hz, 1H), 4.33 (dt, J = 3.3, 7.9 Hz, 1H), 3.99-3.90 (m, 1H), 3.11-2.97 (m, 1H), 2.87 (dddd, J = 12.2, 8.9, 6.8, 3.1 Hz, 1H), 2.38 (dddd, J = 12.4, 9.5, 7.8, 6.0 Hz, 1H), 2.16 (dtd, J = 12.6, 8.0, 5.9 Hz, 1H), 1.78-1.66 (m, 1H). | LC-MS (Method A): m/z = 272.0 [M + H]⁺, 0.96 min. |

-continued

| Comp. No. | Name | Structure | ¹H NMR | M + H⁺ |
|---|---|---|---|---|
| 237 | (3S)-2-(2,2-difluorocyclopropane-carbonyl)-3-(4-fluorophenyl)-1,2-oxazolidine Diastereoisomer 2 | DIASTEREOISOMER 2 | ¹H NMR (400 MHz, CDCl₃) δ 7.34-7.26 (m, 2H), 7.09-7.00 (m, 2H), 5.47-5.36 (m, 1H), 4.31 (dt, J = 3.6, 7.7 Hz, 1H), 3.98 (q, J = 8.1 Hz, 1H), 3.03 (br. s., 1H), 2.93-2.82 (m, 1H), 2.45-2.33 (m, 1H), 2.21-2.09 (m, 1H), 1.76-1.64 (m, 1H) | LC-MS (Method A): m/z = 272.3 [M + H]⁺, 0.97 min. |
| 238 | 4-[(3S)-2-(cubane-1-carbonyl)-1,2-oxazolidin-3-yl]benzonitrile | 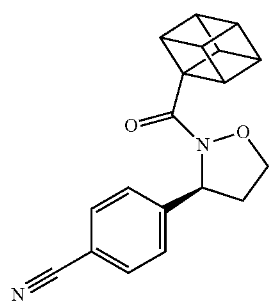 [SMILES: N#Cc1ccc([C@@H]2CCON2C(=O)C23C4C5C6C4C2C6C53)cc1] | ¹H NMR (300 MHz, CD₃OD) δ 7.69 (d, J = 8.4 Hz, 2H), 7.48 (d, J = 8.4 Hz, 2H), 5.44-5.32 (m, 1H), 4.31-4.20 (m, 4H), 4.05-3.83 (m, 5H), 3.04-2.91 (m, 1H), 2.32-2.17 (m, 1H). | LC-MS (Method E): m/z = 305.1 [M + H]⁺, 2.902 min. |
| 239 | 3-[(3S)-2-(3,3-difluoro-2,2-dimethylpropanoyl)-1,2-oxazolidin-3-yl]benzonitrile | 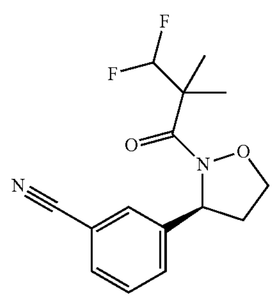 [SMILES: CC(C)(C(=O)N1OCC[C@H]1c1cccc(C#N)c1)C(F)F] | ¹H NMR (400 MHz, CD₃OD) δ 7.64-7.58 (m, 3H), 7.58-7.52 (m, 1H), 6.38 (t, J = 57.2 Hz, 1H), 5.45-5.38 (m, 1H), 4.41-4.36 (m, 1H), 4.04-3.98 (m, 1H), 2.98-2.94 (m, 1H), 2.34-2.26 (m, 1H), 1.34 (s, 3H), 1.33 (s, 3H). | LC-MS (Method E): m/z = 295.1 [M + H]⁺, 2.991 min. |
| 240 | 5-[(3S)-2-[1-(trifluoromethyl)cyclo-propanecarbonyl]-1,2-oxazolidin-3-yl]pyridine-3-carbonitrile | 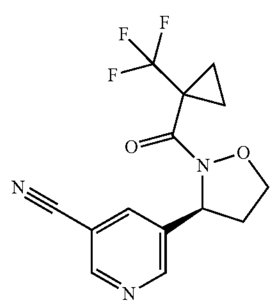 [SMILES: N#Cc1cncc([C@@H]2CCON2C(=O)C2(C(F)(F)F)CC2)c1] | ¹H NMR (400 MHz, CDCl₃) δ 8.83 (d, J = 1.8 Hz, 1H), 8.79 (d, J = 2.3 Hz, 1H), 7.88 (t, J = 2.1 Hz, 1H), 5.49 (dd, 8.8, 6.5 Hz, 1H), 4.38 (dt, J = 2.9, 8.0 Hz, 1H), 4.03 (ddd, J = 9.7, 8.4, 6.5 Hz, 1H), 2.99 (dddd, J = 12.3, 9.2, 6.5, 2.9 Hz, 1H), 2.47-2.32 (m, 1H), 1.47-1.20 (m, 4H). | LC-MS (Method A): m/z = 312.2 [M + H]⁺, 0.85 min. |
| 241 | 5-[(3S)-2-(3,3,3-trifluoro-2,2-dimethylpropanoyl)-1,2-oxazolidin-3-yl]pyridine-3-carbonitrile | 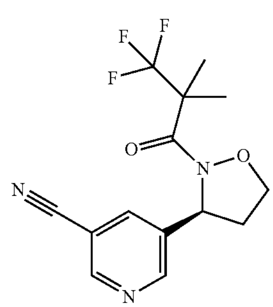 [SMILES: CC(C)(C(=O)N1OCC[C@H]1c1cncc(C#N)c1)C(F)(F)F] | ¹H NMR (400 MHz, CDCl₃) δ 8.83 (d, J = 2.0 Hz, 1H), 8.79 (d, J = 2.3 Hz, 1H), 7.88 (t, J = 2.1 Hz, 1H), 5.49 (dd, J = 8.8, 7.3 Hz, 1H), 4.40 (dt, J = 2.4, 8.0 Hz, 1H), 3.99 (ddd, J = 10.2, 8.3, 6.3 Hz, 1H), 3.03-2.90 (m, 1H), 2.36 (tdd, J = 7.4, 12.5, 10.2 Hz, 1H), 1.58 (s, 3H), 1.57 (s, 3H). | LC-MS (Method A): m/z = 314.2 [M + H]⁺, 0.94 min. |

| Comp. No. | Name | Structure | ¹H NMR | M + H⁺ |
|---|---|---|---|---|
| 242 | 5-[(3S)-2-(tricyclopropylacetyl)-1,2-oxazolidin-3-yl]pyridine-3-carbonitrile | 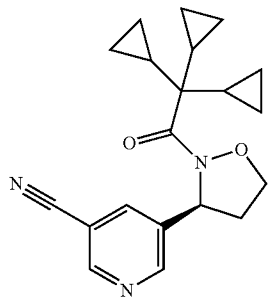 [SMILES: N#Cc1cncc([C@@H]2CCON2C(=O)C(C2CC2)(C2CC2)C2CC2)c1] | ¹H NMR (400 MHz, CDCl₃) δ 8.80 (s, 2H), 7.91 (t, J = 1.9 Hz, 1H), 5.55 (dd, J = 8.8, 7.1 Hz, 1H), 4.31 (dt, J = 1.8, 7.9 Hz, 1H), 3.97 (ddd, J = 10.4, 8.1, 6.3 Hz, 1H), 2.98-2.88 (m, 1H), 2.28 (tdd, J = 7.5, 12.0, 10.4 Hz, 1H), 0.86 (tt, J = 8.5, 5.7 Hz, 3H), 0.69-0.62 (m, 6H), 0.46-0.36 (m, 6H). | LC-MS (Method B): m/z = 338.3 [M + H]⁺, 1.11 min. |
| 243 | 5-[(3S)-2-(4,4-difluoro-2,2-dimethylbutanoyl)-1,2-oxazolidin-3-yl]pyridine-3-carbonitrile | 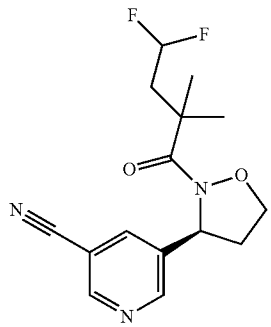 [SMILES: CC(C)(CC(F)F)C(=O)N1OCC[C@H]1c1cncc(C#N)c1] | ¹H NMR (400 MHz, DMSO-d₆) δ 8.94 (d, J = 2.0 Hz, 1H), 8.77 (d, J = 2.0 Hz, 1H), 8.16 (t, J = 2.1 Hz, 1H), 6.13 (tt, J = 56.5, 5.05 Hz, 1H), 5.43-5.34 (m, 1H), 4.36 (dt, J = 2.6, 7.7 Hz, 1H), 3.95 (ddd, J = 9.7, 8.2, 6.0 Hz, 1H), 2.92 (dddd, J = 12.1, 9.0, 6.1, 2.9 Hz, 1H), 2.36-2.20 (m, 3H), 1.28 (s, 3H), 1.26 (s, 3H). | LC-MS (Method A): m/z = 310.2 [M + H]⁺, 0.90 min. |
| 244 | 5-[(3S)-2-(3-cyclopropyl-3,3-difluoro-2,2-dimethylpropanoyl)-1,2-oxazolidin-3-yl]pyridine-3-carbonitrile | 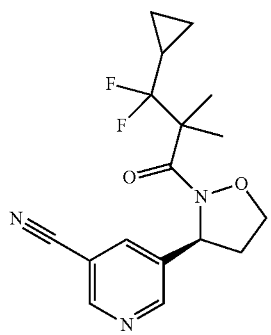 [SMILES: CC(C)(C(=O)N1OCC[C@H]1c1cncc(C#N)c1)C(F)(F)C1CC1] | | |
| 245 | 5-[(3S)-2-(2-(difluoromethyl)-2-methylbutanoyl)-1,2-oxazolidin-3-yl]pyridine-3-carbonitrile | 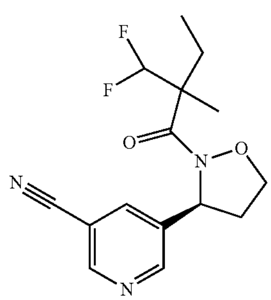 [SMILES: CCC(C)(C(=O)N1OCC[C@H]1c1cncc(C#N)c1)C(F)F] | | |
| 246 | 5-[(3S)-2-(3,3,3-trifluoro-2-methylpropanoyl)-1,2-oxazolidin-3-yl]pyridine-3-carbonitrile | 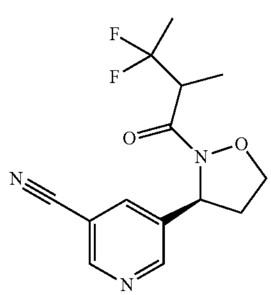 [SMILES: CC(C(=O)N1OCC[C@H]1c1cncc(C#N)c1)C(C)(F)F] | | |

| Comp. No. | Name | Structure | ¹H NMR | M + H⁺ |
|---|---|---|---|---|
| 247 | 5-[(3S)-2-(2,2-dicyclopropyl-5,5-difluoropentanoyl)-1-oxazolidin-3-yl]pyridine-3-carbonitrile | 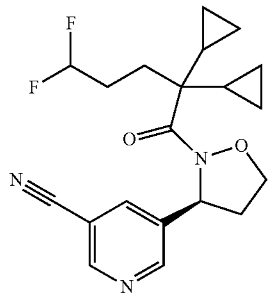 [SMILES: N#Cc1cncc([C@@H]2CCON2C(=O)C(CCC(F)F)(C2CC2)C2CC2)c1] | | |

Further details for the separation of the compounds described herein are as follows:

| No. | RT first eluting* | RT second eluting* | e.e. | Flow rate/column preparative | Flow rate/column analytical | Solvent | Comment |
|---|---|---|---|---|---|---|---|
| Int 28 | 4.6 | 14.0 | 90.6 | | 1 mL/min/as described | as described | second eluting enantiomer is major enantiomer 4.7:95.3 |
| 2 | 6.4 | 13.9 | 97.6 | 18 mL/min/as described | 1 mL/min/as described, column (25 × 0.46 cm) | as described | only first eluting enantiomer is described |
| 23 | 6.0 | 7.6 | 100 | 18 mL/min/as described | 1 mL/min/as described, column (25 × 0.46 cm) | as described | only first eluting enantiomer is described |
| 61 and 62 | 5.0 | 6.9 | 100 and 100 | 16 mL/min/as described | 1 mL/min/as described | as described | |
| 61 | 5.0 | 7.1 | 100 | 18 mL/min/as described | 1 mL/min/as described | as described | Only second eluting enantiomer is described |
| 73 and 74 | 4.7 | 6.3 | 100 and 100 | 18 mL/min/as described | 1 mL/min/as described | as described | |
| 30 | | 7.7 | 100 | 18 mL/min/Whelk O-1 (R, R) (25 × 2.0 cm) 10 mM | 1 mL/min/Whelk O-1 (R, R) (25 × 0.46 cm) 10 mM | n-hexane/ (EtOH/MeOH 1/1) 30/70% v/v | |
| 31 | 3.8 | | 100 | 18 mL/min/Whelk O-1 (R, R) (25 × 2.0 cm) 10 mM | 1 mL/min/Whelk O-1 (R, R) (25 × 0.46 cm) 10 mM | n-hexane/ (EtOH/MeOH 1/1) 30/70% v/v | |
| 35 | | 10.1 | 100 | 18 mL/min/ Chiralpak AD-H (25 × 2.0 cm) 5 mM | 1 mL/min/ Chiralpak AD-H (25 × 0.46 cm) 5 mM | n-hexane/EtOH 50/50% v/v | |
| 36 | 5.8 | | 100 | 18 mL/min/ Chiralpak AD-H (25 × 2.0 cm) 5 mM | 1 mL/min/ Chiralpak AD-H (25 × 0.46 cm) 5 mM | n-hexane/EtOH 50/50% v/v | |
| 40 | 12.0 | | 100 | 17 mL/min/ Chiralpak AD-H (25 × 2.0 cm) 5 mM | 1 mL/min/ Chiralpak AD-H (25 × 0.46 cm) 5 mM | n-hexane/EtOH 75/25% v/v | |
| 41 | | 17.0 | 100 | 17 mL/min/ Chiralpak AD-H (25 × 2.0 cm) 5 mM | 1 mL/min/ Chiralpak AD-H (25 × 0.46 cm) 5 mM | n-hexane/EtOH 75/25% v/v | |
| 45 | | 8.1 | 100 | 18 mL/min/ Chiralpak IC (25 × 2.0 cm) 5 mM | 1 mL/min/ Chiralpak IC (25 × 0.46 cm) 5 mM | n-hexane/EtOH 50/50% v/v | |
| 46 | 5.0 | | 100 | 18 mL/min/ Chiralpak IC | 1 mL/min/ Chiralpak IC | n-hexane/EtOH 50/50% v/v | |

-continued

| No. | RT first eluting* | RT second eluting* | e.e. | Flow rate/column preparative | Flow rate/column analytical | Solvent | Comment |
|---|---|---|---|---|---|---|---|
| 47 |  | 6.1 | 100 | (25 × 2.0 cm) 5 mM 18 mL/min/ Chiralpak IC | (25 × 0.46 cm) 5 mM 1 mL/min/ Chiralpak IC | n-hexane/EtOH 80/20% v/v |  |
| 48 | 4.7 |  | 100 | (25 × 2.0 cm) 5 mM 18 mL/min/ Chiralpak IC | (25 × 0.46 cm) 5 mM 1 mL/min/ Chiralpak IC | n-hexane/EtOH 80/20% v/v |  |
| 50 |  | 9.8 | 100 | (25 × 2.0 cm) 5 mM 45 mL/min/ Chiralpak IC | (25 × 0.46 cm) 5 mM 2.5 mL/min/ Chiralpak IC | 2-propanol 4% SFC |  |
| 51 | 6.0 |  | 100 | (25 × 2.0 cm) 5 mM 45 mL/min/ Chiralpak IC | (25 × 0.46 cm) 5 mM 2.5 mL/min/ Chiralpak IC | 2-propanol 4% SFC |  |
| 52 |  |  |  |  |  |  | Separated by column chromatography (Cyclohexane-EtOAc, 95:5 to 50:50) |
| 53 |  |  |  |  |  |  | Separated by column chromatography (Cyclohexane-EtOAc, 95:5 to 50:50) |
| 59 |  | 15.7 | 100 | 40 mL/min/Whelk O-1 (R, R) (25 × 3.0 cm) 10 mM | 1 mL/min/Whelk O-1 (R, R) (25 × 0.46 cm) 10 mM | n-hexane/EtOH 40/60% v/v |  |
| 60 | 6.7 |  | 100 | 40 mL/min/Whelk O-1 (R, R) (25 × 3.0 cm) 10 mM | 1 mL/min/Whelk O-1 (R, R) (25 × 0.46 cm) 10 mM | n-hexane/EtOH 40/60% v/v |  |
| 64 |  | 8.1 | 100 | 18 mL/min/ Chiralpak OJ-H (25 × 2.0 cm) 5 mM | 1 mL/min/ Chiralpak OJ-H (25 × 0.46 cm) 5 mM | n-hexane/EtOH 70/30% v/v |  |
| 65 | 4.8 |  | 100 | 18 mL/min/ Chiralpak OJ-H (25 × 2.0 cm) 5 mM | 1 mL/min/ Chiralpak OJ-H (25 × 0.46 cm) 5 mM | n-hexane/EtOH 70/30% v/v |  |
| 63 |  | 6.8 | 97 | 18 mL/min/ Chiralpak AD-H (25 × 2.0 cm) 5 mM | 1 mL/min/ Chiralpak AD-H (25 × 0.46 cm) 5 mM | n-hexane/EtOH 82/18% v/v |  |
| 66 | 5.8 |  | 100 | 18 mL/min/ Chiralpak AD-H (25 × 2.0 cm) 5 mM | 1 mL/min/ Chiralpak AD-H (25 × 0.46 cm) 5 mM | n-hexane/EtOH 82/18% v/v |  |
| 67 |  | 8.0 | 100 | 40 mL/min/Whelk O-1 (R, R) (25 × 3.0 cm) 10 mM | 1 mL/min/Whelk O-1 (R, R) (25 × 0.46 cm) 10 mM | n-hexane/EtOH 65/35% v/v |  |
| 68 | 5.5 |  | 100 | 40 mL/min/Whelk O-1 (R, R) (25 × 3.0 cm) 10 mM | 1 mL/min/Whelk O-1 (R, R) (25 × 0.46 cm) 10 mM | n-hexane/EtOH 65/35% v/v |  |

*Enantiomer or Diastereomer

In Vitro Assay 1

Receptor Interacting Protein Kinase 1 Inhibition by Compounds of Structure (I)

Compound potency at receptor interacting protein kinase 1 and selectivity at receptor interacting protein kinase 2 and receptor interacting protein kinase 3 was determined in autophosphorylation mode, using an ADP-Glo luminescence assay, which measures the conversion of ATP to ADP. GST-hRIPK1 (8-327) enzyme was generated by Proteros GmbH by Baculovirus expression system. GST-hRIPK2 (1-299) and GST-hRIPK3 (1-518) enzymes were purchased from SignalChem. Test compounds were diluted in DMSO and 0.1 μL of solution was dispensed to each well of a 384-well white solid microplates. The assay buffer was 50 mM HEPES pH 7.5, 50 mM NaCl, 30 mM $MgCl_2$. The buffer was supplemented with 0.02% CHAPS, 0.01% of Pluronic F127, 0.1 mg/mL BSA and 1 mM DTT. Only for receptor interacting protein kinase 1 5 mM MnCl2, was included in the assay buffer on the day of the experiment. The enzymatic reaction consisted of 1.5 µg/mL GST-hRIPK1 (8-327) and 50 µM ATP for receptor interacting protein kinase 1, 0.4 µg/mL GST-hRIPK2 (1-299) and 150 µM ATP, 0.4 µg/mL GST-hRIPK3 (1-518) and 15 µM ATP. 5 µL of enzyme and 5 µL of ATP were added to the plate at twice the final assay concentration and incubated at room temperature for 3 hours. Following this reaction, 10 µL of ADP-Glo reagent (Promega) was added to each well and incubated for 40 minutes at room temperature. This stops the kinase reaction and depletes any remaining ATP. 20 µL of ADP-Glo detection reagent was then added to each well and incubated at room temperature for at least 15 minutes. The detection reagent converts ADP to ATP and introduces luciferase and luciferin to detect ATP. The luminescence is then measured with the Envision (PerkinElmer) plate reader. Test compound inhibition was expressed as percent inhibition of internal assay controls. For concentration response curves, normalized data is fit and $pIC_{50}$ determined using XL-fit (IDBS) for Excel. The $pIC_{50}$ were averaged to determine a mean value, for a minimum of two independent experiments.

Fluorescent Polarization Binding (FP Binding) assay (Berger S. B. et al. (2015) Cell Death Discovery, 1: 15009; Maki J. L. et al. (2012) Anal Biochem., 427(2): 164-174) was performed in polystyrene low volume 384-well black plate, at Room Temperature (RT) in a final volume of 10.1 µl/well using 10 nM of GST-hRIPK1 (8-327) enzyme and 5 nM of fluorescent-labeled ligand (14-(2-{[3-({2-{[4-(cyanomethyl)phenyl]amino}-6-[(5-cyclopropyl-1H-pyrazol-3-yl)amino]-4-pyrimidinyl}amino) propyl]amino}-2-oxoethyl)-16,16,18,18-tetramethyl-6,7,7a,8a,9,10,16,18-octahydrobenzo[2"3"]indolizino[8", 0.7":5',6']pyrano[3',2':3,4]pyrido[1,2-a]indol-5-ium-2-sulfonate.

Test compounds were serially diluted in DMSO at 100 fold final concentrations in the assay (1% DMSO final). In each well of a 384-well Plate were dispensed 0.1 µL of compound solution (or DMSO for controls) followed by 5 µL of GST-hRIPK1 (8-327) at twice the final concentrations in assay-buffer (50 mM HEPES pH 7.5, 10 mM NaCl, 50 mM $MgCl_2$, 0.02% CHAPS, 0.5 mM DTT and 0.01% Pluronic F127). For negative control the enzyme addition was replaced by assay buffer only.

After addition of 5 µL of fluorescent-labeled ligand at twice the final concentrations in assay buffer, the plate was incubated at RT for 30 min. At the end, the binding was measured as FP value with the Envision (PerkinElmer) plate reader using filter for an excitation λ=531 nm FP and an emission λ=595 nm FP (S & P-pol).

Certain compounds were tested in the following. Compound potency at receptor interacting protein kinase 1 and selectivity at receptor interacting protein kinase 2 and receptor interacting protein kinase 3 was determined in autophosphorylation mode, using an ADP-Glo luminescence assay (Berger S. B. et al. (2015) Cell Death Discovery, 1: 15009), which measures the conversion of ATP to ADP.

GST-hRIPK1 (8-327) enzyme was generated by Proteros GmbH by Baculovirus expression system.

Test compounds were diluted in DMSO and 0.1 µL of solution was dispensed to each well of a 384-well white solid microplate. The assay buffer was 50 mM HEPES pH 7.5, 50 mM NaCl, 30 mM MgCl2. The buffer was supplemented with 0.02% CHAPS, 0.01% of Pluronic F127, 0.1 mg/mL BSA and 1 mM DTT. Only for receptor interacting protein kinase 1 5 mM MnCl2, was included in the assay buffer on the day of the experiment. The enzymatic reaction comprised 1.5 µg/mL GST-hRIPK1 (8-327) and 50 µM ATP for receptor interacting protein kinase 1 and 15 µM ATP. 5 µL of enzyme and 5 µL of ATP were added to the plate at twice the final assay concentration and incubated at room temperature for 3 hours. Following this reaction, 10 µL of ADP-Glo reagent (Promega) was added to each well and incubated for 40 minutes at room temperature. This stops the kinase reaction and depletes any remaining ATP. 20 µL of ADP-Glo detection reagent was then added to each well and incubated at room temperature for at least 15 minutes. The detection reagent converts ADP to ATP and introduces luciferase and luciferin to detect ATP. The luminescence is then measured with the Envision (PerkinElmer) plate reader. Test compound inhibition was expressed as percent inhibition of internal assay controls. For concentration response curves, normalized data is fit and $IC_{50}$ determined using XL-fit (IDBS) for Excel. The $IC_{50}$ were averaged to determine a mean value, for a minimum of two independent experiments.

Test compound inhibition was expressed as percent inhibition of internal assay controls. For concentration response curves, normalized data is fit and $IC_{50}$ determined using XL-fit (IDBS) for Excel. $IC_{50}$ were averaged to determine a mean value, for a minimum of two independent experiments.

Receptor interacting protein kinase 1 activity of exemplary compounds was determined according to the above general procedures. Results are summarized in Table 2.

TABLE 2

| No | ADP $IC_{50}$ | FP $IC_{50}$ |
| --- | --- | --- |
| 1 | +++ | +++ |
| 2 | +++ | +++ |
| 3 | +++ | |
| 4 | +++ | +++ |
| 5 | ++ | |
| 6 | ++ | |
| 7 | ++ | |
| 8 | +++ | +++ |
| 9 | + | |
| 10 | + | |
| 11 | ++ | |
| 12 | +++ | +++ |
| 13 | ++ | |
| 14 | + | |
| 15 | | + |
| 16 | +++ | +++ |
| 17 | +++ | +++ |
| 18 | +++ | +++ |
| 19 | +++ | +++ |
| 20 | +++ | +++ |
| 21 | | ++ |
| 22 | ++ | |
| 23 | +++ | +++ |
| 28 | | +++ |
| 29 | | +++ |
| 30 | | +++ |
| 31 | | +++ |
| 32 | | +++ |
| 33 | | +++ |
| 34 | | +++ |
| 35 | | +++ |
| 36 | | +++ |
| 37 | | +++ |
| 38 | | +++ |
| 39 | | +++ |
| 40 | | +++ |
| 41 | | +++ |
| 42 | | + |
| 43 | | + |

TABLE 2-continued

| No | ADP IC$_{50}$ | FP IC$_{50}$ |
|---|---|---|
| 44 |  | ++ |
| 45 |  | ++ |
| 46 |  | +++ |
| 47 |  | +++ |
| 48 |  | + |
| 49 |  | +++ |
| 50 |  | +++ |
| 51 |  | ++ |
| 52 |  | + |
| 53 |  | ++ |
| 54 |  | +++ |
| 55 |  | +++ |
| 56 |  | +++ |
| 57 |  | +++ |
| 58 |  | +++ |
| 59 |  | + |
| 60 |  | +++ |
| 61 |  | +++ |
| 62 |  | ++ |
| 63 |  | ++ |
| 64 | +++ | +++ |
| 65 |  | + |
| 66 |  | +++ |
| 67 |  | ++ |
| 68 |  | +++ |
| 69 | +++ | +++ |
| 70 | +++ | +++ |
| 71 | +++ | +++ |
| 72 | +++ | +++ |
| 73 | +++ | +++ |
| 74 |  | + |
| 75 |  | ++ |
| 76 |  | ++ |
| 77 | +++ | +++ |
| 78 | +++ | +++ |
| 79 | +++ | +++ |
| 80 | +++ | +++ |
| 81 | +++ | +++ |
| 82 |  | ++ |
| 83 | ++ |  |
| 84 | + |  |
| 85 | + |  |
| 87 | +++ | +++ |
| 88 | +++ | +++ |
| 89 |  | +++ |
| 90 |  | +++ |
| 91 |  | +++ |
| 92 |  | +++ |
| 93 |  | ++ |
| 94 |  | +++ |
| 95 |  | +++ |
| 96 |  | +++ |
| 97 | +++ | +++ |
| 98 |  | +++ |
| 99 |  | +++ |
| 100 |  | +++ |
| 101 | +++ | +++ |
| 102 |  | +++ |
| 103 |  | +++ |
| 104 |  | +++ |
| 105 |  | +++ |
| 106 | +++ | +++ |
| 107 |  | +++ |
| 108 | +++ | +++ |
| 109 |  | +++ |
| 110 |  | +++ |
| 111 |  | ++ |
| 112 |  | +++ |
| 113 |  | +++ |
| 114 |  | +++ |
| 115 |  | +++ |
| 116 |  | +++ |
| 117 |  | +++ |
| 118 |  | N/A |
| 119 |  | N/A |
| 120 |  | +++ |
| 121 |  | +++ |
| 122 |  | +++ |
| 123 |  | ++ |
| 124 |  | +++ |
| 125 |  | +++ |
| 126 |  | +++ |
| 127 |  | +++ |
| 128 |  | +++ |
| 129 |  | +++ |
| 130 |  | +++ |
| 131 |  | +++ |
| 132 |  | +++ |
| 133 |  | +++ |
| 134 |  | +++ |
| 135 |  | +++ |
| 136 |  | ++ |
| 137 |  | ++ |
| 138 |  | +++ |
| 139 |  | +++ |
| 140 |  | +++ |
| 141 |  | +++ |
| 142 |  | +++ |
| 143 |  | +++ |
| 144 |  | +++ |
| 145 |  | +++ |
| 146 |  | +++ |
| 147 |  | +++ |
| 148 |  | +++ |
| 149 |  | ++ |
| 150 |  | +++ |
| 151 |  | +++ |
| 152 |  | +++ |
| 153 |  | +++ |
| 154 |  | +++ |
| 155 |  | +++ |
| 156 |  | ++ |
| 157 |  | ++ |
| 158 |  | +++ |
| 159 |  | +++ |
| 160 |  | ++ |
| 161 |  | +++ |
| 162 |  | +++ |
| 163 |  | +++ |
| 164 |  | +++ |
| 165 |  | +++ |
| 166 |  | ++ |
| 167 |  | +++ |
| 168 |  | +++ |
| 169 |  | +++ |
| 170 |  | +++ |
| 171 |  | +++ |
| 172 |  | +++ |
| 173 |  | +++ |
| 174 |  | +++ |
| 175 |  | +++ |
| 176 |  | +++ |
| 177 |  | +++ |
| 178 |  | +++ |
| 179 |  | +++ |
| 180 |  | +++ |
| 181 |  | +++ |
| 182 |  | +++ |
| 183 |  | +++ |
| 184 |  | +++ |
| 185 |  | ++ |
| 186 |  | ++ |
| 187 |  | +++ |
| 188 |  | +++ |
| 189 |  | +++ |
| 190 |  | +++ |
| 191 |  | +++ |
| 192 |  | +++ |
| 193 |  | +++ |
| 194 |  | ++ |
| 195 |  | +++ |
| 196 |  | +++ |
| 198 |  | +++ |
| 200 |  | +++ |
| 202 |  | +++ |
| 203 |  | +++ |

TABLE 2-continued

| No | ADP IC$_{50}$ | FP IC$_{50}$ |
|---|---|---|
| 204 | | +++ |
| 205 | | +++ |
| 206 | | ++ |
| 207 | | +++ |
| 208 | | +++ |
| 209 | | +++ |
| 210 | | ++ |
| 211 | | +++ |
| 212 | | +++ |
| 213 | | +++ |
| 214 | | +++ |
| 215 | | +++ |
| 216 | | ++ |
| 217 | | +++ |
| 218 | | +++ |
| 219 | | +++ |
| 220 | | +++ |
| 221 | | +++ |
| 222 | | +++ |
| 223 | | +++ |
| 225 | | ++ |
| 226 | | +++ |
| 227 | | +++ |
| 228 | | +++ |
| 229 | | +++ |
| 230 | | +++ |
| 231 | | +++ |
| 232 | | +++ |
| 233 | | +++ |
| 236 | | +++ |
| 237 | | +++ |
| 238 | | +++ |
| 239 | | +++ |

+++ indicates IC$_{50}$ less than 1 μM
++ indicates IC$_{50}$ from 1 μM to 10 μM
+ indicates IC$_{50}$ greater than 10 μM Receptor interacting protein kinase 1 activity of certain compounds was determined according to the above general procedures. These results in nM are summarized in Table 3.

TABLE 3

| No | FP IC$_{50}$ (nM) |
|---|---|
| 61 | 28 |
| 88 | 16 |
| 101 | 8 |
| 109 | 7 |
| 171 | 11 |
| 193 | 5 |
| 195 | 10 |
| 196 | 9 |
| 198 | 51 |
| 200 | 9 |
| 221 | 70 |
| 242 | 5 |

Although various embodiments of the disclosure are disclosed herein, many adaptations and modifications may be made within the scope of the disclosure in accordance with the common general knowledge of those skilled in this art. Such modifications include the substitution of known equivalents for any aspect of the disclosure in order to achieve the same result in substantially the same way. Numeric ranges are inclusive of the numbers defining the range. The word "comprising" is used herein as an open-ended term, substantially equivalent to the phrase "including, but not limited to" and the word "comprises" has a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present disclosure. Any priority document(s) and all publications, including but not limited to patents and patent applications, cited in this specification are incorporated herein by reference as if each individual publication were specifically and individually indicated to be incorporated by reference herein and as though fully set forth herein. The disclosure includes all embodiments and variations substantially as hereinbefore described and with reference to the examples and drawings.

The invention claimed is:
1. A compound having the following structure (Xa):

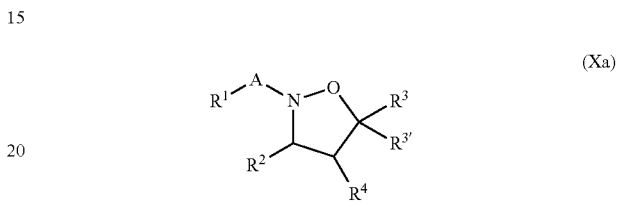

or a pharmaceutically acceptable salt, prodrug, stereoisomer or a mixture of stereoisomers thereof, wherein:

A is —C(=O)—, —S(=O)—, —S(=O)$_2$— or —S(=O)(=NH)—;

R$^1$ is —NR$^5$R$^6$, C$_{1-6}$ alkyl, C$_{3-6}$ alkoxy, C$_{3-10}$ cycloalkyl, heterocyclyl or heteroaryl;

R$^2$ is aryl or heteroaryl;

R$^3$ is hydrogen, deuterium, C$_{1-6}$ alkyl or C$_{3-10}$ cycloalkyl;

R$^{3'}$ is hydrogen or deuterium;

R$^4$ is hydrogen, halo, C$_{1-6}$ alkyl or C$_{3-10}$ cycloalkyl;

R$^5$ and R$^6$ are each independently H, C$_{1-6}$ alkyl, C$_{3-10}$ cycloalkyl, aryl, heteroaryl or heterocyclyl, wherein each C$_{1-6}$ alkyl, C$_{3-6}$ alkoxy, C$_3$-C$_{10}$ cycloalkyl, heterocyclyl, heteroaryl and aryl group of R$^1$, R$^2$, R$^3$, R$^{3'}$, R$^4$, R$^5$ and R$^6$ is optionally substituted with one, two or three R$^{10}$;

R$^{10}$ in each instance is independently deuterium, halo, hydroxy, cyano, nitro, C$_{1-6}$ alkyl, C$_{1-6}$ alkoxy, C$_{2-6}$ alkenyl, C$_{2-6}$ alkynyl, C$_{3-10}$ cycloalkyl, heterocyclyl, aryl, heteroaryl, —C(=O)R$^{11}$, —C(=O)OR$^{11}$, —C(=O)NR$^{11}$R$^{11}$, —S(=O)R$^{11}$, —S(=O)$_2$R$^{11}$, —NR$^{11}$R$^{11}$, —NR$^{11}$C(=O)R$^{11}$ or —NR$^{11}$C(=O) OR$^{11}$;

wherein the C$_{1-6}$ alkyl, C$_{1-6}$ alkoxy, C$_{2-6}$ alkenyl, C$_{2-6}$ alkynyl, C$_{3-10}$ cycloalkyl, heterocyclyl, aryl and heteroaryl of R$^{10}$ are optionally substituted with one, two or three substituents independently selected from halo, hydroxy, cyano, amino, nitro, C$_{1-6}$ alkyl, C$_{1-6}$ alkoxy, C$_{1-6}$ haloalkoxy, C$_{2-6}$ alkenyl, C$_{2-6}$ alkynyl, C$_{3-10}$ cycloalkyl, heterocyclyl, aryl or heteroaryl; and R$^{11}$ in each instance is independently hydrogen, C$_{1-6}$ alkyl, C$_{3-10}$ cycloalkyl, heterocyclyl, heteroaryl or aryl; wherein the C$_{3-10}$ cycloalkyl, heterocyclyl, heteroaryl or aryl of R$^{11}$ is optionally substituted with one, two or three C$_{1-6}$ alkyl;

provided the compound is not ethyl 3-phenylisoxazolidine-2-carboxylate, benzyl 3-(4-amino-2-oxopyrimidin-1 (2H)-yl)isoxazolidine-2-carboxylate, 2-(methyl sulfonyl)-3-phenyl-isoxazolidine, tert-butyl 5-benzyl-3-phenylisoxazolidine-2-carboxylate, tert-butyl 5-(naphthalen-2-ylmethyl)-3-phenylisoxazolidine-2-carboxylate, tert-butyl 5-([1,1'-biphenyl]-4-ylmethyl)-3-phenylisoxazolidine-2-carboxylate or 2,2-dimethyl- 1-(3-phenylisoxazolidin-2-yl)butan-1-one or 2,2-dimethyl-1-(3-phenylisoxazolidin-2-yl)but-3-en-1-one.

2. The compound of claim 1, wherein $R^1$ is optionally substituted $C_{1-6}$ alkyl, $C_{3-6}$ alkoxy, $C_{3-10}$ cycloalkyl or heterocyclyl.

3. The compound of claim 1, wherein $R^1$ is optionally substituted $C_{1-6}$ alkyl.

4. The compound of claim 2, wherein $R^1$ is substituted with at least one substituent selected from deuterium, hydroxy, halo, $C_{1-6}$ alkyl, $C_{1-6}$ haloalkyl, $C_{1-6}$ alkoxy, $C_{1-6}$ haloalkoxy, cyano, $C_{3-10}$ cycloalkyl, heterocyclyl and heteroaryl;
wherein the heterocyclyl or heteroaryl is optionally substituted with one, two or three $C_{1-6}$ alkyl.

5. The compound of claim 3, wherein $R^1$ is substituted with at least one substituent selected from hydroxy, halo, $C_{1-6}$ haloalkyl, $C_{1-6}$ alkoxy, $C_{1-6}$ haloalkoxy and cyano.

6. The compound of claim 1, wherein $R^1$ is optionally substituted $C_{3-6}$ alkoxy.

7. The compound of claim 6, wherein $R^1$ is t-butoxy.

8. The compound of claim 1, wherein $R^1$ is —$NR^5R^6$ and at least one of $R^5$ or $R^6$ is optionally substituted $C_{1-6}$ alkyl or optionally substituted aryl.

9. The compound of claim 8, wherein $R^1$ is dimethylamino, t-butylamino or phenylamino.

10. The compound of claim 1, wherein $R^1$ is optionally substituted $C_{3-10}$ cycloalkyl.

11. The compound of claim 10, wherein the $C_{3-10}$ cycloalkyl is substituted with at least one substituent selected from hydroxy, halo, cyano, $C_{1-6}$ alkoxy, $C_{1-6}$ haloalkoxy, $C_{1-6}$ alkyl, $C_{1-6}$ haloalkyl, $C_{1-6}$ hydroxyalkyl and $C_{1-6}$ alkoxyalkyl.

12. The compound of claim 10, wherein $C_{3-10}$ cycloalkyl is cyclopropyl, cyclobutyl, or bicyclo[1.1.1]pentyl.

13. The compound of claim 1, wherein $R^1$ is optionally substituted heterocyclyl or optionally substituted heteroaryl.

14. The compound of claim 13, wherein $R^1$ is oxetanyl, pyrrolidinyl, tetrahydropyranyl or azetidinyl.

15. The compound of claim 13, wherein $R^1$ is pyrrolyl, pyrazolopyridinyl or benzoisoxazolyl.

16. The compound as in claim 13, wherein $R^1$ is optionally substituted with a $C_{1-6}$ alkyl, cyano or both.

17. The compound as in claim 1, wherein $R^2$ is aryl.

18. The compound of claim 17, wherein $R^2$ is phenyl.

19. The compound as in claim 1, wherein $R^2$ is heteroaryl.

20. The compound of claim 19, wherein $R^2$ is pyridinyl.

21. The compound as in claim 17, wherein $R^2$ is unsubstituted.

22. The compound as in claim 17, wherein $R^2$ is substituted.

23. The compound of claim 22, wherein $R^2$ is substituted with one or more halo.

24. A compound selected from:

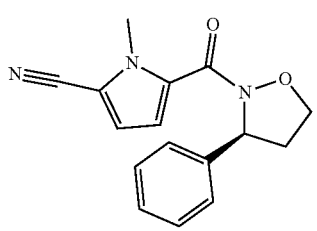
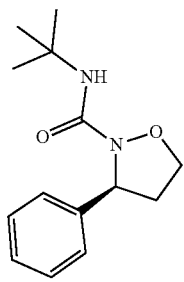

-continued

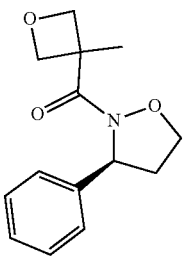
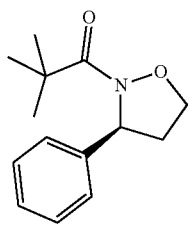

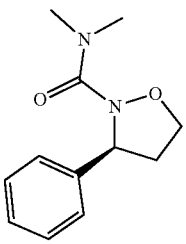
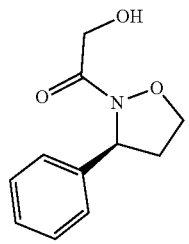

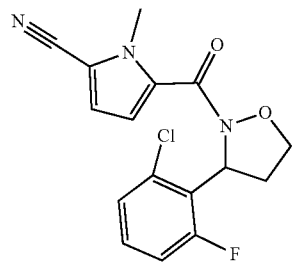
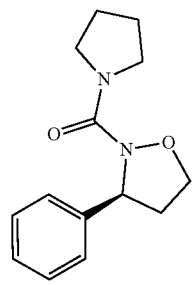

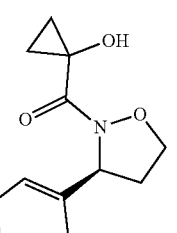
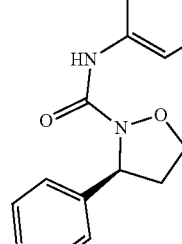

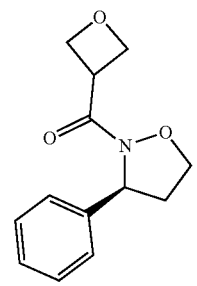
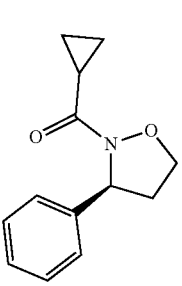

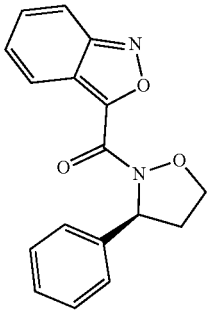
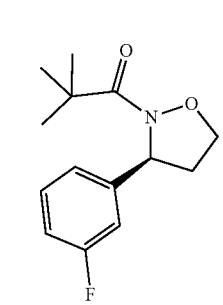

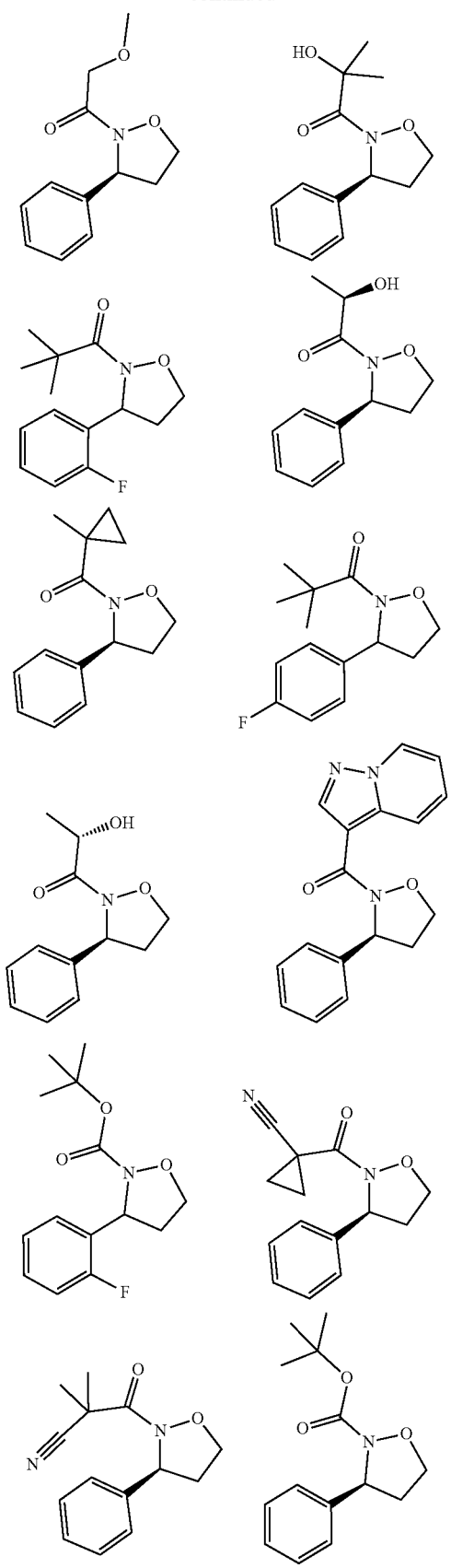
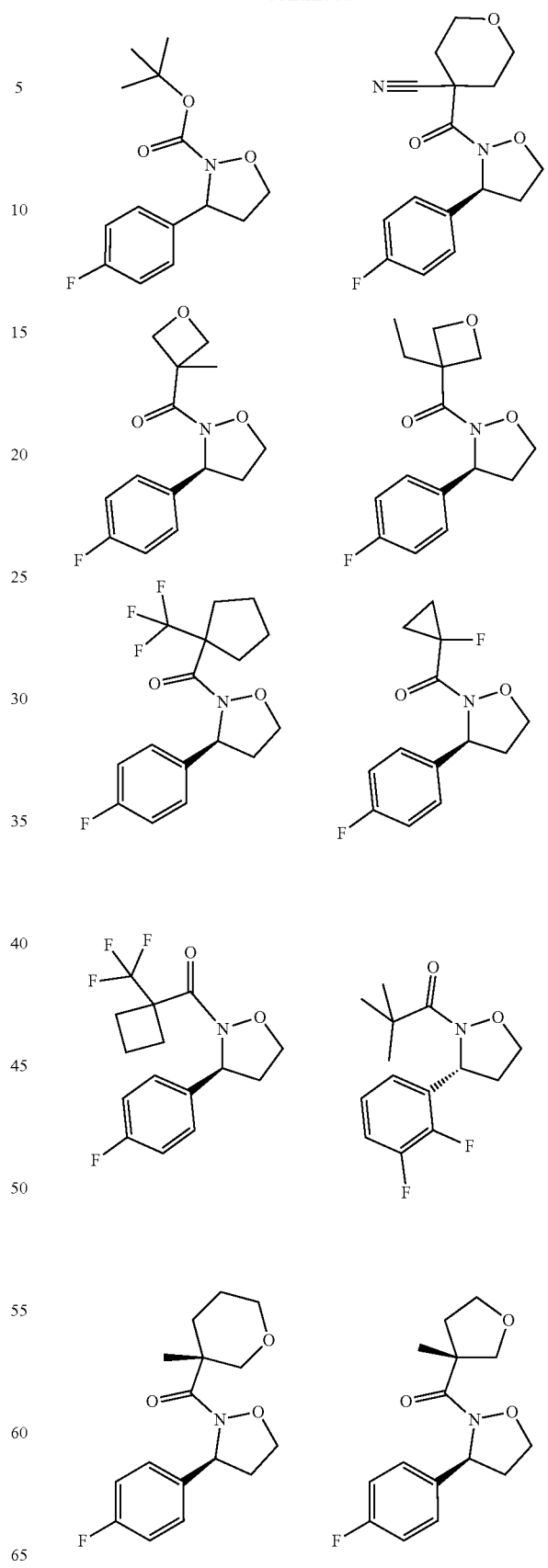

291
-continued
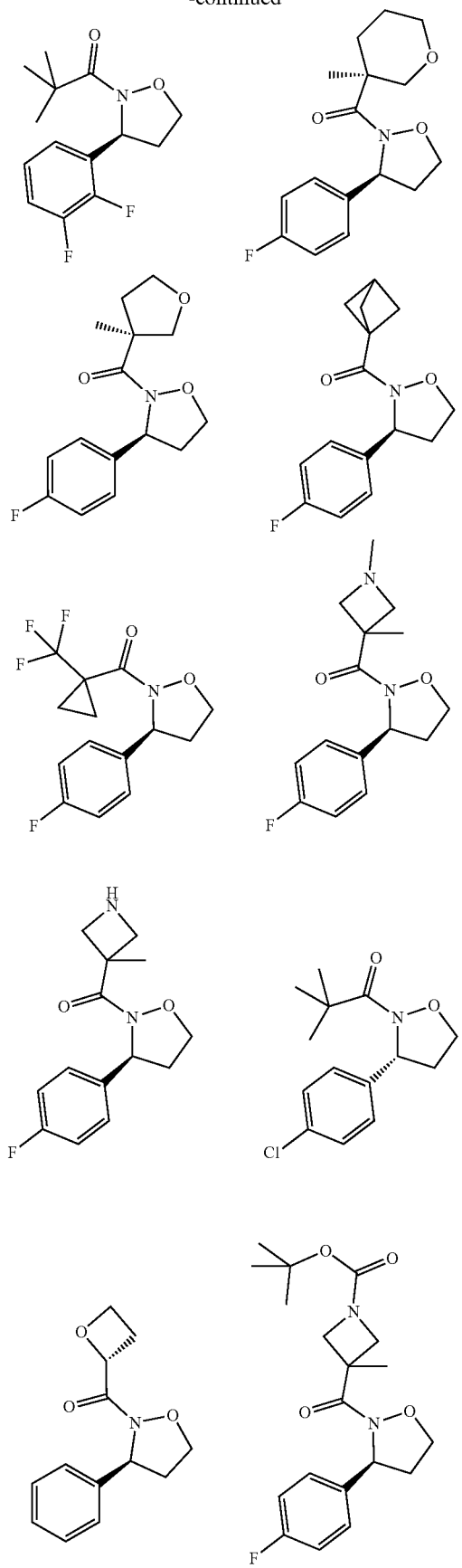
292
-continued
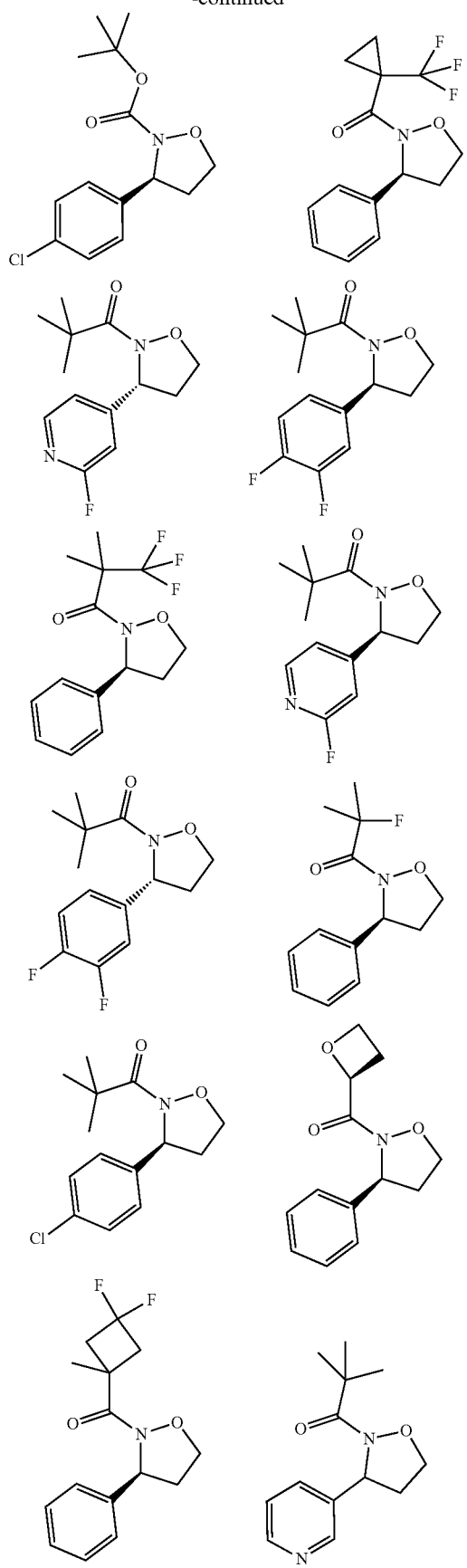

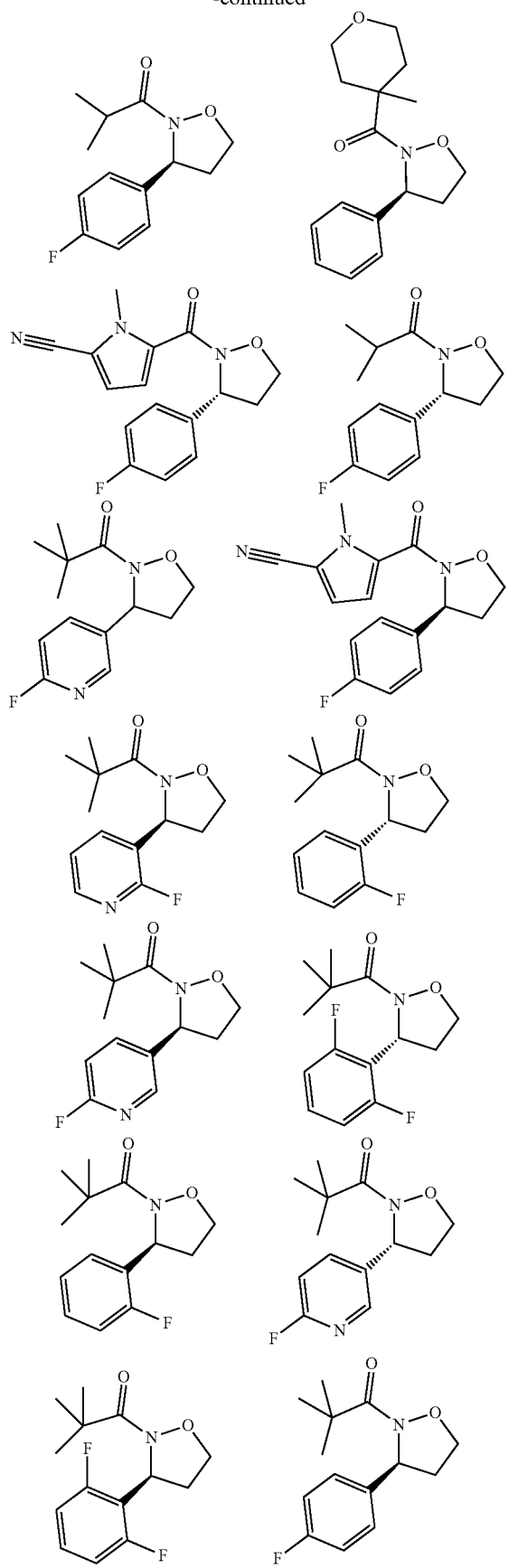
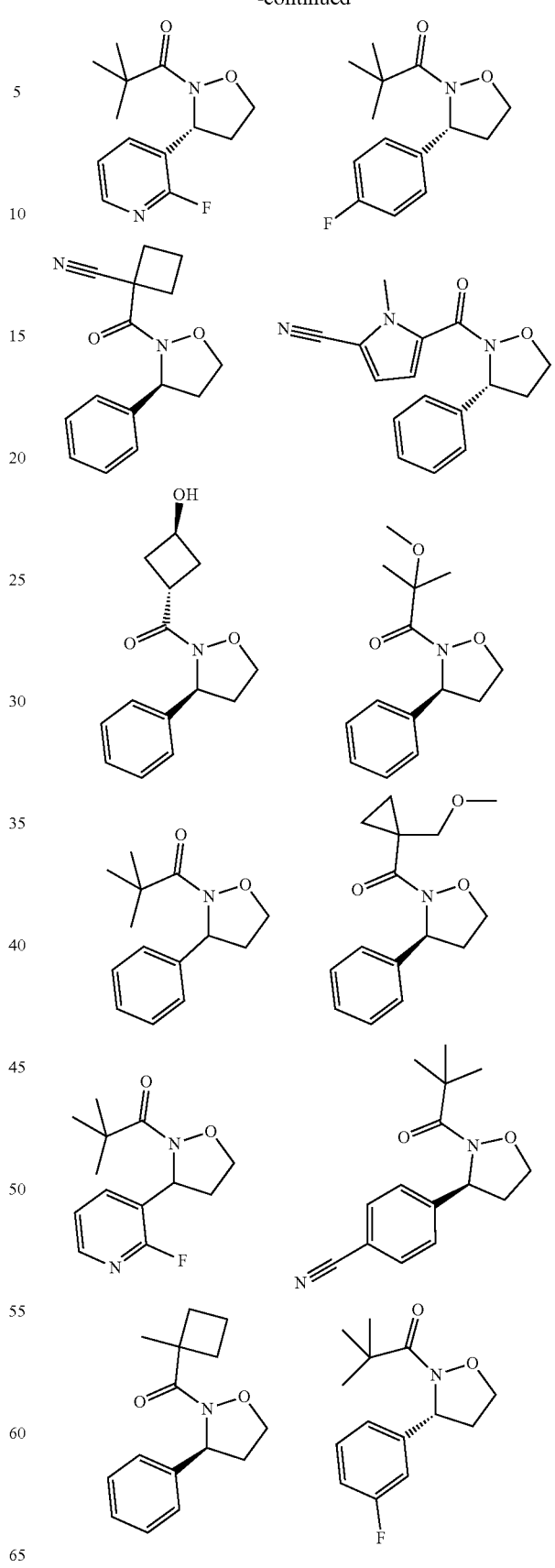

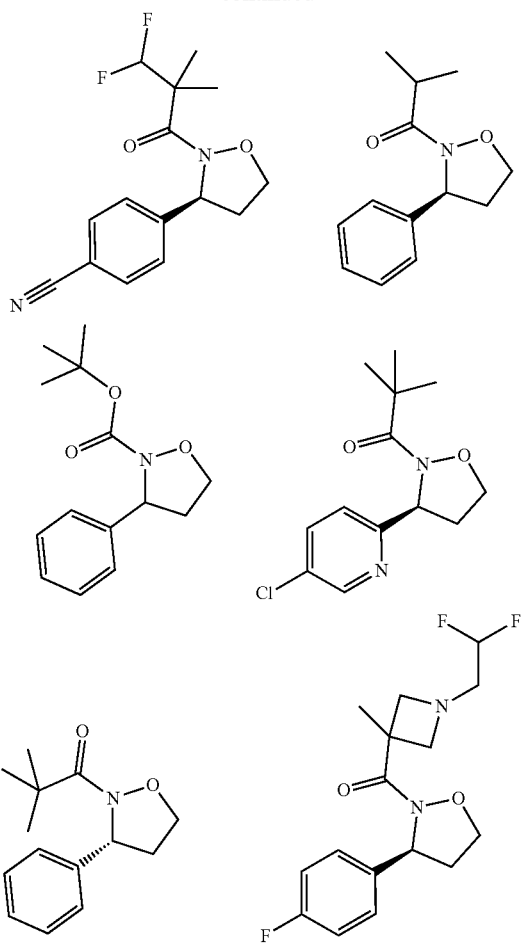
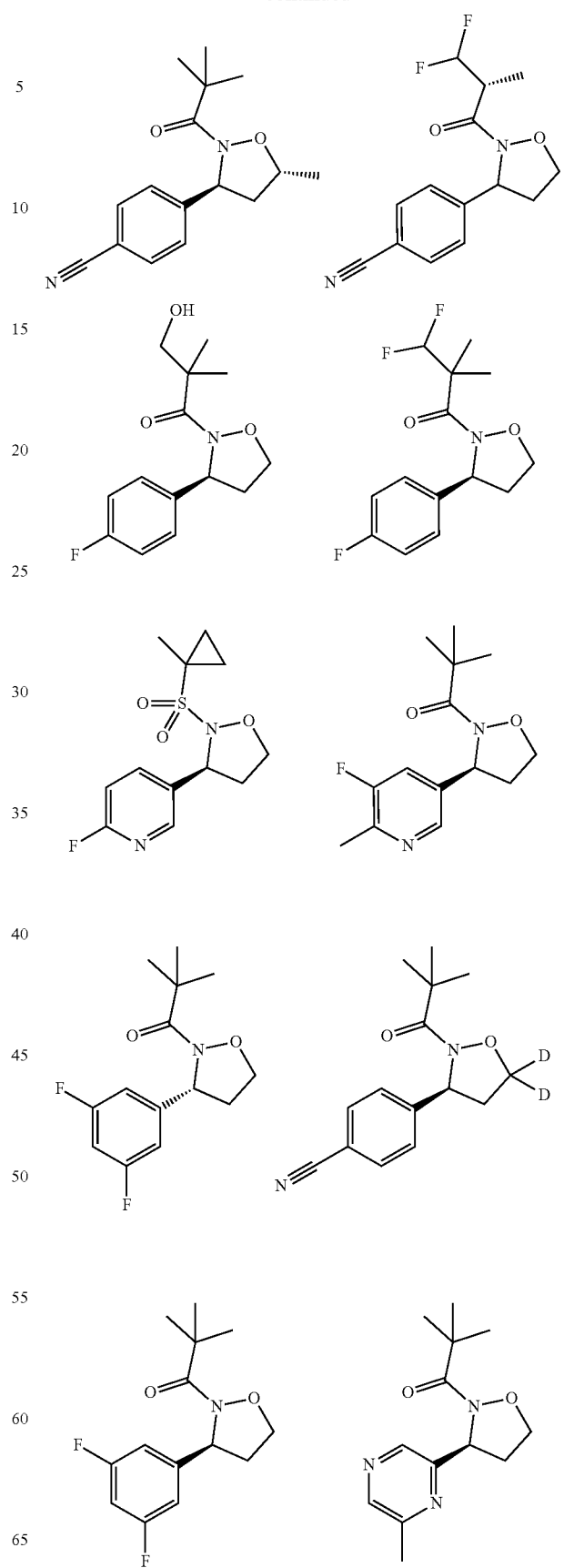

-continued
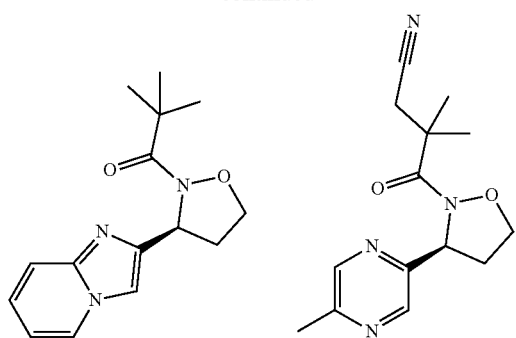
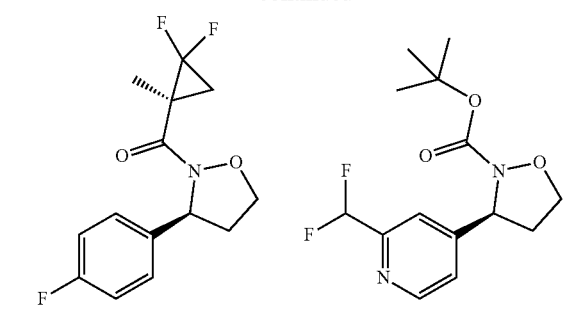
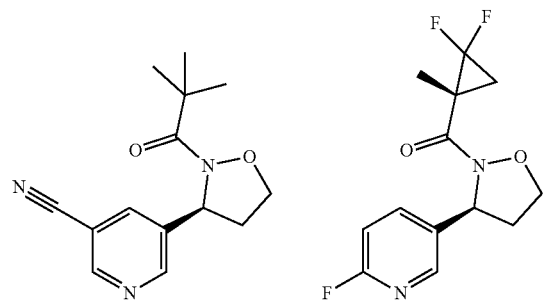
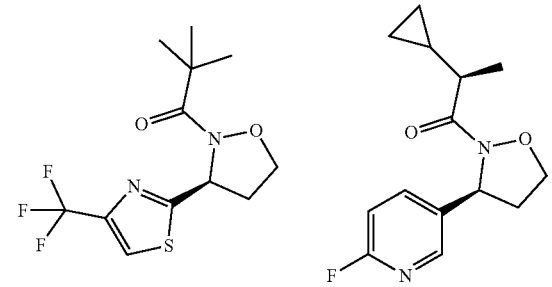
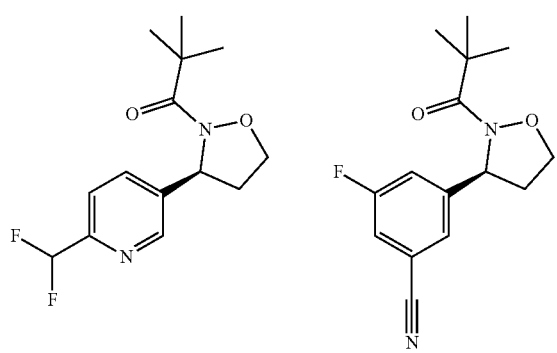
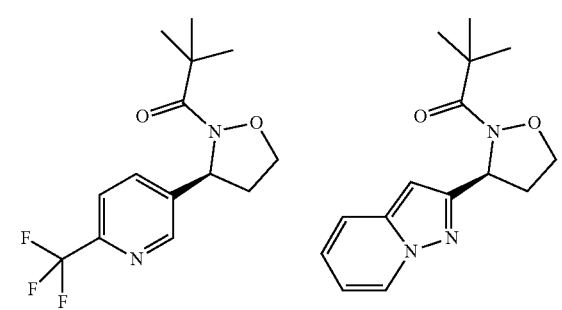
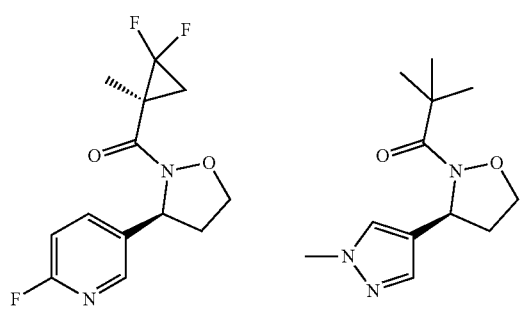
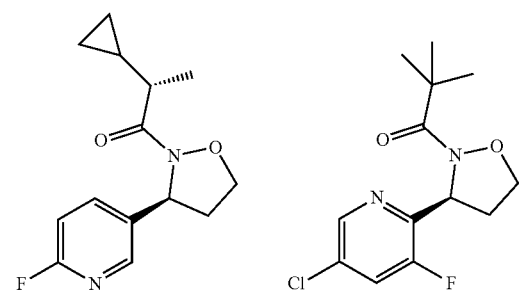
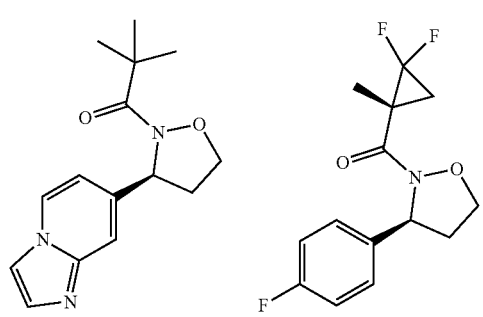
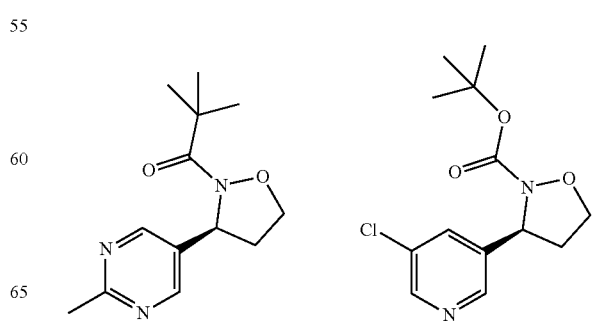

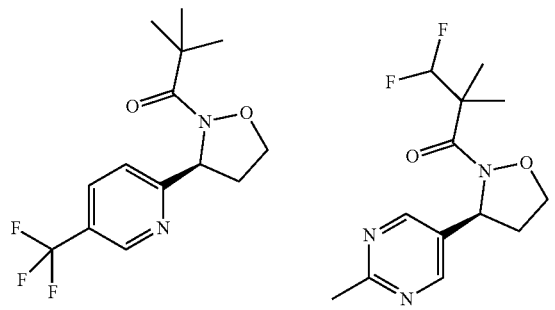
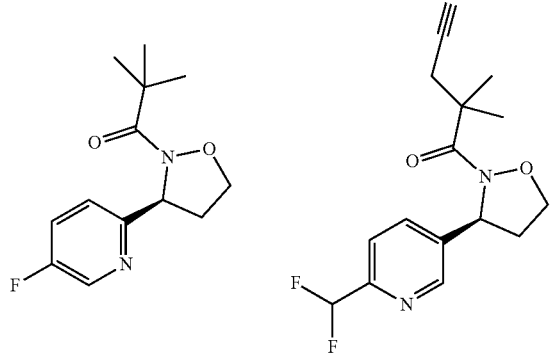
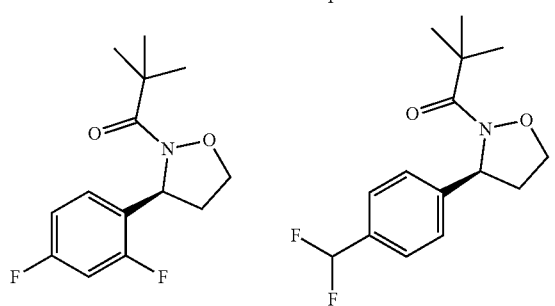
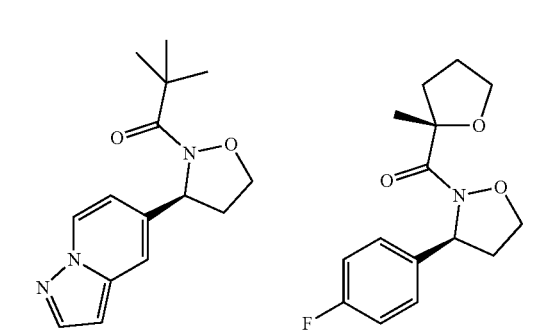
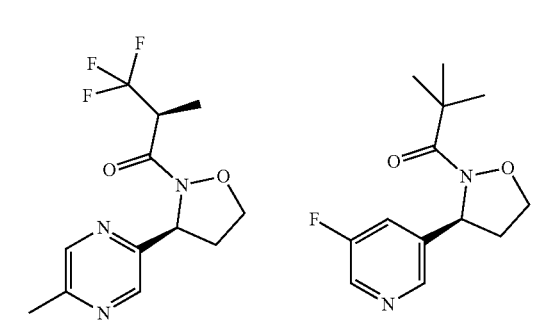
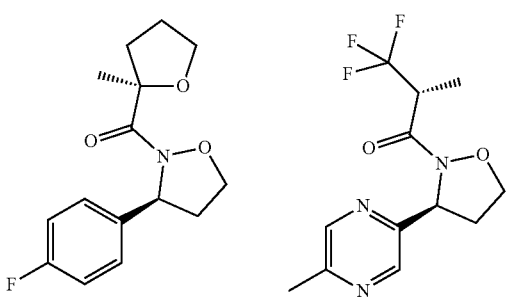
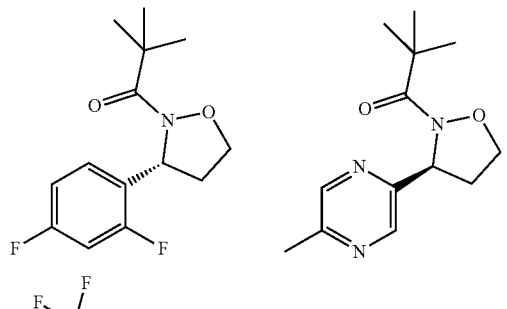
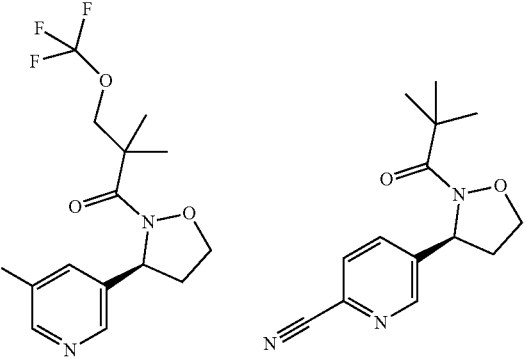
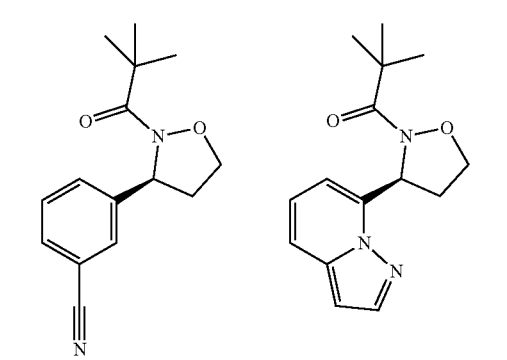
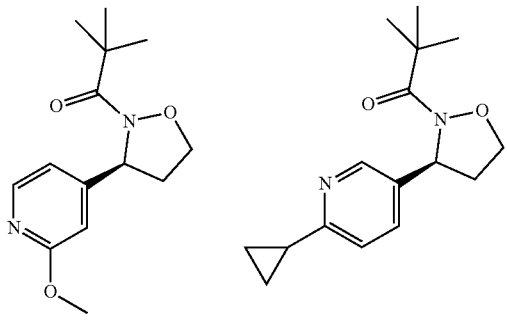

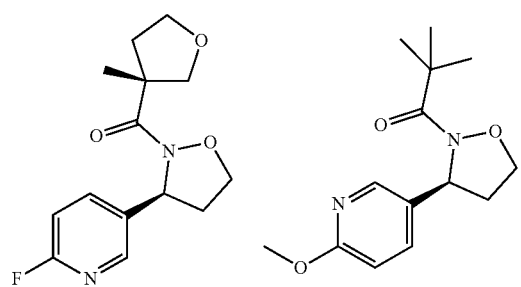
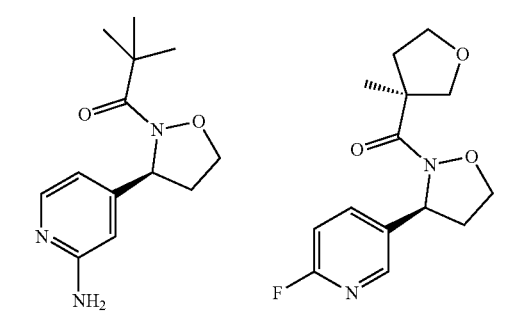
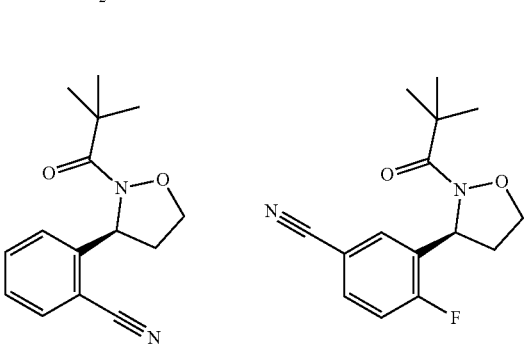
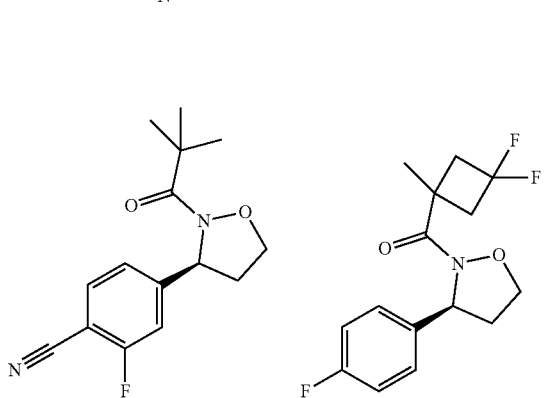
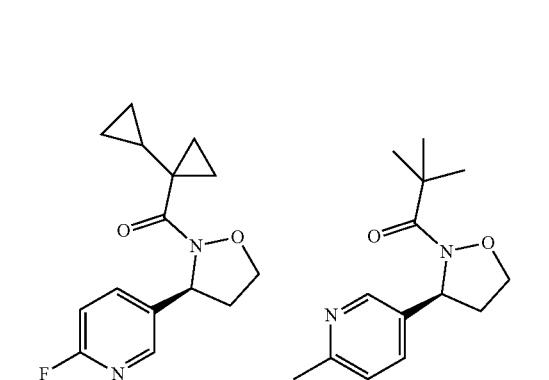
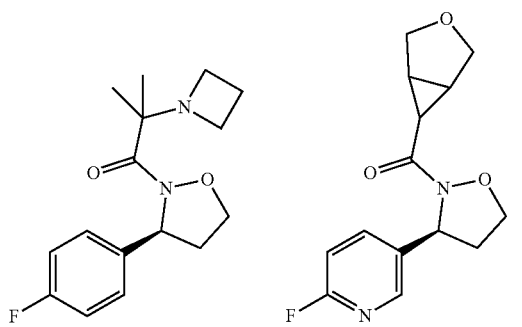
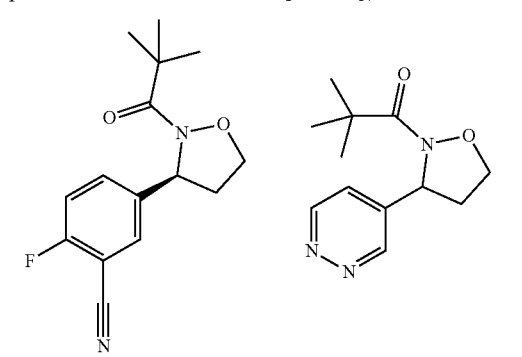
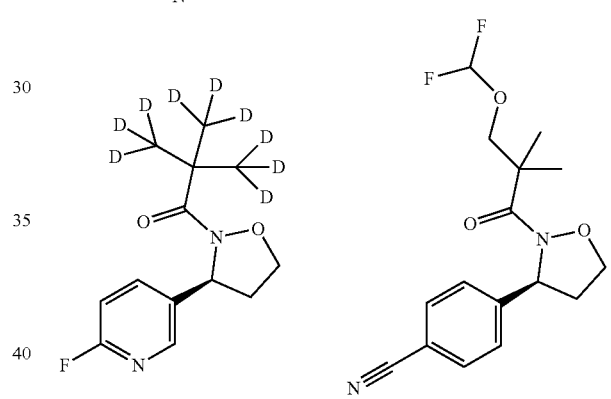
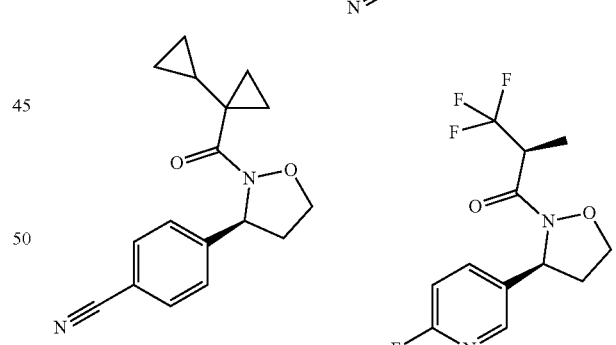
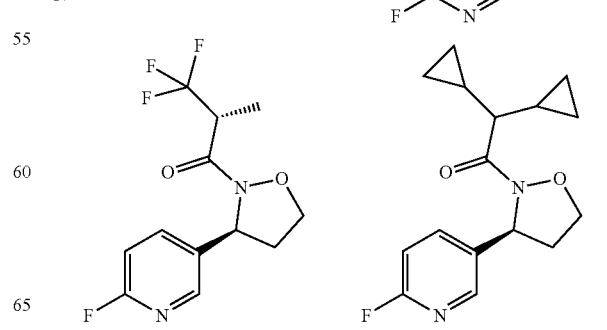

303
-continued
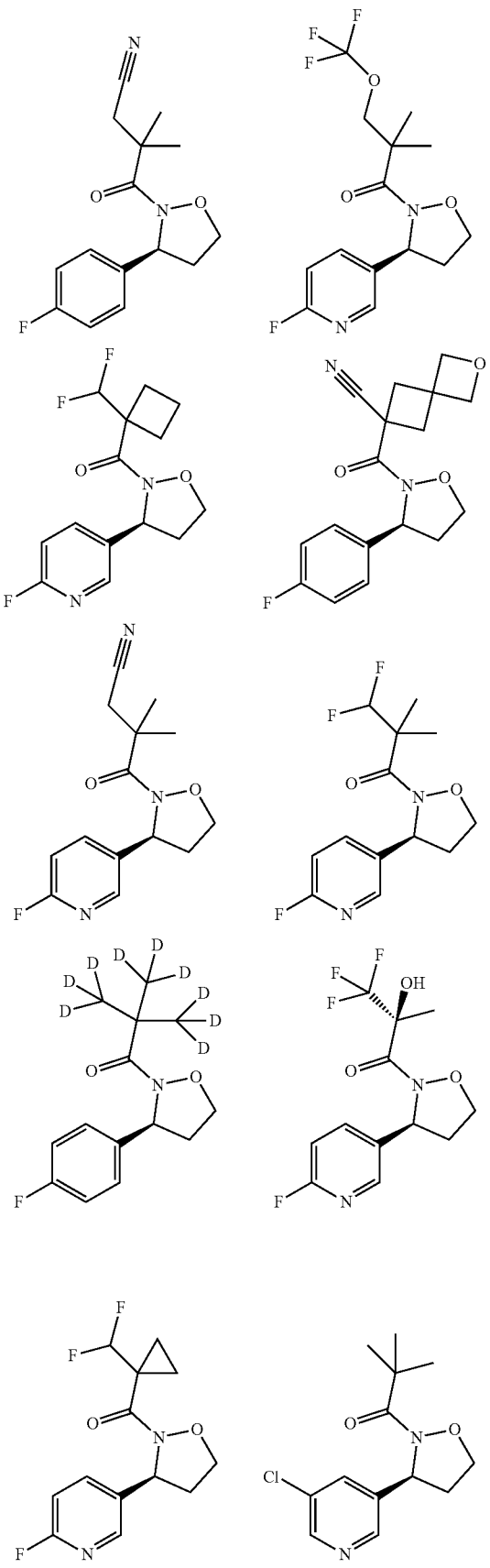
304
-continued
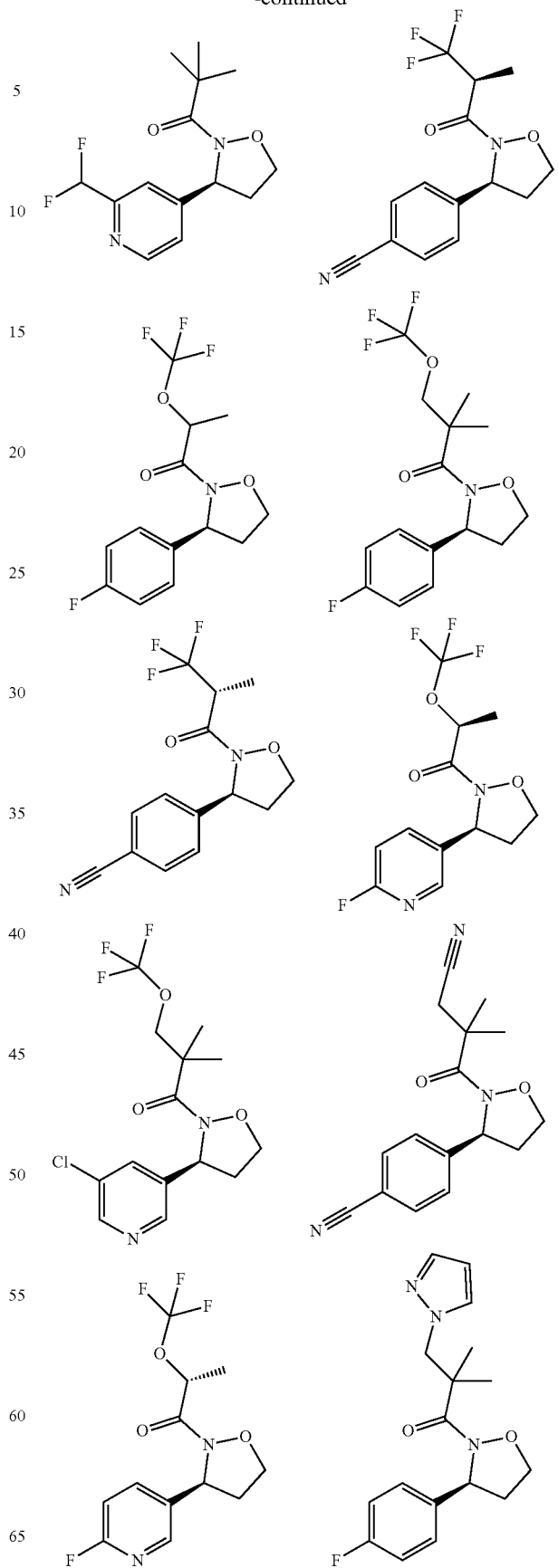

305
-continued
306
-continued
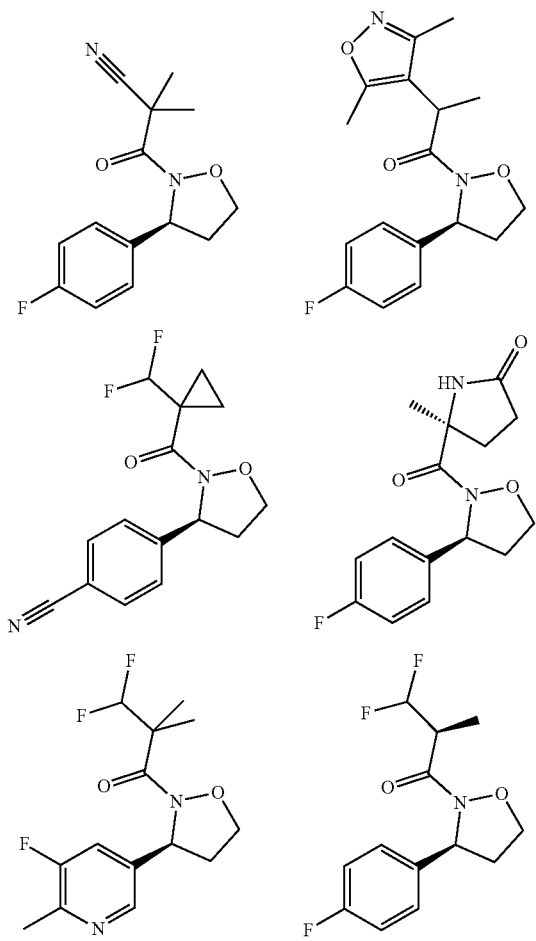
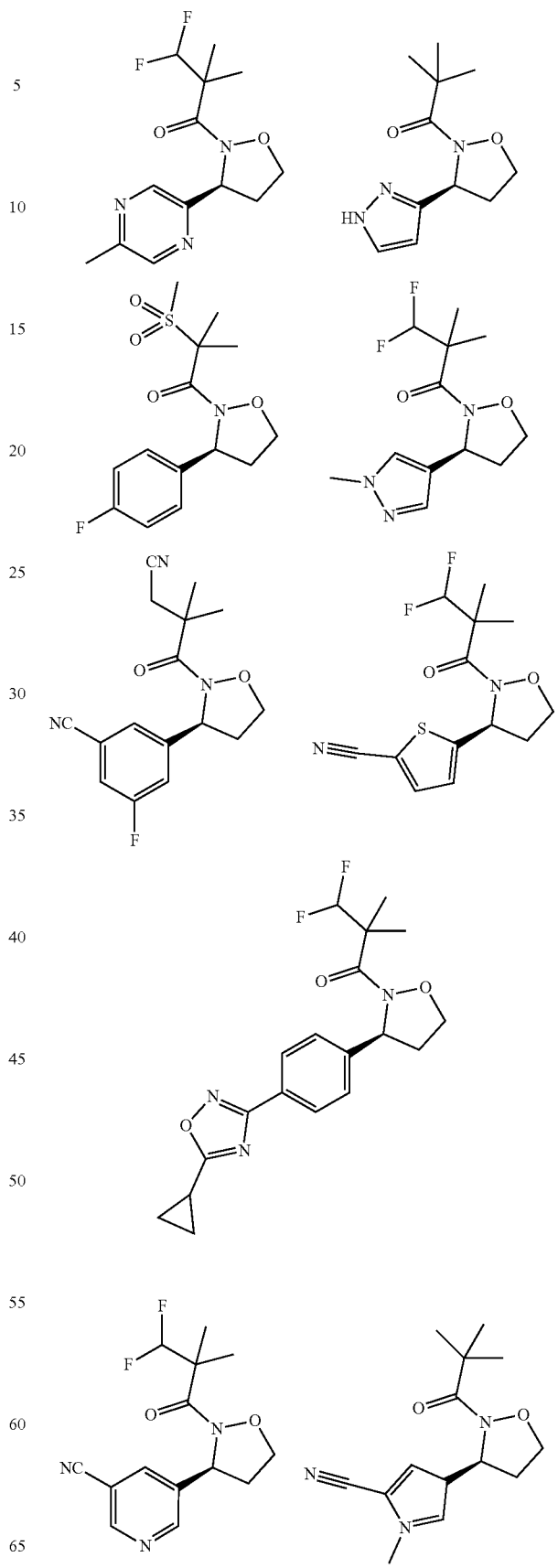

307
-continued
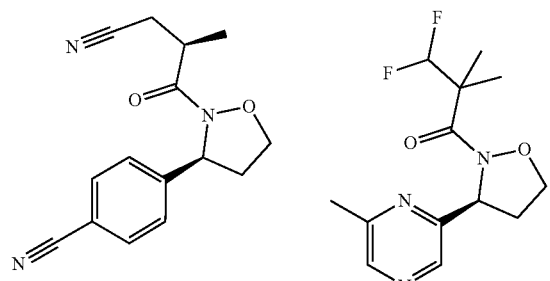
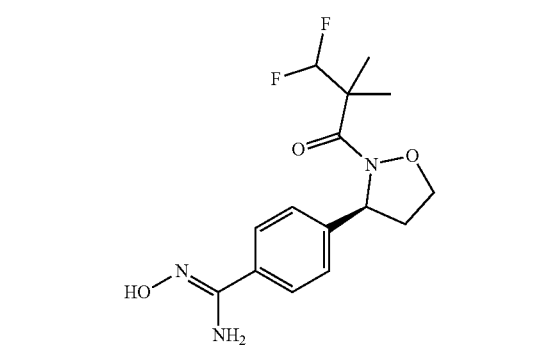
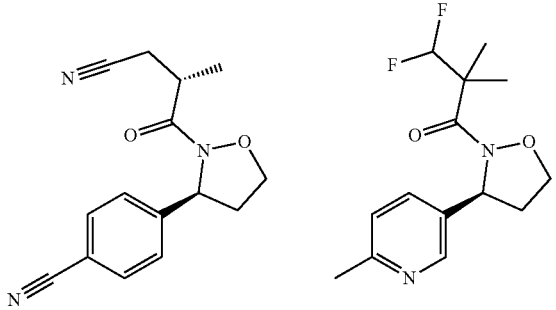
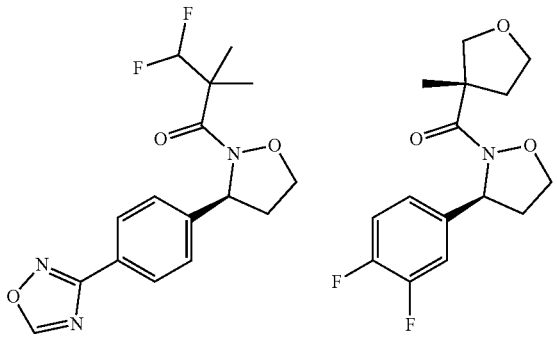
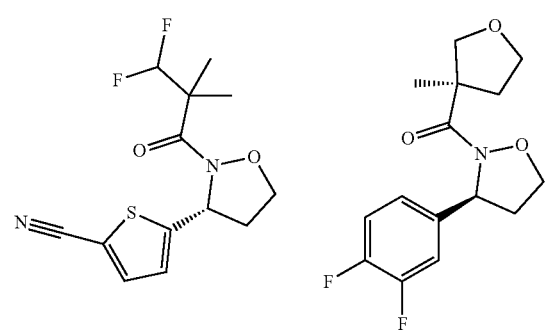
308
-continued
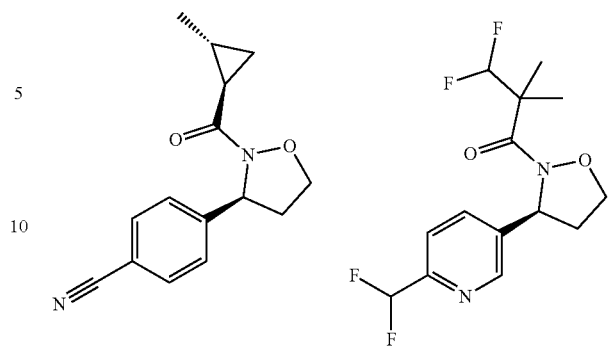
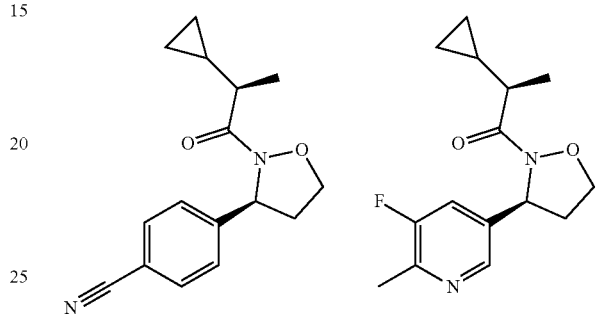
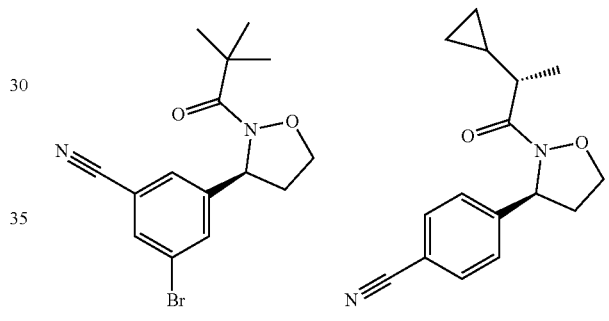
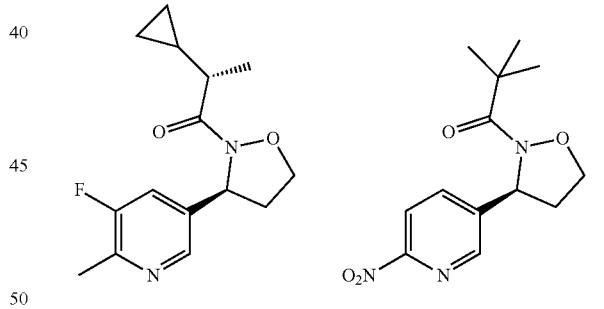
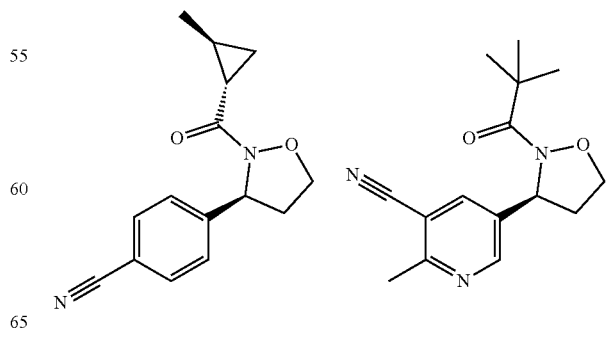

309
-continued
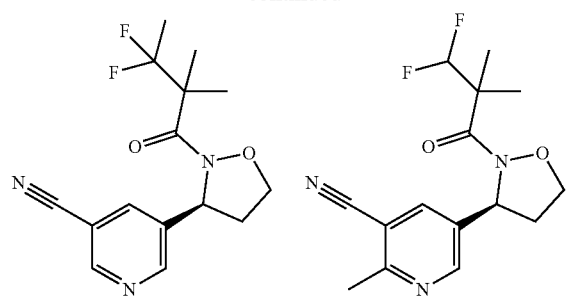
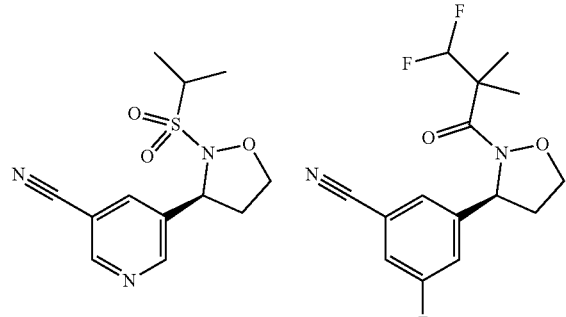
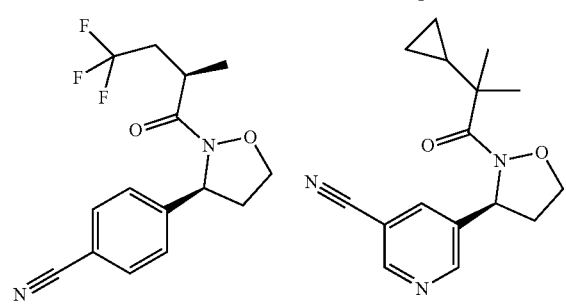
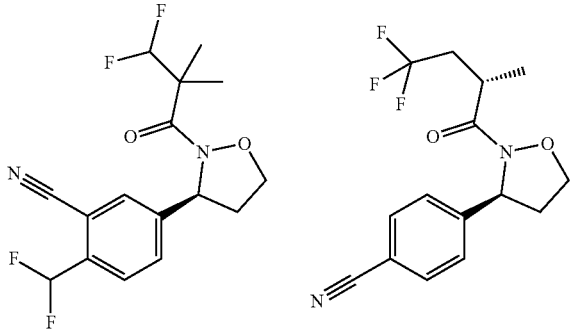
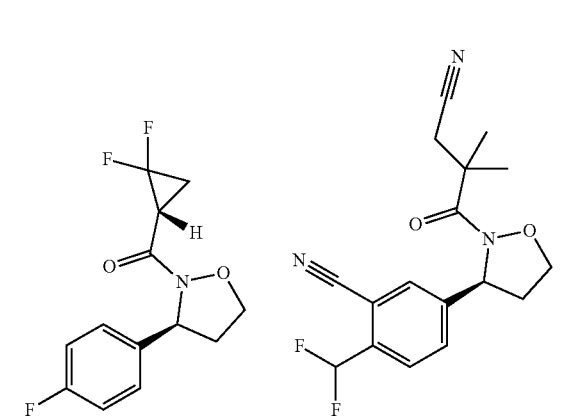
310
-continued
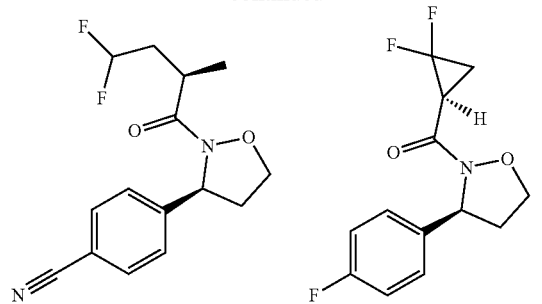
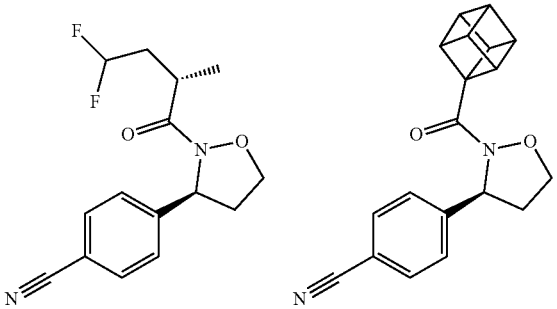
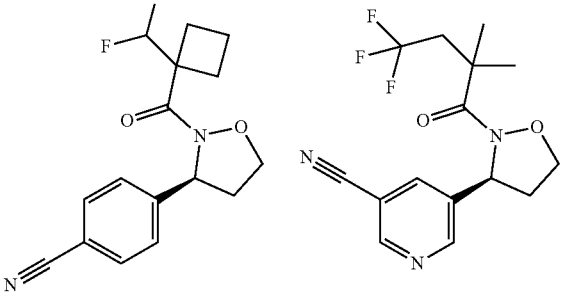
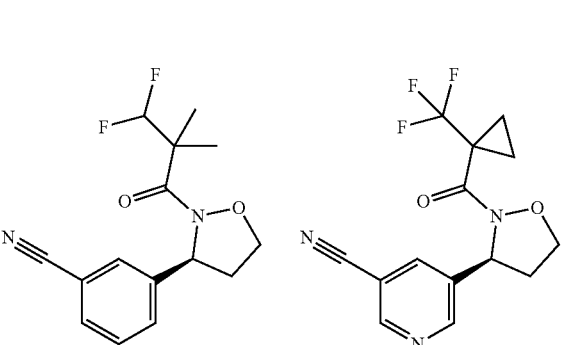
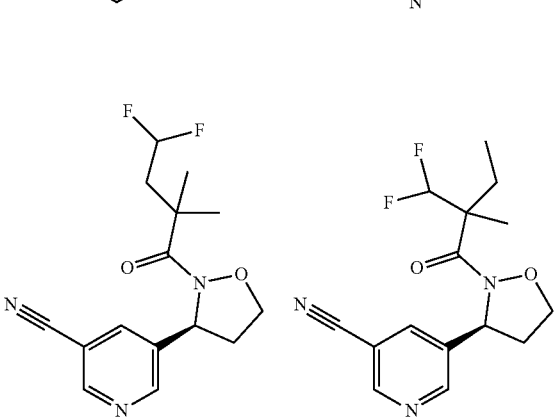

-continued

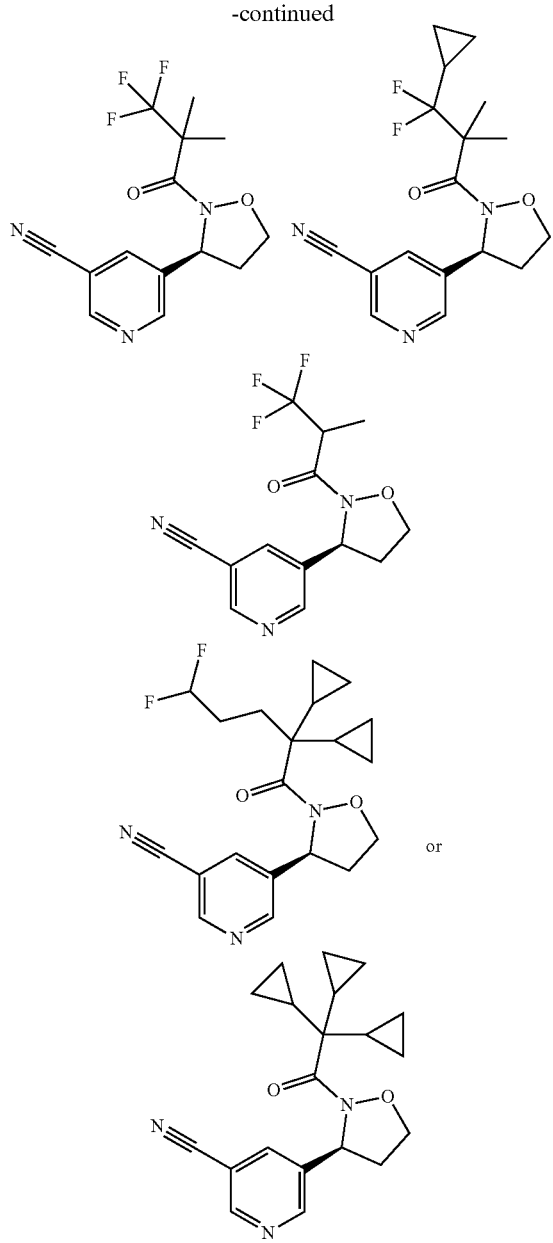

or a pharmaceutically acceptable salt, prodrug, stereoisomer or a mixture of stereoisomers thereof.

25. A composition comprising a pharmaceutically acceptable carrier and a compound as in claim 1.

26. A method for treating a necrotic cell disease or an inflammatory disorder, the method comprising administering an effective amount of the composition of claim 25 to a subject in need thereof.

27. The method of claim 26, wherein the necrotic cell disease or inflammatory disorder is trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis, inflammatory bowel disease, Crohn's disease, or ulcerative colitis.

28. A method of preparing a compound of structure (Xa) of claim 1, comprising coupling a compound of formula (A-2):

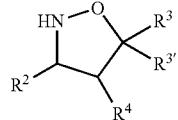

(A-2)

with a compound of formula (B-2):

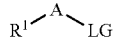

(B-2)

under conditions to provide the compound of structure (Xa), wherein A, $R^1$, $R^2$, $R^3$, $R^{3'}$, and $R^4$ are as defined in claim 4 and LG is a leaving group.

* * * * *